US011958877B2

(12) United States Patent
Graham et al.

(10) Patent No.: US 11,958,877 B2
(45) Date of Patent: *Apr. 16, 2024

(54) NUCLEOTIDE ANALOGUES

(71) Applicant: Singular Genomics Systems, Inc., San Diego, CA (US)

(72) Inventors: Ronald Graham, Carlsbad, CA (US); Olga Adelfinskaya, San Marcos, CA (US); Megha Cila, San Diego, CA (US); Rodrigo Rodriguez, San Diego, CA (US); Abrehet Abdu, San Diego, CA (US); Eli N. Glezer, Del Mar, CA (US)

(73) Assignee: Singular Genomics Systems, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/178,802

(22) Filed: Mar. 6, 2023

(65) Prior Publication Data

US 2023/0203083 A1 Jun. 29, 2023

Related U.S. Application Data

(63) Continuation of application No. 17/287,255, filed as application No. PCT/US2019/057842 on Oct. 24, 2019.

(60) Provisional application No. 62/841,146, filed on Apr. 30, 2019, provisional application No. 62/789,877, filed on Jan. 8, 2019, provisional application No. 62/750,552, filed on Oct. 25, 2018.

(51) Int. Cl.
| | |
|---|---|
| *C07H 19/14* | (2006.01) |
| *C07H 19/10* | (2006.01) |
| *C07H 19/20* | (2006.01) |
| *C12Q 1/6869* | (2018.01) |
| *C12Q 1/6876* | (2018.01) |

(52) U.S. Cl.
CPC .......... *C07H 19/14* (2013.01); *C07H 19/10* (2013.01); *C07H 19/20* (2013.01); *C12Q 1/6869* (2013.01); *C12Q 1/6876* (2013.01)

(58) Field of Classification Search
CPC ...... C07H 19/14; C07H 19/10; C12Q 1/6869; C12Q 1/6876

See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,804,386 A | 9/1998 | Ju |
| 5,814,454 A | 9/1998 | Ju |
| 5,876,936 A | 3/1999 | Ju |
| 5,952,180 A | 9/1999 | Ju |
| 6,046,005 A | 4/2000 | Ju et al. |
| 6,485,944 B1 | 11/2002 | Church et al. |
| 6,627,748 B1 | 9/2003 | Ju et al. |
| 6,664,079 B2 | 12/2003 | Ju et al. |
| 7,074,597 B2 | 7/2006 | Ju |
| 7,279,563 B2 | 10/2007 | Kwiatkowski |
| 7,345,159 B2 | 3/2008 | Ju et al. |
| 7,414,116 B2 | 8/2008 | Milton et al. |
| 7,541,444 B2 | 6/2009 | Milton et al. |
| 7,566,537 B2 | 7/2009 | Barnes et al. |
| 7,622,279 B2 | 11/2009 | Ju |
| 7,635,578 B2 | 12/2009 | Ju et al. |
| 7,713,698 B2 | 5/2010 | Ju et al. |
| 7,771,973 B2 | 8/2010 | Milton et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,071,739 B2 | 12/2011 | Milton et al. |
| 8,088,575 B2 | 1/2012 | Ju et al. |
| 8,114,973 B2 | 2/2012 | Siddiqi et al. |
| 8,298,792 B2 | 10/2012 | Ju et al. |
| 8,399,188 B2 | 3/2013 | Zhao et al. |
| 8,597,881 B2 | 12/2013 | Milton et al. |
| 8,796,432 B2 | 8/2014 | Ju et al. |
| 8,889,348 B2 | 11/2014 | Ju |
| 8,900,810 B2 | 12/2014 | Gordon et al. |
| 9,115,163 B2 | 8/2015 | Ju et al. |
| 9,121,060 B2 | 9/2015 | Milton et al. |
| 9,121,062 B2 | 9/2015 | Balasubramanian et al. |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,388,464 B2 | 7/2016 | Milton et al. |
| 9,410,200 B2 | 8/2016 | Balasubramanian et al. |
| 9,528,151 B2 | 12/2016 | Ju et al. |

(Continued)

FOREIGN PATENT DOCUMENTS

| | | |
|---|---|---|
| EP | 2876166 A1 | 5/2015 |
| EP | 2876166 B1 | 12/2016 |

(Continued)

OTHER PUBLICATIONS

Bentley, D. R. et al. (Nov. 6, 2008). "Accurate whole human genome sequencing using reversible terminator chemistry," *Nature* 456(7218): 53-59.

Bergen, K. et al. (Jun. 17, 2013, e-published Jun. 3, 2013). "Structures of KOD and 9°N DNA polymerases complexed with primer template duplex," *Chembiochem* 14(9): 1058-1062.

Bergseid, M. et al. (Nov. 2000, e-published Aug. 29, 2018). "Small molecule-based chemical affinity system for the purification of proteins," *BioTechniques* 29(5): 1126-1133.

Binauld, S. et al. (Mar. 14, 2013). "Acid-degradable polymers for drug delivery: a decade of innovation," *Chem Commun* 49(21): 2082-2102.

(Continued)

Primary Examiner — Jezia Riley

(74) Attorney, Agent, or Firm — Mintz, Levin, Cohn, Ferris, Glovsky, Popeo, P.C.; Zachary L. Terranova

(57) ABSTRACT

Disclosed herein, interalia, are compounds, compositions, and methods of using the same for the sequencing of a nucleic acid.

21 Claims, 6 Drawing Sheets

(56) References Cited

U.S. PATENT DOCUMENTS

| | | |
|---|---|---|
| 9,593,373 B2 | 3/2017 | Liu et al. |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu et al. |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,336,785 B2 | 7/2019 | Marma et al. |
| 10,738,072 B1 | 8/2020 | Graham et al. |
| 10,822,653 B1 | 11/2020 | Graham et al. |
| 11,085,076 B2 | 8/2021 | Ju et al. |
| 2002/0015961 A1 | 2/2002 | Kwiatkowski |
| 2002/0064782 A1 | 5/2002 | Shinoki et al. |
| 2003/0027140 A1 | 2/2003 | Ju et al. |
| 2004/0023207 A1 | 2/2004 | Polansky |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov et al. |
| 2009/0047699 A1 | 2/2009 | Graham |
| 2011/0014611 A1 | 1/2011 | Ju et al. |
| 2012/0142006 A1 | 6/2012 | Ju et al. |
| 2012/0156671 A1 | 6/2012 | Liu et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2015/0037788 A1 | 2/2015 | Ju |
| 2015/0080232 A1 | 3/2015 | Ju et al. |
| 2015/0140561 A1 | 5/2015 | Bergmann et al. |
| 2015/0197800 A1 | 7/2015 | Ju et al. |
| 2015/0368710 A1 | 12/2015 | Fuller et al. |
| 2016/0002721 A1 | 1/2016 | Liu et al. |
| 2016/0024570 A1 | 1/2016 | Ju et al. |
| 2016/0041179 A1 | 2/2016 | Ju et al. |
| 2016/0108382 A1 | 4/2016 | Efcavitch et al. |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain et al. |
| 2016/0369336 A1 | 12/2016 | Stupi et al. |
| 2017/0002407 A1 | 1/2017 | Balasubramanian et al. |
| 2017/0058335 A1 | 3/2017 | Tao et al. |
| 2017/0137869 A1 | 5/2017 | Marma et al. |
| 2017/0166961 A1 | 6/2017 | Liu et al. |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Ju et al. |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0077726 A1 | 3/2019 | Graham et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |
| 2020/0102609 A1 | 4/2020 | Glezer et al. |

FOREIGN PATENT DOCUMENTS

| | | |
|---|---|---|
| EP | 3356381 A1 | 8/2018 |
| WO | WO-2002/022883 A1 | 3/2002 |
| WO | WO-2002/029003 A3 | 7/2002 |
| WO | WO-2008/037568 A3 | 10/2008 |
| WO | WO-2008/144315 A1 | 11/2008 |
| WO | WO-2009/054922 A1 | 4/2009 |
| WO | WO-2012/083249 A3 | 4/2013 |
| WO | WO-2013/191793 A1 | 12/2013 |
| WO | WO-2012/162429 A3 | 5/2014 |
| WO | WO-2014/144883 A1 | 9/2014 |
| WO | WO-2014/144898 A1 | 9/2014 |
| WO | WO-2013/154999 A3 | 11/2014 |
| WO | WO-2015/148402 A1 | 10/2015 |
| WO | WO-2015/123430 A3 | 11/2015 |
| WO | WO-2016/063059 A1 | 4/2016 |
| WO | WO-2016/144973 A1 | 9/2016 |
| WO | WO-2016/154215 A1 | 9/2016 |
| WO | WO-2017/058953 A1 | 4/2017 |
| WO | WO-2017/087887 A1 | 5/2017 |
| WO | WO-2017/079498 A3 | 7/2017 |
| WO | WO-2017/176677 A1 | 10/2017 |
| WO | WO-2017/176679 A1 | 10/2017 |
| WO | WO-2017/205336 A1 | 11/2017 |
| WO | WO-2018/165207 A1 | 9/2018 |
| WO | WO-2018/183538 A1 | 10/2018 |
| WO | WO-2019/105421 A1 | 6/2019 |
| WO | WO-2019/164977 A1 | 8/2019 |
| WO | WO-2020/086834 A1 | 4/2020 |
| WO | WO-2020/146397 A1 | 7/2020 |
| WO | WO-2020/146497 A1 | 7/2020 |

OTHER PUBLICATIONS

Blackman, M. L. et al. (Oct. 15, 2008, e-published Sep. 18, 2008). "The Tetrazine ligation: fast bioconjugation based on inverse-electron-demand Diels-Alder reactivity," *J Am Chem Soc* 130(41): 13518-13519.

Debets, M. F. et al. (Oct. 14, 2013, e-published Aug. 23, 2013). "Bioorthogonal labelling of biomolecules: new functional handles and ligation methods," *Org Biomol Chem* 11(38): 6439-6455.

Extended European Search Report dated May 10, 2019, for EP Patent Application No. 16852516.0, 7 pages.

Fuller, C. W. et al. (May 10, 2016, e-published Apr. 18, 2016). "Real-time single-molecule electronic DNA sequencing by synthesis using polymer-tagged nucleotides on a nanopore array," *PNAS USA* 113(19): 5233-5238.

Guillier, F. et al. (Jun. 1, 2000, e-published May 6, 2000). "Linkers and cleavage strategies in solid-phase organic synthesis and combinatorial chemistry," *Chem Rev* 100(6): 2091-2158.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27): 9145-9150.

Hutter, D. et al. (Nov. 2010, e-published Dec. 1, 2010). "Labeled nucleoside triphosphates with reversibly terminating aminoalkoxyl groups," *Nucleosides Nucleotides Nucleic Acids* 29(11): 879-895.

Inoue, T. et al. (Nov. 5, 2015, e-published May 13, 2005). "Synthesis of trifluoromethyl ethers and difluoro(methylthio)methyl ethers by the reaction of dithiocarbonates with $IF_5$- pyridine-HF," *Journal of Fluorine Chemistry* 179: 48-52.

International Search Report mdated Dec. 29, 2016, for PCT Application No. PCT/US2016/054236, filed Sep. 28, 2016, 4 pages.

International Search Report dated Jun. 1, 2018 for PCT Application No. PCT/US2018/021219, filed Mar. 6, 2018, 3 pages.

International Search Report dated Jun. 25, 2019, for PCT Application No. PCT/US2019/018810, filed Feb. 20, 2019, 4 pages.

(56) References Cited

OTHER PUBLICATIONS

International Search Report dated Jan. 6, 2020 for PCT Application No. PCT/US2019/57842, filed Oct. 24, 2019, 3 pages.
International Search Report dated Apr. 2, 2020 for PCT Application No. PCT/US2020/012595, filed Jan. 7, 2020, 3 pages.
Jewett, J. C. et al. (Mar. 24, 2010, e-published Feb. 26, 2010). "Rapid Cu-free click chemistry with readily synthesized biarylazacyclooctynones," *J Am Chem Soc* 132(11): 3688-3690.
Ju, J. et al. (Dec. 26, 2006, e-published Dec. 14, 2006). "Four-color DNA sequencing by synthesis using cleavable fluorescent nucleotide reversible terminators," *PNAS USA* 103(52): 19635-19640.
Kumar, S. et al. (2012, e-published Sep. 21, 2012). "PEG-labeled nucleotides and nanopore detection for single molecule DNA sequencing by synthesis," *Sci Rep* 2: 684.
Leicher, T. et al. (Dec. 25, 1998). "Coexpression of the KCNA3B gene product with Kv1.5 leads to a novel A-type potassium channel," *J Biol Chem* 273(52): 35095-35101.
Leriche, G. et al. (Aug. 2, 2010). "Optimization of the azobenzene scaffold for reductive cleavage by dithionite; development of an azobenzene cleavable linker for proteomic applications," *European Journal of Organic Chemistry* 23: 4360-4364.
Marcus-Sekura, C. J. et al. (Aug. 1, 1988, e-published Nov. 24, 2004). "Techniques for using antisense oligodeoxyribonucleotides to study gene expression," *Anal Biochem* 172(2): 289-295.
Needleman, S. B. et al. (Mar. 28, 1970, e-published Oct. 28, 2004). "A general method applicable to the search for similarities in the amino acid sequence of two proteins," *J Mol Biol* 48(3): 443-453.
Partial European Search Report dated Jul. 18, 2022, for European Application No. 19875948.2, filed Oct. 24, 2019, 16 pages.
Pearson, W. R. et al. (Apr. 1, 1988). "Improved tools for biological sequence comparison," *PNAS USA* 85(8): 2444-2448.
PubChem Compound Summary for CID 121486816 (Aug. 16, 2016). Located at <https:pubchem.ncbi.nlm.nih.gov/compound/121486816> last visited Apr. 22, 2019, 7 pages.
PubChem Compound Summary for CID 69188114 (Nov. 30, 2012). Located at <https:pubchem.ncbi.nlm.nih.gov/compound/69188114> last visited Apr. 22, 2019, 7 pages.
Rathod, K. M. et al. (2013). "Synthesis and Antimicrobial Activity of Azo Compounds Containing m-Cresol Moiety," *Chem Sci Trans* 2(1): 25-28.
Rosenblum, B. B. et al. (Nov. 15, 1997). "New dye-labeled terminators for improved DNA sequencing patterns," *Nucleic Acids Res* 25(22): 4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," *PNAS USA* 102(17): 5932-5937.
Schumacher, W. et al. (Jun. 16, 1997, e-published Nov. 7, 1997). "Redox chemistry of cobalamin and iron-sulfur cofactors in the tetrachloroethene reductase of *Dehalobacter restrictus,*" *FEBS Lett* 409(3): 421-425.
Shenoi, R. A. et al. (Sep. 12, 2012, e-published Aug. 30, 2012). "Branched multifunctional polyether polyketals: variation of ketal group structure enables unprecedented control over polymer degradation in solution and within cells," *J Am Chem Soc* 134(36): 14945-14957.
Smith, T. F. et al. (Dec. 1981, e-published Sep. 3, 2004). "Comparison of biosequences," *Adv Appl Math* 2(4): 482-489.
Southworth, M. W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11): 5281-5285.
Švagera, Z. et al. (Mar. 2012, e-published Feb. 15, 2012). "Study of disulfide reduction and alkyl chloroformate derivatization of plasma sulfur amino acids using gas chromatography-mass spectrometry," *Anal Bioanal Chem* 402(9): 2953-2963.
Tang et al. (Nov. 2014). "Synthesis and Application of Four Fluorescence Labeled Nucleotides Through Disulfide as Reversible Terminators in DNA Sequencing by Synthesis," *Chemical Journal of Chinese Universities* 35(11): 2346-2352, including an English language abstract.
Uhlmann, E. et al. (Jun. 1, 1990, e-published May 1, 2002). "Antisense oligonucleotides: a new therapeutic principle," *Chemical Reviews* 90(4): 543-584.
Weintraub, H. M. (Jan. 1990). "Antisense RNA and DNA," *Sci Am* 262(1): 40-46.
Written Opinion dated Dec. 29, 2016, for PCT Application No. PCT/US2016/054236, filed Sep. 28, 2016, 4 pages.
Written Opinion dated Jun. 1, 2018 for PCT Application No. PCT/US2018/021219, filed Mar. 6, 2018, 9 pages.
Written Opinion dated Jun. 25, 2019, for PCT Application No. PCT/US2019/018810, filed Feb. 20, 2019, 5 pages.
Written Opinion dated Jan. 6, 2020 for PCT Application No. PCT/US2019/57842, filed Oct. 24, 2019, 11 pages.
Written Opinion dated Apr. 2, 2020 for PCT Application No. PCT/US2020/012595, filed Jan. 7, 2020, 3 pages.
Wu, J. et al. (Oct. 16, 2007, e-published Oct. 8, 2007). "3'-O-modified nucleotides as reversible terminators for pyrosequencing," *PNAS USA* 104(42): 16462-16467.
Zhu, Z. et al. (Aug. 25, 1994). "Directly labeled DNA probes using fluorescent nucleotides with different length linkers," *Nucleic Acids Res* 22(16): 3418-3422.
Extended European Examination Report dated Aug. 30, 2023, for EP Application No. 21793126.0, PCT/US2021/028839, 8 pages.

calculated Exact Mass: 1853.32
LCMS observed: 1853 calculated Exact Mass: 1853.32
LCMS observed: 1853 calculated Exact Mass: 1545.21
LCMS observed: 1545

NUCLEOTIDE ANALOGUES

CROSS-REFERENCES TO RELATED APPLICATIONS

This application is a continuation of U.S. Utility application Ser. No. 17/287,255 filed Apr. 21, 2021, which is the national stage filing under 35 U.S.C. § 371 of International Application No. PCT/US2019/057842 filed Oct. 24, 2019, which claims the benefit of U.S. Provisional Application No. 62/750,552, filed Oct. 25, 2018; U.S. Provisional Application No. 62/789,877, filed Jan. 8, 2019; and U.S. Provisional Application No. 62/841,146, filed Apr. 30, 2019; which are incorporated herein by reference in their entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound of Formula (I):

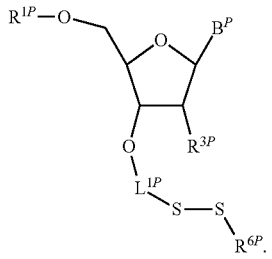

(I$^P$)

$B^P$ is a nucleobase. $R^{1P}$ is independently hydrogen or 5'-nucleoside protecting group, or —$OR^{1P}$ is a monophosphate, or polyphosphate. $R^{3P}$ is hydrogen or —$OR^{3AP}$, wherein $R^{3AP}$ is hydrogen or a polymerase-compatible cleavable moiety. $R^{6P}$ is a substituted or unsubstituted alkyl. $L^{1P}$ is substituted or unsubstituted $C_1$-$C_4$ alkylene.

In an aspect is provided a compound of Formula (IB$^P$):

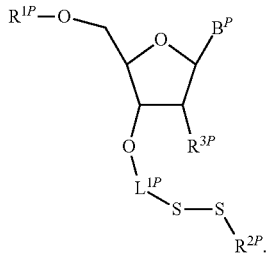

(IB$^P$)

$R^{1P}$, $R^{3P}$, $R^{2P}$, $L^{1P}$ and $B^P$ are described herein.

$R^{2P}$ is -$L^{2P}$-$R^{4P}$, -$L^{2P}$-3'-nucleoside, -$L^{2P}$-3'-nucleotide, or -$L^{2P}$-3'-nucleic acid. $L^{2P}$ is a bond, substituted or unsubstituted $C_1$-$C_4$ alkylene. $R^{4P}$ is substituted or unsubstituted $C_1$-$C_6$ alkyl.

In an aspect is provided a compound of Formula (IC$^P$),

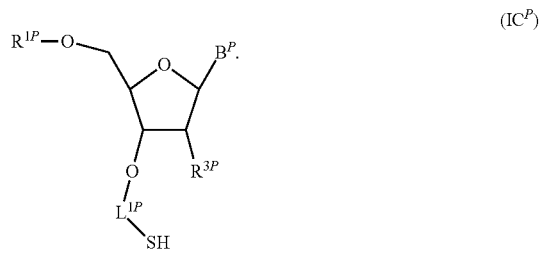

(IC$^P$)

$R^{1P}$, $R^{3P}$, $L^{1P}$ and $B^P$ are described herein.

In an aspect is provided a method of making a compound of Formula I$^P$:

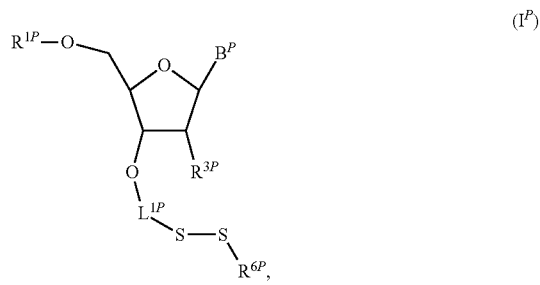

(I$^P$)

the method comprising mixing compound (IB$^P$) and compound (II$^P$) or compound (III$^P$) together in a reaction vessel; wherein the compound of Formula IB$^P$ has the formula:

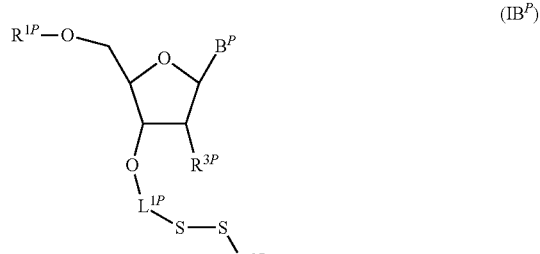

(IB$^P$)

the compound II$^P$ has the formula:

(II$^P$)

the compound III$^P$ has the formula:

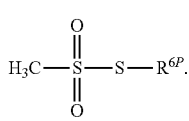

(III$^P$)

B$^P$ is a nucleobase. R$^{1P}$ is independently hydrogen or 5'-nucleoside protecting group, or —OR$^{1P}$ is a monophosphate, or polyphosphate. R$^{2P}$ is -L$^{2P}$-R$^{4P}$, -L$^{2P}$-3'-nucleoside, -L$^{2P}$-3'-nucleotide, or -L$^{2P}$-3'-nucleic acid. R$^{3P}$ is independently hydrogen or —OR$^{3.4P}$, wherein R$^{3.4P}$ is hydrogen or a polymerase-compatible cleavable moiety. R$^{4P}$ is substituted or unsubstituted C$_1$-C$_6$ alkyl. R$^{6P}$ is a substituted or unsubstituted alkyl. L$^{1P}$ is substituted or unsubstituted C$_1$-C$_4$ alkylene; and L$^{2P}$ is a bond, substituted or unsubstituted C$_1$-C$_4$ alkylene.

Other aspects of the invention are disclosed infra.

In an aspect is provided a compound having the formula:

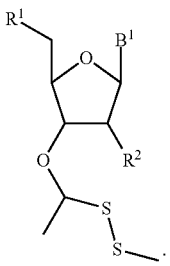

(I)

B$^1$ is a monovalent nucleobase.

R$^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

R$^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

In an aspect is provided a nucleic acid polymerase complex, wherein the nucleic acid polymerase is bound (e.g., non-covalently bound) to a compound described herein, including embodiments.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein.

In an aspect is provided a method for sequencing a nucleic acid, including: incorporating in series with a nucleic acid polymerase, within a reaction vessel, a compound into a primer to create an extension strand, wherein the primer is hybridized to the nucleic acid and wherein the compound includes a detectable label; detecting the detectable label of the incorporated compound, so as to thereby identify the incorporated compound in the extension strand, thereby sequencing the nucleic acid; wherein the compound is independently a compound described herein.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein.

DETAILED DESCRIPTION

I. Definitions

Figure 1:
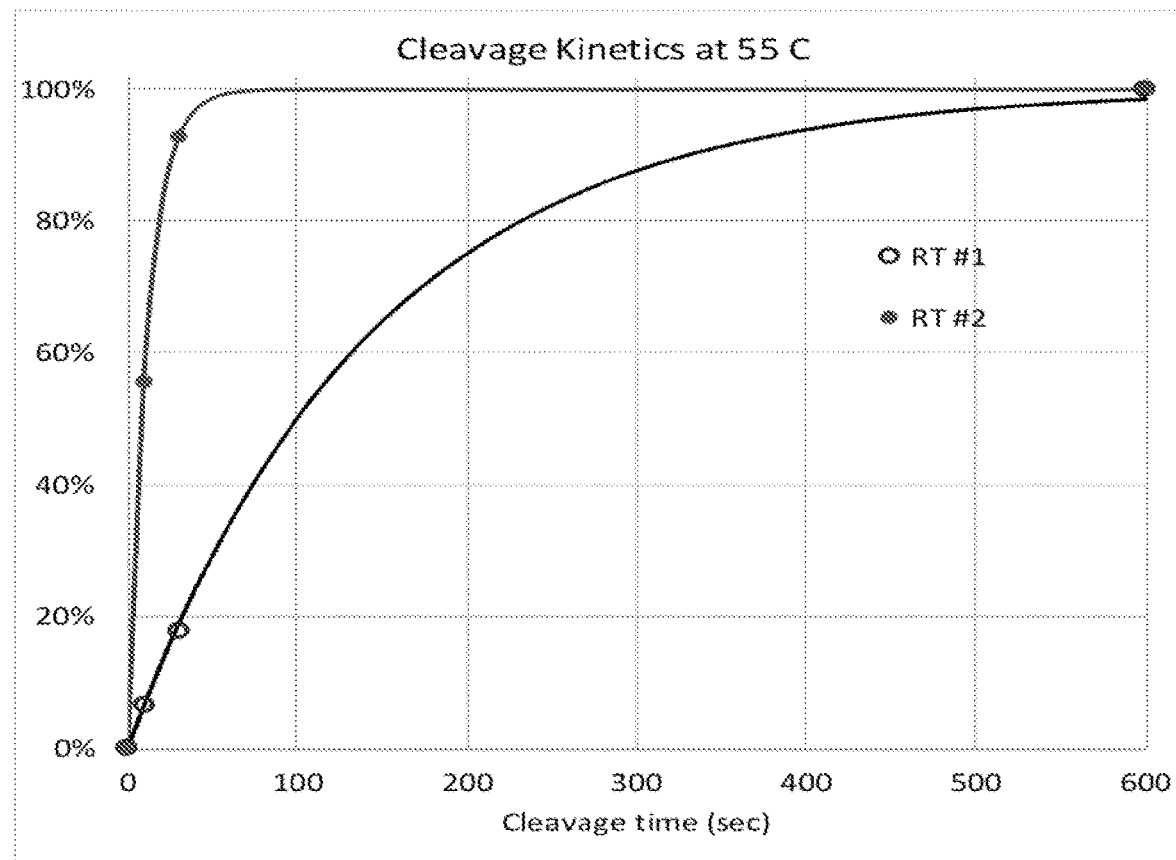
FIG. 1. Cleavage kinetics of two reversible terminators, RT #1 and RT #2. RT #1 is 3'O—CH$_2$—S—S—CH$_3$ and RT #2 is a moiety as described herein. In both cases, a dTTP nucleotide with the reversible terminator was incorporated into a growing DNA strand immobilized on a solid support.
Figure 2A:
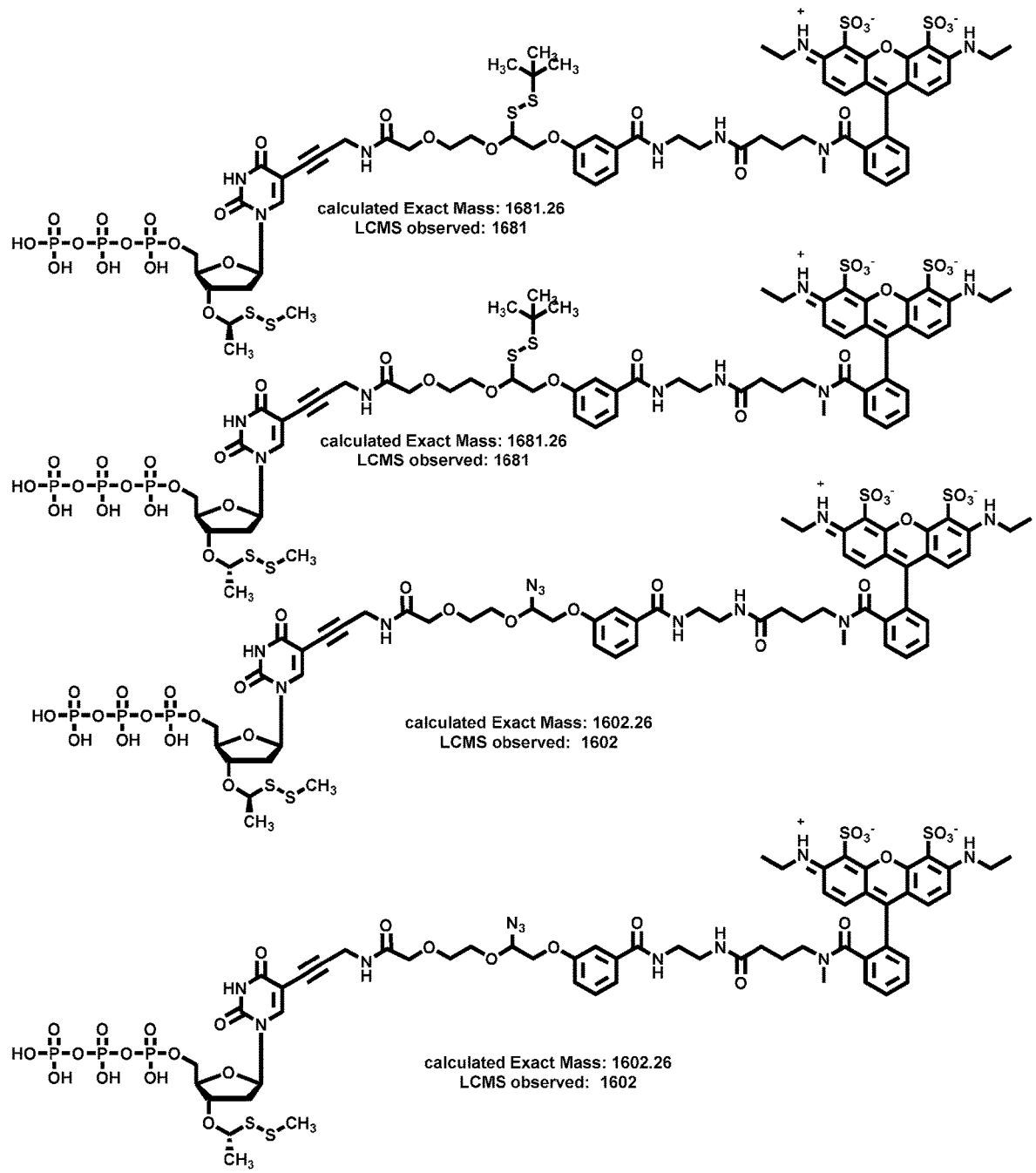
FIGS. 2A-2C. Nucleotides covalently linked to labels and LCMS data.
Figure 2B:
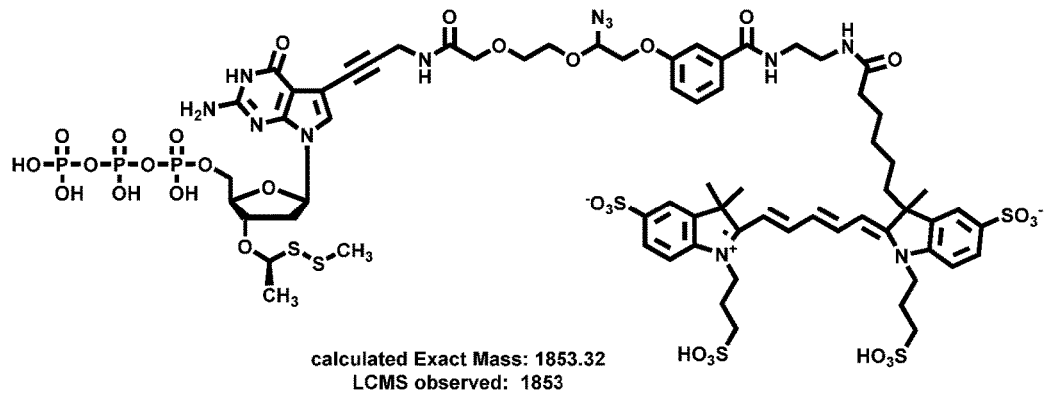
Figure 2B:
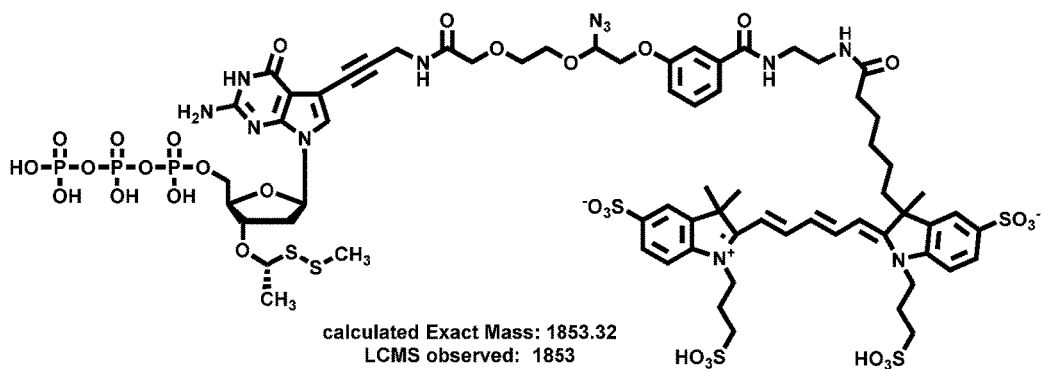
Figure 2B:
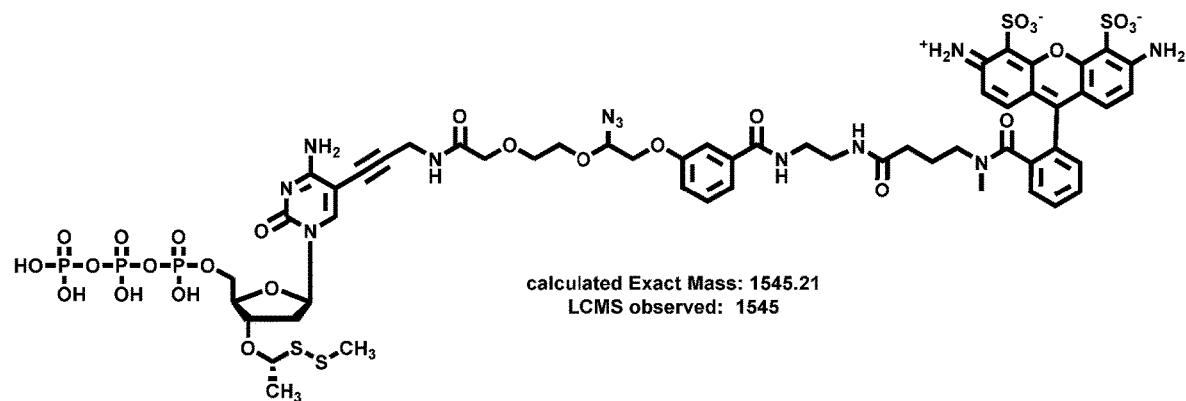
Figure 2C:
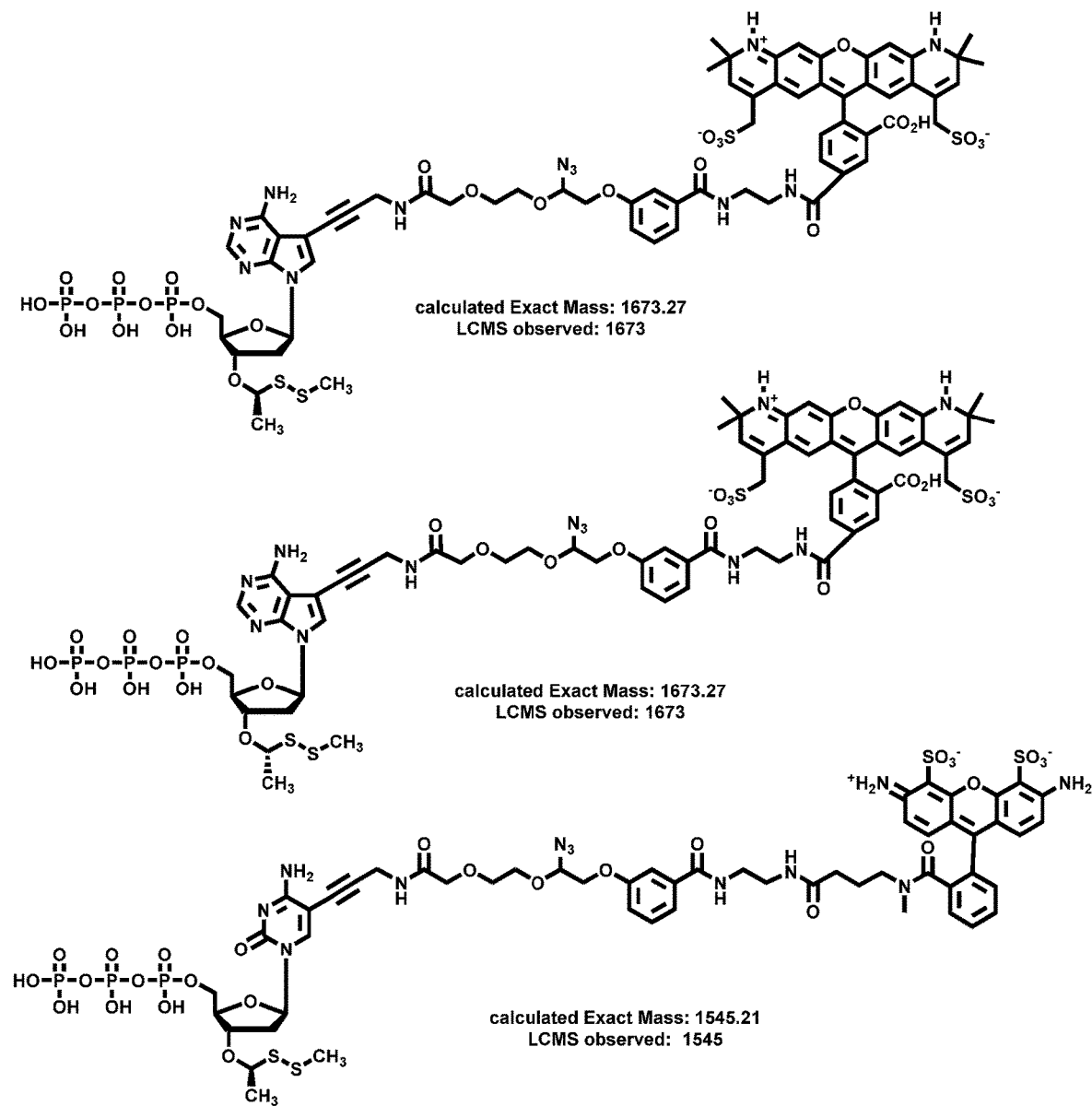
Figure 3:
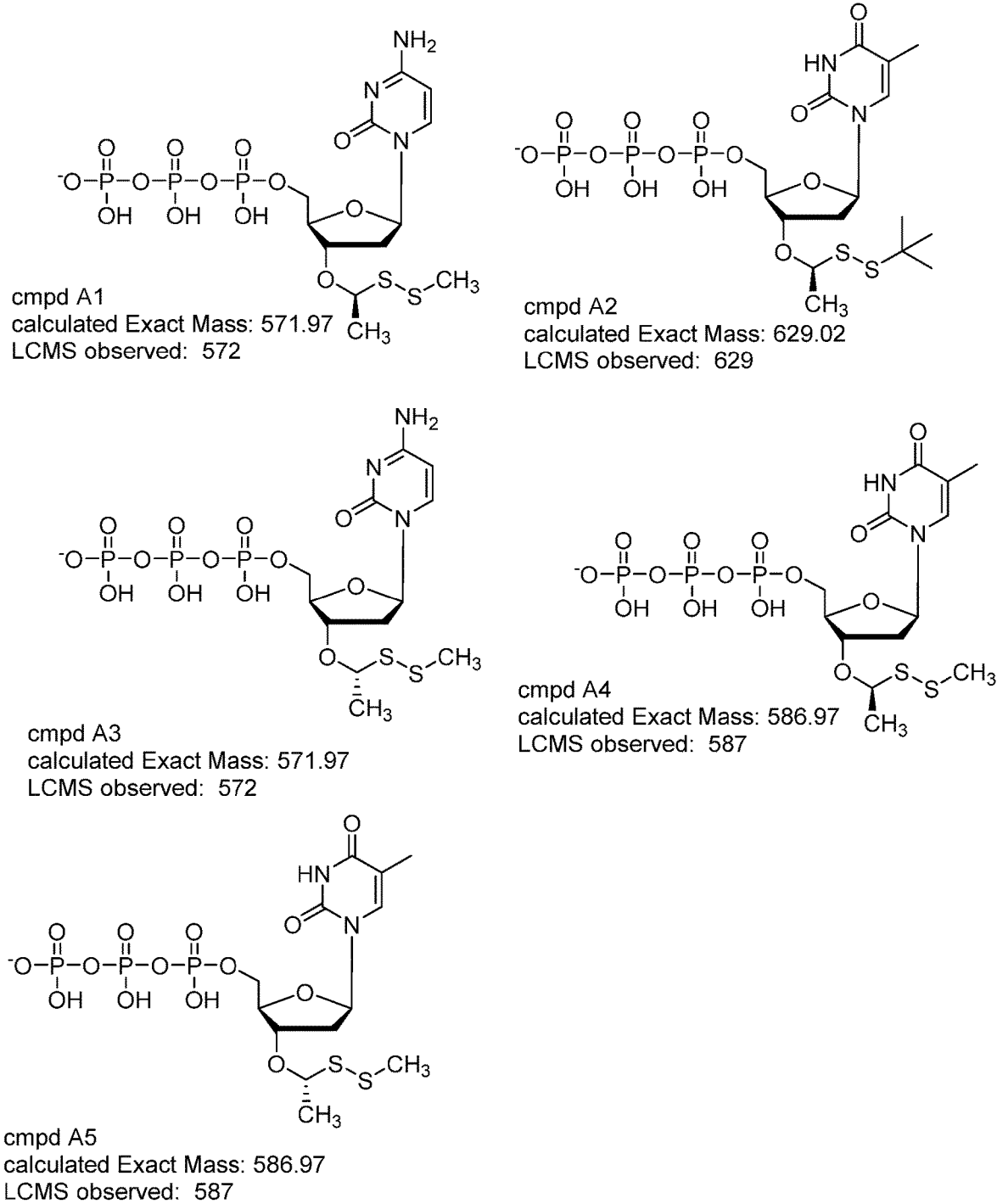
FIG. 3. Nucleotides and LCMS data.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

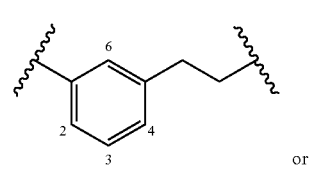

or

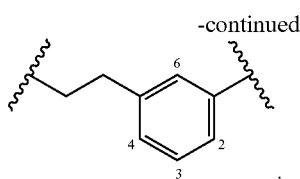

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R', —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R', —NR"C(O)$_2$R', —NR—C(NR'R")=NR'", —S(O)R', —S(O)$_2$R', —S(O)$_2$NR'R", —NRSO$_2$R', —NR'NR"R'", —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^3$ substituents are present, each $R^3$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^3$ and optionally differently.

A "detectable agent," "detectable compound," "detectable label," or "detectable moiety" is a substance (e.g., element), molecule, or composition detectable by spectroscopic, photochemical, biochemical, immunochemical, chemical, magnetic resonance imaging, or other physical means. For example, detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

The terms "fluorophore" or "fluorescent agent" or "fluorescent dye" are used interchangeably and refer to a substance, compound, agent (e.g., a detectable agent), or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5, DRAQ7, or CyTRAK Orange), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF Dye™, DRAQ™, CyTRAK™, BODIPY™, Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™, RPE™, and/or BPE™. A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners). In embodiments, the fluorophore is an aromatic (e.g., polyaromatic) moiety having a conjugated π-electron system. In embodiments, the fluorophore is a fluorescent dye moiety, that is, a monovalent fluorophore. In embodiments, the fluorescent dye moiety is

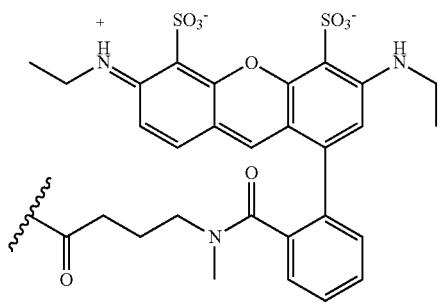

In embodiments, the fluorescent dye moiety is

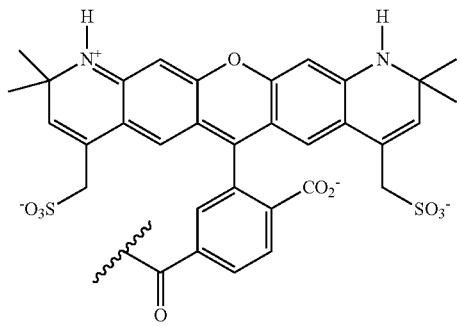

In embodiments, the fluorescent dye moiety is

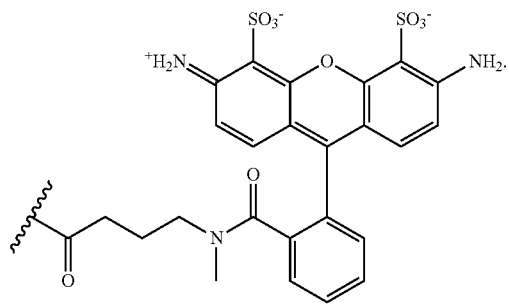

In embodiments, the fluorescent dye moiety is

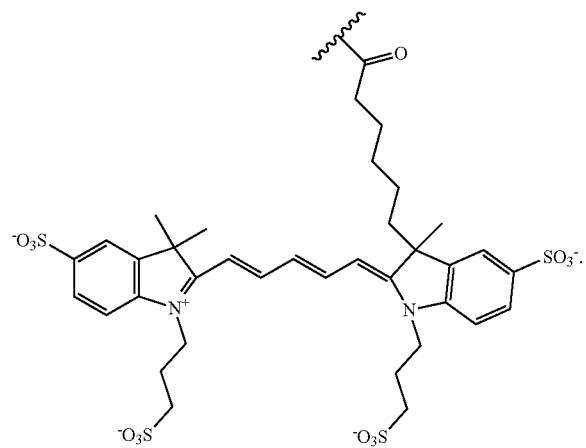

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent moiety or fluorescent dye moiety. In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+ sup>moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2', 7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the detectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl)Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyanl, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Bluegreen algae, BO-PRO-1, BO-PRO-3, BOBO-A, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kntzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu2O3 nanoparticles, Eu (Soini), Eu(tta)3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*—Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazinl, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1. In embodiments, $R^4$ is a monovalent moiety of a compound described within this paragraph.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

As used herein, the term "salt" refers to acid or base salts of the compounds described herein. Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, and it is understood an appropriate counter-ion (e.g., chloride ion, fluoride ion, or acetate ion) may also be present, though not explicitly shown. Likewise, for compounds having a negative charge (e.g.,

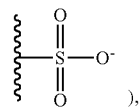 [SMILES: *S(=O)(=O)[O-]]
), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g.,

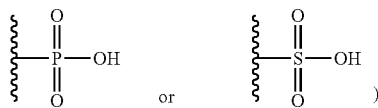

or an ionic state (e.g.,

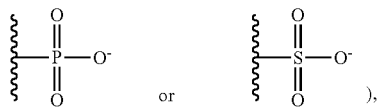

and it is understood these are interchangeable. In embodiments, the counter-ion is represented by the symbol M (e.g., $M^+$ or $M^-$).

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a target-inhibitor interaction means positively affecting (e.g., increasing) the activity or function of the target (e.g., protein) relative to the activity or function of the target (e.g., protein) in the absence of the activator. In embodiments activation means positively affecting (e.g., increasing) the concentration or levels of the target (e.g., protein) relative to the concentration or level of the target (e.g., protein) in the absence of the activator. The terms may reference activation, or activating, sensitizing, or up-regulating signal transduction or enzymatic activity or the amount of a target (e.g., protein) decreased in a disease. Thus, activation may include, at least in part, partially or totally increasing stimulation, increasing or enabling activation, or activating, sensitizing, or up-regulating signal transduction or enzymatic activity or the amount of a target (e.g., protein) associated with a disease (e.g., a target (e.g., protein) which is decreased in a disease relative to a non-diseased control). Activation may include, at least in part, partially or totally increasing stimulation, increasing or enabling activation, or activating, sensitizing, or up-regulating signal transduction or enzymatic activity or the amount of a target (e.g., protein).

The terms "agonist," "activator," "upregulator," etc. refer to a substance capable of detectably increasing the expression or activity of a given target (e.g., gene or protein). The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition," "inhibit," "inhibiting" and the like in reference to a target-inhibitor interaction means negatively affecting (e.g., decreasing) the activity or function of the target (e.g., protein) relative to the activity or function of the target (e.g., protein) in the absence of the inhibitor. In embodiments inhibition means negatively affecting (e.g., decreasing) the concentration or levels of the target (e.g., protein) relative to the concentration or level of the target (e.g., protein) in the absence of the inhibitor. In embodiments inhibition refers to reduction of a disease or symptoms of disease. In embodiments, inhibition refers to a reduction in the activity of a particular target (e.g., protein). Thus, inhibition includes, at least in part, partially or totally blocking stimulation, decreasing, preventing, or delaying activation, or inactivating, desensitizing, or down-regulating signal transduction or enzymatic activity or the amount of a target (e.g., protein). In embodiments, inhibition refers to a reduction of activity of a target (e.g., protein) resulting from a direct interaction (e.g., an inhibitor binds to the target (e.g., protein)). In embodiments, inhibition refers to a reduction of activity of a target (e.g., protein) from an indirect interaction (e.g., an inhibitor binds to a target (e.g., protein) that activates the target (e.g., protein), thereby preventing target (e.g., protein) activation).

The terms "inhibitor," "repressor," "antagonist," or "downregulator" interchangeably refer to a substance capable of detectably decreasing the expression or activity of a given target (e.g., gene or protein). The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. Nucleosides may be modified at the base and/or and the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

"Nucleotide," as used herein, refers to a nucleoside-5'-polyphosphate compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as adenine (A), cytosine (C), guanine (G), thymine (T), uracil (U), or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In an embodiment, the nucleotide is a deoxyribonucleotide. In another embodiment, the nucleotide is a ribonucleotide. In embodiments, nucleotides comprise 3 phosphate groups (e.g., a triphosphate group).

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base A, G, C, T or U), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

A "nucleoside" is structurally similar to a nucleotide, but is missing the phosphate moieties. An example of a nucleoside analogue would be one in which the label is linked to the base and there is no phosphate group attached to the sugar molecule.

"Nucleoside," as used herein, refers to a glycosyl compound consisting of a nucleobase and a 5-membered ring sugar (e.g., either ribose or deoxyribose). Nucleosides may comprise bases such as adenine (A), cytosine (C), guanine (G), thymine (T), uracil (U), or analogues thereof. Nucleosides may be modified at the base and/or and the sugar. In an embodiment, the nucleoside is a deoxyribonucleoside. In another embodiment, the nucleoside is a ribonucleoside.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., $-NH_2$, $-COOH$, $-N$-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The term "monophosphate" is used in accordance with its ordinary meaning in the arts and refers to a moiety having the formula:

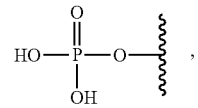

or ionized forms thereof. The term "polyphosphate" refers to at least two phosphate groups, having the formula:

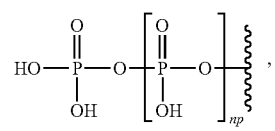

or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

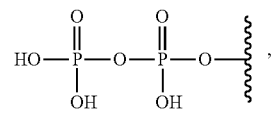 [SMILES: *OP(=O)(O)OP(=O)(O)O]

or ionized forms thereof. The term "triphosphate" is used in accordance with its ordinary meaning in the arts and refers to a moiety having the formula:

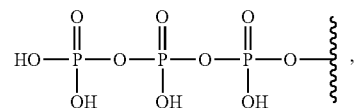 [SMILES: *OP(=O)(O)OP(=O)(O)OP(=O)(O)O]

or ionized forms thereof. In embodiments, a polyphosphate is a diphosphate. In embodiments, a polyphosphate is a triphosphate.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified. In embodiments, the base is

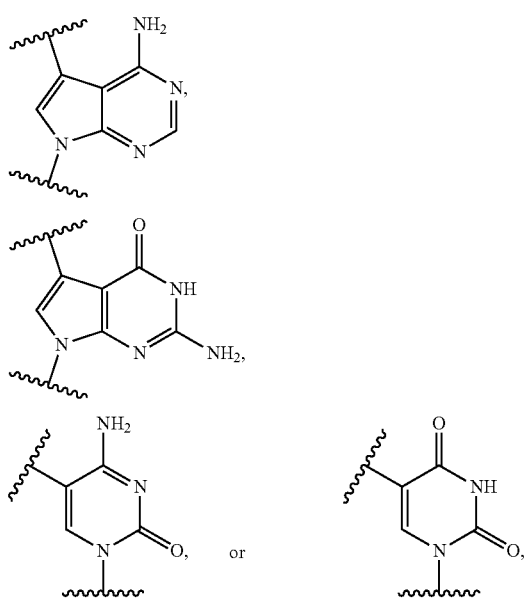

which may be optionally substituted or modified. In embodiments, the base includes

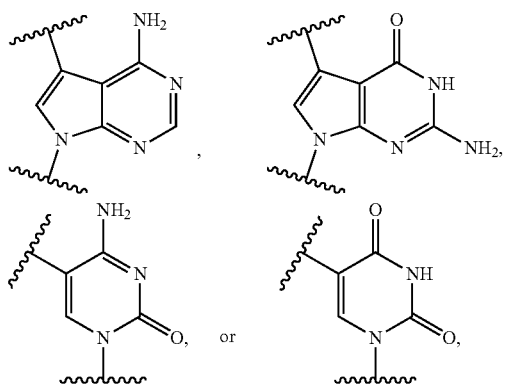

which may be optionally substituted or modified. In embodiments, the base is

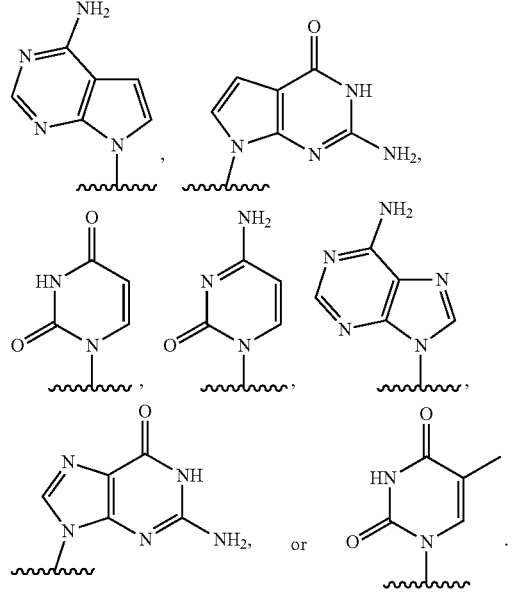

In embodiments, the nucleobase is,

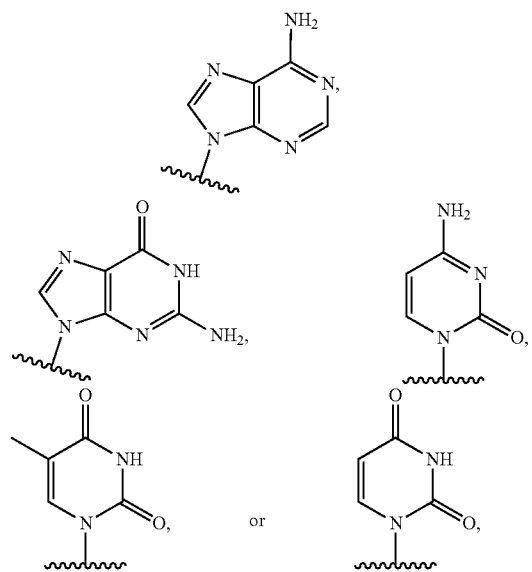

which may be optionally substituted or modified. In embodiments, the nucleobase includes a substituted or unsubstituted propargyl amine moiety, which may further include S—S linker, fluorophores or protecting group. In embodiments, the nucleobase is

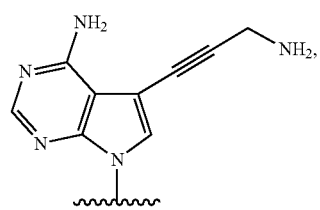

-continued

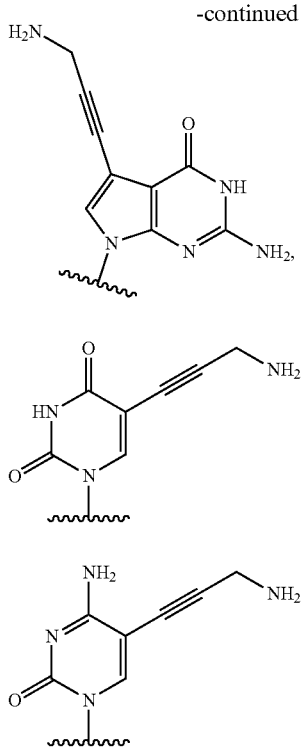

which may be further substituted or modified. In embodiments, the propargyl amine moiety may further include at least one or more fluorophores. In embodiments, the propargyl amine moiety may further be linked to a S—S— linker, which may be connected to at least one or more flurorophores. In embodiments, the propargyl amine moiety may further include at least one or more protecting groups. In embodiments, the propargyl amine moiety may further be linked to a S—S— linker, which may be connected to at least one or more protecting groups. In some embodiments, the nucleobase

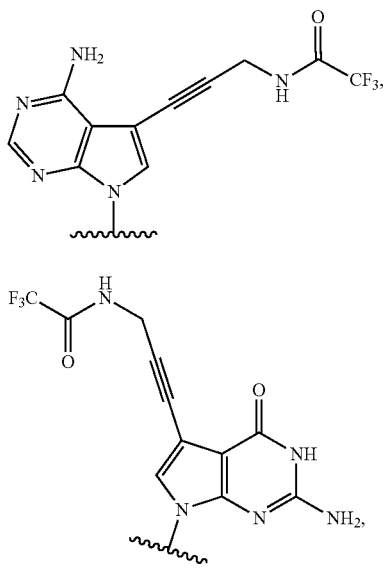

-continued

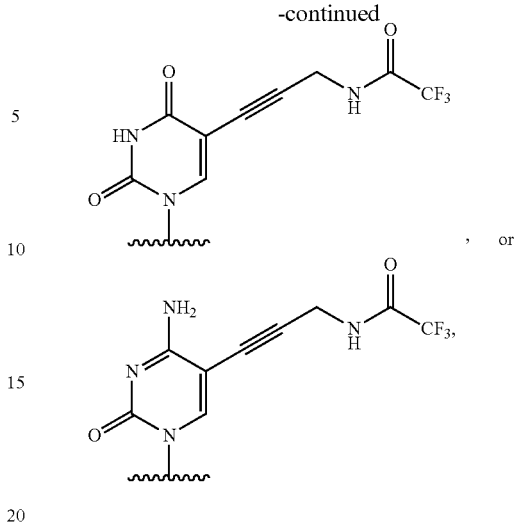

which may be optionally substituted or modified.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group, complementary anchor moiety binder). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Blackman, M. L., et al., *J. Am. Chem. Soc.*, 2008, 130, 13518-13519; Debets, M. F., et al. *Org. Biomol. Chem.*, 2013, 11, 6439-6455) and phenyl boric acid (PBA) (Bergseid M., et al., *BioTechniques*, 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.*, 2010, 132, 3688-3690), tetrazine (TZ) moiety, salicylhydroxamic acid (SHA) moiety).

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/ basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation). The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A "photocleavable linker" (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., tris(3-hydroxypropyl)phosphine). In embodiments, the cleavable linker is a dialkylketal linker (Binaulda S., et al., Chem. Commun., 2013, 49, 2082-2102; Shenoi R. A., et al., J. Am. Chem. Soc., 2012, 134, 14945-14957), an azo linker (Rathod, K. M., et al., Chem. Sci. Tran., 2013, 2, 25-28; Leriche G., et al., Eur. J. Org. Chem., 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers to a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) Proc Natl Acad Sci USA 103(52):19635-19640; Ruparel H. et al. (2005) Proc Natl Acad Sci USA 102(17):5932-5937; Wu J. et al. (2007) Proc Natl Acad Sci USA 104(104):16462-16467; Guo J. et al. (2008) Proc Natl Acad Sci USA 105(27): 9145-9150 Bentley D. R. et al. (2008) Nature 456(7218): 53-59; or Hutter D. et al. (2010) Nucleosides Nucleotides & Nucleic Acids 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is $-NH_2$, $-CN$, $-CH_3$, $C_2-C_6$ allyl (e.g., $-CH_2-CH=CH_2$), methoxyalkyl (e.g., $-CH_2-O-CH_3$), or $-CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with the function of a polymerase (e.g., DNA polymerase, modified DNA polymerase).

The term "allyl" as described herein refers to an unsubstituted methylene attached to a vinyl group (i.e., $-CH=CH_2$), having the formula

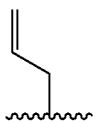

An "allyl linker" refers to a divalent unsubstituted methylene attached to a vinyl group, having the formula

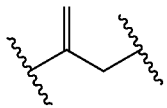

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

The term "polymerase-compatible moiety" as used herein refers a moiety which does not interfere with the function of a polymerase (e.g., DNA polymerase, modified DNA polymerase) in incorporating the nucleotide to which the polymerase-compatible moiety is attached to the 3' end of the newly formed nucleotide strand. The polymerase-compatible moiety does, however, interfere with the polymerase function by preventing the addition of another nucleotide to the 3' oxygen of the nucleotide to which the polymerase-compatible moiety is attached. Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible moiety includes hydrogen, —$N_3$, —CN, or halogen. In embodiments, a polymerase-compatible moiety is a moiety on a nucleotide, nucleobase, nucleoside, or nucleic acid that does not interfere with the function of a polymerase (e.g., DNA polymerase, modified DNA polymerase).

The term "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Terminator γ, 9° N polymerase (exo-), Terminator II, Terminator III, or Terminator IX).

The term "thermophilic nucleic acid polymerase" as used herein refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS*. 1996; 93(11):5281-5285). A thermophilic nucleic acid polymerase is a member of the family B DNA polymerases. Site-directed mutagenesis of the 3'-5' exo motif I (Asp-Ile-Glu) to Asp-Ile-Asp resulted in reduction of 3'-5' exonuclease activity to <1% of wild-type, while maintaining other properties of the polymerase including its high strand displacement activity. Subsequent mutagenesis of key amino acids results in an increased ability of the enzyme to incorporate dideoxynucleotides, ribonucleotides and acyclonucleotides (e.g., Terminator II enzyme from New England Biolabs with D141A/E143A/Y409V/A485L mutations); 3'-amino-dNTPs, 3'-azido-dNTPs and other 3'-modified nucleotides (e.g., NEB Terminator III DNA Polymerase with D141A/E143A/L408S/Y409A/P410V mutations, NEB Terminator IX DNA polymerase), or γ-phosphate labeled nucleotides (e.g., Terminator γ: D141A/E143A/W355A/L408W/R460A/Q461S/K464E/D480V/R484W/A485L). Typically these enzymes do not have 5'-3' exonuclease activity. Additional information about thermophilic nucleic acid polymerases may be found in (Southworth M. W., et al. *PNAS*. 1996; 93(11):5281-5285; Bergen K., et al. *ChemBioChem*. 2013; 14(9):1058-1062; Kumar S., et al. *Scientific Reports*. 2012; 2:684; Fuller C. W., et al. 2016; 113(19): 5233-5238; Guo J., et al. *Proceedings of the National Academy of Sciences of the United States of America*. 2008; 105(27):9145-9150), which are incorporated herein in their entirety for all purposes.

The term "primer," as used herein, is defined to be one or more nucleic acid fragments that specifically hybridize to a nucleic acid template. A primer can be of any length depending on the particular technique it will be used for. For example, PCR primers are generally between 10 and 40 nucleotides in length. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations. The primer permits the addition of a nucleotide residue thereto, or oligonucleotide or polynucleotide synthesis therefrom, under suitable conditions well-known in the art. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer.

"Primer" as used herein (a primer sequence) is a short, usually chemically synthesized oligonucleotide, of appropriate length, for example about 18-24 bases, sufficient to hybridize to a target nucleic acid (e.g. a single stranded nucleic acid) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase, Taq DNA polymerase, DNA polymerase from Bacillus stearothermophilus, Bst 2.0 DNA polymerase, 9° N polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

The term "thio-trigger moiety" refers to a substituent having the formula

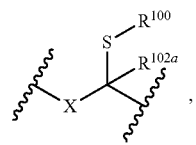

wherein X is —O—, —NH—, or —S—; $R^{100}$ is —$SR^{102}$ or —CN; and $R^{102}$ and $R^{102a}$ are independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula:

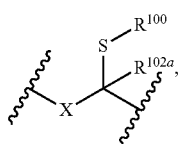

wherein X is —O—, and $R^{100}$ and $R^{102a}$ are as described herein.

A "thio-trigger containing linker" refers to a covalent linker that includes a thio-trigger moiety. When a reducing agent (e.g., dithiothreitol, THPP, or TCEP) contacts a thio-trigger containing linker, the heteroatom represented by the symbol X (e.g., oxygen) of the thio-trigger moiety is reduced, and breaks the linker, according to the mechanism:

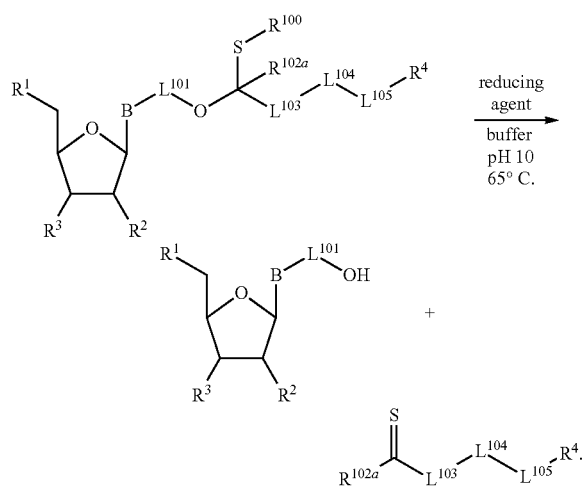

$R^1$, $R^2$, $R^3$, $R^4$, $R^{100}$, $R^{102a}$, $L^{101}$, $L^{103}$, $L^{104}$, and $L^{105}$ are as described herein, including in embodiments.

Where a range of values is provided herein, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various embodiments of the invention are shown and described herein, it will be understood by those skilled in the art that such embodiments are provided by way of example only. Numerous variations, changes, and substitutes may occur to those skilled in the art without departing from the invention. It should be understood that various alternatives to the embodiments of the invention described herein may be employed.

As used herein, and unless stated otherwise, each of the following terms shall have the definition set forth below:
A—Adenine; C—Cytosine; DNA—Deoxyribonucleic acid; G—Guanine; RNA—Ribonucleic acid; T—Thymine; and U—Uracil.

All embodiments of U.S. Pat. No. 6,664,079 (the contents of which are hereby incorporated by reference) with regard to sequencing a nucleic acid are specifically envisioned here.

"Alkyldithiomethyl" refers to a compound or moiety or portion thereof, comprising a dithio group, where one of the sulfurs is directly connected to a methyl group (i.e., a methylene linking group) and the other sulfur is directly connected to an alkyl group. An example is the structure

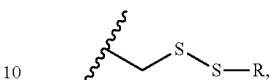

wherein R is an alkyl group (e.g., methyl or ethyl) and the wavy line (e.g., ) represents a point of connection to another portion of the compound. In some cases, the alkyldithiomethyl is methyldithiomethyl, ethyldithiomethyl, propyldithiomethyl, isopropyldithiomethyl, butyldithiomethyl, t-butyldithiomethyl, or phenyldithiomethyl.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts). In embodiments, the protecting group is a nucleoside protecting group. In embodiments, the protecting group is a 5'-nucleoside protecting group.

The term "5'-nucleoside protecting group" as used herein refers to a moiety covalently bound to a heteroatom (e.g., O) on the 5' position of sugar to prevent reactivity of the heteroatom during one or more chemical reactions performed prior to removal of the protecting group. Typically a protecting group is bound to a heteroatom (e.g., O) during a part of a multipart synthesis wherein it is not desired to have the heteroatom react (e.g., during a chemical reduction) with the reagent. Following protection the protecting group may be removed by any appropriate means (e.g., by modulating the pH). Non-limiting examples of 5'-nucleoside protecting groups include silyl ethers (e.g., tert-butyl-diphenylsilyl (TBDPS), or primary and secondary tert-butyldimethylsilyl (TBDMS)) or trityl (e.g., 4,4'-dimethoxytrityl (DMT)). In embodiments, $R^{1P}$ includes a protecting group found in Green's Protective Groups in Organic Chemistry, Wiley, Fourth edition, 2007, Peter G. M. Wuts and Theodora W. Greene, and *Current Protocols in Nucleic Acid Chemistry* (2000) 2.3.1-2.3.34, John Wiley & Sons, Inc. which is incorporated herein by reference in its entirety for all purposes. In embodiments, $R^1$ includes a protecting group found in Green's Protective Groups in Organic Chemistry, Wiley, Fourth edition, 2007, Peter G. M. Wuts and Theodora W. Greene, and *Current Protocols in Nucleic Acid Chemis-* try (2000) 2.3.1-2.3.34, John Wiley & Sons, Inc. which is incorporated herein by reference in its entirety for all purposes.

The term "deprotect" or "deprotecting" is used in accordance with its ordinary meaning in organic chemistry and refers a process or chemical reaction that remove a protecting group, which is covalently bound to a heteroatom, heterocycloalkyl, or heteroaryl, to recover reactivity of the heteroatom, heterocycloalkyl, or heteroaryl for subsequent chemical reactions or metabolic pathway. The "deprotecting agent" or "deprotecting reagent" is used in accordance with its ordinary meaning in organic chemistry and refers to a molecule used for deprotecting. In embodiments, the deprotecting agent is an acid or a base. In embodiments, the deprotecting agent includes alpha-hydroxy amines (amino alcohol), primary amines and secondary amines. In embodiments, the deprotecting agent is ammonium salt (e.g., ammonium hydroxide, ammonium hydrogen sulfate, ceric ammonium nitrate, or ammonium fluoride). In embodiments, the deprotecting agent is concentrated ammonium hydroxide.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer).

The term "thiolation reagent" is used in accordance with its plain ordinary meaning in the arts and refers to a substance (e.g., a compound or solution) which participates in chemical reaction and results in the formation of a dithio containing moiety (e.g., —SS—R$^{6P}$ or —SSCH$_3$) (e.g., between bioconjugate reactive moieties, between a bioconjugate reactive moiety and the thiolation reagent) in aqueous solution. In embodiments, the thiolation reagent is capable of converting —SH to —SSMe in water. In embodiments, the thiolation reagent is

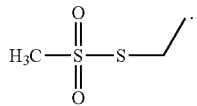

In embodiments the thiolation reagent is

In embodiments, the thiolation reagent is

In embodiments, the thiolation reagent is a compound (e.g., a reagent) described in Mandal and Basu (RSC Adv., 2014, 4, 13854) or Musiejuk and Witt (Organic Preparations and Procedures International, 47:95-131, 2015), which are incorporated by reference in their entirety for all purposes. Non-limiting examples of a thiolation reagent include 1,2-propanediol, 3-(2-pyridinyldithio)-; 1,4,7,10-tetraazacyclododecane, 1-[2-(2-pyridinyldithio)ethyl]-; 1,4,7,10-tetraazacyclododecane-1,4,7-triacetic acid, α1,α4,α7,2,5,8,11-heptamethyl-10-[(1s)-1-methyl-2-oxo-2-[[2-(2-pyridinyldithio)ethyl]amino]ethyl]-, (α1s,α4s,α7s,2s,5s,8s,11s)-; 1-butanol, 4-(2-pyridinyldithio)-; 1h,7h-pyrazolo[1,2-a]pyrazole-1,7-dione, 2,3,6-trimethyl-5-[(2-pyridinyldithio)methyl]-; 1-hexanol, 6-(2-pyridinyldithio)-; 1h-thieno[3,4-d]imidazole-4-pentanamide, hexahydro-2-oxo-n-[2-(2-pyridinyldithio)ethyl]-, (4s)-; 1h-thieno[3,4-d]imidazole-4-pentanamide, hexahydro-2-oxo-n-[2-(2-pyridinyldithio)ethyl]-, [3as-(3aα,4β,6aα)]-(9ci); 1h-thieno[3,4-d]imidazole-4-pentanamide, hexahydro-2-oxo-n-[6-[[1-oxo-3-(2-pyridinyldithio)propyl]amino]hexyl]-, (3as,4s,6ar)-; 1h-thieno[3,4-d]imidazole-4-pentanamide, hexahydro-2-oxo-n-[6-[[1-oxo-3-(2-pyridinyldithio)propyl]amino]hexyl]-, (4s)-; 1-propanamine, 2-methyl-2-(2-pyridinyldithio)-; 1-propanamine, 3-(2-pyridinyldithio)-; 1-propanol, 3-(2-pyridinyldithio)-; 2(1h)-pyridinone, 6-(2-pyridinyldithio)-; 2-buten-1-ol, 3-methyl-4-(2-pyridinyldithio)-, (2e)-; 2-naphthalenol, 6-(2-pyridinyldithio)-; 2-propenamide, n-[2-(2-pyridinyldithio)ethyl]-; 2-pyridinamine, 6-(2-pyridinyldithio)-; 2-pyridinecarbonitrile, 6-(2-pyridinyldithio)-; 3,6,9,12,15-pentaoxaheptadecan-1-amine, 17-(2-pyridinyldithio)-; 3-buten-1-ol, 2-(2-pyridinyldithio)-; 3-pyridinamine, 2-(2-pyridinyldithio)-; 3-pyridinamine, 6-(2-pyridinyldithio)-; 3-pyridinecarbonitrile, 2-(2-pyridinyldithio)-; 3-pyridinecarbonitrile, 6-(2-pyridinyldithio)-; 3-pyridinol, 2-(2-pyridinyldithio)-; 3-pyridinol, 6-(2-pyridinyldithio)-; 4,7,10,13,16,19-hexaoxa-22-azapentacosanoic acid, 23-oxo-25-(2-pyridinyldithio)-, 1,1-dimethylethyl ester; 4,7,10,13-tetraoxa-16-azanonadecanoic acid, 17-oxo-19-(2-pyridinyldithio)-, 2,5-dioxo-1-pyrrolidinyl ester; 4,7,10,13-tetraoxapentadecanoic acid, 15-(2-pyridinyldithio)-, 2,5-dioxo-1-pyrrolidinyl ester; 4-pyridinamine, 2-(2-pyridinyldithio)-; 4-pyridinecarbonitrile, 2-(2-pyridinyldithio)-; 4-pyridinol, 2-(2-pyridinyldithio)-; acetamide, 2-(aminooxy)-n-[2-(2-pyridinyldithio)ethyl]-; acetamide, 2-amino-n-[2-(2-pyridinyldithio)ethyl]-; acetamide, 2-chloro-n-[2-(2-pyridinyldithio)ethyl]-; acetamide, n-[(2-pyridinyldithio)methyl]-; acetamide, n-[2-(2-pyridinyldithio)ethyl]-; acetic acid, 2-[[16-oxo-18-(2-pyridinyldithio)-3,6,9,12-tetraoxa-15-azaoctadec-1-yl]oxy]-, 2,5-dioxo-1-pyrrolidinyl ester; adenosine, 3'-deoxy-3'-(2-pyridinyldithio)-(9ci); benzamide, 4-hydrazinyl-n-[2-(2-pyridinyldithio)ethyl]-; benzenamine, 2-(2-pyridinyldithio)-; benzenamine, 2,4-dinitro-n-[2-(2-pyridinyldithio)ethyl]-; benzenemethanol, 2-(2-pyridinyldithio)-; benzenemethanol, 3-(2-pyridinyldithio)-; benzenemethanol, 4-(2-pyridinyldithio)-; benzenepropanamide, α-(acetylamino)-n-[2-(2-pyridinyldithio)ethyl]-, (αs)-; benzenesulfonamide, 4-methyl-n-[2-(2-pyridinyldithio)ethyl]-; benzoic acid, 2-(2-pyridinyldithio)-, 1,1'-(3-oxospiro[isobenzofuran-1(3h),9'-[9h]xanthene]-3',6'-diyl)

ester; benzoic acid, 2-(2-pyridinyldithio)-, 6'-methoxy-3-oxospiro[isobenzofuran-1(3h),9'-[9h]xanthen]-3'-yl ester; benzoic acid, 2-[[3,5-dichloro-4-[[14-(2-pyridinyldithio)-3,6,9,12-tetraoxatetradec-1-yl]oxy]phenyl]amino]-; benzoic acid, 2-[[3,5-dichloro-4-[[17-(2-pyridinyldithio)-3,6,9,12,15-pentaoxaheptadec-1-yl]oxy]phenyl]amino]-; benzoic acid, 2-[[3,5-dichloro-4-[2-(2-pyridinyldithio)ethoxy]phenyl]amino]-; benzoic acid, 2-[[3,5-dichloro-4-[2-[2-(2-pyridinyldithio)ethoxy]ethoxy]phenyl]amino]-; benzoic acid, 2-[[3,5-dichloro-4-[2-[2-[2-(2-pyridinyldithio)ethoxy]ethoxy]ethoxy]phenyl]amino]-; benzoic acid, 2-[[3,5-dichloro-4-[2-[2-[2-[2-(2-pyridinyldithio)ethoxy]ethoxy]ethoxy]ethoxy]phenyl]amino]-; benzoic acid, 4-[(2-pyridinyldithio)methyl]-; benzoic acid, 4-[(2-pyridinyldithio)methyl]-, 2,5-dioxo-1-pyrrolidinyl ester; benzoic acid, 4-[1-(2-pyridinyldithio)ethyl]-, 2,5-dioxo-1-pyrrolidinyl ester; benzothiazole, 2-(2-pyridinyldithio)-; butanamide, 2-(acetylamino)-4-(2-pyridinyldithio)-, (s)-(9ci); butanamide, 2-[(1-oxo-2-propenyl)amino]-4-(2-pyridinyldithio)-, (s)-(9ci); butanimidamide, 4-(2-pyridinyldithio)-; butanoic acid, 2-(dimethylamino)-4-(2-pyridinyldithio)-; butanoic acid, 2-(dimethylamino)-4-(2-pyridinyldithio)-, 2,5-dioxo-1-pyrrolidinyl ester; butanoic acid, 3-(2-pyridinyldithio)-, (r)-(9ci); butanoic acid, 3-(2-pyridinyldithio)-, 2,5-dioxo-1-pyrrolidinyl ester; butanoic acid, 3-methyl-3-(2-pyridinyldithio)-; butanoic acid, 3-methyl-3-(2-pyridinyldithio)-, 2,5-dioxo-1-pyrrolidinyl ester; butanoic acid, 3-methyl-3-(2-pyridinyldithio)-, hydrazide; butanoic acid, 4-(2-pyridinyldithio)-; butanoic acid, 4-(2-pyridinyldithio)-, 2,3,4,5,6-pentafluorophenyl ester; butanoic acid, 4-(2-pyridinyldithio)-, 2,5-dioxo-1-pyrrolidinyl ester; butanoic acid, 4-(2-pyridinyldithio)-, 2,5-dioxo-3-sulfo-1-pyrrolidinyl ester; butanoic acid, 4-(2-pyridinyldithio)-, hydrazide; butanoic acid, 4-(2-pyridinyldithio)-2-sulfo-; butanoic acid, 4-(2-pyridinyldithio)-2-sulfo-, 1-(2,5-dioxo-1-pyrrolidinyl) ester; butanoic acid, 4-[[1-oxo-3-(2-pyridinyldithio)propyl]amino]-, 2,5-dioxo-1-pyrrolidinyl ester; butanoic acid, 4-[2-[2-(2-pyridinyldithio)ethoxy]ethoxy]-, 2,5-dioxo-1-pyrrolidinyl ester; butanoic acid, 4-oxo-4-[[4-(2-pyridinyldithio)phenyl]amino]-, hydrazide; carbamic acid, [2-(2-pyridinyldithio)ethyl]-, 1,1-dimethylethyl ester (9ci); carbamic acid, [2-oxo-2-[[2-(2-pyridinyldithio)ethyl]amino]ethoxy]-, 1,1-dimethylethyl ester (9ci); carbamic acid, [3-(methylthio)-1-[(2-pyridinyldithio)methyl]propyl]-, 1,1-dimethylethyl ester, (s)-(9ci); carbamic acid, n-methyl-n-[2-(2-pyridinyldithio)ethyl]-, 1,1-dimethylethyl ester; carbonic acid, 1h-benzotriazol-1-yl 2-(2-pyridinyldithio)ethyl ester; carbonic acid, 2-methyl-2-(2-pyridinyldithio)propyl 4-nitrophenyl ester; carbonic acid, 4-nitrophenyl 2-(2-pyridinyldithio)ethyl ester; carbonic acid, 4-nitrophenyl 2-(2-pyridinyldithio)propyl ester; carbonochloridic acid, 2-(2-pyridinyldithio)ethyl ester; carbonochloridic acid, 3-(2-pyridinyldithio)propyl ester; cas index name; cytidine, n-[1-oxo-3-(2-pyridinyldithio)propyl]-(9ci); d-phenylalanine, n-acetyl-, 2-(2-pyridinyldithio)ethyl ester; ethanamine, 2-(2-pyridinyldithio)-; ethanamine, n,n-dimethyl-2-(2-pyridinyldithio)-; ethanol, 2-(2-pyridinyldithio)-; ethanol, 2-[2-(2-pyridinyldithio)ethoxy]-; ethanol, 2-[2-[2-(2-pyridinyldithio)ethoxy]ethoxy]ethoxy]-; glycine, n-[2-[bis(carboxymethyl)amino]ethyl]-n-[2-oxo-2-[[2-(2-pyridinyldithio)ethyl]amino]ethyl]-; guanosine, 3'-deoxy-3'-(2-pyridinyldithio)-(9ci); heptanoic acid, 7-[[1-oxo-3-(2-pyridinyldithio)propyl]amino]-, 2,5-dioxo-1-pyrrolidinyl ester; hexadecanoic acid, 16-(2-pyridinyldithio)-; hexanamide, 2,6-diamino-n-[2-(2-pyridinyldithio)ethyl]-, (2s)-; hexanamide, n-(2-ethoxy-1,3-dioxan-5-yl)-6-(2-pyridinyldithio)-; hexanamide, n-(cis-2-methoxy-1,3-dioxan-5-yl)-6-(2-pyridinyldithio)-; hexanamide, n-(trans-2-methoxy-1,3-dioxan-5-yl)-6-(2-pyridinyldithio)-; hexanamide, n-[2-(2-propyn-1-yloxy)-1,1-bis[(2-propyn-1-yloxy)methyl]ethyl]-6-(2-pyridinyldithio)-; hexanamide, n-[2-hydroxy-1-(hydroxymethyl)ethyl]-6-(2-pyridinyldithio)-; hexanoic acid, 6-(2-pyridinyldithio)-; hexanoic acid, 6-(2-pyridinyldithio)-, 2,5-dioxo-1-pyrrolidinyl ester; hexanoic acid, 6-[[1-oxo-3-(2-pyridinyldithio)propyl]amino]-; hexanoic acid, 6-[[1-oxo-3-(2-pyridinyldithio)propyl]amino]-, 2,5-dioxo-1-pyrrolidinyl ester; hexanoic acid, 6-[[1-oxo-3-(2-pyridinyldithio)propyl]amino]-, 2,5-dioxo-3-sulfo-1-pyrrolidinyl ester; hydrazinecarboxylic acid, 2-(2-pyridinyldithio)ethyl ester; hydrazinecarboxylic acid, 2-[1-oxo-3-(2-pyridinyldithio)propyl]-, 1,1-dimethylethyl ester; index name not yet assigned; l-alanine, 3-(2-pyridinyldithio)-; l-ornithinamide, 1-valyl-n5-(aminocarbonyl)-n-[4-[[[[[2-(2-pyridinyldithio)ethyl]amino]carbonyl]oxy]methyl]phenyl]-; octanoic acid, 6,8-bis(2-pyridinyldithio)-; pentanamide, $^2$-amino-4-methyl-n-[2-(2-pyridinyldithio)ethyl]-, (2s)-; pentanediamide, 2-amino-n1-[2-(2-pyridinyldithio)ethyl]-, (2s)-; pentanoic acid, 4-(2-pyridinyldithio)-; pentanoic acid, 4-(2-pyridinyldithio)-, (4s)-; pentanoic acid, 4-(2-pyridinyldithio)-, 2,3,4,5,6-pentafluorophenyl ester; pentanoic acid, 4-(2-pyridinyldithio)-, 2,5-dioxo-1-pyrrolidinyl ester; pentanoic acid, 4-(2-pyridinyldithio)-, 2,5-dioxo-1-pyrrolidinyl ester, (4s)-; pentanoic acid, 4-(2-pyridinyldithio)-, 2,5-dioxo-3-sulfo-1-pyrrolidinyl ester; pentanoic acid, 4-methyl-4-(2-pyridinyldithio)-; pentanoic acid, 4-methyl-4-(2-pyridinyldithio)-, 2,3,4,5,6-pentafluorophenyl ester; pentanoic acid, 4-methyl-4-(2-pyridinyldithio)-, 2,5-dioxo-1-pyrrolidinyl ester; pentanoic acid, 4-methyl-4-(2-pyridinyldithio)-, 2,5-dioxo-3-sulfo-1-pyrrolidinyl ester; pentanoic acid, 5-(2-pyridinyldithio)-; pentanoic acid, 5-(2-pyridinyldithio)-, 2,5-dioxo-1-pyrrolidinyl ester; phenol, 2-(2-pyridinyldithio)-; propanamide, 3-(2-pyridinyldithio)-; propanamide, 3-(2-pyridinyldithio)-n-[(3,3a,7,7a-tetrahydro-1,3-dioxo-4,7-epoxyisobenzofuran-4(1h)-yl)methyl]-; propanamide, n-(2-aminoethyl)-3-(2-pyridinyldithio)-; propanamide, n-(2-hydroxyethyl)-3-(2-pyridinyldithio)-; propanamide, n-(3-aminopropyl)-3-(2-pyridinyldithio)-; propanamide, n-(6-aminohexyl)-3-(2-pyridinyldithio)-; propanamide, n,n'-1,4-butanediylbis[3-(2-pyridinyldithio)-; propanamide, n,n'-1,6-hexanediylbis[3-(2-pyridinyldithio)-; propanamide, n-[[(3as,4r,7s,7ar)-1,3,3a,4,7,7a-hexahydro-1,3-dioxo-4,7-epoxyisobenzofuran-4-yl]methyl]-3-(2-pyridinyldithio)-; propanamide, n-octadecyl-3-(2-pyridinyldithio)-; propanenitrile, 3-(2-pyridinyldithio)-; propanoic acid, 2-bromo-2-methyl-, 2-(2-pyridinyldithio)ethyl ester; propanoic acid, 2-bromo-2-methyl-, 3-(2-pyridinyldithio)propyl ester; propanoic acid, 3-(2-pyridinyldithio)-; propanoic acid, 3-(2-pyridinyldithio)-, 2,3,4,5,6-pentafluorophenyl ester; propanoic acid, 3-(2-pyridinyldithio)-, 2,5-dihydro-2,5-dioxo-1h-pyrrol-1-yl ester; propanoic acid, 3-(2-pyridinyldithio)-, 2,5-dioxo-1-pyrrolidinyl ester; propanoic acid, 3-(2-pyridinyldithio)-, 2,5-dioxo-3-sulfo-1-pyrrolidinyl ester; propanoic acid, 3-(2-pyridinyldithio)-, hydrazide; propanoic acid, 3-(2-pyridinyldithio)-, methyl ester; propanoic acid, 3-[[13-oxo-15-(2-pyridinyldithio)-3,6,9-trioxa-12-azapentadec-1-yl]oxy]-; propanoic acid, 3-[[19-oxo-21-(2-pyridinyldithio)-3,6,9,12,15-pentaoxa-18-azaheneicos-1-yl]oxy]-; propanoic acid, 3-[[19-oxo-21-(2-pyridinyldithio)-3,6,9,12,15-pentaoxa-18-azaheneicos-1-yl]oxy]-, 2,5-dioxo-1-pyrrolidinyl ester; propanoic acid, 3-[[25-oxo-27-(2-pyridinyldithio)-3,6,9,12,15,18,21-heptaoxa-24-azaheptacos-1-yl]oxy]-; propanoic acid, 3-[[25-oxo-27-(2-pyridinyldithio)-3,6,9,12,15,18,21-heptaoxa-24-azaheptacos-1-yl]oxy]-, 2,5-dioxo-1-pyrrolidinyl ester; propanoic acid, 3-[2-[2-(2-pyridinyldithio)ethoxy] ethoxy]-, 1,1-dimethylethyl ester; propanoic acid, 3-[2-[2-[2-(2-pyridinyldithio)ethoxy]ethoxy]ethoxy]-; propanoic acid, 3-[2-[2-[2-[[1-oxo-3-(2-pyridinyldithio)propyl]amino] ethoxy]ethoxy]ethoxy]-; propanoic acid, 3-[2-[2-[2-[[1-oxo-3-(2-pyridinyldithio)propyl]amino]ethoxy]ethoxy]ethoxy]-, 2,5-dioxo-1-pyrrolidinyl ester; pyridine, 2-(2-naphthalenyl-dithio)-; pyridine, 2-(2-propen-1-yldithio)-; pyridine, 2-(3,6,9,12-tetraoxapentadec-14-yn-1-yldithio)-; pyridine, 2-(butyldithio)-; pyridine, 2-(cyclohexyldithio)-; pyridine, 2-(ethyldithio)-; pyridine, 2-(hexyldithio)-; pyridine, 2-(methyldithio)-; pyridine, 2-(phenyldithio)-; pyridine, 2-(propyldithio)-; pyridine, 2,2'-[1,2-ethanediylbis(dithio)] bis-(9ci); pyridine, 2,2'-[1,2-ethanediylbis(oxy-2,1-eth-anediyldithio)]bis-; pyridine, 2,2'-dithiobis-; pyridine, 2-[(1,1-diethylpropyl)dithio]-; pyridine, 2-[(1,1-dimethylethyl) dithio]-; pyridine, 2-[(1-methylethyl)dithio]-; pyridine, 2-[(1-methylpropyl)dithio]-; pyridine, 2-[(2,4,6-trimeth-ylphenyl)dithio]-; pyridine, 2-[(2,4-dinitrophenyl)dithio]-; pyridine, 2-[(2-isocyanatoethyl)dithio]-; pyridine, 2-[(2-ni-trophenyl)dithio]-; pyridine, 2-[(3p)-cholest-5-en-3-yldi-thio]-; pyridine, 2-[(4-chlorophenyl)dithio]-; pyridine, 2-[(4-methylphenyl)dithio]-; pyridine, 2-[(4-nitrophenyl)di-thio]-; pyridine, 2-[(phenylmethyl)dithio]-; pyridine, 2-[[2-(tetrahydro-2h-thiopyran-2-yl)ethyl]dithio]-; pyridine, 2-[[2-[2-(2-methoxyethoxy)ethoxy]ethyl]dithio]-; pyridine, 2-[[3-(trimethoxysilyl)propyl]dithio]-; pyridine, 2-bromo-6-(2-pyridinyldithio)-; pyridine, 3-bromo-2-(2-pyridinyldi-thio)-; pyridine, 4-bromo-2-(2-pyridinyldithio)-; pyridine, 4-chloro-2-(2-pyridinyldithio)-; pyridine, 5-bromo-2-(2-pyridinyldithio)-; thymidine 5'-(tetrahydrogen triphos-phate), 3'-deoxy-3'-[[1-oxo-3-(2-pyridinyldithio)propyl] amino]-(9ci); uridine 5'-(tetrahydrogen triphosphate), 2'-deoxy-5-[2-[[1-oxo-3-(2-pyridinyldithio)propyl]amino] ethenyl]-; uridine 5'-(tetrahydrogen triphosphate), 2'-deoxy-5-[2-oxo-2-[[6-[[1-oxo-3-(2-pyridinyldithio)propyl]amino] hexyl]amino]ethyl]-(9ci); uridine 5'-(tetrahydrogen triphosphate), 2'-deoxy-5-[3-[[1-oxo-3-(2-pyridinyldithio) propyl]amino]-1-propen-1-yl]-; uridine, 2'-amino-2',3'-dide-oxy-3'-(2-pyridinyldithio)-(9ci); uridine, 2'-deoxy-5-[3-oxo-3-[[2-[[1-oxo-3-(2-pyridinyldithio)propyl]amino]ethyl] amino]propyl]-(9ci); uridine, 5'-o-[bis(4-methoxyphenyl) phenylmethyl]-2'-deoxy-5-[3-oxo-3-[[2-[[1-oxo-3-(2-pyridinyldithio)propyl]amino]ethyl]amino]propyl]-(9ci); or β-alanine, n-[1-oxo-3-(2-pyridinyldithio)propyl]-2,5-dioxo-1-pyrrolidinyl ester.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate contain-ers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subpor-tion of the total kit components. The containers may be delivered to the intended recipient together or separately. For example, a first container may contain an enzyme for use in an assay, while a second container contains oligonucle-otides. In contrast, a "combined kit" refers to a delivery system containing all of the components of a reaction assay in a single container (e.g., in a single box housing each of the desired components). The term "kit" includes both frag-mented and combined kits.

II. Compositions

In an aspect is provided a compound of the formula:

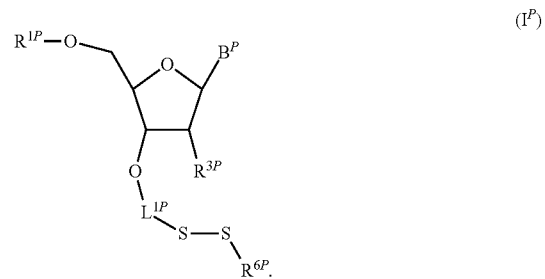

$B^P$ is a nucleobase, which may be optionally substituted. $L^{1P}$ is a covalent linker. $R^{1P}$ is independently hydrogen or 5'-nucleoside protecting group, or $-OR^{1P}$ is a monophos-phate, or polyphosphate. $R^{3P}$ is hydrogen or $-OR^{3AP}$. $R^{3AP}$ is hydrogen or a polymerase-compatible cleavable moiety. $R^{6P}$ is hydrogen, substituted or unsubstituted alkyl, substi-tuted or unsubstituted heteroalkyl, substituted or unsubsti-tuted cycloalkyl, substituted to unsubstituted heterocycloal-kyl, substituted or unsubstituted aryl, or substituted or unsubstituted heteroaryl.

$B^P$ is a nucleobase, which may be optionally substituted. $L^{1P}$ is a covalent linker. $R^{1P}$ is independently hydrogen or 5'-nucleoside protecting group, or $-OR^{1P}$ is a monophos-phate, or polyphosphate. $R^{3P}$ is hydrogen or $-OR^{3AP}$. $R^{3AP}$ is hydrogen or a polymerase-compatible cleavable moiety. In embodiments, $R^{6P}$ is a substituted or unsubstituted alkyl.

In embodiments, $B^P$ is a cytosine moiety or a derivative thereof, guanine moiety or a derivative thereof, adenine or a derivative thereof, thymine moiety or a derivative thereof, uracil moiety or a derivative thereof, hypoxanthine moiety or a derivative thereof, xanthine moiety or a derivative thereof, deaza-adenine moiety or a derivative thereof, deaza-guanine moiety or a derivative thereof, deaza-hypoxanthine moiety or a derivative thereof, 7-methylguanine moiety or a derivative thereof, 5,6-dihydrouracil moiety or a derivative thereof, 5-methylcytosine moiety or a derivative thereof, or 5-hydroxymethylcytosine moiety or a derivative thereof. In embodiments, $B^P$ is a cytosine moiety or a derivative thereof. In embodiments, $B^P$ is a guanine moiety or a derivative thereof. In embodiments, $B^P$ is an adenine moiety or a derivative thereof. In embodiments, $B^P$ is a thymine moiety or a derivative thereof. In embodiments, $B^P$ is a uracil moiety or a derivative thereof. In embodiments, $B^P$ is a hypoxanthine moiety or a derivative thereof. In embodi-ments, $B^P$ is a xanthine moiety or a derivative thereof. In embodiments, $B^P$ is a deaza-adenine moiety or a derivative thereof. In embodiments, $B^P$ is a deaza-guanine moiety or a derivative thereof. In embodiments, $B^P$ is a deaza-hypoxan-thine moiety or a derivative thereof. In embodiments, $B^P$ is a 7-methylguanine moiety or a derivative thereof. In embodiments, $B^P$ is a 5,6-dihydrouracil moiety or a deriva-tive thereof. In embodiments, $B^P$ is a 5-methylcytosine moiety or a derivative thereof. In embodiments, $B^P$ is a 5-hydroxymethylcytosine moiety or a derivative thereof.

In embodiments, $B^P$ is
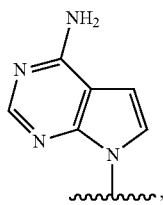 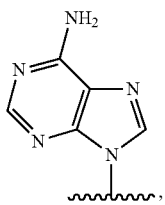
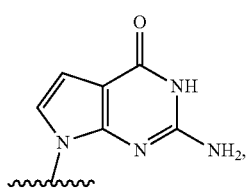 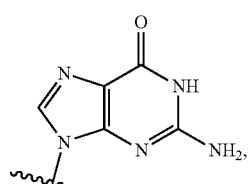
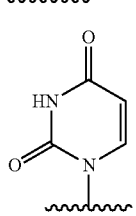, or 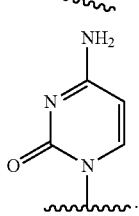.
In embodiments, $B^P$ is
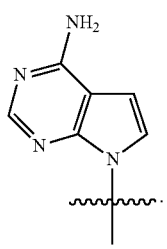 [SMILES: *n1ccc2c(N)ncnc21]
In embodiments, $B^P$ is
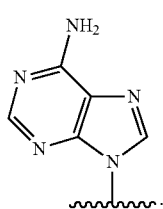 [SMILES: *n1cnc2c(N)ncnc21]
In embodiments, $B^P$ is
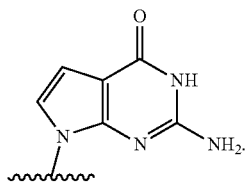 [SMILES: *n1ccc2c(=O)[nH]c(N)nc21]
In embodiments, $B^P$ is
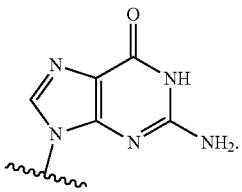 [SMILES: *n1cnc2c(=O)[nH]c(N)nc21]
In embodiments, $B^P$ is
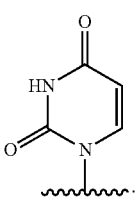
In embodiments, $B^P$ is
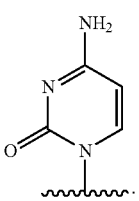
In embodiments, $B^P$ is
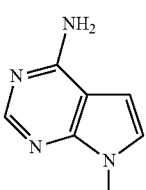, 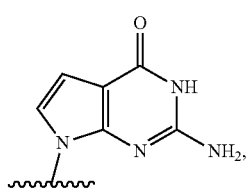
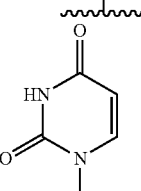, or 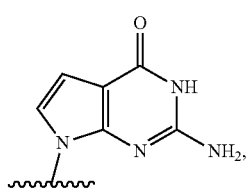.
In embodiments, $B^P$ is
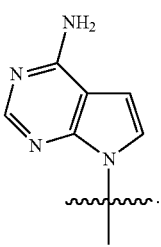 [SMILES: *n1ccc2c(N)ncnc21]

In embodiments, B$^P$ is
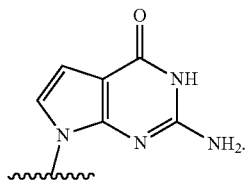 [SMILES: *n1ccc2c(=O)[nH]c(N)nc21]
In embodiments, B$^P$ is
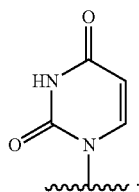
In embodiments, B$^P$ is
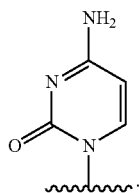 [SMILES: *n1ccc(N)nc1=O]
In embodiments, B$^P$ is
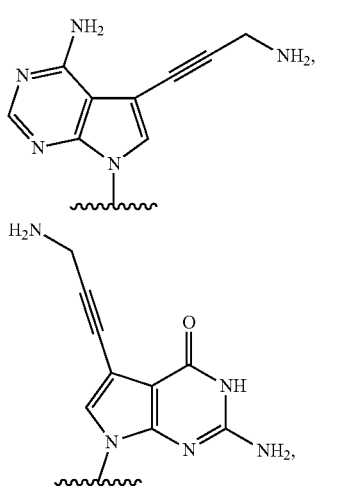
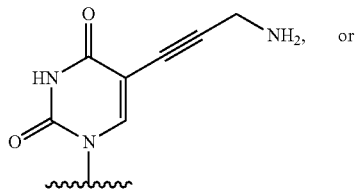
or
-continued
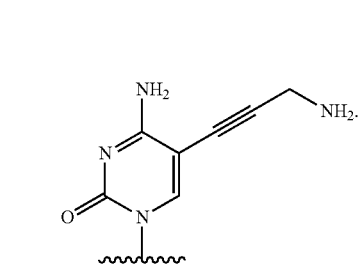 [SMILES: *n1cc(C#CCN)c(N)nc1=O]
In embodiments, B$^P$ is
In embodiments, B$^P$ is
In embodiments, B$^P$ is In embodiments, $B^P$ is

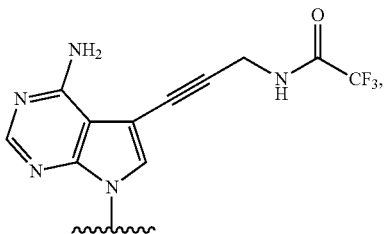 [SMILES: *n1cc(C#CCNC(=O)C(F)(F)F)c2c(N)ncnc21]

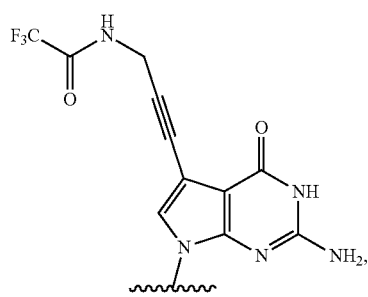 [SMILES: *n1cc(C#CCNC(=O)C(F)(F)F)c2c(=O)[nH]c(N)nc21]

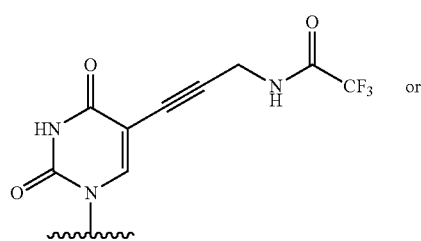 or

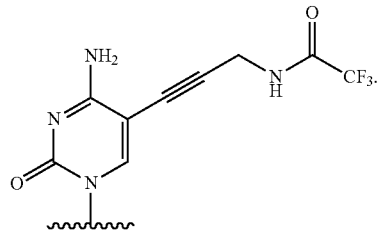 [SMILES: *n1cc(C#CCNC(=O)C(F)(F)F)c(N)nc1=O]

In embodiments, $B^P$ is

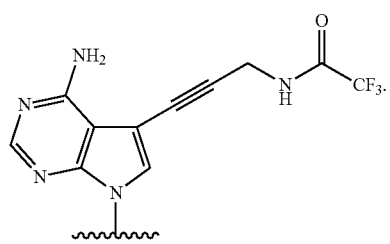

In embodiments, $B^P$ is

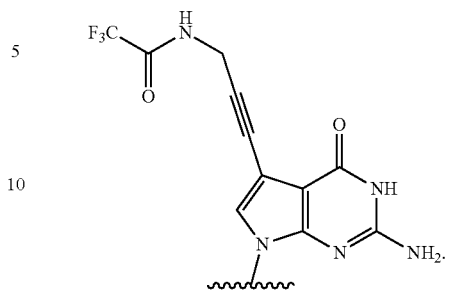

In embodiments, $B^P$ is

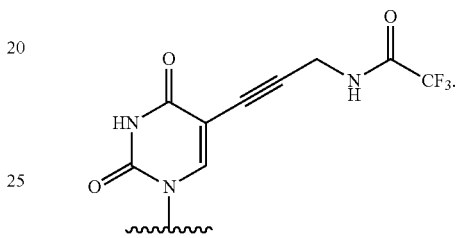

In embodiments, $B^P$ is

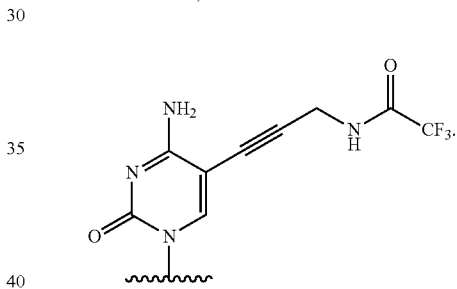

In embodiments, $R^{31}$ is hydrogen. In embodiments, $R^{3P}$ is —$OR^{3AP}$; and $R^{3AP}$ is hydrogen. In embodiments, $R^{3P}$ is —$OR^{3AP}$; and $R^{3AP}$ is a polymerase-compatible cleavable moiety. In embodiments, $R^{3P}$ is —$OR^{3AP}$; and $R^{3AP}$ is a polymerase-compatible cleavable moiety including an azido moiety. In embodiments, $R^{3P}$ is —$OR^{3AP}$; and $R^{3AP}$ is a polymerase-compatible cleavable moiety including a dithiol linker. In embodiments, $R^{3P}$ is —$OR^{3AP}$; $R^{3AP}$ is a polymerase-compatible cleavable moiety; and the polymerase-compatible cleavable moiety is —$CH_2N_3$. In embodiments, $R^{3P}$ is —$OR^{3AP}$; and $R^{3AP}$ is a polymerase-compatible cleavable moiety comprising a dithiol linker, an allyl group, or a 2-nitrobenzyl group.

In embodiments, $R^{6P}$ is hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{6P}$ is hydrogen, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered).

In embodiments, a substituted $R^{6P}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{6P}$ is substituted with a plurality of groups selected from substituent groups, size-limited substituent groups, and lower substituent groups; each substituent group, size-limited substituent group, and/or lower substituent group may optionally be different. In embodiments, when $R^{6P}$ is substituted, it is substituted with at least one substituent group. In embodiments, when $R^{6P}$ is substituted, it is substituted with at least one size-limited substituent group. In embodiments, when $R^{6P}$ is substituted, it is substituted with at least one lower substituent group. In embodiments, when $R^{6P}$ is substituted, it is substituted with 1 to 10 substituent groups. In embodiments, when $R^{6P}$ is substituted, it is substituted with 1 to 10 size-limited substituent groups. In embodiments, when $R^{6P}$ is substituted, it is substituted with 1 to 10 lower substituent groups. In embodiments, when $R^{6P}$ is substituted, it is substituted with 1 to 5 substituent groups. In embodiments, when $R^{6P}$ is substituted, it is substituted with 1 to 5 size-limited substituent groups. In embodiments, when $R^{6P}$ is substituted, it is substituted with 1 to 5 lower substituent groups. In embodiments, when $R^{6P}$ is substituted, it is substituted with a substituent group. In embodiments, when $R^{6P}$ is substituted, it is substituted with a size-limited substituent group. In embodiments, when $R^{6P}$ is substituted, it is substituted with a lower substituent group.

In embodiments, $R^{6P}$ is a substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$). In embodiments, $R^{6P}$ is a substituted (e.g., substituted with a substituent group, size-limited substituent group, or lower substituent group) or unsubstituted $C_1$-$C_8$ alkyl. In embodiments, $R^{6P}$ is substituted (e.g., substituted with a substituent group, size-limited substituent group, or lower substituent group) or unsubstituted $C_1$-$C_6$ alkyl. In embodiments, $R^{6P}$ is a substituted (e.g., substituted with a substituent group, size-limited substituent group, or lower substituent group) or unsubstituted $C_1$-$C_4$ alkyl. In embodiments, $R^{6P}$ is a substituted (e.g., substituted with a substituent group, size-limited substituent group, or lower substituent group) or unsubstituted methyl, or ethyl. In embodiments, $R^{6P}$ is a substituted (e.g., substituted with a substituent group, size-limited substituent group, or lower substituent group) $C_1$-$C_8$ alkyl. In embodiments, $R^{6P}$ is a substituted (e.g., substituted with a substituent group, size-limited substituent group, or lower substituent group) $C_1$-$C_6$ alkyl. In embodiments, $R^{6P}$ is substituted (e.g., substituted with a substituent group, size-limited substituent group, or lower substituent group) $C_1$-$C_4$ alkyl. In embodiments, $R^{6P}$ is a substituted (e.g., substituted with a substituent group, size-limited substituent group, or lower substituent group) methyl, or ethyl. In embodiments, $R^{6P}$ is unsubstituted $C_1$-$C_8$ alkyl. In embodiments, $R^{6P}$ is substituted or unsubstituted $C_1$-$C_6$ alkyl. In embodiments, $R^{6P}$ is unsubstituted $C_1$-$C_4$ alkyl. In embodiments, $R^{6P}$ is unsubstituted methyl, or unsubstituted ethyl. In embodiments, $R^{6P}$ is —$CH_3$. In embodiments, $R^{6P}$ is —$CH_2CH_3$.

In embodiments, the compounds of Formulae $I^P$, $IA^P$, and $IB^P$ include alkyldithiomethyl or portion thereof, comprising a dithio group, where one of the sulfurs is directly connected to a methylene (e.g., a substituted or unsubstituted methylene) group at 3' end of the compounds and the other sulfur is directly connected to an alkyl group (e.g., $C_1$-$C_8$, $C_1$-$C_6$, $C_1$-$C_4$, or $C_1$-$C_2$). An example is the structure

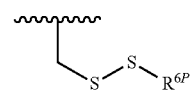

and the symbol "〰" represents a point of connection to another portion of the compound. In embodiments, $R^{6P}$ is an alkyl group as described above (i.e., a substituted or unsubstituted alkyl (e.g., $C_1$-$C_8$, $C_1$-$C_6$, $C_1$-$C_4$, or $C_1$-$C_2$)). In embodiments, the alkyldithiomethyl is methyldithiomethyl, ethyldithiomethyl, propyldithiomethyl, isopropyldithiomethyl, butyldithiomethyl, t-butyldithiomethyl, or phenyldithiomethyl. In embodiments, the alkyldithiomethyl is methyldithiomethyl. In embodiments, the alkyldithiomethyl is ethyldithiomethyl. In embodiments, the alkyldithiomethyl is propyldithiomethyl. In embodiments, the alkyldithiomethyl is isopropyldithiomethyl. In embodiments, the alkyldithiomethyl is butyldithiomethyl. In embodiments, the alkyldithiomethyl is t-butyldithiomethyl.

In embodiments, the moiety of —S—S—$R^{6P}$ is a polymerase-compatible cleavable moiety. In embodiments, the moiety

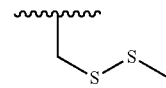

is a polymerase-compatible cleavable moiety. In embodiments, the moiety

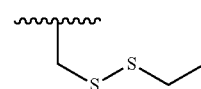

is a polymerase-compatible cleavable moiety. In embodiments, the moiety

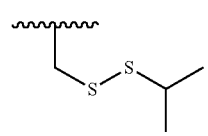 [SMILES: *CSSC(C)C]

is a polymerase-compatible cleavable moiety. In embodiments, the moiety

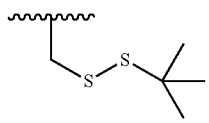 [SMILES: *CSSC(C)(C)C]

is a polymerase-compatible cleavable moiety.

In embodiments, the moiety

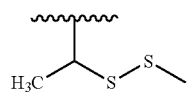

is a polymerase-compatible cleavable moiety. In embodiments, the moiety

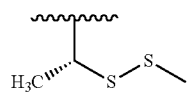

is a polymerase-compatible cleavable moiety. In embodiments, the moiety

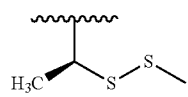

is a polymerase-compatible cleavable moiety. In embodiments, the moiety

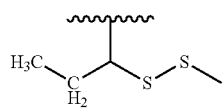

is a polymerase-compatible cleavable moiety. In embodiments, the moiety

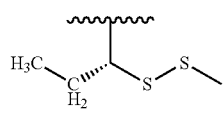

is a polymerase-compatible cleavable moiety. In embodiments, the moiety

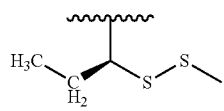

is a polymerase-compatible cleavable moiety. In embodiments, the moiety

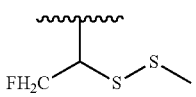

is a polymerase-compatible cleavable moiety. In embodiments, the moiety

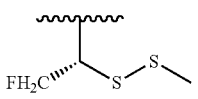

is a polymerase-compatible cleavable moiety. In embodiments, the moiety

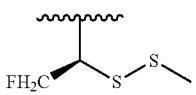

is a polymerase-compatible cleavable moiety. In embodiments, the moiety

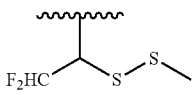

is a polymerase-compatible cleavable moiety. In embodiments, the moiety

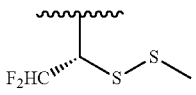

is a polymerase-compatible cleavable moiety. In embodiments, the moiety

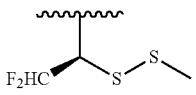

is a polymerase-compatible cleavable moiety. In embodiments, the moiety

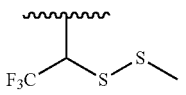

is a polymerase-compatible cleavable moiety. In embodiments, the moiety

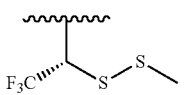

is a polymerase-compatible cleavable moiety. In embodiments, the moiety

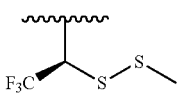

is a polymerase-compatible cleavable moiety. In embodiments, the moiety

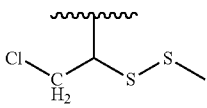 [SMILES: *C(CCl)SSC]

is a polymerase-compatible cleavable moiety. In embodiments, the moiety

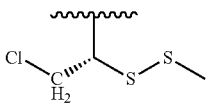 [SMILES: *[C@@H](CCl)SSC]

is a polymerase-compatible cleavable moiety. In embodiments, the moiety

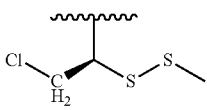

is a polymerase-compatible cleavable moiety. In embodiments, the moiety

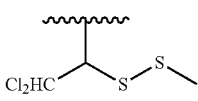

is a polymerase-compatible cleavable moiety. In embodiments, the moiety

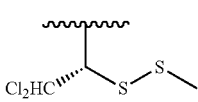

is a polymerase-compatible cleavable moiety. In embodiments, the moiety

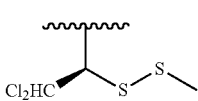

is a polymerase-compatible cleavable moiety. In embodiments, the moiety

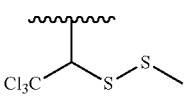

is a polymerase-compatible cleavable moiety. In embodiments, the moiety

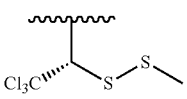

is a polymerase-compatible cleavable moiety. In embodiments, the moiety

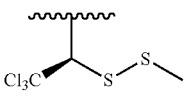

is a polymerase-compatible cleavable moiety. In embodiments, the moiety

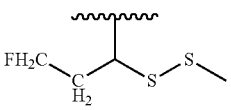

is a polymerase-compatible cleavable moiety. In embodiments, the moiety

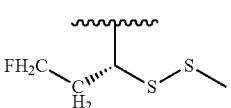

is a polymerase-compatible cleavable moiety. In embodiments, the moiety

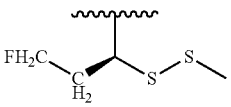

is a polymerase-compatible cleavable moiety. In embodiments, the moiety

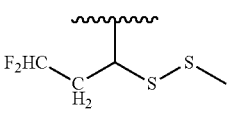

is a polymerase-compatible cleavable moiety. In embodiments, the moiety

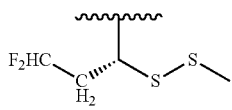

is a polymerase-compatible cleavable moiety. In embodiments, the moiety

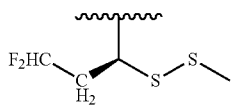

is a polymerase-compatible cleavable moiety. In embodiments, the moiety

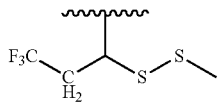

is a polymerase-compatible cleavable moiety. In embodiments, the moiety

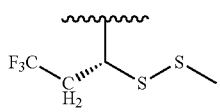

is a polymerase-compatible cleavable moiety. In embodiments, the moiety

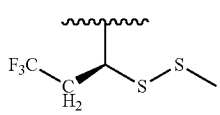

is a polymerase-compatible cleavable moiety. In embodiments, the moiety

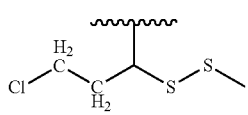

is a polymerase-compatible cleavable moiety. In embodiments, the moiety

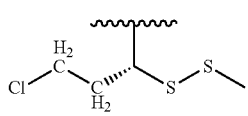

is a polymerase-compatible cleavable moiety. In embodiments, the moiety

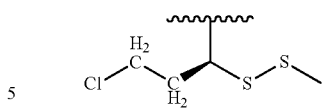

is a polymerase-compatible cleavable moiety. In embodiments, the moiety

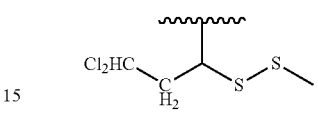

is a polymerase-compatible cleavable moiety. In embodiments, the moiety

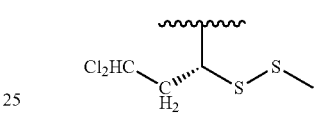

is a polymerase-compatible cleavable moiety. In embodiments, the moiety

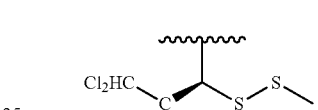

is a polymerase-compatible cleavable moiety. In embodiments, the moiety

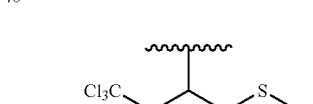

is a polymerase-compatible cleavable moiety. In embodiments, the moiety

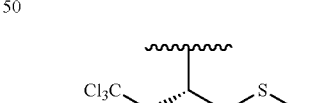

is a polymerase-compatible cleavable moiety. In embodiments, the moiety

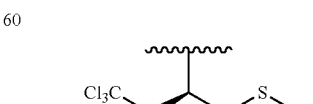

is a polymerase-compatible cleavable moiety.

In embodiments, the moiety

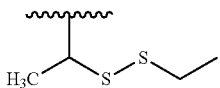

is a polymerase-compatible cleavable moiety. In embodiments, the moiety

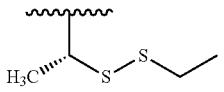

is a polymerase-compatible cleavable moiety. In embodiments, the moiety

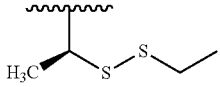

is a polymerase-compatible cleavable moiety. In embodiments, the moiety

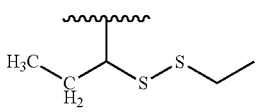

is a polymerase-compatible cleavable moiety. In embodiments, the moiety

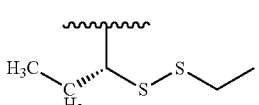

is a polymerase-compatible cleavable moiety. In embodiments, the moiety

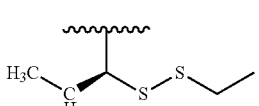

is a polymerase-compatible cleavable moiety. In embodiments, the moiety

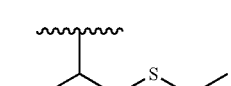

is a polymerase-compatible cleavable moiety. In embodiments, the moiety

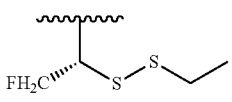

is a polymerase-compatible cleavable moiety. In embodiments, the moiety

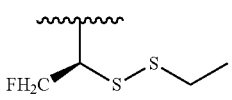

is a polymerase-compatible cleavable moiety. In embodiments, the moiety

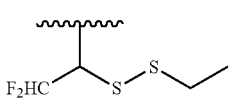

is a polymerase-compatible cleavable moiety. In embodiments, the moiety

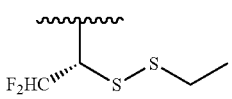

is a polymerase-compatible cleavable moiety. In embodiments, the moiety

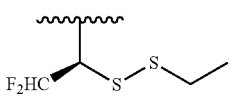

is a polymerase-compatible cleavable moiety. In embodiments, the moiety

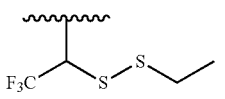

is a polymerase-compatible cleavable moiety. In embodiments, the moiety

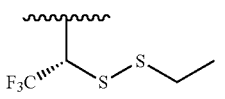

is a polymerase-compatible cleavable moiety. In embodiments, the moiety

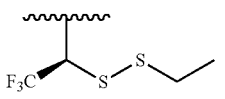

is a polymerase-compatible cleavable moiety. In embodiments, the moiety

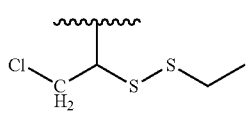

is a polymerase-compatible cleavable moiety. In embodiments, the moiety

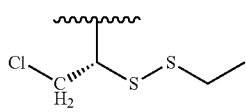 [SMILES: *[C@@H](CCl)SSCC]

is a polymerase-compatible cleavable moiety. In embodiments, the moiety

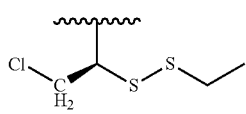

is a polymerase-compatible cleavable moiety. In embodiments, the moiety

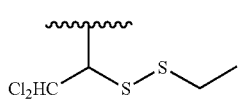

is a polymerase-compatible cleavable moiety. In embodiments, the moiety

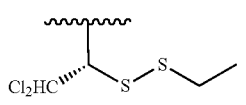

is a polymerase-compatible cleavable moiety. In embodiments, the moiety

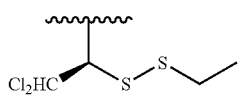

is a polymerase-compatible cleavable moiety. In embodiments, the moiety

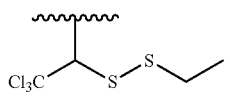

is a polymerase-compatible cleavable moiety. In embodiments, the moiety

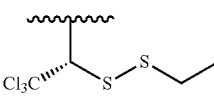

is a polymerase-compatible cleavable moiety. In embodiments, the moiety

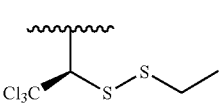

is a polymerase-compatible cleavable moiety. In embodiments, the moiety

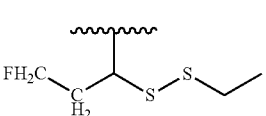

is a polymerase-compatible cleavable moiety. In embodiments, the moiety

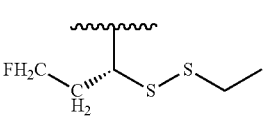

is a polymerase-compatible cleavable moiety. In embodiments, the moiety

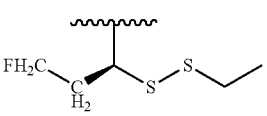

is a polymerase-compatible cleavable moiety. In embodiments, the moiety

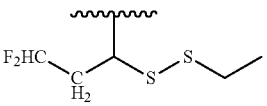

is a polymerase-compatible cleavable moiety. In embodiments, the moiety

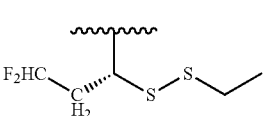

is a polymerase-compatible cleavable moiety. In embodiments, the moiety

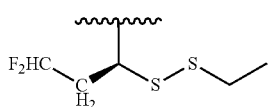

is a polymerase-compatible cleavable moiety. In embodiments, the moiety

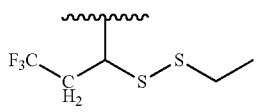

is a polymerase-compatible cleavable moiety. In embodiments, the moiety

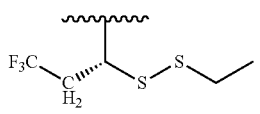

is a polymerase-compatible cleavable moiety. In embodiments, the moiety

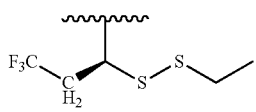

is a polymerase-compatible cleavable moiety. In embodiments, the moiety

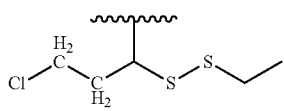

is a polymerase-compatible cleavable moiety. In embodiments, the moiety

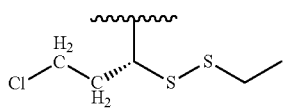 [SMILES: *[C@@H](CCCl)SSCC]

is a polymerase-compatible cleavable moiety. In embodiments, the moiety

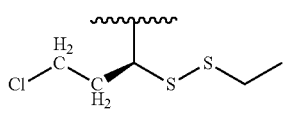 [SMILES: *[C@H](CCCl)SSCC]

is a polymerase-compatible cleavable moiety. In embodiments, the moiety

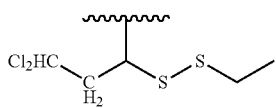

is a polymerase-compatible cleavable moiety. In embodiments, the moiety

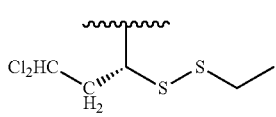

is a polymerase-compatible cleavable moiety. In embodiments, the moiety

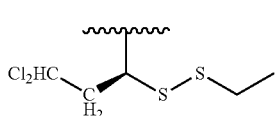

is a polymerase-compatible cleavable moiety. In embodiments, the moiety

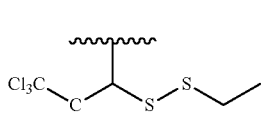

is a polymerase-compatible cleavable moiety. In embodiments, the moiety

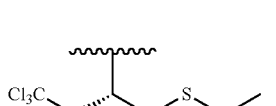

is a polymerase-compatible cleavable moiety. In embodiments, the moiety

is a polymerase-compatible cleavable moiety. In embodiments, the moiety

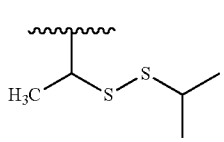

is a polymerase-compatible cleavable moiety. In embodiments, the moiety

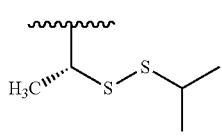 [SMILES: *[C@H](SSC(C)C)C(F)(F)F]

is a polymerase-compatible cleavable moiety. In embodiments, the moiety

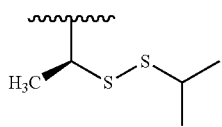 [SMILES: *[C@@H](SSC(C)C)C(F)(F)F]

is a polymerase-compatible cleavable moiety. In embodiments, the moiety


is a polymerase-compatible cleavable moiety. In embodiments, the moiety

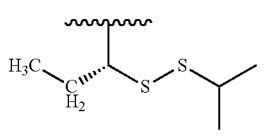

is a polymerase-compatible cleavable moiety. In embodiments, the moiety


is a polymerase-compatible cleavable moiety. In embodiments, the moiety


is a polymerase-compatible cleavable moiety. In embodiments, the moiety


is a polymerase-compatible cleavable moiety. In embodiments, the moiety

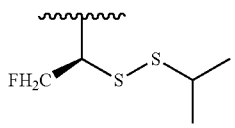

is a polymerase-compatible cleavable moiety. In embodiments, the moiety

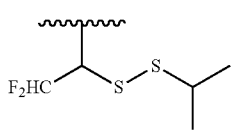

is a polymerase-compatible cleavable moiety. In embodiments, the moiety

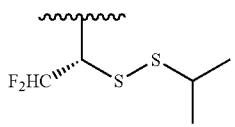

is a polymerase-compatible cleavable moiety. In embodiments, the moiety

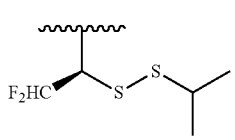

is a polymerase-compatible cleavable moiety. In embodiments, the moiety

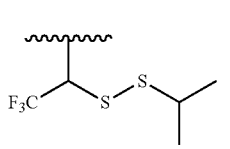

is a polymerase-compatible cleavable moiety. In embodiments, the moiety

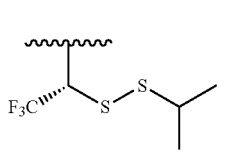

is a polymerase-compatible cleavable moiety. In embodiments, the moiety

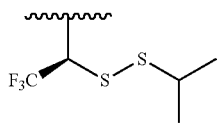

is a polymerase-compatible cleavable moiety. In embodiments, the moiety

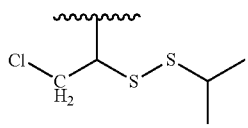

is a polymerase-compatible cleavable moiety. In embodiments, the moiety

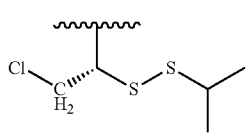 [SMILES: *C(CCl)SSC(C)C]

is a polymerase-compatible cleavable moiety. In embodiments, the moiety

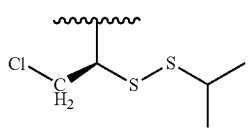 [SMILES: *[C@H](CCl)SSC(C)C]

is a polymerase-compatible cleavable moiety. In embodiments, the moiety

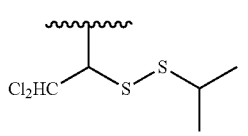

is a polymerase-compatible cleavable moiety. In embodiments, the moiety

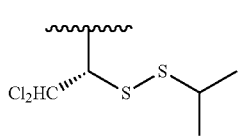

is a polymerase-compatible cleavable moiety. In embodiments, the moiety

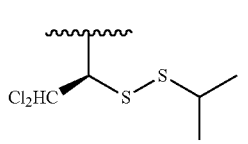

is a polymerase-compatible cleavable moiety. In embodiments, the moiety

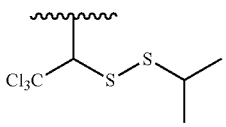

is a polymerase-compatible cleavable moiety. In embodiments, the moiety

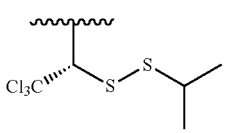

is a polymerase-compatible cleavable moiety. In embodiments, the moiety

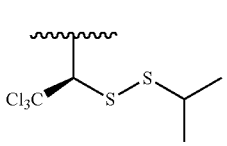

is a polymerase-compatible cleavable moiety. In embodiments, the moiety

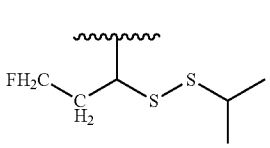

is a polymerase-compatible cleavable moiety. In embodiments, the moiety

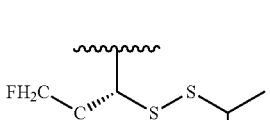

is a polymerase-compatible cleavable moiety. In embodiments, the moiety

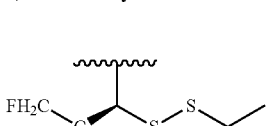

is a polymerase-compatible cleavable moiety. In embodiments, the moiety

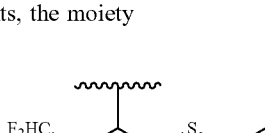

is a polymerase-compatible cleavable moiety. In embodiments, the moiety

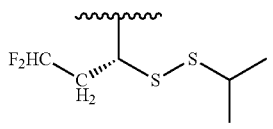

is a polymerase-compatible cleavable moiety. In embodiments, the moiety

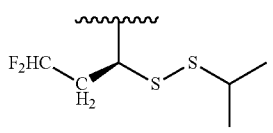 [SMILES: *[C@H](CC(F)F)SSC(C)C]

is a polymerase-compatible cleavable moiety. In embodiments, the moiety


is a polymerase-compatible cleavable moiety. In embodiments, the moiety

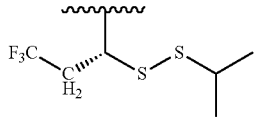 [SMILES: *[C@@H](CC(F)(F)F)SSC(C)C]

is a polymerase-compatible cleavable moiety. In embodiments, the moiety

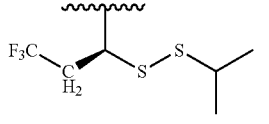

is a polymerase-compatible cleavable moiety. In embodiments, the moiety

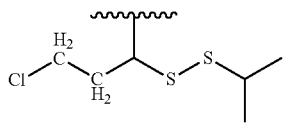 [SMILES: *C(CCCl)SSC(C)C]

is a polymerase-compatible cleavable moiety. In embodiments, the moiety

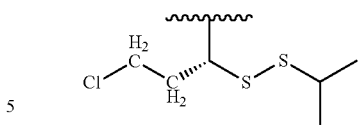

is a polymerase-compatible cleavable moiety. In embodiments, the moiety

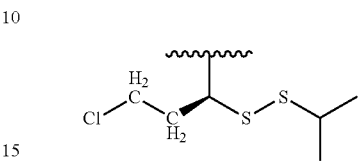

is a polymerase-compatible cleavable moiety. In embodiments, the moiety

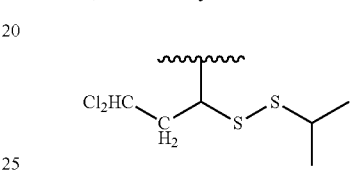

is a polymerase-compatible cleavable moiety. In embodiments, the moiety

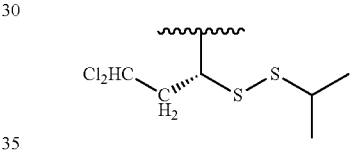

is a polymerase-compatible cleavable moiety. In embodiments, the moiety

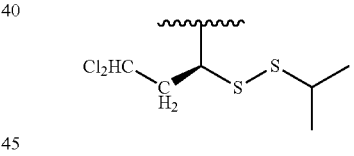

is a polymerase-compatible cleavable moiety. In embodiments, the moiety

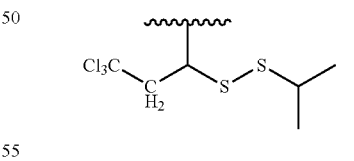

is a polymerase-compatible cleavable moiety. In embodiments, the moiety

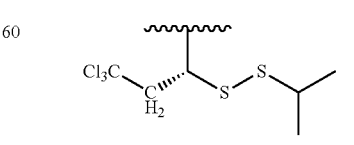

is a polymerase-compatible cleavable moiety. In embodiments, the moiety

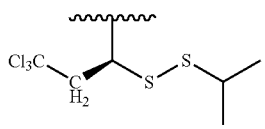

is a polymerase-compatible cleavable moiety. In embodiments, the moiety

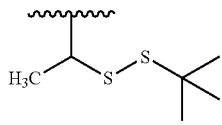

is a polymerase-compatible cleavable moiety. In embodiments, the moiety


is a polymerase-compatible cleavable moiety. In embodiments, the moiety


is a polymerase-compatible cleavable moiety. In embodiments, the moiety

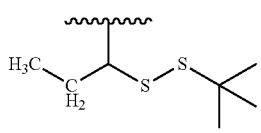

is a polymerase-compatible cleavable moiety. In embodiments, the moiety

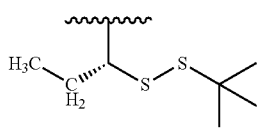

is a polymerase-compatible cleavable moiety. In embodiments, the moiety

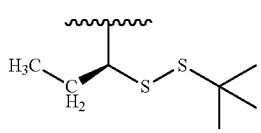 [SMILES: *[C@H](CC)SSC(C)(C)C]

is a polymerase-compatible cleavable moiety. In embodiments, the moiety

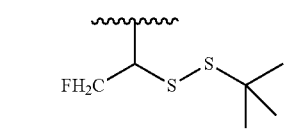

is a polymerase-compatible cleavable moiety. In embodiments, the moiety

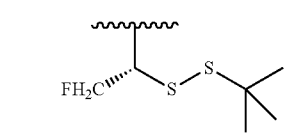

is a polymerase-compatible cleavable moiety. In embodiments, the moiety

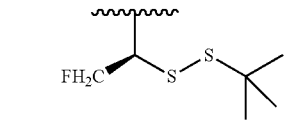

is a polymerase-compatible cleavable moiety. In embodiments, the moiety

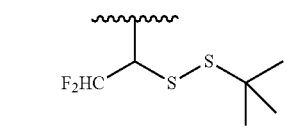 [SMILES: *C(SSC(C)(C)C)C(F)F]

is a polymerase-compatible cleavable moiety. In embodiments, the moiety

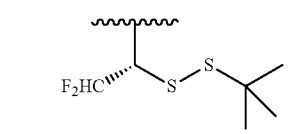

is a polymerase-compatible cleavable moiety. In embodiments, the moiety

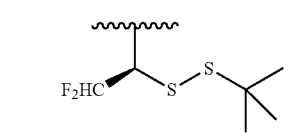

is a polymerase-compatible cleavable moiety. In embodiments, the moiety

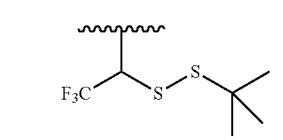

is a polymerase-compatible cleavable moiety. In embodiments, the moiety is a polymerase-compatible cleavable moiety. In embodiments, the moiety


is a polymerase-compatible cleavable moiety. In embodiments, the moiety

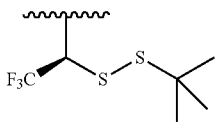 [SMILES: *[C@@H](SSC(C)(C)C)C(F)(F)F]

is a polymerase-compatible cleavable moiety. In embodiments, the moiety

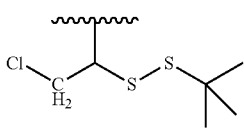 [SMILES: *C(CCl)SSC(C)(C)C]

is a polymerase-compatible cleavable moiety. In embodiments, the moiety

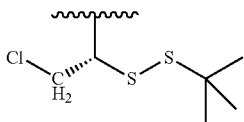 [SMILES: *[C@@H](CCl)SSC(C)(C)C]

is a polymerase-compatible cleavable moiety. In embodiments, the moiety

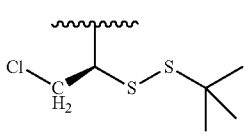 [SMILES: *[C@H](CCl)SSC(C)(C)C]

is a polymerase-compatible cleavable moiety

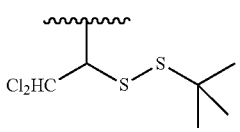

is a polymerase-compatible cleavable moiety. In embodiments, the moiety

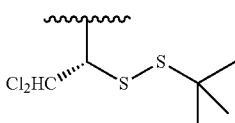

is a polymerase-compatible cleavable moiety. In embodiments, the moiety

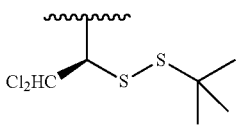

is a polymerase-compatible cleavable moiety. In embodiments, the moiety

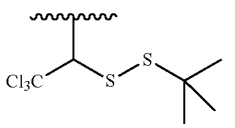

is a polymerase-compatible cleavable moiety. In embodiments, the moiety

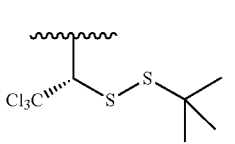

is a polymerase-compatible cleavable moiety. In embodiments, the moiety

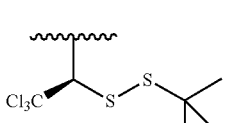

is a polymerase-compatible cleavable moiety. In embodiments, the moiety

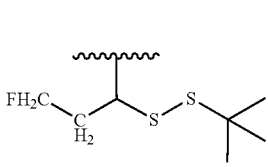

is a polymerase-compatible cleavable moiety. In embodiments, the moiety

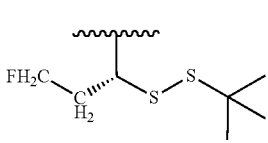

is a polymerase-compatible cleavable moiety. In embodiments, the moiety

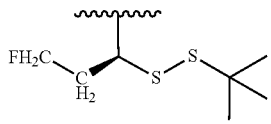

is a polymerase-compatible cleavable moiety. In embodiments, the moiety

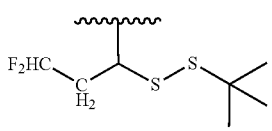

is a polymerase-compatible cleavable moiety. In embodiments, the moiety


is a polymerase-compatible cleavable moiety. In embodiments, the moiety

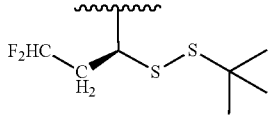 [SMILES: *[C@H](CC(F)F)SSC(C)(C)C]

is a polymerase-compatible cleavable moiety. In embodiments, the moiety

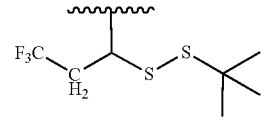

is a polymerase-compatible cleavable moiety. In embodiments, the moiety

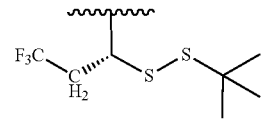

is a polymerase-compatible cleavable moiety. In embodiments, the moiety

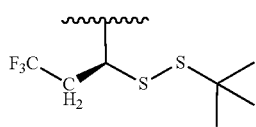

is a polymerase-compatible cleavable moiety. In embodiments, the moiety

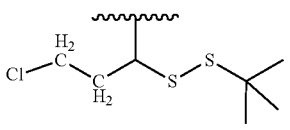 [SMILES: *C(CCCl)SSC(C)(C)C]

is a polymerase-compatible cleavable moiety. In embodiments, the moiety

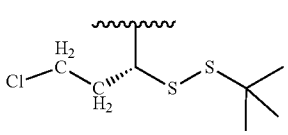

is a polymerase-compatible cleavable moiety. In embodiments, the moiety

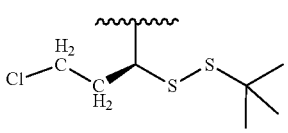 [SMILES: *[C@H](CCCl)SSC(C)(C)C]

is a polymerase-compatible cleavable moiety. In embodiments, the moiety

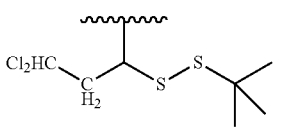

is a polymerase-compatible cleavable moiety. In embodiments, the moiety

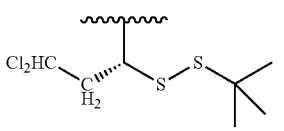

is a polymerase-compatible cleavable moiety. In embodiments, the moiety

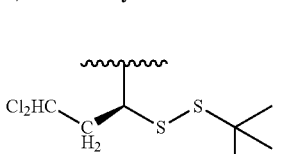
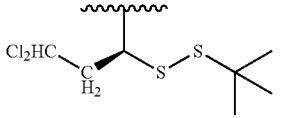
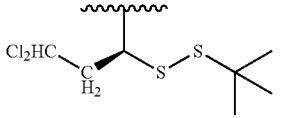
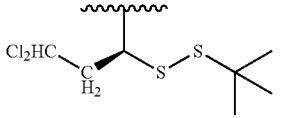
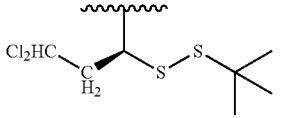
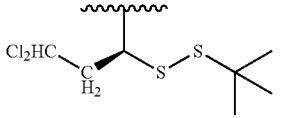

is a polymerase-compatible cleavable moiety. In embodiments, the moiety

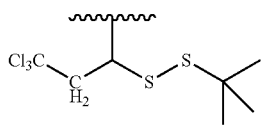

is a polymerase-compatible cleavable moiety. In embodiments, the moiety

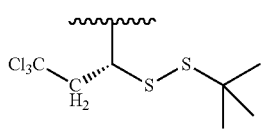

is a polymerase-compatible cleavable moiety. In embodiments, the moiety

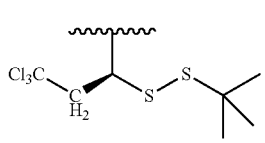

is a polymerase-compatible cleavable moiety.

In embodiments, $-L^{1P}\text{-S}-\text{S}-R^{6P}$ is

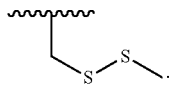

In embodiments, $-L^{1P}\text{-S}-\text{S}-R^{6P}$ is

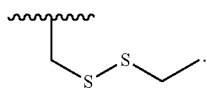

In embodiments, $-L^{1P}\text{-S}-\text{S}-R^{6P}$ is

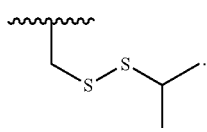

In embodiments, $-L^{1P}\text{-S}-\text{S}-R^{6P}$ is

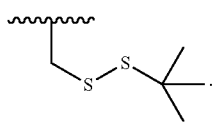 [SMILES: *CSSC(C)(C)C]

In embodiments, $-L^{1P}\text{-S}-\text{S}-R^{6P}$ is

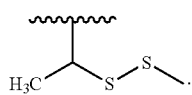

In embodiments, $-L^{1P}\text{-S}-\text{S}-R^{6P}$ is

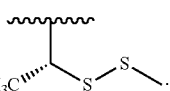

In embodiments, $-L^{1P}\text{-S}-\text{S}-R^{6P}$ is

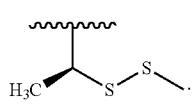

In embodiments, $-L^{1P}\text{-S}-\text{S}-R^{6P}$ is

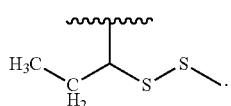

In embodiments, $-L^{1P}\text{-S}-\text{S}-R^{6P}$ is

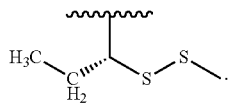

In embodiments, $-L^{1P}\text{-S}-\text{S}-R^{6P}$ is

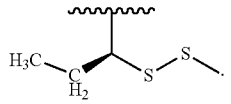

In embodiments, $-L^{1P}\text{-S}-\text{S}-R^{6P}$ is

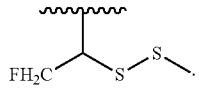

In embodiments, $-L^{1P}\text{-S}-\text{S}-R^{6P}$ is

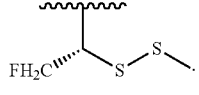

In embodiments, -L$^{1P}$-S—S—R$^{6P}$ is

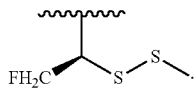

In embodiments, -L$^{1P}$-S—S—R$^{6P}$ is

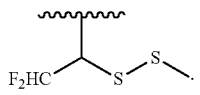

In embodiments, -L$^{1P}$-S—S—R$^{6P}$ is

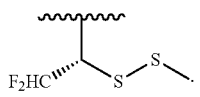

In embodiments, -L$^{1P}$-S—S—R$^{6P}$ is

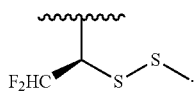

In embodiments, -L$^{1P}$-S—S—R$^{6P}$ is

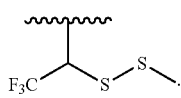

In embodiments, -L$^{1P}$-S—S—R$^{6P}$ is

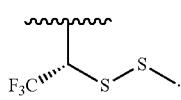

In embodiments, -L$^{1P}$-S—S—R$^{6P}$ is

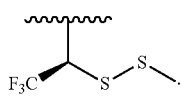

In embodiments, -L$^{1P}$-S—S—R$^{6P}$ is

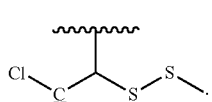

In embodiments, -L$^{1P}$-S—S—R$^{6P}$ is

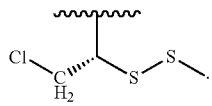

In embodiments, -L$^{1P}$-S—S—R$^{6P}$ is

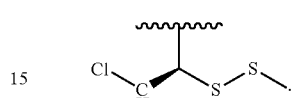

In embodiments, -L$^{1P}$-S—S—R$^{6P}$ is

In embodiments, -L$^{1P}$-S—S—R$^{6P}$ is

In embodiments, -L$^{1P}$-S—S—R$^{6P}$ is

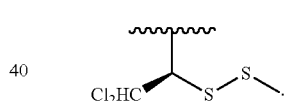

In embodiments, -L$^{1P}$-S—S—R$^{6P}$ is

In embodiments, -L$^{1P}$-S—S—R$^{6P}$ is

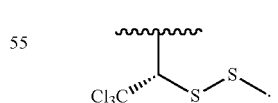

In embodiments, -L$^{1P}$-S—S—R$^{6P}$ is

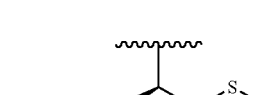

In embodiments, -L$^{1P}$-S—S—R$^{6P}$ is

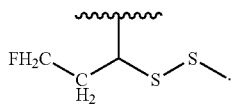

In embodiments, -L$^{1P}$-S—S—R$^{6P}$ is

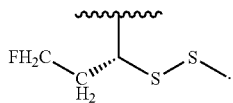

In embodiments, -L$^{1P}$-S—S—R$^{6P}$ is

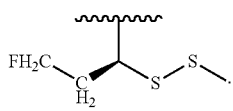

In embodiments, -L$^{1P}$-S—S—R$^{6P}$ is

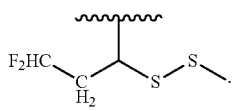

In embodiments, -L$^{1P}$-S—S—R$^{6P}$ is

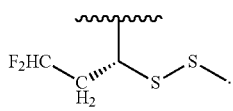

In embodiments, -L$^{1P}$-S—S—R$^{6P}$ is

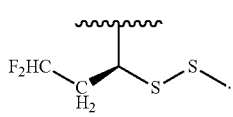

In embodiments, -L$^{1P}$-S—S—R$^{6P}$ is

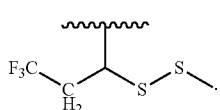

In embodiments, -L$^{1P}$-S—S—R$^{6P}$ is

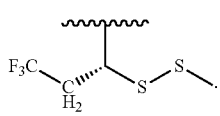

In embodiments, -L$^{1P}$-S—S—R$^{6P}$ is

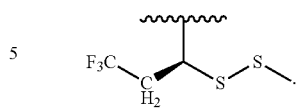

In embodiments, -L$^{1P}$-S—S—R$^{6P}$ is

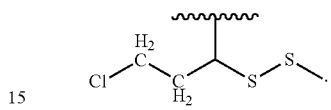

In embodiments, -L$^{1P}$-S—S—R$^{6P}$ is

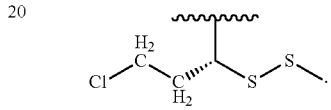

In embodiments, -L$^{1P}$-S—S—R$^{6P}$ is

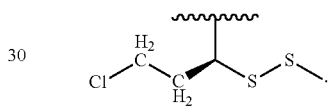

In embodiments, -L$^{1P}$-S—S—R$^{6P}$ is

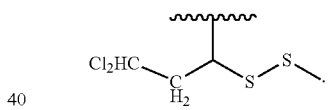

In embodiments, -L$^{1P}$-S—S—R$^{6P}$ is

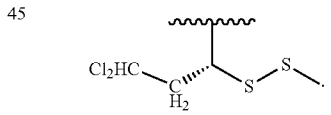

In embodiments, -L$^{1P}$-S—S—R$^{6P}$ is

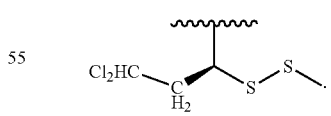

In embodiments, -L$^{1P}$-S—S—R$^{6P}$ is

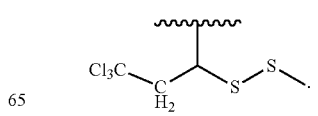

In embodiments, -L$^{1P}$-S—S—R$^{6P}$ is

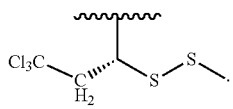

In embodiments, -L$^{1P}$-S—S—R$^{6P}$ is

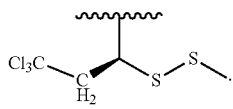

In embodiments, -L$^{1P}$-S—S—R$^{6P}$ is


In embodiments, -L$^{1P}$-S—S—R$^{6P}$ is

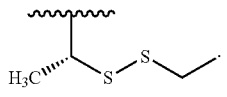

In embodiments, -L$^{1P}$-S—S—R$^{6P}$ is

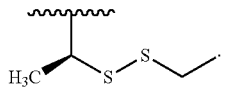

In embodiments, -L$^{1P}$-S—S—R$^{6P}$ is

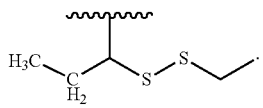

In embodiments, -L$^{1P}$-S—S—R$^{6P}$ is

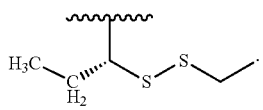

In embodiments, -L$^{1P}$-S—S—R$^{6P}$ is

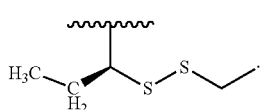

In embodiments, -L$^{1P}$-S—S—R$^{6P}$ is

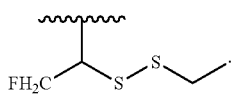

In embodiments, -L$^{1P}$-S—S—R$^{6P}$ is

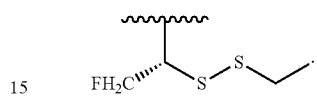

In embodiments, -L$^{1P}$-S—S—R$^{6P}$ is

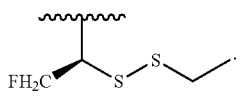

In embodiments, -L$^{1P}$-S—S—R$^{6P}$ is

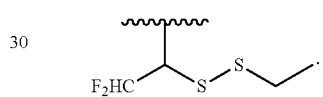

In embodiments, -L$^{1P}$-S—S—R$^{6P}$ is

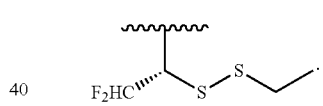

In embodiments, -L$^{1P}$-S—S—R$^{6P}$ is

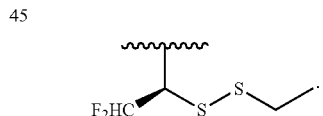

In embodiments, -L$^{1P}$-S—S—R$^{6P}$ is

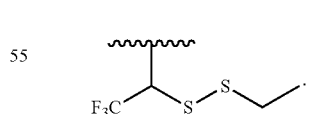

In embodiments, -L$^{1P}$-S—S—R$^{6P}$ is

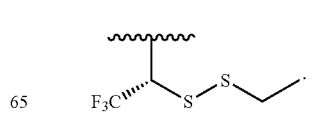

In embodiments, -L$^{1P}$-S—S—R$^{6P}$ is

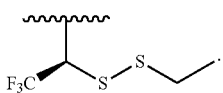

In embodiments, -L$^{1P}$-S—S—R$^{6P}$ is

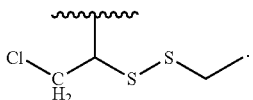

In embodiments, -L$^{1P}$-S—S—R$^{6P}$ is

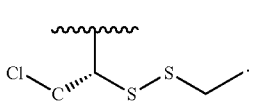

In embodiments, -L$^{1P}$-S—S—R$^{6P}$ is

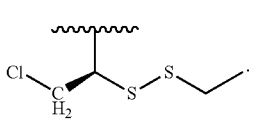

In embodiments, -L$^{1P}$-S—S—R$^{6P}$ is

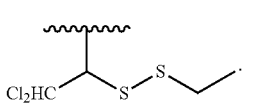

In embodiments, -L$^{1P}$-S—S—R$^{6P}$ is

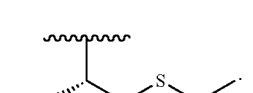

In embodiments, -L$^{1P}$-S—S—R$^{6P}$ is

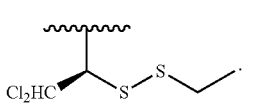

In embodiments, -L$^{1P}$-S—S—R$^{6P}$ is

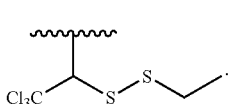

In embodiments, -L$^{1P}$-S—S—R$^{6P}$ is

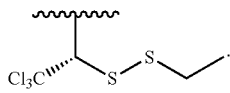

In embodiments, -L$^{1P}$-S—S—R$^{6P}$ is

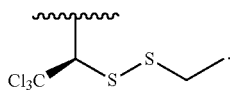

In embodiments, -L$^{1P}$-S—S—R$^{6P}$ is

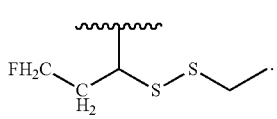

In embodiments, -L$^{1P}$-S—S—R$^{6P}$ is

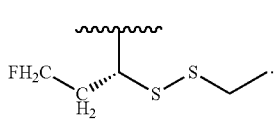

In embodiments, -L$^{1P}$-S—S—R$^{6P}$ is

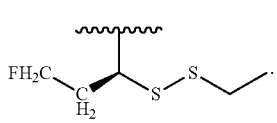

In embodiments, -L$^{1P}$-S—S—R$^{6P}$ is

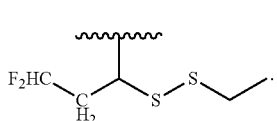

In embodiments, -L$^{1P}$-S—S—R$^{6P}$ is

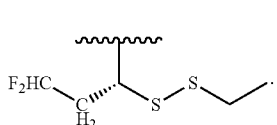

In embodiments, -L$^{1P}$-S—S—R$^{6P}$ is

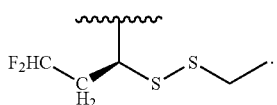

In embodiments, -L$^{1P}$-S—S—R$^{6P}$ is

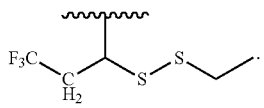

In embodiments, -L$^{1P}$-S—S—R$^{6P}$ is


In embodiments, -L$^{1P}$-S—S—R$^{6P}$ is

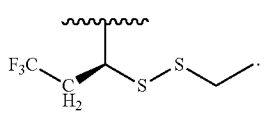

In embodiments, -L$^{1P}$-S—S—R$^{6P}$ is

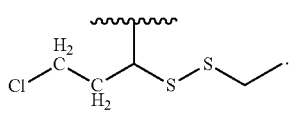 [SMILES: *C(CCCl)SSCC]

In embodiments, -L$^{1P}$-S—S—R$^{6P}$ is

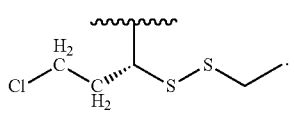

In embodiments, -L$^{1P}$-S—S—R$^{6P}$ is

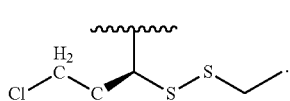

In embodiments, -L$^{1P}$-S—S—R$^{6P}$ is

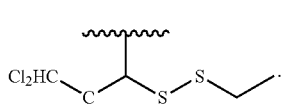

In embodiments, -L$^{1P}$-S—S—R$^{6P}$ is

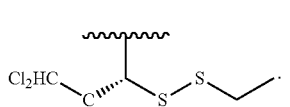

In embodiments, -L$^{1P}$-S—S—R$^{6P}$ is

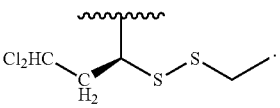

In embodiments, -L$^{1P}$-S—S—R$^{6P}$ is

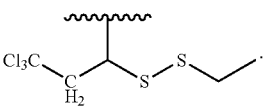

In embodiments, -L$^{1P}$-S—S—R$^{6P}$ is

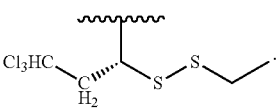

In embodiments, -L$^{1P}$-S—S—R$^{6P}$ is

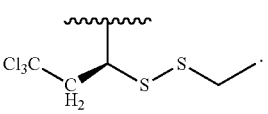

In embodiments, -L$^{1P}$-S—S—R$^{6P}$ is

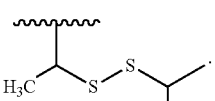

In embodiments, -L$^{1P}$-S—S—R$^{6P}$ is

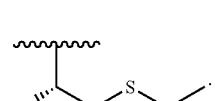

In embodiments, -L$^{1P}$-S—S—R$^{6P}$ is

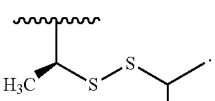

In embodiments, -L$^{1P}$-S—S—R$^{6P}$ is

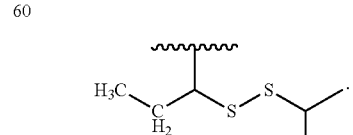

In embodiments, -L$^{1P}$-S—S—R$^{6P}$ is

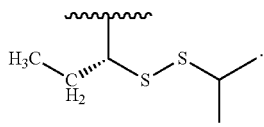

In embodiments, -L$^{1P}$-S—S—R$^{6P}$ is

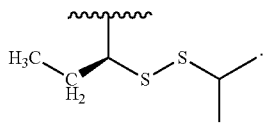

In embodiments, -L$^{1P}$-S—S—R$^{6P}$ is


In embodiments, -L$^{1P}$-S—S—R$^{6P}$ is


In embodiments, -L$^{1P}$-S—S—R$^{6P}$ is

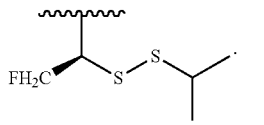

In embodiments, -L$^{1P}$-S—S—R$^{6P}$ is

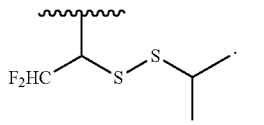 [SMILES: *C(SSC(C)C)C(F)F]

In embodiments, -L$^{1P}$-S—S—R$^{6P}$ is

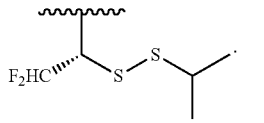 [SMILES: *[C@H](SSC(C)C)C(F)F]

In embodiments, -L$^{1P}$-S—S—R$^{6P}$ is

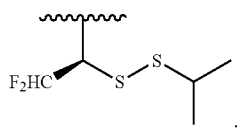 [SMILES: *[C@@H](SSC(C)C)C(F)F]

In embodiments, -L$^{1P}$-S—S—R$^{6P}$ is

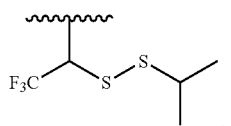

In embodiments, -L$^{1P}$-S—S—R$^{6P}$ is

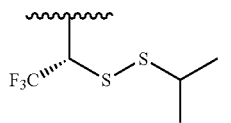

In embodiments, -L$^{1P}$-S—S—R$^{6P}$ is

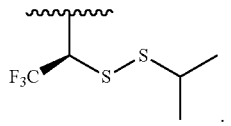

In embodiments, -L$^{1P}$-S—S—R$^{6P}$ is

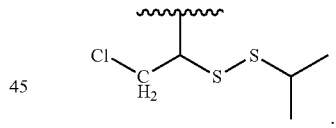

In embodiments, -L$^{1P}$-S—S—R$^{6P}$ is

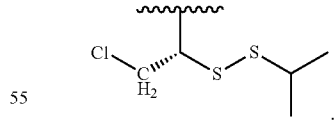

In embodiments, -L$^{1P}$-S—S—R$^{6P}$ is

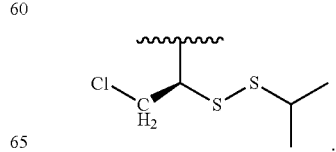

In embodiments, -L$^{1P}$-S—S—R$^{6P}$ is

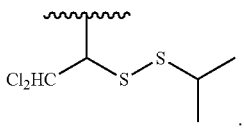

In embodiments, -L$^{1P}$-S—S—R$^{6P}$ is

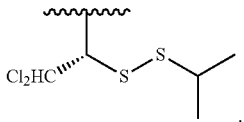

In embodiments, -L$^{1P}$-S—S—R$^{6P}$ is

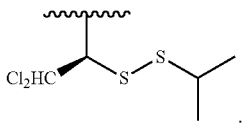

In embodiments, -L$^{1P}$-S—S—R$^{6P}$ is

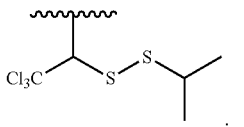

In embodiments, -L$^{1P}$-S—S—R$^{6P}$ is

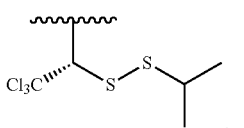

In embodiments, -L$^{1P}$-S—S—R$^{6P}$ is

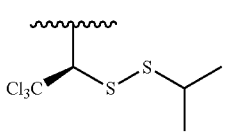

In embodiments, -L$^{1P}$-S—S—R$^{6P}$ is

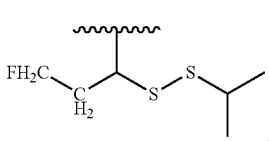

In embodiments, -L$^{1P}$-S—S—R$^{6P}$ is

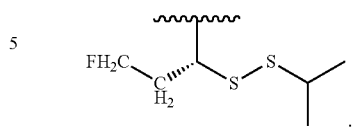

In embodiments, -L$^{1P}$-S—S—R$^{6P}$ is

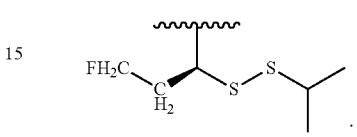

In embodiments, -L$^{1P}$-S—S—R$^{6P}$ is

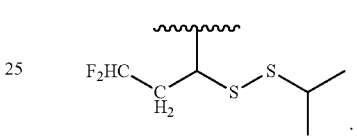

In embodiments, -L$^{1P}$-S—S—R$^{6P}$ is

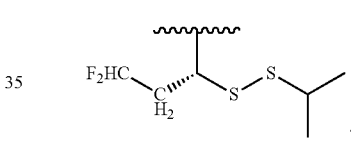

In embodiments, -L$^{1P}$-S—S—R$^{6P}$ is

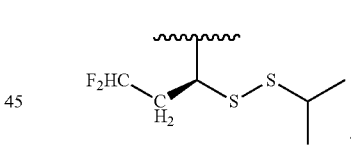

In embodiments, -L$^{1P}$-S—S—R$^{6P}$ is

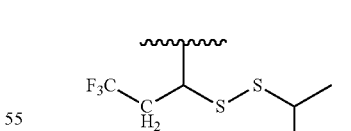

In embodiments, -L$^{1P}$-S—S—R$^{6P}$ is

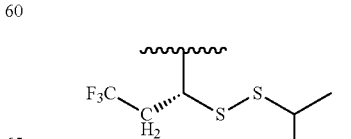

In embodiments, -L$^{1P}$-S—S—R$^{6P}$ is

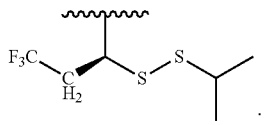

In embodiments, -L$^{1P}$-S—S—R$^{6P}$ is

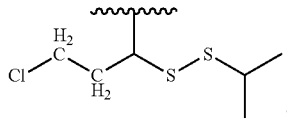

In embodiments, -L$^{1P}$-S—S—R$^{6P}$ is

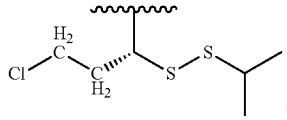

In embodiments, -L$^{1P}$-S—S—R$^{6P}$ is

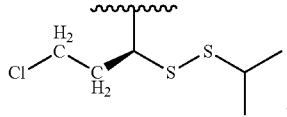

In embodiments, -L$^{1P}$-S—S—R$^{6P}$ is

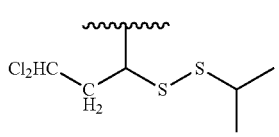

In embodiments, -L$^{1P}$-S—S—R$^{6P}$ is

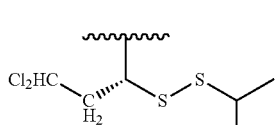

In embodiments, -L$^{1P}$-S—S—R$^{6P}$ is

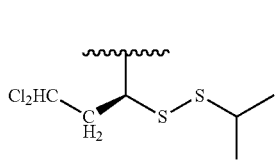

In embodiments, -L$^{1P}$-S—S—R$^{6P}$ is

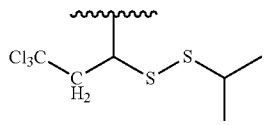

In embodiments, -L$^{1P}$-S—S—R$^{6P}$ is

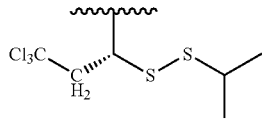

In embodiments, -L$^{1P}$-S—S—R$^{6P}$ is


In embodiments, -L$^{1P}$-S—S—R$^{6P}$ is

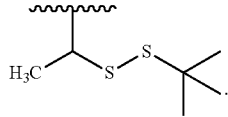 [SMILES: *C(C)SSC(C)(C)C]

In embodiments, -L$^{1P}$-S—S—R$^{6P}$ is

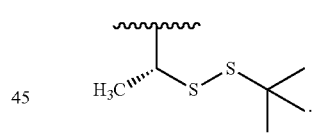

In embodiments, -L$^{1P}$-S—S—R$^{6P}$ is


In embodiments, -L$^{1P}$-S—S—R$^{6P}$ is

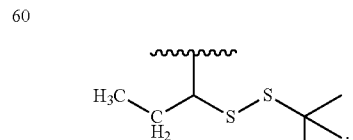

In embodiments, -L$^{1P}$-S—S—R$^{6P}$ is

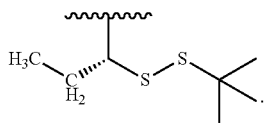 [SMILES: *[C@@H](CC)SSC(C)(C)C]

In embodiments, -L$^{1P}$-S—S—R$^{6P}$ is


In embodiments, -L$^{1P}$-S—S—R$^{6P}$ is


In embodiments, -L$^{1P}$-S—S—R$^{6P}$ is

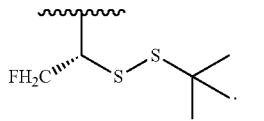

In embodiments, -L$^{1P}$-S—S—R$^{6P}$ is

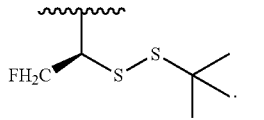

In embodiments, -L$^{1P}$-S—S—R$^{6P}$ is

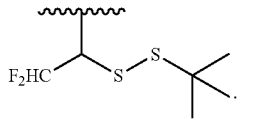

In embodiments, -L$^{1P}$-S—S—R$^{6P}$ is

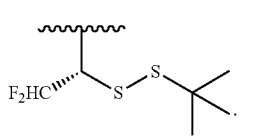

In embodiments, -L$^{1P}$-S—S—R$^{6P}$ is

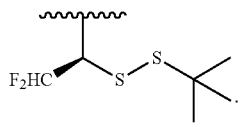

In embodiments, -L$^{1P}$-S—S—R$^{6P}$ is

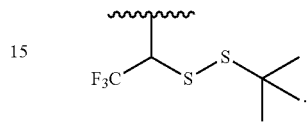

In embodiments, -L$^{1P}$-S—S—R$^{6P}$ is

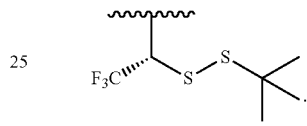

In embodiments, -L$^{1P}$-S—S—R$^{6P}$ is

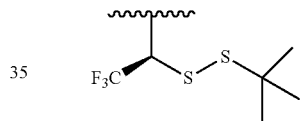

In embodiments, -L$^{1P}$-S—S—R$^{6P}$ is

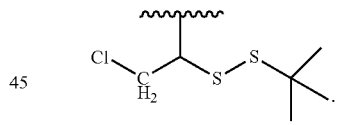

In embodiments, -L$^{1P}$-S—S—R$^{6P}$ is

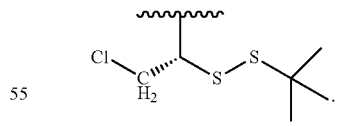

In embodiments, -L$^{1P}$-S—S—R$^{6P}$ is

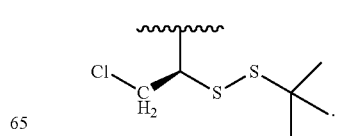

In embodiments, -L$^{1P}$-S—S—R$^{6P}$ is

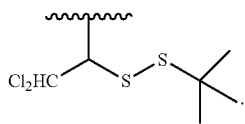

In embodiments, -L$^{1P}$-S—S—R$^{6P}$ is

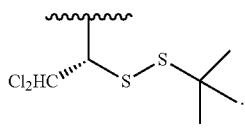

In embodiments, -L$^{1P}$-S—S—R$^{6P}$ is

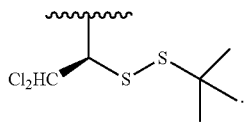

In embodiments, -L$^{1P}$-S—S—R$^{6P}$ is

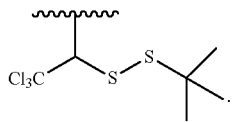

In embodiments, -L$^{1P}$-S—S—R$^{6P}$ is

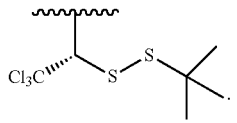

In embodiments, -L$^{1P}$-S—S—R$^{6P}$ is

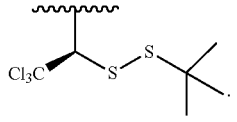

In embodiments, -L$^{1P}$-S—S—R$^{6P}$ is

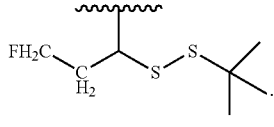

In embodiments, -L$^{1P}$-S—S—R$^{6P}$ is

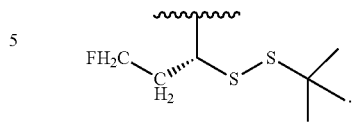

In embodiments, -L$^{1P}$-S—S—R$^{6P}$ is

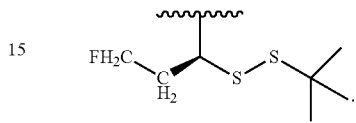

In embodiments, -L$^{1P}$-S—S—R$^{6P}$ is

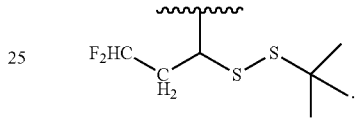

In embodiments, -L$^{1P}$-S—S—R$^{6P}$ is

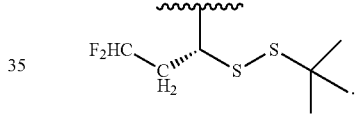

In embodiments, -L$^{1P}$-S—S—R$^{6P}$ is

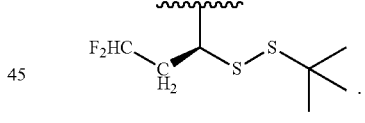

In embodiments, -L$^{1P}$-S—S—R$^{6P}$ is

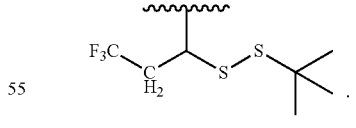

In embodiments, -L$^{1P}$-S—S—R$^{6P}$ is

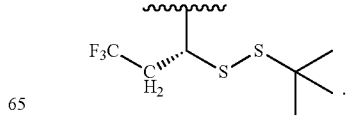

In embodiments, -L$^{1P}$-S—S—R$^{6P}$ is
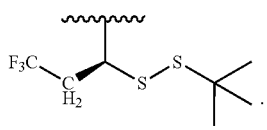
In embodiments, -L$^{1P}$-S—S—R$^{6P}$ is
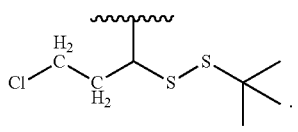 [SMILES: *C(CCCl)SSC(C)(C)C]
In embodiments, -L$^{1P}$-S—S—R$^{6P}$ is
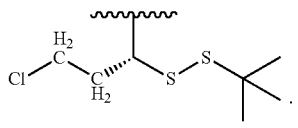 [SMILES: *[C@@H](CCCl)SSC(C)(C)C]
In embodiments, -L$^{1P}$-S—S—R$^{6P}$ is
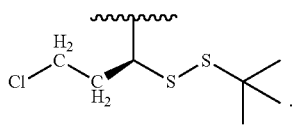
In embodiments, -L$^{1P}$-S—S—R$^{6P}$ is
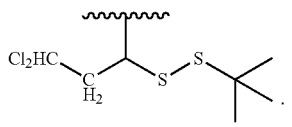
In embodiments, -L$^{1P}$-S—S—R$^{6P}$ is
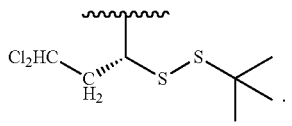
In embodiments, -L$^{1P}$-S—S—R$^{6P}$ is
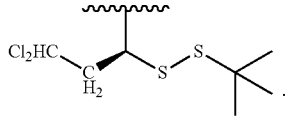
In embodiments, -L$^{1P}$-S—S—R$^{6P}$ is
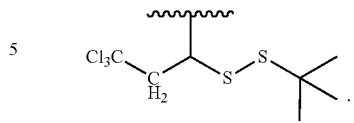
In embodiments, -L$^{1P}$-S—S—R$^{6P}$ is
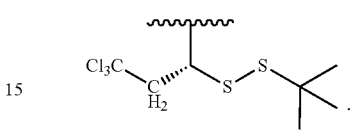
In embodiments, -L$^{1P}$-S—S—R$^{6P}$ is
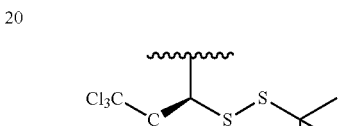
In embodiments, -L$^{1P}$-S—S—R$^{6P}$ is:
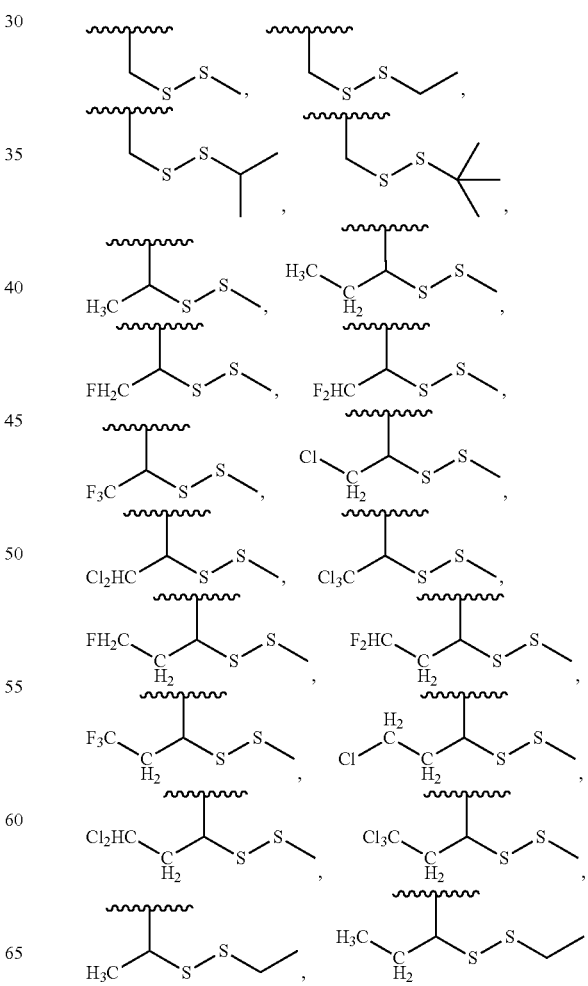

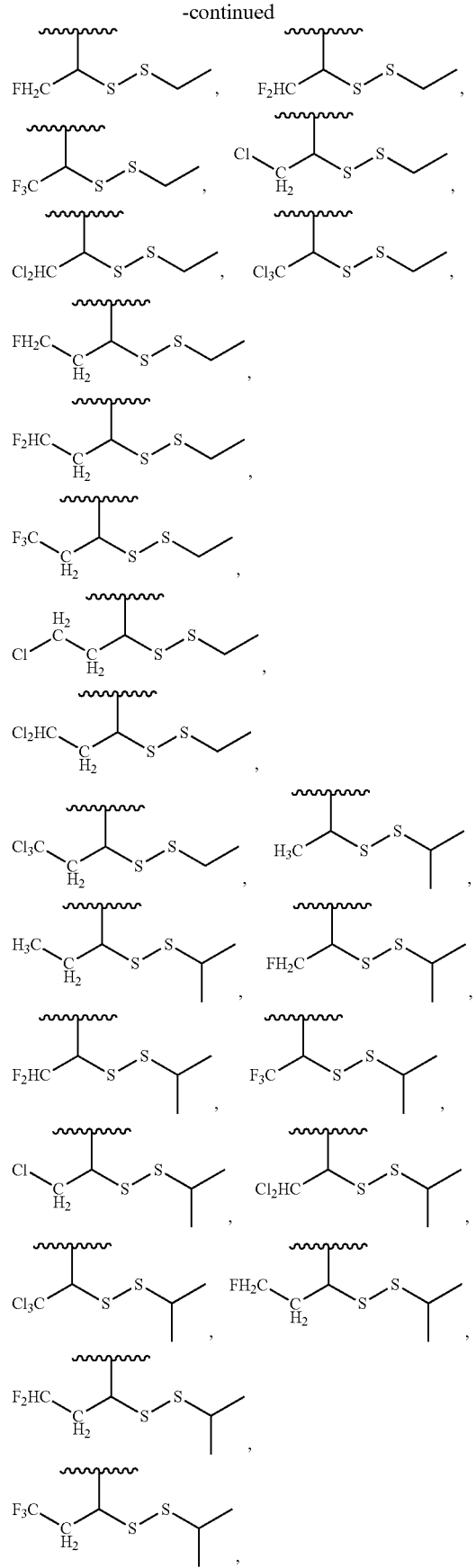
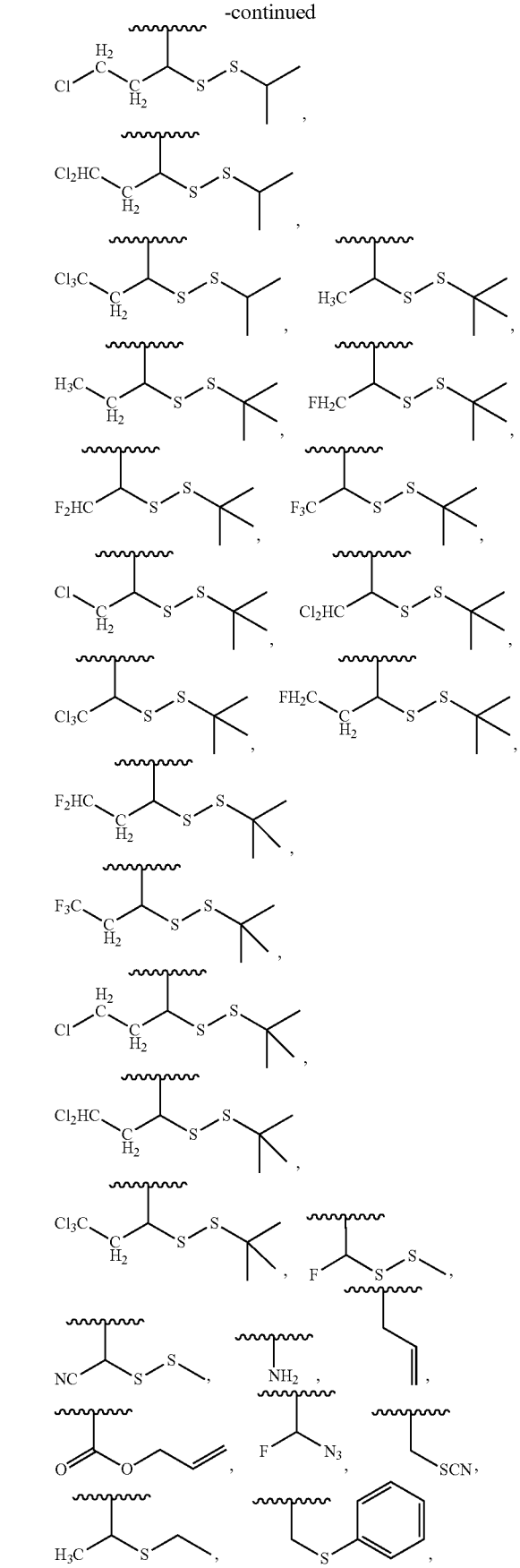

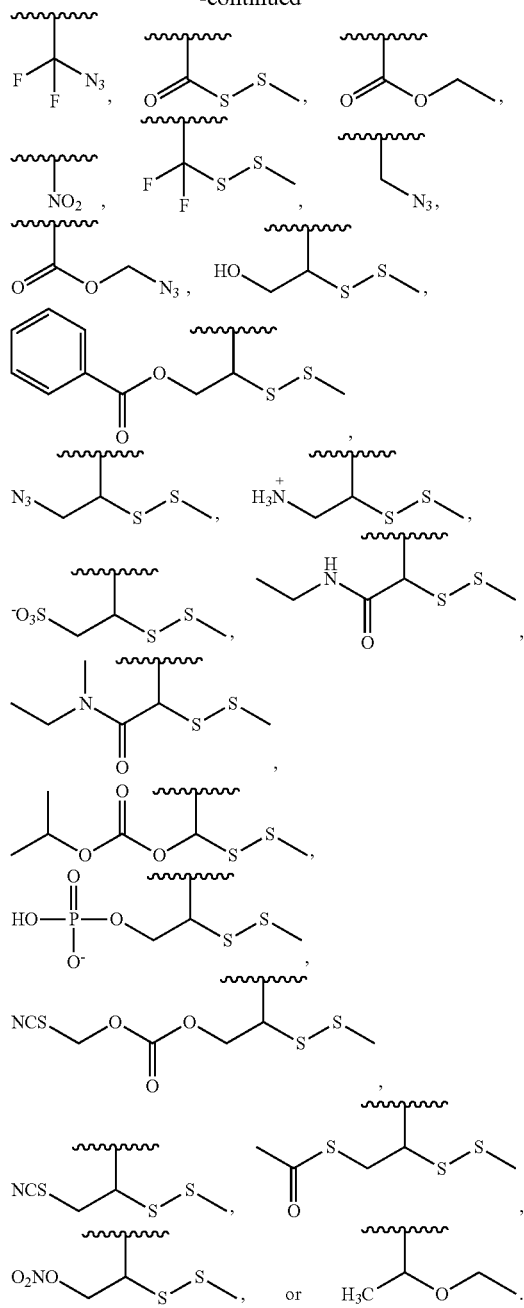
In embodiments, -L$^{1P}$-S—S—R$^{6P}$ is:
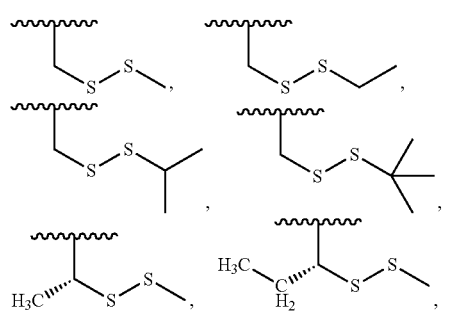
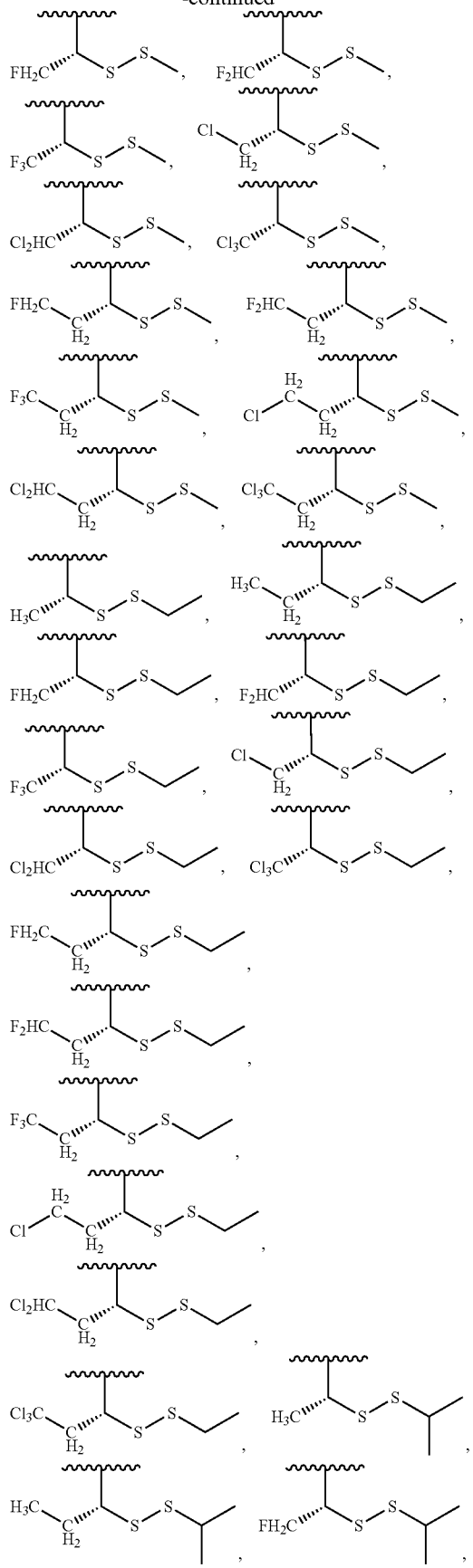

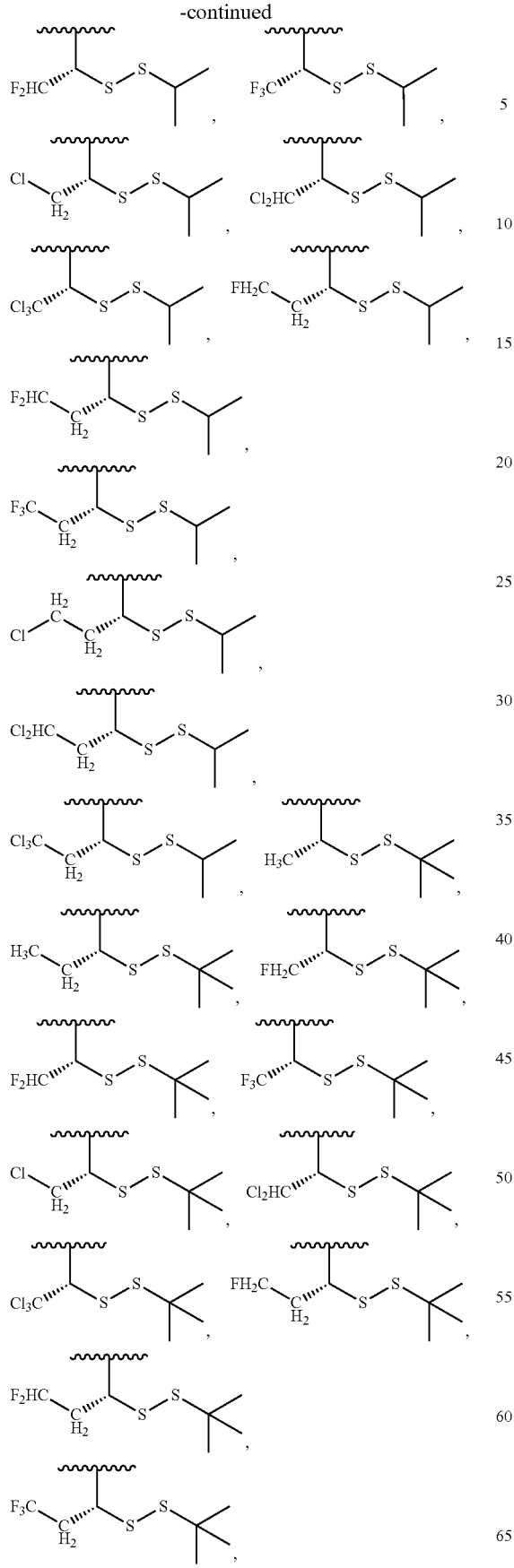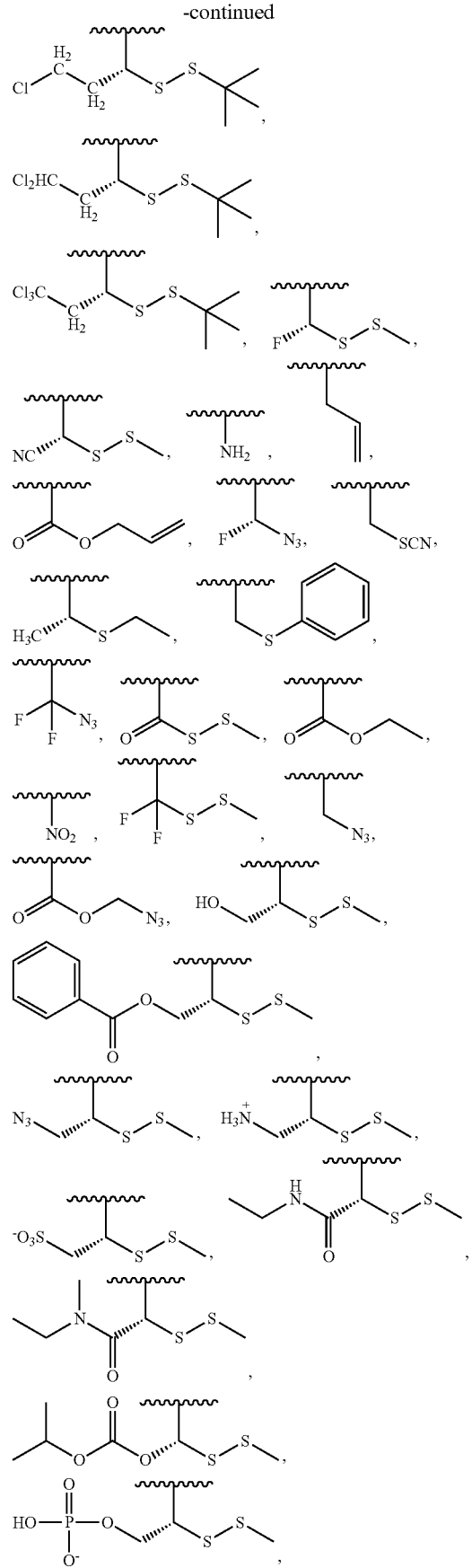

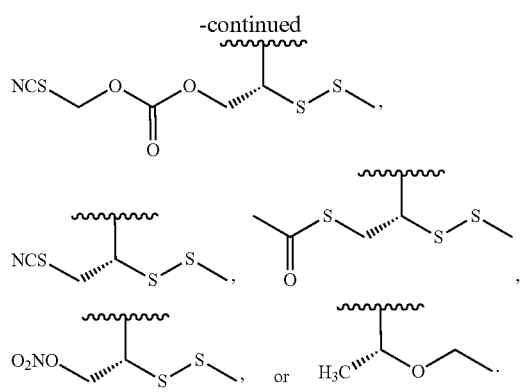
In embodiments, -L$^{1P}$-S—S—R$^{6P}$ is:
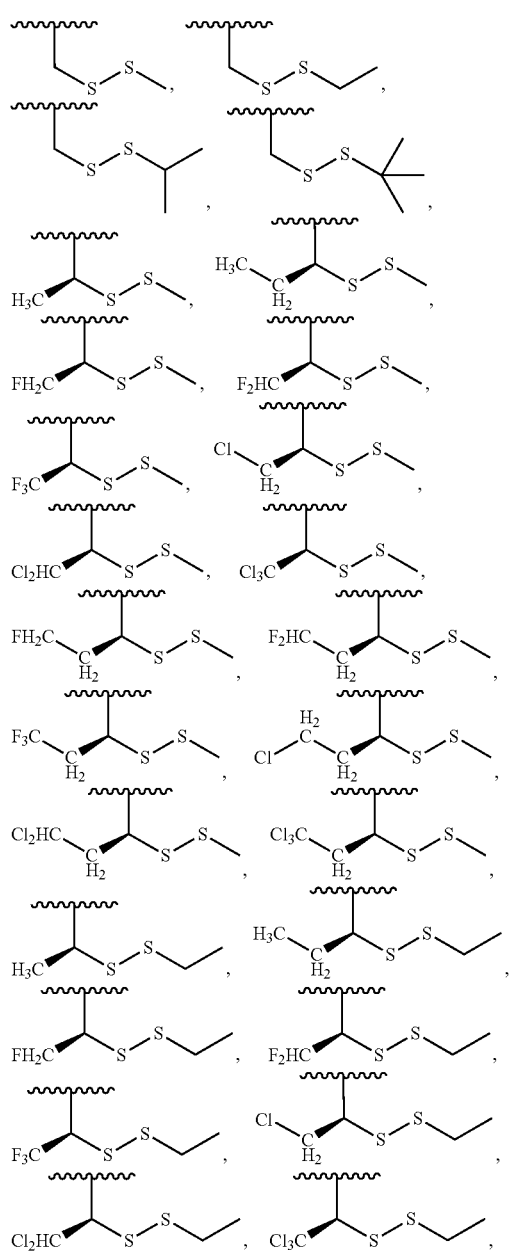
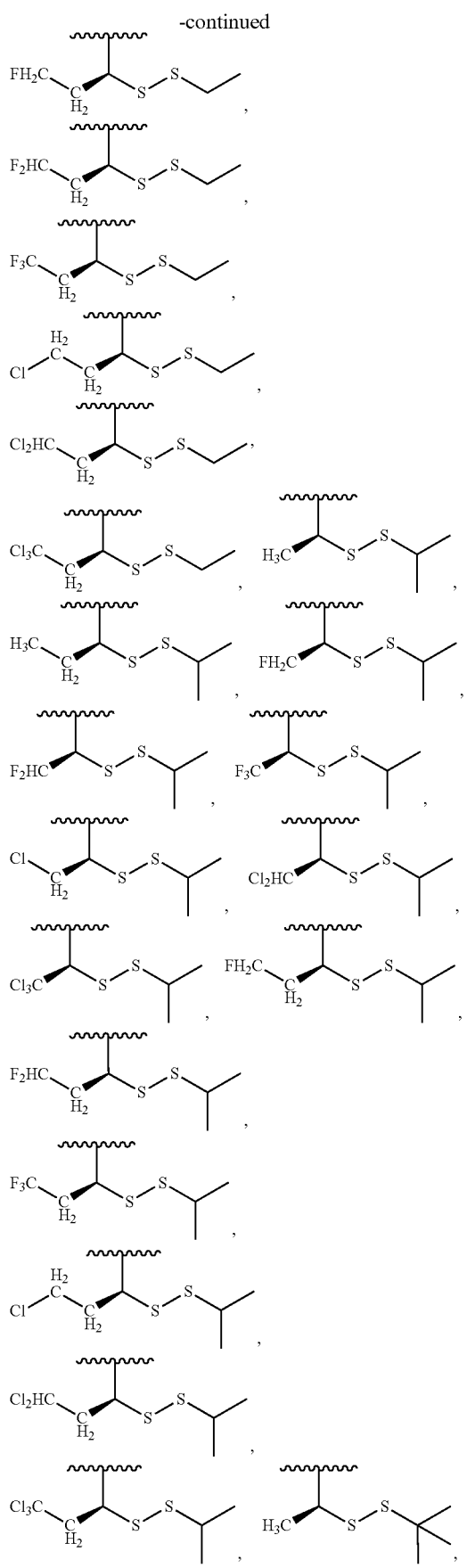

121
-continued

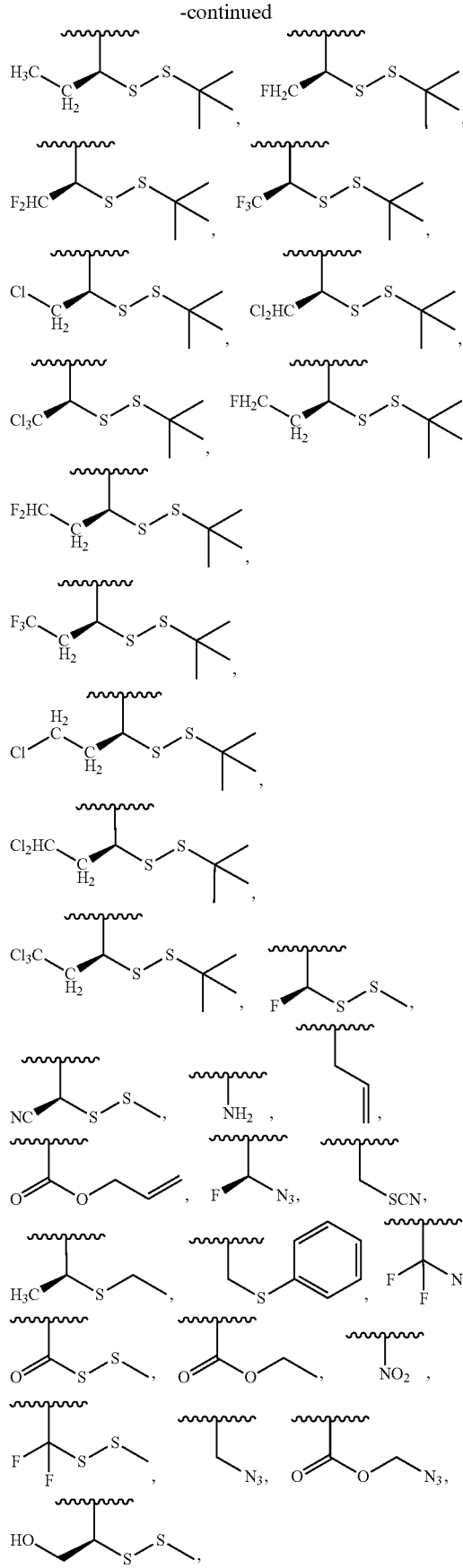

122
-continued

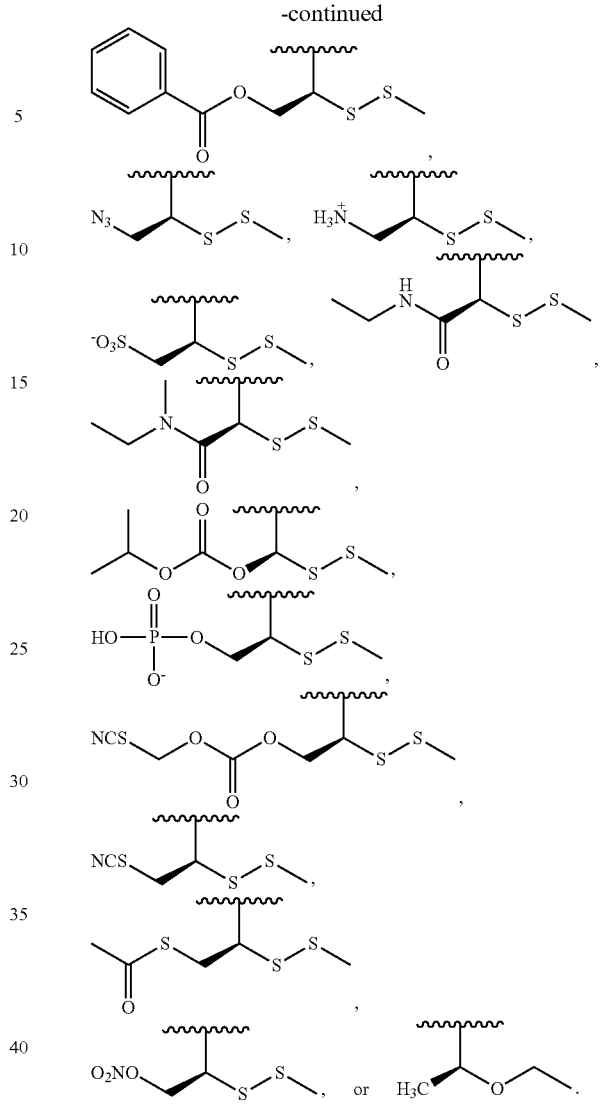

In embodiments, $L^{1P}$ is a bond, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{1P}$ is a bond, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, a substituted $L^{1P}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{1P}$ is substituted with a plurality of groups selected from substituent groups, size-limited substituent groups, and lower substituent groups; each substituent group, size-limited substituent group, and/or lower substituent group may optionally be different. In embodiments, when $L^{1P}$ is substituted, it is substituted with at least one substituent group. In embodiments, when $L^{1P}$ is substituted, it is substituted with at least one size-limited substituent group. In embodiments, when $L^{1P}$ is substituted, it is substituted with at least one lower substituent group. In embodiments, when $L^{1P}$ is substituted, it is substituted with 1 to 10 substituent groups. In embodiments, when $L^{1P}$ is substituted, it is substituted with 1 to 10 size-limited substituent groups. In embodiments, when $L^{1P}$ is substituted, it is substituted with 1 to 10 lower substituent groups. In embodiments, when $L^{1P}$ is substituted, it is substituted with 1 to 5 substituent groups. In embodiments, when $L^{1P}$ is substituted, it is substituted with 1 to 5 size-limited substituent groups. In embodiments, when $L^{1P}$ is substituted, it is substituted with 1 to 5 lower substituent groups. In embodiments, when $L^{1P}$ is substituted, it is substituted with a substituent group. In embodiments, when $L^{1P}$ is substituted, it is substituted with a size-limited substituent group. In embodiments, when $L^{1P}$ is substituted, it is substituted with a lower substituent group.

In embodiments, $L^{1P}$ is a bond, substituted (e.g., substituted with a substituent group, size-limited substituent group, or lower substituent group) or unsubstituted $C_1$-$C_8$ alkylene (e.g., saturated alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^{1P}$ is a bond, substituted (e.g., substituted with a substituent group, size-limited substituent group, or lower substituent group) or unsubstituted $C_1$-$C_6$ alkylene (e.g., saturated alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^{1P}$ is a bond, substituted (e.g., substituted with a substituent group, size-limited substituent group, or lower substituent group) or unsubstituted $C_1$-$C_4$ alkylene (e.g., saturated alkylene, alkenylene, or alkynylene), substituted (e.g., substituted with a substituent group, size-limited substituent group, or lower substituent group) or unsubstituted 2 to 4 membered heteroalkylene (e.g., heteroalkylene, heteroalkenylene, or heteroalkynylene), substituted (e.g., substituted with a substituent group, size-limited substituent group, or lower substituent group) or unsubstituted $C_5$-$C_6$ cycloalkylene, substituted (e.g., substituted with a substituent group, size-limited substituent group, or lower substituent group) or unsubstituted 5 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^{1P}$ is a bond, substituted (e.g., substituted with a substituent group, size-limited substituent group, or lower substituent group) or unsubstituted $C_1$-$C_2$ alkylene (e.g., saturated alkylene, alkenylene, or alkynylene), substituted (e.g., substituted with a substituent group, size-limited substituent group, or lower substituent group).

In embodiments, $L^{1P}$ is a bond. In embodiments, $L^{1P}$ is substituted (e.g., substituted with a substituent group, size-limited substituent group, or lower substituent group) or unsubstituted $C_1$-$C_6$ alkylene (e.g., saturated alkylene, alkenylene, or alkynylene).

In embodiments, $L^{1P}$ is substituted (e.g., substituted with a substituent group, size-limited substituent group, or lower substituent group) $C_1$-$C_6$ alkylene (e.g., saturated alkylene, alkenylene, or alkynylene). In embodiments, $L^{1P}$ is unsubstituted $C_1$-$C_6$ alkylene (e.g., saturated alkylene, alkenylene, or alkynylene).

In embodiments, $L^{1P}$ is substituted (e.g., substituted with a substituent group, size-limited substituent group, or lower substituent group) or unsubstituted $C_1$-$C_4$ alkylene (e.g., saturated alkylene, alkenylene, or alkynylene). In embodiments, $L^{1P}$ is substituted (e.g., substituted with a substituent group, size-limited substituent group, or lower substituent group) $C_1$-$C_4$ alkylene (e.g., saturated alkylene, alkenylene, or alkynylene). In embodiments, $L^{1P}$ is unsubstituted $C_1$-$C_4$ alkylene (e.g., saturated alkylene, alkenylene, or alkynylene).

In embodiments, $L^{1P}$ is substituted (e.g., substituted with a substituent group, size-limited substituent group, or lower substituent group) or unsubstituted $C_1$-$C_2$ alkylene (e.g., saturated alkylene, alkenylene, or alkynylene). In embodiments, $L^{1P}$ is substituted (e.g., substituted with a substituent group, size-limited substituent group, or lower substituent group) $C_1$-$C_2$ alkylene (e.g., saturated alkylene, alkenylene, or alkynylene). In embodiments, $L^{1P}$ is —CH$_2$— or —CH$_2$CH$_2$—. In embodiments, $L^{1P}$ is —CH$_2$—. In embodiments, $L^{1P}$ is —CH$_2$CH$_2$—. In embodiments, $L^{1P}$ is —CH=CH—. In embodiments, $L^{1P}$ is substituted methylene. In embodiments, $L^{1P}$ is substituted methylene substituted with $C_1$-$C_4$ haloalkyl or unsubstituted $C_1$-$C_4$ alkyl. In embodiments, $L^{1P}$ is

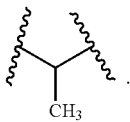

In embodiments, $L^{1P}$ is

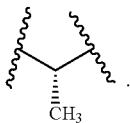

In embodiments, $L^{1P}$ is

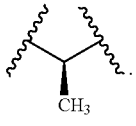

In embodiments, $L^{1P}$ is

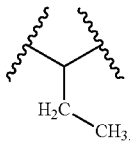

In embodiments, $L^{1P}$ is

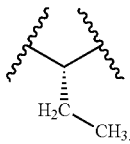

In embodiments, $L^{1P}$ is

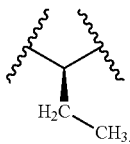

In embodiments, $L^{1P}$ is

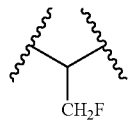

In embodiments, $L^{1P}$ is

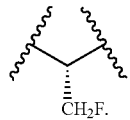

In embodiments, $L^{1P}$ is

In embodiments, $L^{1P}$ is

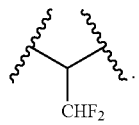

In embodiments, $L^{1P}$ is

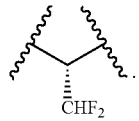

In embodiments, $L^{1P}$ is

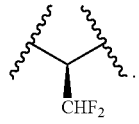

In embodiments, $L^{1P}$ is

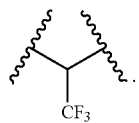

In embodiments, $L^{1P}$ is
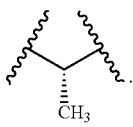
In embodiments, $L^{1P}$ is
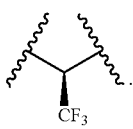
In embodiments, $L^{1P}$ is
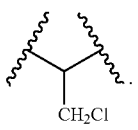
In embodiments, $L^{1P}$ is
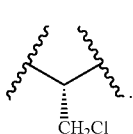
In embodiments, $L^{1P}$ is
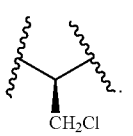
In embodiments, $L^{1P}$ is
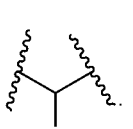
In embodiments, $L^{1P}$ is
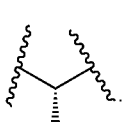
In embodiments, $L^{1P}$ is
In embodiments, $L^{1P}$ is
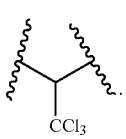
In embodiments, $L^{1P}$ is
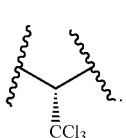
In embodiments, $L^{1P}$ is
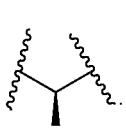
In embodiments, $L^{1P}$ is
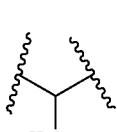
In embodiments, $L^{1P}$ is
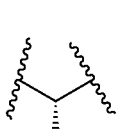
In embodiments, $L^{1P}$ is
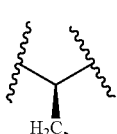

In embodiments, $L^{1P}$ is
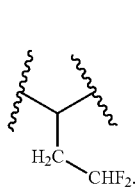
In embodiments, $L^{1P}$ is
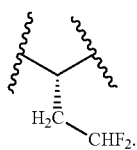
In embodiments, $L^{1P}$ is
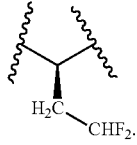
In embodiments, $L^{1P}$ is
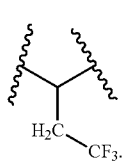
In embodiments, $L^{1P}$ is
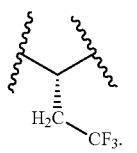
In embodiments, $L^{1P}$ is
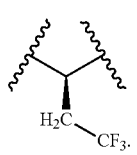
In embodiments, $L^{1P}$ is
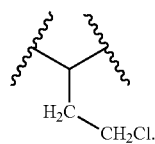
In embodiments, $L^{1P}$ is
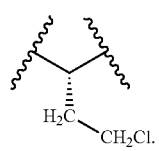
In embodiments, $L^{1P}$ is
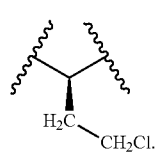
In embodiments, $L^{1P}$ is
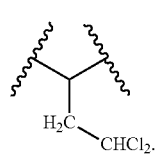
In embodiments, $L^{1P}$ is
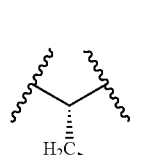
In embodiments, $L^{1P}$ is
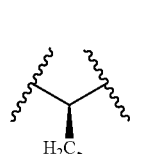
In embodiments, $L^{1P}$ is
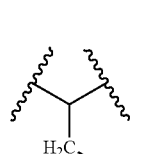

In embodiments, $L^{1P}$ is

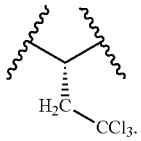

In embodiments, $L^{1P}$ is

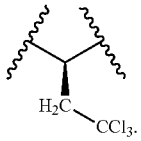

In embodiments, $R^{3P}$ is $—OR^{3AP}$; and $R^{3AP}$ is hydrogen. In embodiments, $R^{3P}$ is $—OR^{3AP}$; and $R^{3AP}$ is a polymerase-compatible cleavable moiety. In embodiments, $R^{3AP}$ is a polymerase-compatible cleavable moiety including an azido moiety. In embodiments, $R^{3AP}$ is a polymerase-compatible cleavable moiety including a dithiol linker. In embodiments, $R^{3AP}$ is $—CH_2N_3$. In embodiments, $R^{3AP}$ is

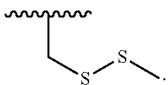

In embodiments, $R^{3AP}$ is

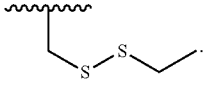 [SMILES: *CSSCC]

In embodiments, $R^{3AP}$ is

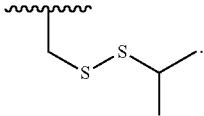 [SMILES: *CSSC(C)C]

In embodiments, $R^{3AP}$ is

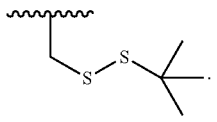 [SMILES: *CSSC(C)(C)C]

In embodiments, $R^{3AP}$ is a polymerase-compatible cleavable moiety comprising an allyl group. In embodiments, $R^{3AP}$ is a polymerase-compatible cleavable moiety comprising a 2-nitrobenzyl group. In embodiments, $R^{3AP}$ is $—NH_2$. In embodiments, $R^{3AP}$ is

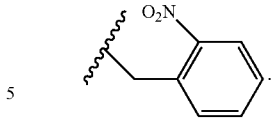

In embodiments, $R^{3AP}$ is

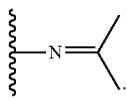

In embodiments, $R^{3AP}$ is

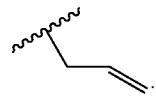 [SMILES: *CC=C]

In embodiments, $R^{3AP}$ is

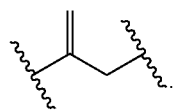

In embodiments, $R^{3AP}$ is $—CH_2—O—CH_3$.

In an aspect is provided a compound having the formula:

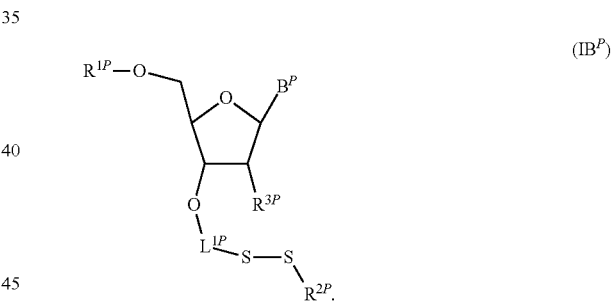

(IB$^P$)

$B^P$ is a nucleobase, which may be optionally substituted. $L^{1P}$ is a covalent linker. $R^{1P}$ is independently hydrogen or 5'-nucleoside protecting group, or $—OR^{1P}$ is a monophosphate, or polyphosphate. $R^{3P}$ is hydrogen or $—OR^{3AP}$. $R^{3AP}$ is hydrogen or a polymerase-compatible cleavable moiety.

$R^{2P}$ is $-L^{2P}-R^{4P}$, $-L^{2P}$-3'-nucleoside, $-L^{2P}$-3'-nucleotide, or $-L^{2P}$-3'-nucleic acid. $L^{2P}$ is a bond, $—NN—$, $—NHC(O)—$, $—C(O)NH—$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{4P}$ is substituted or unsubstituted alkyl.

$R^{2P}$ is $-L^{2P}-R^{4P}$, $-L^{2P}$-3'-nucleoside, $-L^{2P}$-3'-nucleotide, or $-L^{2P}$-3'-nucleic acid. In embodiments, $L^{2P}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{4P}$ is substituted or unsubstituted alkyl.

$R^{2P}$ is $-L^{2P}-R^{4P}$, $-L^{2P}-3'$-nucleoside, $-L^{2P}-3'$-nucleotide, or $-L^{2P}-3'$-nucleic acid. In embodiments, $L^{2P}$ is a bond, substituted or unsubstituted $C_1$-$C_4$ alkylene. In embodiments, $R^{4P}$ is substituted or unsubstituted $C_1$-$C_6$ alkyl.

In embodiments, $R^{2P}$ includes a protecting group. In embodiments, $R^{2P}$ is $-L^{2P}$-protecting group. In embodiments, $R^{2P}$ is $-L^{2P}-R^{4P}$, $-L^{2P}-3'$-nucleoside, $-L^{2P}-3'$-nucleotide, or $-L^{2P}-3'$-nucleic acid. In embodiments, $R^{4P}$ is substituted or unsubstituted $C_1$-$C_6$ alkyl.

In embodiments, the compound has the formula:

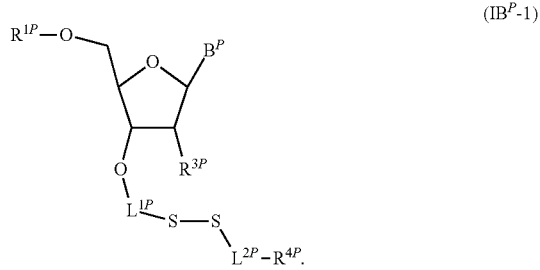

(IB$^P$-1)

In embodiments, $L^{2P}$ is a bond. In embodiments, $L^{2P}$ is $L^{2AP}-L^{2BP}-L^{2CP}-L^{2DP}-L^{2EP}$; and $L^{2AP}$, $L^{2BP}$, $L^{2CP}$, $L^{2DP}$, and $L^{2EP}$ are independently a bond, —NN—, —NHC(O)—, —C(O)NH—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered); wherein at least one of $L^{2AP}$, $L^{2BP}$, $L^{2CP}$, $L^{2DP}$, and $L^{2EP}$ is not a bond.

In embodiments, $L^{2P}$ is a bond. In embodiments, $L^{2P}$ is $L^{2AP}-L^{2BP}-L^{2CP}-L^{2DP}-L^{2EP}$; and $L^{2AP}$, $L^{2BP}$, $L^{2CP}$, $L^{2DP}$, and $L^{2EP}$ are independently a bond, —NN—, —NHC(O)—, —C(O)NH—, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2AP}$, $L^{2BP}$, $L^{2CP}$, $L^{2DP}$, and $L^{2EP}$ is not a bond.

In embodiments, a substituted $L^{2AP}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2AP}$ is substituted with a plurality of groups selected from substituent groups, size-limited substituent groups, and lower substituent groups; each substituent group, size-limited substituent group, and/or lower substituent group may optionally be different. In embodiments, when $L^{2AP}$ is substituted, it is substituted with at least one substituent group. In embodiments, when $L^{2AP}$ is substituted, it is substituted with at least one size-limited substituent group. In embodiments, when $L^{2AP}$ is substituted, it is substituted with at least one lower substituent group. In embodiments, when $L^{2AP}$ is substituted, it is substituted with 1 to 10 substituent groups. In embodiments, when $L^{2AP}$ is substituted, it is substituted with 1 to 10 size-limited substituent groups. In embodiments, when $L^{2AP}$ is substituted, it is substituted with 1 to 10 lower substituent groups. In embodiments, when $L^{2AP}$ is substituted, it is substituted with 1 to 5 substituent groups. In embodiments, when $L^{2AP}$ is substituted, it is substituted with 1 to 5 size-limited substituent groups. In embodiments, when $L^{2AP}$ is substituted, it is substituted with 1 to 5 lower substituent groups. In embodiments, when $L^{2AP}$ is substituted, it is substituted with a substituent group. In embodiments, when $L^{2AP}$ is substituted, it is substituted with a size-limited substituent group. In embodiments, when $L^{2AP}$ is substituted, it is substituted with a lower substituent group.

In embodiments, a substituted $L^{2BP}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2BP}$ is substituted with a plurality of groups selected from substituent groups, size-limited substituent groups, and lower substituent groups; each substituent group, size-limited substituent group, and/or lower substituent group may optionally be different. In embodiments, when $L^{2BP}$ is substituted, it is substituted with at least one substituent group. In embodiments, when $L^{2BP}$ is substituted, it is substituted with at least one size-limited substituent group. In embodiments, when $L^{2BP}$ is substituted, it is substituted with at least one lower substituent group. In embodiments, when $L^{2BP}$ is substituted, it is substituted with 1 to 10 substituent groups. In embodiments, when $L^{2BP}$ is substituted, it is substituted with 1 to 10 size-limited substituent groups. In embodiments, when $L^{2BP}$ is substituted, it is substituted with 1 to 10 lower substituent groups. In embodiments, when $L^{2BP}$ is substituted, it is substituted with 1 to 5 substituent groups. In embodiments, when $L^{2BP}$ is substituted, it is substituted with 1 to 5 size-limited substituent groups. In embodiments, when $L^{2BP}$ is substituted, it is substituted with 1 to 5 lower substituent groups. In embodiments, when $L^{2BP}$ is substituted, it is substituted with a substituent group. In embodiments, when $L^{2BP}$ is substituted, it is substituted with a size-limited substituent group. In embodiments, when $L^{2BP}$ is substituted, it is substituted with a lower substituent group.

In embodiments, a substituted $L^{2CP}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2CP}$ is substituted with a plurality of groups selected from substituent groups, size-limited substituent groups, and lower substituent groups; each substituent group, size-limited substituent group, and/or lower substituent group may optionally be different. In embodiments, when $L^{2CP}$ is substituted, it is substituted with at least one substituent group. In embodiments, when $L^{2CP}$ is substituted, it is substituted with at least one size-limited substituent group. In embodiments, when $L^{2CP}$ is substituted, it is substituted with at least one lower substituent group. In embodiments, when $L^{2CP}$ is substituted, it is substituted with 1 to 10 substituent groups. In embodiments, when $L^{2CP}$ is substituted, it is substituted with 1 to 10 size-limited substituent groups. In embodiments, when $L^{2CP}$ is substituted, it is substituted with 1 to 10 lower substituent groups. In embodiments, when $L^{2CP}$ is substituted, it is substituted with 1 to 5 substituent groups. In embodiments, when $L^{2CP}$ is substituted, it is substituted with 1 to 5 size-limited substituent groups. In embodiments, when $L^{2CP}$ is substituted, it is substituted with 1 to 5 lower substituent groups. In embodiments, when $L^{2CP}$ is substituted, it is substituted with a substituent group. In embodiments, when $L^{2CP}$ is substituted, it is substituted with a size-limited substituent group. In embodiments, when $L^{2CP}$ is substituted, it is substituted with a lower substituent group.

In embodiments, a substituted $L^{2DP}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2DP}$ is substituted with a plurality of groups selected from substituent groups, size-limited substituent groups, and lower substituent groups; each substituent group, size-limited substituent group, and/or lower substituent group may optionally be different. In embodiments, when $L^{2DP}$ is substituted, it is substituted with at least one substituent group. In embodiments, when $L^{2DP}$ is substituted, it is substituted with at least one size-limited substituent group. In embodiments, when $L^{2DP}$ is substituted, it is substituted with at least one lower substituent group. In embodiments, when $L^{2DP}$ is substituted, it is substituted with 1 to 10 substituent groups. In embodiments, when $L^{2DP}$ is substituted, it is substituted with 1 to 10 size-limited substituent groups. In embodiments, when $L^{2DP}$ is substituted, it is substituted with 1 to 10 lower substituent groups. In embodiments, when $L^{2DP}$ is substituted, it is substituted with 1 to 5 substituent groups. In embodiments, when $L^{2DP}$ is substituted, it is substituted with 1 to 5 size-limited substituent groups. In embodiments, when $L^{2D}P$ is substituted, it is substituted with 1 to 5 lower substituent groups. In embodiments, when $L^{2DP}$ is substituted, it is substituted with a substituent group. In embodiments, when $L^{2DP}$ is substituted, it is substituted with a size-limited substituent group. In embodiments, when $L^{2DP}$ is substituted, it is substituted with a lower substituent group.

In embodiments, a substituted $L^{2EP}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2EP}$ is substituted with a plurality of groups selected from substituent groups, size-limited substituent groups, and lower substituent groups; each substituent group, size-limited substituent group, and/or lower substituent group may optionally be different. In embodiments, when $L^{2EP}$ is substituted, it is substituted with at least one substituent group. In embodiments, when $L^{2EP}$ is substituted, it is substituted with at least one size-limited substituent group. In embodiments, when $L^{2EP}$ is substituted, it is substituted with at least one lower substituent group. In embodiments, when $L^{2EP}$ is substituted, it is substituted with 1 to 10 substituent groups. In embodiments, when $L^{2EP}$ is substituted, it is substituted with 1 to 10 size-limited substituent groups. In embodiments, when $L^{2EP}$ is substituted, it is substituted with 1 to 10 lower substituent groups. In embodiments, when $L^{2EP}$ is substituted, it is substituted with 1 to 5 substituent groups. In embodiments, when $L^{2EP}$ is substituted, it is substituted with 1 to 5 size-limited substituent groups. In embodiments, when $L^{2EP}$ is substituted, it is substituted with 1 to 5 lower substituent groups. In embodiments, when $L^{2EP}$ is substituted, it is substituted with a substituent group. In embodiments, when $L^{2EP}$ is substituted, it is substituted with a size-limited substituent group. In embodiments, when $L^{2EP}$ is substituted, it is substituted with a lower substituent group.

In embodiments, $L^{2P}$ is $L^{2AP}$-$L^{2BP}$-$L^{2CP}$-$L^{2DP}$-$L^{2EP}$; and $L^{2AP}$, $L^{2BP}$, $L^{2CP}$, $L^{2DP}$ and $L^{2EP}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., saturated alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{2AP}$, $L^{2BP}$, $L^{2CP}$, $L^{2DP}$, and $L^{2EP}$ is not a bond.

In embodiments, $L^{2P}$ is $L^{2AP}$-$L^{2BP}$-$L^{2CP}$-$L^{2DP}$-$L^{2EP}$; and $L^{2AP}$, $L^{2BP}$, $L^{2CP}$, $L^{2DP}$ and $L^{2EP}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., saturated alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{2AP}$, $L^{2BP}$, $L^{2CP}$, $L^{2DP}$, and $L^{2EP}$ is not a bond.

In embodiments, $L^{2P}$ is $L^{2AP}$-$L^{2BP}$-$L^{2CP}$-$L^{2DP}$-$L^{2EP}$; and $L^{2AP}$, $L^{2BP}$, $L^{2CP}$, $L^{2DP}$ and $L^{2EP}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., saturated alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{2AP}$, $L^{2BP}$, $L^{2CP}$, $L^{2DP}$, and $L^{2EP}$ is not a bond.

In embodiments, $L^{2P}$ is $L^{2AP}$-$L^{2BP}$-$L^{2CP}$-$L^{2DP}$-$L^{2EP}$; $L^{2AP}$ is a bond, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene). $L^{2BP}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2CP}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2DP}$ is a bond, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{2EP}$ is a bond, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2AP}$, $L^{2BP}$, $L^{2CP}$, $L^{2DP}$, and $L^{2EP}$ is not a bond.

In embodiments, $L^{2P}$ is a bond, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^{2P}$ is a bond, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene. In embodiments, $L^{2P}$ is a bond, substituted (e.g., substituted with a substituent group, size-limited substituent group, or lower substituent group) or unsubstituted $C_1$-$C_{20}$alkylene (e.g., saturated alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene. In embodiments, $L^{2P}$ is a bond, substituted (e.g., substituted with a substituent group, size-limited substituent group, or lower substituent group) or unsubstituted $C_1$-$C_8$ alkylene (e.g., saturated alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene. In embodiments, $L^{2P}$ is a bond, substituted (e.g., substituted with a substituent group, size-limited substituent group, or lower substituent group) or unsubstituted $C_1$-$C_6$ alkylene (e.g., saturated alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, a substituted $L^{2P}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2P}$ is substituted with a plurality of groups selected from substituent groups, size-limited substituent groups, and lower substituent groups; each substituent group, size-limited substituent group, and/or lower substituent group may optionally be different. In embodiments, when $L^{2P}$ is substituted, it is substituted with at least one substituent group. In embodiments, when $L^{2P}$ is substituted, it is substituted with at least one size-limited substituent group. In embodiments, when $L^{2P}$ is substituted, it is substituted with at least one lower substituent group. In embodiments, when $L^{2P}$ is substituted, it is substituted with 1 to 10 substituent groups. In embodiments, when $L^{2P}$ is substituted, it is substituted with 1 to 10 size-limited substituent groups. In embodiments, when $L^{2P}$ is substituted, it is substituted with 1 to 10 lower substituent groups. In embodiments, when $L^{2P}$ is substituted, it is substituted with 1 to 5 substituent groups. In embodiments, when $L^{2P}$ is substituted, it is substituted with 1 to 5 size-limited substituent groups. In embodiments, when $L^{2P}$ is substituted, it is substituted with 1 to 5 lower substituent groups. In embodiments, when $L^{2P}$ is substituted, it is substituted with a substituent group. In embodiments, when $L^{2P}$ is substituted, it is substituted with a size-limited substituent group. In embodiments, when $L^{2P}$ is substituted, it is substituted with a lower substituent group.

In embodiments, $L^{2P}$ is a substituted (e.g., substituted with a substituent group, size-limited substituent group, or lower substituent group) or unsubstituted $C_1$-$C_8$ alkylene (e.g., saturated alkylene, alkenylene, or alkynylene). In embodiments, $L^{2P}$ is a substituted (e.g., substituted with a substituent group, size-limited substituent group, or lower substituent group) or unsubstituted $C_1$-$C_6$ alkylene (e.g., saturated alkylene, alkenylene, or alkynylene). In embodiments, $L^{2P}$ is a substituted (e.g., substituted with a substituent group, size-limited substituent group, or lower substituent group) or unsubstituted $C_1$-$C_3$ alkylene (e.g., saturated alkylene, alkenylene, or alkynylene).

In embodiments, $L^{2P}$ is a bond, substituted or unsubstituted $C_1$-$C_4$ alkylene.

In embodiments, $L^{2P}$ is unsubstituted $C_1$-$C_8$ alkylene (e.g., saturated alkylene, alkenylene, or alkynylene). In embodiments, $L^{2P}$ is unsubstituted $C_1$-$C_6$ alkylene (e.g., saturated alkylene, alkenylene, or alkynylene). In embodiments, $L^{2P}$ is unsubstituted $C_1$-$C_3$ saturated alkylene. In embodiments, $L^{2P}$ is —$CH_2$— or —$CH_2CH_2$—. In embodiments, $L^{2P}$ is —$CH_2$—. In embodiments, $L^{2P}$ is —$CH_2CH_2$—.

In embodiments, $R^{4P}$ is substituted or unsubstituted alkyl (e.g., $C_1$-$C_6$, $C_1$-$C_4$, or $C_1$-$C_2$). In embodiments, $R^{4P}$ is substituted (e.g., substituted with a substituent group, size-limited substituent group, or lower substituent group) or unsubstituted alkyl (e.g., $C_1$-$C_6$, $C_1$-$C_4$, or $C_1$-$C_2$). In embodiments, $R^{4P}$ is substituted (e.g., substituted with a substituent group, size-limited substituent group, or lower substituent group) or unsubstituted $C_1$-$C_6$ alkyl. In embodiments, $R^{4P}$ is a substituted (e.g., substituted with a substituent group, size-limited substituent group, or lower substituent group) or unsubstituted neopentyl

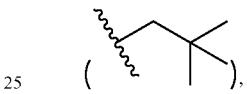

or thexyl

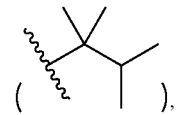

In embodiments, $R^{4P}$ is substituted (e.g., substituted with a substituent group, size-limited substituent group, or lower substituent group) or unsubstituted $C_1$-$C_4$ alkyl. In embodiments, $R^{4P}$ is substituted (e.g., substituted with a substituent group, size-limited substituent group, or lower substituent group) or unsubstituted methyl, or ethyl. In embodiments, $R^{4P}$ is substituted or unsubstituted $C_1$-$C_6$ alkyl. In embodiments, $R^{4P}$ is unsubstituted $C_1$-$C_4$ alkyl. In embodiments, $R^{4P}$ is unsubstituted methyl, or unsubstituted ethyl. In embodiments, $R^{4P}$ is —$CH_3$. In embodiments, $R^{4P}$ is —$CH_2CH_3$. In embodiments, $R^{4P}$ is unsubstituted $C_3$ alkyl. In embodiments, $R^{4P}$ is unsubstituted $C_4$ alkyl. In embodiments, $R^{4P}$ is unsubstituted $C_5$ alkyl. In embodiments, $R^{4P}$ is unsubstituted $C_6$ alkyl. In embodiments, $R^{4P}$ is unsubstituted t-butyl. In embodiments, $R^{4P}$ is unsubstituted neopentyl. In embodiments, $R^{4P}$ is unsubstituted thexyl.

In embodiments, a substituted $R^{4P}$ (e.g., substituted alkyl) is substituted with at least one substituent group, size-limited substituent group, or lower substituent group; wherein if the substituted $R^{4P}$ is substituted with a plurality of groups selected from substituent groups, size-limited substituent groups, and lower substituent groups; each substituent group, size-limited substituent group, and/or lower substituent group may optionally be different. In embodiments, when $R^{4P}$ is substituted, it is substituted with at least one substituent group. In embodiments, when $R^{4P}$ is substituted, it is substituted with at least one size-limited substituent group. In embodiments, when $R^{4P}$ is substituted, it is substituted with at least one lower substituent group. In embodiments, when $R^{4P}$ is substituted, it is substituted with 1 to 10 substituent groups. In embodiments, when $R^{4P}$ is substituted, it is substituted with 1 to 10 size-limited substituent groups. In embodiments, when $R^{4P}$ is substituted, it is substituted with 1 to 10 lower substituent groups. In embodiments, when $R^{4P}$ is substituted, it is substituted with 1 to 5 substituent groups. In embodiments, when $R^{4P}$ is substituted, it is substituted with 1 to 5 size-limited substituent groups. In embodiments, when $R^{4P}$ is substituted, it is substituted with 1 to 5 lower substituent groups. In embodiments, when $R^{4P}$ is substituted, it is substituted with a substituent group. In embodiments, when $R^{4P}$ is substituted, it is substituted with a size-limited substituent group. In embodiments, when $R^{4P}$ is substituted, it is substituted with a lower substituent group.

In embodiments, $L^{2P}$ is a bond and $R^{2P}$ is a protecting group. In embodiments, the protecting group in $R^{2P}$ may be stable under the treatment with concentrated ammonium hydroxide. In embodiments, a moiety of —S—S—$R^2$ in formula $IB^P$ may be stable under the treatment with concentrated ammonium hydroxide. In embodiments, a moiety of -$L^{1P}$-S—S—$R^{2P}$ at 3'OH of nucleotide in formula $IB^P$ may be stable under the treatment with concentrated ammonium hydroxide.

In embodiments, $L^{2P}$ is a bond and $R^{4P}$ is —C(CH$_3$)$_3$. In embodiments, $L^{2P}$ is a bond and $R^{4P}$ is unsubstituted propyl. In embodiments, $L^{2P}$ is a bond and $R^{4P}$ is unsubstituted isopropyl. In embodiments, $L^{2P}$ is a bond and $R^{4P}$ is unsubstituted butyl. In embodiments, $L^{2P}$ is a bond and $R^{4P}$ is unsubstituted t-butyl. In embodiments, $L^{2P}$ is a bond and $R^{4P}$ is unsubstituted t-pentyl. In embodiments, $L^{2P}$ is a bond and $R^{4P}$ is unsubstituted neopentyl. In embodiments, $L^{2P}$ is a bond and $R^{4P}$ is unsubstituted hexyl. In embodiments, $L^{2P}$ is a bond and $R^{4P}$ is unsubstituted thexyl. In embodiments, $L^{2P}$ is unsubstituted methylene and $R^{4P}$ is —C(CH$_3$)$_3$. In embodiments, $L^{2P}$ is unsubstituted methylene and $R^{4P}$ is unsubstituted propyl. In embodiments, $L^{2P}$ is unsubstituted methylene and $R^{4P}$ is unsubstituted isopropyl. In embodiments, $L^{2P}$ is unsubstituted methylene and $R^{4P}$ is unsubstituted butyl. In embodiments, $L^{2P}$ is unsubstituted methylene and $R^{4P}$ is unsubstituted t-butyl.

In embodiments, $L^{2P}$ is a bond and $R^{4P}$ is —C(CH$_3$)$_3$. In embodiments, $L^{2P}$ is a bond and $R^{4P}$ is propyl. In embodiments, $L^{2P}$ is a bond and $R^{4P}$ is isopropyl. In embodiments, $L^{2P}$ is a bond and $R^{4P}$ is butyl. In embodiments, $L^{2P}$ is a bond and $R^{4P}$ is t-butyl. In embodiments, $L^{2P}$ is a bond and $R^{4P}$ is t-pentyl. In embodiments, $L^{2P}$ is a bond and $R^{4P}$ is neopentyl. In embodiments, $L^{2P}$ is a bond and $R^{4P}$ is hexyl. In embodiments, $L^{2P}$ is a bond and $R^{4P}$ is thexyl. In embodiments, $L^{2P}$ is unsubstituted methylene and $R^{4P}$ is —C(CH$_3$)$_3$. In embodiments, $L^{2P}$ is unsubstituted methylene and $R^{4P}$ is propyl. In embodiments, $L^{2P}$ is unsubstituted methylene and $R^{4P}$ is isopropyl. In embodiments, $L^{2P}$ is unsubstituted methylene and $R^{4P}$ is butyl. In embodiments, $L^{2P}$ is unsubstituted methylene and $R^{4P}$ is t-butyl. In embodiments, $L^{2P}$ is unsubstituted methylene and $R^{4P}$ is unsubstituted methyl.

In embodiments, a moiety of —S—S—$R^{2P}$ in formula $IB^P$ may be stable under the treatment with concentrated ammonium hydroxide. In embodiments, a moiety of -$L^{1P}$-S—S—$R^{2P}$ at 3'OH of nucleotide in formula $IB^P$ may be stable under the treatment with concentrated ammonium hydroxide.

In embodiments, $L^{2P}$ is substituted methylene and $R^{2P}$ is a protecting group. In embodiments, the protecting group in $R^{2P}$ may be stable under the treatment with concentrated ammonium hydroxide. In embodiments, a moiety of —S—S—$R^{2P}$ in formula $IB^P$ may be stable under the treatment with concentrated ammonium hydroxide. In embodiments, a moiety of -$L^{1P}$-S—S—$R^{2P}$ at 3'OH of nucleotide in formula $IB^P$ may be stable under the treatment with concentrated ammonium hydroxide. In embodiments, $L^{2P}$ is unsubstituted methylene and $R^{2P}$ is —C(CH$_3$)$_3$. In embodiments, $L^{2P}$ is substituted methylene and $R^{2P}$ is unsubstituted propyl. In embodiments, $L^{2P}$ is substituted methylene and $R^{2P}$ is unsubstituted isopropyl. In embodiments, $L^{2P}$ is substituted methylene and $R^{2P}$ is unsubstituted butyl.

In embodiments, $L^{2P}$ is substituted methylene and $R^{2P}$ is a protecting group. In embodiments, the protecting group in $R^{2P}$ may be stable under the treatment with concentrated ammonium hydroxide. In embodiments, a moiety of —S—S—$R^{2P}$ in formula $IB^P$ may be stable under the treatment with concentrated ammonium hydroxide. In embodiments, a moiety of -$L^{1P}$-S—S—$R^{2P}$ at 3'OH of nucleotide in formula $IB^P$ may be stable under the treatment with concentrated ammonium hydroxide. In embodiments, $L^{2P}$ is unsubstituted methylene and $R^{2P}$ is —C(CH$_3$)$_3$. In embodiments, $L^{2P}$ is substituted methylene and $R^{2P}$ is propyl. In embodiments, $L^{2P}$ is substituted methylene and $R^{2P}$ is isopropyl. In embodiments, $L^{2P}$ is substituted methylene and $R^{2P}$ is butyl.

In embodiments, $L^{2P}$ is unsubstituted C$_1$-C$_4$ alkylene and $R^{2P}$ is -$L^{2P}$-3'-nucleoside, -$L^{2P}$-3'-nucleotide, or -$L^{2P}$-3'-nucleic acid. In embodiments, $L^{2P}$ is —CH$_2$— or —CH$_2$CH$_2$—; and and $R^{2P}$ is -$L^{2P}$-3'-nucleoside, -$L^{2P}$-3'-nucleotide, or -$L^{2P}$-3'-nucleic acid. In embodiments, $L^{2P}$ is —CH$_2$—; and $R^{2P}$ is -$L^{2P}$-3'-nucleoside, -$L^{2P}$-3'-nucleotide, or -$L^{2P}$-3'-nucleic acid. In embodiments, $L^{2P}$ is —CH$_2$CH$_2$—; and $R^{2P}$ is -$L^{2P}$-3'-nucleoside, -$L^{2P}$-3'-nucleotide, or -$L^{2P}$-3'-nucleic acid.

In embodiments, $R^{2P}$ is

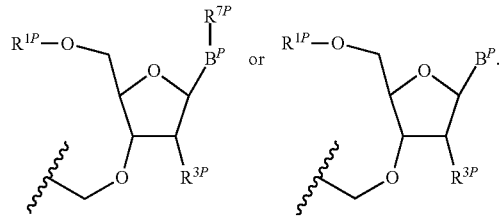

$R^{1P}$, $R^{3P}$, and $B^P$ are independently as described herein. $R^{7P}$ is a moiety including a protecting group. In embodiments, $R^{7P}$ is a propargyl amine moiety, which may be substituted with a protecting group. In embodiments, $R^{7P}$ is a propargyl amine moiety that may be substituted with a protecting group. In embodiments, $R^{7P}$ is

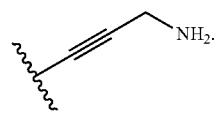 [SMILES: *C#CCN]

In embodiments, $R^{7P}$ is

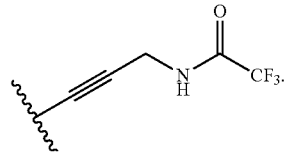 [SMILES: *C#CCNC(=O)C(F)(F)F]

In embodiments, R$^{2P}$ is
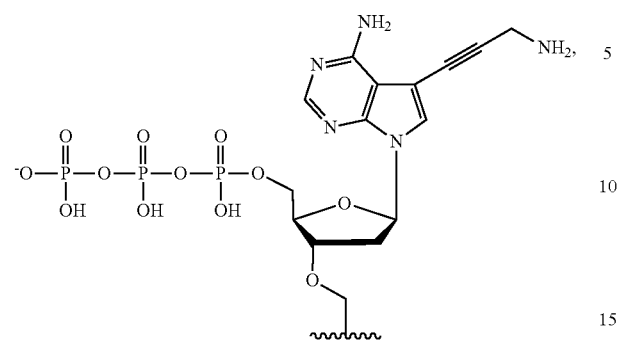
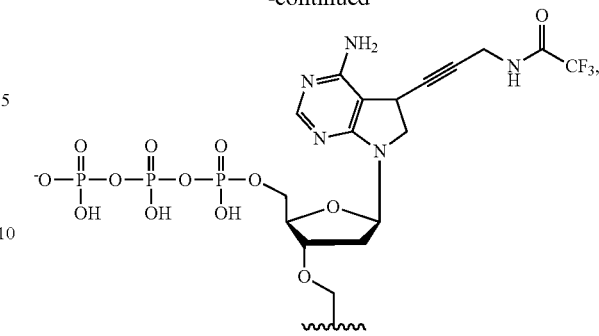
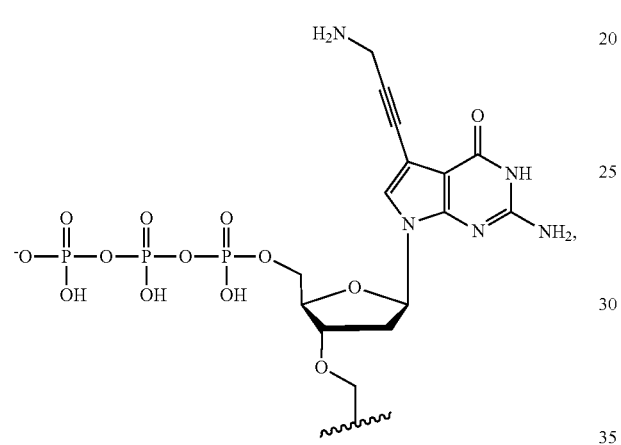
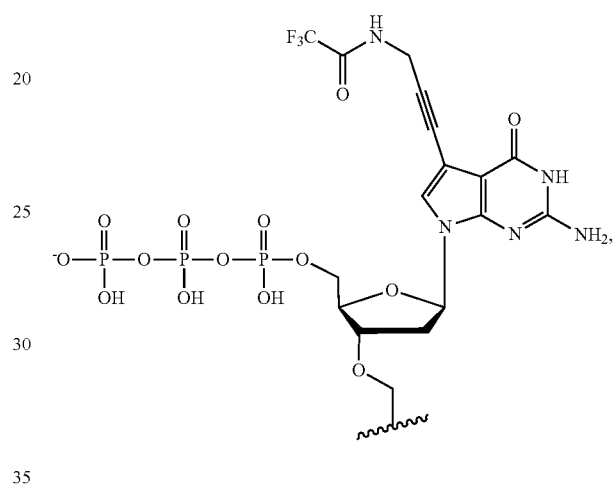
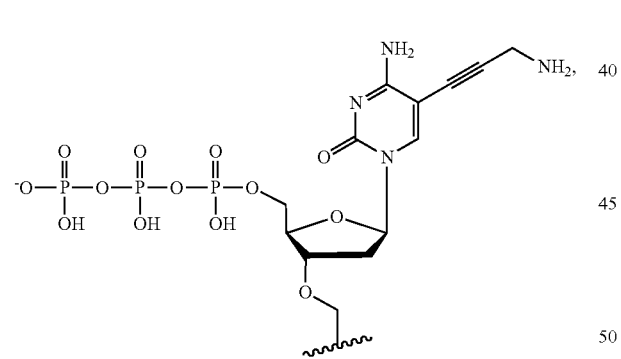
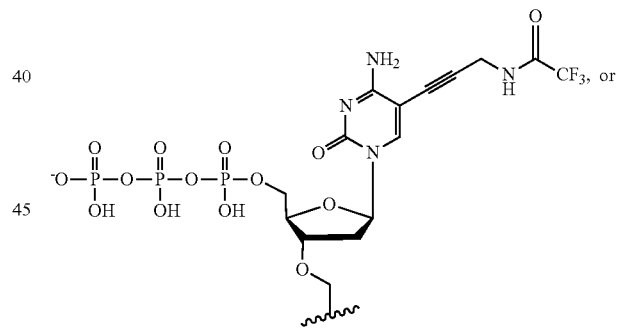
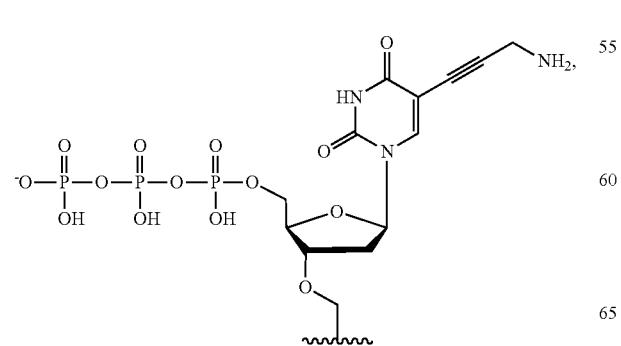
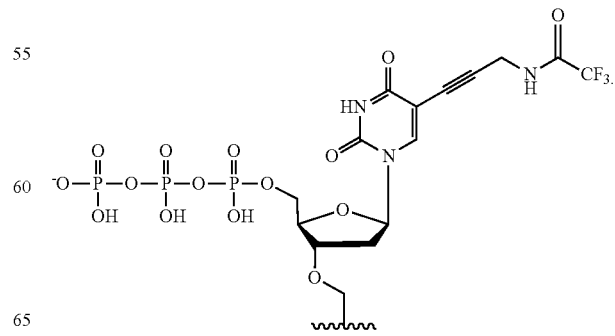

In embodiments, $R^{2P}$ is
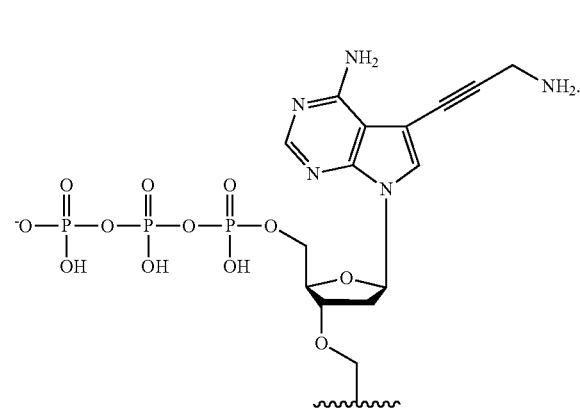
In embodiments, $R^{2P}$ is
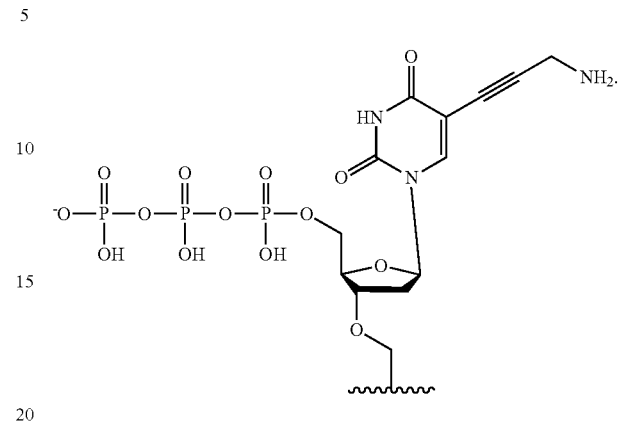
In embodiments, $R^{2P}$ is
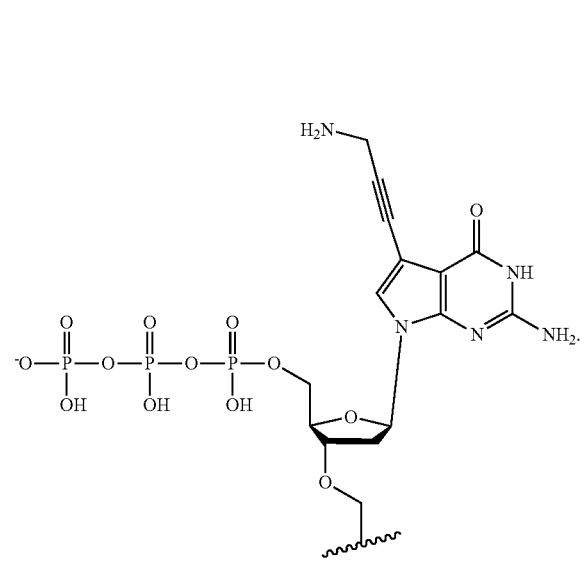
In embodiments, $R^{2P}$ is
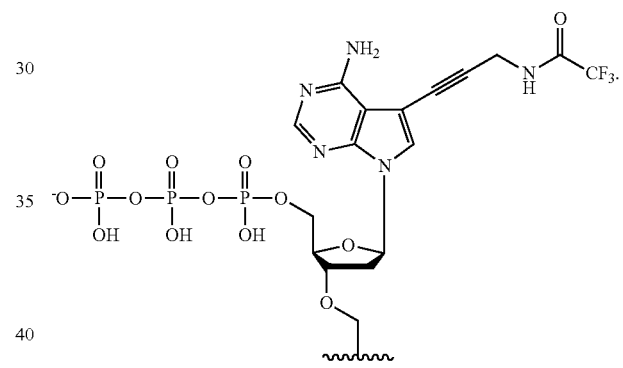
In embodiments, $R^{2P}$ is
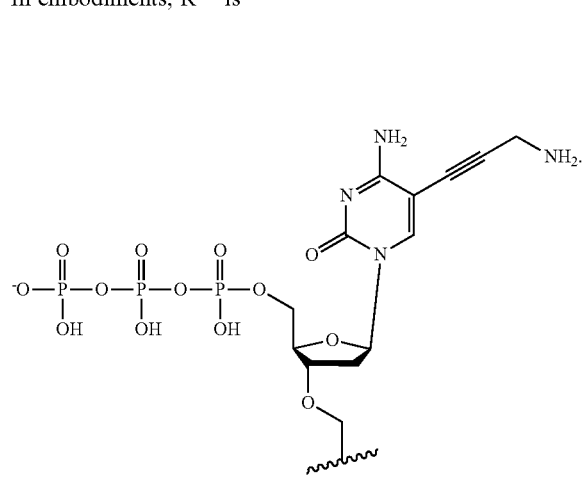
In embodiments, $R^{2P}$ is
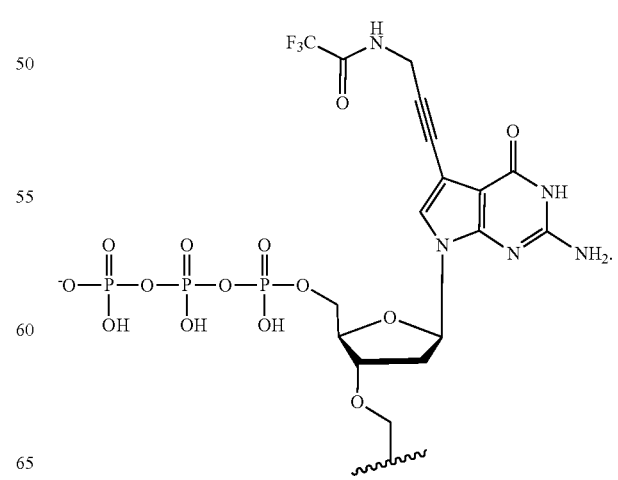

In embodiments, $R^{2P}$ is
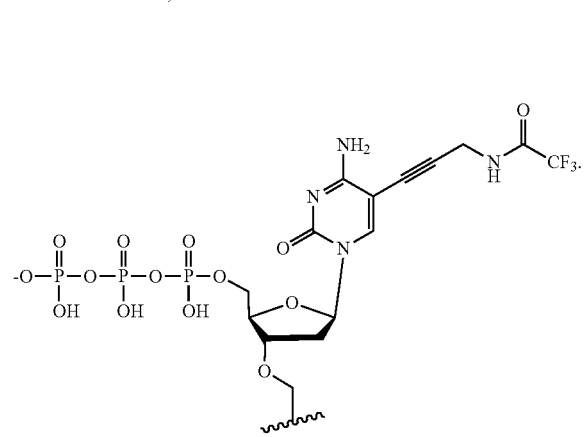
In embodiments, $R^{2P}$ is
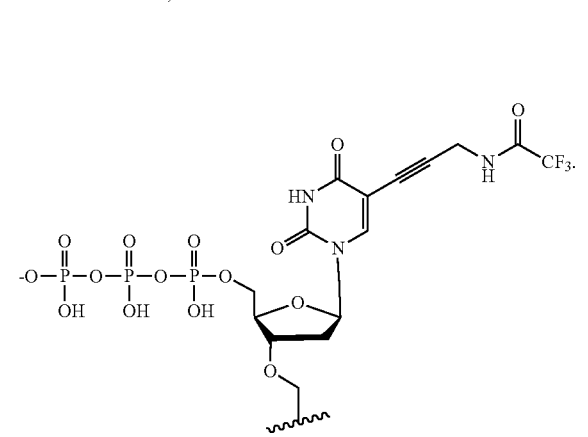
In embodiments, $R^{2P}$ is:
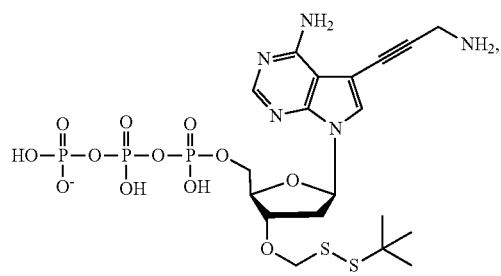
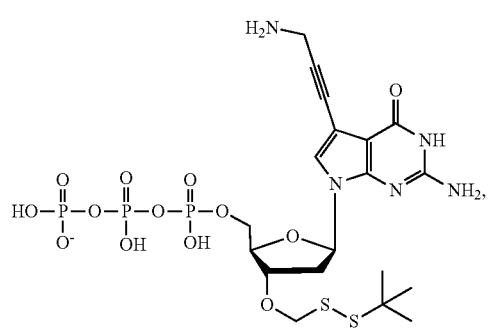
-continued
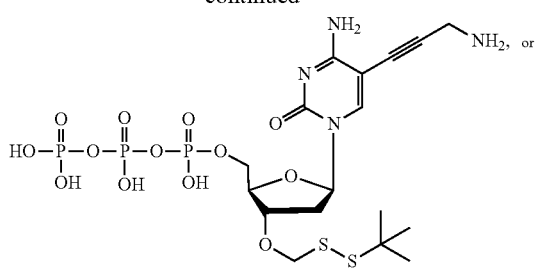
In embodiments, $R^{2P}$ is
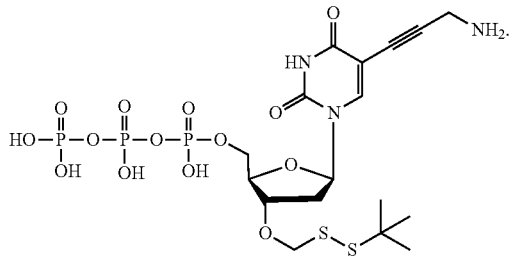
In embodiments, $R^{2P}$ is
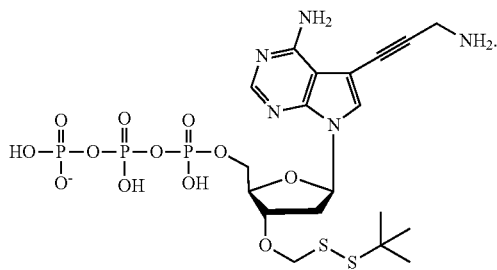 [SMILES: CC(C)(C)SSCO[C@@H]1C[C@H](Cn2cc(C#CCN)c3c(N)ncnc32)O[C@@H]1COP(=O)(O)OP(=O)(O)OP(=O)([O-])O]
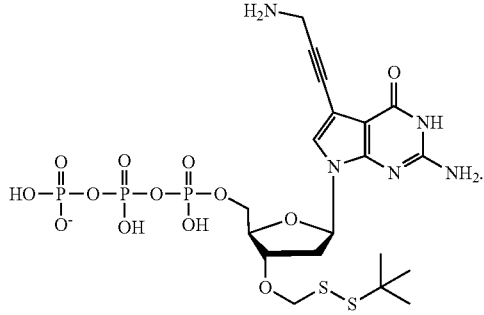 [SMILES: CC(C)(C)SSCO[C@@H]1C[C@H](Cn2cc(C#CCN)c3c(=O)[nH]c(N)nc32)O[C@@H]1COP(=O)(O)OP(=O)(O)OP(=O)([O-])O]

In embodiments, $R^{2P}$ is

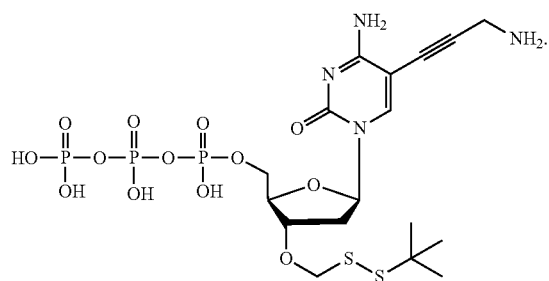 [SMILES: CC(C)(C)SSCO[C@@H]1C[C@H](Cn2cc(C#CCN)c(N)nc2=O)O[C@@H]1COP(=O)(O)OP(=O)(O)OP(=O)(O)O]

In embodiments, $R^{2P}$ is

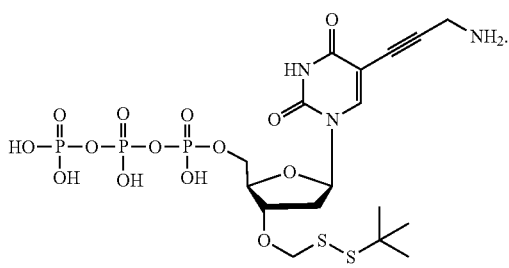 [SMILES: CC(C)(C)SSCO[C@@H]1C[C@H](Cn2cc(C#CCN)c(=O)[nH]c2=O)O[C@@H]1COP(=O)(O)OP(=O)(O)OP(=O)(O)O]

Provided herein is a compound having the formula:

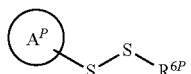

$R^{6P}$ is as described herein.

Ring $A^P$ is substituted (e.g., substituted with a substituent group, size-limited substituent group, or lower substituent group) or unsubstituted heteroaryl (e.g., 5 to 10 membered heteroaryl, 5 to 9 membered heteroaryl, or 5 to 6 membered heteroaryl). In embodiments, Ring $A^P$ is substituted (e.g., substituted with a substituent group, size-limited substituent group, or lower substituent group) heteroaryl (e.g., 5 to 10 membered heteroaryl, 5 to 9 membered heteroaryl, or 5 to 6 membered heteroaryl). In embodiments, Ring $A^P$ is unsubstituted heteroaryl (e.g., 5 to 10 membered heteroaryl, 5 to 9 membered heteroaryl, or 5 to 6 membered heteroaryl).

In embodiments, a substituted Ring $A^P$ (e.g., substituted heteroaryl) is substituted with at least one substituent group, size-limited substituent group, or lower substituent group; wherein if the substituted Ring $A^P$ is substituted with a plurality of groups selected from substituent groups, size-limited substituent groups, and lower substituent groups; each substituent group, size-limited substituent group, and/or lower substituent group may optionally be different. In embodiments, when Ring $A^P$ is substituted, it is substituted with at least one substituent group. In embodiments, when Ring $A^P$ is substituted, it is substituted with at least one size-limited substituent group. In embodiments, when Ring $A^P$ is substituted, it is substituted with at least one lower substituent group. In embodiments, when Ring $A^P$ is substituted, it is substituted with 1 to 10 substituent groups. In embodiments, when Ring $A^P$ is substituted, it is substituted with 1 to 10 size-limited substituent groups. In embodiments, when Ring $A^P$ is substituted, it is substituted with 1 to 10 lower substituent groups. In embodiments, when Ring $A^P$ is substituted, it is substituted with 1 to 5 substituent groups. In embodiments, when Ring $A^P$ is substituted, it is substituted with 1 to 5 size-limited substituent groups. In embodiments, when Ring $A^P$ is substituted, it is substituted with 1 to 5 lower substituent groups. In embodiments, when Ring $A^P$ is substituted, it is substituted with a substituent group. In embodiments, when Ring $A^P$ is substituted, it is substituted with a size-limited substituent group. In embodiments, when Ring $A^P$ is substituted, it is substituted with a lower substituent group.

In embodiments, Ring $A^P$ is substituted (e.g., substituted with a substituent group, size-limited substituent group, or lower substituent group) or unsubstituted 5 to 10 membered heteroaryl. In embodiments, Ring $A^P$ is substituted (e.g., substituted with a substituent group, size-limited substituent group, or lower substituent group) or unsubstituted 5 to 9 membered heteroaryl. In embodiments, Ring $A^P$ is substituted (e.g., substituted with a substituent group, size-limited substituent group, or lower substituent group) or unsubstituted 5 to 6 membered heteroaryl. In embodiments, Ring $A^P$ is substituted (e.g., substituted with a substituent group, size-limited substituent group, or lower substituent group) or unsubstituted 6 membered heteroaryl. In embodiments, Ring $A^P$ is substituted (e.g., substituted with a substituent group, size-limited substituent group, or lower substituent group) or unsubstituted 5 membered heteroaryl. In embodiments, Ring $A^P$ is substituted (e.g., substituted with a substituent group, size-limited substituent group, or lower substituent group) 5 to 10 membered heteroaryl. In embodiments, Ring $A^P$ is substituted (e.g., substituted with a substituent group, size-limited substituent group, or lower substituent group) 5 to 9 membered heteroaryl. In embodiments, Ring $A^P$ is substituted (e.g., substituted with a substituent group, size-limited substituent group, or lower substituent group) 5 to 6 membered heteroaryl. In embodiments, Ring $A^P$ is substituted (e.g., substituted with a substituent group, size-limited substituent group, or lower substituent group) 6 membered heteroaryl. In embodiments, Ring $A^P$ is substituted (e.g., substituted with a substituent group, size-limited substituent group, or lower substituent group) 5 membered heteroaryl. In embodiments, Ring $A^P$ is unsubstituted 5 to 10 membered heteroaryl. In embodiments, Ring $A^P$ is unsubstituted 5 to 9 membered heteroaryl. In embodiments, Ring $A^P$ is substituted unsubstituted 5 to 6 membered heteroaryl. In embodiments, Ring $A^P$ is unsubstituted 6 membered heteroaryl. In embodiments, Ring $A^P$ is unsubstituted 5 membered heteroaryl.

In embodiments, Ring $A^P$ is substituted (e.g., substituted with a substituent group, size-limited substituent group, or lower substituent group) or unsubstituted thienyl. In embodiments, Ring $A^P$ is substituted (e.g., substituted with a substituent group, size-limited substituent group, or lower substituent group) or unsubstituted furanyl. In embodiments, Ring $A^P$ is substituted (e.g., substituted with a substituent group, size-limited substituent group, or lower substituent group) or unsubstituted pyrrolyl. In embodiments, Ring $A^P$ is substituted (e.g., substituted with a substituent group, size-limited substituent group, or lower substituent group) or unsubstituted imidazolyl. In embodiments, Ring $A^P$ is substituted (e.g., substituted with a substituent group, size-limited substituent group, or lower substituent group) or unsubstituted pyrazolyl. In embodiments, Ring $A^P$ is substituted (e.g., substituted with a substituent group, size-limited substituent group, or lower substituent group) or unsubstituted oxazolyl. In embodiments, Ring $A^P$ is substituted (e.g., substituted with a substituent group, size-limited substituent group, or lower substituent group) or unsubstituted isoxazolyl. In embodiments, Ring $A^P$ is substituted (e.g., substituted with a substituent group, size-limited substituent group, or lower substituent group) or unsubstituted pyridinyl. In embodiments, Ring $A^P$ is substituted (e.g., substituted with a substituent group, size-limited substituent group, or lower substituent group) or unsubstituted pyridyl. In embodiments, Ring $A^P$ is substituted (e.g., substituted with a substituent group, size-limited substituent group, or lower substituent group) or unsubstituted pyrazinyl. Ring $A^P$ is substituted (e.g., substituted with a substituent group, size-limited substituent group, or lower substituent group) or unsubstituted pyrimidinyl. In embodiments, Ring $A^P$ is substituted (e.g., substituted with a substituent group, size-limited substituent group, or lower substituent group) or unsubstituted pyridazinyl. In embodiments, Ring $A^P$ is substituted (e.g., substituted with a substituent group, size-limited substituent group, or lower substituent group) or unsubstituted 1,2,3-triazinyl. In embodiments, Ring $A^P$ is substituted (e.g., substituted with a substituent group, size-limited substituent group, or lower substituent group) or unsubstituted 1,2,4-triazinyl. In embodiments, Ring $A^P$ is substituted (e.g., substituted with a substituent group, size-limited substituent group, or lower substituent group) or unsubstituted 1,3,5-triazinyl. In embodiments, Ring $A^P$ is unsubstituted thienyl. In embodiments, Ring $A^P$ is unsubstituted furanyl. In embodiments, Ring $A^P$ is unsubstituted pyrrolyl. In embodiments, Ring $A^P$ is unsubstituted imidazolyl. In embodiments, Ring $A^P$ is unsubstituted pyrazolyl. In embodiments, Ring $A^P$ is unsubstituted oxazolyl. In embodiments, Ring $A^P$ is unsubstituted isoxazolyl. In embodiments, Ring $A^P$ is unsubstituted pyridinyl. In embodiments, Ring $A^P$ is unsubstituted pyridyl. In embodiments, Ring $A^P$ is unsubstituted pyrazinyl. In embodiments, Ring $A^P$ is unsubstituted pyrimidinyl. In embodiments, Ring $A^P$ is unsubstituted pyridazinyl. In embodiments, Ring $A^P$ is unsubstituted 1,2,3-triazinyl. In embodiments, Ring $A^P$ is unsubstituted 1,2,4-triazinyl. In embodiments, Ring $A^P$ is unsubstituted 1,3,5-triazinyl.

In embodiments, Ring $A^P$ is substituted (e.g., substituted with a substituent group, size-limited substituent group, or lower substituent group) or unsubstituted 2-pyridyl. In embodiments, Ring $A^P$ is substituted (e.g., substituted with a substituent group, size-limited substituent group, or lower substituent group) or unsubstituted 3-pyridyl. In embodiments, Ring $A^P$ is substituted (e.g., substituted with a substituent group, size-limited substituent group, or lower substituent group) or unsubstituted 4-pyridyl. In embodiments, Ring $A^P$ is substituted (e.g., substituted with a substituent group, size-limited substituent group, or lower substituent group) 2-pyridyl. In embodiments, Ring $A^P$ is substituted (e.g., substituted with a substituent group, size-limited substituent group, or lower substituent group) 3-pyridyl. In embodiments, Ring $A^P$ is substituted (e.g., substituted with a substituent group, size-limited substituent group, or lower substituent group) 4-pyridyl. In embodiments, Ring $A^P$ is unsubstituted 2-pyridyl. In embodiments, Ring $A^P$ is unsubstituted 3-pyridyl. In embodiments, Ring $A^P$ is unsubstituted 4-pyridyl.

In embodiments, the compound has the formula ($II^P$):

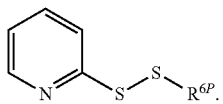

(II$^P$)

$R^{6P}$ is described herein. In embodiments, the compound has the formula ($II^{P'}$):

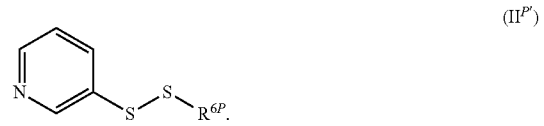

(II$^{P'}$)

In embodiments, the compound has the formula ($II^{P''}$):

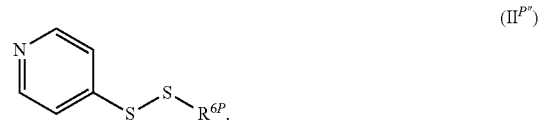

(II$^{P''}$)

In embodiments, the compound of formula IB$^P$ is formed by deprotecting a compound of the formula IA$^P$:

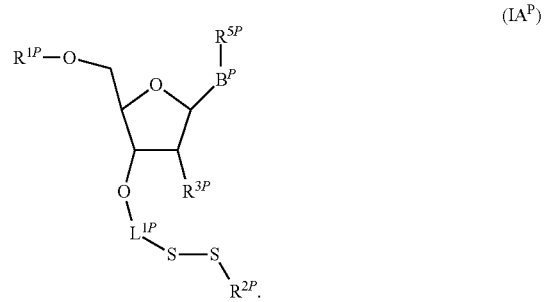

(IA$^P$)

$R^{1P}$, $R^{2P}$, $R^{3P}$, $L^{1P}$ and $B^P$ are described herein. $R^{5P}$ is a moiety including a protecting group.

In embodiments, the deprotecting includes cleaving the protecting group. In embodiments, the deprotecting includes cleaving the protecting group and at least one or more atoms connected to the protecting group.

In embodiments, $R^{5P}$ is a propargyl amine moiety, which may be substituted with a protecting group. In embodiments, $R^{5P}$ is a propargyl amine moiety that may be substituted with a protecting group. In embodiments, $R^{5P}$ is

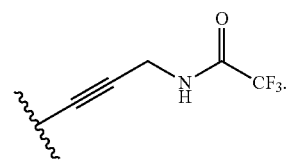 [SMILES: *C#CCNC(=O)C(F)(F)F]

In embodiments, the deprotecting produces

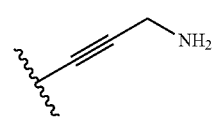

from

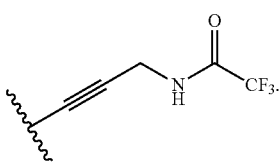 [SMILES: *C#CCNC(=O)C(F)(F)F]

In embodiments, the deprotecting agent may cleave propargyl amine moiety of $R^{5P}$. In embodiments, the deprotecting agent includes $K_2CO_2$ or $Na_2CO_3$. In embodiments, the deprotecting agent includes $K_2CO_2$ or $Na_2CO_3$ in methanol. In embodiments, the deprotecting agent includes $K_2CO_2$ or $Na_2CO_3$ in methanol and water. In embodiments, the deprotecting agent includes LiOH. In embodiments, the deprotecting agent includes LiOH and THF. In embodiments, the deprotecting agent includes LiOH, methanol, in methanol. In embodiments, the deprotecting agent includes LiOH, methanol, in methanol and water. In embodiments, the deprotecting agent includes $NH_3$. In embodiments, the deprotecting agent includes $NH_3$ in methanol.

In embodiments, the deprotecting agent further includes $K_2CO_2$ or $Na_2CO_3$. In embodiments, the deprotecting agent further includes $K_2CO_2$ or $Na_2CO_3$ in methanol. In embodiments, the deprotecting agent further includes $K_2CO_2$ or $Na_2CO_3$ in methanol and water. In embodiments, the deprotecting agent further includes LiOH. In embodiments, the deprotecting agent further includes LiOH and THF. In embodiments, the deprotecting agent further includes LiOH, methanol, in methanol. In embodiments, the deprotecting agent further includes LiOH, methanol, in methanol and water. In embodiments, the deprotecting agent further includes $NH_3$. In embodiments, the deprotecting agent further includes $NH_3$ in methanol. In embodiments, the deprotecting process or the agent thereof is maintained at room temperature.

In embodiments, $R^{5P}$ is a fluorenylmethyloxycarbonyl moiety (FMOC), which may be substituted with a protecting group. In embodiments, the deprotecting agent may cleave FMOC from $R^{5P}$. In embodiments, the deprotecting agent includes piperidine. In embodiments, the deprotecting agent includes morpholine. In embodiments, the compound of formula ($IA^P$) is deprotected by removing FMOC.

In embodiments, the compound of formula $IB^P$ is formed by deprotecting a compound of the formula $IA^P$-1:

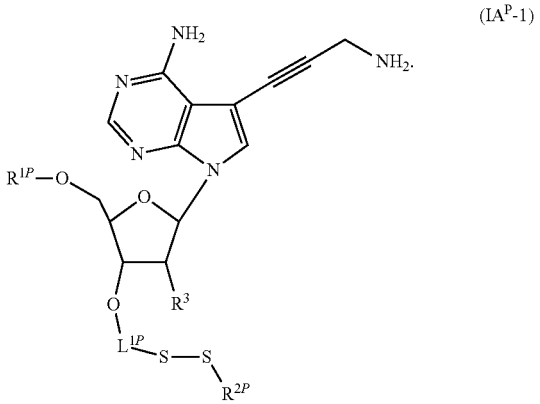

(IA$^P$-1)

In embodiments, the compound of formula $IB^P$ is formed by deprotecting a compound of the formula $IA^P$-2:

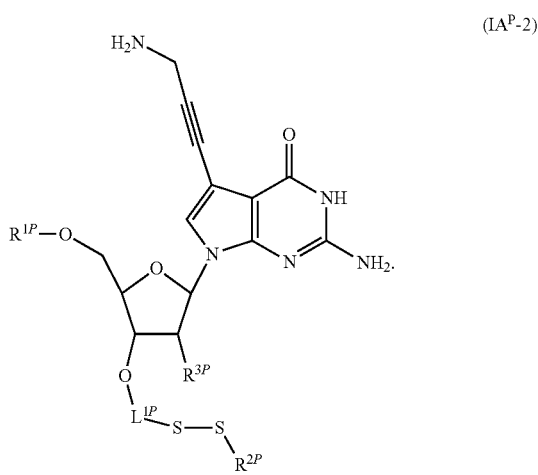

(IA$^P$-2)

In embodiments, the compound of formula $IB^P$ is formed by deprotecting a compound of the formula $IA^P$-3:

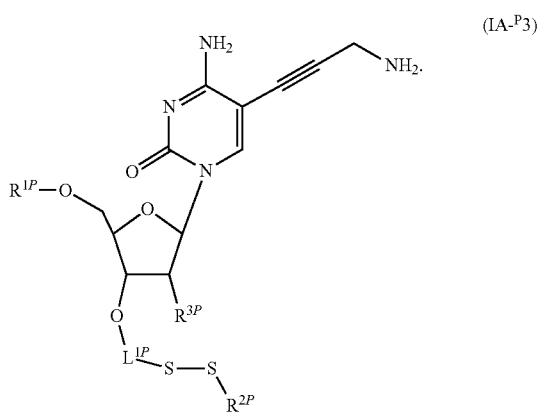

(IA-$^{P3}$)

In embodiments, the compound of formula $IB^P$ is formed by deprotecting a compound of the formula $IA^P$-4:

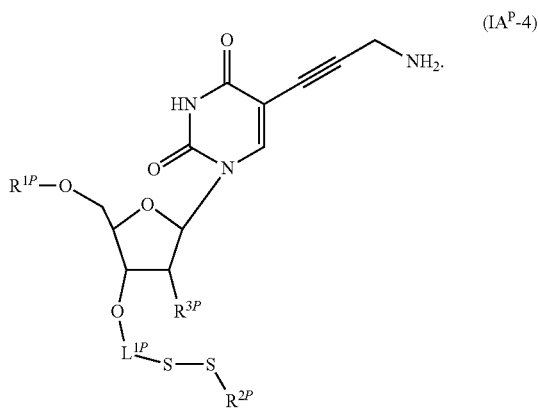

(IA$^P$-4)

In embodiments, the compound of formula IB$^P$ is formed by deprotecting a compound of the formula IA$^P$-5:

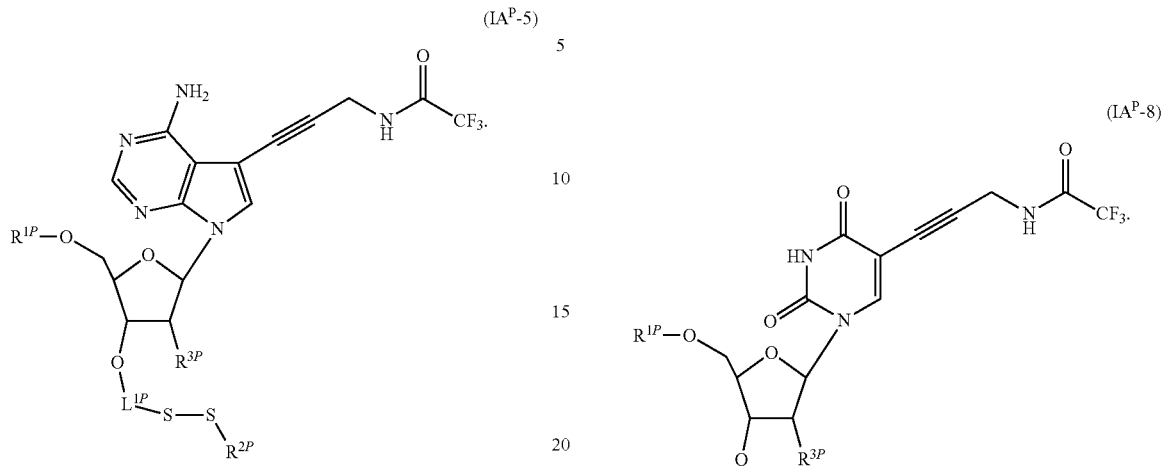

(IA$^P$-5)

In embodiments, the compound of formula IB$^P$ is formed by deprotecting a compound of the formula IA$^P$-6:

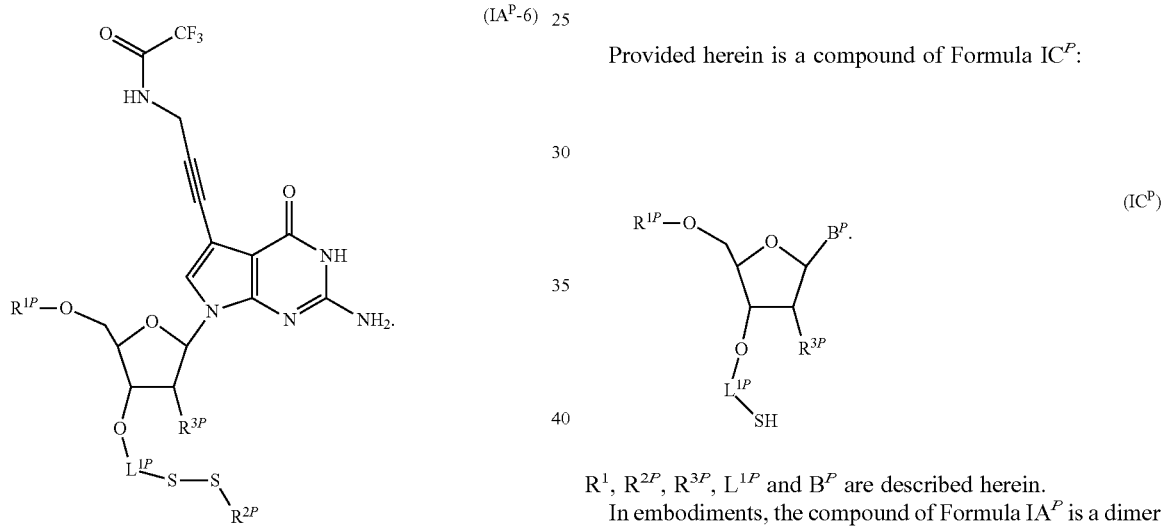

(IA$^P$-6)

In embodiments, the compound of formula IB$^P$ is formed by deprotecting a compound of the formula IA$^P$-7:

(IA$^P$-7)

In embodiments, the compound of formula IB$^P$ is formed by deprotecting a compound of the formula IA$^P$-8:

(IA$^P$-8)

Provided herein is a compound of Formula IC$^P$:

(IC$^P$)

$R^1$, $R^{2P}$, $R^{3P}$, $L^{1P}$ and $B^P$ are described herein.

In embodiments, the compound of Formula IA$^P$ is a dimer of nucleotides. In embodiments, the compound of Formula IA$^P$ is a dimer of nucleosides. In embodiments, the dimer compound of Formula IA$^P$ is not symmetrical. In embodiments, the dimer compound of Formula IA$^P$ is symmetrical. In embodiments, the dimer compound of Formula IA$^P$ is not symmetrical along the disulfanyl bond. In embodiments, the dimer compound of Formula IA$^P$ is symmetrical along the disulfanyl bond.

In embodiments, the compound of Formula IB$^P$ is

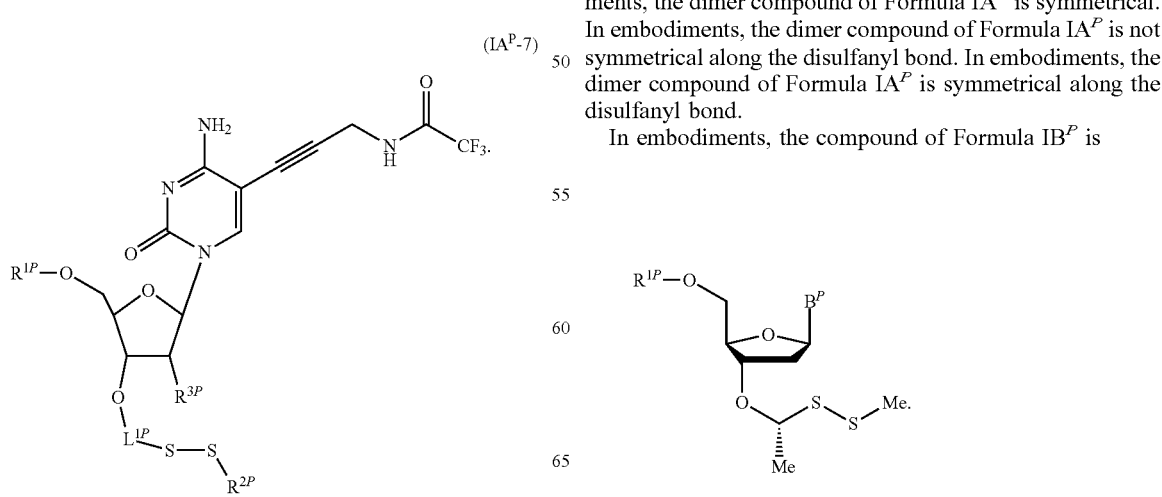

In embodiments, the compound of Formula IB$^F$ is

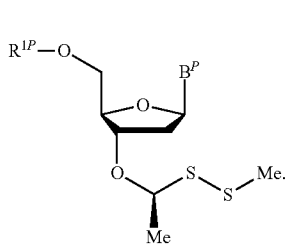

In embodiments, the compound of Formula IB$^P$ is

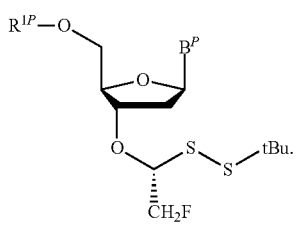

In embodiments, the compound of Formula IB$^P$ is

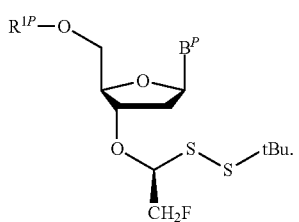

In embodiments, the compound of Formula IB$^P$ is

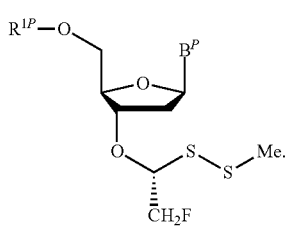

In embodiments, the compound of Formula IB$^P$ is

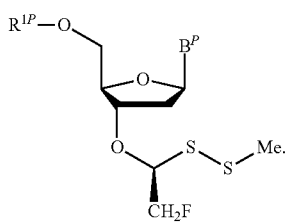

In embodiments, the compound of Formula IB$^P$ is

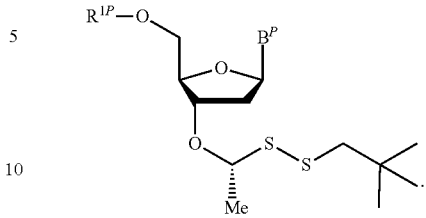

In embodiments, the compound of Formula IB$^P$ is

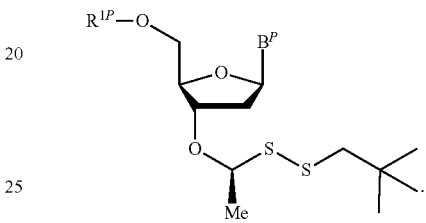

In embodiments, the compound of Formula IB$^P$ is

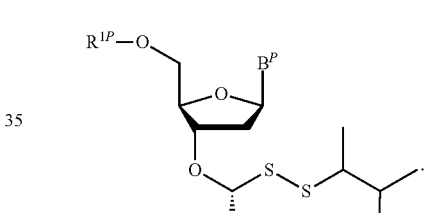

In embodiments, the compound of Formula IB$^P$ is


In embodiments, the compound of Formula IB$^P$ is

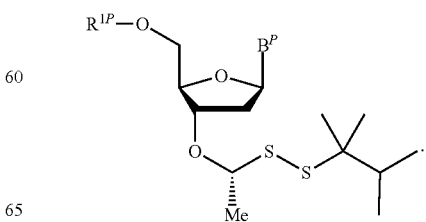

In embodiments, the compound of Formula IB$^P$ is
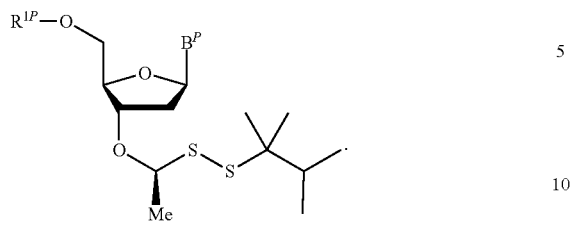
In embodiments, the compound of formula IB$^P$ is:
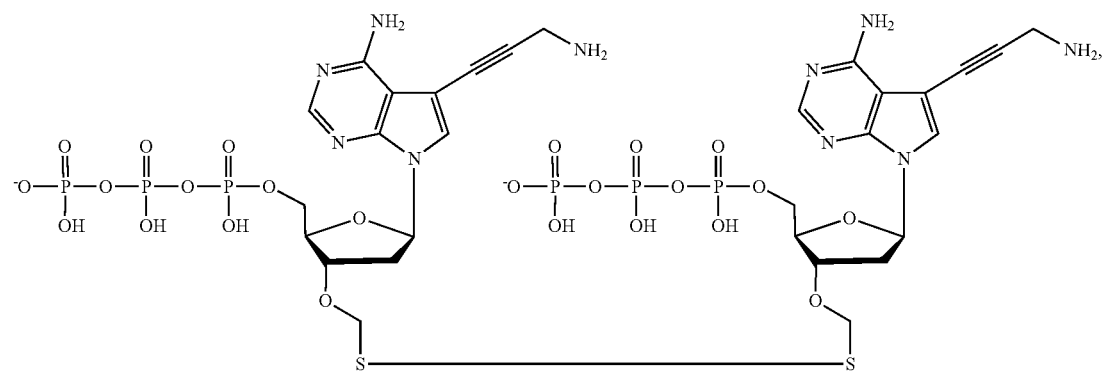
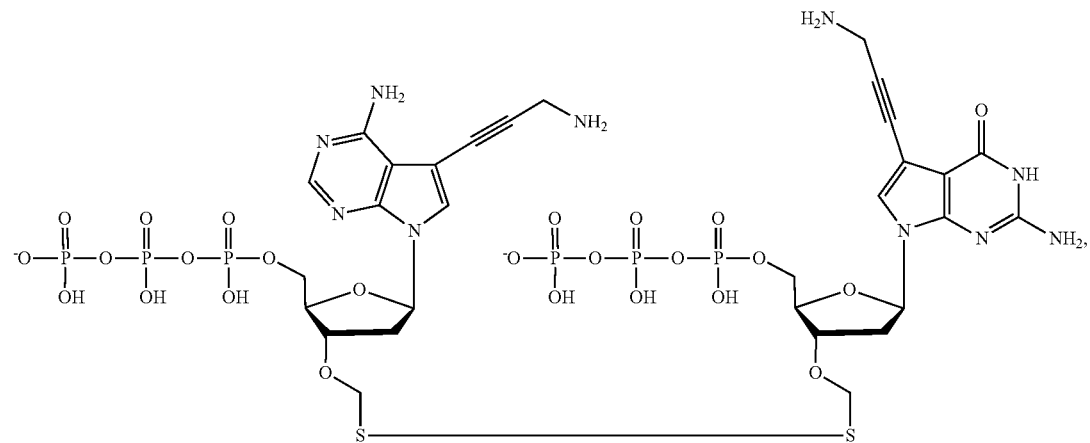
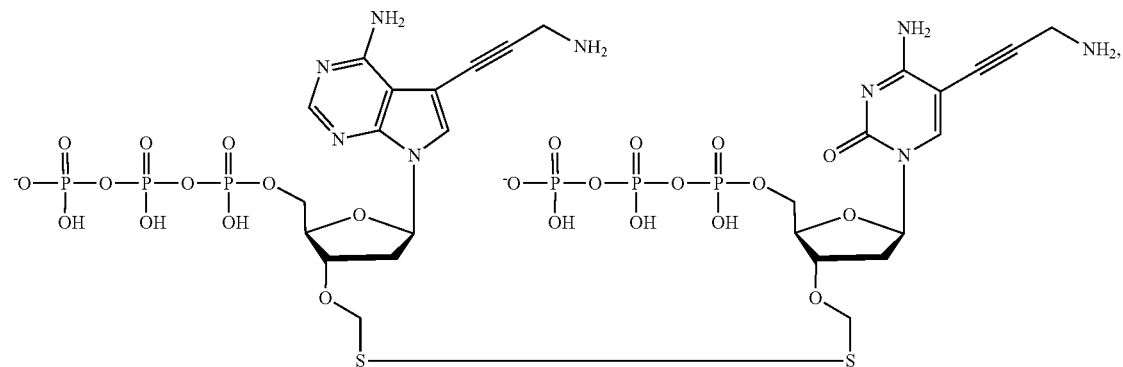

161
162
-continued
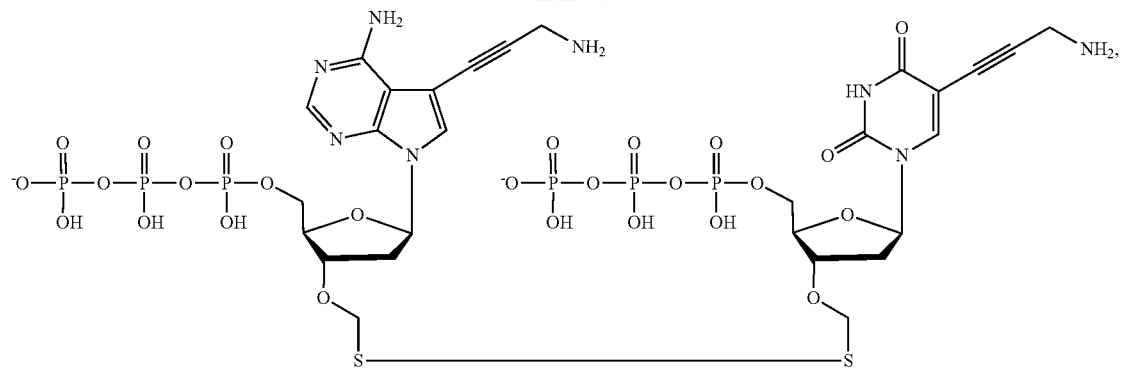
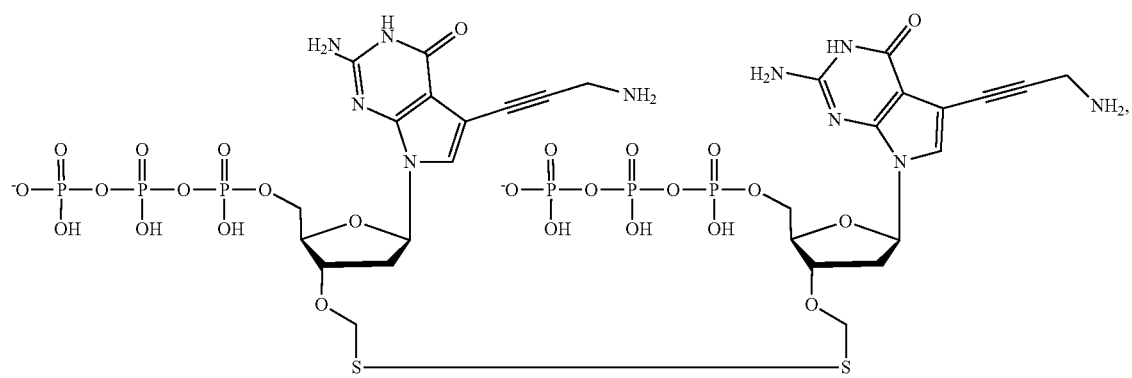
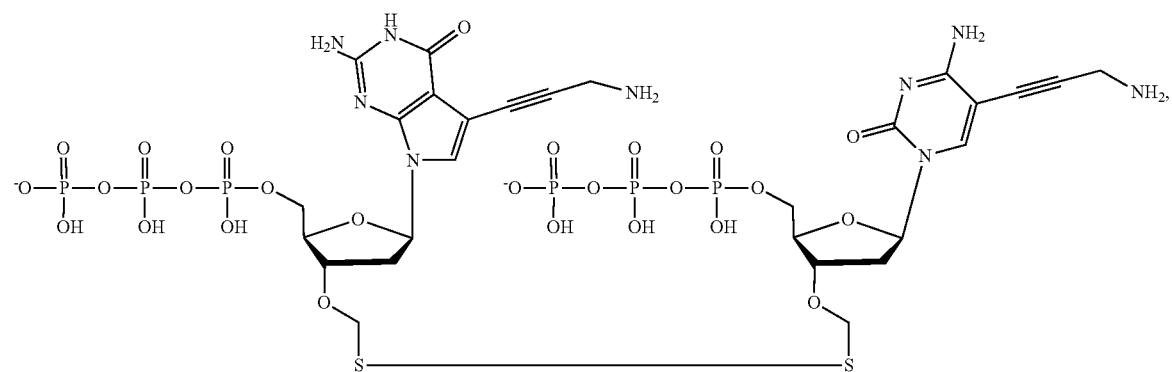
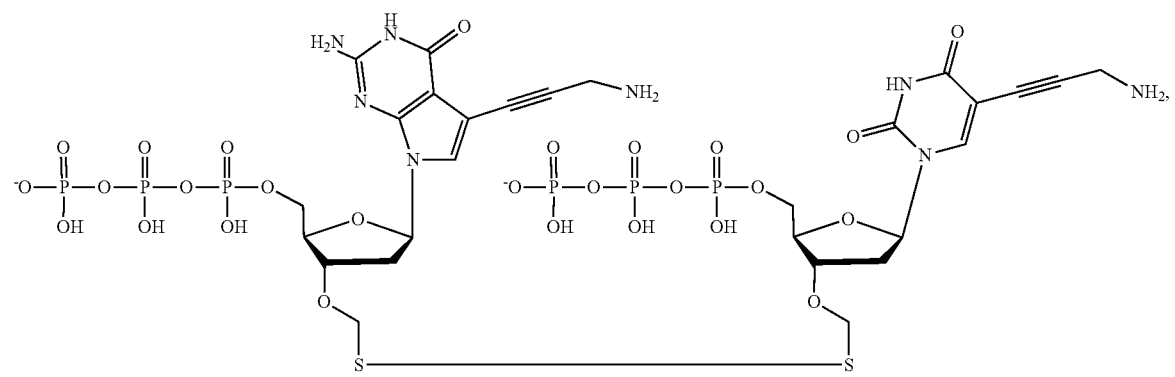

-continued
163
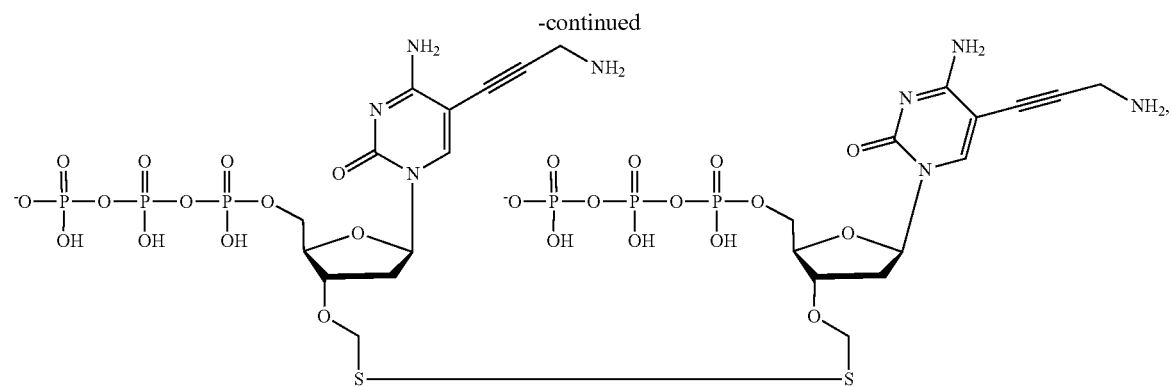
164
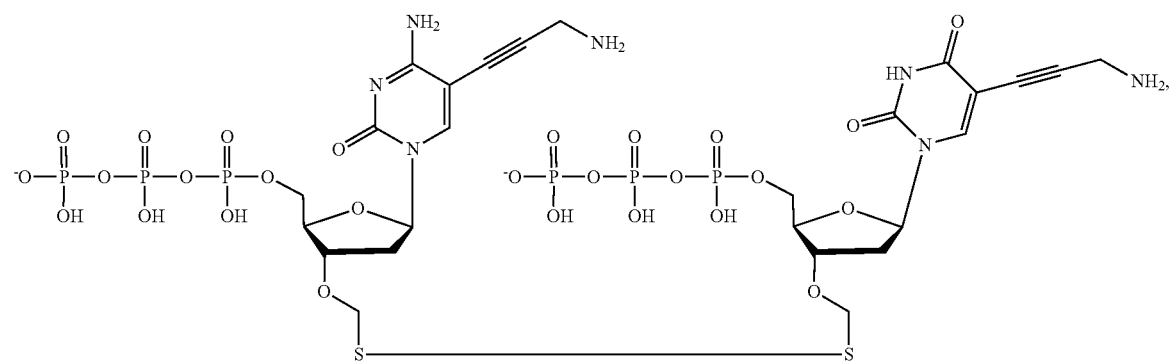
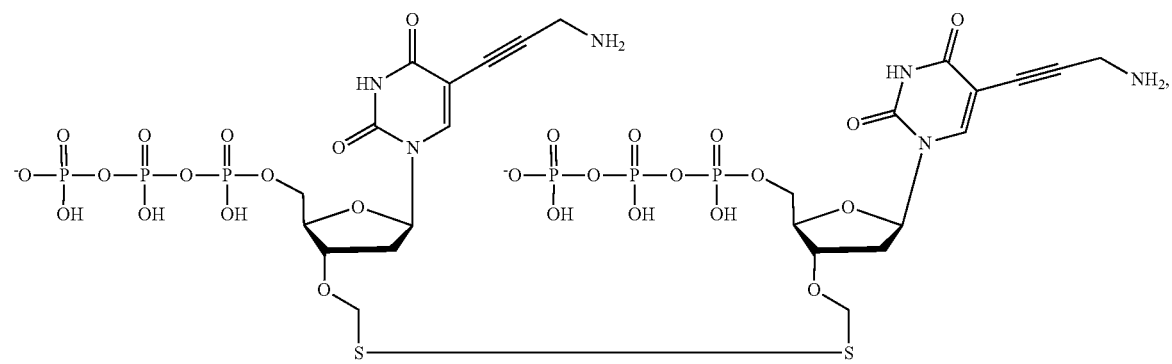
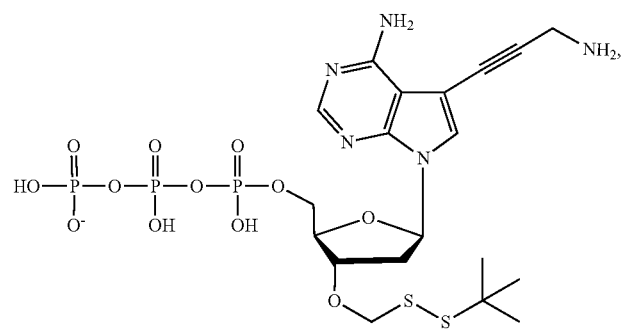

-continued
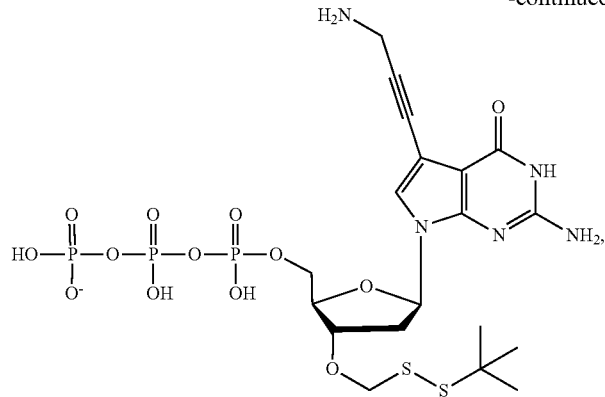
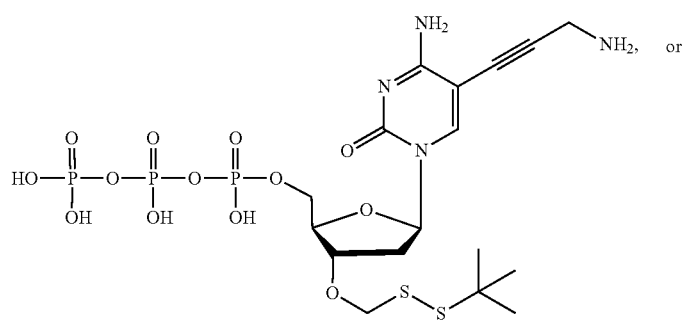
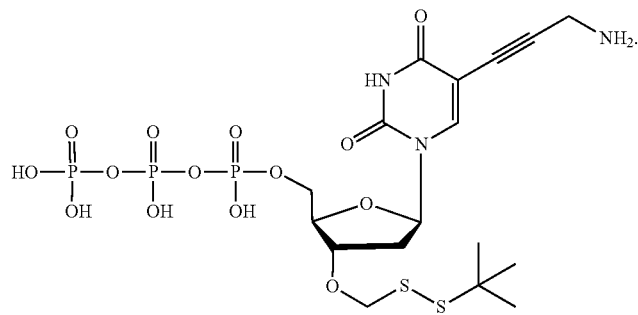
In embodiments, the compound of formula IB$^P$ is
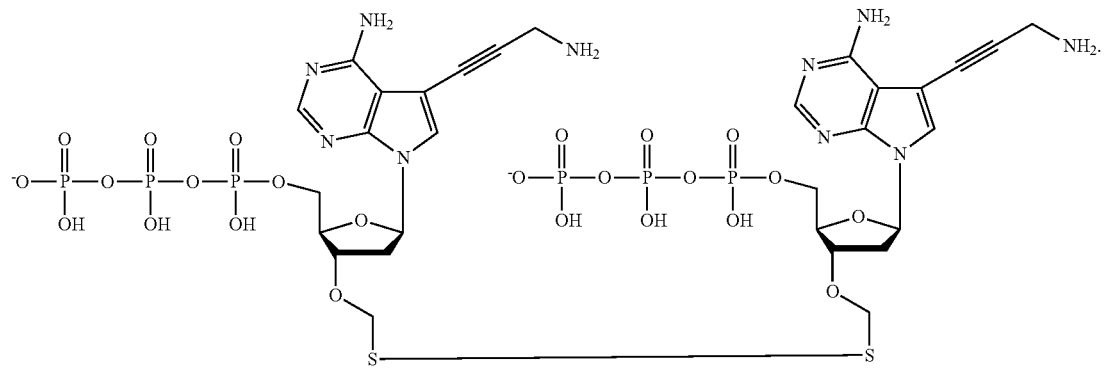

In embodiments, the compound of Formula IB$^P$ is
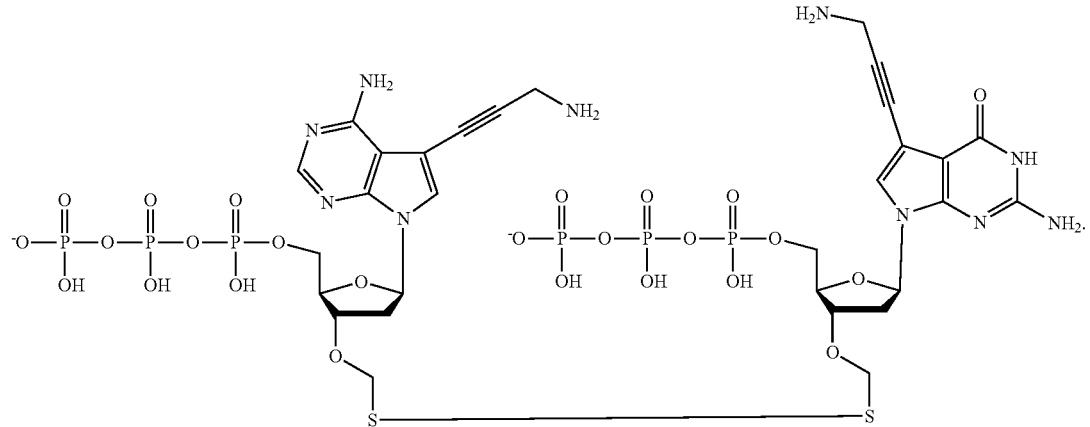
In embodiments, the compound of Formula IB$^P$ is
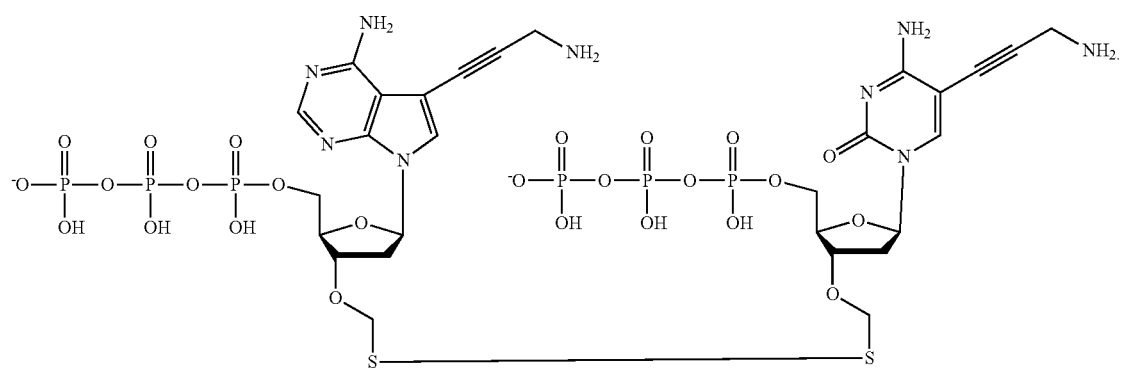
In embodiments, the compound of Formula IB$^P$ is
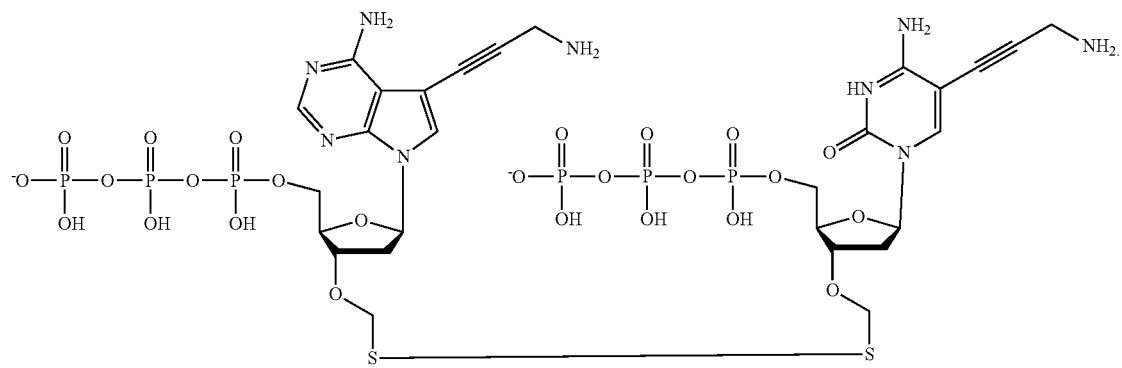

In embodiments, the compound of Formula IB$^P$ is
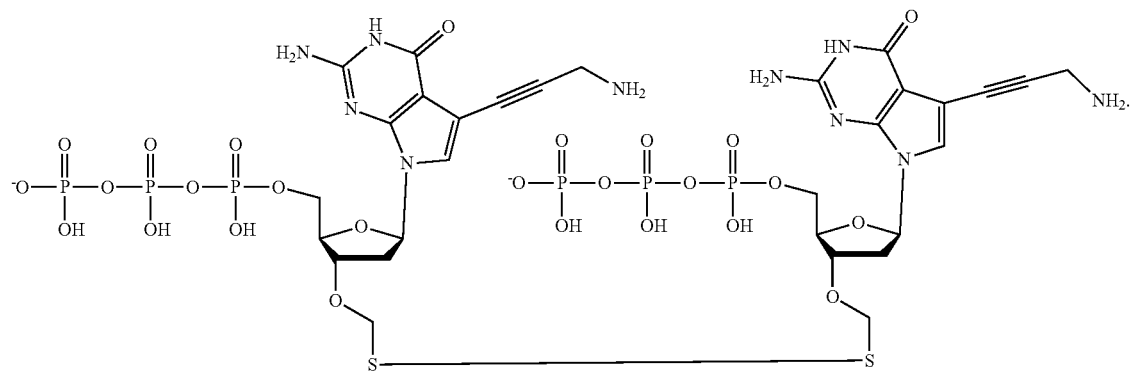
In embodiments, the compound of Formula IB$^P$ is
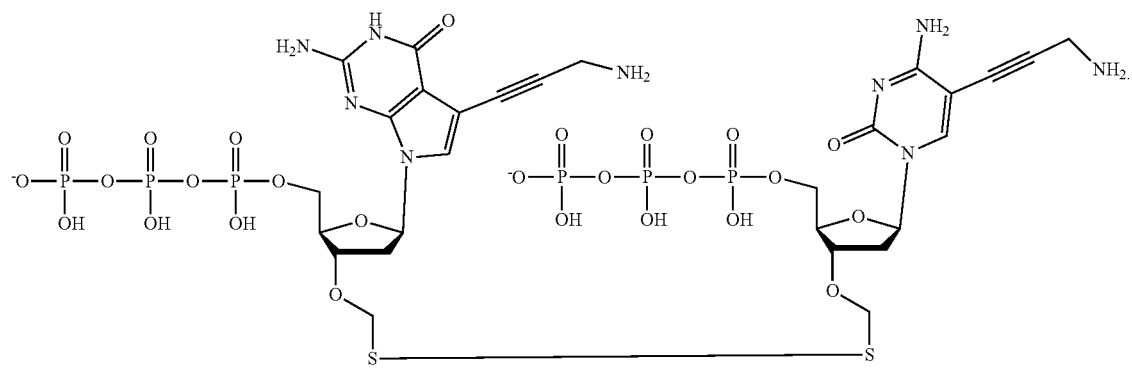
In embodiments, the compound of Formula IB$^P$ is
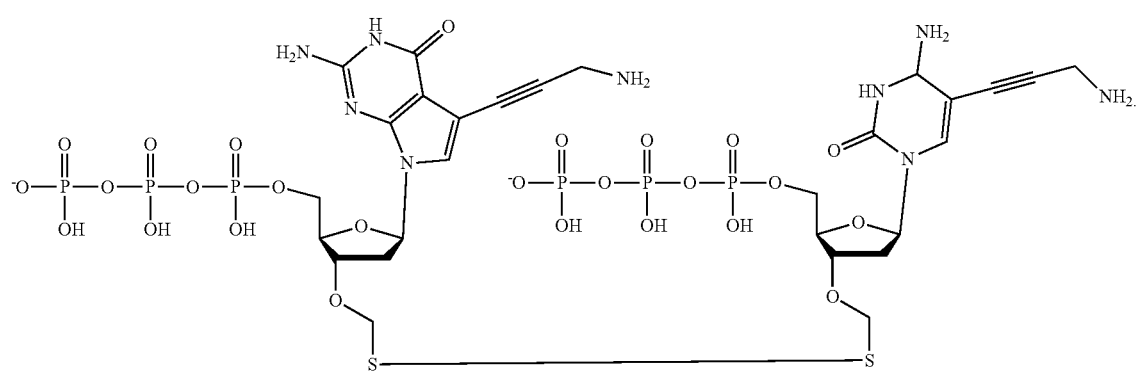

In embodiments, the compound of Formula IB$^P$ is
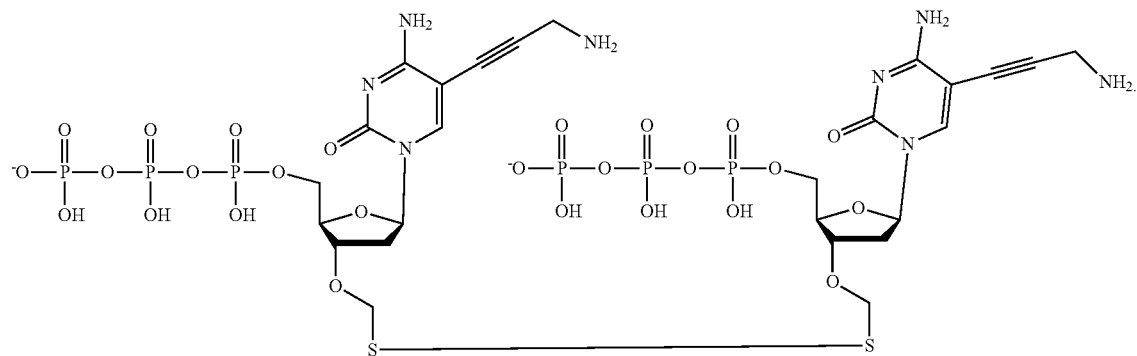
In embodiments, the compound of Formula IB$^P$ is
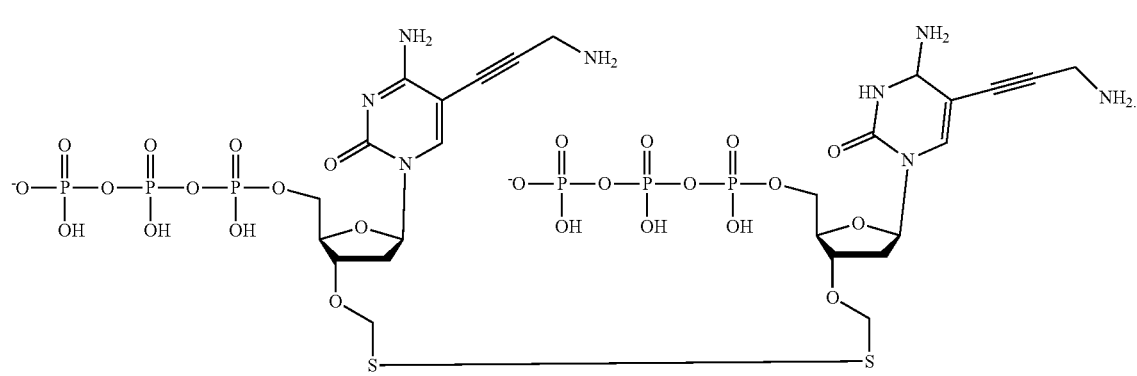
In embodiments, the compound of Formula IB$^P$ is
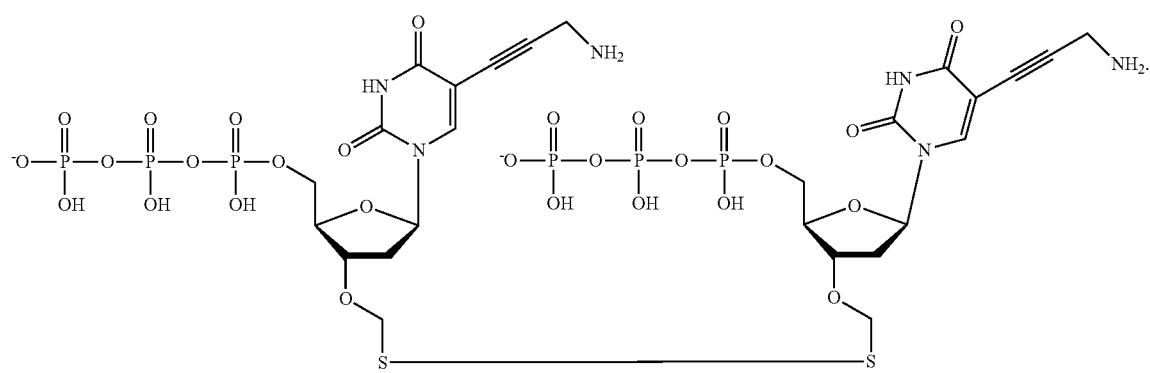
In embodiments, the compound of Formula IB$^P$ is    In embodiments, the compound of Formula IB$^P$ is
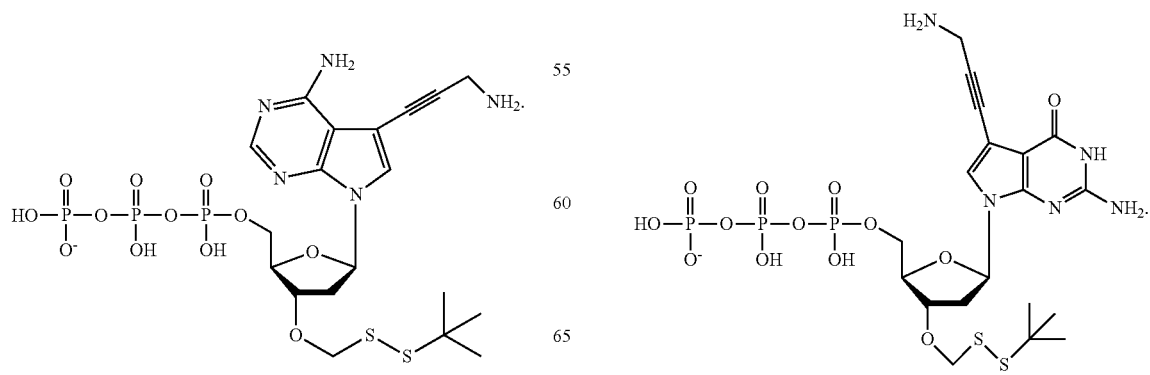

In embodiments, the compound of Formula IB$^P$ is

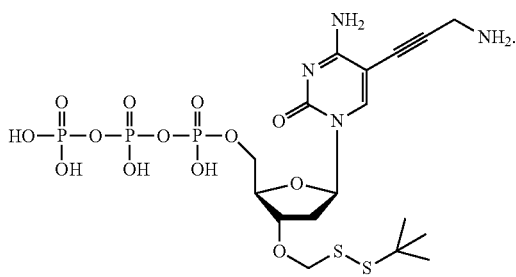 [SMILES: CC(C)(C)SSCO[C@@H]1C[C@H](n2cc(C#CCN)c(N)nc2=O)O[C@@H]1COP(=O)(O)OP(=O)(O)OP(=O)(O)O]

In embodiments, the compound of Formula IB$^P$ is

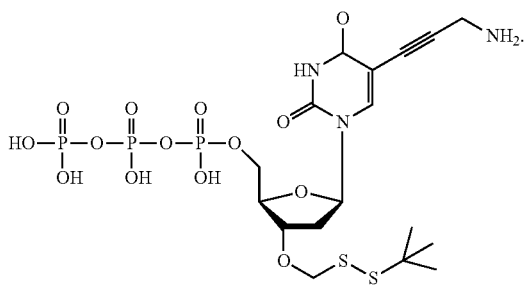 [SMILES: CC(C)(C)SSCO[C@@H]1C[C@H](N2C=C(C#CCN)C(O)NC2=O)O[C@@H]1COP(=O)(O)OP(=O)(O)OP(=O)(O)O]

In embodiments, the compound is not a compound described in WO 2017/079498.

In an aspect is provided a compound having the formula:

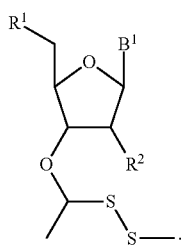

(I)

B$^1$ is a monovalent nucleobase (e.g., a monovalent nucleobase including a covalent linker optionally bonded to a detectable moiety, for example as described herein). In embodiments, B$^1$ is a substituted or unsubstituted monovalent nucleobase (e.g., —B-L$^{100}$-R$^4$).

R$^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

R$^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

R$^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety, —OR$^{2A}$, or an —O-polymerase-compatible cleavable moiety.

In embodiments, R$^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

In embodiments, the compound has the formula:

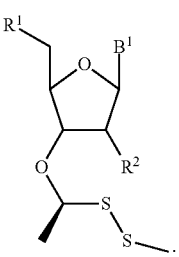

(IA)

In embodiments, the compound has the formula:

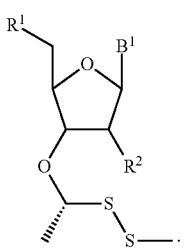

(IB)

In embodiments, the compound has the formula:

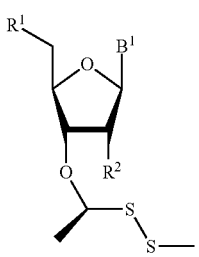

(IAD)

In embodiments, the compound has the formula:

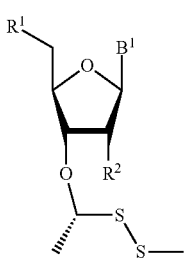

(IBD)

In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a 5'-nucleoside protecting group; or $R^1$ is a monophosphate moiety, polyphosphate moiety, or nucleic acid moiety. In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^1$ is a 5'-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is —OH.

In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a 5'-nucleoside protecting group; or —OR$^1$ is a monophosphate moiety, polyphosphate moiety, or nucleic acid moiety. In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^1$ is a 5'-nucleoside protecting group. In embodiments, R, is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is —OH.

In embodiments, $R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_2$NH$_2$, —NHNH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered), or a 5'-nucleoside protecting group; or $R^1$ is a monophosphate moiety, polyphosphate moiety, or nucleic acid moiety. In embodiments, $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_2NH_2$, —$NHNH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered). In embodiments, $R^1$ is a 5'-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is —OH.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group. In embodiments, when $R^1$ is substituted, it is substituted with 1 to 10 substituent groups. In embodiments, when $R^1$ is substituted, it is substituted with 1 to 10 size-limited substituent groups. In embodiments, when $R^1$ is substituted, it is substituted with 1 to 10 lower substituent groups. In embodiments, when $R^1$ is substituted, it is substituted with 1 to 5 substituent groups. In embodiments, when $R^1$ is substituted, it is substituted with 1 to 5 size-limited substituent groups. In embodiments, when $R^1$ is substituted, it is substituted with 1 to 5 lower substituent groups. In embodiments, when $R^1$ is substituted, it is substituted with a substituent group. In embodiments, when $R^1$ is substituted, it is substituted with a size-limited substituent group. In embodiments, when $R^1$ is substituted, it is substituted with a lower substituent group.

In embodiments, $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety. In embodiments, $R^1$ is independently a monophosphate moiety including a phosphodiester derivative. In embodiments, $R^1$ is independently a polyphosphate moiety including a phosphodiester derivative. In embodiments, $R^1$ is independently a nucleic acid moiety including a phosphodiester derivative. In embodiments, $R^1$ is independently a phosphoramidate moiety. In embodiments, $R^1$ is independently a polyphosphate moiety including a phosphoramidate. In embodiments, $R^1$ is independently a nucleic acid moiety including a phosphoramidate. In embodiments, $R^1$ is independently a phosphorothioate moiety. In embodiments, $R^1$ is independently a polyphosphate moiety including a phosphorothioate. In embodiments, $R^1$ is independently a nucleic acid moiety including a phosphorothioate. In embodiments, $R^1$ is independently a phosphorodithioate moiety. In embodiments, $R^1$ is independently a polyphosphate moiety including a phosphorodithioate. In embodiments, $R^1$ is independently a nucleic acid moiety including a phosphorodithioate. In embodiments, $R^1$ is independently an O-methylphosphoroamidite moiety. In embodiments, $R^1$ is independently a polyphosphate moiety including an O-methylphosphoroamidite. In embodiments, $R^1$ is independently a nucleic acid moiety including an O-methylphosphoroamidite. In embodiments, $R^1$ is independently a nucleic acid moiety including a nucleotide analog. In embodiments, $R^1$ is independently a nucleic acid moiety including a plurality of optionally different nucleotide analogs.

In embodiments, $R^1$ is independently a 5'-nucleoside protecting group; and the 5'-nucleoside protecting group is

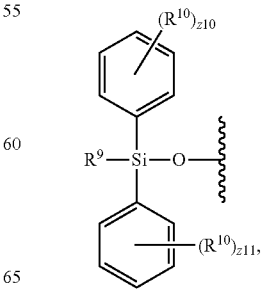

wherein $R^9$ is substituted or unsubstituted $C_1$-$C_4$ alkyl. $R^{10}$ and $R^{11}$ are each independently halogen, —$CF_3$, —$Cl_3$, —$CI_3$, —$CBr_3$, —$CHF_2$, —$CHCl_2$, —$CHI_2$, —$CHBr_2$, —$CH_2Cl$, —$CH_2Br$, —$CH_2F$, —$CH_2I$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCI_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. The symbols z10 and z11 are each independently integers from 0 to 5. In embodiments, z10 and z11 are 0.

In embodiments, $R^9$ is independently substituted (e.g., substituted with a substituent group, a size-limited substituent group, or lower substituent group) $C_1$-$C_4$ alkyl. In embodiments, $R^9$ is an unsubstituted methyl. In embodiments, $R^9$ is an unsubstituted $C_2$ alkyl. In embodiments, $R^9$ is an unsubstituted $C_3$ alkyl. In embodiments, $R^9$ is an unsubstituted $C_4$ alkyl. In embodiments, $R^9$ is an unsubstituted tert-butyl.

In embodiments, a substituted $R^9$ (e.g., substituted alkyl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group. In embodiments, when $R^9$ is substituted, it is substituted with 1 to 10 substituent groups. In embodiments, when $R^9$ is substituted, it is substituted with 1 to 10 size-limited substituent groups. In embodiments, when $R^9$ is substituted, it is substituted with 1 to 10 lower substituent groups. In embodiments, when $R^9$ is substituted, it is substituted with 1 to 5 substituent groups. In embodiments, when $R^9$ is substituted, it is substituted with 1 to 5 size-limited substituent groups. In embodiments, when $R^9$ is substituted, it is substituted with 1 to 5 lower substituent groups. In embodiments, when $R^9$ is substituted, it is substituted with a substituent group. In embodiments, when $R^9$ is substituted, it is substituted with a size-limited substituent group. In embodiments, when $R^9$ is substituted, it is substituted with a lower substituent group.

In embodiments, $R^{10}$ and $R^{11}$ are each independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{10}$ and $R^{11}$ are each independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{10}$ and $R^{11}$ are each independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{10}$ and $R^{11}$ are each independently unsubstituted alkyl, unsubstituted heteroalkyl, unsubstituted cycloalkyl, unsubstituted heterocycloalkyl, unsubstituted aryl, or unsubstituted heteroaryl.

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group. In embodiments, when $R^{10}$ is substituted, it is substituted with 1 to 10 substituent groups. In embodiments, when $R^{10}$ is substituted, it is substituted with 1 to 10 size-limited substituent groups. In embodiments, when $R^{10}$ is substituted, it is substituted with 1 to 10 lower substituent groups. In embodiments, when $R^{10}$ is substituted, it is substituted with 1 to 5 substituent groups. In embodiments, when $R^{10}$ is substituted, it is substituted with 1 to 5 size-limited substituent groups. In embodiments, when $R^{10}$ is substituted, it is substituted with 1 to 5 lower substituent groups. In embodiments, when $R^{10}$ is substituted, it is substituted with a substituent group. In embodiments, when $R^{10}$ is substituted, it is substituted with a size-limited substituent group. In embodiments, when $R^{10}$ is substituted, it is substituted with a lower substituent group.

In embodiments, a substituted $R^{11}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when R¹¹ is substituted, it is substituted with at least one substituent group. In embodiments, when R¹ is substituted, it is substituted with at least one size-limited substituent group. In embodiments, when R¹ is substituted, it is substituted with at least one lower substituent group. In embodiments, when R¹ is substituted, it is substituted with 1 to 10 substituent groups. In embodiments, when R¹¹ is substituted, it is substituted with 1 to 10 size-limited substituent groups. In embodiments, when R¹¹ is substituted, it is substituted with 1 to 10 lower substituent groups. In embodiments, when R¹ is substituted, it is substituted with 1 to 5 substituent groups. In embodiments, when R¹¹ is substituted, it is substituted with 1 to 5 size-limited substituent groups. In embodiments, when R¹¹ is substituted, it is substituted with 1 to 5 lower substituent groups. In embodiments, when R¹¹ is substituted, it is substituted with a substituent group. In embodiments, when R¹¹ is substituted, it is substituted with a size-limited substituent group. In embodiments, when R¹ is substituted, it is substituted with a lower substituent group.

In embodiments, R² is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, R² is independently a polymerase-compatible cleavable moiety. In embodiments, R² is independently an —O-polymerase-compatible cleavable moiety.

In embodiments, R² is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, a substituted R² (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted R² is substituted with a plurality of groups selected from substituent groups, size-limited substituent groups, and lower substituent groups; each substituent group, size-limited substituent group, and/or lower substituent group may optionally be different. In embodiments, when R² is substituted, it is substituted with at least one substituent group. In embodiments, when R² is substituted, it is substituted with at least one size-limited substituent group. In embodiments, when R² is substituted, it is substituted with at least one lower substituent group. In embodiments, when R² is substituted, it is substituted with 1 to 10 substituent groups. In embodiments, when R² is substituted, it is substituted with 1 to 10 size-limited substituent groups. In embodiments, when R² is substituted, it is substituted with 1 to 10 lower substituent groups. In embodiments, when R² is substituted, it is substituted with 1 to 5 substituent groups. In embodiments, when R² is substituted, it is substituted with 1 to 5 size-limited substituent groups. In embodiments, when R² is substituted, it is substituted with 1 to 5 lower substituent groups. In embodiments, when R² is substituted, it is substituted with a substituent group. In embodiments, when R² is substituted, it is substituted with a size-limited substituent group. In embodiments, when R² is substituted, it is substituted with a lower substituent group.

In embodiments, R² is independently hydrogen, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —N₃, R²ᴬ-substituted or unsubstituted alkyl (e.g., $C_1$-$C_{20}$, $C_{10}$-$C_{20}$, $C_1$-$C_8$, $C_1$-$C_6$, or $C_1$-$C_4$), R²ᴬ-substituted or unsubstituted heteroalkyl (e.g., 2 to 20 membered, 8 to 20 membered, 2 to 10 membered, 2 to 8 membered, 2 to 6 membered, or 2 to 4 membered), R²ᴬ-substituted or unsubstituted cycloalkyl (e.g., $C_3$-$C_8$, $C_3$-$C_6$, or $C_5$-$C_6$), R²ᴬ-substituted or unsubstituted heterocycloalkyl (e.g., 3 to 8 membered, 3 to 6 membered, or 5 to 6 membered), R²ᴬ-substituted or unsubstituted aryl (e.g., $C_6$-$C_{10}$, $C_{10}$, or phenyl), or R²ᴬ-substituted or unsubstituted heteroaryl (e.g., 5 to 10 membered, 5 to 9 membered, or 5 to 6 membered), or —OR²ᴬ. In embodiments, R² is independently —OR²ᴬ.

In embodiments, R² is hydrogen. In embodiments, R² is —OH. In embodiments, R² is —O-polymerase-compatible cleavable moiety.

In embodiments, R² is a polymerase-compatible cleavable moiety or an —O-polymerase-compatible cleavable moiety; and the polymerase-compatible cleavable moiety is

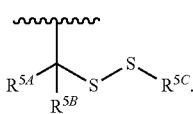

R⁵ᴬ is independently hydrogen, halogen, —CX⁵ᴬ₃, —CHX⁵ᴬ₂, —CH₂X⁵ᴬ, —OCX⁵ᴬ₃, —OCH₂X⁵ᴬ, —OCHX⁵ᴬ₂, —CN, —OH, —SH, —NH₂, —COOH, —CONH₂, —NO₂, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —N₃, —SF₅, —NH₃⁺, —SO₃⁻, —OPO₃H⁻, —SCN, —ONO₂, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{5A}$ and $R^{5B}$ are combined to form an oxo. $R^{5C}$ is hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, and $X^{5C}$ are independently —F, —Cl, —Br, or —I.

In embodiments, $R^2$ is a polymerase-compatible cleavable moiety or an —O-polymerase-compatible cleavable moiety; and the polymerase-compatible cleavable moiety is

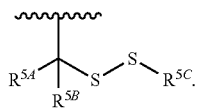

$R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{5A}$ and $R^{5B}$ are combined to form an oxo. $R^{5C}$ is hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted (e.g., substituted with a substituent group, size-limited substituent group, or lower substitutent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, and $X^{5C}$ are independently —F, —Cl, —Br, or —I.

In embodiments, a substituted $R^{5A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{5A}$ is substituted, it is substituted with at least one substituent group. In embodiments, when $R^{5A}$ is substituted, it is substituted with at least one size-limited substituent group. In embodiments, when $R^{5A}$ is substituted, it is substituted with at least one lower substituent group. In embodiments, when $R^{5A}$ is substituted, it is substituted with 1 to 10 substituent groups. In embodiments, when $R^{5A}$ is substituted, it is substituted with 1 to 10 size-limited substituent groups. In embodiments, when $R^{5A}$ is substituted, it is substituted with 1 to 10 lower substituent groups. In embodiments, when $R^{5A}$ is substituted, it is substituted with 1 to 5 substituent groups. In embodiments, when $R^{5A}$ is substituted, it is substituted with 1 to 5 size-limited substituent groups. In embodiments, when $R^{5A}$ is substituted, it is substituted with 1 to 5 lower substituent groups. In embodiments, when $R^{5A}$ is substituted, it is substituted with a substituent group. In embodiments, when $R^{5A}$ is substituted, it is substituted with a size-limited substituent group. In embodiments, when $R^{5A}$ is substituted, it is substituted with a lower substituent group.

In embodiments, a substituted $R^{5B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5B}$ is substituted with a plurality of groups selected from substituent groups, size-limited substituent groups, and lower substituent groups; each substituent group, size-limited substituent group, and/or lower substituent group may optionally be different. In embodiments, when $R^{5B}$ is substituted, it is substituted with at least one substituent group. In embodiments, when $R^{5B}$ is substituted, it is substituted with at least one size-limited substituent group. In embodiments, when $R^{5B}$ is substituted, it is substituted with at least one lower substituent group. In embodiments, when $R^{5B}$ is substituted, it is substituted with 1 to 10 substituent groups. In embodiments, when $R^{5B}$ is substituted, it is substituted with 1 to 10 size-limited substituent groups. In embodiments, when $R^{5B}$ is substituted, it is substituted with 1 to 10 lower substituent groups. In embodiments, when $R^{5B}$ is substituted, it is substituted with 1 to 5 substituent groups. In embodiments, when $R^{5B}$ is substituted, it is substituted with 1 to 5 size-limited substituent groups. In embodiments, when $R^{5B}$ is substituted, it is substituted with 1 to 5 lower substituent groups. In embodiments, when $R^{5B}$ is substituted, it is substituted with a substituent group. In embodiments, when $R^{5B}$ is substituted, it is substituted with a size-limited substituent group. In embodiments, when $R^{5B}$ is substituted, it is substituted with a lower substituent group.

In embodiments, a substituted $R^{5C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{5C}$ is substituted with a plurality of groups selected from substituent groups, size-limited substituent groups, and lower substituent groups; each substituent group, size-limited substituent group, and/or lower substituent group may optionally be different. In embodiments, when $R^{5C}$ is substituted, it is substituted with at least one substituent group. In embodiments, when $R^{5C}$ is substituted, it is substituted with at least one size-limited substituent group. In embodiments, when $R^{5C}$ is substituted, it is substituted with at least one lower substituent group. In embodiments, when $R^{5C}$ is substituted, it is substituted with 1 to 10 substituent groups. In embodiments, when $R^{5C}$ is substituted, it is substituted with 1 to 10 size-limited substituent groups. In embodiments, when $R^{5C}$ is substituted, it is substituted with 1 to 10 lower substituent groups. In embodiments, when $R^{5C}$ is substituted, it is substituted with 1 to 5 substituent groups. In embodiments, when $R^{5C}$ is substituted, it is substituted with 1 to 5 size-limited substituent groups. In embodiments, when $R^{5C}$ is substituted, it is substituted with 1 to 5 lower substituent groups. In embodiments, when $R^{5C}$ is substituted, it is substituted with a substituent group. In embodiments, when $R^{5C}$ is substituted, it is substituted with a size-limited substituent group. In embodiments, when $R^{5C}$ is substituted, it is substituted with a lower substituent group.

In embodiments, $R^2$ is a polymerase-compatible cleavable moiety or an —O-polymerase-compatible cleavable moiety; and the polymerase-compatible cleavable moiety is

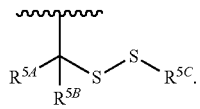

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl. $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl. $R^{5E}$ is independently halogen, oxo, —$CX^{5E}_3$, —$CHX^{5E}_2$, —$CH_2X^{5E}$, —$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5F}$-substituted or unsubstituted alkyl, $R^{5F}$-substituted or unsubstituted heteroalkyl, $R^{5F}$-substituted or unsubstituted cycloalkyl, $R^{5F}$-substituted or unsubstituted heterocycloalkyl, $R^{5F}$-substituted or unsubstituted aryl, or $R^{5F}$-substituted or unsubstituted heteroaryl. $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl, $R^{5G}$-substituted or unsubstituted heteroalkyl, $R^{5G}$-substituted or unsubstituted cycloalkyl, $R^{5G}$-substituted or unsubstituted heterocycloalkyl, $R^{5G}$-substituted or unsubstituted aryl, or $R^{5G}$-substituted or unsubstituted heteroaryl. $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5H}$-substituted or unsubstituted alkyl, $R^{5H}$-substituted or unsubstituted heteroalkyl, $R^{5H}$-substituted or unsubstituted cycloalkyl, $R^{5H}$-substituted or unsubstituted heterocycloalkyl, $R^{5H}$-substituted or unsubstituted aryl, or $R^{5H}$-substituted or unsubstituted heteroaryl. $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl, $R^{5I}$-substituted or unsubstituted heteroalkyl, $R^{5I}$-substituted or unsubstituted cycloalkyl, $R^{5I}$-substituted or unsubstituted heterocycloalkyl, $R^{5I}$-substituted or unsubstituted aryl, or $R^{5I}$-substituted or unsubstituted heteroaryl. $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^2$ is a polymerase-compatible cleavable moiety or an —O-polymerase-compatible cleavable moiety; and the polymerase-compatible cleavable moiety is

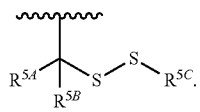

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5D}$-substituted or unsubstituted alkyl (e.g., $C_1$-$C_8$, $C_1$-$C_6$, $C_1$-$C_4$, or $C_1$-$C_2$), $R^{5D}$-substituted or unsubstituted heteroalkyl (e.g., 2 to 8 membered, 2 to 6 membered, 4 to 6 membered, 2 to 3 membered, or 4 to 5 membered), $R^{5D}$-substituted or unsubstituted cycloalkyl (e.g., $C_3$-$C_8$, $C_3$-$C_6$, $C_4$-$C_6$, or $C_5$-$C_6$), $R^{5D}$-substituted or unsubstituted heterocycloalkyl (e.g., 3 to 8 membered, 3 to 6 membered, 4 to 6 membered, 4 to 5 membered, or 5 to 6 membered), $R^{5D}$-substituted or unsubstituted aryl (e.g., $C_6$-$C_{10}$ or phenyl), or $R^{5D}$-substituted or unsubstituted heteroaryl (e.g., 5 to 10 membered, 5 to 9 membered, or 5 to 6 membered). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl (e.g., $C_1$-$C_8$, $C_1$-$C_6$, $C_1$-$C_4$, or $C_1$-$C_2$), $R^{5E}$-substituted or unsubstituted heteroalkyl (e.g., 2 to 8 membered, 2 to 6 membered, 4 to 6 membered, 2 to 3 membered, or 4 to 5 membered), $R^{5E}$-substituted or unsubstituted cycloalkyl (e.g., $C_3$-$C_8$, $C_3$-$C_6$, $C_4$-$C_6$, or $C_5$-$C_6$), $R^{5E}$-substituted or unsubstituted heterocycloalkyl (e.g., 3 to 8 membered, 3 to 6 membered, 4 to 6 membered, 4 to 5 membered, or 5 to 6 membered), $R^{5E}$-substituted or unsubstituted aryl (e.g., $C_6$-$C_{10}$ or phenyl), or $R^{5E}$-substituted or unsubstituted heteroaryl (e.g., 5 to 10 membered, 5 to 9 membered, or 5 to 6 membered). In embodiments, $R^{5E}$ is independently halogen, oxo, —$CX^{5E}_3$, —$CHX^{5E}_2$, —$CH_2X^{5E}$, —$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5F}$-substituted or unsubstituted alkyl (e.g., $C_1$-$C_8$, $C_1$-$C_6$, $C_1$-$C_4$, or $C_1$-$C_2$), $R^{5F}$-substituted or unsubstituted heteroalkyl (e.g., 2 to 8 membered, 2 to 6 membered, 4 to 6 membered, 2 to 3 membered, or 4 to 5 membered), $R^{5F}$-substituted or unsubstituted cycloalkyl (e.g., $C_3$-$C_8$, $C_3$-$C_6$, $C_4$-$C_6$, or $C_5$-$C_6$), $R^{5F}$-substituted or unsubstituted heterocycloalkyl (e.g., 3 to 8 membered, 3 to 6 membered, 4 to 6 membered, 4 to 5 membered, or 5 to 6 membered), $R^{5F}$-substituted or unsubstituted aryl (e.g., $C_6$-$C_{10}$ or phenyl), or $R^{5F}$-substituted or unsubstituted heteroaryl (e.g., 5 to 10 membered, 5 to 9 membered, or 5 to 6 membered). In embodiments, $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl (e.g., $C_1$-$C_8$, $C_1$-$C_6$, $C_1$-$C_4$, or $C_1$-$C_2$), $R^{5G}$-substituted or unsubstituted heteroalkyl (e.g., 2 to 8 membered, 2 to 6 membered, 4 to 6 membered, 2 to 3 membered, or 4 to 5 membered), $R^{5G}$-substituted or unsubstituted cycloalkyl (e.g., $C_3$-$C_8$, $C_3$-$C_6$, $C_4$-$C_6$, or $C_5$-$C_6$), $R^{5G}$-substituted or unsubstituted heterocycloalkyl (e.g., 3 to 8 membered, 3 to 6 membered, 4 to 6 membered, 4 to 5 membered, or 5 to 6 membered), $R^{5G}$-substituted or unsubstituted aryl (e.g., $C_6$-$C_{10}$ or phenyl), or $R^{5G}$-substituted or unsubstituted heteroaryl (e.g., 5 to 10 membered, 5 to 9 membered, or 5 to 6 membered). In embodiments, $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H$, —SCN, —$ONO_2$, $R^{5H}$-substituted or unsubstituted alkyl (e.g., $C_1$-$C_8$, $C_1$-$C_6$, $C_1$-$C_4$, or $C_1$-$C_2$), $R^{5H}$-substituted or unsubstituted heteroalkyl (e.g., 2 to 8 membered, 2 to 6 membered, 4 to 6 membered, 2 to 3 membered, or 4 to 5 membered), $R^{5H}$-substituted or unsubstituted cycloalkyl (e.g., $C_3$-$C_8$, $C_3$-$C_6$, $C_4$-$C_6$, or $C_5$-$C_6$), $R^{5H}$-substituted or unsubstituted heterocycloalkyl (e.g., 3 to 8 membered, 3 to 6 membered, 4 to 6 membered, 4 to 5 membered, or 5 to 6 membered), $R^{5H}$-substituted or unsubstituted aryl (e.g., $C_6$-$C_{10}$ or phenyl), or $R^{5H}$-substituted or unsubstituted heteroaryl (e.g., 5 to 10 membered, 5 to 9 membered, or 5 to 6 membered). In embodiments, $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl (e.g., $C_1$-$C_8$, $C_1$-$C_6$, $C_1$-$C_4$, or $C_1$-$C_2$), $R^{5I}$-substituted or unsubstituted heteroalkyl (e.g., 2 to 8 membered, 2 to 6 membered, 4 to 6 membered, 2 to 3 membered, or 4 to 5 membered), $R^{5I}$-substituted or unsubstituted cycloalkyl (e.g., $C_3$-$C_8$, $C_3$-$C_6$, $C_4$-$C_6$, or $C_5$-$C_6$), $R^{5I}$-substituted or unsubstituted heterocycloalkyl (e.g., 3 to 8 membered, 3 to 6 membered, 4 to 6 membered, 4 to 5 membered, or 5 to 6 membered), $R^{5I}$-substituted or unsubstituted aryl (e.g., $C_6$-$C_{10}$ or phenyl), or $R^{5I}$-substituted or unsubstituted heteroaryl (e.g., 5 to 10 membered, 5 to 9 membered, or 5 to 6 membered). In embodiments, $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, —$ONO_2$, $R^{5D}$-substituted $C_1$-$C_4$ alkyl (e.g., $R^{5D}$-substituted $C_1$-$C_3$ alkyl, $R^{5D}$-substituted $C_1$-$C_2$ alkyl, or $R^{5D}$-substituted methyl) or $R^{5D}$-substituted 2 to 8 membered heteroalkyl (e.g., $R^{5D}$-substituted 2 to 6 membered heteroalkyl, $R^{5D}$-substituted 2 to 5 membered heteroalkyl, or $R^{5D}$-substituted 2 to 4 membered heteroalkyl). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3^-$, —$OPO_3H^-$, —SCN, or —$ONO_2$. In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$N_3$, —$SF_5$, —$NH_3^+$, —$SO_3$, —$OPO_3H^-$, —SCN, —$ONO_2$, $R^{5F}$-substituted $C_1$-$C_4$ alkyl, (e.g., $R^{5F}$-substituted $C_1$-$C_3$ alkyl, $R^{5F}$-substituted $C_1$-$C_2$ alkyl, or $R^{5F}$-substituted methyl) or $R^{5F}$-substituted 2 to 8 membered heteroalkyl (e.g., $R^{5F}$-substituted 2 to 6 membered heteroalkyl, $R^{5F}$-substituted 2 to 5 membered heteroalkyl, or $R^{5F}$-substituted 2 to 4 membered heteroalkyl). In embodiments, $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, or —$ONO_2$. In embodiments, $R^{5A}$ and $R^{5B}$ are be combined to form an oxo. The symbols $X^{5A}$, $X^{5B}$, $X^{5D}$, and $X^{5F}$ are independently —F, —Cl, —Br, or —I.

In embodiments, $R^2$ is independently hydrogen, oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8 membered, 3 to 6 membered, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10 membered, 5 to 9 membered, or 5 to 6 membered), or —$OR^{2A}$. In embodiments, $R^2$ is independently —$OR^{2A}$.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8 membered, 3 to 6 membered, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10 membered, 5 to 9 membered, or 5 to 6 membered), or a polymerase-compatible cleavable moiety. In embodiments, $R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8 membered, 3 to 6 membered, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10 membered, 5 to 9 membered, or 5 to 6 membered). In embodiments, $R^{2A}$ is independently a polymerase-compatible cleavable moiety.

$R^{2B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2C}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2C}$-substituted or unsubstituted cycloalkyl (e.g., $C_3$-$C_8$, $C_3$-$C_6$, or $C_5$-$C_6$), $R^{2C}$-substituted or unsubstituted heterocycloalkyl (e.g., 3 to 8 membered, 3 to 6 membered, or 5 to 6 membered), $R^{2C}$-substituted or unsubstituted aryl (e.g., $C_6$-$C_{10}$, $C_{10}$, or phenyl), or $R^{2C}$-substituted or unsubstituted heteroaryl (e.g., 5 to 10 membered, 5 to 9 membered, or 5 to 6 membered).

$R^{2C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^{2A}$ is a polymerase-compatible cleavable moiety; and the polymerase-compatible cleavable moiety is

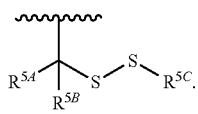

$R^{5A}$, $R^{5B}$, and $R^{5C}$ are as described herein, including in embodiments. In embodiments, $R^2$ is —$OR^{2A}$.

In embodiments, $R^{2A}$ is independently:

-continued

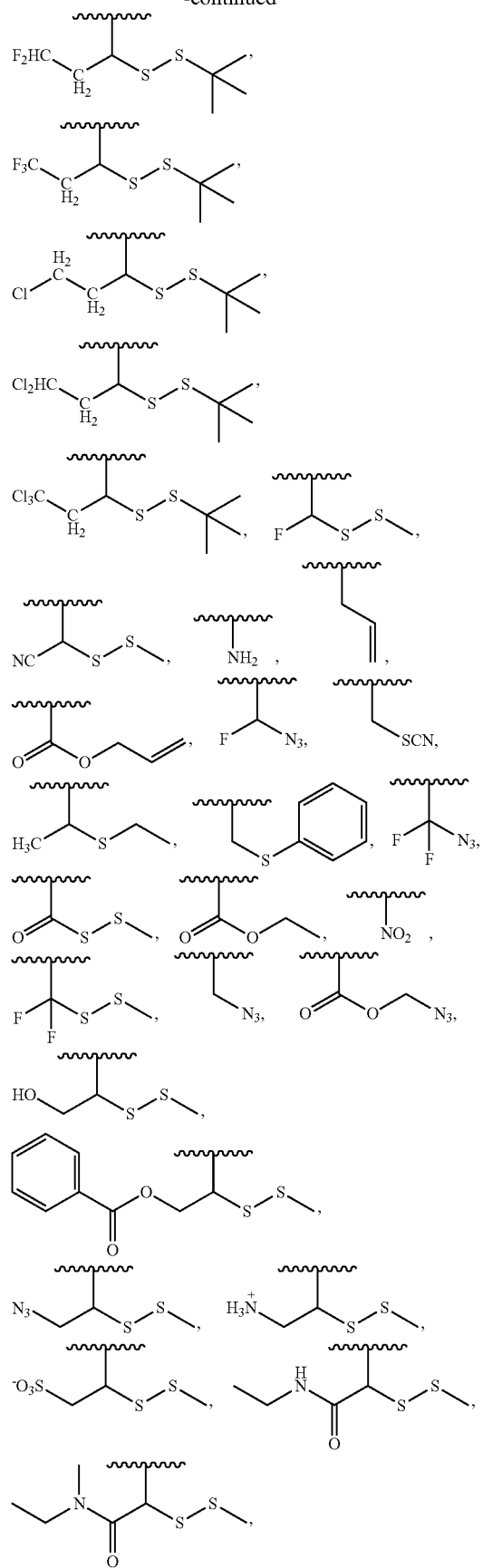
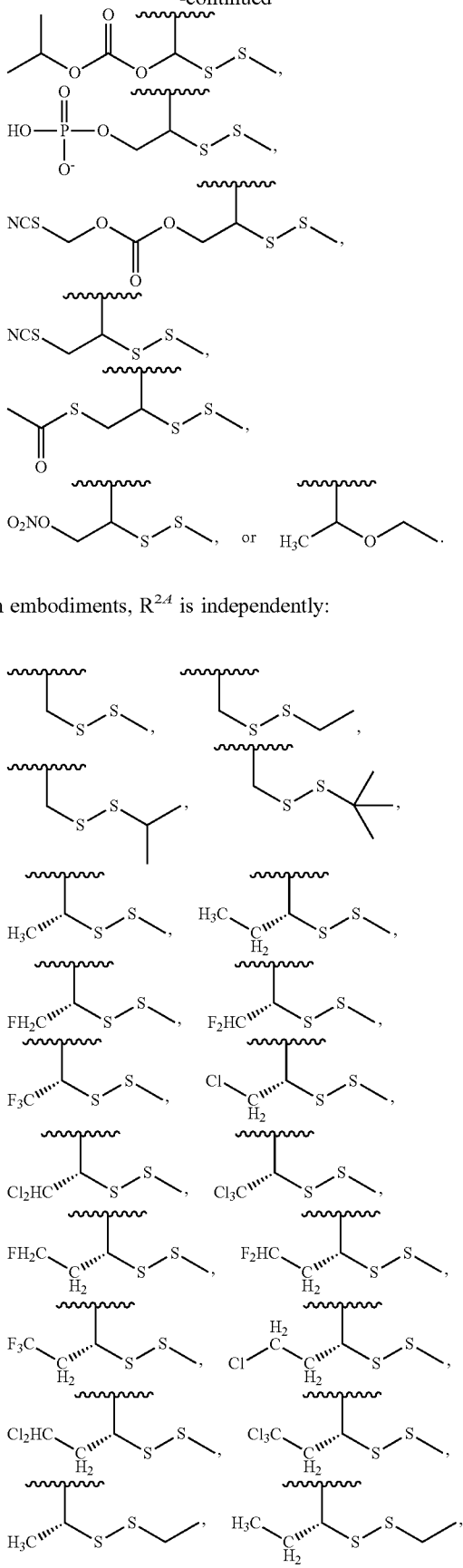
In embodiments, $R^{2A}$ is independently:

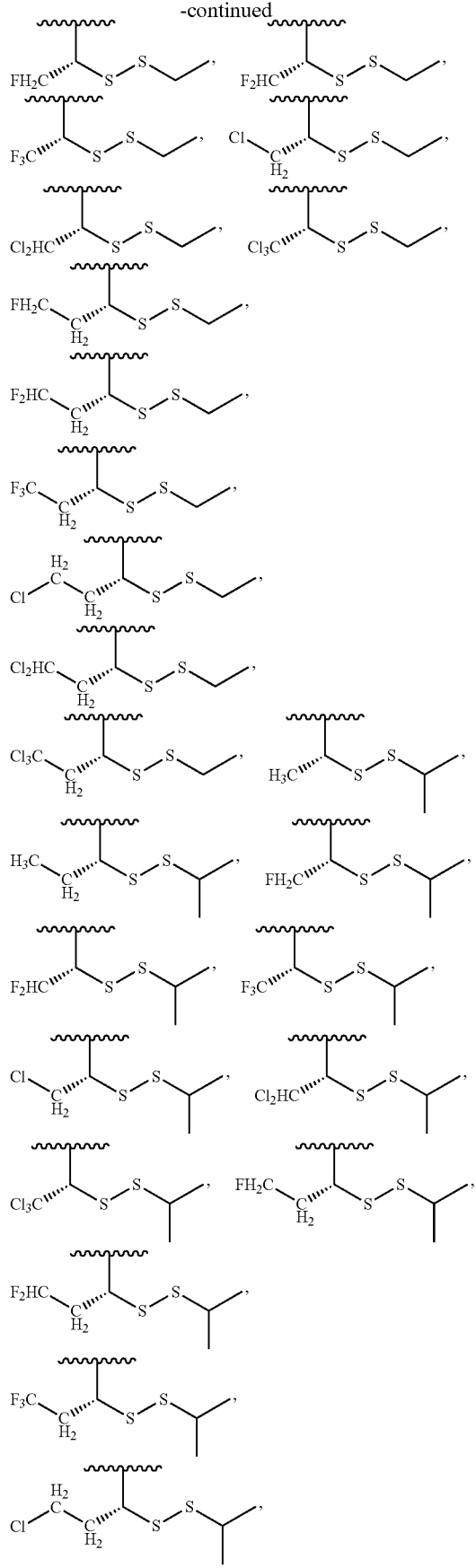
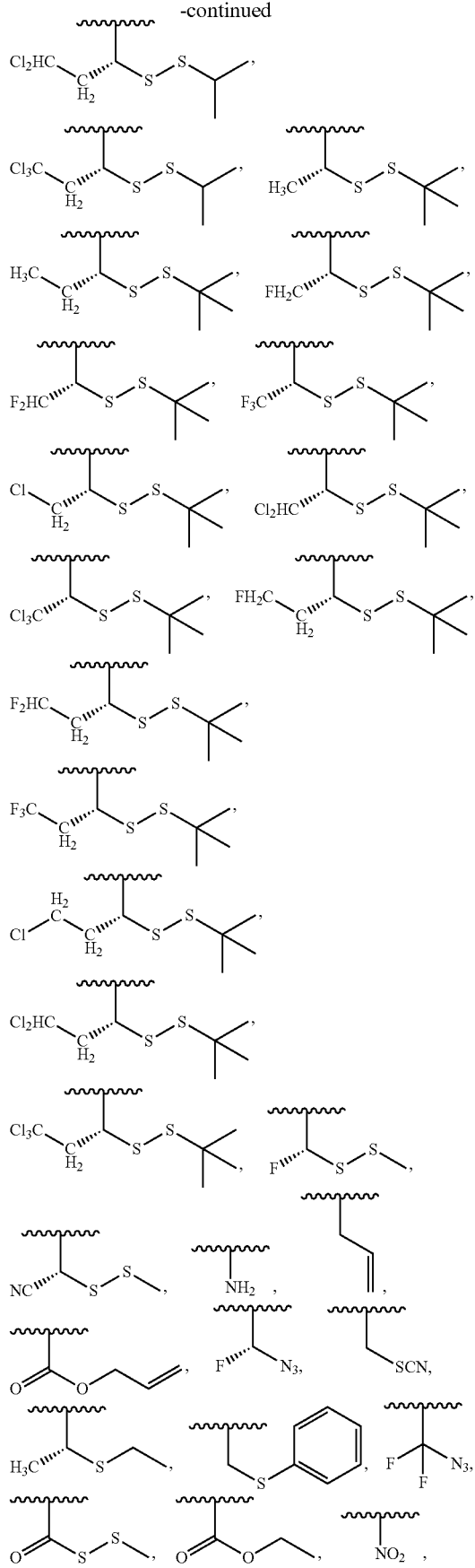

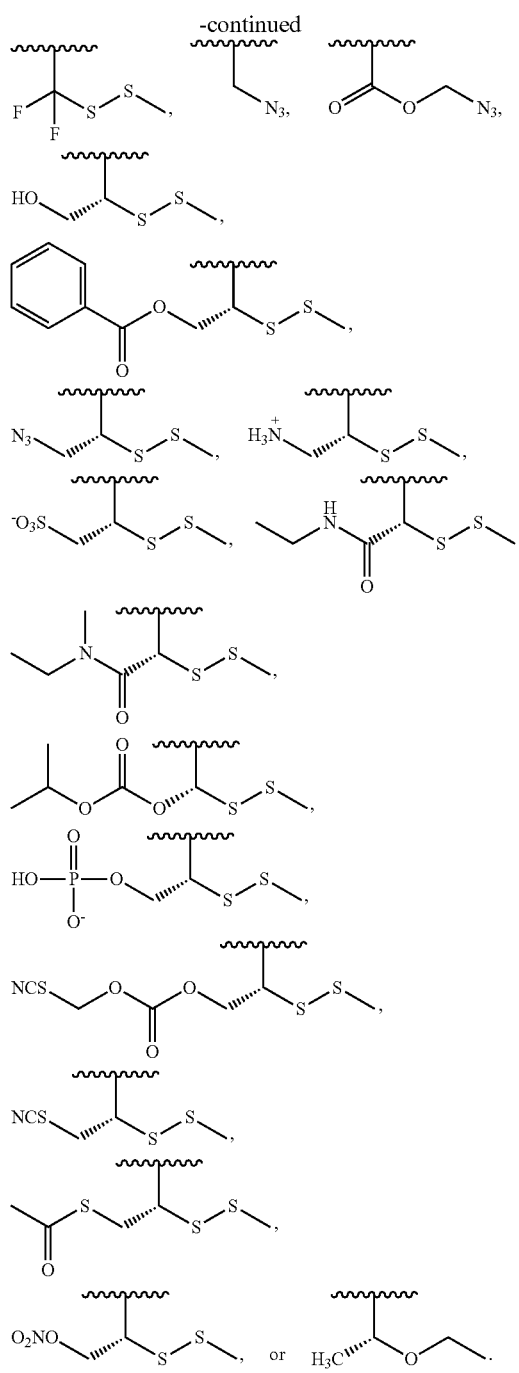
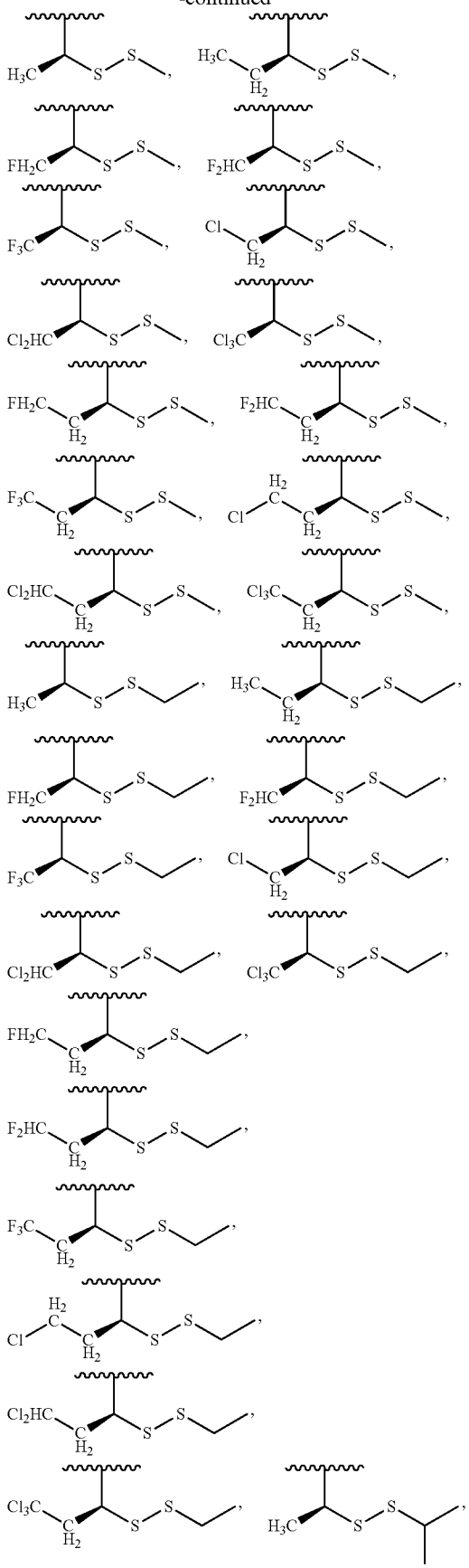
In embodiments, $R^2$ is $-OR^{2A}$.
In embodiments, $R^{2A}$ independently
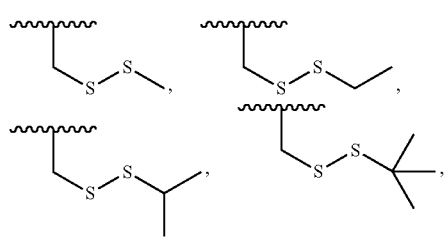

201
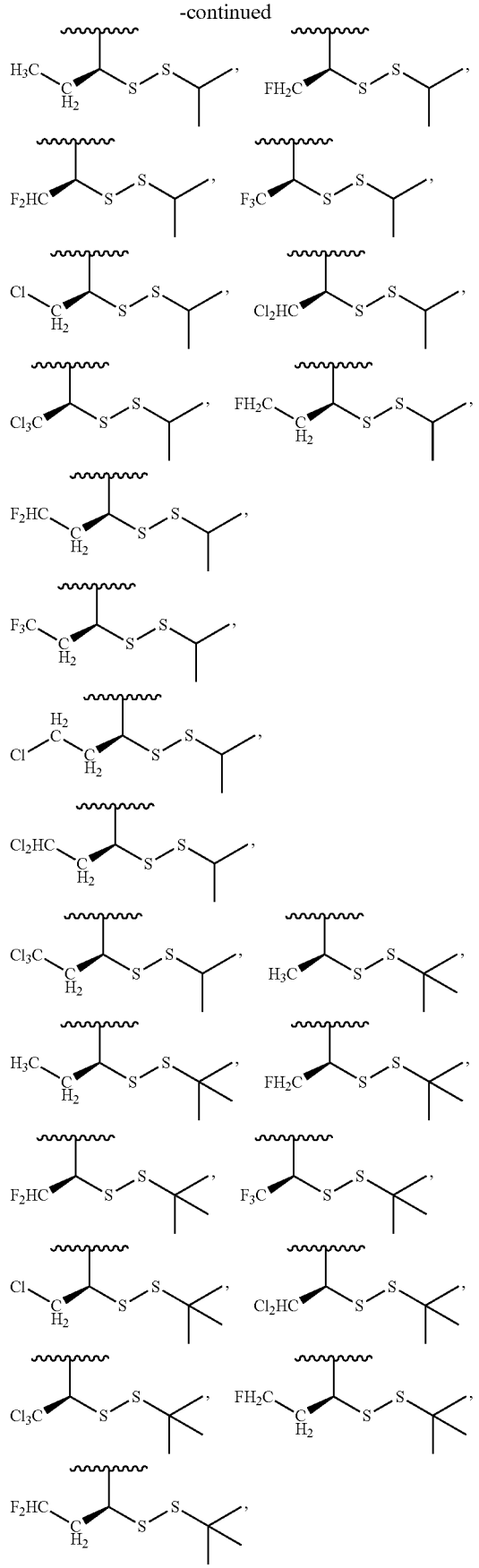
202
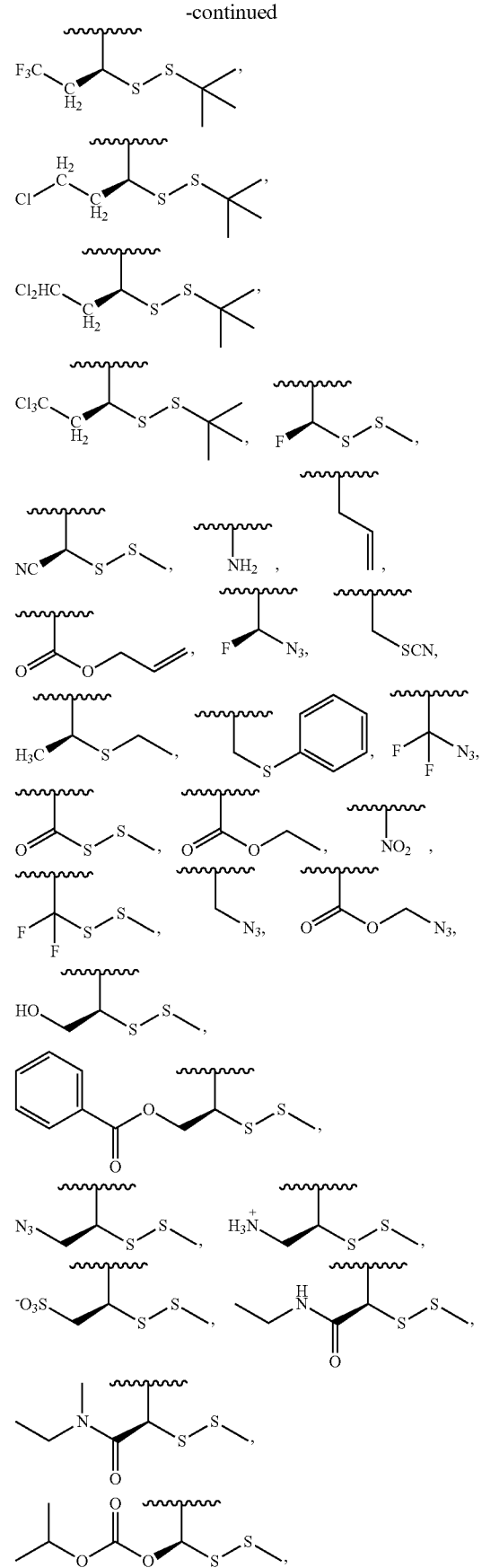

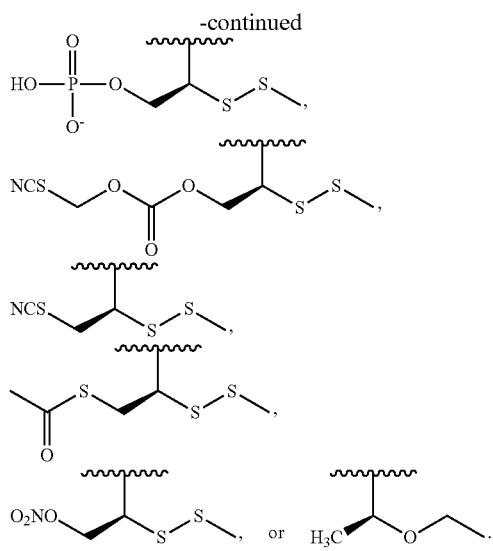
In embodiments, $R^2$ is —$OR^{2A}$.
In embodiments, $R^{2A}$ is independently:
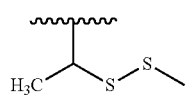
In embodiments, $R^2$ is —$OR^{2A}$.
In embodiments, $R^{2A}$ is independently
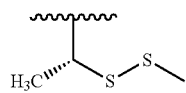
In embodiments, $R^2$ is —$OR^{2A}$.
In embodiments, $R^{2A}$ is independently
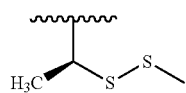
In embodiments, $R^2$ is —$OR^{2A}$.
In embodiments, the-polymerase-compatible cleavable moiety is:
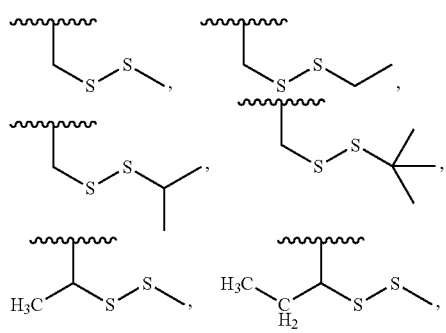
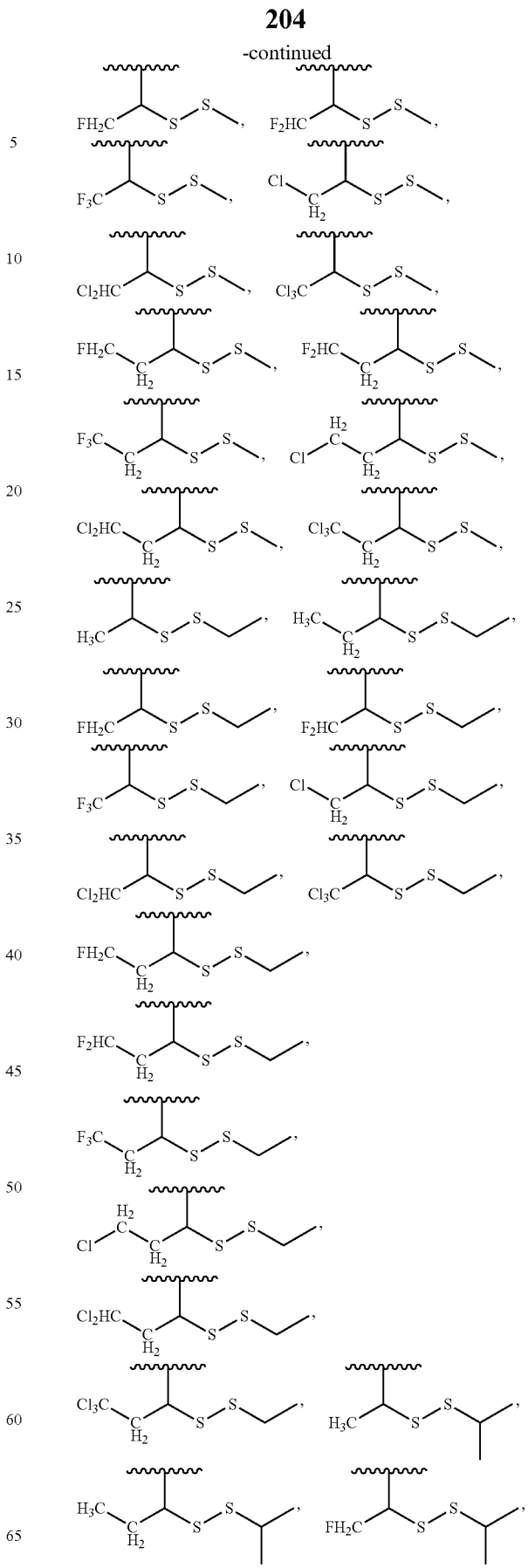

-continued
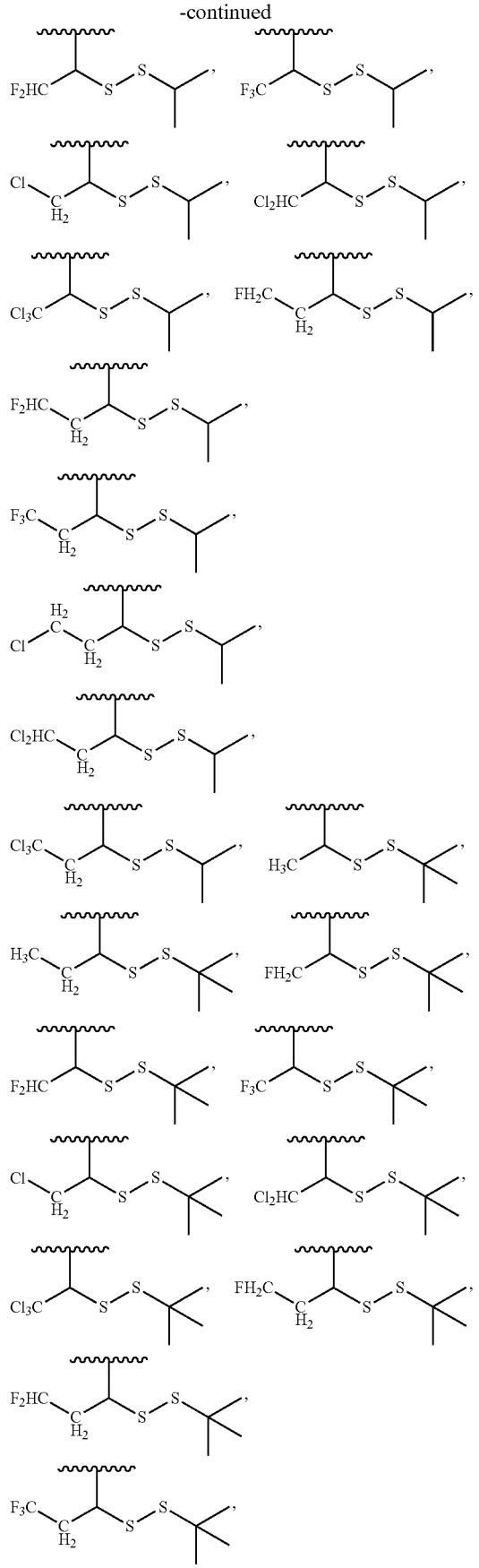
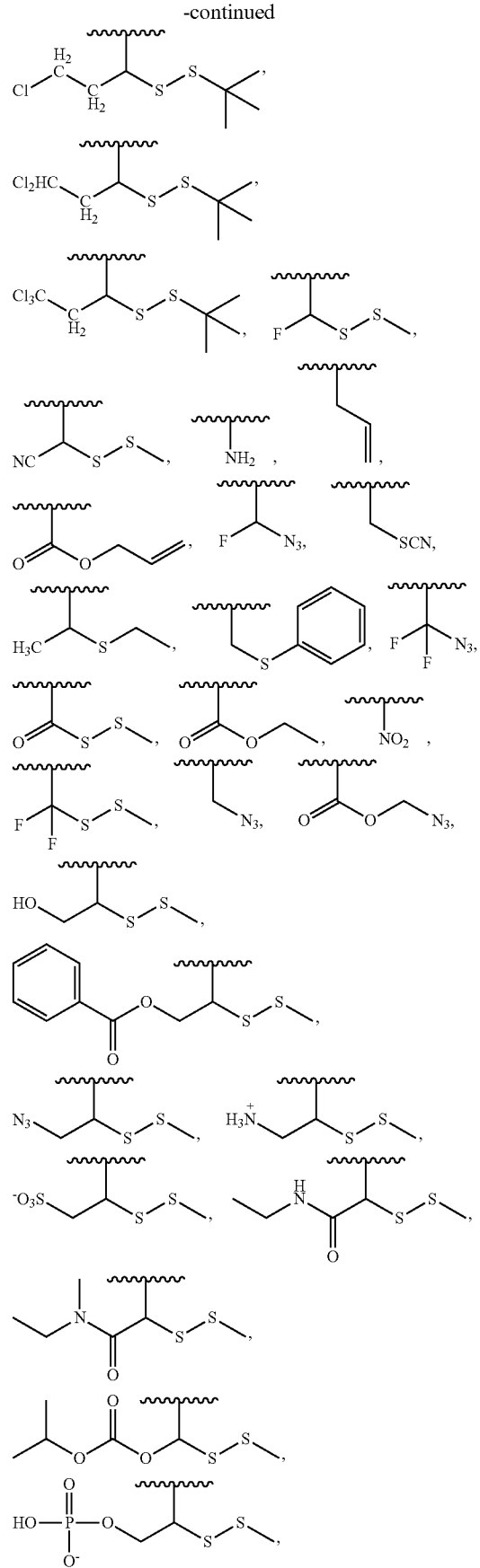

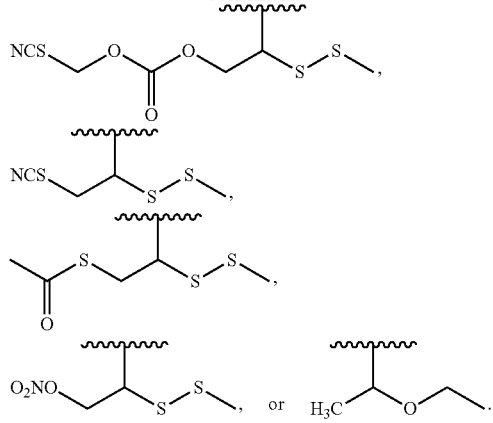
In embodiments, $R^2$ is the polymerase-compatible cleavable moiety.
In embodiments, the polymerase-compatible cleavable moiety is:
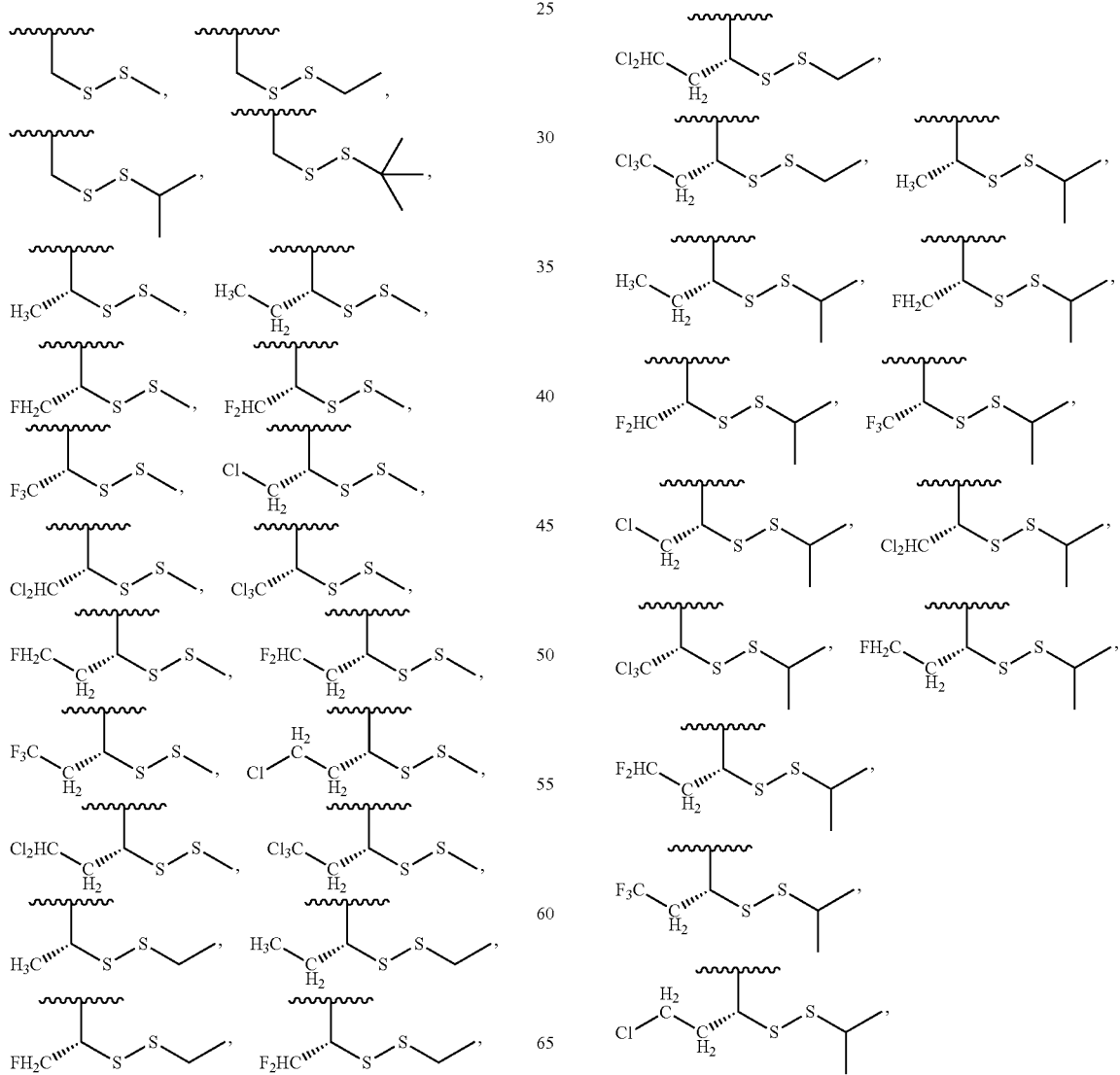

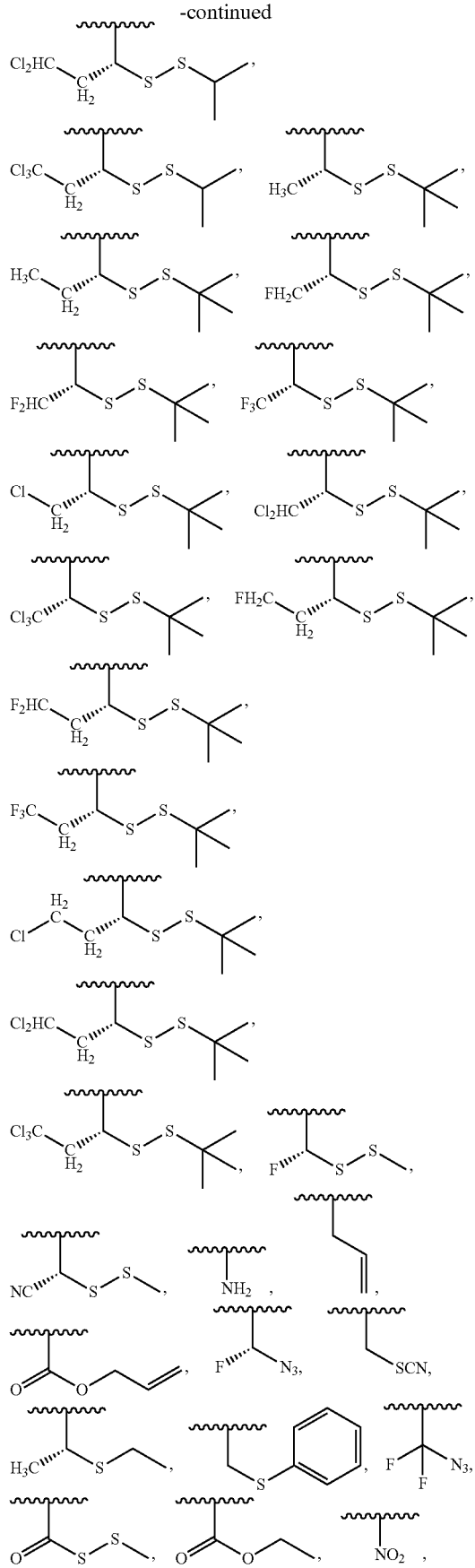
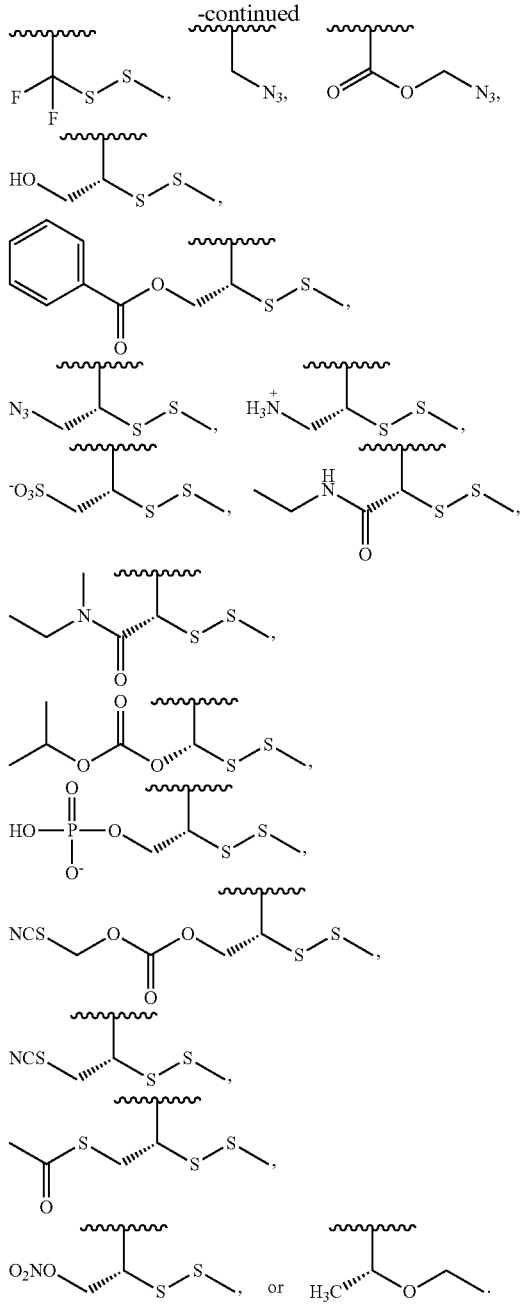
In embodiments, $R^2$ is the polymerase-compatible cleavable moiety.
In embodiments, the-polymerase-compatible cleavable moiety is:
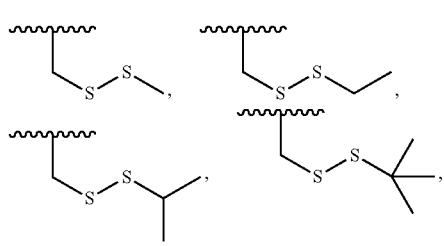

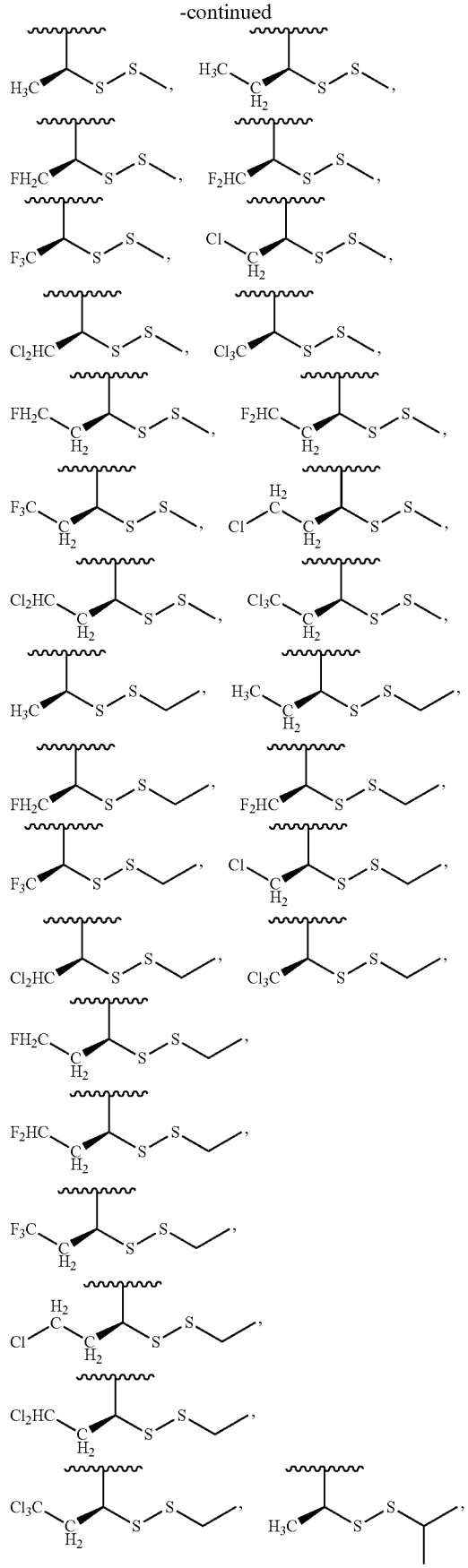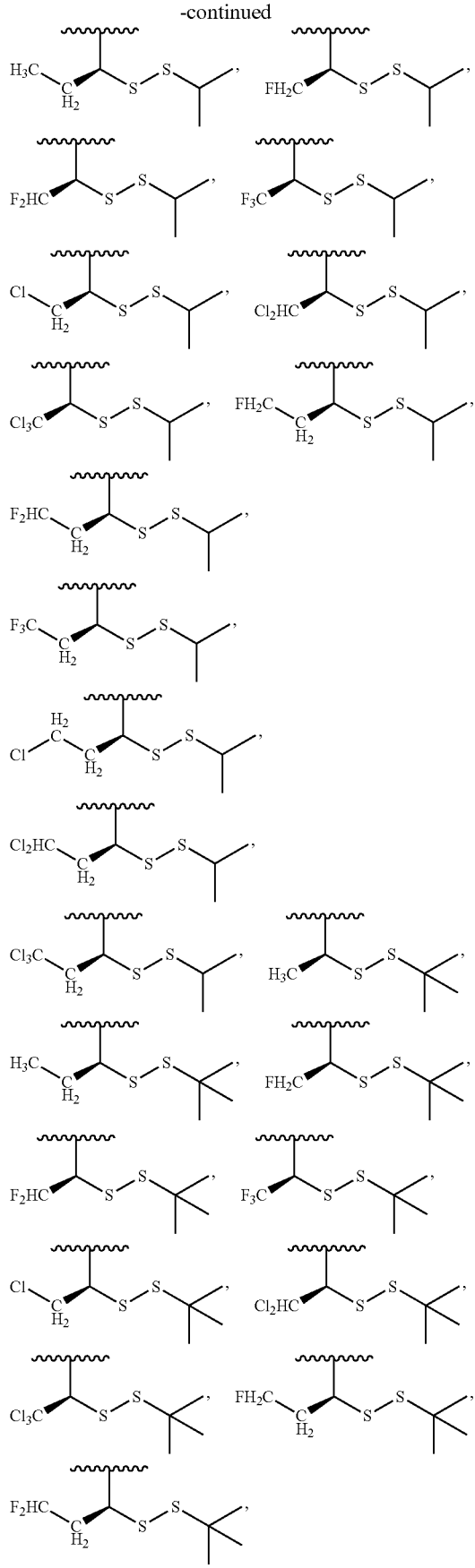

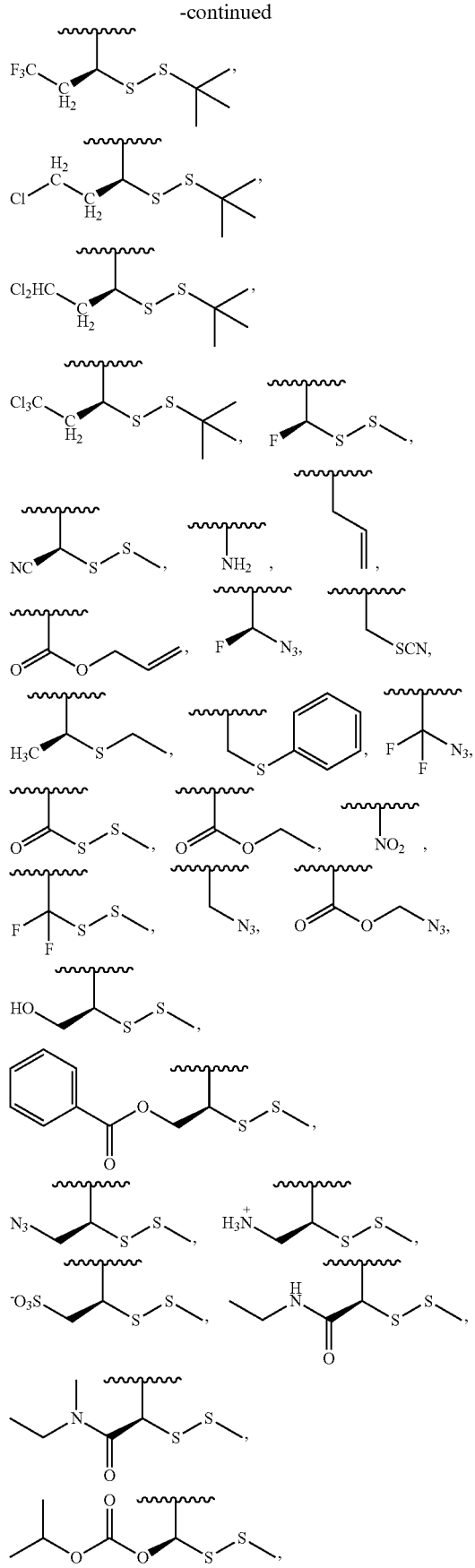

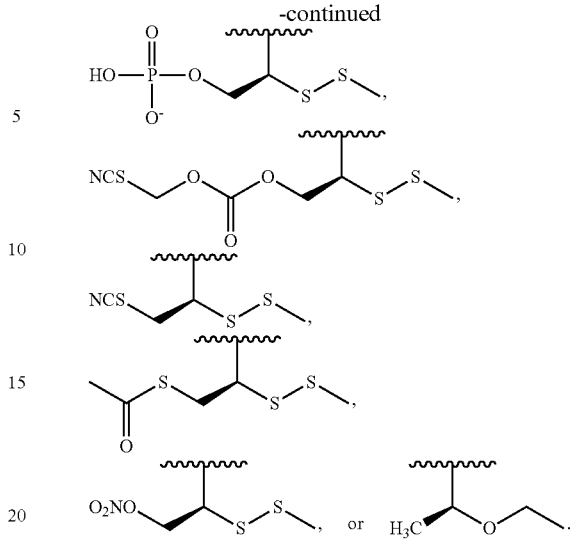

In embodiments, $R^2$ is the polymerase-compatible cleavable moiety.

In embodiments, the-polymerase-compatible cleavable moiety is:

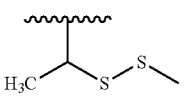

In embodiments, $R^2$ is the polymerase-compatible cleavable moiety.

In embodiments, the-polymerase-compatible cleavable moiety is:

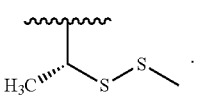

In embodiments, $R^2$ is the polymerase-compatible cleavable moiety.

In embodiments, the-polymerase-compatible cleavable moiety is:

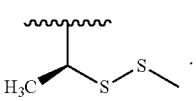

In embodiments, $R^2$ is the polymerase-compatible cleavable moiety.

In embodiments, $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof.

In embodiments, B¹ is a monovalent cytosine or a derivative thereof. In embodiments, B¹ is a monovalent guanine or a derivative thereof. In embodiments, B¹ is a monovalent adenine or a derivative thereof. In embodiments, B¹ is a monovalent thymine or a derivative thereof. In embodiments, B¹ is a monovalent uracil or a derivative thereof. In embodiments, B¹ is a monovalent hypoxanthine or a derivative thereof. In embodiments, B¹ is a monovalent xanthine or a derivative thereof. In embodiments, B¹ is a monovalent 7-methylguanine or a derivative thereof. In embodiments, B¹ is a monovalent 5,6-dihydrouracil or a derivative thereof. In embodiments, B¹ is a monovalent 5-methylcytosine or a derivative thereof. In embodiments, B¹ is a monovalent 5-hydroxymethylcytosine or a derivative thereof.

In embodiments, B¹ is a monovalent cytosine. In embodiments, B¹ is a monovalent guanine. In embodiments, B¹ is a monovalent adenine. In embodiments, B¹ is a monovalent thymine. In embodiments, B¹ is a monovalent uracil. In embodiments, B¹ is a monovalent hypoxanthine. In embodiments, B¹ is a monovalent xanthine. In embodiments, B¹ is a monovalent 7-methylguanine. In embodiments, B¹ is a monovalent 5,6-dihydrouracil. In embodiments, B¹ is a monovalent 5-methylcytosine. In embodiments, B¹ is a monovalent 5-hydroxymethylcytosine.

In embodiments, B¹ is

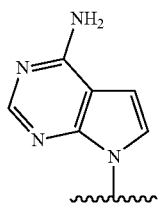 , 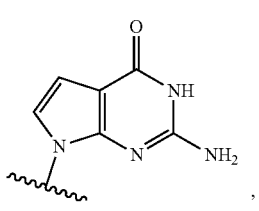 ,

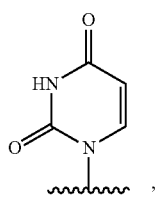 , 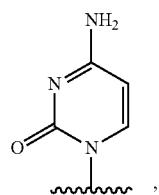 ,

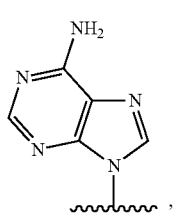 , 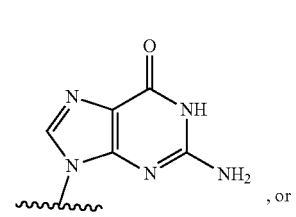 , or

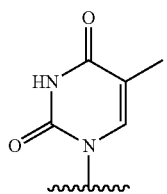 .

In embodiments, B¹ is

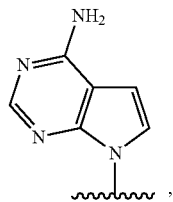 [SMILES: *n1ccc2c(N)ncnc21] ,

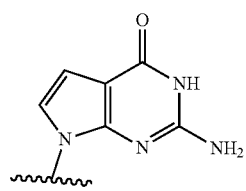 , 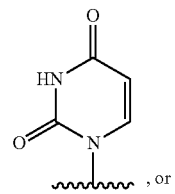 , or

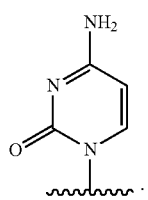 .

In embodiments, B¹ is

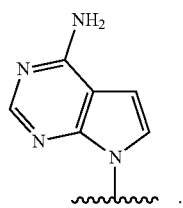 [SMILES: *n1ccc2c(N)ncnc21] .

In embodiments, B¹ is

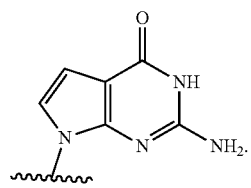 [SMILES: *n1ccc2c(=O)[nH]c(N)nc21] .

In embodiments, B¹ is

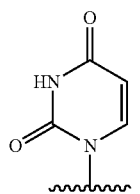 .

In embodiments, B¹ is
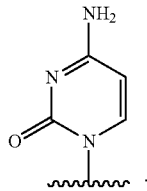 [SMILES: *n1ccc(N)nc1=O]
In embodiments, B¹ is
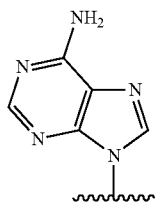
In embodiments, B¹ is
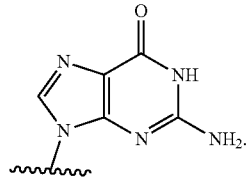 [SMILES: *n1cnc2c(=O)[nH]c(N)nc21]
In embodiments, B¹ is
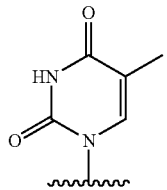
In embodiments, B¹ is
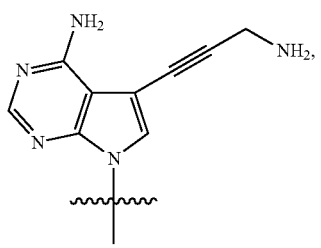 [SMILES: *n1cc(C#CCN)c2c(N)ncnc21]
-continued
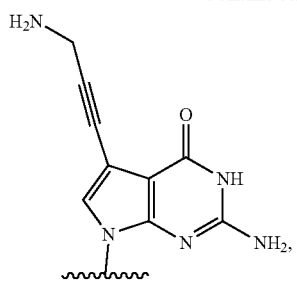 [SMILES: *n1cc(C#CCN)c2c(=O)[nH]c(N)nc21]
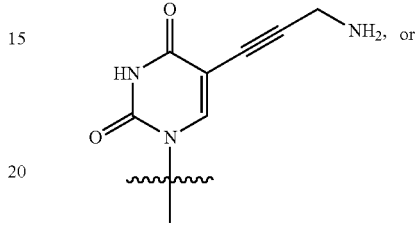, or
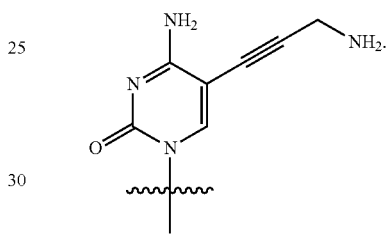
In embodiments, B¹ is
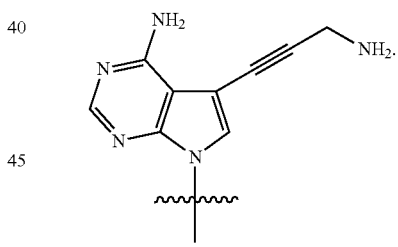
In embodiments, B¹ is
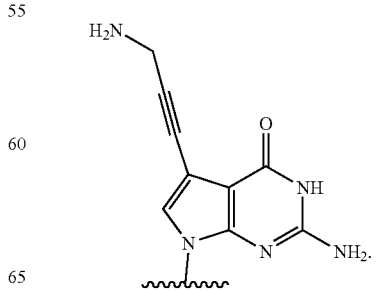

In embodiments, B¹ is
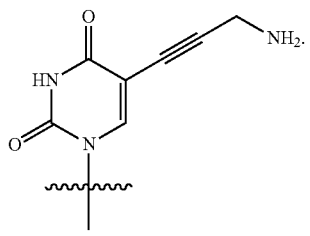 [SMILES: *n1cc(C#CCN)c(=O)[nH]c1=O]
In embodiments, B¹ is
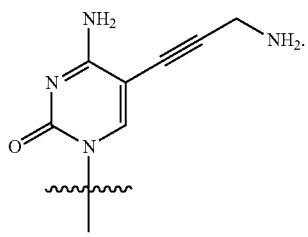 [SMILES: *n1cc(C#CCN)c(N)nc1=O]
In embodiments, B¹ is
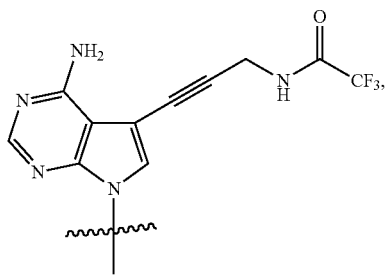 [SMILES: *n1cc(C#CCNC(=O)C(F)(F)F)c2c(N)ncnc21]
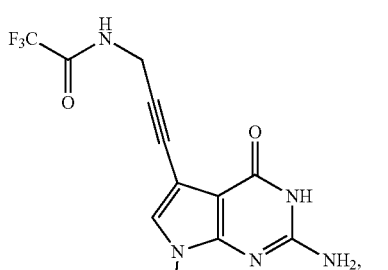
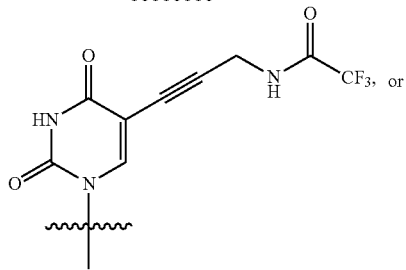
In embodiments, B¹ is
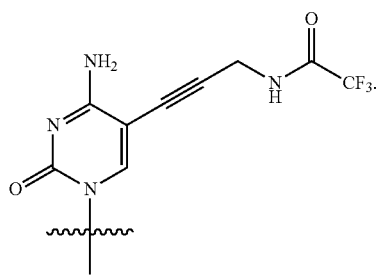 [SMILES: *n1cc(C#CCNC(=O)C(F)(F)F)c(N)nc1=O]
In embodiments, B¹ is
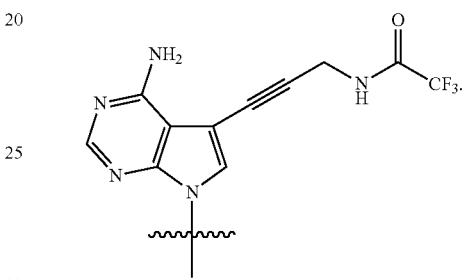
In embodiments, B¹ is
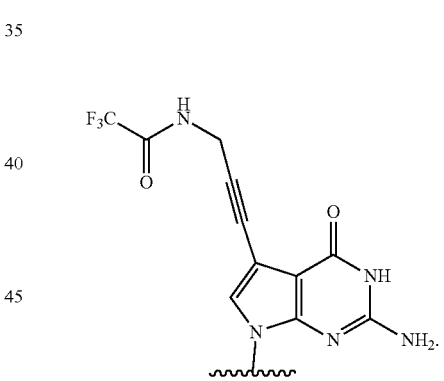
In embodiments, B¹ is
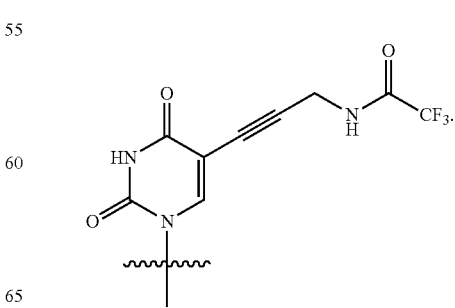

In embodiments, $B^1$ is

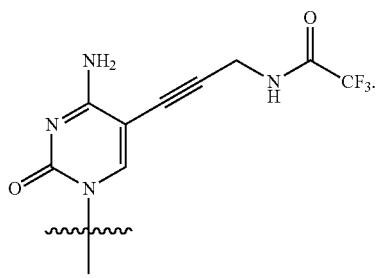

In embodiments, $B^1$ is —B-$L^{100}$-$R^4$.
B is a divalent nucleobase.
$L^{100}$ is a divalent linker.
$R^4$ is a detectable moiety.

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments, B is

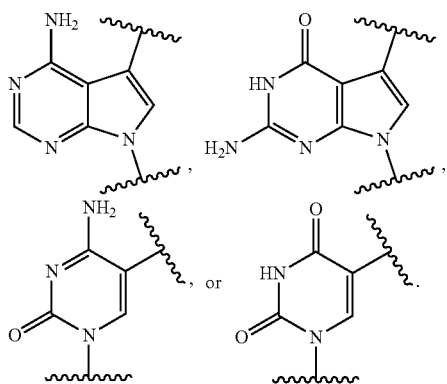

In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof.

In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine.

In embodiments, B is a divalent 5,6-dihydrouracil. In embodiments, B is a divalent 5-methylcytosine. In embodiments, B is a divalent 5-hydroxymethylcytosine.

In embodiments, B is independently

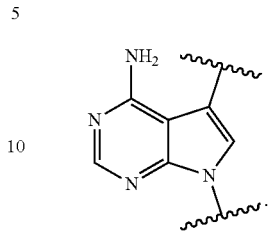

In embodiments, B is independently

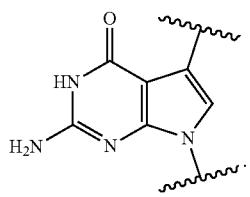 [SMILES: *c1cn(*)c2nc(N)[nH]c(=O)c12]

In embodiments, B is independently

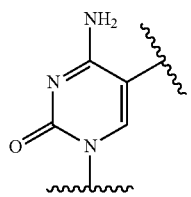

In embodiments, B is independently

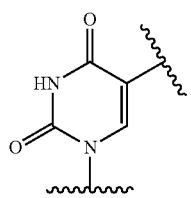

In embodiments, $L^{100}$ is -$L^{101}$-$L^{102}$-$L^{103}$-$L^{104}$-$L^{105}$-. In embodiments, $L^{100}$ is independently a bioconjugate linker; a cleavable linker, a self-immolative linker, a linker capable of dendritic amplification of signal (e.g., capable of increasing fluorescence by releasing fluorophores from the remainder of the linker, optionally wherein the fluorescence is increased following release), a trivalent linker, or a self-immolative dendrimer linker (e.g., capable of increasing fluorescence by releasing fluorophores from the remainder of the linker). In embodiments, $L^{100}$ is independently a bioconjugate linker. In embodiments, $L^{100}$ is independently a cleavable linker. In embodiments, $L^{100}$ is independently a self-immolative linker. In embodiments, $L^{100}$ is independently a linker capable of dendritic amplification of signal (e.g., capable of increasing fluorescence by releasing fluorophores). In embodiments, $L^{100}$ is independently a trivalent linker. In embodiments, $L^{100}$ is independently a self-immolative dendrimer linker (e.g., capable of increasing fluorescence by releasing fluorophores).

$L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker). In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; or a cleavable linker.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker). In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, $L^{101}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, a substituted $L^{101}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{101}$ is substituted with a plurality of groups selected from substituent groups, size-limited substituent groups, and lower substituent groups; each substituent group, size-limited substituent group, and/or lower substituent group may optionally be different. In embodiments, when $L^{101}$ is substituted, it is substituted with at least one substituent group. In embodiments, when $L^{101}$ is substituted, it is substituted with at least one size-limited substituent group. In embodiments, when $L^{101}$ is substituted, it is substituted with at least one lower substituent group. In embodiments, when $L^{101}$ is substituted, it is substituted with 1 to 10 substituent groups. In embodiments, when $L^{101}$ is substituted, it is substituted with 1 to 10 size-limited substituent groups. In embodiments, when $L^{101}$ is substituted, it is substituted with 1 to 10 lower substituent groups. In embodiments, when $L^{101}$ is substituted, it is substituted with 1 to 5 substituent groups. In embodiments, when $L^{101}$ is substituted, it is substituted with 1 to 5 size-limited substituent groups. In embodiments, when $L^{101}$ is substituted, it is substituted with 1 to 5 lower substituent groups. In embodiments, when $L^{101}$ is substituted, it is substituted with a substituent group. In embodiments, when $L^{101}$ is substituted, it is substituted with a size-limited substituent group. In embodiments, when $L^{101}$ is substituted, it is substituted with a lower substituent group.

In embodiments, $L^{102}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, a substituted $L^{102}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{102}$ is substituted with a plurality of groups selected from substituent groups, size-limited substituent groups, and lower substituent groups; each substituent group, size-limited substituent group, and/or lower substituent group may optionally be different. In embodiments, when $L^{102}$ is substituted, it is substituted with at least one substituent group. In embodiments, when $L^{102}$ is substituted, it is substituted with at least one size-limited substituent group. In embodiments, when $L^{102}$ is substituted, it is substituted with at least one lower substituent group. In embodiments, when $L^{102}$ is substituted, it is substituted with 1 to 10 substituent groups. In embodiments, when $L^{102}$ is substituted, it is substituted with 1 to 10 size-limited substituent groups. In embodiments, when $L^{102}$ is substituted, it is substituted with 1 to 10 lower substituent groups. In embodiments, when $L^{102}$ is substituted, it is substituted with 1 to 5 substituent groups. In embodiments, when $L^{102}$ is substituted, it is substituted with 1 to 5 size-limited substituent groups. In embodiments, when $L^{102}$ is substituted, it is substituted with 1 to 5 lower substituent groups. In embodiments, when $L^{112}$ is substituted, it is substituted with a substituent group. In embodiments, when $L^{102}$ is substituted, it is substituted with a size-limited substituent group. In embodiments, when $L^{102}$ is substituted, it is substituted with a lower substituent group.

In embodiments, $L^{103}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, a substituted $L^{103}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{103}$ is substituted with a plurality of groups selected from substituent groups, size-limited substituent groups, and lower substituent groups; each substituent group, size-limited substituent group, and/or lower substituent group may optionally be different. In embodiments, when $L^{103}$ is substituted, it is substituted with at least one substituent group. In embodiments, when $L^{103}$ is substituted, it is substituted with at least one size-limited substituent group. In embodiments, when $L^{103}$ is substituted, it is substituted with at least one lower substituent group. In embodiments, when $L^{103}$ is substituted, it is substituted with 1 to 10 substituent groups. In embodiments, when $L^{103}$ is substituted, it is substituted with 1 to 10 size-limited substituent groups. In embodiments, when $L^{103}$ is substituted, it is substituted with 1 to 10 lower substituent groups. In embodiments, when $L^{103}$ is substituted, it is substituted with 1 to 5 substituent groups. In embodiments, when $L^{103}$ is substituted, it is substituted with 1 to 5 size-limited substituent groups. In embodiments, when $L^{103}$ is substituted, it is substituted with 1 to 5 lower substituent groups. In embodiments, when $L^{103}$ is substituted, it is substituted with a substituent group. In embodiments, when $L^{103}$ is substituted, it is substituted with a size-limited substituent group. In embodiments, when $L^{103}$ is substituted, it is substituted with a lower substituent group.

In embodiments, $L^{104}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, a substituted $L^{104}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{104}$ is substituted with a plurality of groups selected from substituent groups, size-limited substituent groups, and lower substituent groups; each substituent group, size-limited substituent group, and/or lower substituent group may optionally be different. In embodiments, when $L^{104}$ is substituted, it is substituted with at least one substituent group. In embodiments, when $L^{104}$ is substituted, it is substituted with at least one size-limited substituent group. In embodiments, when $L^{104}$ is substituted, it is substituted with at least one lower substituent group. In embodiments, when $L^{104}$ is substituted, it is substituted with 1 to 10 substituent groups. In embodiments, when $L^{104}$ is substituted, it is substituted with 1 to 10 size-limited substituent groups. In embodiments, when $L^{104}$ is substituted, it is substituted with 1 to 10 lower substituent groups. In embodiments, when $L^{104}$ is substituted, it is substituted with 1 to 5 substituent groups. In embodiments, when $L^{104}$ is substituted, it is substituted with 1 to 5 size-limited substituent groups. In embodiments, when $L^{104}$ is substituted, it is substituted with 1 to 5 lower substituent groups. In embodiments, when $L^{104}$ is substituted, it is substituted with a substituent group. In embodiments, when $L^{104}$ is substituted, it is substituted with a size-limited substituent group. In embodiments, when $L^{104}$ is substituted, it is substituted with a lower substituent group.

In embodiments, $L^{105}$ is independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, substituted (e.g., substituted with a substituent group, size-limited substituent group, or lower substituent group) or unsubstituted alkylene (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkylene (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted arylene (e.g., $C_6$-$C_{10}$ or phenylene), or substituted (e.g., substituted with a substituent group, size-limited substituent group, or lower substituent group) or unsubstituted heteroarylene (e.g., 5 to 10 membered, 5 to 9 membered, or 5 to 6 membered); a bioconjugate linker; or a cleavable linker.

In embodiments, a substituted $L^{105}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{105}$ is substituted with a plurality of groups selected from substituent groups, size-limited substituent groups, and lower substituent groups; each substituent group, size-limited substituent group, and/or lower substituent group may optionally be different. In embodiments, when $L^{105}$ is substituted, it is substituted with at least one substituent group. In embodiments, when $L^{105}$ is substituted, it is substituted with at least one size-limited substituent group. In embodiments, when $L^{105}$ is substituted, it is substituted with at least one lower substituent group. In embodiments, when $L^{105}$ is substituted, it is substituted with 1 to 10 substituent groups. In embodiments, when $L^{105}$ is substituted, it is substituted with 1 to 10 size-limited substituent groups. In embodiments, when $L^{105}$ is substituted, it is substituted with 1 to 10 lower substituent groups. In embodiments, when $L^{105}$ is substituted, it is substituted with 1 to 5 substituent groups. In embodiments, when $L^{105}$ is substituted, it is substituted with 1 to 5 size-limited substituent groups. In embodiments, when $L^{105}$ is substituted, it is substituted with 1 to 5 lower substituent groups. In embodiments, when $L^{105}$ is substituted, it is substituted with a substituent group. In embodiments, when $L^{105}$ is substituted, it is substituted with a size-limited substituent group. In embodiments, when $L^{105}$ is substituted, it is substituted with a lower substituent group.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; or a cleavable linker.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{102}$, $L^{103}$, $L^{104}$, or $L^{105}$ is independently a bioconjugate linker. In embodiments, $L^{101}$, $L^{102}$, $L^{103}$, $L^{104}$, or $L^{105}$ is independently a cleavable linker. In embodiments, $L^{101}$, $L^{102}$, $L^{103}$, $L^{104}$, or $L^{105}$ is independently a self-immolative linker. In embodiments, $L^{101}$, $L^{102}$, $L^{103}$, $L^{104}$, or $L^{105}$ is independently a linker capable of dendritic amplification of signal (e.g., capable of increasing fluorescence by releasing fluorophores). In embodiments, $L^{101}$, $L^{102}$, $L^{103}$, $L^{104}$, or $L^{105}$ is independently a trivalent linker. In embodiments, $L^{101}$, $L^{102}$, $L^{103}$, $L^{104}$, or $L^{105}$ is independently a self-immolative dendrimer linker (e.g., capable of increasing fluorescence by releasing fluorophores).

In embodiments, $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$, $L^{102}$, $L^{103}$, $L^{104}$, and/or $L^{105}$ are independently a bond, —NH—, —S—, —O—, —C(O)—, —C(O)O—, —OC(O)—, —CH(OH)—, —NHC(O)—, —C(O)NH—, —NHC(O)NH—, —NHC(NH)NH—, —C(S)—, or —C(CH$_2$)—.

In embodiments, $L^{100}$ is -$L^{101}$-O—CH(—SR$^{100}$)-$L^{103}$-$L^{104}$-$L^{105}$- or -$L^{101}$-O—C(CH$_3$)(—SR$^{100}$)-$L^{103}$-$L^{104}$-$L^{105}$-. $R^{100}$ is —SR$^{102}$ or —CN. In embodiments, $R^{100}$ is —SR$^{102}$. In embodiments, $R^{100}$ is —CN. $R^{102}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^{100}$ is -$L^{101}$-O—CH(—SR$^{100}$)-$L^{103}$-$L^{104}$-$L^{105}$- or -$L^{101}$-O—C(CH$_3$)(—SR$^{100}$)-$L^{103}$-$L^{104}$-$L^{105}$-. $R^{100}$ is —SR$^{102}$ or —CN. In embodiments, $R^{100}$ is —SR$^{102}$. In embodiments, $R^{100}$ is —CN. In embodiments, $R^{102}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered).

In embodiments, a substituted $R^{102}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102}$ is substituted with a plurality of groups selected from substituent groups, size-limited substituent groups, and lower substituent groups; each substituent group, size-limited substituent group, and/or lower substituent group may optionally be different. In embodiments, when $R^{102}$ is substituted, it is substituted with at least one substituent group. In embodiments, when $R^{102}$ is substituted, it is substituted with at least one size-limited substituent group. In embodiments, when $R^{102}$ is substituted, it is substituted with at least one lower substituent group. In embodiments, when $R^{102}$ is substituted, it is substituted with 1 to 10 substituent groups. In embodiments, when $R^{102}$ is substituted, it is substituted with 1 to 10 size-limited substituent groups. In embodiments, when $R^{102}$ is substituted, it is substituted with 1 to 10 lower substituent groups. In embodiments, when $R^{102}$ is substituted, it is substituted with 1 to 5 substituent groups. In embodiments, when $R^{102}$ is substituted, it is substituted with 1 to 5 size-limited substituent groups. In embodiments, when $R^{102}$ is substituted, it is substituted with 1 to 5 lower substituent groups. In embodiments, when $R^{102}$ is substituted, it is substituted with a substituent group. In embodiments, when $R^{102}$ is substituted, it is substituted with a size-limited substituent group. In embodiments, when $R^{102}$ is substituted, it is substituted with a lower substituent group.

In embodiments, $L^{100}$ is -$L^{101}$-O—CH(—SSR$^{102}$)-$L^{103}$-$L^{104}$-$L^{105}$- or -$L^{101}$-O—C(CH$_3$)(—SSR$^{102}$)-$L^{103}$-$L^{104}$-$L^{105}$-.

In embodiments, $L^{100}$ is -$L^{101}$-O—CH(—SSR$^{102}$)-$L^{103}$-$L^{104}$-$L^{105}$-. In embodiments, $L^{100}$ is -$L^{101}$-O—C(CH$_3$)(—SSR$^{102}$)-$L^{103}$-$L^{104}$-$L^{105}$.

In embodiments, $L^{100}$ is -$L^{101}$-O—CH(—SCN)-$L^{103}$-$L^{104}$-$L^{105}$- or -$L^{101}$-O—C(CH$_3$)(—SCN)-$L^{103}$-$L^{104}$-$L^{105}$-.

In embodiments, $L^{100}$ is -$L^{101}$-O—CH(—SCN)-$L^{103}$-$L^{104}$-$L^{105}$-. In embodiments, $L^{100}$ is -$L^{101}$-O—C(CH$_3$)(—SCN)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is unsubstituted $C_1$-$C_4$ alkyl.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $R^{102}$ is unsubstituted $C_1$-$C_4$ alkyl.

In embodiments, $L^{100}$ is -$L^{101}$-O—CH(—SR$^{100}$)-$L^{103}$-$L^{104}$-$L^{105}$- or -$L^{101}$-O—C(CH$_3$)(—SR$^{100}$)-$L^{103}$-$L^{104}$-$L^{105}$-. In embodiments, $L^{100}$ is -$L^{101}$-O—CH(—SR$^{100}$)-$L^{103}$-$L^{104}$-$L^{105}$-. In embodiments, $L^{100}$ is -$L^{101}$-O—C(CH$_3$)(—SR$^{100}$)-$L^{103}$-$L^{104}$-$L^{105}$-.

In embodiments, $L^{100}$ is -$L^{101}$-O—CH(—SSR$^{102}$)-$L^{103}$-$L^{104}$-$L^{105}$- or -$L^{101}$-O—C(CH$_3$)(—SSR$^{102}$)-$L^{103}$-$L^{104}$-$L^{105}$. In embodiments, $L^{100}$ is -$L^{101}$-O—CH(—SSR$^{102}$)-$L^{103}$-$L^{104}$-$L^{105}$-. In embodiments, $L^{100}$ is -$L^{101}$-O—C(CH$_3$)(—SSR$^{102}$)-$L^{103}$-$L^{104}$-$L^{105}$.

In embodiments, $L^{100}$ is -$L^{101}$-O—CH(—SCN)-$L^{103}$-$L^{104}$-$L^{105}$- or -$L^{101}$-O—C(CH$_3$)(—SCN)-$L^{103}$-$L^{104}$-$L^{105}$-. In embodiments, $L^{100}$ is -$L^{101}$-O—CH(—SCN)-$L^{103}$-$L^{104}$-$L^{105}$. In embodiments, $L^{100}$ is -$L^{101}$-O—C(CH$_3$)(—SCN)-$L^{103}$-$L^{104}$-$L^{105}$.

In embodiments, $L^{101}$ is independently a substituted or unsubstituted C$_1$-C$_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; and $R^{102}$ is unsubstituted C$_1$-C$_4$ alkyl. In embodiments, $L^{101}$ is independently a substituted or unsubstituted C$_1$-C$_4$ alkylene or substituted or unsubstituted 8 to 20 membered heteroalkylene. In embodiments, $L^{103}$ is independently a bond or substituted or unsubstituted 2 to 10 membered heteroalkylene. In embodiments, $L^{104}$ is independently a bond, substituted or unsubstituted 4 to 18 membered heteroalkylene, or substituted or unsubstituted phenylene. In embodiments, $L^{105}$ is independently bond or substituted or unsubstituted 4 to 18 membered heteroalkylene.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; and $R^{102}$ is unsubstituted C$_1$-C$_4$ alkyl. In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{104}$ is unsubstituted phenylene.

In embodiments, $L^{100}$ is -$L^{101}$-O—CH(N$_3$)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted C$_1$-C$_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; and $L^{105}$ is independently bond or substituted or unsubstituted 4 to 18 membered heteroalkylene. In embodiments, $L^{101}$ is independently a substituted or unsubstituted C$_1$-C$_4$ alkylene or substituted or unsubstituted 8 to 20 membered heteroalkylene. In embodiments, $L^{101}$ is independently an oxo-substituted C$_1$-C$_4$ alkylene or an oxo-substituted 8 to 20 membered heteroalkylene. In embodiments, $L^{103}$ is independently a bond or substituted or unsubstituted 2 to 10 membered heteroalkylene. In embodiments, $L^{103}$ is independently a bond or an unsubstituted 2 to 10 membered heteroalkylene. In embodiments, $L^{104}$ is independently a bond, substituted or unsubstituted 4 to 18 membered heteroalkylene, or substituted or unsubstituted phenylene. In embodiments, $L^{105}$ is independently a bond or substituted or unsubstituted 4 to 18 membered heteroalkylene. In embodiments, $L^{105}$ is independently a bond or an oxo-substituted 4 to 18 membered heteroalkylene. In embodiments, $L^{105}$ is independently a bond or an unsubstituted 4 to 18 membered heteroalkylene.

In embodiments, $L^{100}$ is -$L^{101}$-O—CH(N$_3$)—CH$_2$—O-$L^{104}$-$L^{105}$-;

In embodiments, $L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{104}$ is unsubstituted phenylene. In embodiments, $L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$ is oxo-substituted heteroalkylene. In embodiments, $L^{104}$ is unsubstituted phenylene. In embodiments, $L^{105}$ is oxo-substituted heteroalkylene.

In embodiments, $L^{100}$ is -$L^{101}$-SS-$L^{103}$-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{103}$ is a bond or unsubstituted phenylene.

In embodiments, $L^{101}$ is independently a substituted or unsubstituted 8 to 20 membered heteroalkylene; $L^{103}$ is independently a bond or substituted or unsubstituted phenylene; $L^{104}$ is independently a bond or substituted or unsubstituted 4 to 18 membered heteroalkylene; and $L^{105}$ is independently a bond or substituted or unsubstituted 4 to 18 membered heteroalkylene. In embodiments, $L^{101}$ is independently a substituted or unsubstituted 8 to 20 membered heteroalkylene. In embodiments, $L^{101}$ is independently an oxo-substituted 8 to 20 membered heteroalkylene. In embodiments, $L^{103}$ is independently a bond. In embodiments, $L^{103}$ is independently a substituted phenylene. In embodiments, $L^{103}$ is independently an unsubstituted phenylene. In embodiments, $L^{103}$ is independently In embodiments, $L^{101}$ is independently a bond, or substituted or unsubstituted 4 to 18 membered heteroalkylene. In embodiments, $L^{104}$ is independently a bond or an oxo-substituted 4 to 18 membered heteroalkylene. In embodiments, $L^{105}$ is independently a bond or substituted or unsubstituted 4 to 18 membered heteroalkylene. In embodiments, $L^{105}$ is independently a bond or an unsubstituted 4 to 18 membered heteroalkylene.

In embodiments, $L^{100}$ is -$L^{101}$-SS—C(CH$_3$)$_2$-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 8 to 20 membered heteroalkylene; $L^{104}$ is independently a bond or substituted or unsubstituted 4 to 18 membered heteroalkylene; and $L^{105}$ is independently bond or substituted or unsubstituted 4 to 18 membered heteroalkylene. In embodiments, $L^{101}$ is independently a substituted or unsubstituted 8 to 20 membered heteroalkylene. In embodiments, $L^{101}$ is independently an oxo-substituted 8 to 20 membered heteroalkylene. In embodiments, $L^{104}$ is independently a bond, or substituted or unsubstituted 4 to 18 membered heteroalkylene. In embodiments, $L^{104}$ is independently a bond or an oxo-substituted 4 to 18 membered heteroalkylene. In embodiments, $L^{105}$ is independently a bond or substituted or unsubstituted 4 to 18 membered heteroalkylene. In embodiments, $L^{105}$ is independently a bond or an unsubstituted 4 to 18 membered heteroalkylene.

In embodiments, $L^{100}$ is -($L^{101}$)-SS-($L^{103}$)-($L^{104}$)-($L^{105}$)-. $L^{101}$, $L^{103}$, $L^{104}$, and $L^{105}$ are as described herein. In embodiments, $L^{100}$ is -($L^{101}$)-OCH(R$^{102}$)—SS-($L^{103}$)-($L^{104}$)-($L^{105}$). $L^{101}$, $L^{104}$, and $L^{105}$ are as described herein.

In embodiments, $L^{100}$ is -$L^{101}$-CH(OH)—CH(OH)-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 3 to 10 membered heteroalkylene; $L^{104}$ is independently a bond or substituted or unsubstituted 2 to 10 membered heteroalkylene; and $L^{105}$ is independently bond or substituted or unsubstituted 2 to 10 membered heteroalkylene. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{104}$ is independently a bond or substituted or unsubstituted 2 to 10 membered heteroalkylene. In embodiments, $L^{104}$ is independently a bond or oxo-substituted 2 to 10 membered heteroalkylene. In embodiments, $L^{105}$ is independently a bond or substituted or unsubstituted 2 to 10 membered heteroalkylene. In embodiments, $L^{105}$ is independently a bond or unsubstituted 2 to 10 membered heteroalkylene.

In embodiments, $L^{100}$ is -$L^{101}$-C(CH$_2$)-$L^{103}$-$L^{104}$-$L^{105}$-;

In embodiments, $L^{101}$, $L^{1013}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 3 to 10 membered heteroalkylene; $L^{103}$ is independently a bond or substituted or unsubstituted 2 to 10 membered heteroalkylene; $L^{104}$ is independently a bond or substituted or unsubstituted 2 to 10 membered heteroalkylene; and $L^{105}$ is independently bond or substituted or unsubstituted 2 to 10 membered heteroalkylene. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{103}$ is independently a bond or substituted or unsubstituted 2 to 10 membered heteroalkylene. In embodiments, $L^{103}$ is independently a bond or unsubstituted 2 to 10 membered heteroalkylene. In embodiments, $L^{104}$ is independently a bond or substituted or unsubstituted 2 to 10 membered heteroalkylene. In embodiments, $L^{104}$ is independently a bond or unsubstituted 2 to 10 membered heteroalkylene. In embodiments, $L^{105}$ is independently a bond or substituted or unsubstituted 2 to 10 membered heteroalkylene. In embodiments, $L^{105}$ is independently a bond or unsubstituted 2 to 10 membered heteroalkylene.

In embodiments, $L^{100}$ is -$L^{101}$-$L^{102}$-$L^{103}$-$L^{104}$-$L^{105}$-;

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, —N=N—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{102}$ and $L^{104}$ are substituted or unsubstituted phenylene. In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, —N=N—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{103}$ is independently —N=N—. In embodiments, $L^{102}$ is independently a substituted phenylene. In embodiments, $L^{102}$ is independently an unsubstituted phenylene. In embodiments, $L^{102}$ is independently In embodiments, $L^{104}$ is independently a substituted phenylene. In embodiments, $L^{104}$ is independently an unsubstituted phenylene. In embodiments, $L^{104}$ is independently

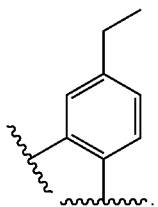

In embodiments, L¹⁰⁴ is independently

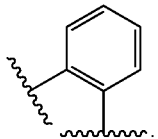

In embodiments, L¹⁰¹ is independently a substituted or unsubstituted 3 to 10 membered heteroalkylene; L¹⁰³ is independently a bond or substituted or unsubstituted 2 to 10 membered heteroalkylene; L¹⁰⁵ is independently bond or substituted or unsubstituted 5 to 16 membered heteroalkylene; and L¹⁰² and L¹⁰⁴ are substituted or unsubstituted phenylene. In embodiments, L¹⁰¹ is independently a substituted or unsubstituted 3 to 10 membered heteroalkylene. In embodiments, L¹⁰¹ is independently oxo-substituted 3 to 10 membered heteroalkylene. In embodiments, L¹⁰³ is independently a bond or substituted or unsubstituted 2 to 10 membered heteroalkylene. In embodiments, L¹⁰³ is independently a bond or substituted 2 to 10 membered heteroalkylene. In embodiments, L¹⁰³ is independently —N=N—. In embodiments, L¹⁰⁵ is independently bond or substituted or unsubstituted 5 to 16 membered heteroalkylene. In embodiments, L¹⁰⁵ is independently bond or unsubstituted 5 to 16 membered heteroalkylene. In embodiments, L¹⁰² is independently a substituted phenylene. In embodiments, L¹⁰² is independently an unsubstituted phenylene. In embodiments, L¹⁰⁴ is independently a substituted phenylene. In embodiments, L¹⁰⁴ is independently an unsubstituted phenylene.

In embodiments, L¹⁰⁰ is -L¹⁰¹-O—CH(R¹⁰²)-L¹⁰³-L¹⁰⁴-L¹⁰⁵-;

In embodiments, L¹⁰¹, L¹⁰³, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R¹⁰² is R¹⁰²ᴮ-substituted C₁-C₄ alkyl. In embodiments, L¹⁰¹, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, R¹⁰² is R¹⁰²ᴮ-substituted C₁-C₄ alkyl. R¹⁰²ᴮ is independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R¹⁰²ᴮ is independently —CN.

In embodiments, L¹⁰¹, L¹⁰³, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R¹⁰² is R¹⁰²ᴮ-substituted C₁-C₄ alkyl. In embodiments, L¹⁰¹, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, R¹⁰² is R¹⁰²ᴮ-substituted C₁-C₄ alkyl. In embodiments, R¹⁰²ᴮ is independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —N₃, unsubstituted alkyl, unsubstituted heteroalkyl, unsubstituted cycloalkyl, unsubstituted heterocycloalkyl, unsubstituted aryl, or unsubstituted heteroaryl. In embodiments, R¹⁰²ᴮ is independently —CN.

In embodiments, L¹⁰¹, L¹⁰³, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and R¹⁰² is R¹⁰²ᴮ-substituted C₁-C₄ alkyl. In embodiments, L¹⁰¹, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH₂)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, R¹⁰² is R¹⁰²ᴮ-substituted C₁-C₄ alkyl. In embodiments, R¹⁰²ᴮ is independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —N₃, unsubstituted alkyl (e.g., C₁-C₈, C₁-C₆, or C₁-C₄), unsubstituted heteroalkyl (e.g., 2 to 10 membered, 2 to 8 membered, 2 to 6 membered, or 2 to 4 membered), unsubstituted cycloalkyl (e.g., C₃-C₈, C₃-C₆, or C₅-C₆), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $R^{102B}$ is independently —CN.

In embodiments, $L^{100}$ is -$L^{101}$-O—CH(CH$_2$R$^{102}$)-$L^{103}$-$L^{104}$-$L^{105}$-;

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is independently oxo, hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_8$, $C_1$-$C_6$, or $C_1$-$C_4$), unsubstituted heteroalkyl (e.g., 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is independently oxo, hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_8$, $C_1$-$C_6$, or $C_1$-$C_4$), unsubstituted heteroalkyl (e.g., 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $R^{102}$ is independently —CN.

In embodiments, $L^{101}$ is independently a substituted or unsubstituted 3 to 10 membered heteroalkylene; $L^{103}$ is independently a bond or substituted or unsubstituted 5 to 16 membered heteroalkylene; $L^{104}$ is independently a bond or substituted or unsubstituted 5 to 16 membered heteroalkylene; $L^{105}$ is independently bond or substituted or unsubstituted 5 to 16 membered heteroalkylene; and $R^{102}$ is independently —CN. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{103}$ is independently a bond or substituted or unsubstituted 5 to 16 membered heteroalkylene. In embodiments, $L^{103}$ is independently a bond or unsubstituted 5 to 16 membered heteroalkylene. In embodiments, $L^{104}$ is independently a bond or substituted or unsubstituted 5 to 16 membered heteroalkylene. In embodiments, $L^{104}$ is independently a bond or unsubstituted 5 to 16 membered heteroalkylene. In embodiments, $L^{105}$ is independently a bond or substituted or unsubstituted 5 to 16 membered heteroalkylene. In embodiments, $L^{105}$ is independently a bond or unsubstituted 5 to 16 membered heteroalkylene. In embodiments, $R^{102}$ is independently —CN.

In embodiments, $L^{100}$ is -$L^{101}$-O—CH(CH$_2$R$^{102}$)—CH$_2$—O-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is independently oxo, hydrogen, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_8$, $C_1$-$C_6$, or $C_1$-$C_4$), unsubstituted heteroalkyl (e.g., 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $R^{102}$ is independently —CN.

In embodiments, $L^{100}$ is -$L^{101}$-O—CH(CH$_2$CN)—CH$_2$—O-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^{100}$ is
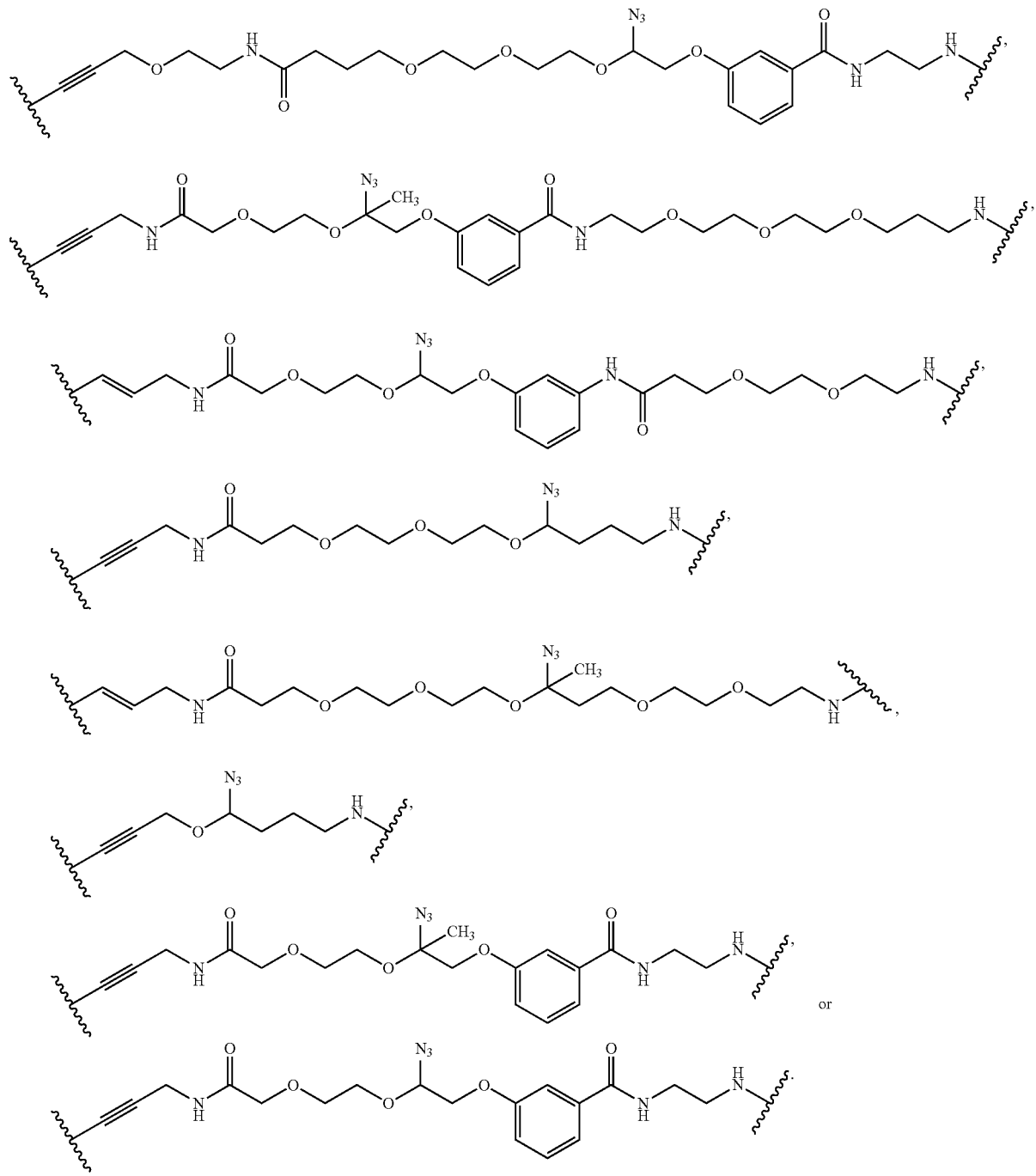
In embodiments, L$^{100}$ is
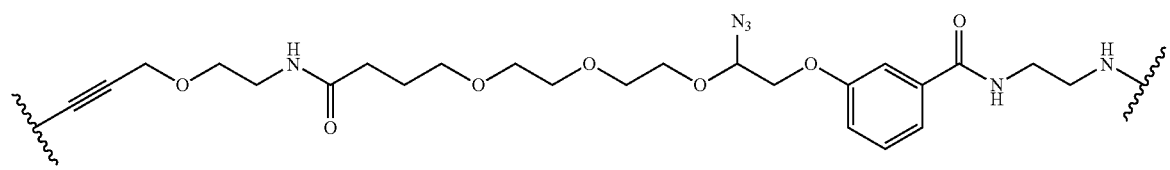 [SMILES: *C#CCOCCNC(=O)CCCOCCOCCOC(COc1cccc(C(=O)NCCN*)c1)N=[N+]=[N-]]

In embodiments, $L^{100}$ is
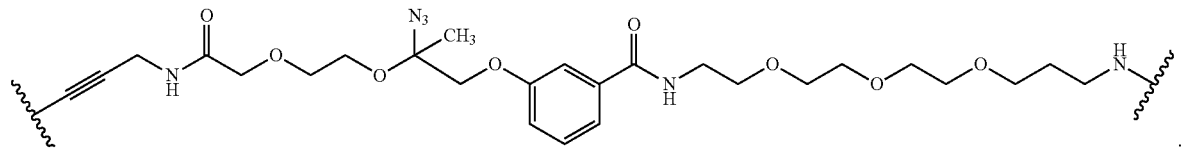 [SMILES: *C#CCNC(=O)COCCOC(C)(COc1cccc(C(=O)NCCOCCOCCOCCCN*)c1)N=[N+]=[N-]]
In embodiments, $L^{100}$ is
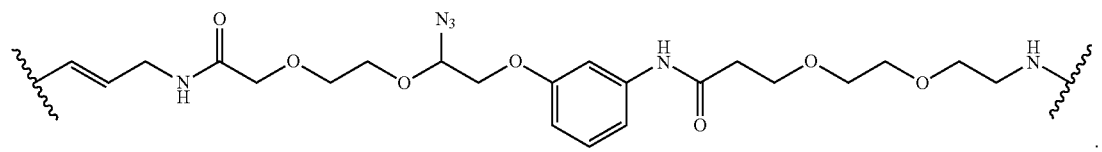 [SMILES: */C=C/CNC(=O)COCCOC(COc1cccc(NC(=O)CCOCCOCCN*)c1)N=[N+]=[N-]]
In embodiments, $L^{100}$ is
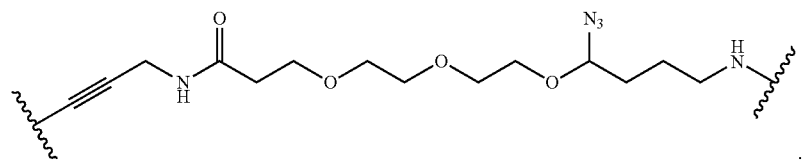 [SMILES: *C#CCNC(=O)CCOCCOCCOC(CCCN*)N=[N+]=[N-]]
In embodiments, $L^{100}$ is
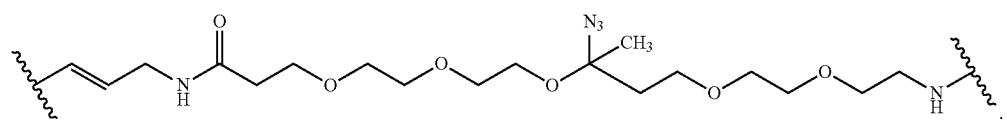 [SMILES: */C=C/CNC(=O)CCOCCOCCOC(C)(CCOCCOCCN*)N=[N+]=[N-]]
In embodiments, $L^{100}$ is
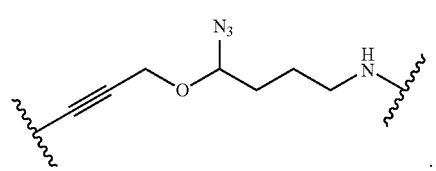 [SMILES: *C#CCOC(CCCN*)N=[N+]=[N-]]
In embodiments, $L^{100}$ is
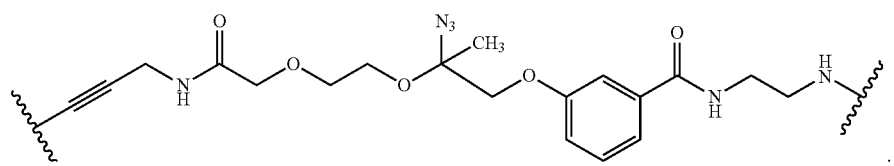 [SMILES: *C#CCNC(=O)COCCOC(C)(COc1cccc(C(=O)NCCN*)c1)N=[N+]=[N-]]

In embodiments, $L^{100}$ is
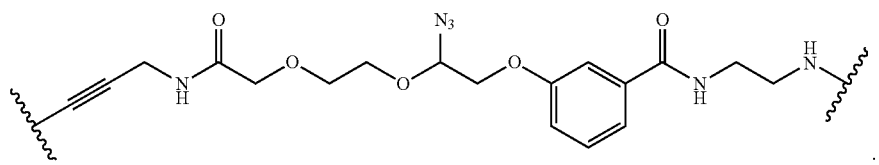 [SMILES: *C#CCNC(=O)COCCOC(COc1cccc(C(=O)NCCN*)c1)N=[N+]=[N-]]
In embodiments, $L^{100}$ is
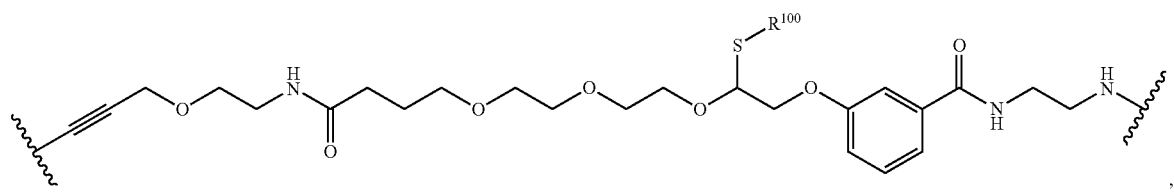
,
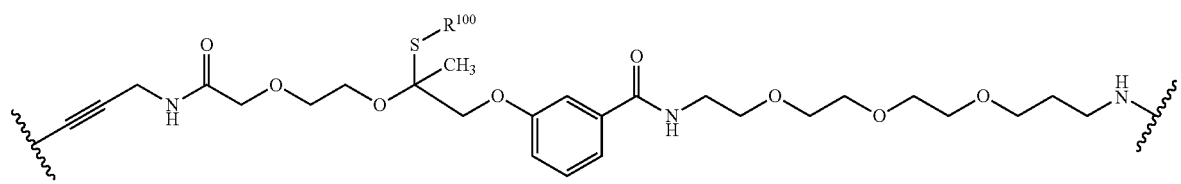
,
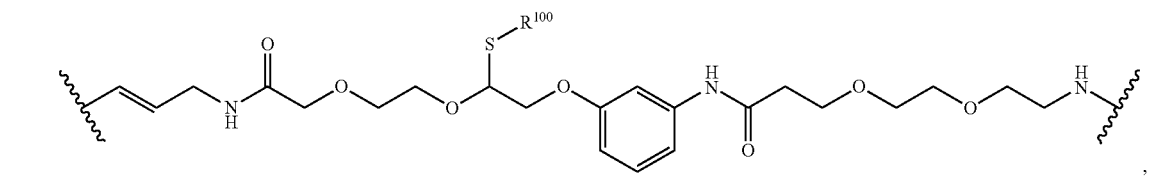
,
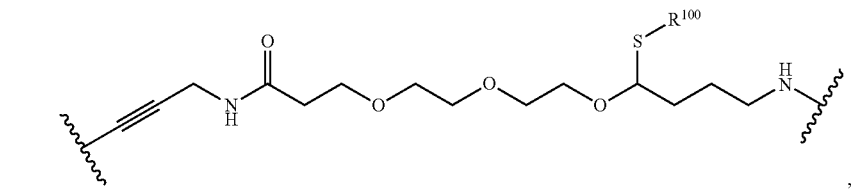
,
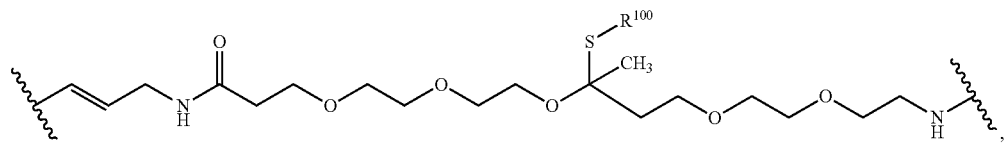
,
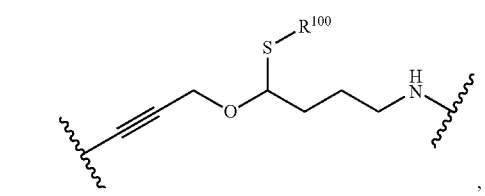
,
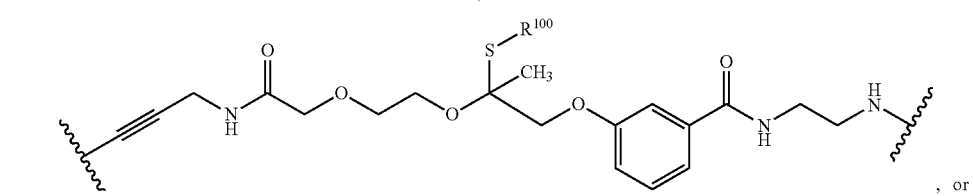
, or -continued
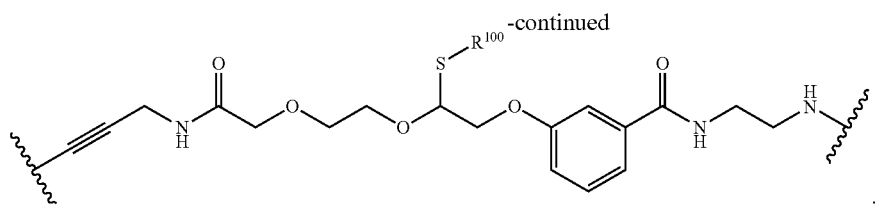
In embodiments, $L^{100}$ is
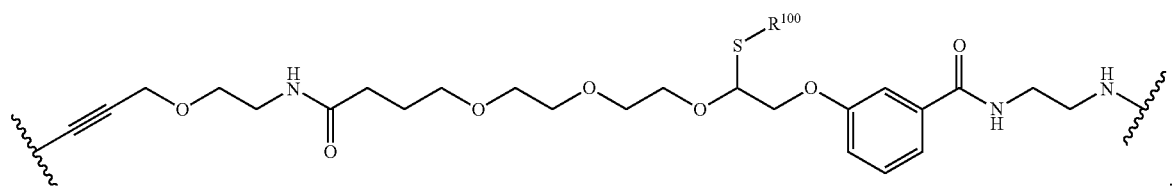
In embodiments, $L^{100}$ is
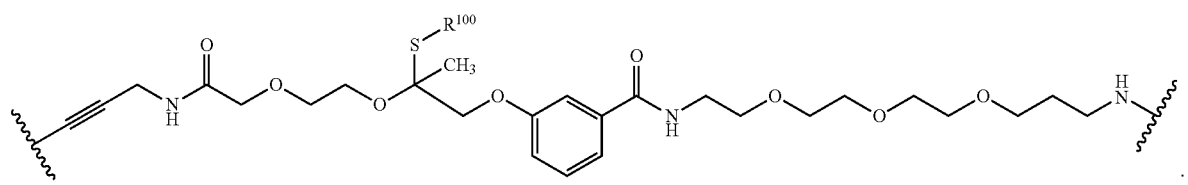
In embodiments, $L^{100}$ is
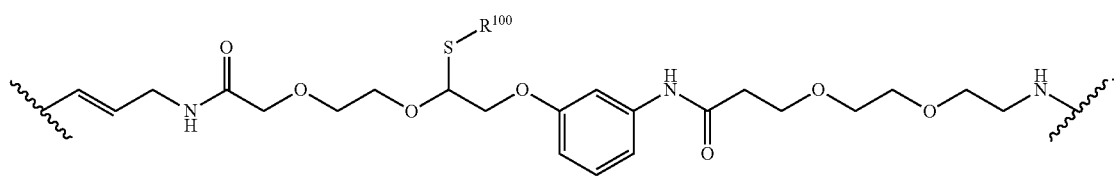
In embodiments, $L^{100}$ is
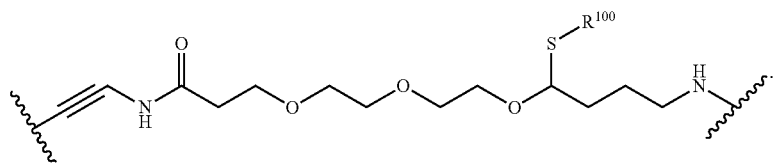
In embodiments, $L^{100}$ is
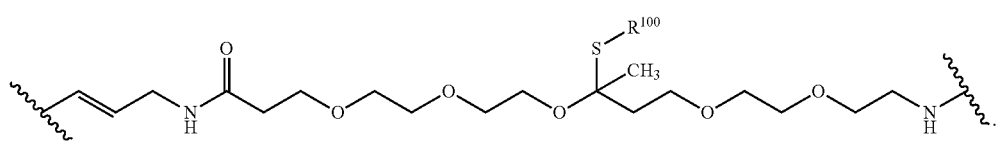

In embodiments, $L^{100}$ is
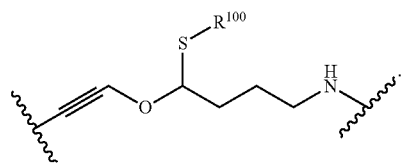
In embodiments, $L^{100}$ is
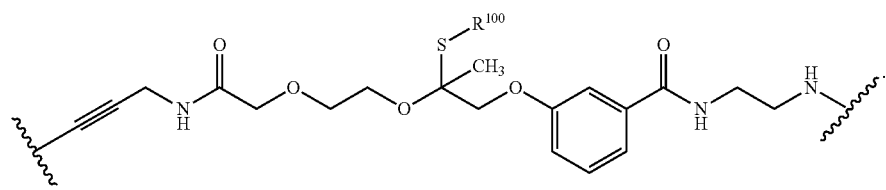
In embodiments, $L^{100}$ is
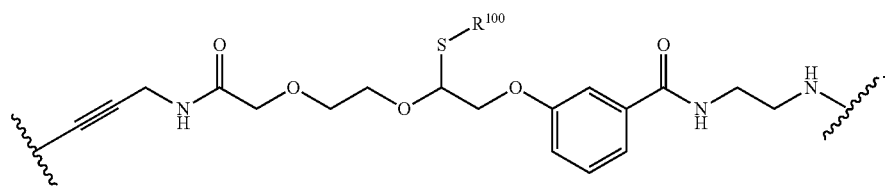
$R^{100}$ is as described herein, including in embodiments.
In embodiments, $L^{100}$ is
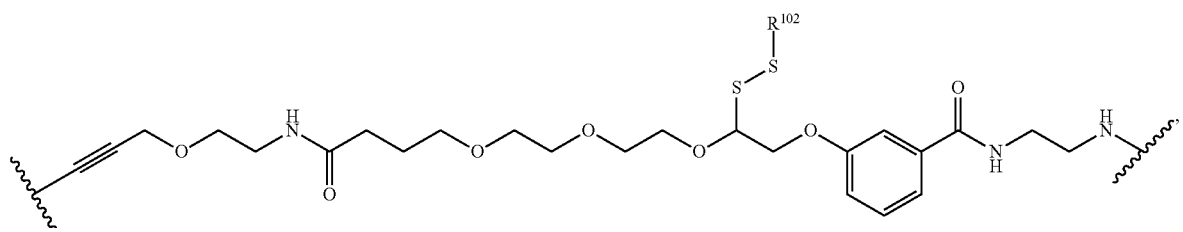
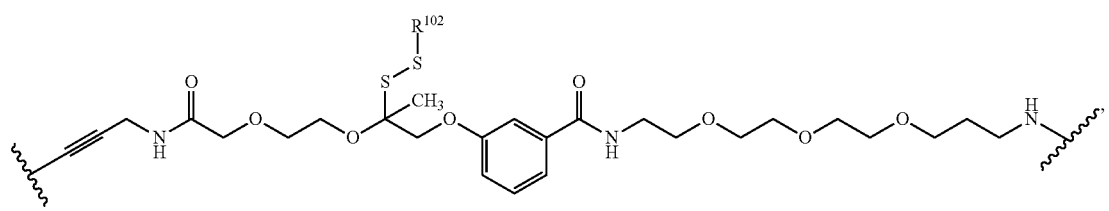
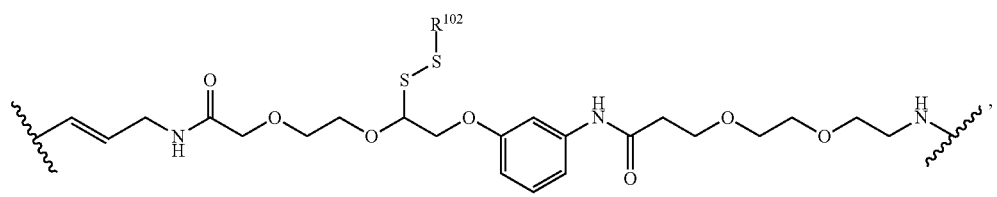

-continued
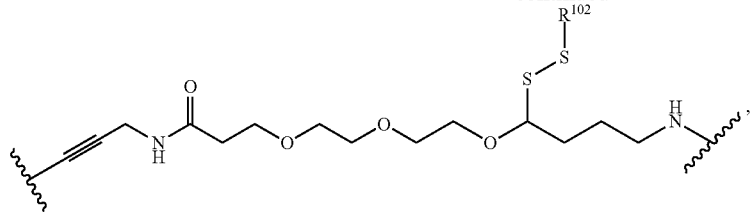
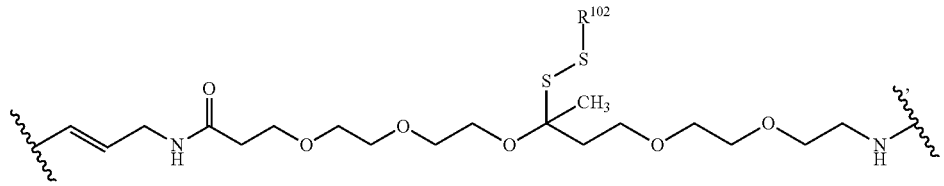
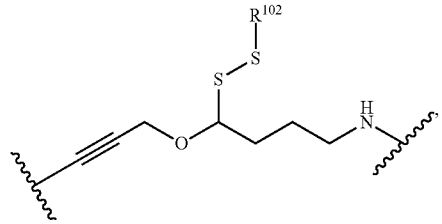
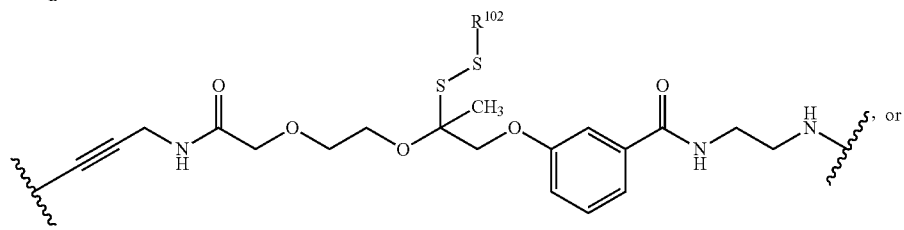
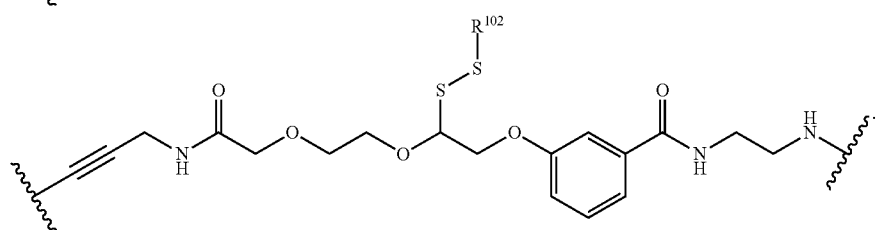
In embodiments, L$^{100}$ is
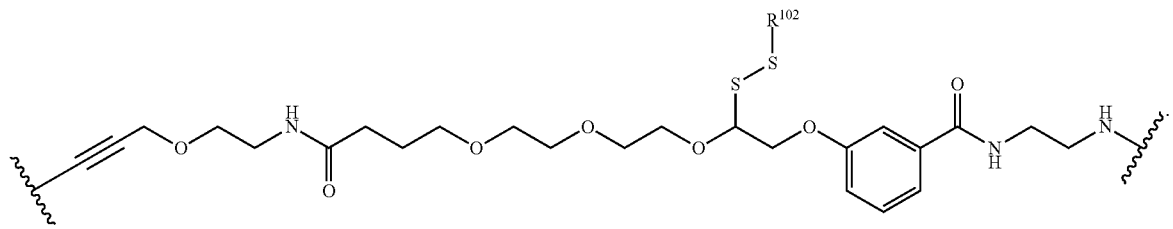
In embodiments, L$^{100}$ is
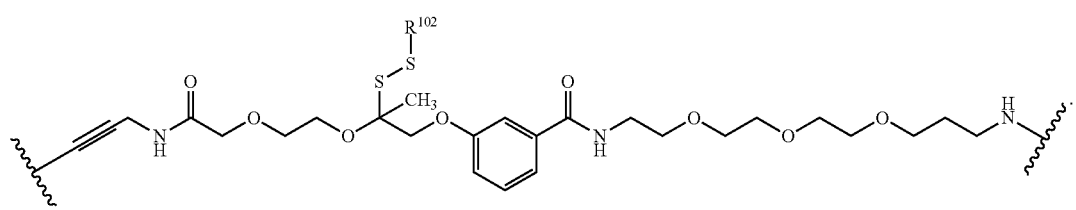

In embodiments, L$^{100}$ is
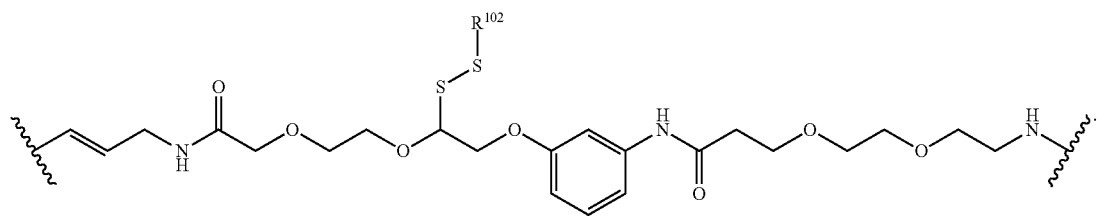
In embodiments, L$^{100}$ is
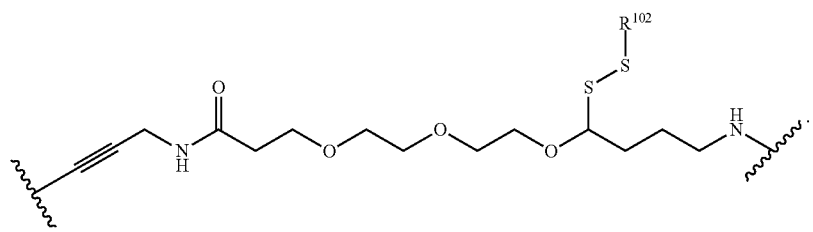
In embodiments, L$^{100}$ is
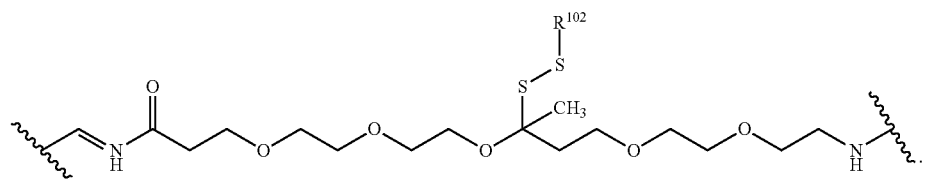
In embodiments, L$^{100}$ is
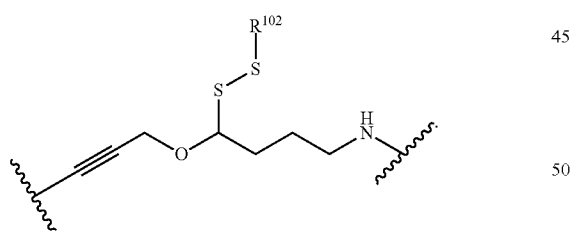
In embodiments, L$^{100}$ is
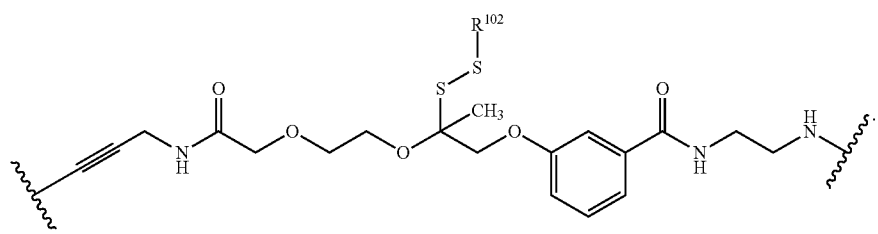

In embodiments, $L^{100}$ is
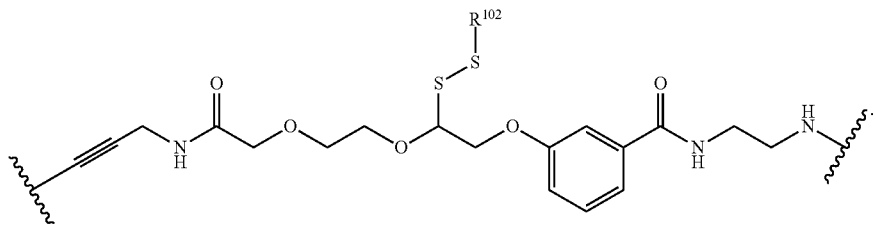
$R^{102}$ is as described herein, including in embodiments.
In embodiments, $L^{100}$ is
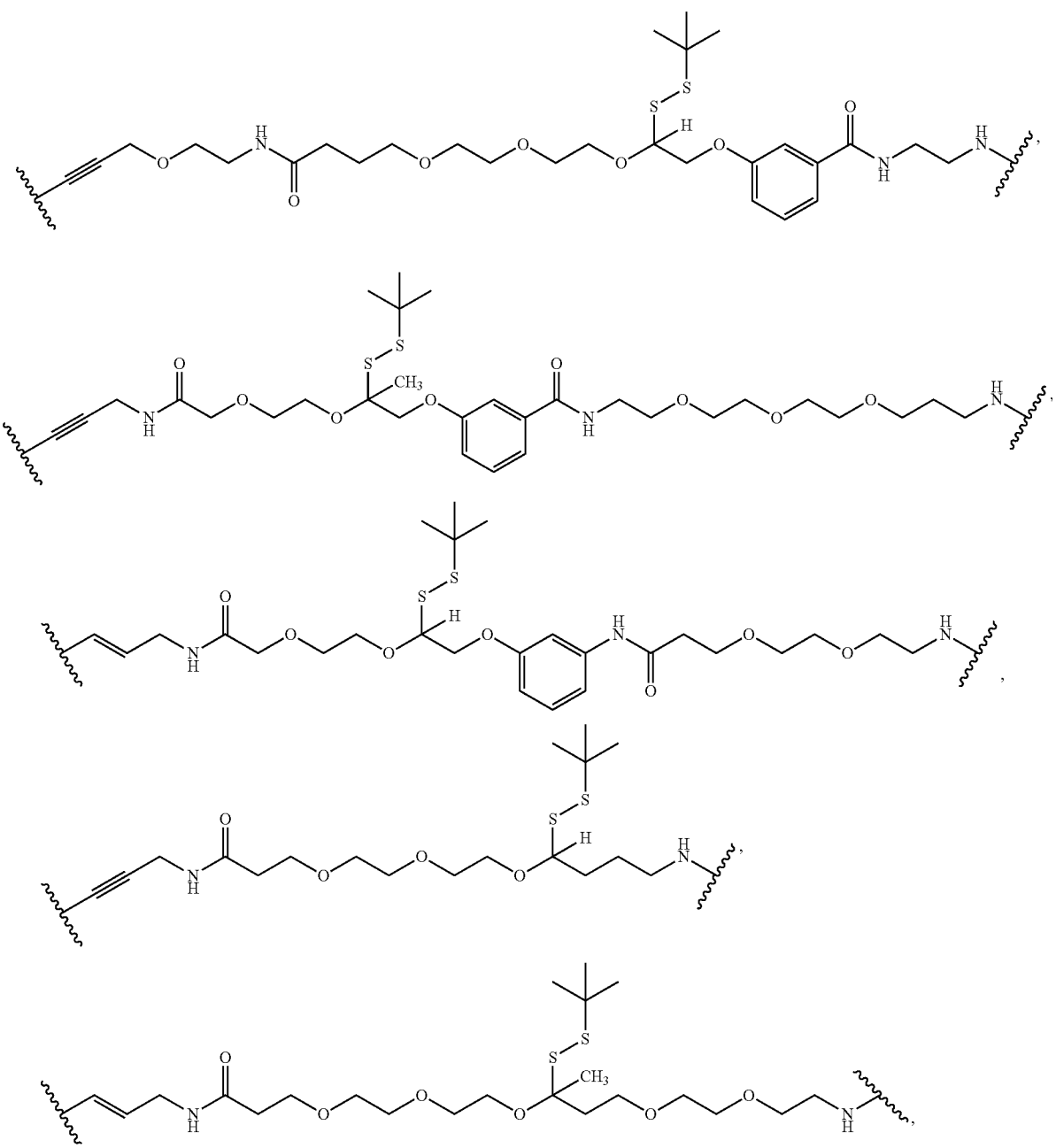

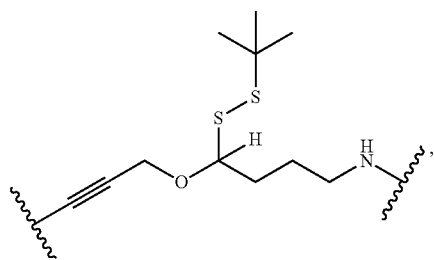
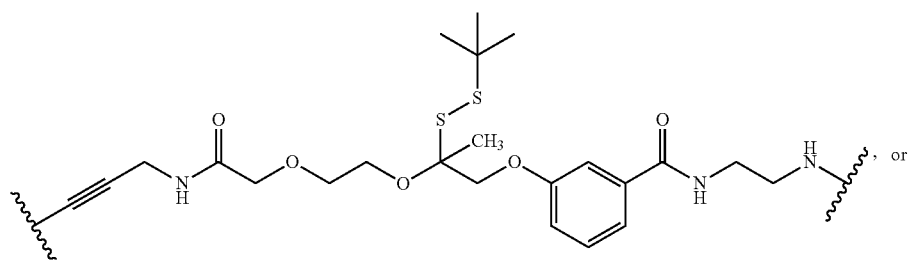
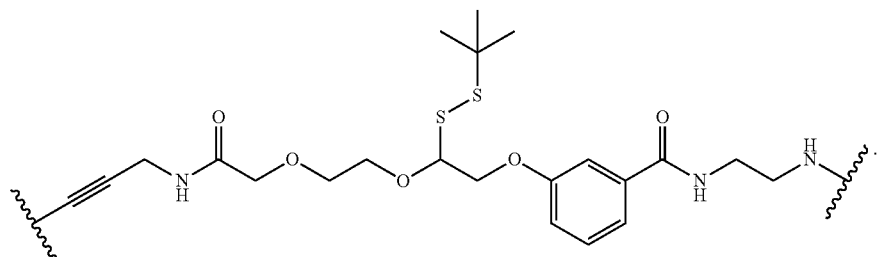 [SMILES: *C#CCNC(=O)COCCOC(COc1cccc(C(=O)NCCN*)c1)SSC(C)(C)C]
In embodiments, $L^{100}$ is
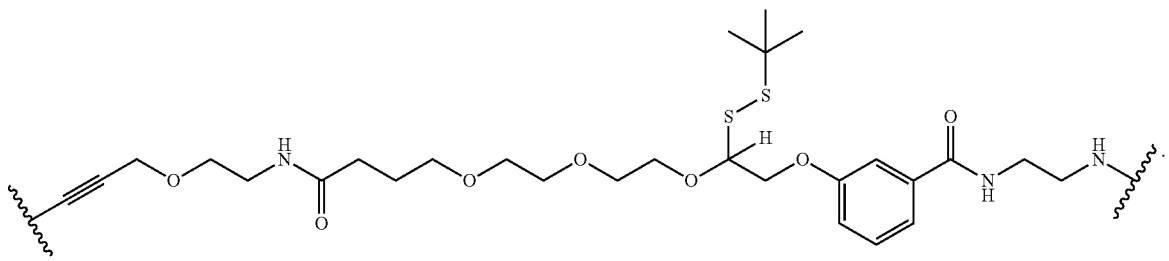 [SMILES: *C#CCOCCNC(=O)CCCOCCOCCOC(COc1cccc(C(=O)NCCN*)c1)SSC(C)(C)C]
In embodiments, $L^{100}$ is
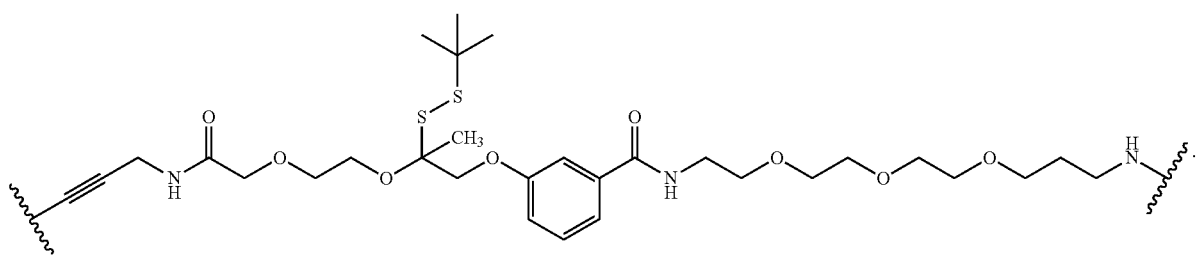 [SMILES: *C#CCNC(=O)COCCOC(C)(COc1cccc(C(=O)NCCOCCOCCOCCCN*)c1)SSC(C)(C)C]

In embodiments, $L^{100}$ is
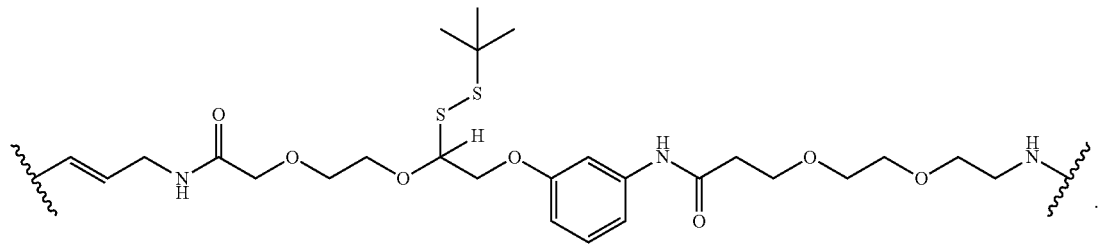 [SMILES: */C=C/CNC(=O)COCCOC(COc1cccc(NC(=O)CCOCCOCCN*)c1)SSC(C)(C)C]
In embodiments, $L^{100}$ is
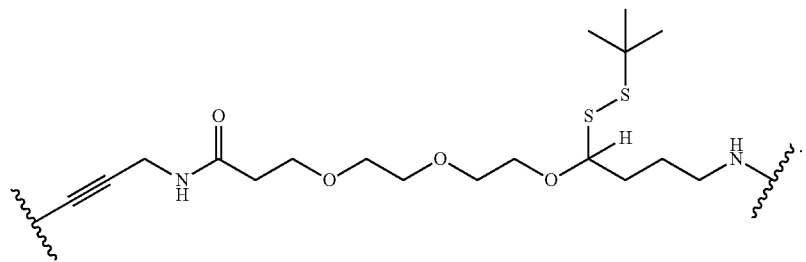 [SMILES: *C#CCNC(=O)CCOCCOCCOC(CCCN*)SSC(C)(C)C]
In embodiments, $L^{100}$ is
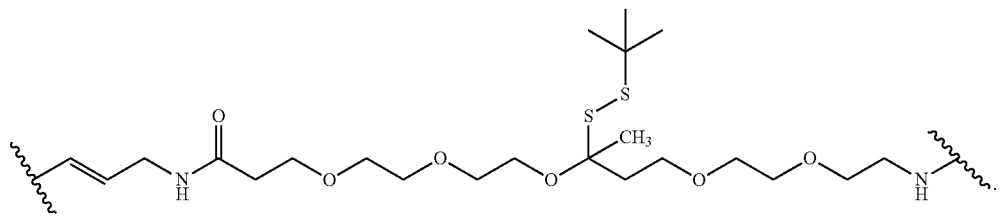 [SMILES: */C=C/CNC(=O)CCOCCOCCOC(C)(CCOCCOCCN*)SSC(C)(C)C]
In embodiments, $L^{100}$ is
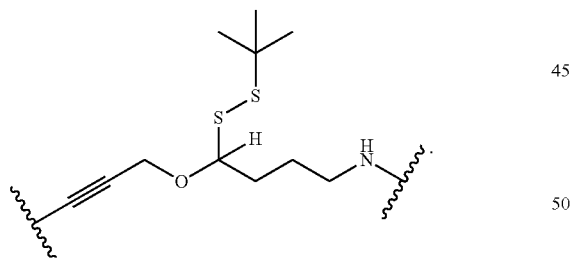
In embodiments, $L^{100}$ is
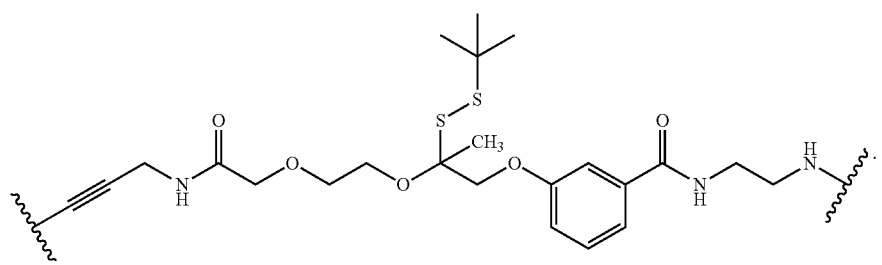 [SMILES: *C#CCNC(=O)COCCOC(C)(COc1cccc(C(=O)NCCN*)c1)SSC(C)(C)C]

In embodiments, L$^{100}$ is
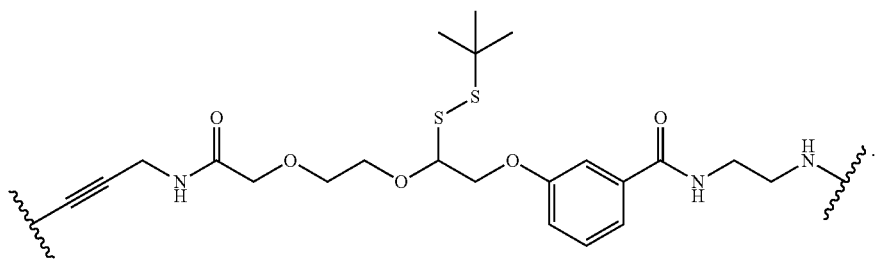 [SMILES: *C#CCNC(=O)COCCOC(COc1cccc(C(=O)NCCN*)c1)SSC(C)(C)C]
In embodiments, L$^{100}$ is
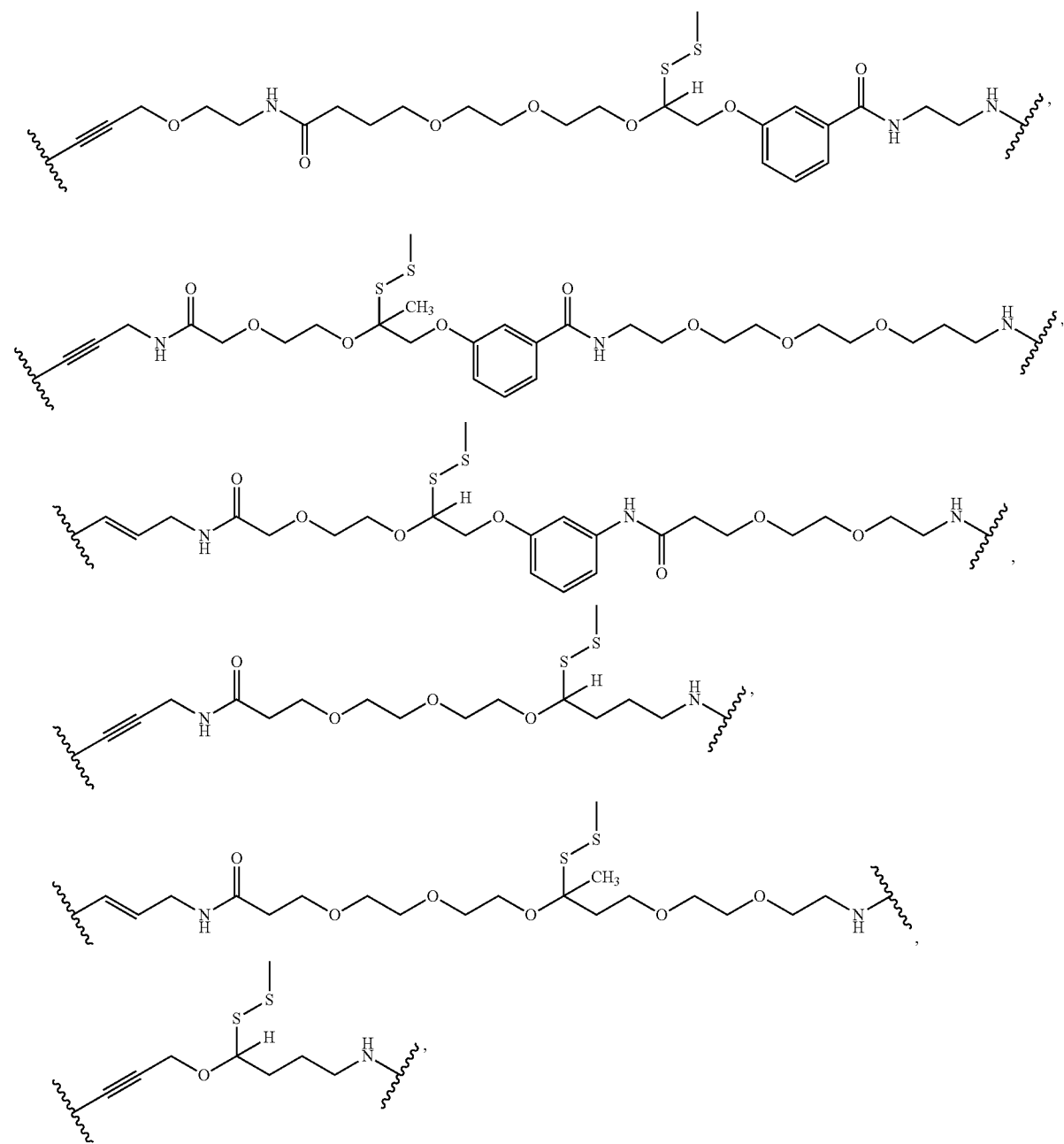

-continued
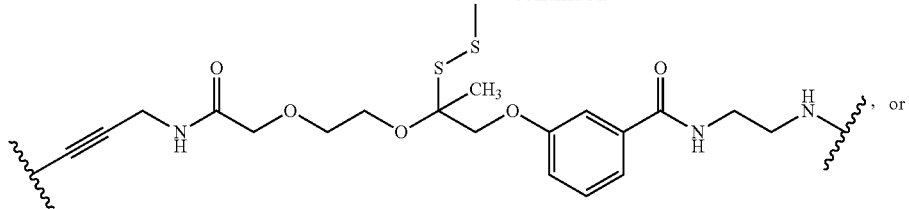, or
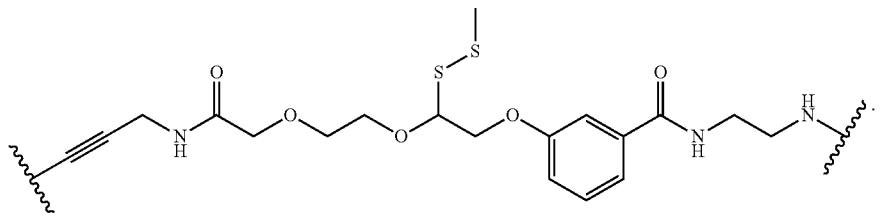
In embodiments, $L^{100}$ is
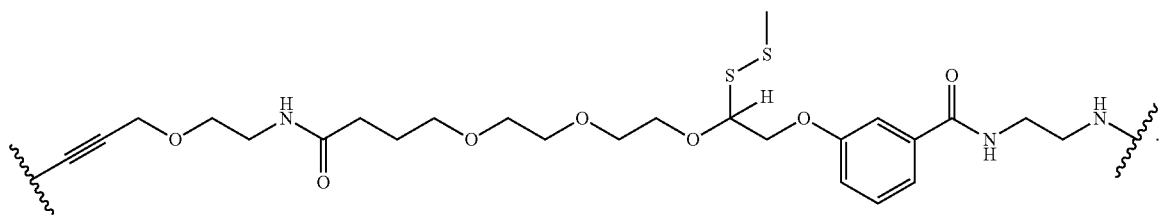 [SMILES: *C#CCOCCNC(=O)CCCOCCOCCOC(COc1cccc(C(=O)NCCN*)c1)SSC]
In embodiments, $L^{100}$ is
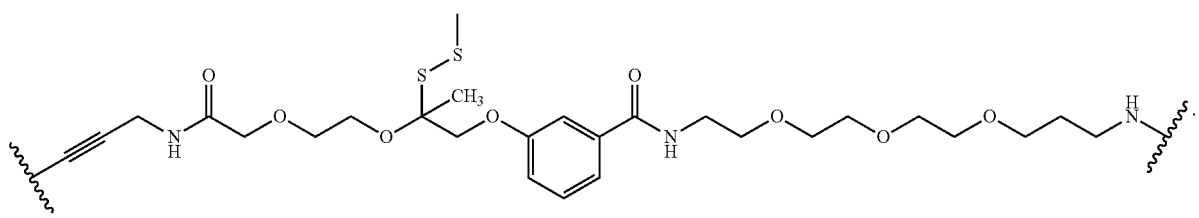 [SMILES: *C#CCNC(=O)COCCOC(C)(COc1cccc(C(=O)NCCOCCOCCOCCCN*)c1)SSC]
In embodiments, $L^{100}$ is
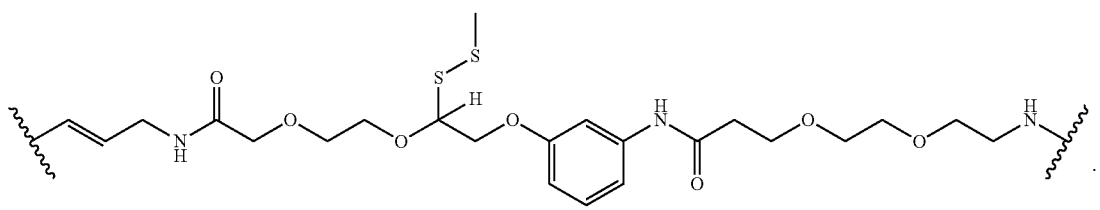 [SMILES: */C=C/CNC(=O)COCCOC(COc1cccc(NC(=O)CCOCCOCCN*)c1)SSC]
In embodiments, $L^{100}$ is
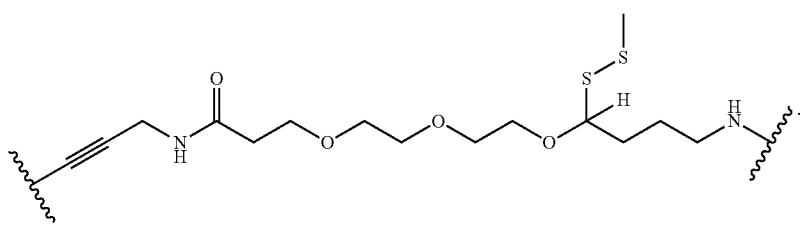 [SMILES: *C#CCNC(=O)CCOCCOCCOC(CCCN*)SSC]

In embodiments, $L^{100}$ is
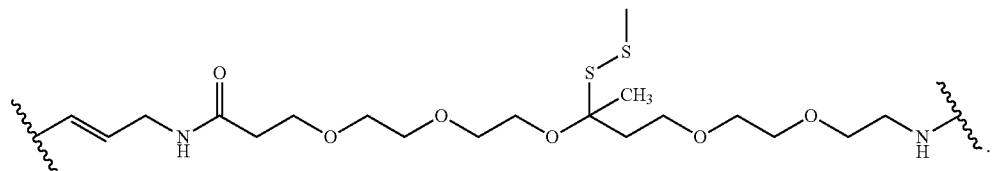 [SMILES: */C=C/CNC(=O)CCOCCOCCOC(C)(CCOCCOCCN*)SSC]
In embodiments, $L^{100}$ is
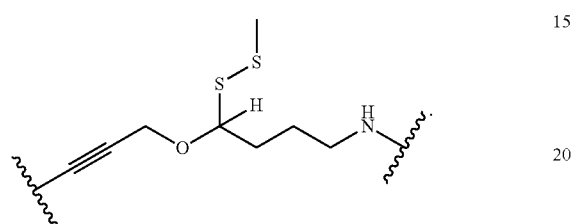
In embodiments, $L^{100}$ is
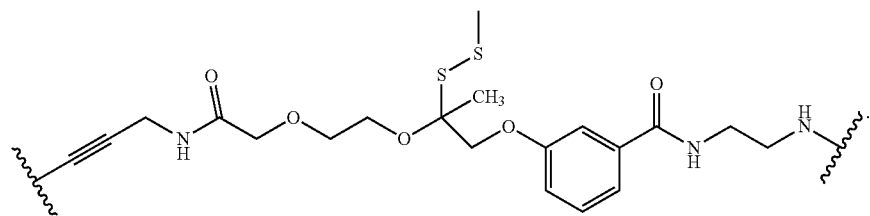 [SMILES: *C#CCNC(=O)COCCOC(C)(COc1cccc(C(=O)NCCN*)c1)SSC]
In embodiments, $L^{100}$ is
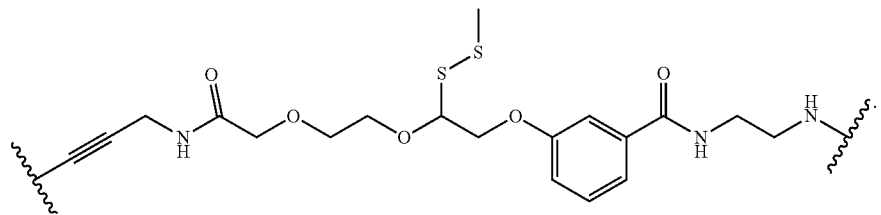 [SMILES: *C#CCNC(=O)COCCOC(COc1cccc(C(=O)NCCN*)c1)SSC]
In embodiments, $L^{100}$ is
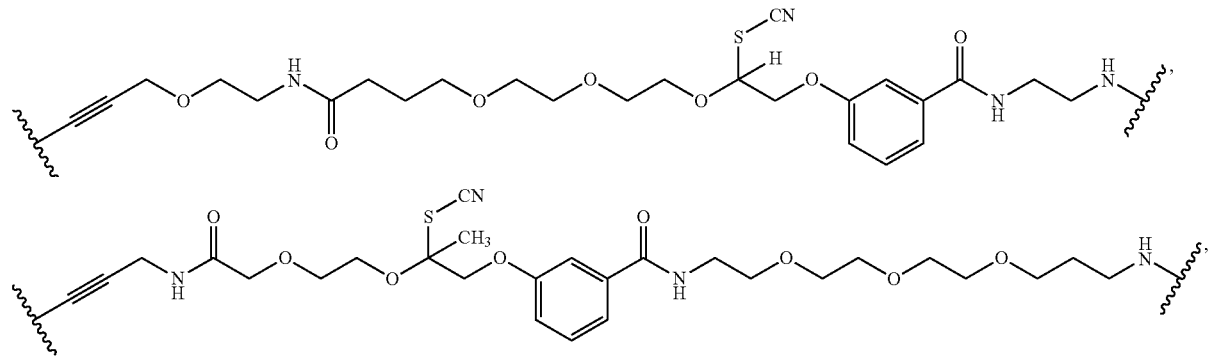

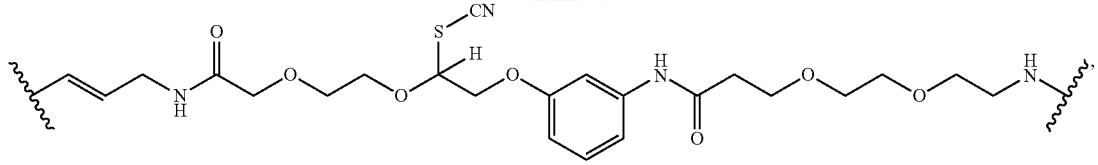
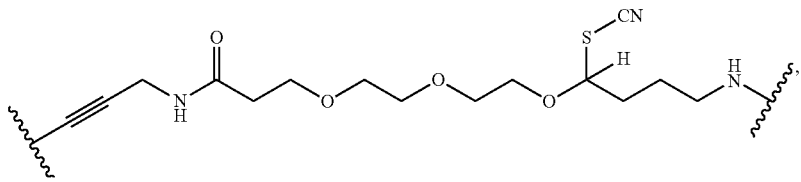
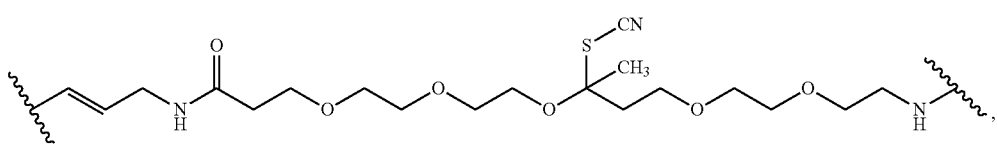
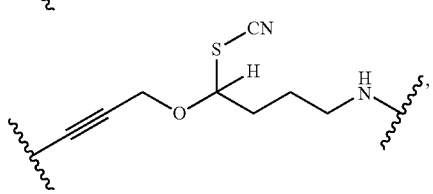
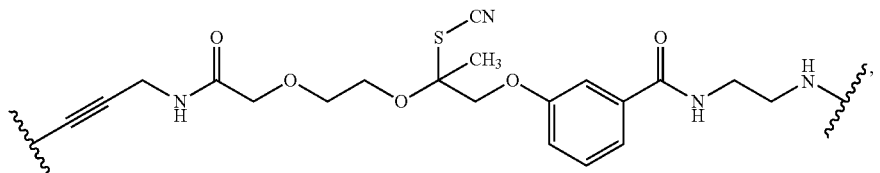
or
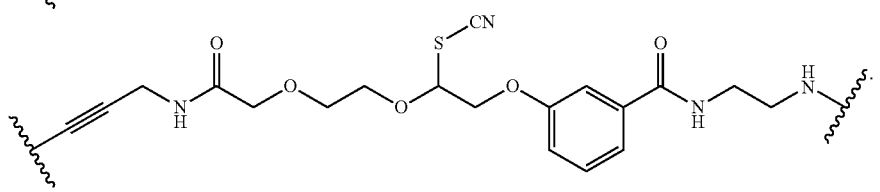
In embodiments, L$^{100}$ is
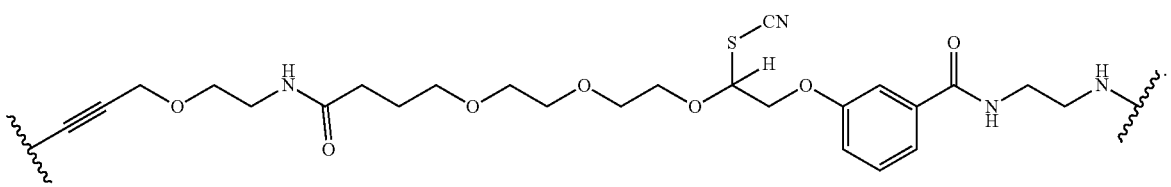 [SMILES: *C#CCOCCNC(=O)CCCOCCOCCOC(COc1cccc(C(=O)NCCN*)c1)SC#N]
In embodiments, L$^{100}$ is
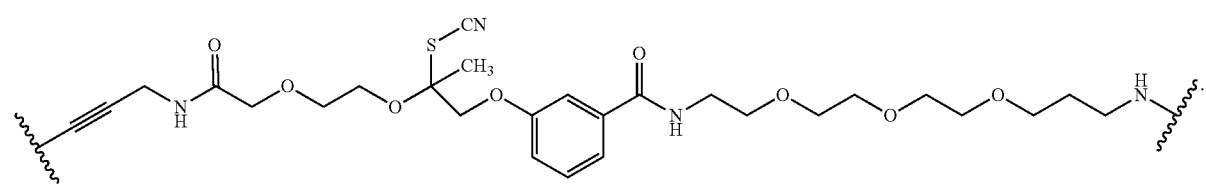 [SMILES: *C#CCNC(=O)COCCOC(C)(COc1cccc(C(=O)NCCOCCOCCOCCCN*)c1)SC#N]

In embodiments, L$^{100}$ is
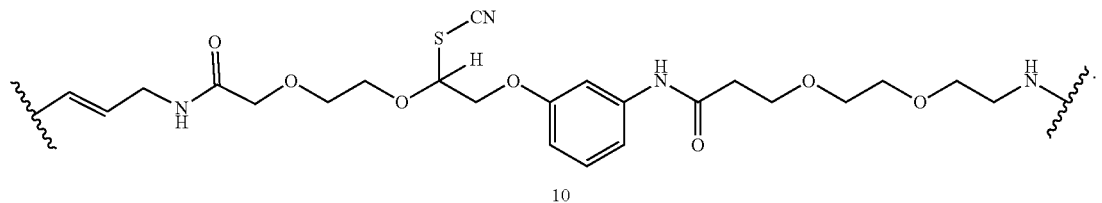
In embodiments, L$^{100}$ is
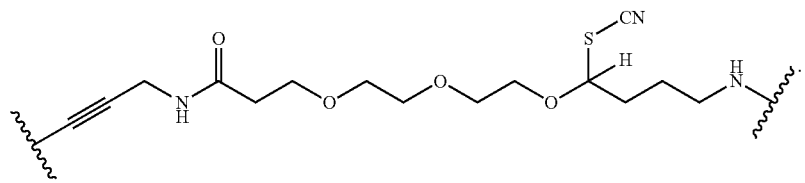 [SMILES: *C#CCNC(=O)CCOCCOCCOC(CCCN*)SC#N]
In embodiments, L$^{100}$ is
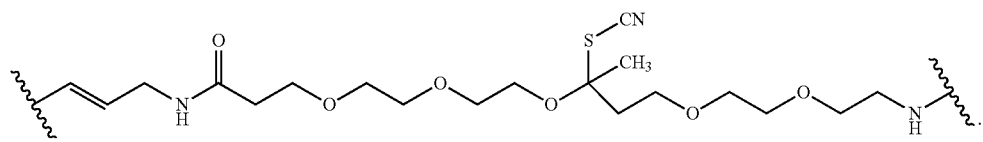 [SMILES: */C=C/CNC(=O)CCOCCOCCOC(C)(CCOCCOCCN*)SC#N]
In embodiments, L$^{100}$ is
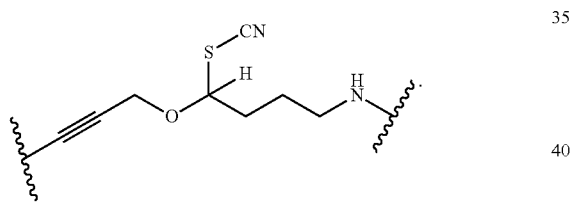
In embodiments, L$^{100}$ is
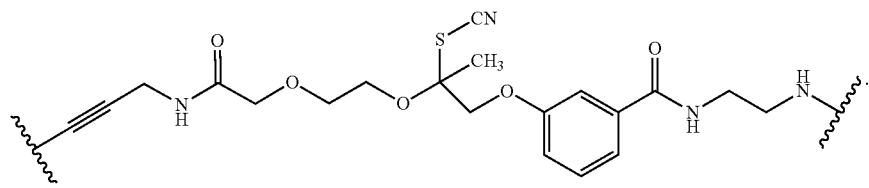 [SMILES: *C#CCNC(=O)COCCOC(C)(COc1cccc(C(=O)NCCN*)c1)SC#N]
In embodiments, L$^{100}$ is
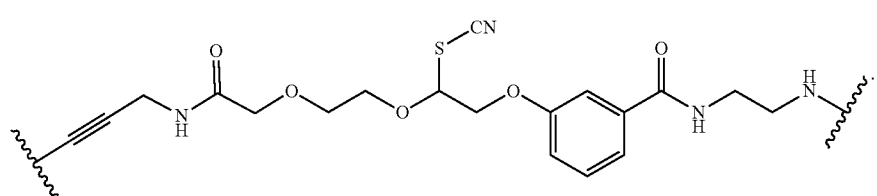 [SMILES: *C#CCNC(=O)COCCOC(COc1cccc(C(=O)NCCN*)c1)SC#N]

In embodiments, $L^{100}$ is
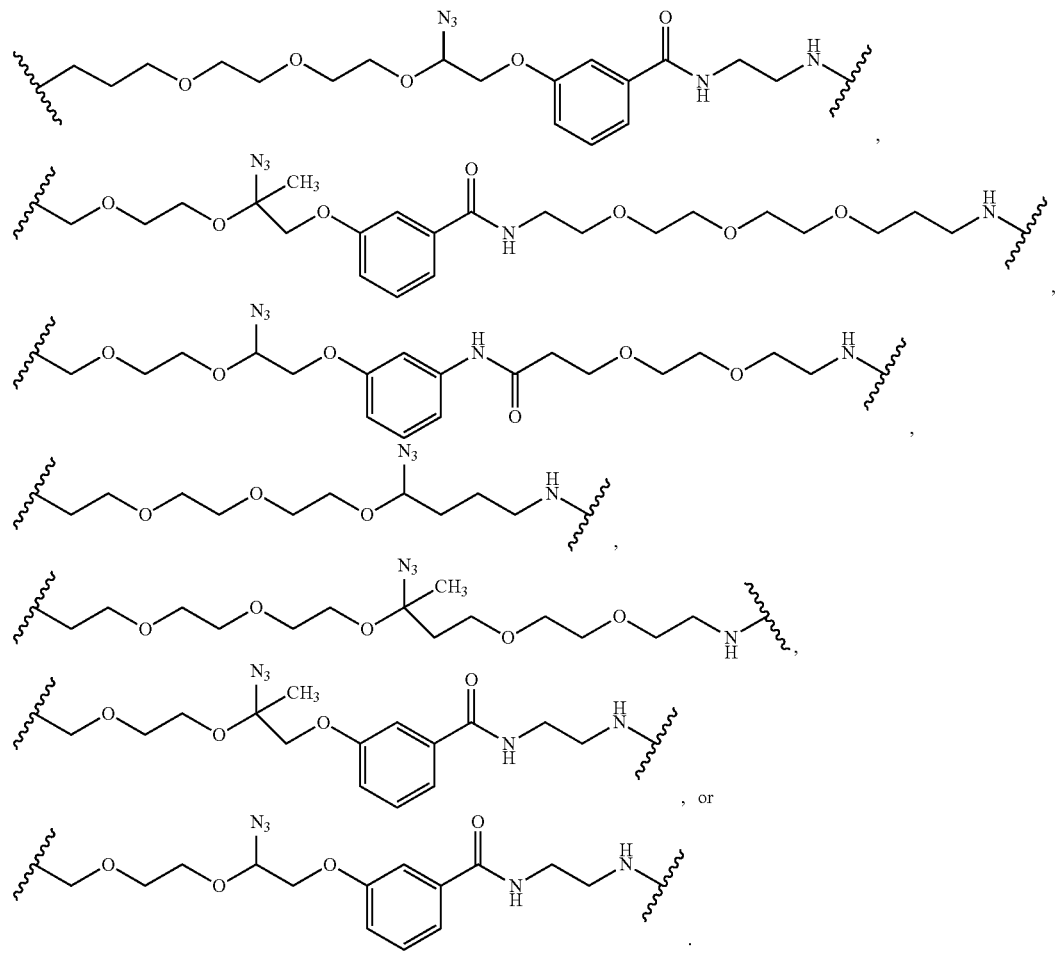
In embodiments, $L^{100}$ is
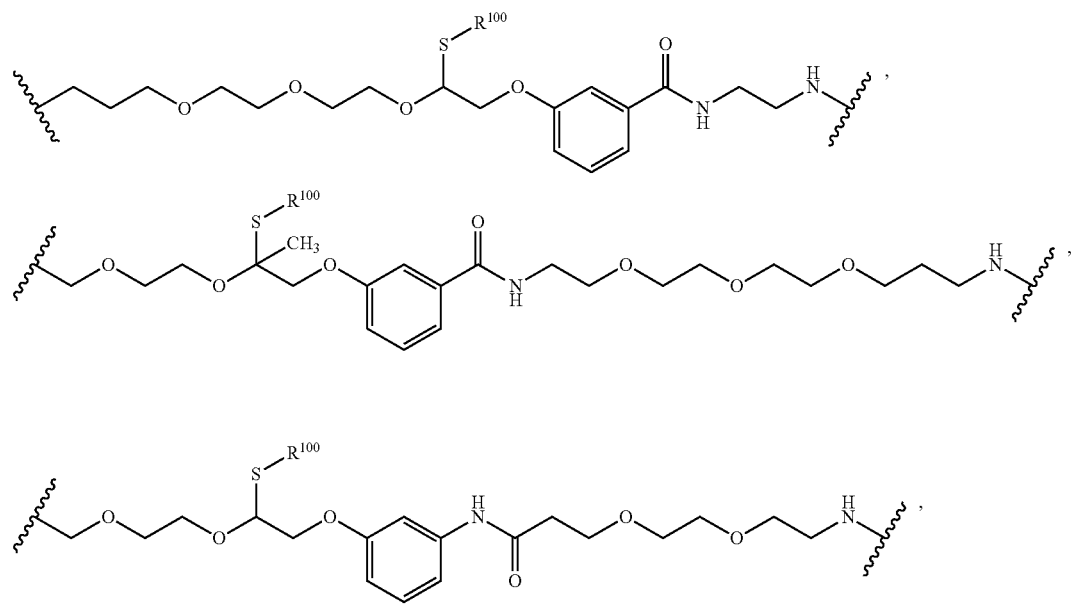

-continued
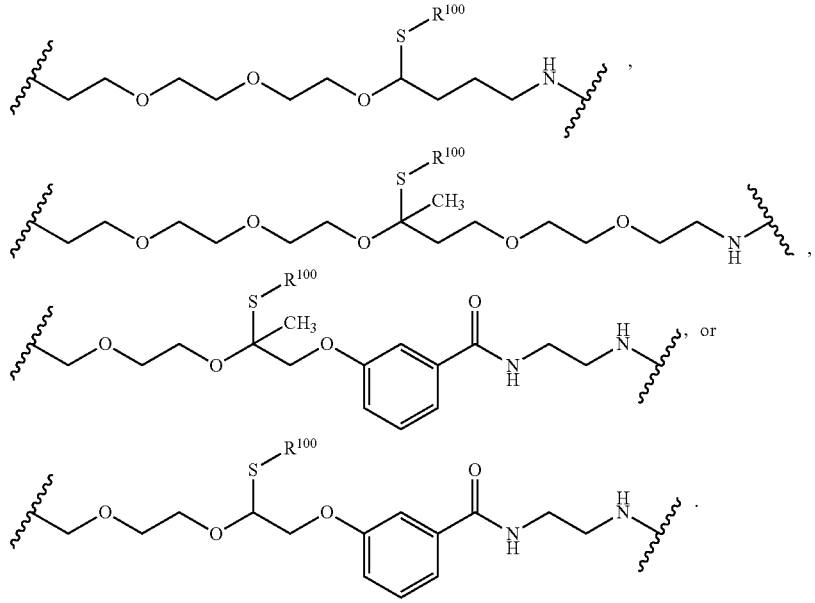
$R^{100}$ is as described herein, including in embodiments.
In embodiments, $L^{100}$ is
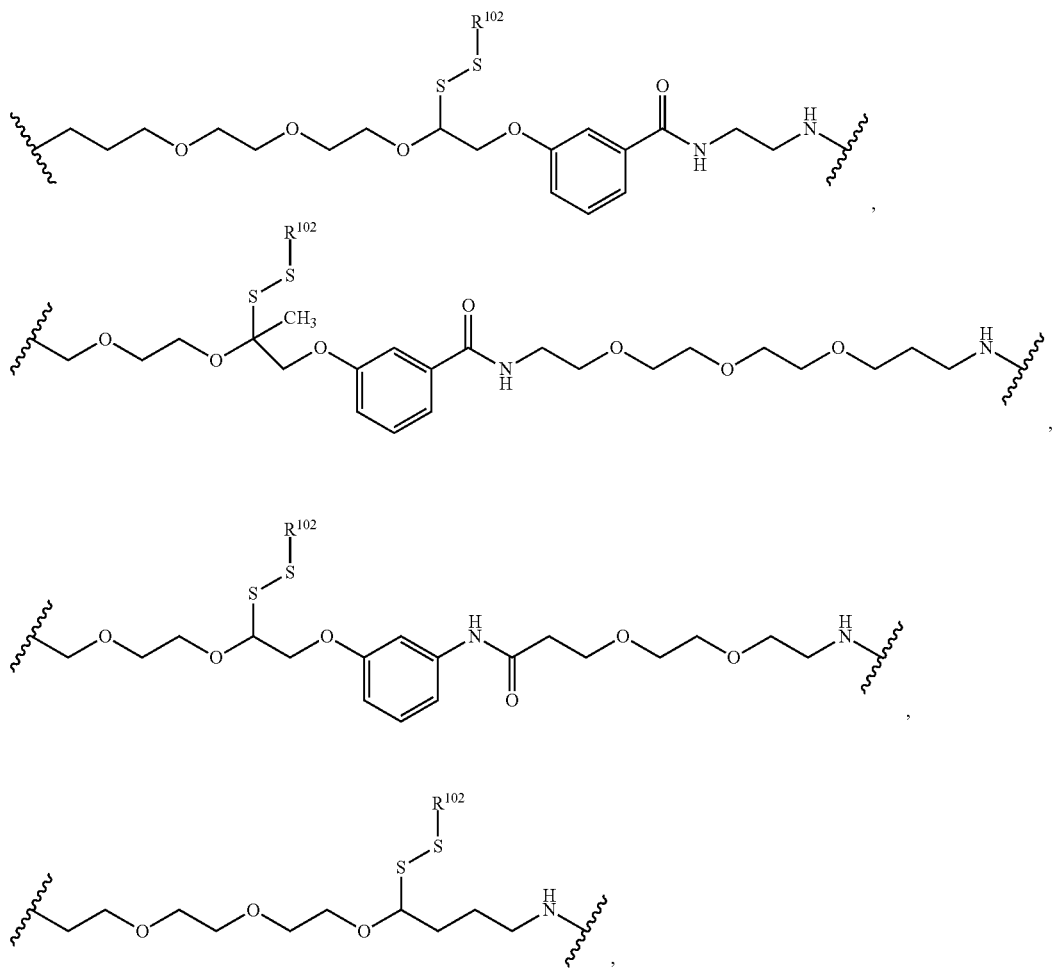

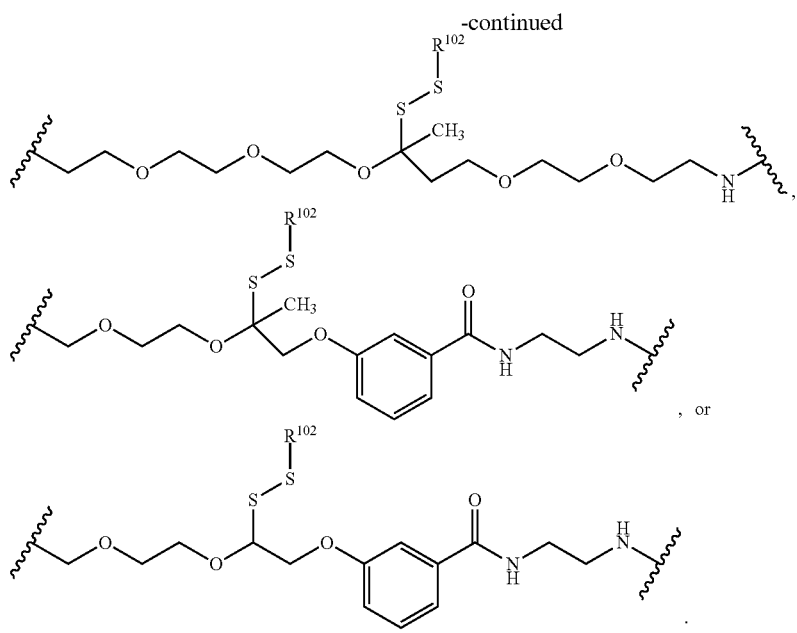
$R^{102}$ is as described herein, including in embodiments.
In embodiments, $L^{100}$ is
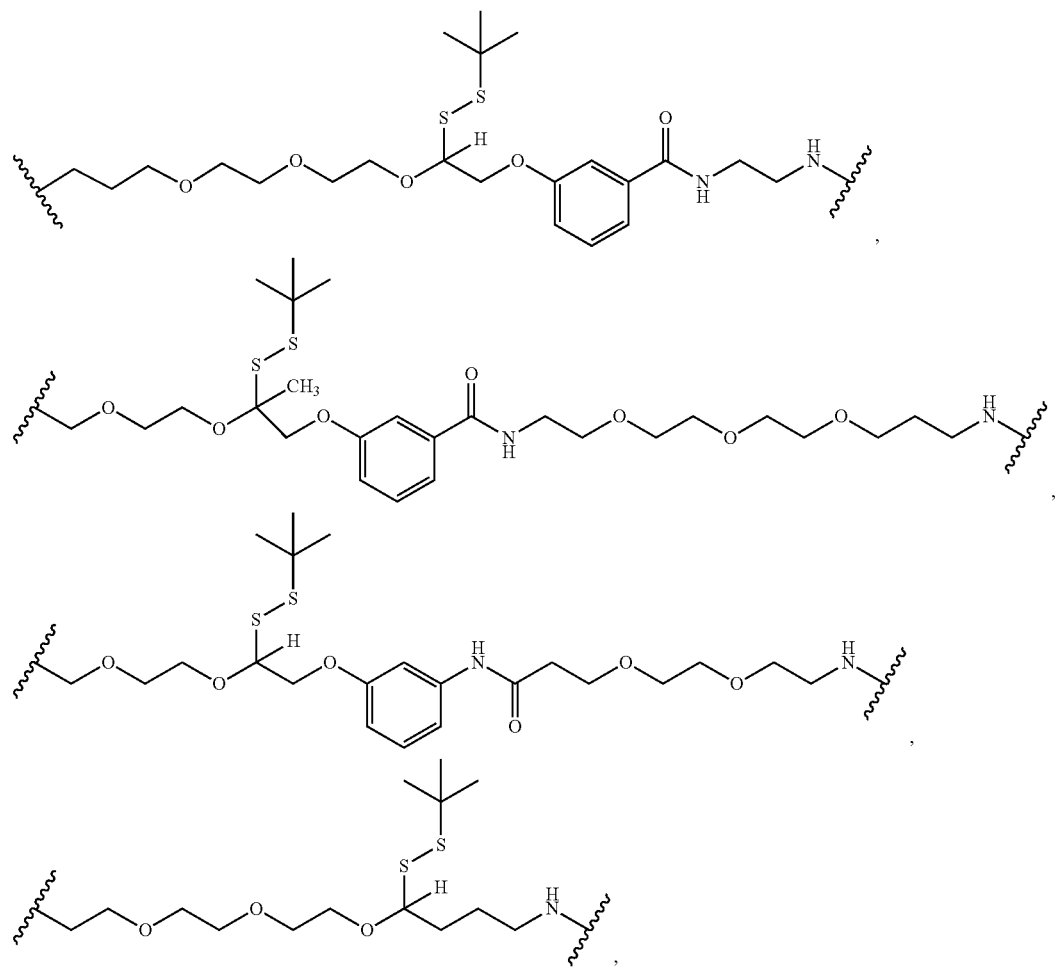

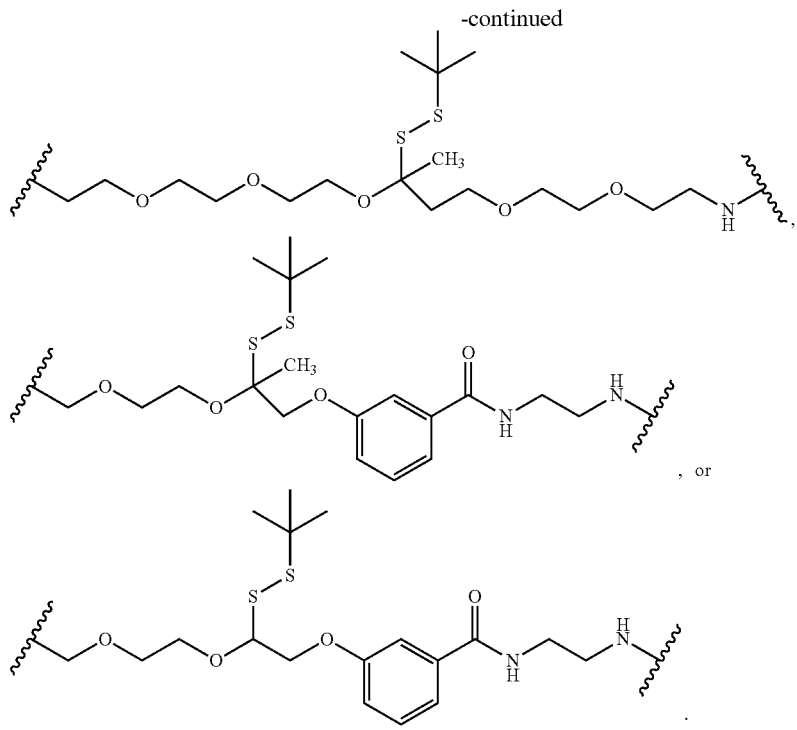
In embodiments, $L^{100}$ is
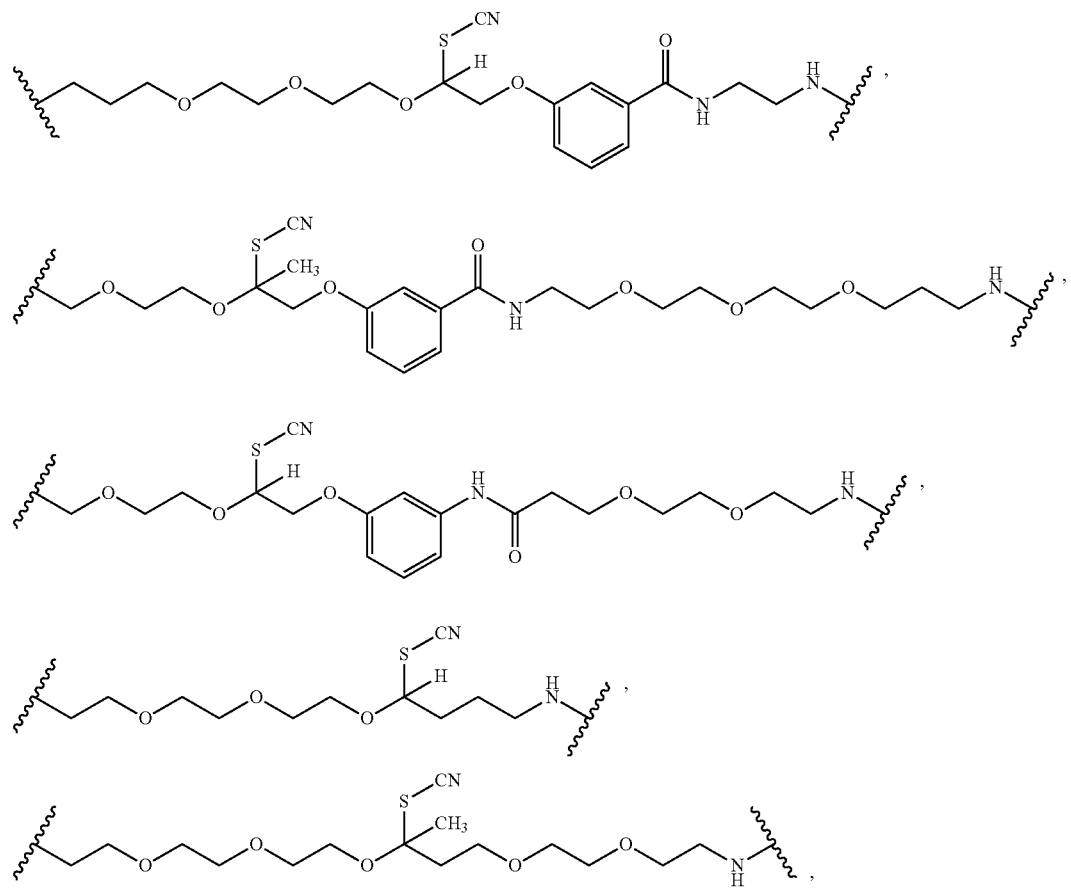

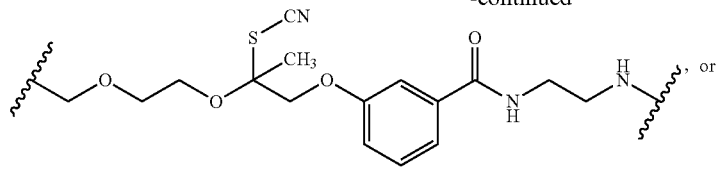, or
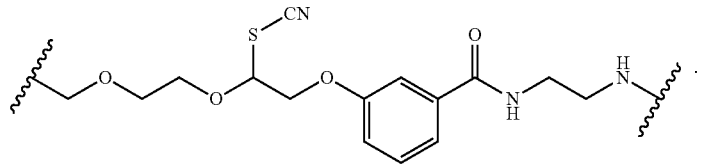
In embodiments, L$^{100}$ is
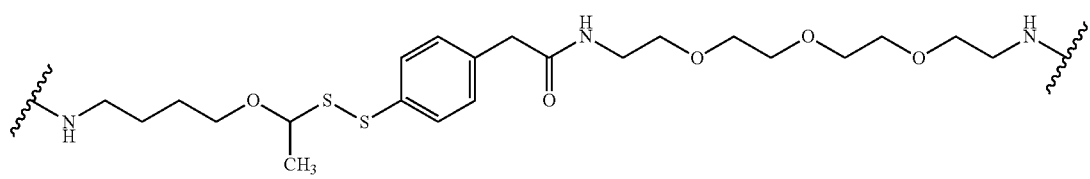,
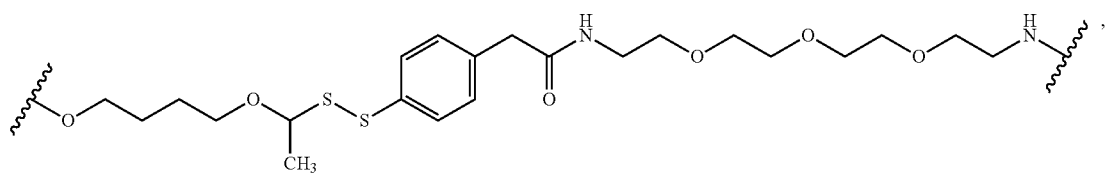,
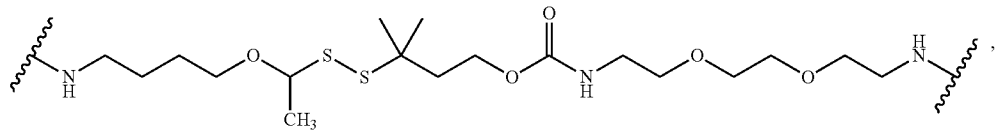,
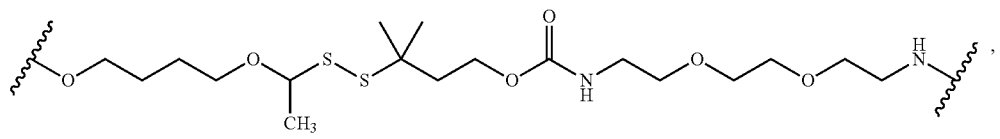,
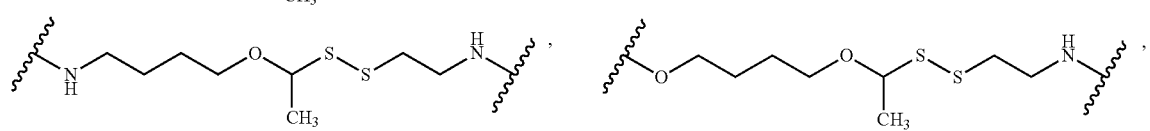,
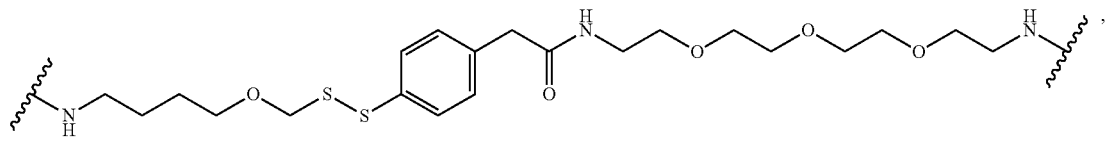,
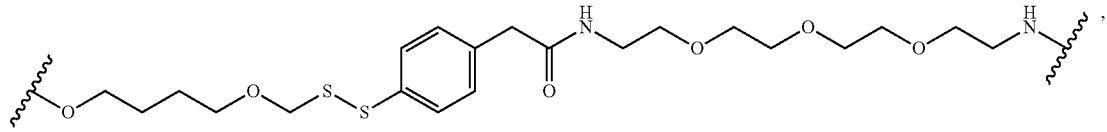,
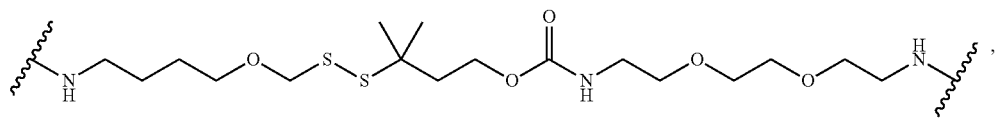,
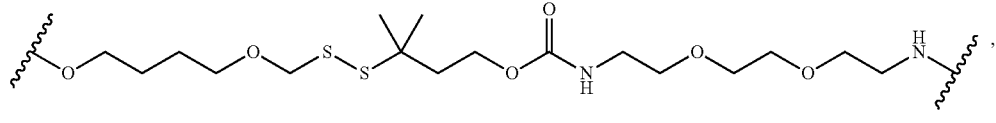, 279
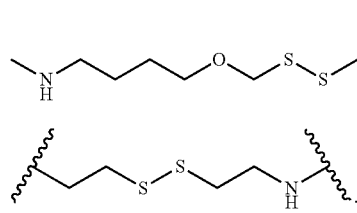
280
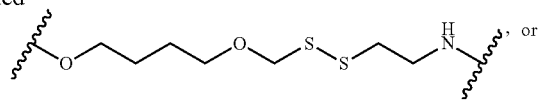
In embodiments, $L^{100}$ is
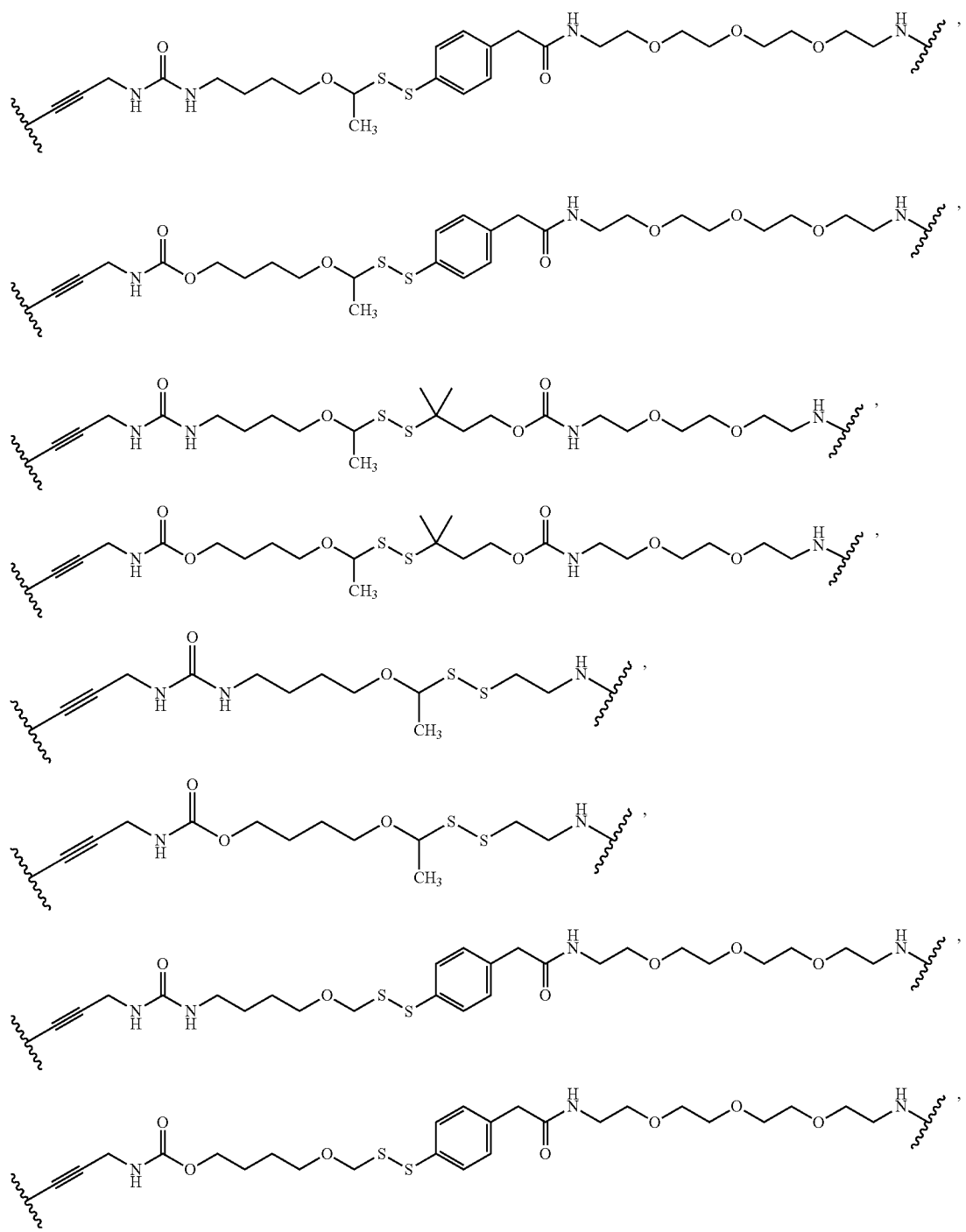

-continued
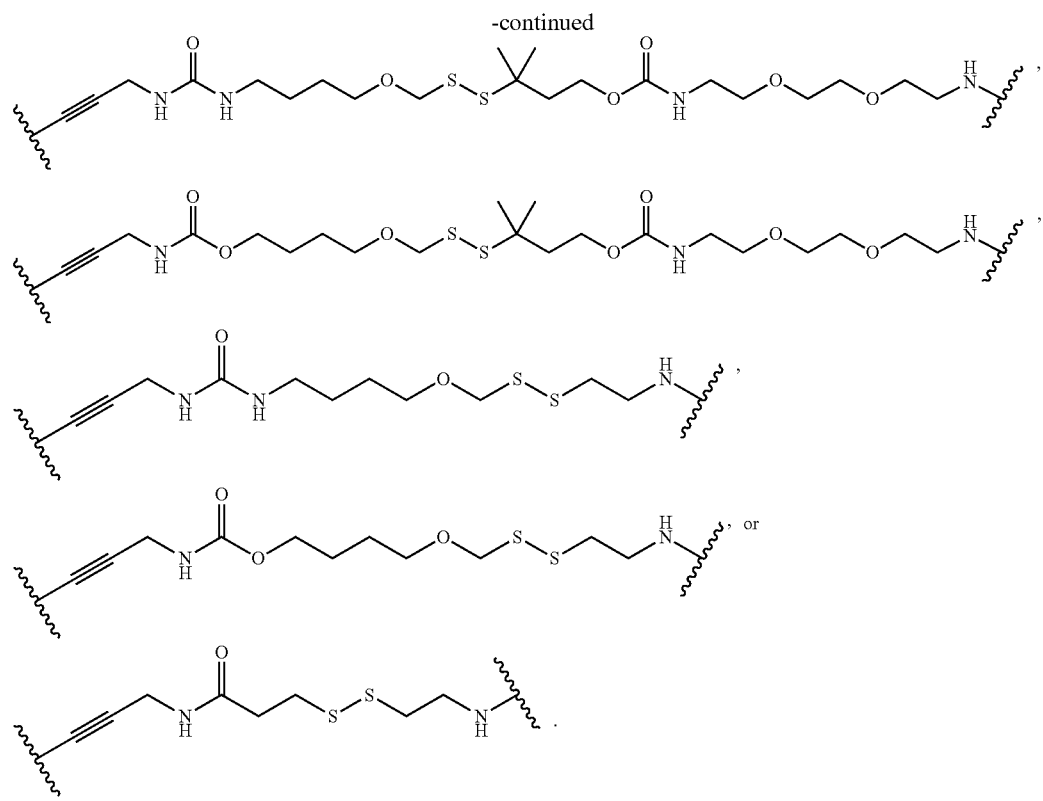
In embodiments, $L^{100}$ is
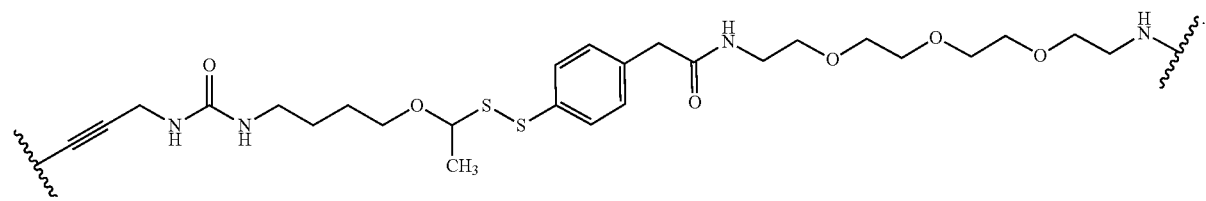 [SMILES: *C#CCNC(=O)NCCCCOC(C)SSc1ccc(CC(=O)NCCOCCOCCOCCN*)cc1]
In embodiments, $L^{100}$ is
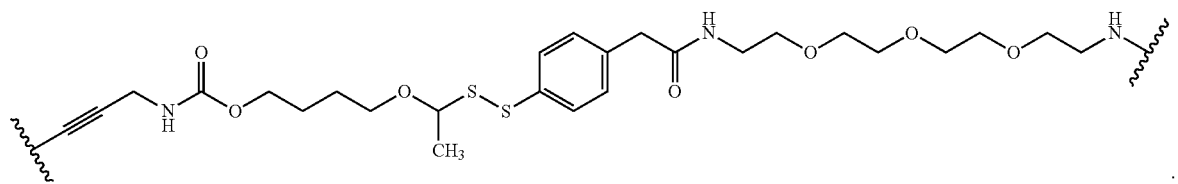 [SMILES: *C#CCNC(=O)OCCCCOC(C)SSc1ccc(CC(=O)NCCOCCOCCOCCN*)cc1]
In embodiments, $L^{100}$ is
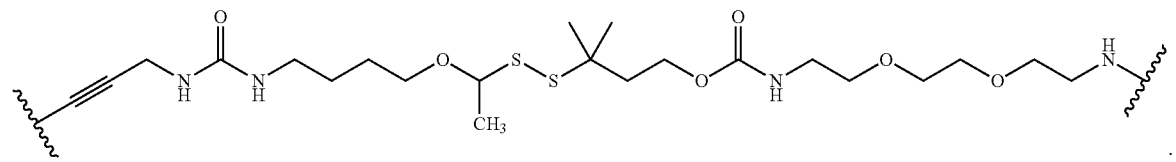 [SMILES: *C#CCNC(=O)NCCCCOC(C)SSC(C)(C)CCOC(=O)NCCOCCOCCN*]

In embodiments, $L^{100}$ is
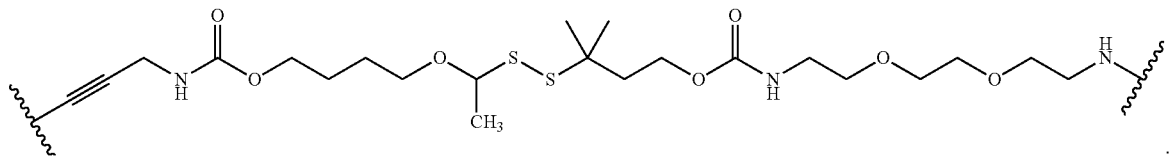 [SMILES: *C#CCNC(=O)OCCCCOC(C)SSC(C)(C)CCOC(=O)NCCOCCOCCN*]
In embodiments, $L^{100}$ is
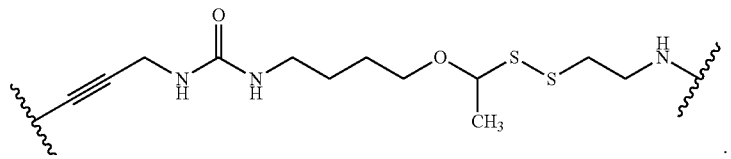 [SMILES: *C#CCNC(=O)NCCCCOC(C)SSCCN*]
In embodiments, $L^{100}$ is
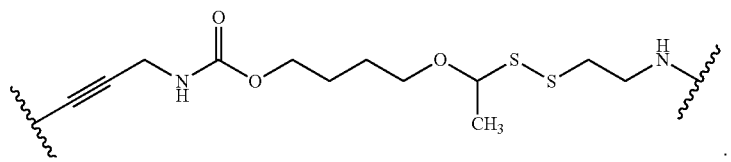 [SMILES: *C#CCNC(=O)OCCCCOC(C)SSCCN*]
In embodiments, $L^{100}$ is
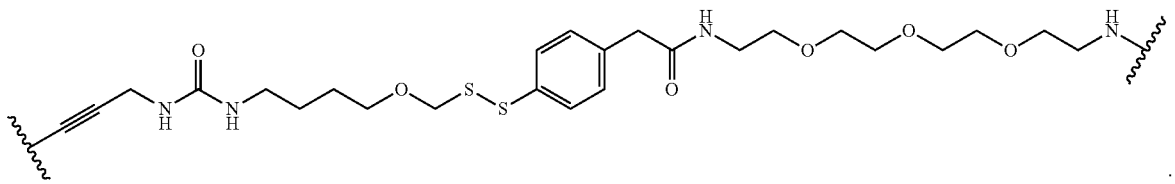 [SMILES: *C#CCNC(=O)NCCCCOCSSc1ccc(CC(=O)NCCOCCOCCOCCN*)cc1]
In embodiments, $L^{100}$ is
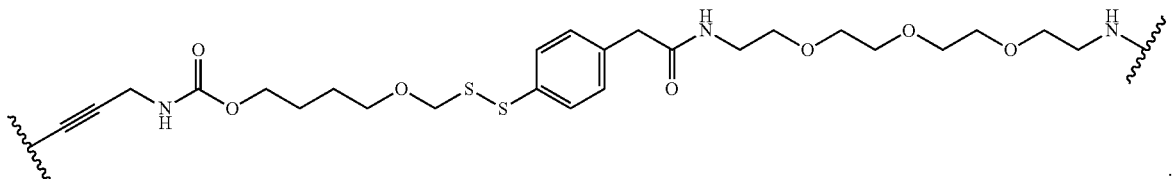 [SMILES: *C#CCNC(=O)OCCCCOCSSc1ccc(CC(=O)NCCOCCOCCOCCN*)cc1]
In embodiments, $L^{100}$ is
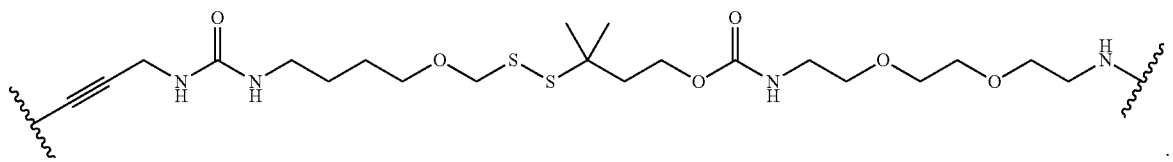 [SMILES: *C#CCNC(=O)NCCCCOCSSC(C)(C)CCOC(=O)NCCOCCOCCN*]

In embodiments, $L^{100}$ is
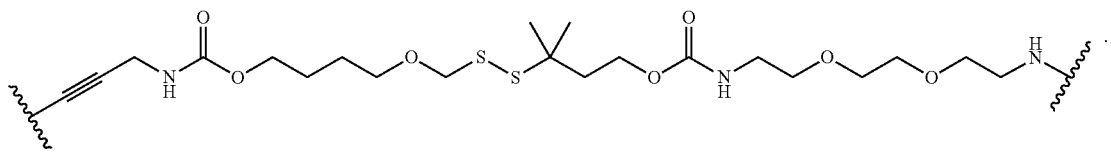 [SMILES: *C#CCNC(=O)OCCCCOCSSC(C)(C)CCOC(=O)NCCOCCOCCN*]
In embodiments, $L^{100}$ is
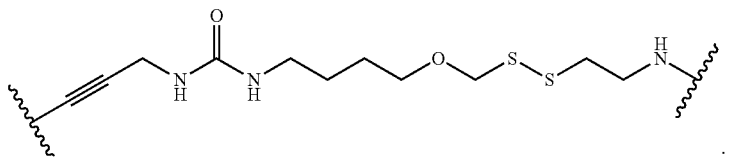 [SMILES: *C#CCNC(=O)NCCCCOCSSCCN*]
In embodiments, $L^{100}$ is
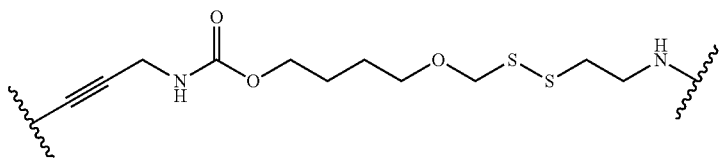
In embodiments, $L^{100}$ is
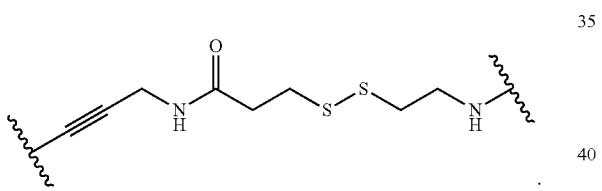
In embodiments, $L^{100}$ is
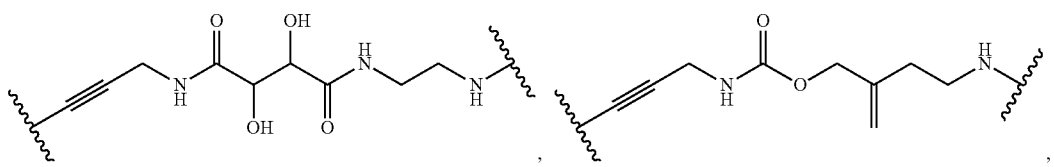
,
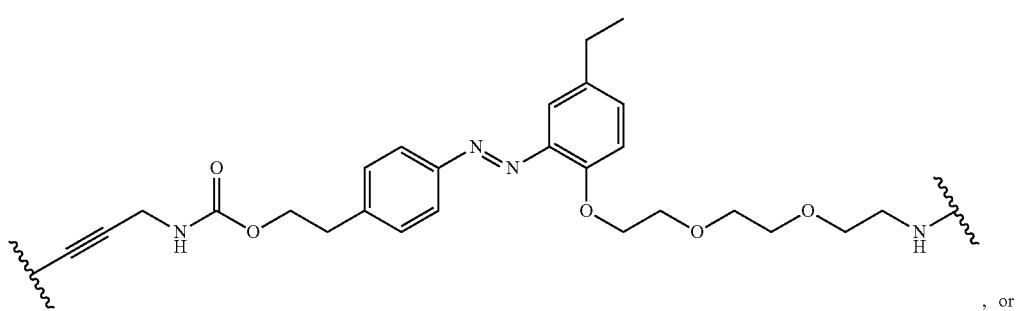
, or -continued
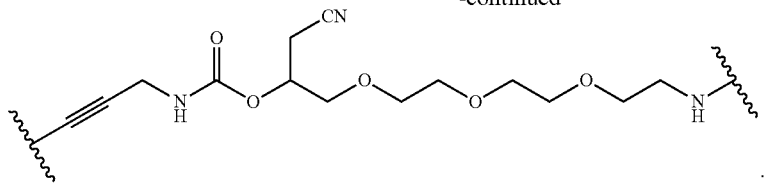
In embodiments, $L^{100}$ is
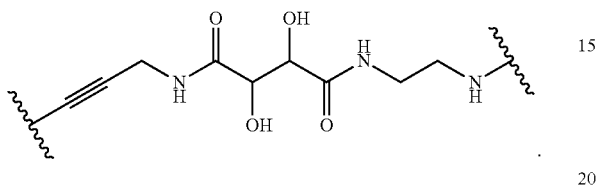
In embodiments, $L^{100}$ is
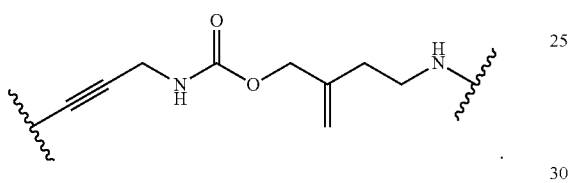
In embodiments, $L^{100}$ is
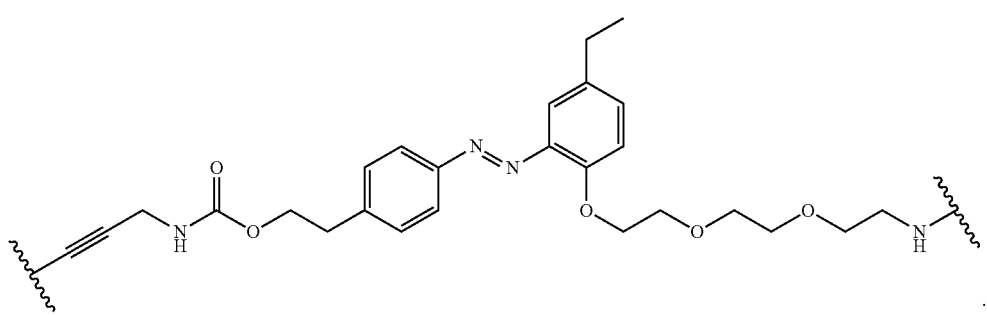 [SMILES: *C#CCNC(=O)OCCc1ccc(/N=N/c2cc(CC)ccc2OCCOCCOCCN*)cc1]
In embodiments, $L^{100}$ is
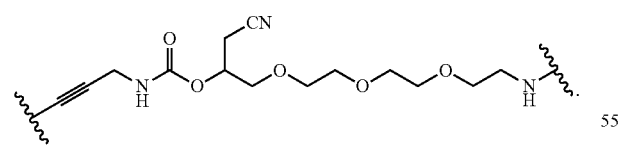
In embodiments, $L^{100}$ is
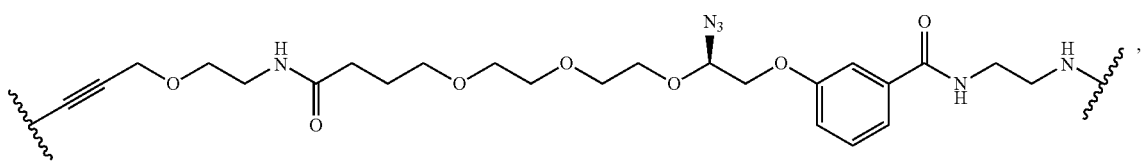

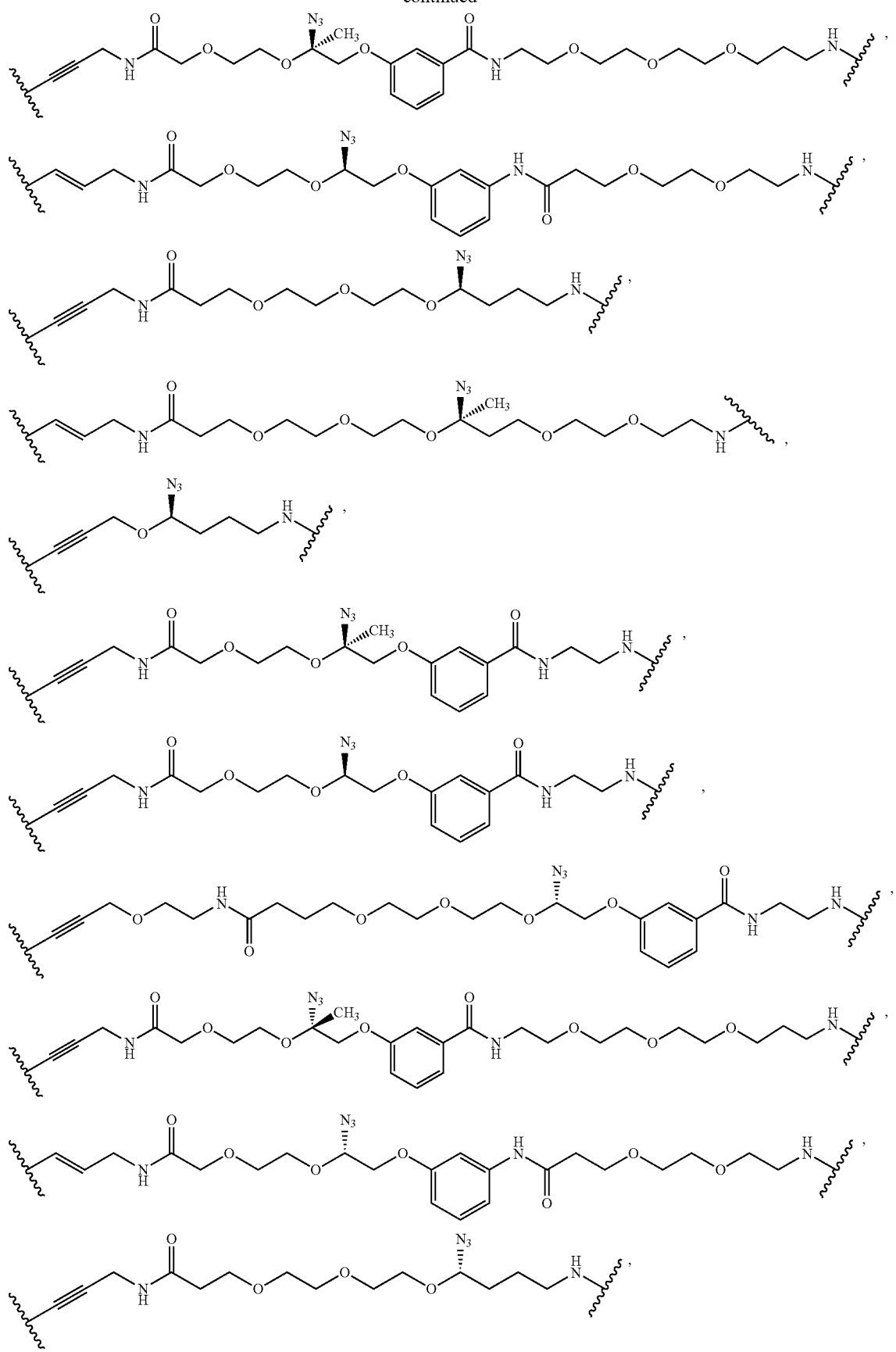

-continued
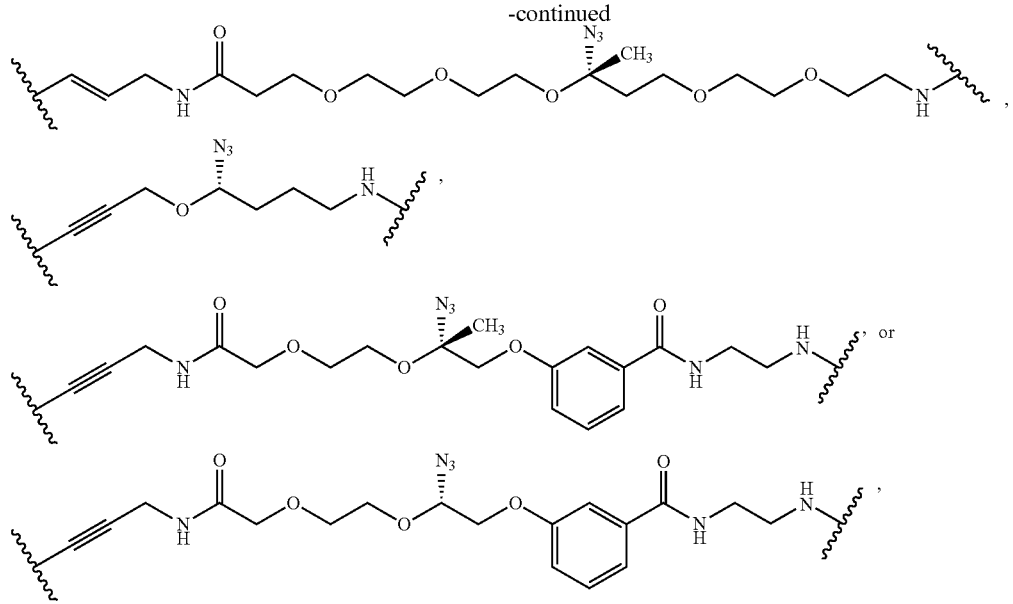
In embodiments, $L^{100}$ is
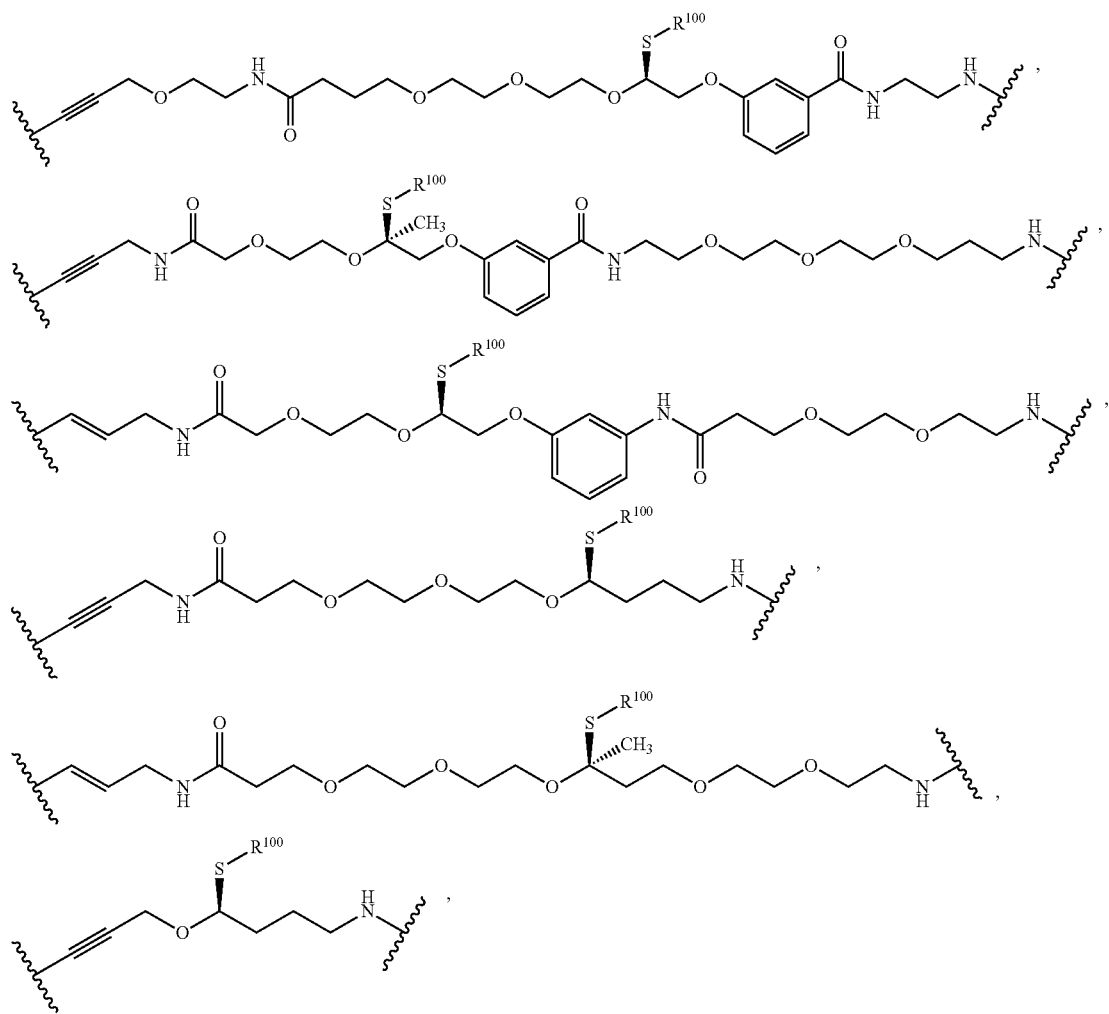

-continued
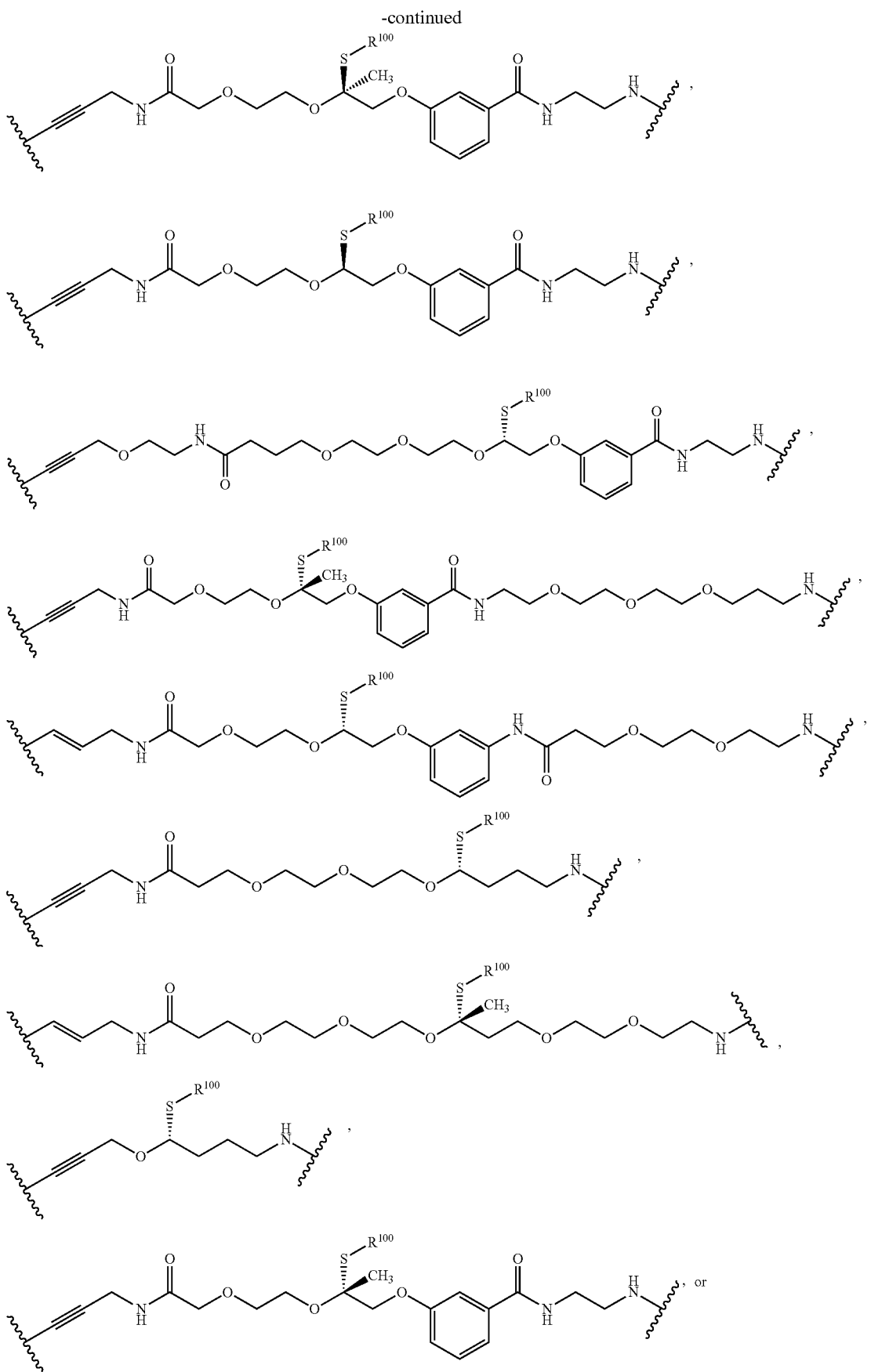

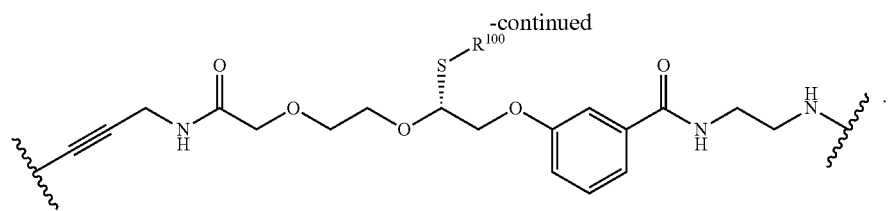
$R^{100}$ is as described herein, including in embodiments.
In embodiments, $L^{100}$ is
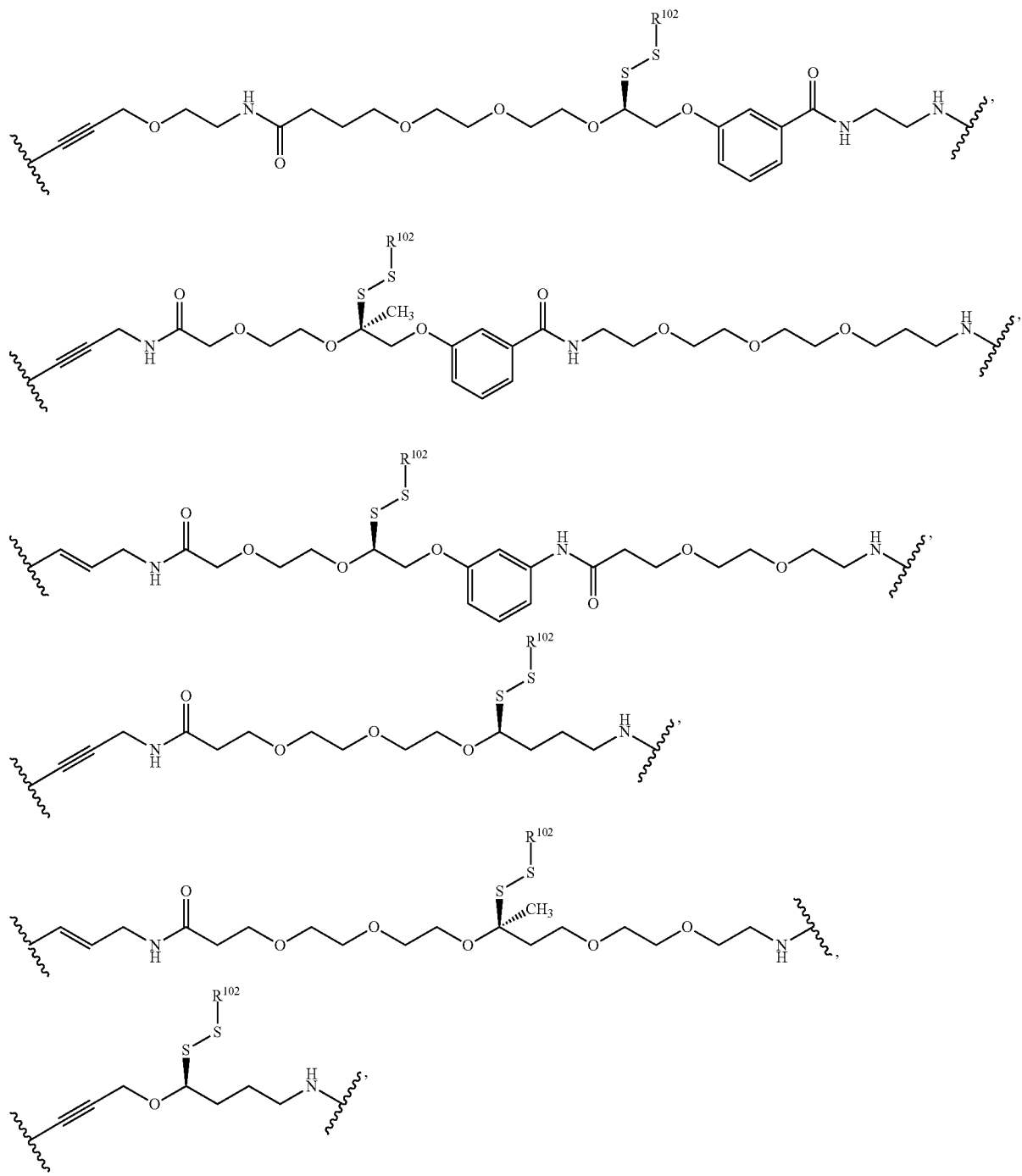

-continued
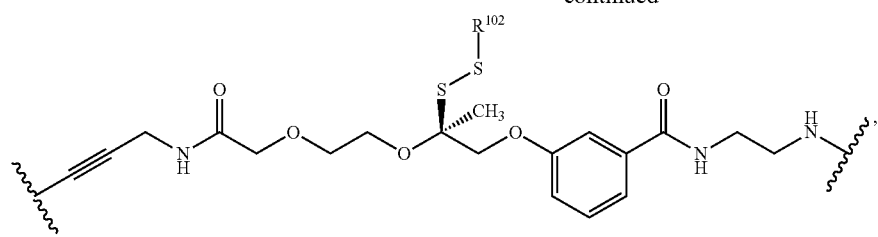
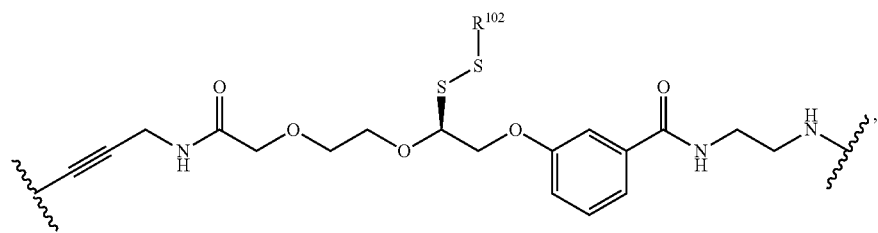
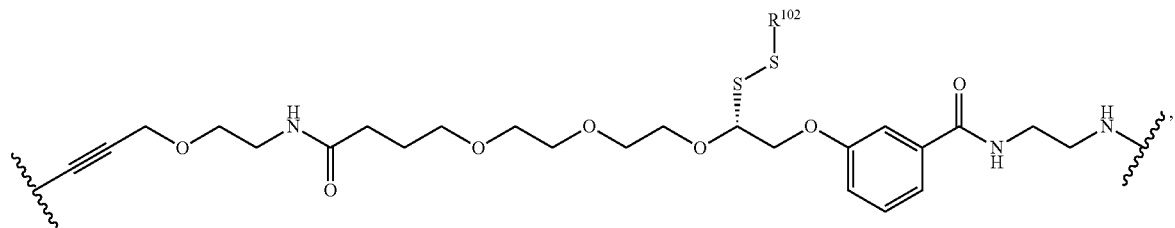
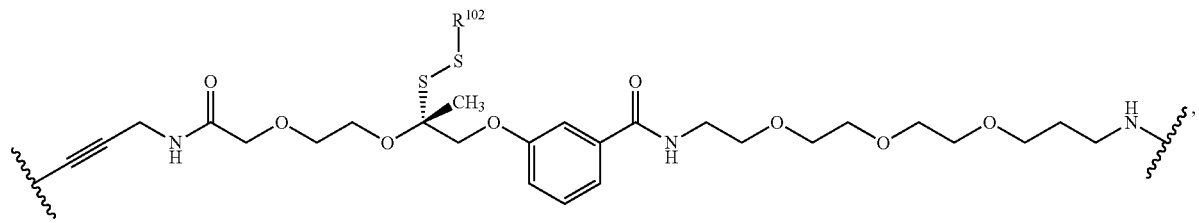
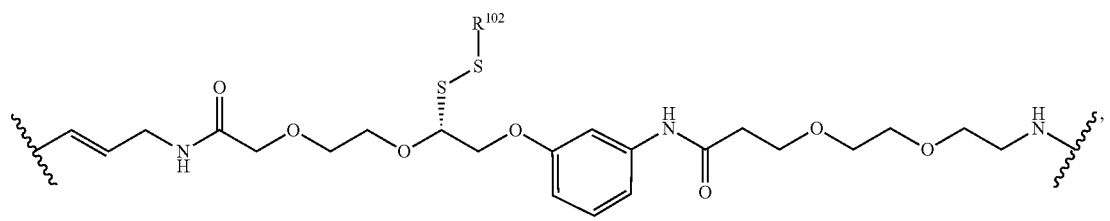
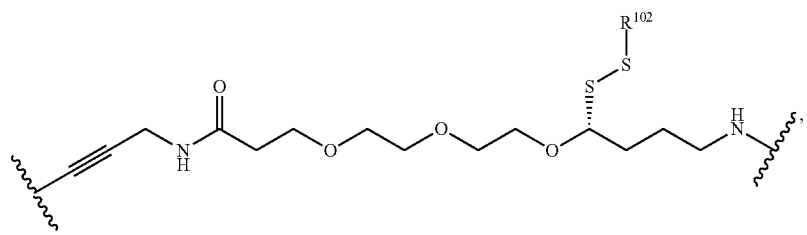
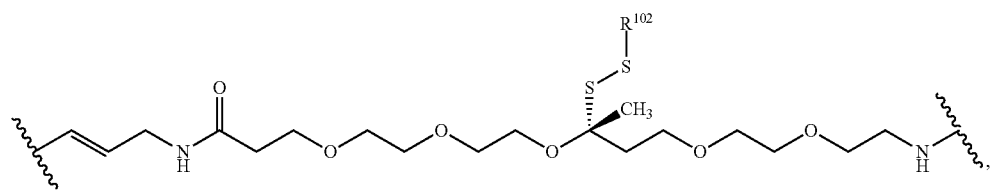

-continued
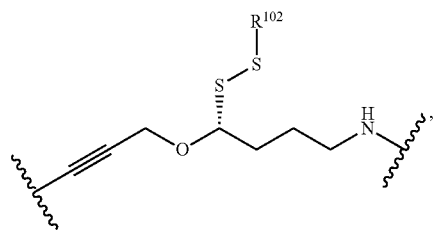
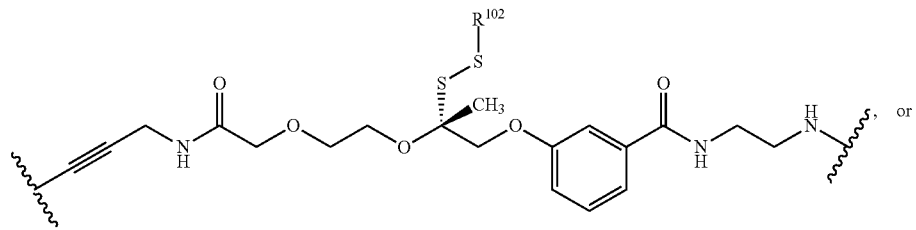, or
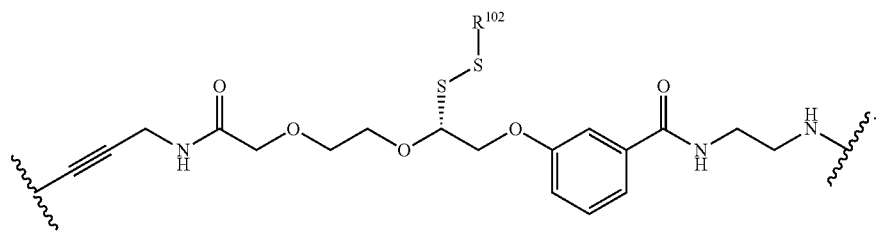
$R^{102}$ is as described herein, including in embodiments.
In embodiments, $L^{100}$ is
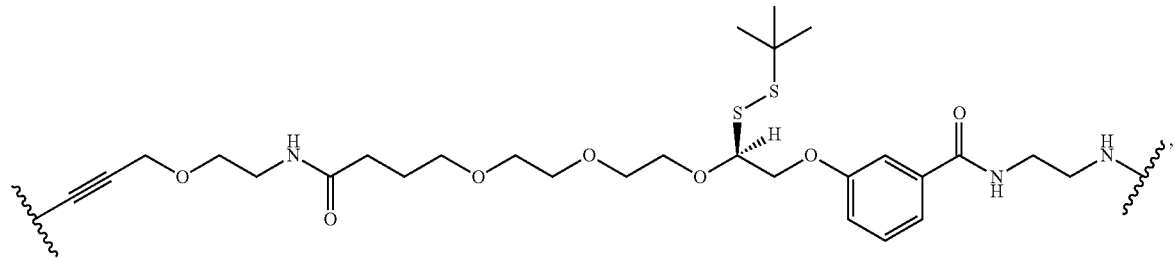,
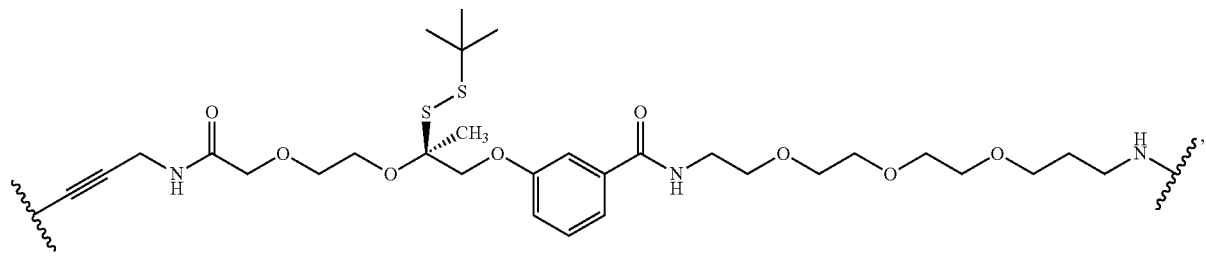,
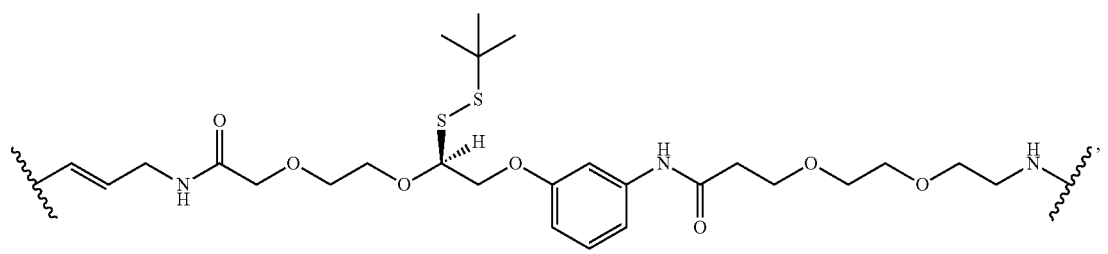, -continued
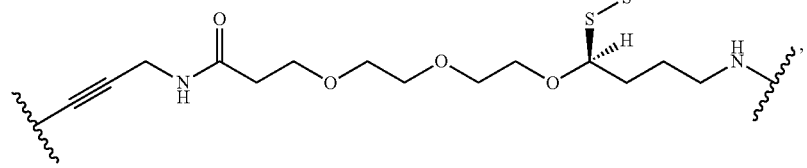
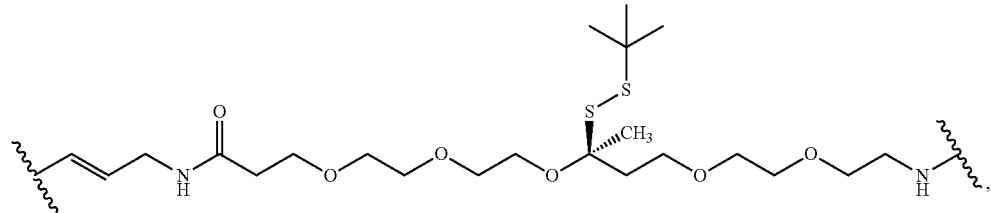
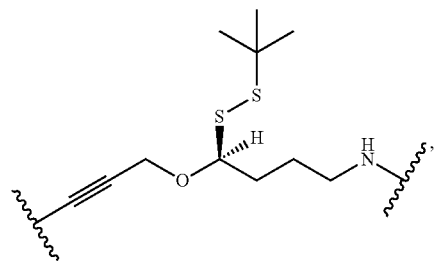
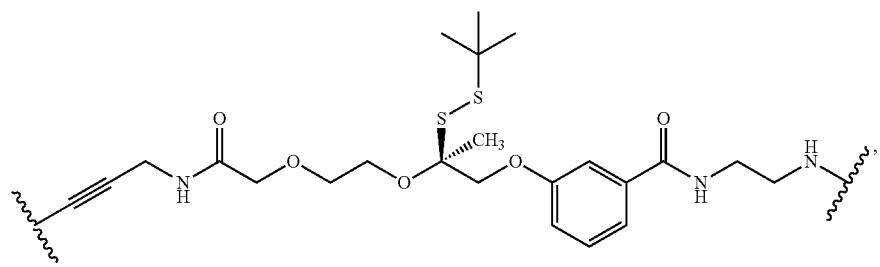
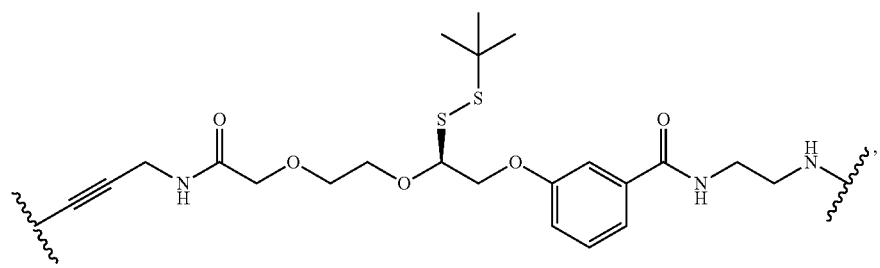
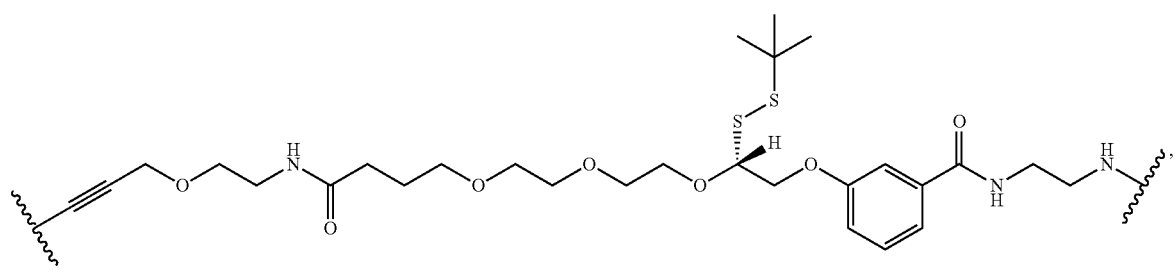

-continued
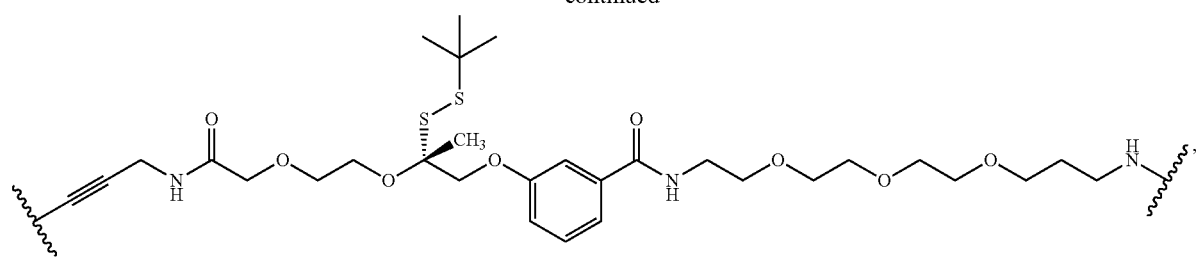
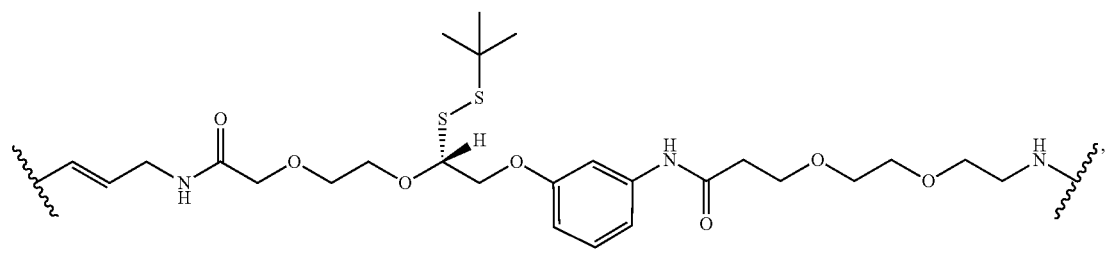
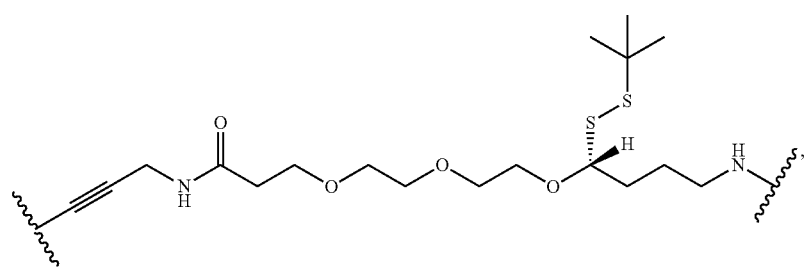
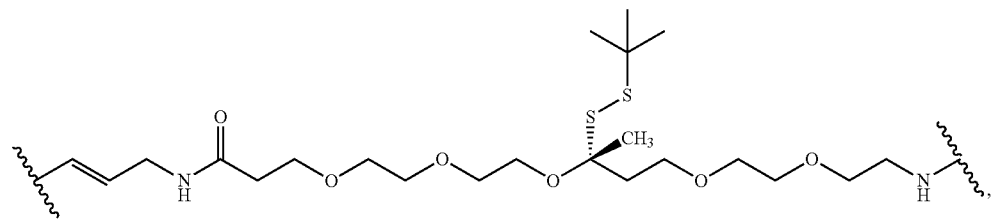
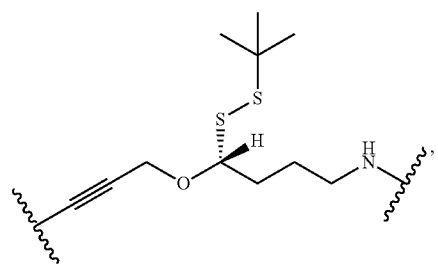
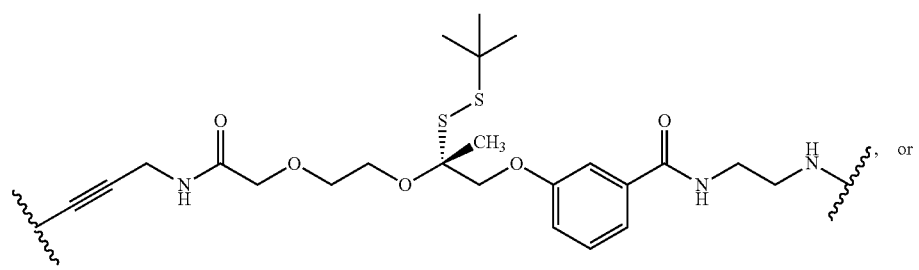

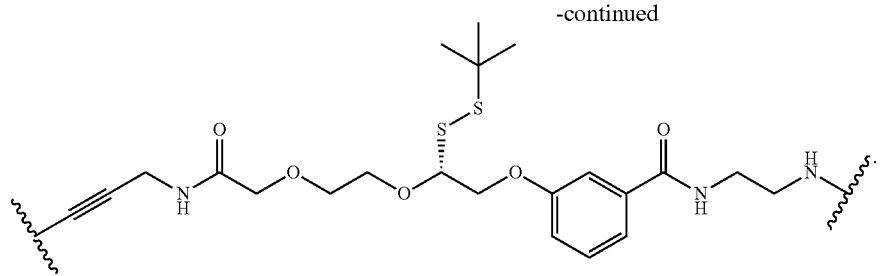
In embodiments, $L^{100}$ is
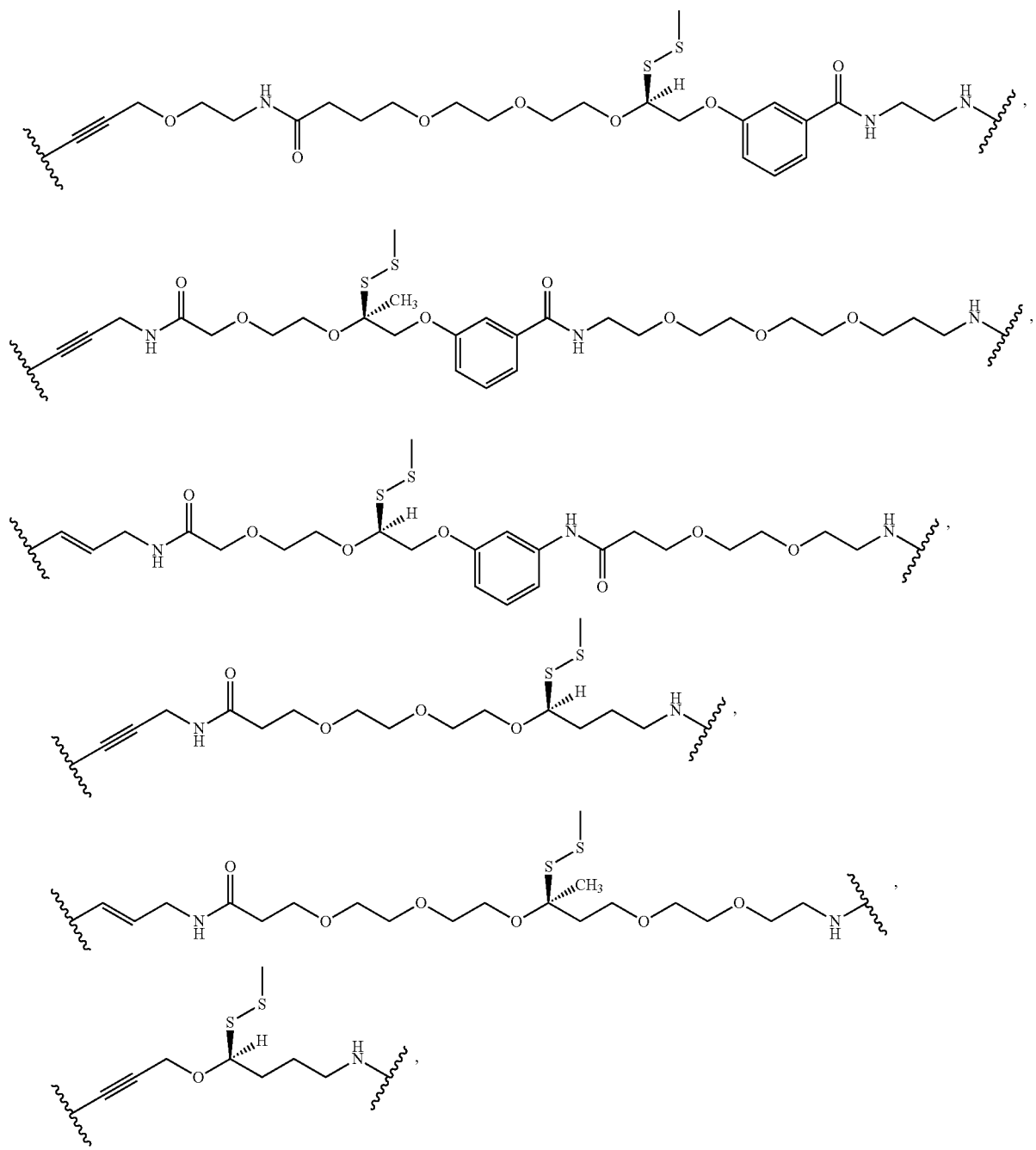

-continued
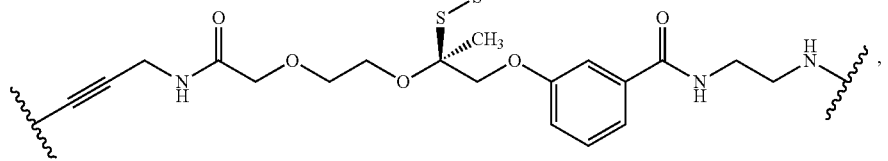
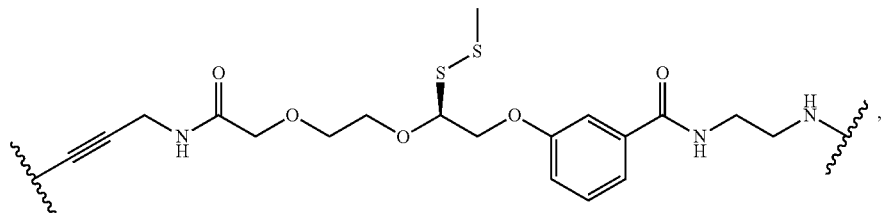
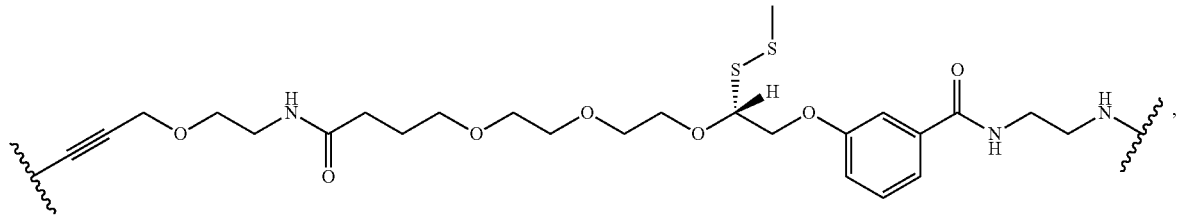
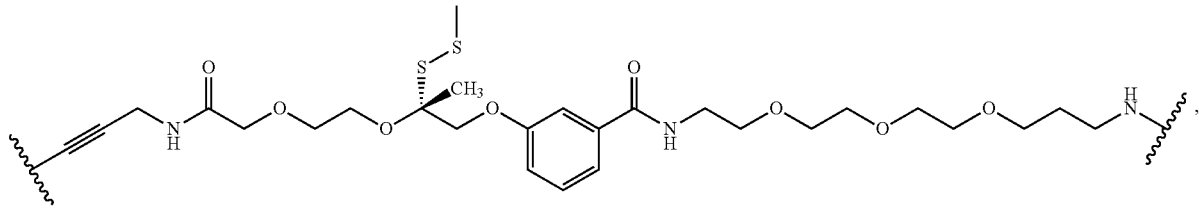
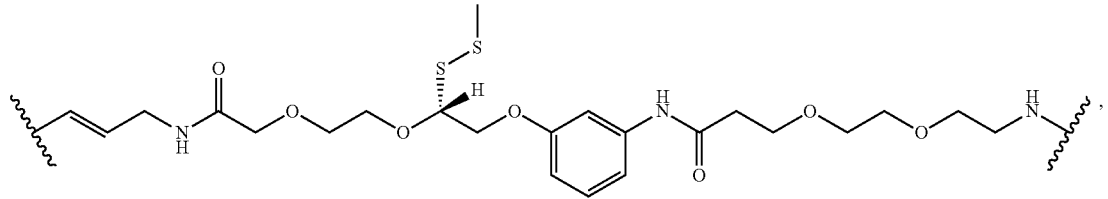
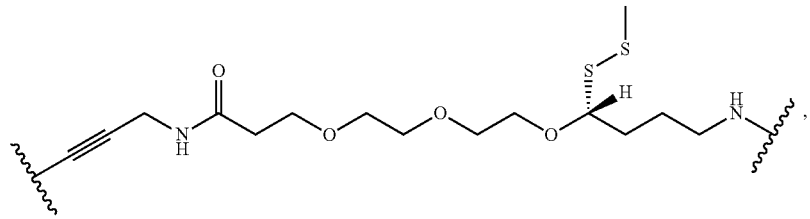
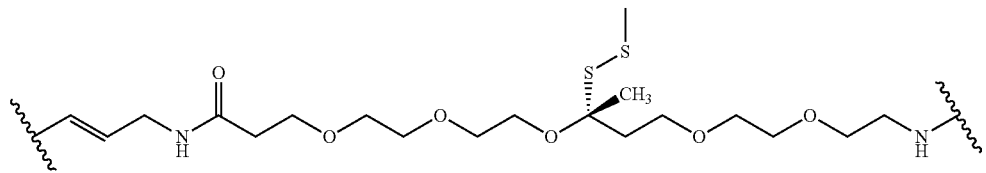
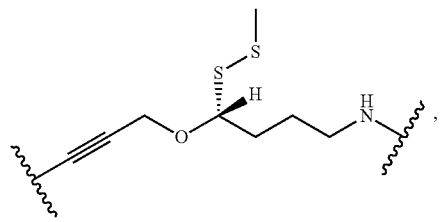

-continued
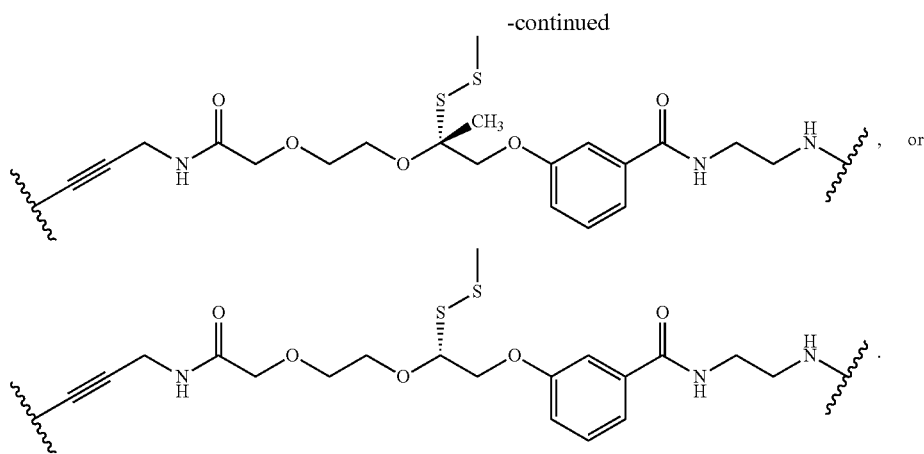
In embodiments, $L^{100}$ is
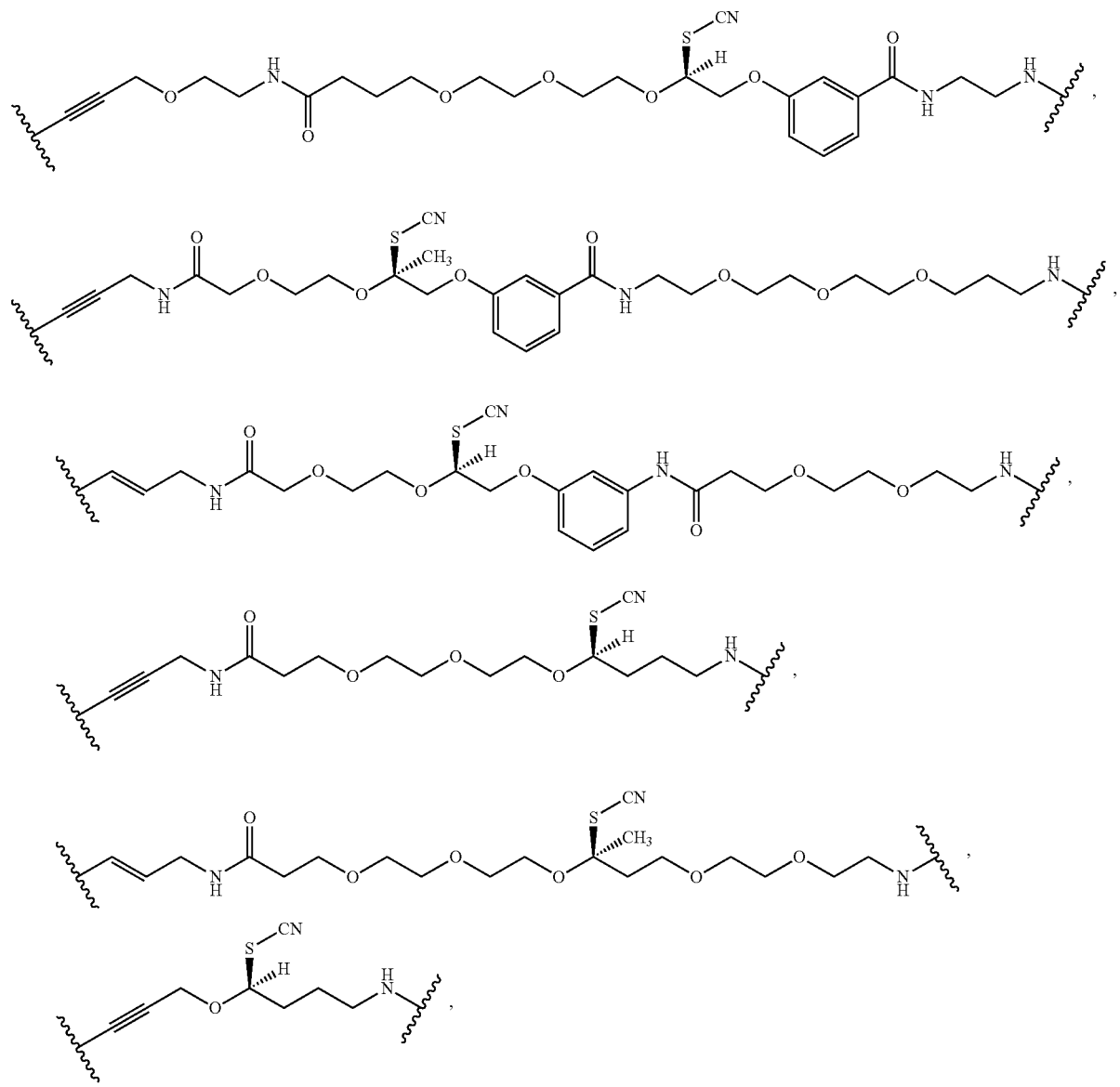

-continued
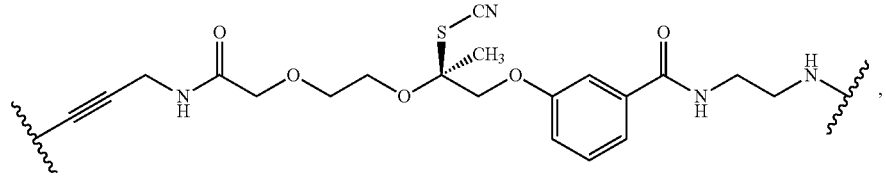
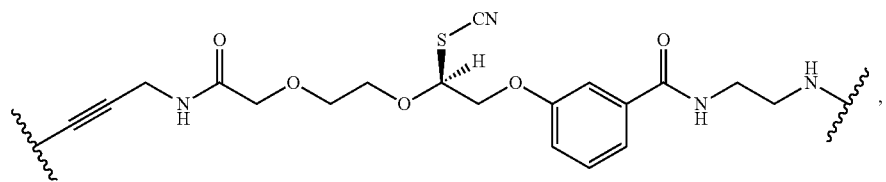
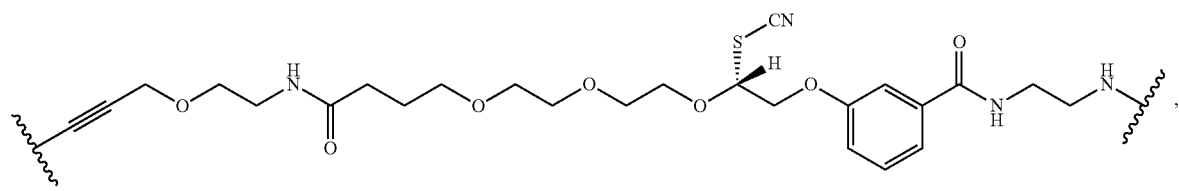
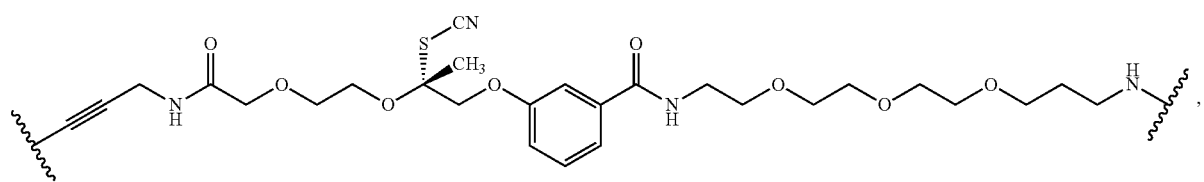
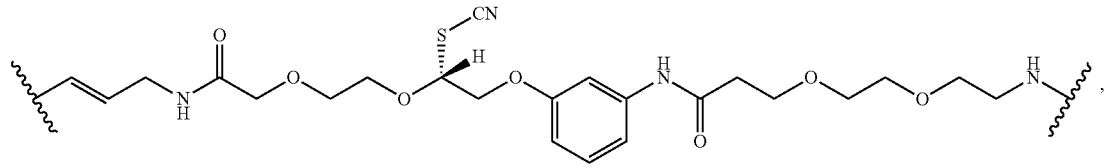
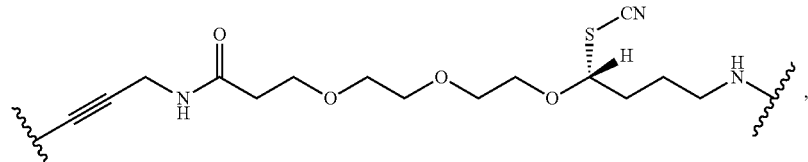
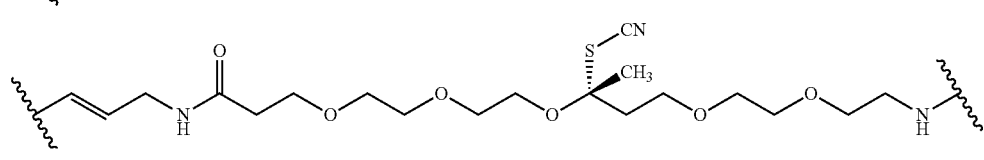
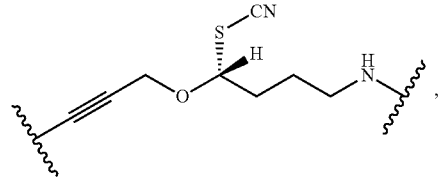
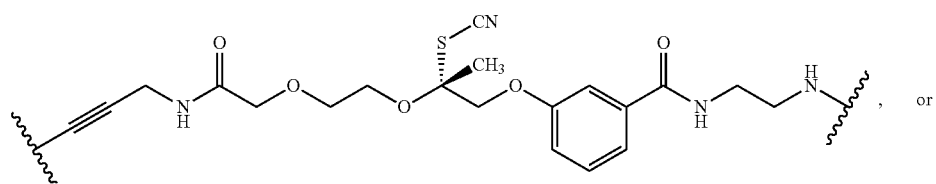, or

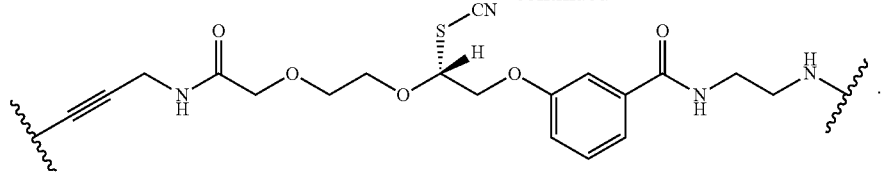
In embodiments, $L^{100}$ is
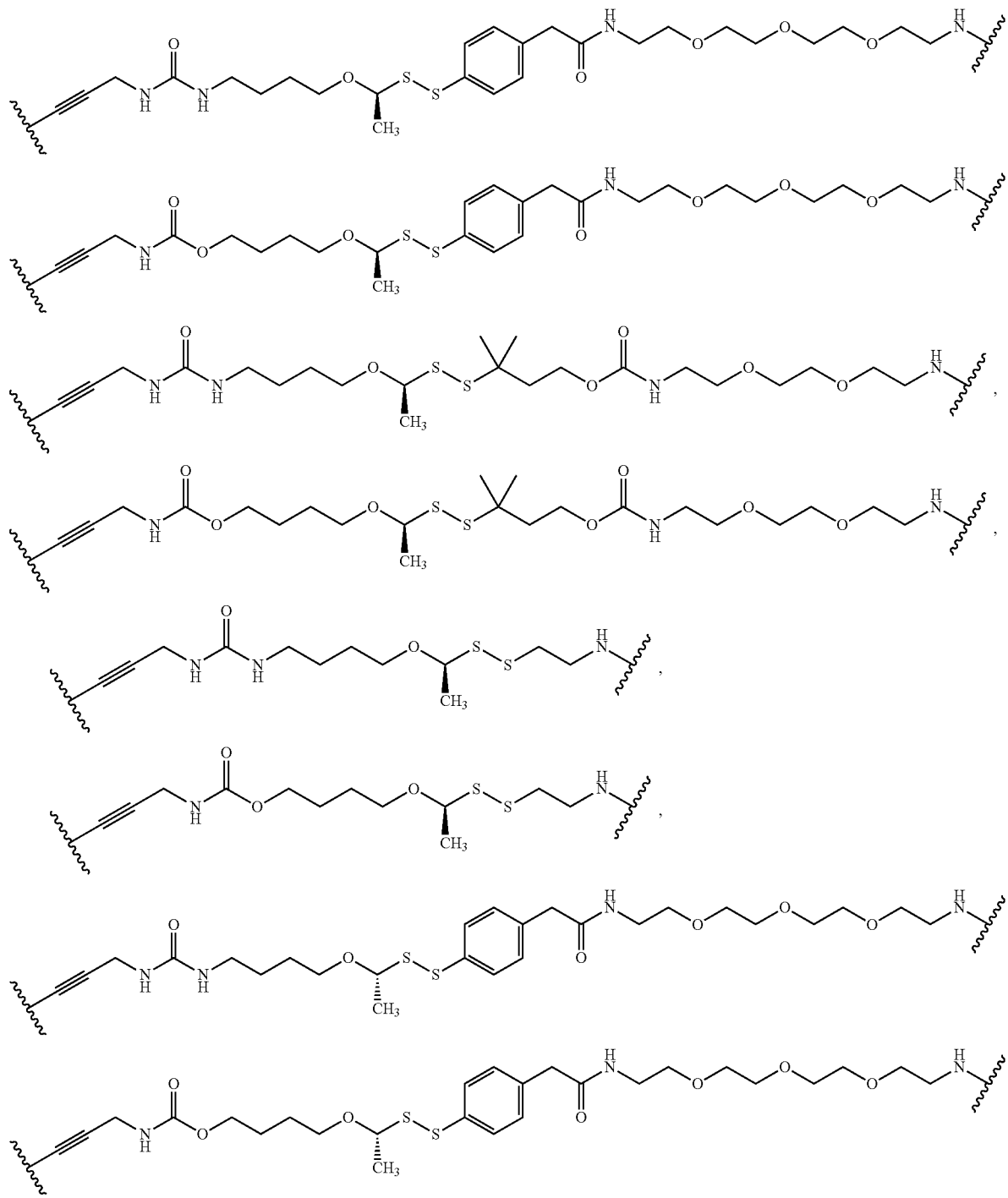

-continued

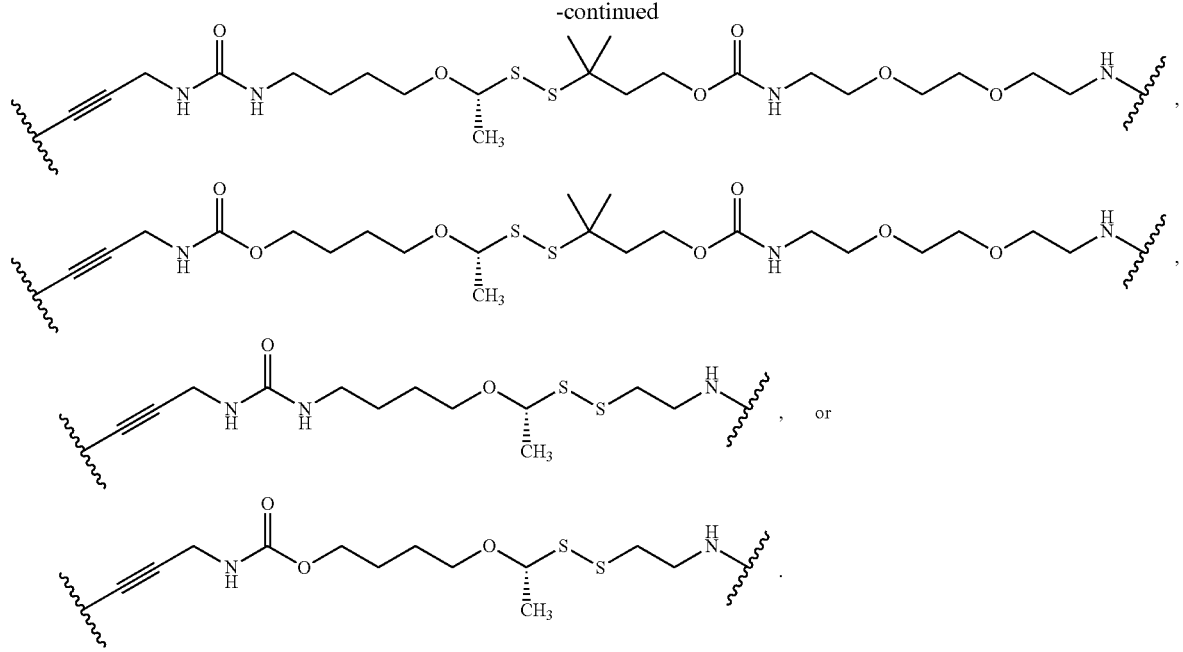

In embodiments, $L^{100}$ is

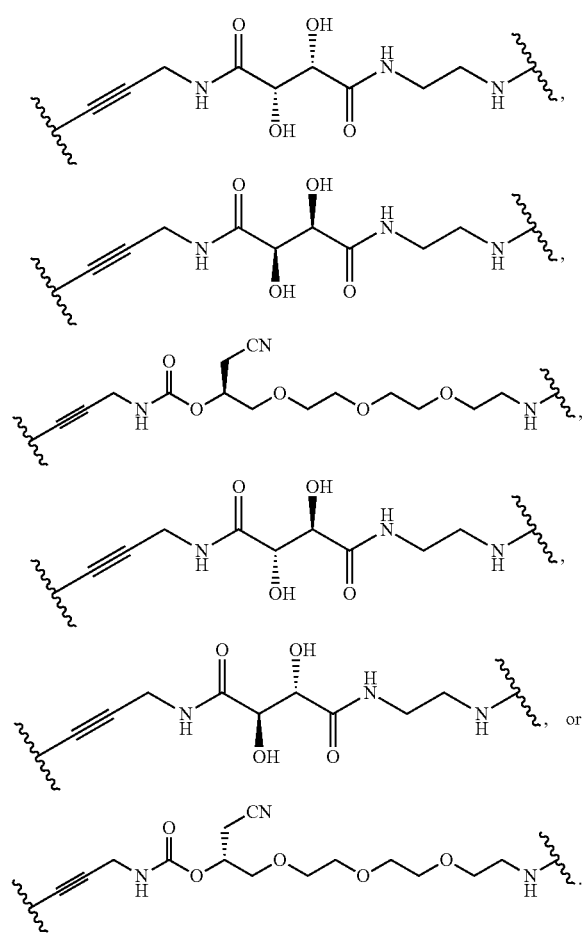 [SMILES: *C#CCNC(=O)[C@@H](O)[C@H](O)C(=O)NCCN* ; *C#CCNC(=O)[C@H](O)[C@@H](O)C(=O)NCCN* ; *C#CCNC(=O)O[C@@H](CC#N)COCCOCCOCCN* ; *C#CCNC(=O)[C@@H](O)[C@@H](O)C(=O)NCCN* ; *C#CCNC(=O)[C@H](O)[C@H](O)C(=O)NCCN* ; *C#CCNC(=O)O[C@H](CC#N)COCCOCCOCCN*]

In embodiments, $L^{101}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{101}$ is a bond, —NH—, —NR$^{101}$—, —S—, —O—, —C(O)—, —C(O)O—, —OC(O)—, —NHC(O)—, —C(O)NH—, —NHC(O)NH—, —NHC(NH)NH—, —C(S)—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8 membered, 3 to 6 membered, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10 membered, 5 to 9 membered, or 5 to 6 membered). In embodiments, $L^{101}$ is a bond. In embodiments, $L^{101}$ is —NH—. In embodiments, $L^{101}$ is —NR$^{101}$—. In embodiments, $L^{101}$ is —S—. In embodiments, $L^{101}$ is —O—. In embodiments, $L^{101}$ is —C(O)—. In embodiments, $L^{101}$ is —C(O)O—. In embodiments, $L^{101}$ is —OC(O)—. In embodiments, $L^{101}$ is —NHC(O)—. In embodiments, $L^{101}$ is —C(O)NH—. In embodiments, $L^{101}$ is —NHC(O)NH—. In embodiments, $L^{101}$ is —NHC(NH)NH—. In embodiments, $L^{101}$ is —C(S)—. In embodiments, $L^{101}$ is $R^{101}$-substituted or unsubstituted $C_1$-$C_{20}$ alkylene. In embodiments, $L^{101}$ is $R^{101}$-substituted or unsubstituted 2 to 20 membered heteroalkylene. In embodiments, $L^{101}$ is $R^{101}$-substituted or unsubstituted 3 to 10 membered heteroalkylene. In embodiments, $L^{101}$ is $R^{101}$-substituted or unsubstituted $C_3$-$C_8$ cycloalkylene. In embodiments, $L^{101}$ is $R^{101}$-substituted or unsubstituted 3 to 8 membered heterocycloalkylene. In embodiments, $L^{101}$ is $R^{101}$-substituted or unsubstituted $C_6$-$C_{10}$ arylene. In embodiments, $L^{101}$ is $R^{101}$-substituted or unsubstituted 5 to 10 membered heteroarylene.

In embodiments, $L^{101}$ is a bond, —NH—, —NR$^{101}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —C(CH$_2$)—. In embodiments, $L^{101}$ is a bond. In embodiments, $L^{101}$ is —NH—. In embodiments, $L^{101}$ is —NR$^{101}$—. In embodiments, $L^{101}$ is —S—. In embodiments, $L^{101}$ is —O—. In embodiments, $L^{101}$ is —C(O)—. In embodiments, $L^{101}$ is —C(O)O—. In embodiments, $L^{101}$ is —OC(O)—. In embodiments, $L^{101}$ is —NHC(O)—. In embodiments, $L^{101}$ is —C(O)NH—. In embodiments, $L^{101}$ is —NHC(O)NH—. In embodiments, $L^{101}$ is —NHC(NH)NH—. In embodiments, $L^{101}$ is —C(S)—. In embodiments, $L^{101}$ is —CH(OH)—. In embodiments, $L^{101}$ is —C(CH$_2$)—.

In embodiments, $L^{101}$ is —(CH$_2$CH$_2$O)$_b$—. In embodiments, $L^{101}$ is CCCH$_2$(OCH$_2$CH$_2$)$_a$—NHC(O)—(CH$_2$)$_c$(OCH$_2$CH$_2$)$_b$—. In embodiments, $L^{101}$ is —CHCHCH$_2$—NHC(O)—(CH$_2$)$_c$(OCH$_2$CH$_2$)$_b$—. In embodiments, $L^{101}$ is —CCCH$_2$—NHC(O)—(CH$_2$)$_c$(OCH$_2$CH$_2$)$_b$—. In embodiments, $L^{101}$ is —CCCH$_2$—. The symbol a is an integer from 0 to 8. In embodiments, a is 1. In embodiments, a is 0. The symbol b is an integer from 0 to 8. In embodiments, b is 0. In embodiments, b is 1 or 2. In embodiments, b is an integer from 2 to 8. In embodiments, b is 1. The symbol c is an integer from 0 to 8. In embodiments, c is 0. In embodiments, c is 1. In embodiments, c is 2. In embodiments, c is 3.

$R^{101}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8 membered, 3 to 6 membered, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10 membered, 5 to 9 membered, or 5 to 6 membered).

In embodiments, $R^{101}$ is independently —NH$_2$. In embodiments, $R^{101}$ is independently —OH. In embodiments, $R^{101}$ is independently halogen. In embodiments, $R^{101}$ is independently —CN. In embodiments, Riot is independently oxo. In embodiments, $R^{101}$ is independently —CF$_3$. In embodiments, $R^{101}$ is independently —COOH. In embodiments, $R^{101}$ is independently —CONH$_2$. In embodiments, $R^{101}$ is independently —F. In embodiments, $R^{101}$ is independently —Cl. In embodiments, $R^{101}$ is independently —Br. In embodiments, $R^{101}$ is independently —I.

$R^{101A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{101B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{101B}$-substituted or unsubstituted cycloalkyl (e.g., $C_3$-$C_8$, $C_3$-$C_6$, or $C_5$-$C_6$), $R^{101B}$-substituted or unsubstituted heterocycloalkyl (e.g., 3 to 8 membered, 3 to 6 membered, or 5 to 6 membered), $R^{101B}$-substituted or unsubstituted aryl (e.g., $C_6$-$C_{10}$, $C_{10}$, or phenyl), or $R^{101B}$-substituted or unsubstituted heteroaryl (e.g., 5 to 10 membered, 5 to 9 membered, or 5 to 6 membered).

$R^{101B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $L^{102}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{102}$ is a bond, —NH—, —OC(—$SR^{100}$)($R^{102a}$)—, —OC(—$SSR^{102}$)($R^{102a}$)—, —OC(—SCN)($R^{102a}$)—, —OC($N_3$)($R^{102a}$)—, —OCH($R^{102}$)—, —OCH($CH_2R^{102}$)—, —OCH($CH_2CN$)—, —S—, —O—, —C(O)—, —C(O)O—, —OC(O)—, —NHC(O)—, —C(O)NH—, —NHC(O)NH—, —NHC(NH)NH—, —C(S)—, —SS—, $R^{102}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{102}$-substituted or unsubstituted heteroalkylene (e.g., 2 to 20 membered, 8 to 20 membered, 2 to 10 membered, 2 to 8 membered, 2 to 6 membered, or 2 to 4 membered), $R^{102}$-substituted or unsubstituted cycloalkylene (e.g., $C_3$-$C_8$, $C_3$-$C_6$, or $C_5$-$C_6$), $R^{102}$-substituted or unsubstituted heterocycloalkylene (e.g., 3 to 8 membered, 3 to 6 membered, or 5 to 6 membered), $R^{102}$-substituted or unsubstituted arylene (e.g., $C_6$-$C_{10}$, $C_{10}$, or phenylene), or $R^{102}$-substituted or unsubstituted heteroarylene (e.g., 5 to 10 membered, 5 to 9 membered, or 5 to 6 membered). In embodiments, $L^{102}$ is a bond. In embodiments, $L^{102}$ is —NH—. In embodiments, $L^{102}$ is —OC(—$SR^{100}$)($R^{102a}$)—. In embodiments, $L^{102}$ is —OC(—$SSR^{102}$)($R^{102a}$)—. In embodiments, $L^{102}$ is —OC(—SCN)($R^{102a}$)—. In embodiments, $L^{102}$ is —OC($N_3$)($R^{102a}$)—. In embodiments, $L^{102}$ is —OC(—$SR^{100}$)($CH_3$)—. In embodiments, $L^{102}$ is —OC(—$SSR^{102}$)($CH_3$)—. In embodiments, $L^{102}$ is —OC(—SCN)($CH_3$)—. In embodiments, $L^{102}$ is —OC($N_3$)($CH_3$)—. In embodiments, $L^{102}$ is —OCH(—$SR^{100}$)—. In embodiments, $L^{102}$ is —OCH(—$SSR^{102}$)—. In embodiments, $L^{102}$ is —OCH(—SCN)—. In embodiments, $L^{102}$ is —OCH($N_3$)—. In embodiments, $L^{102}$ is —OCH($R^{102}$)—. In embodiments, $L^{102}$ is —OCH($CH_2R^{102}$)—. In embodiments, $L^{102}$ is —OCH($CH_2CN$)—. In embodiments, $L^{102}$ is —S—. In embodiments, $L^{102}$ is —O—. In embodiments, $L^{102}$ is —C(O)—. In embodiments, $L^{102}$ is —C(O)O—. In embodiments, $L^{102}$ is —OC(O)—. In embodiments, $L^{102}$ is —NHC(O)—. In embodiments, $L^{102}$ is —C(O)NH—. In embodiments, $L^{102}$ is —NHC(O)NH—. In embodiments, $L^{102}$ is —NHC(NH)NH—. In embodiments, $L^{102}$ is —C(S)—. In embodiments, $L^{102}$ is —SS—. In embodiments, $L^{102}$ is $R^{102}$-substituted or unsubstituted $C_1$-$C_{20}$alkylene. In embodiments, $L^{102}$ is $R^{102}$-substituted or unsubstituted 2 to 20 membered heteroalkylene. In embodiments, $L^{102}$ is $R^{102}$-substituted or unsubstituted $C_3$-$C_8$ cycloalkylene. In embodiments, $L^{102}$ is $R^{102}$-substituted or unsubstituted 3 to 8 membered heterocycloalkylene. In embodiments, $L^{102}$ is $R^{102}$-substituted or unsubstituted $C_6$-$C_{10}$ arylene. In embodiments, $L^{102}$ is $R^{102}$-substituted or unsubstituted phenylene. In embodiments, $L^{102}$ is $R^{102}$-substituted or unsubstituted 5 to 10 membered heteroarylene.

In embodiments, $L^{102}$ is a bond, —NH—, —OC(—$SR^{100}$)($R^{102a}$)—, —OC(—$SSR^{102}$)($R^{102a}$)—, —OC(—SCN)($R^{102a}$)—, —OC($N_3$)($R^{102a}$)—, —OCH($R^{102}$)—, —OCH($CH_2R^{102}$)—, —OCH($CH_2CN$)—, —S—, —O—, —C(O)—, —C(O)O—, —OC(O)—, —NHC(O)—, —C(O)NH—, —NHC(O)NH—, —NHC(NH)NH—, —C(S)—, —SS—, —CH(OH)—, or —C($CH_2$)—. In embodiments, $L^{102}$ is a bond. In embodiments, $L^{102}$ is —NH—. In embodiments, $L^{102}$ is —OC(—$SR^{100}$)($R^{102a}$)—. In embodiments, $L^{102}$ is —OC(—$SSR^{102}$)($R^{102a}$)—. In embodiments, $L^{102}$ is —OC(—SCN)($R^{102a}$)—. In embodiments, $L^{102}$ is —OC($N_3$)($R^{102a}$)—. In embodiments, $L^{102}$ is —OC(—$SR^{100}$)($CH_3$)—. In embodiments, $L^{102}$ is —OC(—$SSR^{102}$)($CH_3$)—. In embodiments, $L^{102}$ is —OC(—SCN)($CH_3$)—. In embodiments, $L^{102}$ is —OC($N_3$)($CH_3$)—. In embodiments, $L^{102}$ is —OCH(—$SR^{100}$)—. In embodiments, $L^{102}$ is —OCH(—$SSR^{102}$)—. In embodiments, $L^{102}$ is —OCH(—SCN)—. In embodiments, $L^{102}$ is —OCH($N_3$)—. In embodiments, $L^{102}$ is —OCH($R^{102}$)—. In embodiments, $L^{102}$ is —OCH($CH_2R^{102}$)—. In embodiments, $L^{102}$ is —OCH($CH_2CN$)—. In embodiments, $L^{102}$ is —S—. In embodiments, $L^{102}$ is —O—. In embodiments, $L^{102}$ is —C(O)—. In embodiments, $L^{102}$ is —C(O)O—. In embodiments, $L^{102}$ is —OC(O)—. In embodiments, $L^{102}$ is —NHC(O)—. In embodiments, $L^{102}$ is —C(O)NH—. In embodiments, $L^{102}$ is —NHC(O)NH—. In embodiments, $L^{102}$ is —NHC(NH)NH—. In embodiments, $L^{102}$ is —C(S)—. In embodiments, $L^{102}$ is —SS—. In embodiments, $L^{102}$ is —CH(OH)—. In embodiments, $L^{102}$ is —C($CH_2$)—.

$R^{100}$ is —$SR^{102}$ or —CN. In embodiments, $R^{100}$ is —$SR^{102}$. In embodiments, $R^{100}$ is —CN.

$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{102}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{102B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{102B}$-substituted or unsubstituted cycloalkyl (e.g., $C_3$-$C_8$, $C_3$-$C_6$, or $C_5$-$C_6$), $R^{102B}$-substituted or unsubstituted heterocycloalkyl (e.g., 3 to 8 membered, 3 to 6 membered, or 5 to 6 membered), $R^{102B}$-substituted or unsubstituted aryl (e.g., $C_6$-$C_{10}$, $C_{10}$, or phenyl), or $R^{102B}$-substituted or unsubstituted heteroaryl (e.g., 5 to 10 membered, 5 to 9 membered, or 5 to 6 membered).

In embodiments, $R^{102}$ is independently —$NH_2$. In embodiments, $R^{102}$ is independently —OH. In embodiments, $R^{102}$ is independently halogen. In embodiments, $R^{102}$ is independently —CN. In embodiments, $R^{102}$ is independently oxo. In embodiments, $R^{102}$ is independently —$CF_3$. In embodiments, $R^{102}$ is independently —COOH. In embodiments, $R^{102}$ is independently —$CONH_2$. In embodiments, $R^{102}$ is independently —F. In embodiments, $R^{102}$ is independently —Cl. In embodiments, $R^{102}$ is independently —Br. In embodiments, $R^{102}$ is independently —I.

In embodiments, $R^{102}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102}$ is independently unsubstituted $C_1$-$C_6$ alkyl. In embodiments, $R^{102}$ is independently unsubstituted $C_1$-$C_4$ alkyl. In embodiments, $R^{102}$ is independently unsubstituted methyl. In embodiments, $R^{102}$ is independently unsubstituted tert-butyl. In embodiments, $R^{102}$ is independently hydrogen.

In embodiments, $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{102C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102C}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{102C}$-substituted or unsubstituted cycloalkyl (e.g., $C_3$-$C_8$, $C_3$-$C_6$, or $C_5$-$C_6$), $R^{102C}$-substituted or unsubstituted heterocycloalkyl (e.g., 3 to 8 membered, 3 to 6 membered, or 5 to 6 membered), $R^{102C}$-substituted or unsubstituted aryl (e.g., $C_6$-$C_{10}$, $C_{10}$, or phenyl), or $R^{102C}$-substituted or unsubstituted heteroaryl (e.g., 5 to 10 membered, 5 to 9 membered, or 5 to 6 membered).

$R^{102C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^{102}$, is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8 membered, 3 to 6 membered, 4 to 6 membered, 4 to 5 membered, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered).

In embodiments, a substituted $R^{102a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102a}$ is substituted with a plurality of groups selected from substituent groups, size-limited substituent groups, and lower substituent groups; each substituent group, size-limited substituent group, and/or lower substituent group may optionally be different. In embodiments, when $R^{102a}$ is substituted, it is substituted with at least one substituent group. In embodiments, when $R^{102a}$ is substituted, it is substituted with at least one size-limited substituent group. In embodiments, when $R^{102a}$ is substituted, it is substituted with at least one lower substituent group. In embodiments, when $R^{102a}$ is substituted, it is substituted with 1 to 10 substituent groups. In embodiments, when $R^{102a}$ is substituted, it is substituted with 1 to 10 size-limited substituent groups. In embodiments, when $R^{102a}$ is substituted, it is substituted with 1 to 10 lower substituent groups. In embodiments, when $R^{102a}$ is substituted, it is substituted with 1 to 5 substituent groups. In embodiments, when $R^{102a}$ is substituted, it is substituted with 1 to 5 size-limited substituent groups. In embodiments, when $R^{102a}$ is substituted, it is substituted with 1 to 5 lower substituent groups. In embodiments, when $R^{102a}$ is substituted, it is substituted with a substituent group. In embodiments, when $R^{102a}$ is substituted, it is substituted with a size-limited substituent group. In embodiments, when $R^{102a}$ is substituted, it is substituted with a lower substituent group.

In embodiments, $R^{102a}$ is independently hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). In embodiments, $R^{102a}$ is independently hydrogen or unsubstituted alkyl (e.g., $C_1$-$C_{20}$, $C_{10}$-$C_{20}$, $C_1$-$C_8$, $C_1$-$C_6$, or $C_1$-$C_4$).

In embodiments, $R^{102a}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102a}$ is independently unsubstituted $C_1$-$C_6$ alkyl. In embodiments, $R^{102a}$ is independently unsubstituted $C_1$-$C_4$ alkyl. In embodiments, $R^{102a}$ is independently unsubstituted methyl. In embodiments, $R^{102a}$ is independently unsubstituted tert-butyl. In embodiments, $R^{102a}$ is independently hydrogen.

In embodiments, $R^{102}$ and $R^{102a}$ are independently hydrogen or unsubstituted alkyl. In embodiments, $R^{102}$ is unsubstituted $C_1$-$C_4$ alkyl. In embodiments, $R^{102a}$ is hydrogen or unsubstituted methyl.

In embodiments, $L^{103}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{103}$ is a bond, —NH—, —NR$^{103}$—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, $R^{103}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{103}$-substituted or unsubstituted heteroalkylene (e.g., 2 to 20 membered, 8 to 20 membered, 5 to 16 membered, 2 to 10 membered, 2 to 8 membered, 2 to 6 membered, or 2 to 4 membered), $R^{103}$-substituted or unsubstituted cycloalkylene (e.g., $C_3$-$C_8$, $C_3$-$C_6$, or $C_5$-$C_6$), $R^{103}$-substituted or unsubstituted heterocycloalkylene (e.g., 3 to 8 membered, 3 to 6 membered, or 5 to 6 membered), $R^{103}$-substituted or unsubstituted arylene (e.g., $C_6$-$C_{10}$, $C_{10}$, or phenylene), or $R^{103}$-substituted or unsubstituted heteroarylene (e.g., 5 to 10 membered, 5 to 9 membered, or 5 to 6 membered). In embodiments, $L^{103}$ is a bond. In embodiments, $L^{103}$ is —NH—. In embodiments, $L^{103}$ is —NR$^{103}$—. In embodiments, $L^{103}$ is —S—. In embodiments, $L^{103}$ is —O—. In embodiments, $L^{103}$ is —C(O)—. In embodiments, $L^{103}$ is —C(O)O—. In embodiments, $L^{103}$ is —OC(O)—. In embodiments, $L^{103}$ is —NHC(O)—. In embodiments, $L^{103}$ is —C(O)NH—. In embodiments, $L^{103}$ is —NHC(O)NH—. In embodiments, $L^{103}$ is —NHC(NH)NH—. In embodiments, $L^{103}$ is —C(S)—. In embodiments, $L^{103}$ is —N=N—. In embodiments, $L^{103}$ is —SS—. In embodiments, $L^{103}$ is $R^{103}$-substituted or unsubstituted $C_1$-$C_{20}$alkylene. In embodiments, $L^{103}$ is $R^{103}$-substituted or unsubstituted 2 to 20 membered heteroalkylene. In embodiments, $L^{103}$ is $R^{103}$-substituted or unsubstituted 5 to 16 membered heteroalkylene. In embodiments, $L^{103}$ is $R^{103}$-substituted or unsubstituted 2 to 10 membered heteroalkylene. In embodiments, $L^{103}$ is $R^{103}$-substituted or unsubstituted $C_3$-$C_8$ cycloalkylene. In embodiments, $L^{103}$ is $R^{103}$-substituted or unsubstituted 3 to 8 membered heterocycloalkylene. In embodiments, $L^{103}$ is $R^{103}$-substituted or unsubstituted $C_6$-$C_{10}$ arylene. In embodiments, $L^{103}$ is $R^{103}$-substituted or unsubstituted 5 to 10 membered heteroarylene.

In embodiments, $L^{103}$ is a bond, —NH—, —NR$^{103}$—, —S—, —O—, —C(O)—, —C(O)O—, —OC(O)—, —NHC(O)—, —C(O)NH—, —NHC(O)NH—, —NHC(NH)NH—, —C(S)—, —N=N—, —SS—, —CH(OH)—, or —C(CH$_2$)—. In embodiments, $L^{103}$ is a bond. In embodiments, $L^{103}$ is —NH—. In embodiments, $L^{103}$ is —NR$^{103}$—. In embodiments, $L^{103}$ is —S—. In embodiments, $L^{103}$ is —O—. In embodiments, $L^{103}$ is —C(O)—. In embodiments, $L^{103}$ is —C(O)O—. In embodiments, $L^{103}$ is —OC(O)—. In embodiments, $L^{103}$ is —NHC(O)—. In embodiments, $L^{103}$ is —C(O)NH—. In embodiments, $L^{103}$ is —NHC(O)NH—. In embodiments, $L^{103}$ is —NHC(NH)NH—. In embodiments, $L^{103}$ is —C(S)—. In embodiments, $L^{103}$ is —N=N—. In embodiments, $L^{103}$ is —SS—. In embodiments, $L^{103}$ is —CH(OH)—. In embodiments, $L^{103}$ is —C(CH$_2$)—.

In embodiments, $L^{103}$ is —(CH$_2$CH$_2$O)$_d$—. In embodiments, $L^{103}$ is —(CH$_2$O)$_d$—. In embodiments, $L^{103}$ is —(CH$_2$)$_d$—. In embodiments, $L^{103}$ is —(CH$_2$)$_d$—NH—. In embodiments, $L^{103}$ is -(unsubstituted phenylene)-. In embodiments, $L^{103}$ is

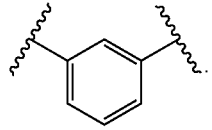 [SMILES: *c1cccc(*)c1]

In embodiments, $L^{103}$ is -(unsubstituted phenylene)-C(O)NH—. In embodiments, $L^{103}$ is

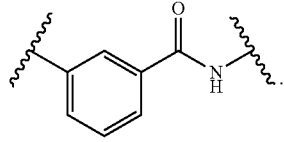 [SMILES: *NC(=O)c1cccc(*)c1]

In embodiments, $L^{103}$ is -(unsubstituted phenylene)-NHC(O)—. In embodiments, $L^{103}$ is

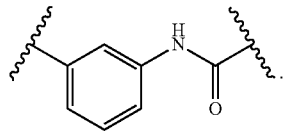 [SMILES: *C(=O)Nc1cccc(*)c1]

The symbol d is an integer from 0 to 8. In embodiments, d is 3. In embodiments, d is 1. In embodiments, d is 2. In embodiments, d is 0.

$R^{103}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{103A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{103A}$-substituted or unsubstituted cycloalkyl (e.g., $C_3$-$C_8$, $C_3$-$C_6$, or $C_5$-$C_6$), $R^{103A}$-substituted or unsubstituted heterocycloalkyl (e.g., 3 to 8 membered, 3 to 6 membered, or 5 to 6 membered), $R^{103A}$-substituted or unsubstituted aryl (e.g., $C_6$-$C_{10}$, $C_{10}$, or phenyl), or $R^{103A}$-substituted or unsubstituted heteroaryl (e.g., 5 to 10 membered, 5 to 9 membered, or 5 to 6 membered).

In embodiments, $R^{103}$ is independently —NH$_2$. In embodiments, $R^{103}$ is independently —OH. In embodiments, $R^{103}$ is independently halogen. In embodiments, $R^{103}$ is independently —CN. In embodiments, $R^{103}$ is independently oxo. In embodiments, $R^{103}$ is independently —CF$_3$. In embodiments, $R^{103}$ is independently —COOH. In embodiments, $R^{103}$ is independently —$CONH_2$. In embodiments, $R^{103}$ is independently —F. In embodiments, $R^{103}$ is independently —Cl. In embodiments, $R^{103}$ is independently —Br. In embodiments, $R^{103}$ is independently —I.

$R^{103A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{103B}$-substituted or unsubstituted cycloalkyl (e.g., $C_3$-$C_8$, $C_3$-$C_6$, or $C_5$-$C_6$), $R^{103B}$-substituted or unsubstituted heterocycloalkyl (e.g., 3 to 8 membered, 3 to 6 membered, or 5 to 6 membered), $R^{103B}$-substituted or unsubstituted aryl (e.g., $C_6$-$C_{10}$, $C_{10}$, or phenyl), or $R^{103B}$-substituted or unsubstituted heteroaryl (e.g., 5 to 10 membered, 5 to 9 membered, or 5 to 6 membered).

$R^{103B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $L^{104}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{104}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 5 to 16 membered, 2 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^{104}$ is a bond, —NH—, —$NR^{104}$—, —S—, —O—, —C(O)—, —C(O)O—, —OC(O)—, —NHC(O)—, —C(O)NH—, —NHC(O)NH—, —NHC(NH)NH—, —C(S)—, $R^{104}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{104}$-substituted or unsubstituted heteroalkylene (e.g., 2 to 20 membered, 8 to 20 membered, 5 to 16 membered, 2 to 10 membered, 2 to 8 membered, 2 to 6 membered, or 2 to 4 membered), $R^{104}$-substituted or unsubstituted cycloalkylene (e.g., $C_3$-$C_8$, $C_3$-$C_6$, or $C_5$-$C_6$), $R^{104}$-substituted or unsubstituted heterocycloalkylene (e.g., 3 to 8 membered, 3 to 6 membered, or 5 to 6 membered), $R^{104}$-substituted or unsubstituted arylene (e.g., $C_6$-$C_{10}$, $C_{10}$, or phenylene), or $R^{104}$-substituted or unsubstituted heteroarylene (e.g., 5 to 10 membered, 5 to 9 membered, or 5 to 6 membered). In embodiments, $L^{104}$ is a bond. In embodiments, $L^{104}$ is —NH—. In embodiments, $L^{104}$ is —$NR^{104}$—. In embodiments, $L^{104}$ is —S—. In embodiments, $L^{104}$ is —O—. In embodiments, $L^{104}$ is —C(O)—. In embodiments, $L^{104}$ is —C(O)O—. In embodiments, $L^{104}$ is —OC(O)—. In embodiments, $L^{104}$ is —NHC(O)—. In embodiments, $L^{104}$ is —C(O)NH—. In embodiments, $L^{104}$ is —NHC(O)NH—. In embodiments, $L^{104}$ is —NHC(NH)NH—. In embodiments, $L^{104}$ is —C(S)—. In embodiments, $L^{104}$ is $R^{104}$-substituted or unsubstituted $C_1$-$C_{20}$alkylene. In embodiments, $L^{104}$ is $R^{104}$-substituted or unsubstituted 2 to 20 membered heteroalkylene. In embodiments, $L^{104}$ is $R^{104}$-substituted or unsubstituted 5 to 16 membered heteroalkylene. In embodiments, $L^{104}$ is $R^{104}$-substituted or unsubstituted 2 to 10 membered heteroalkylene. In embodiments, $L^{104}$ is $R^{104}$-substituted or unsubstituted $C_3$-$C_8$ cycloalkylene. In embodiments, $L^{104}$ is $R^{104}$-substituted or unsubstituted 3 to 8 membered heterocycloalkylene. In embodiments, $L^{104}$ is $R^{104}$-substituted or unsubstituted $C_6$-$C_{10}$ arylene. In embodiments, $L^{104}$ is $R^{104}$-substituted or unsubstituted 5 to 10 membered heteroarylene. In embodiments, $L^{104}$ is $R^{104}$-substituted or unsubstituted phenylene.

In embodiments, $L^{104}$ is a bond, —NH—, —$NR^{104}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —$C(CH_2)$—. In embodiments, $L^{104}$ is a bond. In embodiments, $L^{104}$ is —NH—. In embodiments, $L^{104}$ is —$NR^{104}$—. In embodiments, $L^{104}$ is —S—. In embodiments, $L^{104}$ is —O—. In embodiments, $L^{104}$ is —C(O)—. In embodiments, $L^{104}$ is —C(O)O—. In embodiments, $L^{104}$ is —OC(O)—. In embodiments, $L^{104}$ is —NHC(O)—. In embodiments, $L^{104}$ is —C(O)NH—. In embodiments, $L^{104}$ is —NHC(O)NH—. In embodiments, $L^{104}$ is —NHC(NH)NH—. In embodiments, $L^{104}$ is —C(S)—. In embodiments, $L^{104}$ is —CH(OH)—. In embodiments, $L^{104}$ is —$C(CH_2)$—.

In embodiments, $L^{104}$ is —$(CH_2CH_2O)_e$—. In embodiments, $L^{104}$ is —$(CH_2O)_e$—. In embodiments, $L^{104}$ is —$(CH_2)_e$—. In embodiments, $L^{104}$ is —$(CH_2)_e$—NH—. In embodiments, $L^{104}$ is -(unsubstituted phenylene)-. In embodiments, $L^{104}$ is

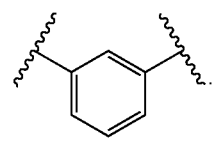

In embodiments, $L^{104}$ is -(unsubstituted phenylene)-C(O)NH—. In embodiments, $L^{104}$ is

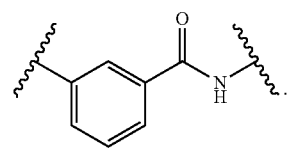 [SMILES: *NC(=O)c1cccc(*)c1]

In embodiments L$^{104}$ is -(unsubstituted phenylene)-NHC(O)—. In embodiments, L$^{104}$ is

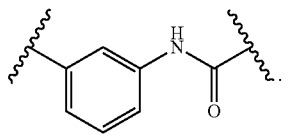 [SMILES: *C(=O)Nc1cccc(*)c1]

The symbol e is an integer from 0 to 8. In embodiments, e is 3. In embodiments, e is 1. In embodiments, e is 2.

R$^{104}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, R$^{104A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{104A}$-substituted or unsubstituted heteroalkyl (e.g., 2 to 20 membered, 8 to 20 membered, 2 to 10 membered, 2 to 8 membered, 2 to 6 membered, or 2 to 4 membered), R$^{104A}$-substituted or unsubstituted cycloalkyl (e.g., C$_3$-C$_8$, C$_3$-C$_6$, or C$_5$-C$_6$), R$^{104A}$-substituted or unsubstituted heterocycloalkyl (e.g., 3 to 8 membered, 3 to 6 membered, or 5 to 6 membered), R$^{104A}$-substituted or unsubstituted aryl (e.g., C$_6$-C$_{10}$, C$_{10}$, or phenyl), or R$^{104A}$-substituted or unsubstituted heteroaryl (e.g., 5 to 10 membered, 5 to 9 membered, or 5 to 6 membered).

In embodiments, R$^{104}$ is independently —NH$_2$. In embodiments, R$^{104}$ is independently —OH. In embodiments, R$^{104}$ is independently halogen. In embodiments, R$^{104}$ is independently —CN. In embodiments, R$^{104}$ is independently oxo. In embodiments, R$^{104}$ is independently —CF$_3$. In embodiments, R$^{104}$ is independently —COOH. In embodiments, R$^{104}$ is independently —CONH$_2$. In embodiments, R$^{104}$ is independently —F. In embodiments, R$^{104}$ is independently —Cl. In embodiments, R$^{104}$ is independently —Br. In embodiments, R$^{104}$ is independently —I.

R$^{104A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, R$^{104B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), R$^{104B}$-substituted or unsubstituted heteroalkyl (e.g., 2 to 20 membered, 8 to 20 membered, 2 to 10 membered, 2 to 8 membered, 2 to 6 membered, or 2 to 4 membered), R$^{104B}$-substituted or unsubstituted cycloalkyl (e.g., C$_3$-C$_8$, C$_3$-C$_6$, or C$_5$-C$_6$), R$^{104B}$-substituted or unsubstituted heterocycloalkyl (e.g., 3 to 8 membered, 3 to 6 membered, or 5 to 6 membered), R$^{104B}$-substituted or unsubstituted aryl (e.g., C$_6$-C$_{10}$, C$_{10}$, or phenyl), or R$^{104B}$-substituted or unsubstituted heteroaryl (e.g., 5 to 10 membered, 5 to 9 membered, or 5 to 6 membered).

R$^{104B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_{10}$, or phenyl), or unsubstituted heteroaryl (e.g., 5 to 10 membered, 5 to 9 membered, or 5 to 6 membered).

In embodiments, L$^{105}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, L$^{105}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., C$_1$-C$_{20}$, C$_{10}$-C$_{20}$, C$_1$-C$_8$, C$_1$-C$_6$, or C$_1$-C$_4$), substituted or unsubstituted heteroalkylene (e.g., 2 to 20 membered, 8 to 20 membered, 5 to 16 membered, 2 to 10 membered, 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8 membered, 3 to 6 membered, or 5 to 6 membered), substituted or unsubstituted arylene (e.g., C$_6$-C$_{10}$, C$_{10}$, or phenylene), or substituted or unsubstituted heteroarylene (e.g., 5 to 10 membered, 5 to 9 membered, or 5 to 6 membered).

In embodiments, L$^{105}$ is a bond, —NH—, —NR$^{105}$—, —S—, —O—, —C(O)—, —C(O)O—, —OC(O)—, —NHC(O)—, —C(O)NH—, —NHC(O)NH—, —NH(NH)NH—, —C(S)—, R$^{105}$-substituted or unsubstituted alkylene (e.g., C$_1$-C$_{20}$, C$_{10}$-C$_{20}$, C$_1$-C$_8$, C$_1$-C$_6$, or C$_1$-C$_4$), R$^{105}$-substituted or unsubstituted heteroalkylene (e.g., 2 to 20 membered, 8 to 20 membered, 5 to 16 membered, 2 to 10 membered, 2 to 8 membered, 2 to 6 membered, or 2 to 4 membered), R$^{105}$-substituted or unsubstituted cycloalkylene (e.g., C$_3$-C$_8$, C$_3$-C$_6$, or C$_5$-C$_6$), R$^{105}$-substituted or unsubstituted heterocycloalkylene (e.g., 3 to 8 membered, 3 to 6 membered, or 5 to 6 membered), R$^{105}$-substituted or unsubstituted arylene (e.g., C$_6$-C$_{10}$, C$_{10}$, or phenylene), or R$^{105}$-substituted or unsubstituted heteroarylene (e.g., 5 to 10 membered, 5 to 9 membered, or 5 to 6 membered). In embodiments, L$^{105}$ is a bond. In embodiments, L$^{105}$ is —NH—. In embodiments, L$^{105}$ is —NR$^{105}$—. In embodiments, L$^{105}$ is —S—. In embodiments, L$^{105}$ is —O—. In embodiments, L$^{105}$ is —C(O)—. In embodiments, L$^{105}$ is —C(O)O—. In embodiments, L$^{105}$ is —OC(O)—. In embodiments, L$^{105}$ is —NHC(O)—. In embodiments, L$^{105}$ is —C(O)NH—. In embodiments, L$^{105}$ is —NHC(O)NH—. In embodiments, L$^{105}$ is —NHC(NH)NH—. In embodiments, L$^{105}$ is —C(S)—. In embodiments, L$^{105}$ is R$^{105}$-substituted or unsubstituted C$_1$-C$_{20}$alkylene. In embodiments, L$^{105}$ is R$^{105}$-substituted or unsubstituted 2 to 20 membered heteroalkylene. In embodiments, L$^{105}$ is R$^{105}$-substituted or unsubstituted 5 to 16 membered heteroalkylene. In embodiments, L$^{105}$ is R$^{105}$-substituted or unsubstituted 2 to 10 membered heteroalkylene. In embodiments, L$^{105}$ is R$^{105}$-substituted or unsubstituted C$_3$-C$_8$ cycloalkylene. In embodiments, L$^{105}$ is R$^{105}$-substituted or unsubstituted 3 to 8 membered heterocycloalkylene. In embodiments, L$^{105}$ is R$^{105}$-substituted or unsubstituted C$_6$-C$_{10}$ arylene. In embodiments, L$^{105}$ is R$^{105}$-substituted or unsubstituted 5 to 10 membered heteroarylene.

In embodiments, $L^{105}$ is a bond, —NH—, —NR$^{105}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —C(CH$_2$)—. In embodiments, $L^{105}$ is a bond. In embodiments, $L^{105}$ is —NH—. In embodiments, $L^{105}$ is —NR$^{105}$—. In embodiments, $L^{105}$ is —S—. In embodiments, $L^{105}$ is —O—. In embodiments, $L^{105}$ is —C(O)—. In embodiments, $L^{105}$ is —C(O)O—. In embodiments, $L^{105}$ is —OC(O)—. In embodiments, $L^{105}$ is —NHC(O)—. In embodiments, $L^{105}$ is —C(O)NH—. In embodiments, $L^{105}$ is —NHC(O)NH—. In embodiments, $L^{105}$ is —NHC(NH)NH—. In embodiments, $L^{105}$ is —C(S)—. In embodiments, $L^{105}$ is —CH(OH)—. In embodiments, $L^{105}$ is —C(CH$_2$)—.

In embodiments, $L^{105}$ is —(CH$_2$CH$_2$O)$_f$—. In embodiments, $L^{105}$ is —(CH$_2$O)$_f$—. In embodiments, $L^{105}$ is —(CH$_2$)$_f$—. In embodiments, $L^{105}$ is —(CH$_2$)$_f$—NH—. In embodiments, $L^{105}$ is —C(O)NH(CH$_2$)$_f$—NH—. In embodiments, $L^{105}$ is —(CH$_2$CH$_2$O)$_f$—(CH$_2$)$_g$—NH—. In embodiments, $L^{105}$ is —(CH$_2$)$_g$—. In embodiments, $L^{105}$ is —(CH$_2$)$_g$—NH—. In embodiments, $L^{105}$ is —NHC(O)—(CH$_2$)$_f$—NH—. In embodiments, $R^{105}$ is —NHC(O)—(CH$_2$)$_f$—NH—. In embodiments, $L^{105}$ is —NHC(O)—(CH$_2$CH$_2$O)$_f$—(CH$_2$)$_g$—NH—. In embodiments, $L^{105}$ is —NHC(O)—(CH$_2$)$_g$—NH—. In embodiments, $L^{105}$ is —C(O)NH(CH$_2$)$_f$—NH—. In embodiments, $L^{105}$ is —C(O)NH—(CH$_2$CH$_2$O)$_f$—(CH$_2$)$_g$—NH—. In embodiments, $L^{105}$ is —C(O)NH—(CH$_2$)$_g$—. In embodiments, $L^{105}$ is —C(O)NH—(CH$_2$)$_g$—NH—. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

$R^{105}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{105A}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{105A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{105A}$-substituted or unsubstituted cycloalkyl (e.g., C$_3$-C$_8$, C$_3$-C$_6$, or C$_5$-C$_6$), $R^{105A}$-substituted or unsubstituted heterocycloalkyl (e.g., 3 to 8 membered, 3 to 6 membered, or 5 to 6 membered), $R^{105A}$-substituted or unsubstituted aryl (e.g., C$_6$-C$_{10}$, C$_{10}$, or phenyl), or $R^{105A}$-substituted or unsubstituted heteroaryl (e.g., 5 to 10 membered, 5 to 9 membered, or 5 to 6 membered).

In embodiments, $R^{105}$ is independently —NH$_2$. In embodiments, $R^{105}$ is independently —OH. In embodiments, $R^{105}$ is independently halogen. In embodiments, $R^{105}$ is independently —CN. In embodiments, $R^{105}$ is independently oxo. In embodiments, $R^{105}$ is independently —CF$_3$. In embodiments, $R^{105}$ is independently —COOH. In embodiments, $R^{105}$ is independently —CONH$_2$. In embodiments, $R^{105}$ is independently —F. In embodiments, $R^{105}$ is independently —Cl. In embodiments, $R^{105}$ is independently —Br. In embodiments, $R^{105}$ is independently —I.

$R^{105A}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, $R^{105B}$-substituted or unsubstituted alkyl (e.g., C$_1$-C$_{20}$, C$_{10}$-C$_{20}$, C$_1$-C$_8$, C$_1$-C$_6$, or C$_1$-C$_4$), $R^{105B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{105B}$-substituted or unsubstituted cycloalkyl (e.g., C$_3$-C$_8$, C$_3$-C$_6$, or C$_5$-C$_6$), $R^{105B}$-substituted or unsubstituted heterocycloalkyl (e.g., 3 to 8 membered, 3 to 6 membered, or 5 to 6 membered), $R^{105B}$-substituted or unsubstituted aryl (e.g., C$_6$-C$_{10}$, C$_{10}$, or phenyl), or $R^{105B}$-substituted or unsubstituted heteroaryl (e.g., 5 to 10 membered, 5 to 9 membered, or 5 to 6 membered).

$R^{105B}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_{20}$, C$_{10}$-C$_{20}$, C$_1$-C$_8$, C$_1$-C$_6$, or C$_1$-C$_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., C$_3$-C$_8$, C$_3$-C$_6$, or C$_5$-C$_6$), unsubstituted heterocycloalkyl (e.g., 3 to 8 membered, 3 to 6 membered, or 5 to 6 membered), unsubstituted aryl (e.g., C$_6$-C$_{10}$, C$_{10}$, or phenyl), or unsubstituted heteroaryl (e.g., 5 to 10 membered, 5 to 9 membered, or 5 to 6 membered).

In embodiments, $L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ and $R^{102a}$ are independently hydrogen or unsubstituted alkyl.

In embodiments, $L^{101}$ is independently a substituted or unsubstituted C$_1$-C$_4$ alkylene or substituted or unsubstituted 8 to 20 membered heteroalkylene.

In embodiments, $L^{103}$ is independently a bond or substituted or unsubstituted 2 to 10 membered heteroalkylene.

In embodiments, $L^{104}$ is independently a bond, substituted or unsubstituted 4 to 18 membered heteroalkylene, or substituted or unsubstituted phenylene.

In embodiments, $L^{105}$ is independently bond or substituted or unsubstituted 4 to 18 membered heteroalkylene.

In embodiments, $L^{101}$ is independently a substituted or unsubstituted C$_1$-C$_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; and $R^{102}$ is unsubstituted C$_1$-C$_4$ alkyl; and $R^{102a}$ is hydrogen or unsubstituted methyl.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{104}$ is unsubstituted phenylene.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; and $R^{102}$ and $R^{102a}$ are independently hydrogen or unsubstituted alkyl.

In embodiments, $L^{101}$ is independently a substituted or unsubstituted $C_1$-$C_4$ alkylene or substituted or unsubstituted 8 to 20 membered heteroalkylene.

In embodiments, $L^{103}$ is independently a bond or substituted or unsubstituted 2 to 10 membered heteroalkylene.

In embodiments, $L^{104}$ is independently an unsubstituted phenylene.

In embodiments, $L^{105}$ is independently bond or substituted or unsubstituted 4 to 18 membered heteroalkylene.

In embodiments, $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently an unsubstituted phenylene; $L^{105}$ is independently bond or substituted or unsubstituted 4 to 18 membered heteroalkylene; and $R^{102}$ is unsubstituted $C_1$-$C_4$ alkyl; and $R^{102a}$ is hydrogen or unsubstituted methyl.

In embodiments, -($L^{101}$)-OC(SS$R^{102}$)($R^{102a}$)-($L^{103}$)-($L^{104}$)-($L^{105}$)- is

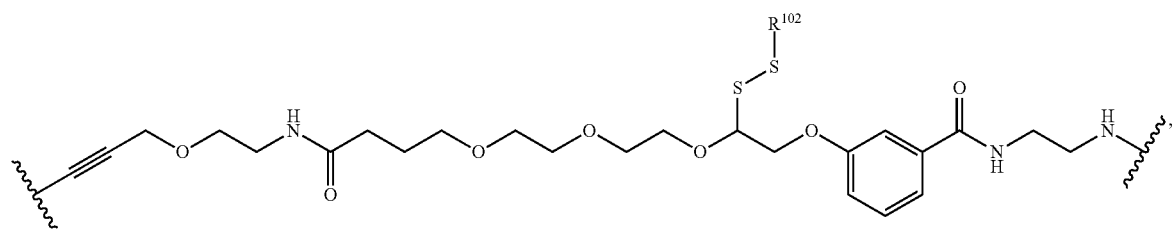

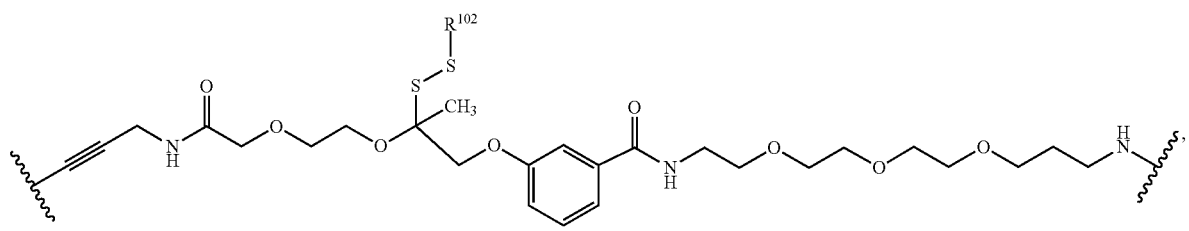

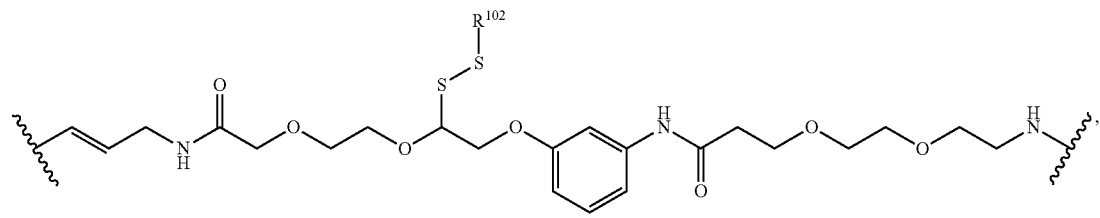

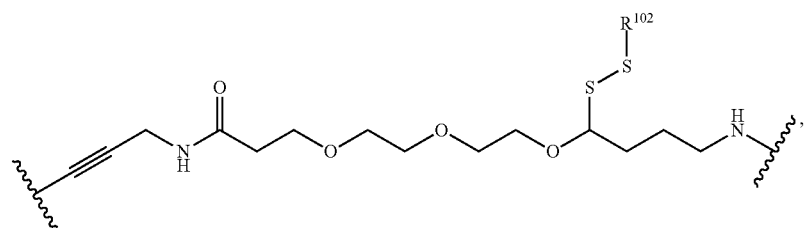

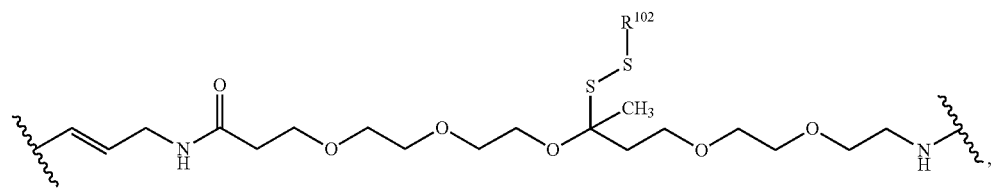

-continued
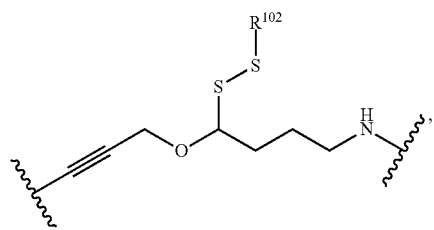
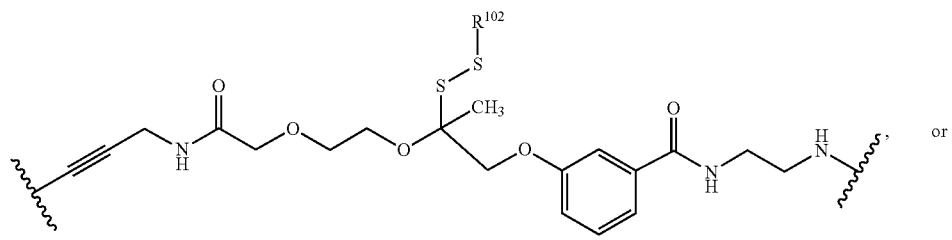 or
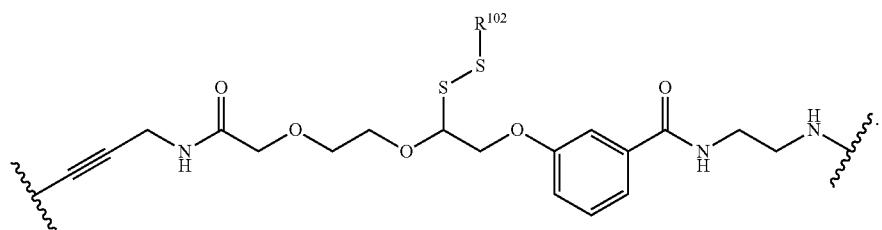
R[102] is as described herein, including in embodiments.
In embodiments, -(L[101])-OC(SSR[102])(R[102a])-(L[103])-(L[104])-(L[105])- is
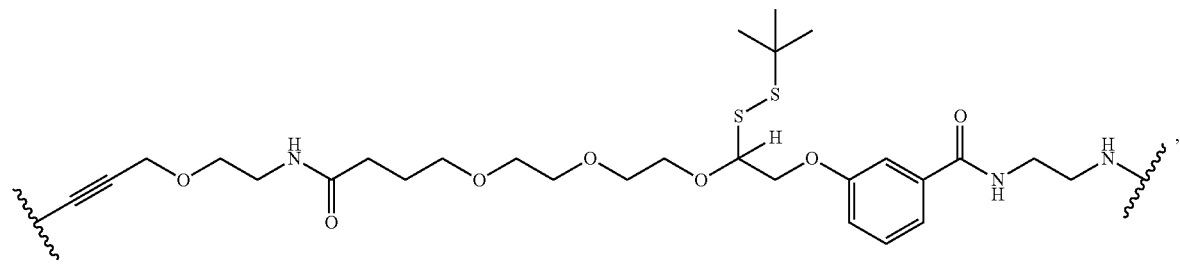
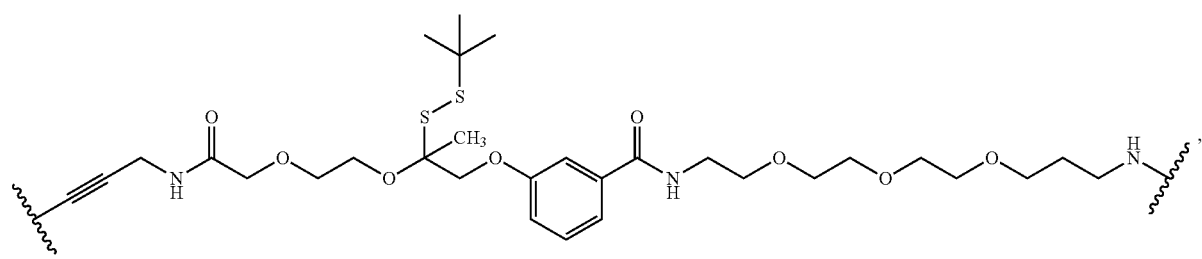
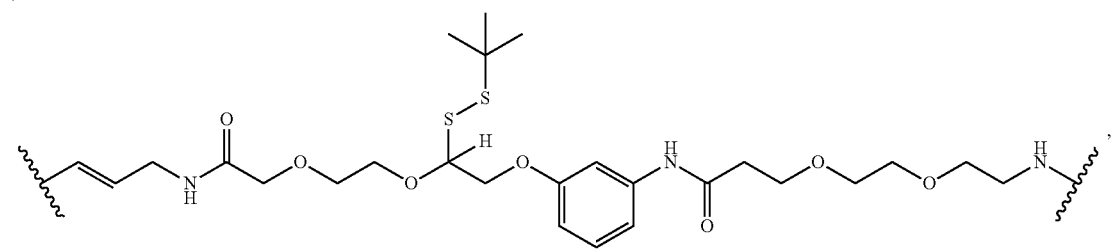

-continued
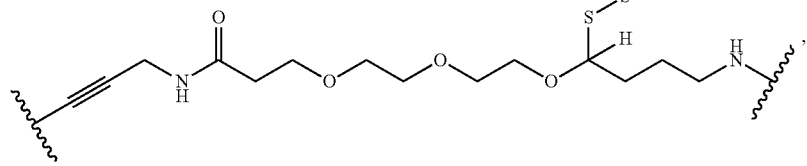
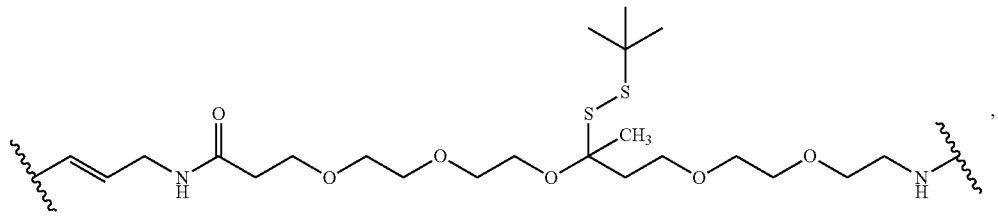
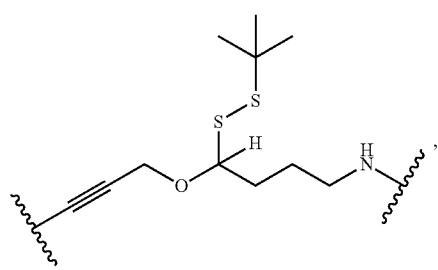
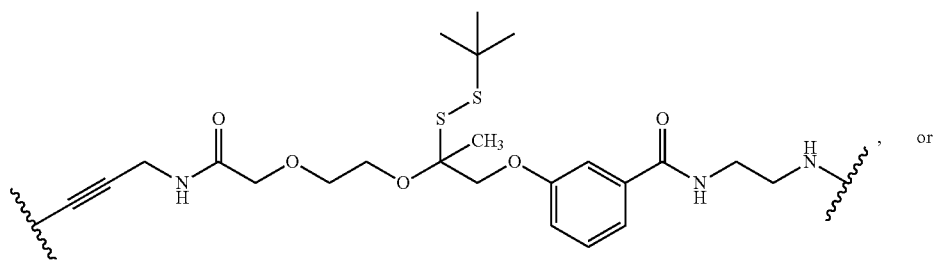, or
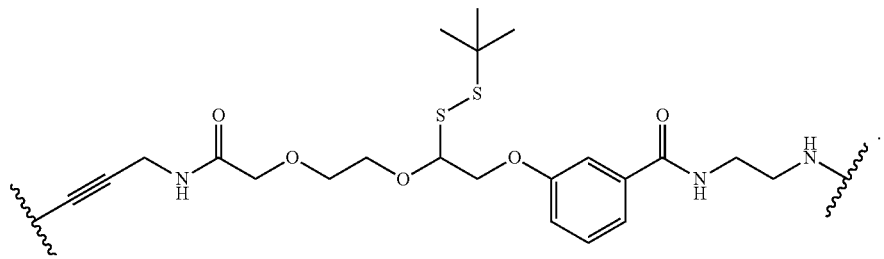 [SMILES: *C#CCNC(=O)COCCOC(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
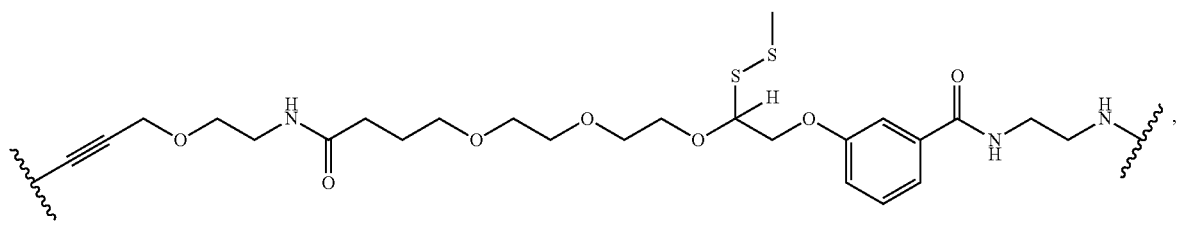, -continued
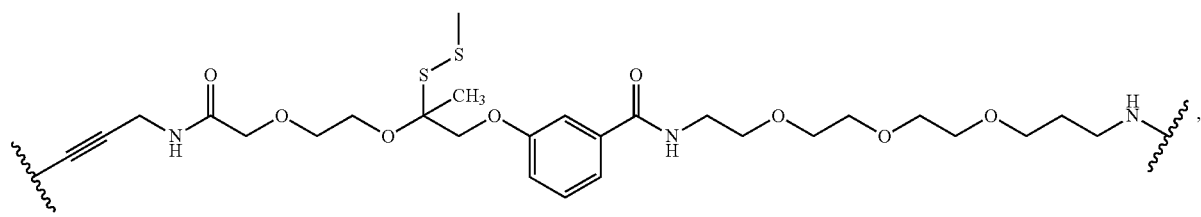
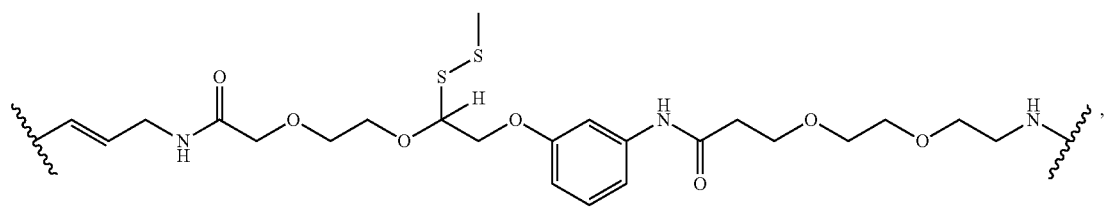
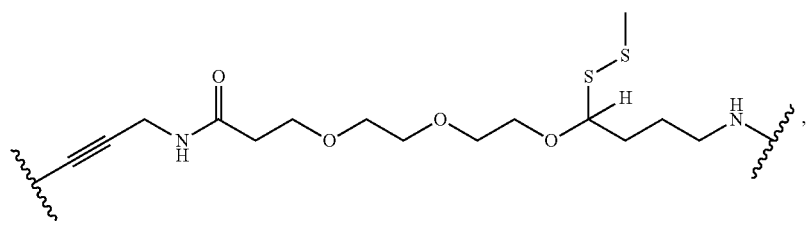
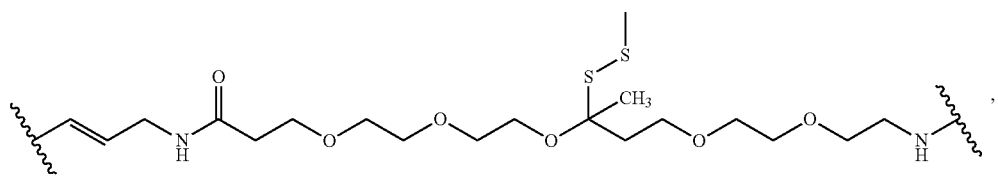
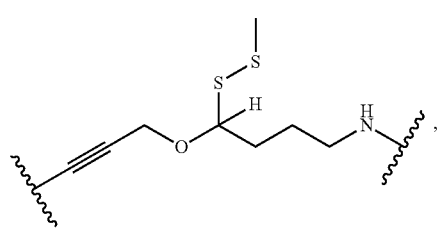
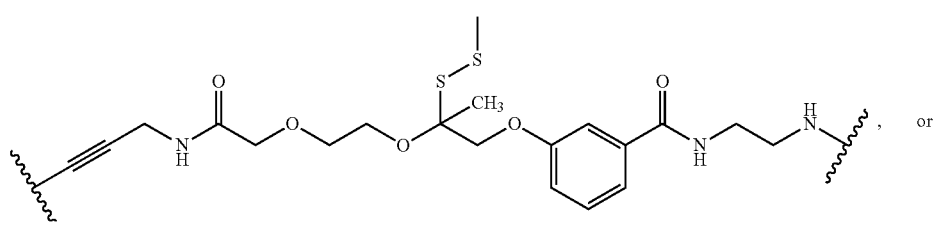, or
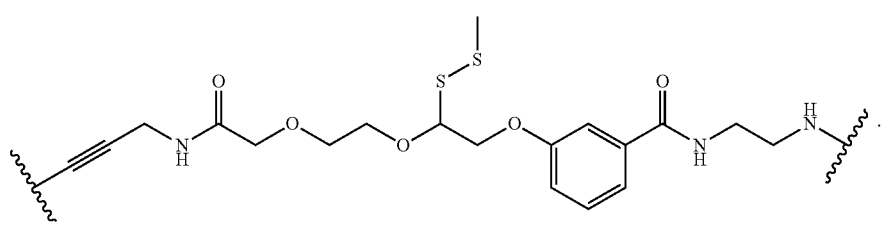 [SMILES: *C#CCNC(=O)COCCOC(COc1cccc(C(=O)NCCN*)c1)SSC].

In embodiments, -(L¹⁰¹)-OC(SSR¹⁰²)(R¹⁰²ᵃ)-(L¹⁰³)-(L¹⁰⁴)-(L¹⁰⁵)- is
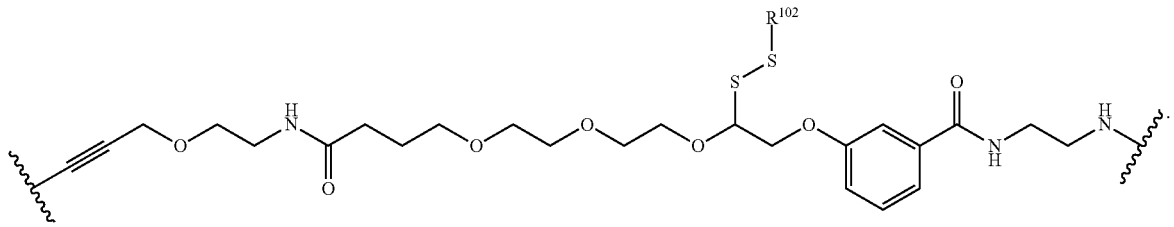
In embodiments, -(L¹⁰¹)-OC(SSR¹⁰²)(R¹⁰²ᵃ)-(L¹⁰³)-(L¹⁰⁴)-(L¹⁰⁵)- is
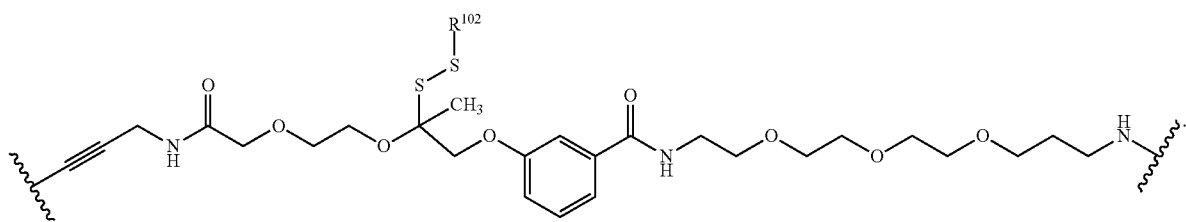
In embodiments, -(L¹⁰¹)-OC(SSR¹⁰²)(R¹⁰²ᵃ)-(L¹⁰³)-(L¹⁰⁴)-(L¹⁰⁵)- is
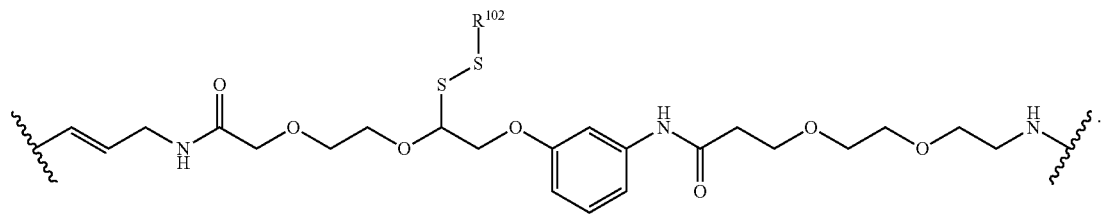
In embodiments, -(L¹⁰¹)-OC(SSR¹⁰²)(R¹⁰²ᵃ)-(L¹⁰³)-(L¹⁰⁴)-(L¹⁰⁵)- is
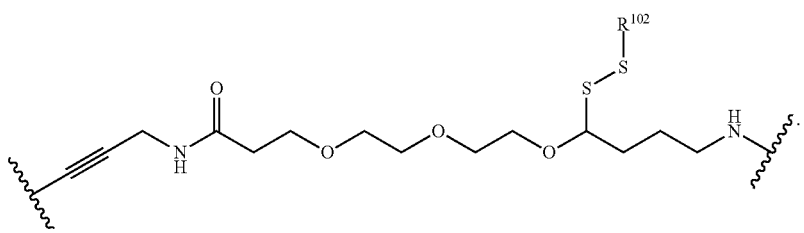
In embodiments, -(L¹⁰¹)-OC(SSR¹⁰²)(R¹⁰²ᵃ)-(L¹⁰³)-(L¹⁰⁴)-(L¹⁰⁵)- is
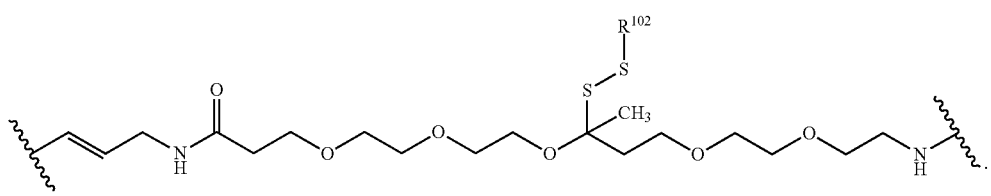

In embodiments, -(L$^{101}$)-OC(SSR$^{102}$)(R$^{102a}$)-(L$^{103}$)-(L$^{104}$)-(L$^{105}$)- is
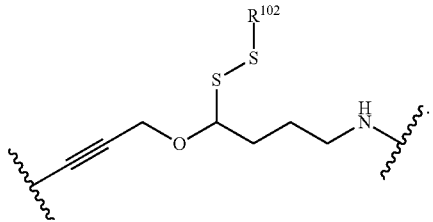
In embodiments, -(L$^{101}$)-OC(SSR$^{102}$)(R$^{102a}$)-(L$^{103}$)-(L$^{104}$)-(L$^{105}$)- is
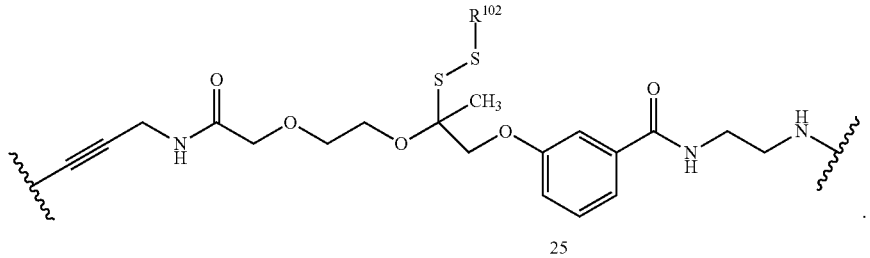
In embodiments, -(L$^{101}$)-OC(SSR$^{102}$)(R$^{102a}$)-(L$^{103}$)-(L$^{104}$)-(L$^{105}$)- is
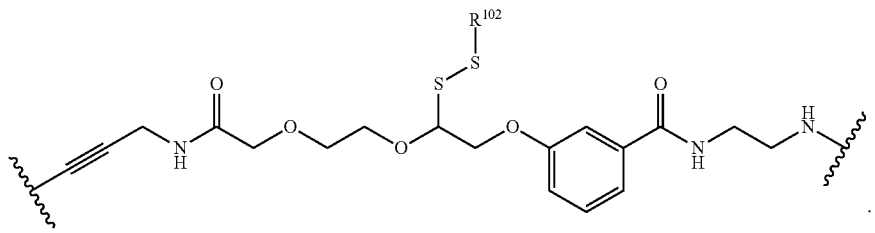
In embodiments, -(L$^{101}$)-OC(SSR$^{102}$)(R$^{102a}$)-(L$^{103}$)-(L$^{104}$)-(L$^{105}$)- is
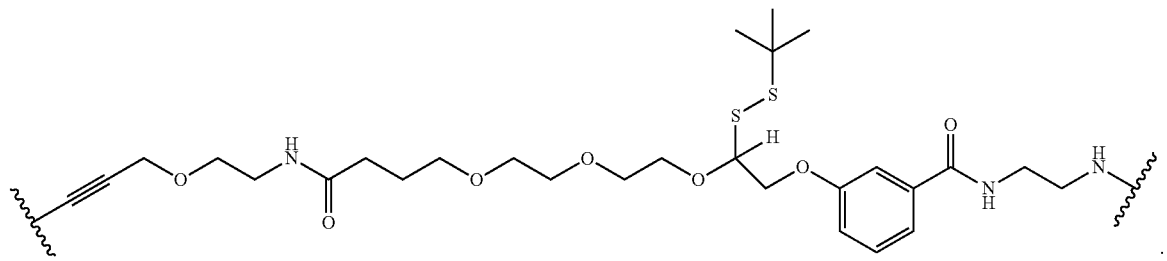 [SMILES: *C#CCOCCNC(=O)CCCOCCOCCOC(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
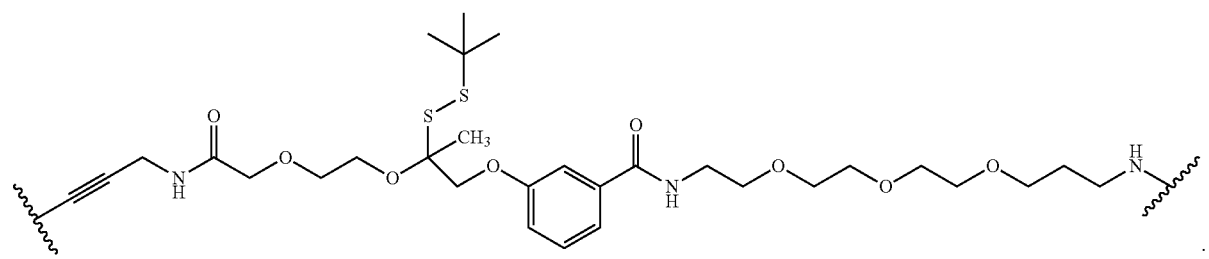 [SMILES: *C#CCNC(=O)COCCOC(C)(COc1cccc(C(=O)NCCOCCOCCOCCCN*)c1)SSC(C)(C)C]

In embodiments, -(L$^{101}$)-OC(SSR$^{102}$)(R$^{102a}$)-(L$^{103}$)-(L$^{104}$)-(L$^{105}$)- is
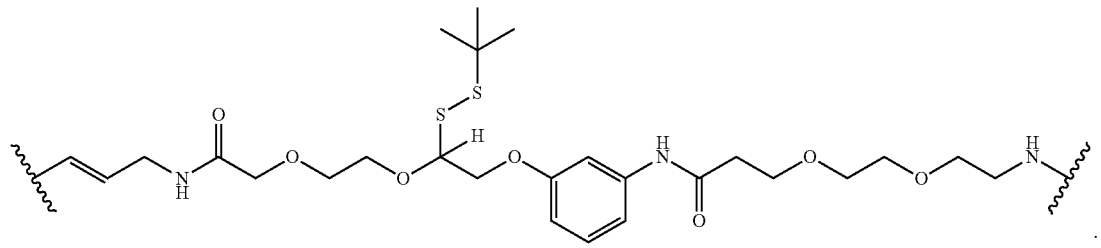 [SMILES: */C=C/CNC(=O)COCCOC(COc1cccc(NC(=O)CCOCCOCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
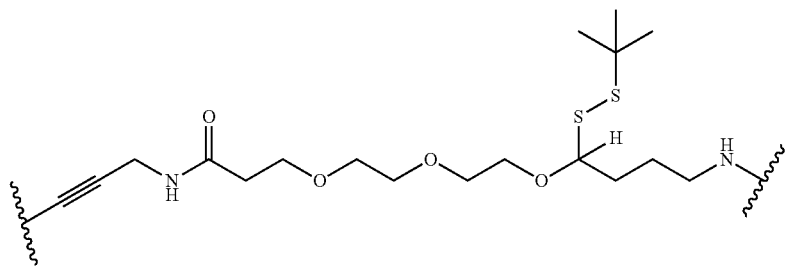 [SMILES: *C#CCNC(=O)CCOCCOCCOC(CCCN*)SSC(C)(C)C]
In embodiments, -(L$^{101}$)-OC(SSR$^{102}$)(R$^{102a}$)-(L$^{103}$)-(L$^{104}$)-(L$^{105}$)- is
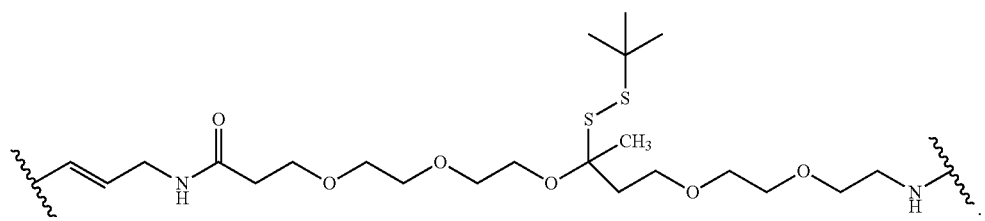 [SMILES: */C=C/CNC(=O)CCOCCOCCOC(C)(CCOCCOCCN*)SSC(C)(C)C]
In embodiments, -(L$^{101}$)-OC(SSR$^{102}$)(R$^{102a}$)-(L$^{103}$)-(L$^{104}$)-(L$^{105}$)- is
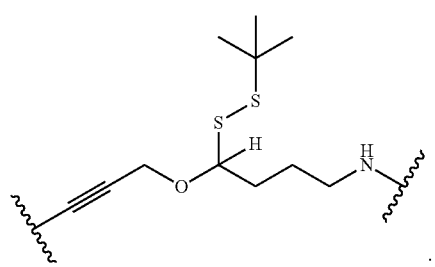 [SMILES: *C#CCOC(CCCN*)SSC(C)(C)C]

In embodiments, -(L$^{101}$)-OC(SSR$^{102}$)(R$^{102a}$)-(L$^{103}$)-(L$^{104}$)-(L$^{105}$)- is
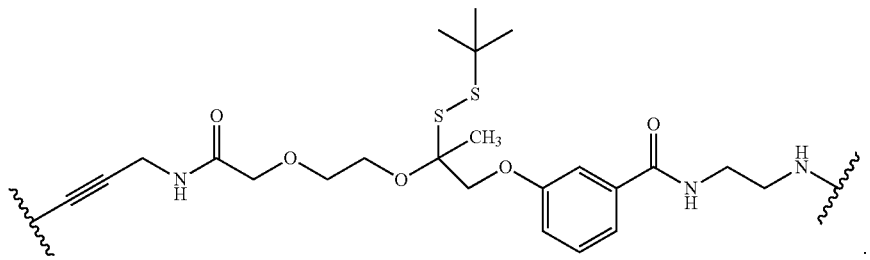 [SMILES: *C#CCNC(=O)COCCOC(C)(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
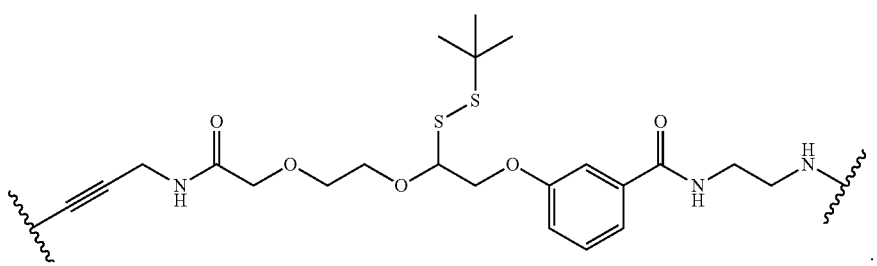 [SMILES: *C#CCNC(=O)COCCOC(COc1cccc(C(=O)NCCN*)c1)SSC(C)(C)C]
In embodiments, -(L$^{101}$)-OC(SSR$^{102}$)(R$^{102a}$)-(L$^{103}$)-(L$^{104}$)-(L$^{105}$)- is
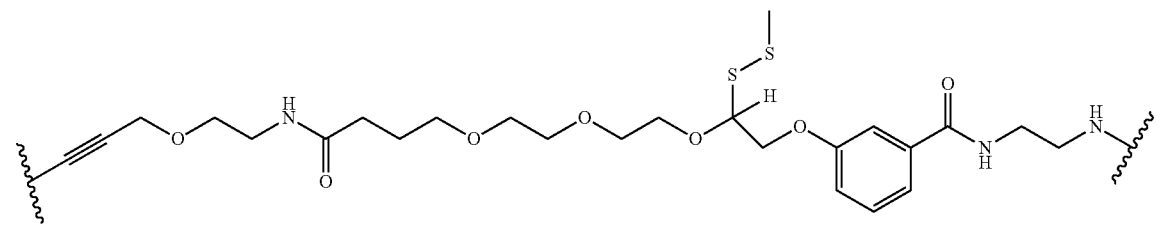 [SMILES: *C#CCOCCNC(=O)CCCOCCOCCOC(COc1cccc(C(=O)NCCN*)c1)SSC]
In embodiments, -(L$^{101}$)-OC(SSR$^{102}$)(R$^{102a}$)-(L$^{103}$)-(L$^{104}$)-(L$^{105}$)- is
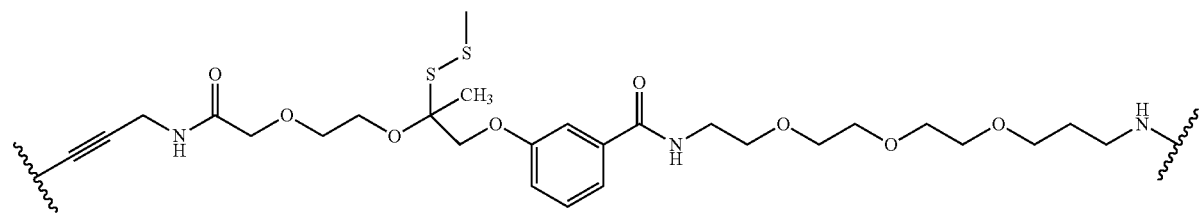 [SMILES: *C#CCNC(=O)COCCOC(C)(COc1cccc(C(=O)NCCOCCOCCOCCCN*)c1)SSC]
In embodiments, -(L$^{101}$)-OC(SSR$^{102}$)(R$^{102a}$)-(L$^{103}$)-(L$^{104}$)-(L$^{105}$)- is
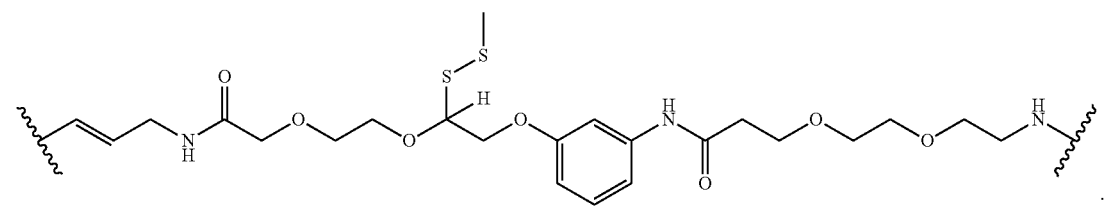 [SMILES: */C=C/CNC(=O)COCCOC(COc1cccc(NC(=O)CCOCCOCCN*)c1)SSC]

In embodiments, -(L$^{101}$)-OC(SSR$^{102}$)(R$^{102a}$)-(L$^{103}$)-(L$^{104}$)-(L$^{105}$)- is
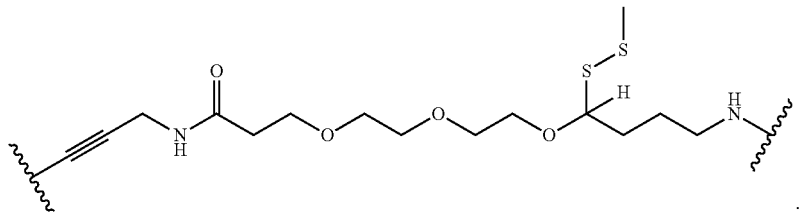 [SMILES: *C#CCNC(=O)CCOCCOCCOC(CCCN*)SSC]
In embodiments, -(L$^{101}$)-OC(SSR$^{102}$)(R$^{102a}$)-(L$^{103}$)-(L$^{104}$)-(L$^{105}$)- is
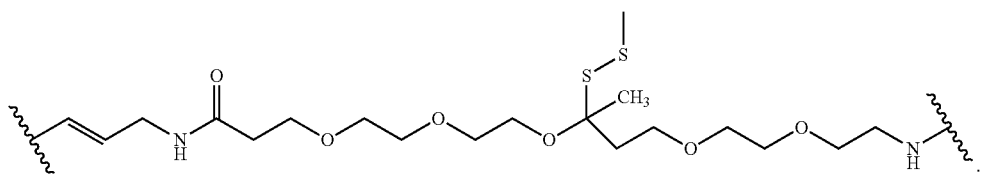 [SMILES: */C=C/CNC(=O)CCOCCOCCOC(C)(CCOCCOCCN*)SSC]
In embodiments, -(L$^{101}$)-OC(SSR$^{102}$)(R$^{102a}$)-(L$^{103}$)-(L$^{104}$)-(L$^{105}$)- is
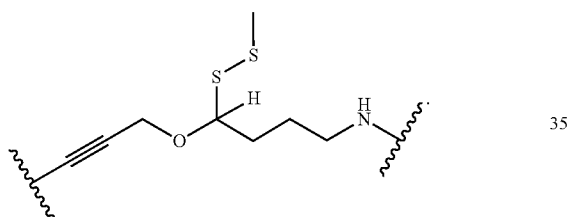
In embodiments, -(L$^{101}$)-OC(SSR$^{102}$)(R$^{102a}$)-(L$^{103}$)-(L$^{104}$)-(L$^{105}$)- is
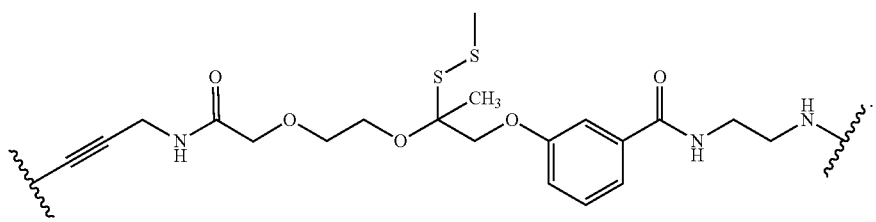 [SMILES: *C#CCNC(=O)COCCOC(C)(COc1cccc(C(=O)NCCN*)c1)SSC]
In embodiments, -(L$^{101}$)-OC(SSR$^{102}$)(R$^{102a}$)-(L$^{103}$)-(L$^{104}$)-(L$^{105}$)- is
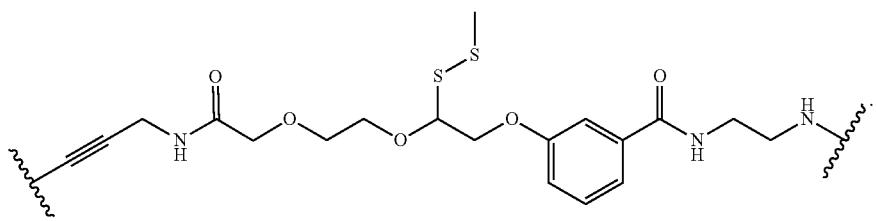 [SMILES: *C#CCNC(=O)COCCOC(COc1cccc(C(=O)NCCN*)c1)SSC]

In embodiments, $-(L^{101})-OC(SSR^{102})(R^{102a})-(L^{103})-(L^{104})-(L^{105})-$ is
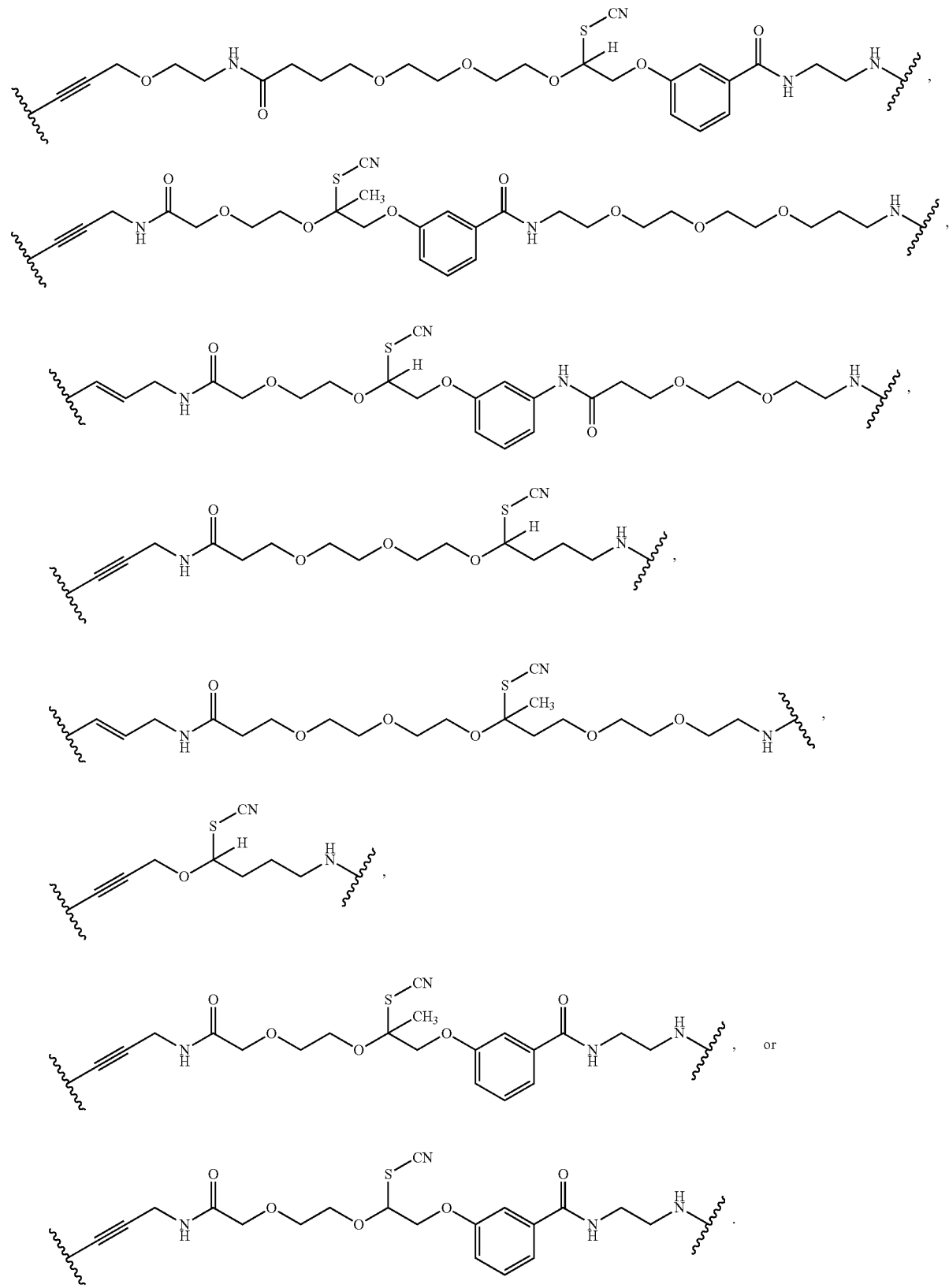

In embodiments, -(L$^{101}$)-OC(SSR$^{102}$)(R$^{102a}$)-(L$^{103}$)-(L$^{104}$)-(L$^{105}$)- is
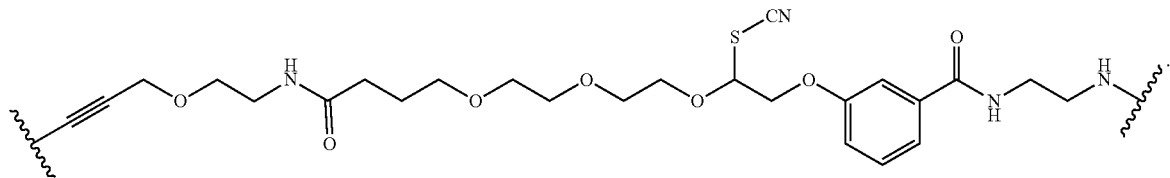 [SMILES: *C#CCOCCNC(=O)CCCOCCOCCOC(COc1cccc(C(=O)NCCN*)c1)SC#N]
In embodiments, -(L$^{101}$)-OC(SSR$^{102}$)(R$^{102a}$)-(L$^{103}$)-(L$^{104}$)-(L$^{105}$)- is
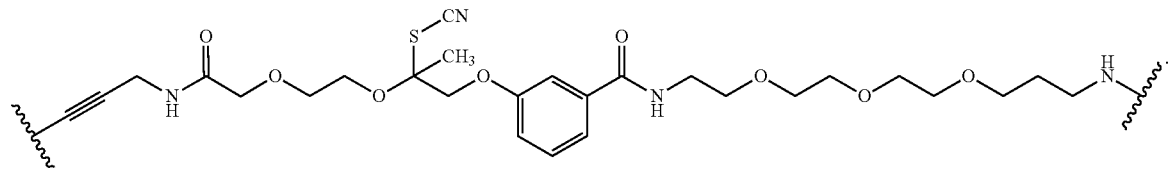 [SMILES: *C#CCNC(=O)COCCOC(C)(COc1cccc(C(=O)NCCOCCOCCOCCCN*)c1)SC#N]
In embodiments, -(L$^{101}$)-OC(SSR$^{102}$)(R$^{102a}$)-(L$^{103}$)-(L$^{104}$)-(L$^{105}$)- is
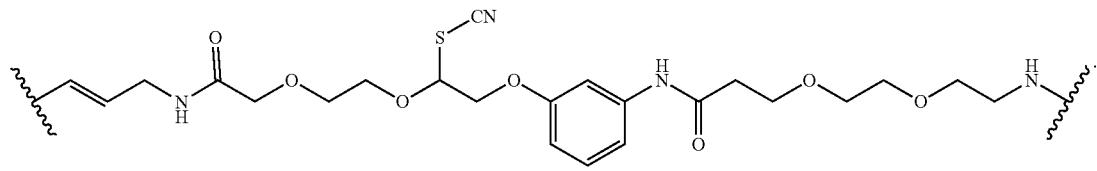 [SMILES: */C=C/CNC(=O)COCCOC(COc1cccc(NC(=O)CCOCCOCCN*)c1)SC#N]
In embodiments, -(L$^{101}$)-OC(SSR$^{102}$)(R$^{102a}$)-(L$^{103}$)-(L$^{104}$)-(L$^{105}$)- is
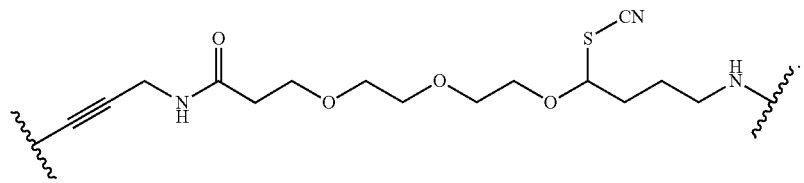 [SMILES: *C#CCNC(=O)CCOCCOCCOC(CCCN*)SC#N]
In embodiments, -(L$^{101}$)-OC(SSR$^{102}$)(R$^{102a}$)-(L$^{103}$)-(L$^{104}$)-(L$^{105}$)- is
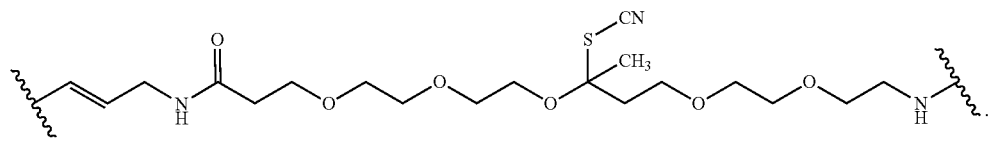 [SMILES: */C=C/CNC(=O)CCOCCOCCOC(C)(CCOCCOCCN*)SC#N]
In embodiments, -(L$^{101}$)-OC(SSR$^{102}$)(R$^{102a}$)-(L$^{103}$)-(L$^{104}$)-(L$^{105}$)- is
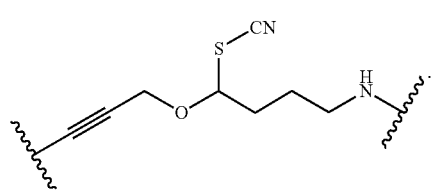 [SMILES: *C#CCOC(CCCN*)SC#N]

In embodiments, -(L$^{101}$)-OC(SSR$^{102}$)(R$^{102a}$)-(L$^{103}$)-(L$^{104}$)-(L$^{105}$)- is

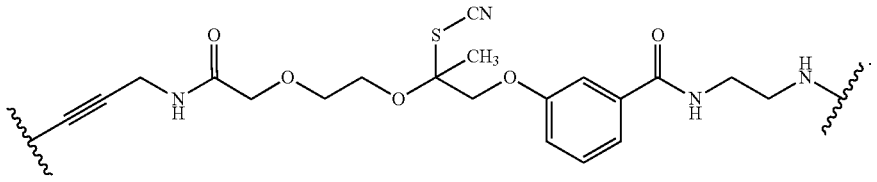 [SMILES: *C#CCNC(=O)COCCOC(C)(COc1cccc(C(=O)NCCN*)c1)SC#N]

In embodiments, -(L$^{101}$)-OC(SSR$^{102}$)(R$^{102a}$)-(L$^{103}$)-(L$^{104}$)-(L$^{105}$)- is

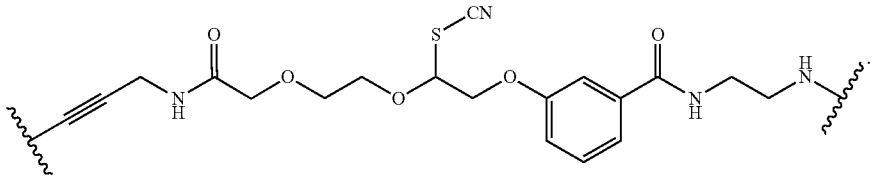 [SMILES: *C#CCNC(=O)COCCOC(COc1cccc(C(=O)NCCN*)c1)SC#N]

In embodiments, L$^{101}$ is —CCCH$_2$—NHC(O)—O—(CH$_2$)$_e$—. In embodiments, L$^{101}$ is —CCCH$_2$—NHC(O)—NH—(CH$_2$)$_c$—. In embodiments, L$^{101}$ is —CCCH$_2$—NHC(O)—(CH$_2$)$_c$—. The symbol c is an integer from 0 to 8. In embodiments, c is 0. In embodiments, c is 1. In embodiments, c is 2. In embodiments, c is 3. In embodiments, c is 4. In embodiments, L$^{101}$ is —CCCH$_2$—NHC(O)—O—(CH$_2$)$_4$—. In embodiments, L$^{101}$ is —CCCH$_2$—NHC(O)—NH—(CH$_2$)$_4$—. In embodiments, L$^{101}$ is —CCCH$_2$—NHC(O)—(CH$_2$)$_2$—. In embodiments, L$^{101}$ is —CCCH$_2$—NHC(O)—O—(CH$_2$)$_c$—OCH(R$^{102}$)—. In embodiments, L$^{101}$ is —CCCH$_2$—NHC(O)—NH—(CH$_2$)$_c$—OCH(R$^{102}$)—.

In embodiments, L$^{102}$ is a bond. In embodiments, L$^{102}$ is —OCH(R$^{102}$)—. In embodiments, L$^{102}$ is —OCH(CH$_3$)—. In embodiments, L$^{102}$ is

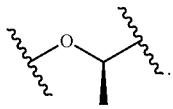 [SMILES: *O[C@@H](*)C]

In embodiments, L$^{102}$ is

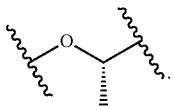

In embodiments, L$^{103}$ is —SS—. In embodiments, R$^{102}$ is —CH$_3$.

In embodiments, L$^{104}$ is a bond. In embodiments, L$^{104}$ is —(CH$_2$CH$_2$O)$_e$—. In embodiments, L$^{104}$ is —(C(CH$_3$)$_2$)—(CH$_2$CH$_2$O)$_e$—. In embodiments, L$^{104}$ is —(CH$_2$)$_e$—. In embodiments, L$^{104}$ is —(CH$_2$)$_e$—NH—. In embodiments, L$^{104}$ is —(C(CH$_3$)$_2$)—(CH$_2$CH$_2$O)—. In embodiments, L$^{104}$ is —(CH$_2$)—NH—. In embodiments, L$^{104}$ is —(CH$_2$)$_2$—NH—. In embodiments, L$^{104}$ is -(unsubstituted phenylene)-. In embodiments, L$^{104}$ is The symbol e is an integer from 0 to 8. In embodiments, e is 3. In embodiments, e is 1. In embodiments, e is 2. In embodiments, e is 0. In embodiments, L$^{104}$ is -(unsubstituted phenylene)-CH$_2$C(O)NH—. In embodiments, L$^{104}$ is —(C(CH$_3$)$_2$)—(CH$_2$CH$_2$O)—C(O)NH—.

In embodiments, L$^{105}$ is a bond. In embodiments, L$^{105}$ is —(CH$_2$)$_f$—NH—. In embodiments, L$^{105}$ is —(CH$_2$)$_2$—NH—. In embodiments, L$^{105}$ is —C(O)NH(CH$_2$)$_f$—NH—. In embodiments, L$^{105}$ is —(CH$_2$CH$_2$O)$_f$—(CH$_2$)$_g$—NH—. In embodiments, L$^{105}$ is —CH$_2$—C(O)NH—(CH$_2$CH$_2$O)$_f$—(CH$_2$)$_g$—NH—. In embodiments, L$^{105}$ is —CH$_2$—C(O)NH—(CH$_2$CH$_2$O)$_3$—(CH$_2$)$_2$—NH—. In embodiments, L$^{105}$ is —C(O)NH—(CH$_2$CH$_2$O)$_f$—(CH$_2$)$_g$—NH—. In embodiments, L$^{105}$ is —C(O)NH—(CH$_2$CH$_2$O)$_2$—(CH$_2$)$_2$—NH—. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

In embodiments, L$^{100}$ is -(L$^{101}$)-(L$^{102}$)-SS-(L$^{104}$)-(L$^{105}$)-. L$^{101}$, L$^{102}$, L$^{104}$, and L$^{105}$ are as described herein. In embodiments, L$^{100}$ is -(L$^{101}$)-OCH(R$^{102}$)—SS-(L$^{104}$)-(L$^{105}$)-. L$^{101}$, L$^{104}$, and L$^{105}$ are as described herein.

In embodiments, -(L$^{101}$)-(L$^{102}$)-SS-(L$^{104}$)-(L$^{105}$)- is
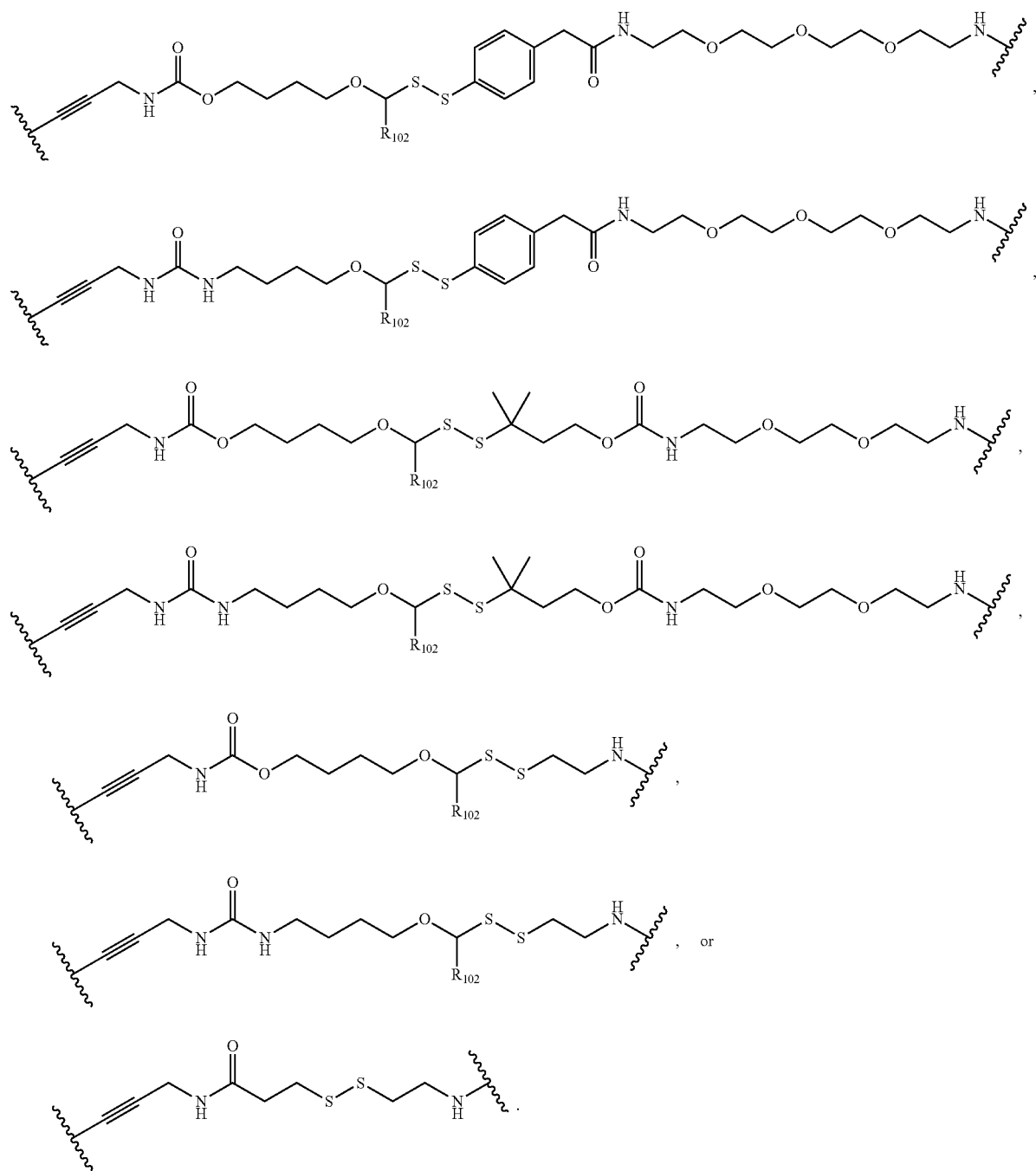
In embodiments, -(L$^{101}$)-(L$^{102}$)-SS-(L$^{104}$)-(L$^{105}$)- is
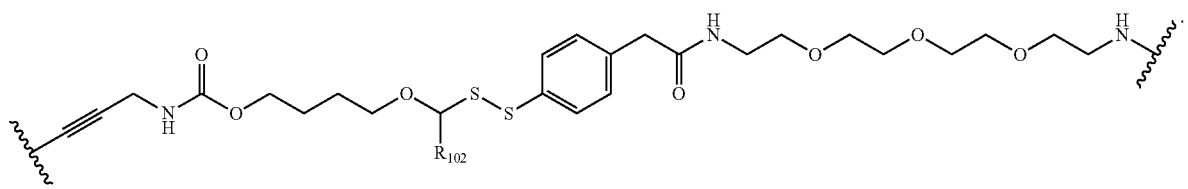

In embodiments, -(L$^{101}$)-(L$^{102}$)-SS-(L$^{104}$)-(L$^{105}$)- is
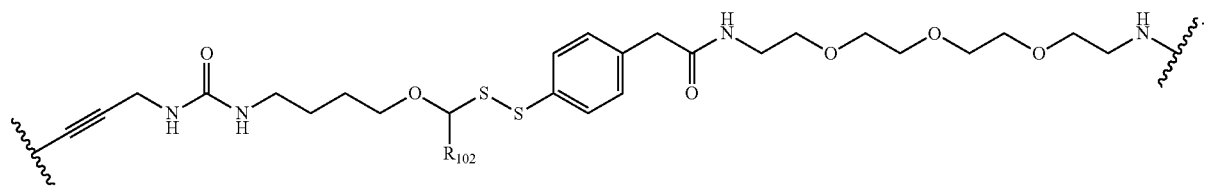
In embodiments, -(L$^{101}$)-(L$^{102}$)-SS-(L$^{104}$)-(L$^{105}$)- is
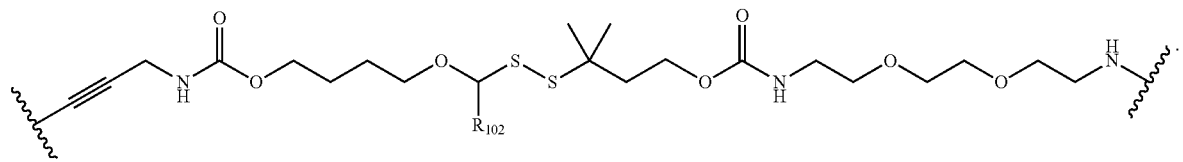
In embodiments, -(L$^{101}$)-(L$^{102}$)-SS-(L$^{104}$)-(L$^{105}$)- is
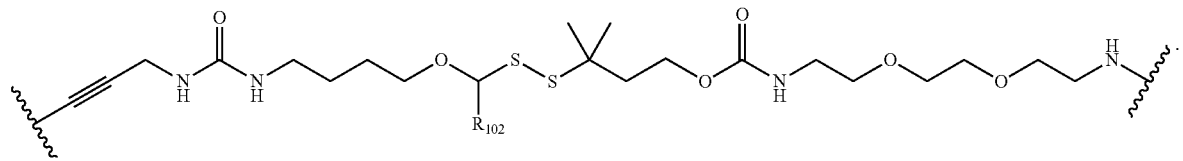
In embodiments, -(L$^{101}$)-(L$^{102}$)-SS-(L$^{104}$)-(L$^{105}$)- is
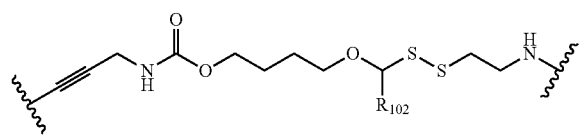
In embodiments, -(L$^{101}$)-(L$^{102}$)-SS-(L$^{104}$)-(L$^{105}$)- is
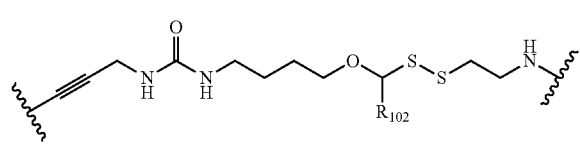
In embodiments, -(L$^{101}$)-(L$^{102}$)-SS-(L$^{104}$)-(L$^{105}$)- is
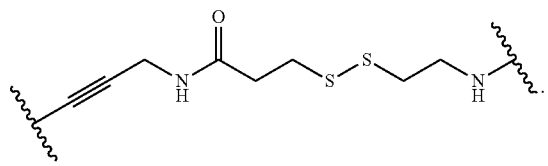 [SMILES: *C#CCNC(=O)CCSSCCN*]
R$^{102}$ is as described herein, including in embodiments.
In embodiments, -(L$^{101}$)-(L$^{102}$)-SS-(L$^{104}$)-(L$^{105}$)- is
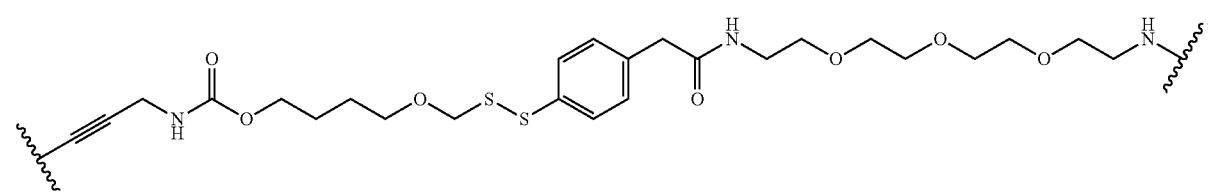

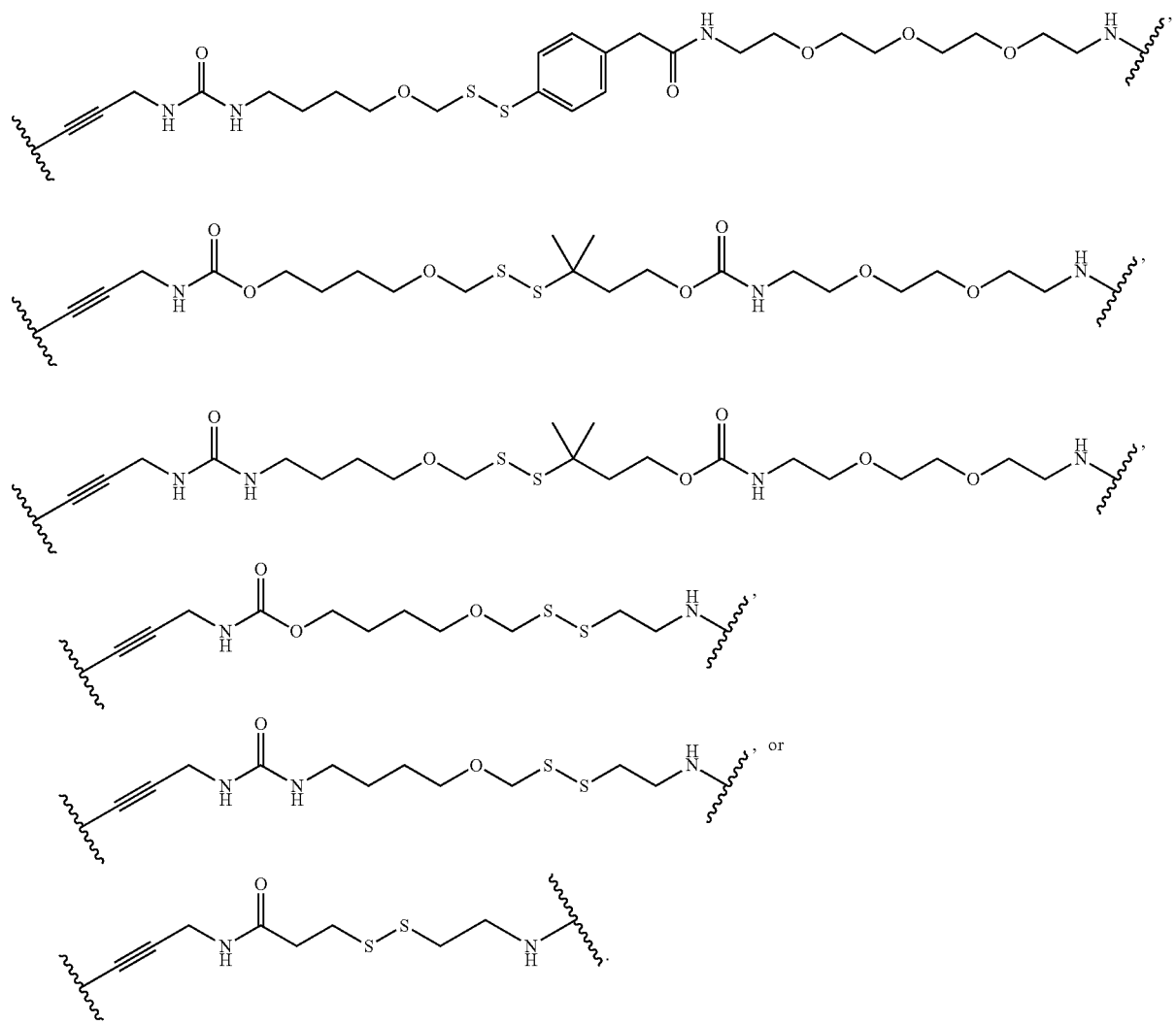
In embodiments, -(L$^{101}$)-(L$^{102}$)-SS-(L$^{104}$)-(L$^{105}$)- is
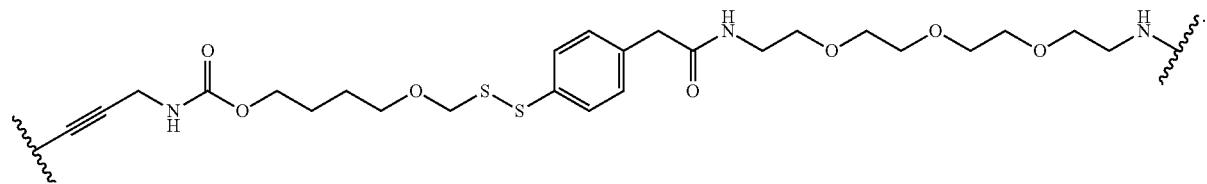 [SMILES: *C#CCNC(=O)OCCCCOCSSc1ccc(CC(=O)NCCOCCOCCOCCN*)cc1]
In embodiments, -(L$^{101}$)-(L$^{102}$)-SS-(L$^{104}$)-(L$^{105}$)- is
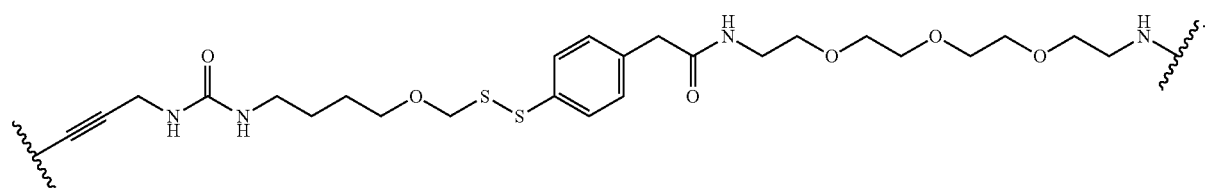

In embodiments, -(L$^{101}$)-(L$^{102}$)-SS-(L$^{104}$)-(L$^{105}$)- is
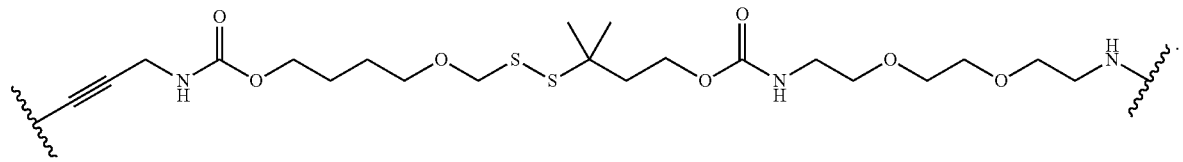 [SMILES: *C#CCNC(=O)OCCCCOCSSC(C)(C)CCOC(=O)NCCOCCOCCN*]
In embodiments, -(L$^{101}$)-(L$^{102}$)-SS-(L$^{104}$)-(L$^{105}$)- is
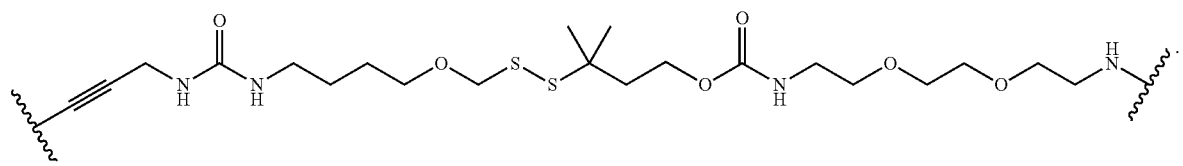 [SMILES: *C#CCNC(=O)NCCCCOCSSC(C)(C)CCOC(=O)NCCOCCOCCN*]
In embodiments, -(L$^{101}$)-(L$^{102}$)-SS-(L$^{104}$)-(L$^{105}$)- is
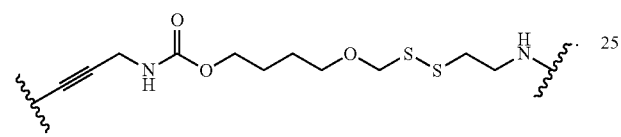
In embodiments, -(L$^{101}$)-(L$^{102}$)-SS-(L$^{104}$)-(L$^{105}$)- is
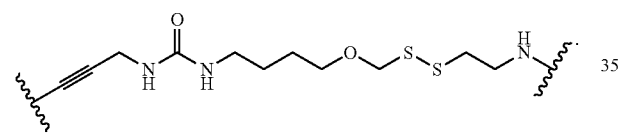
In embodiments, -(L$^{101}$)-(L$^{102}$)-SS-(L$^{104}$)-(L$^{105}$)- is
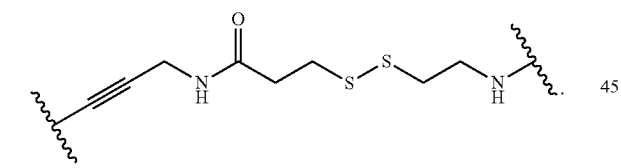
In embodiments, -(L$^{101}$)-(L$^{102}$)-SS-(L$^{104}$)-(L$^{105}$)- is
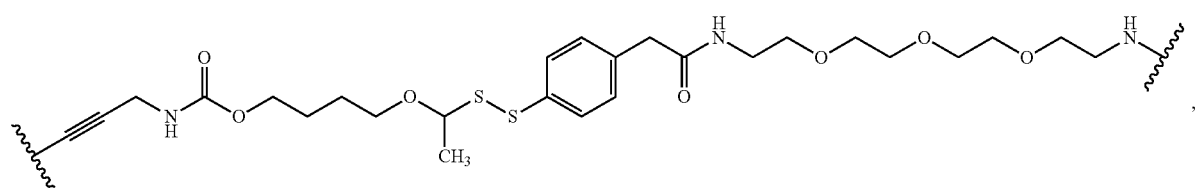
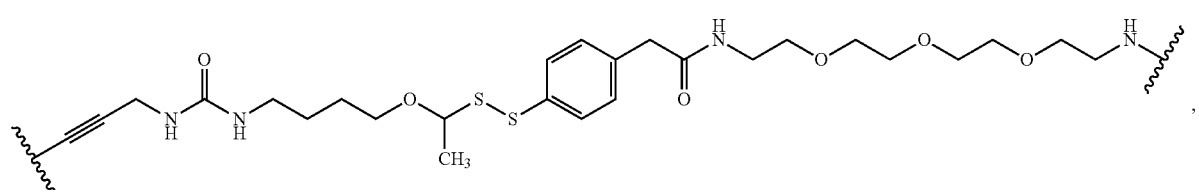

-continued
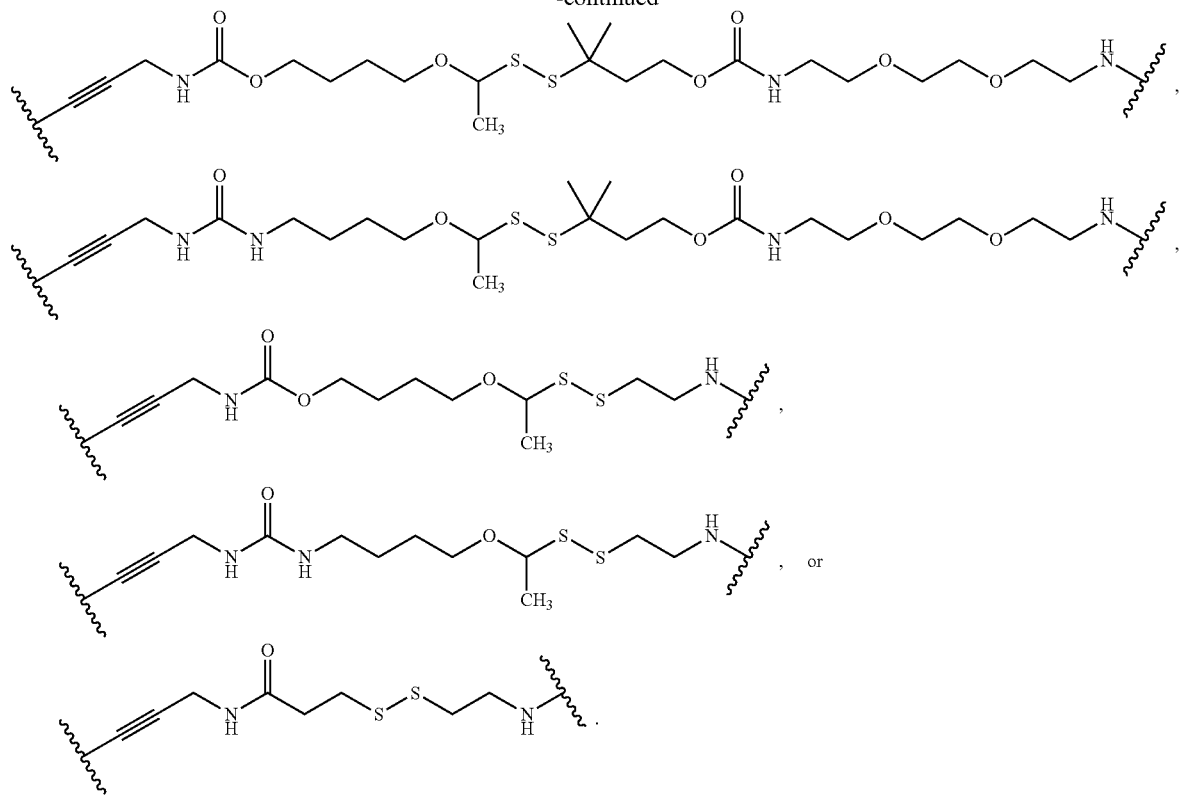
In embodiments, -(L$^{101}$)-(L$^{102}$)-SS-(L$^{104}$)-(L$^{105}$)- is
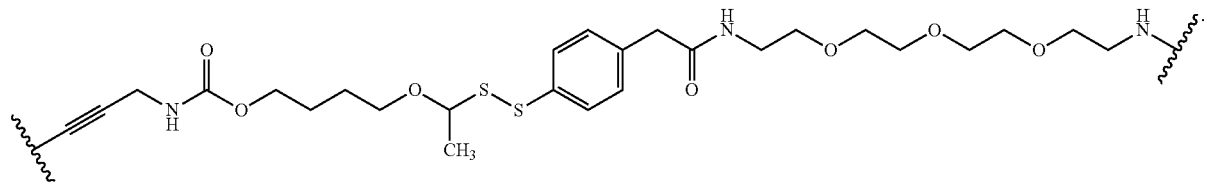 [SMILES: *C#CCNC(=O)OCCCCOC(C)SSc1ccc(CC(=O)NCCOCCOCCOCCN*)cc1]
In embodiments, -(L$^{101}$)-(L$^{102}$)-SS-(L$^{104}$)-(L$^{105}$)- is
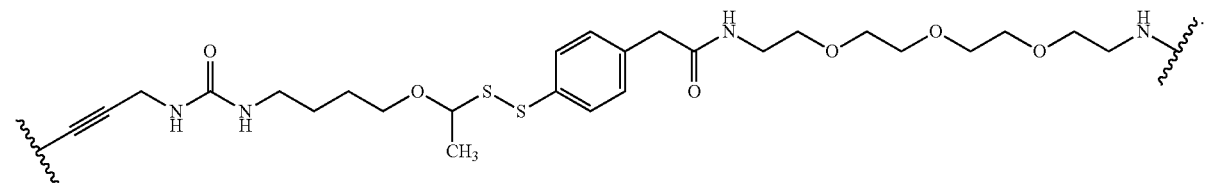
In embodiments, -(L$^{101}$)-(L$^{102}$)-SS-(L$^{104}$)-(L$^{105}$)- is
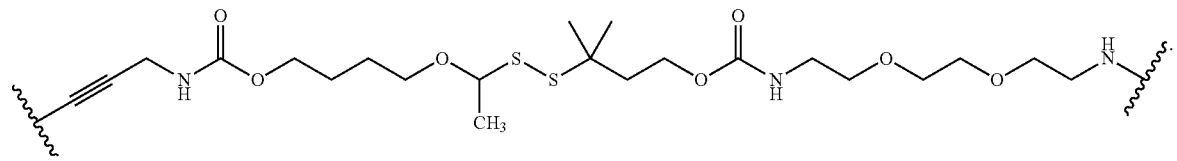 [SMILES: *C#CCNC(=O)OCCCCOC(C)SSC(C)(C)CCOC(=O)NCCOCCOCCN*]

In embodiments, -(L$^{101}$)-(L$^{102}$)-SS-(L$^{104}$)-(L$^{105}$)- is
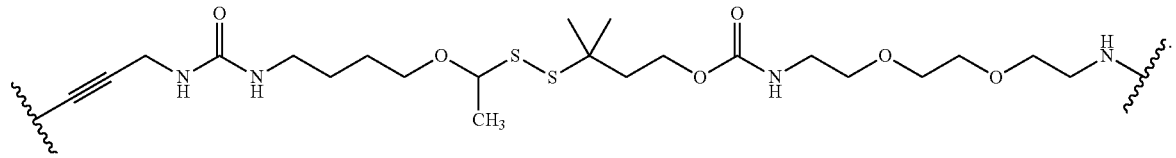 [SMILES: *C#CCNC(=O)NCCCCOC(C)SSC(C)(C)CCOC(=O)NCCOCCOCCN*]
In embodiments, -(L$^{101}$)-(L$^{102}$)-SS-(L$^{104}$)-(L$^{105}$)- is
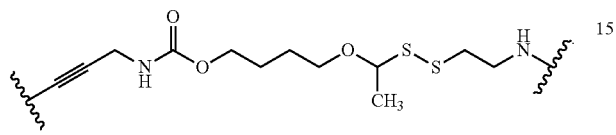
In embodiments, -(L$^{101}$)-(L$^{102}$)-SS-(L$^{104}$)-(L$^{105}$)- is
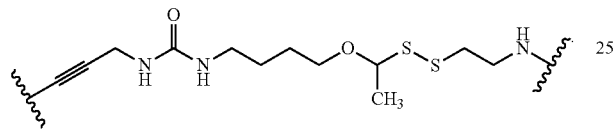
In embodiments, -(L$^{101}$)-(L$^{102}$)-SS-(L$^{104}$)-(L$^{105}$)- is
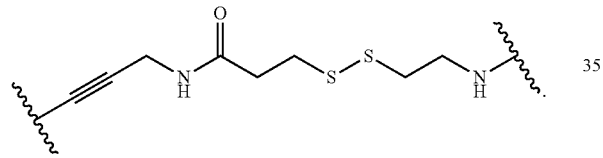
In embodiments, -(L$^{101}$)-(L$^{102}$)-SS-(L$^{104}$)-(L$^{105}$)- is
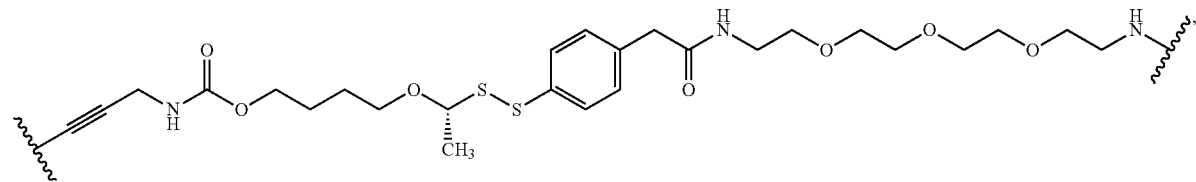
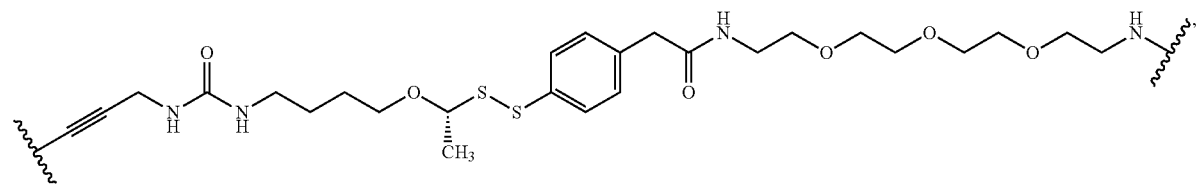
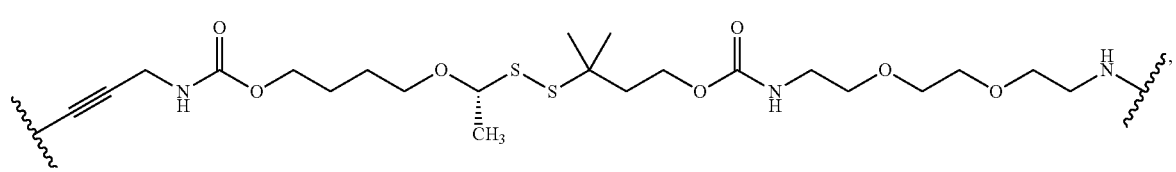

-continued
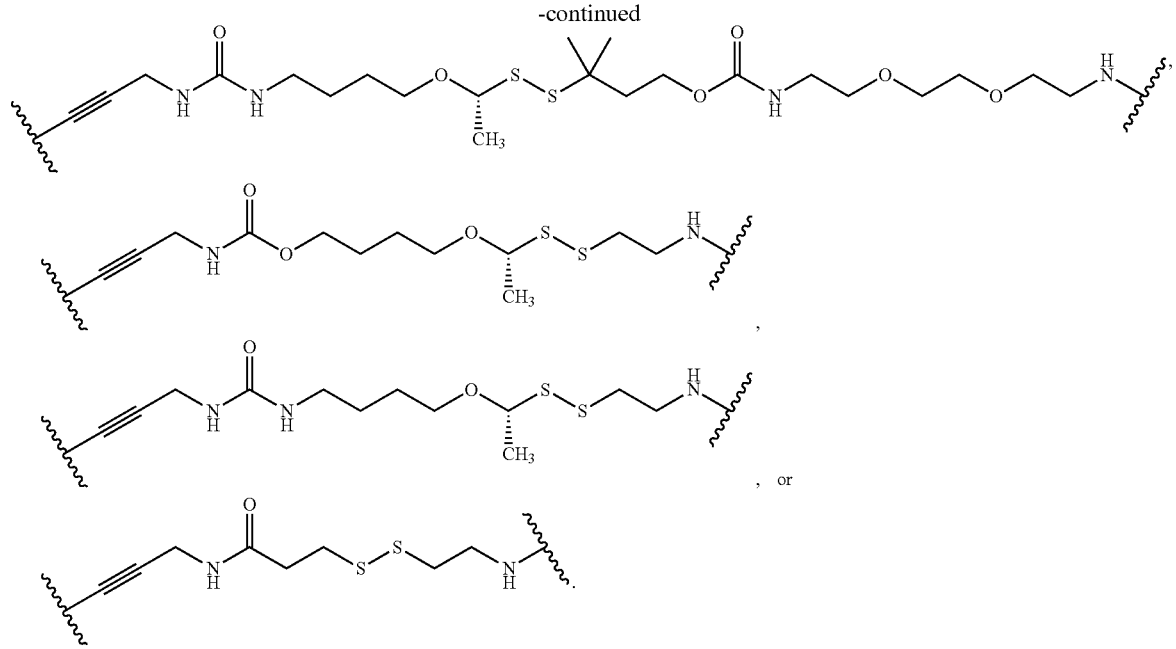
In embodiments, -(L$^{101}$)-(L$^{102}$)-SS-(L$^{104}$)-(L$^{105}$)- is
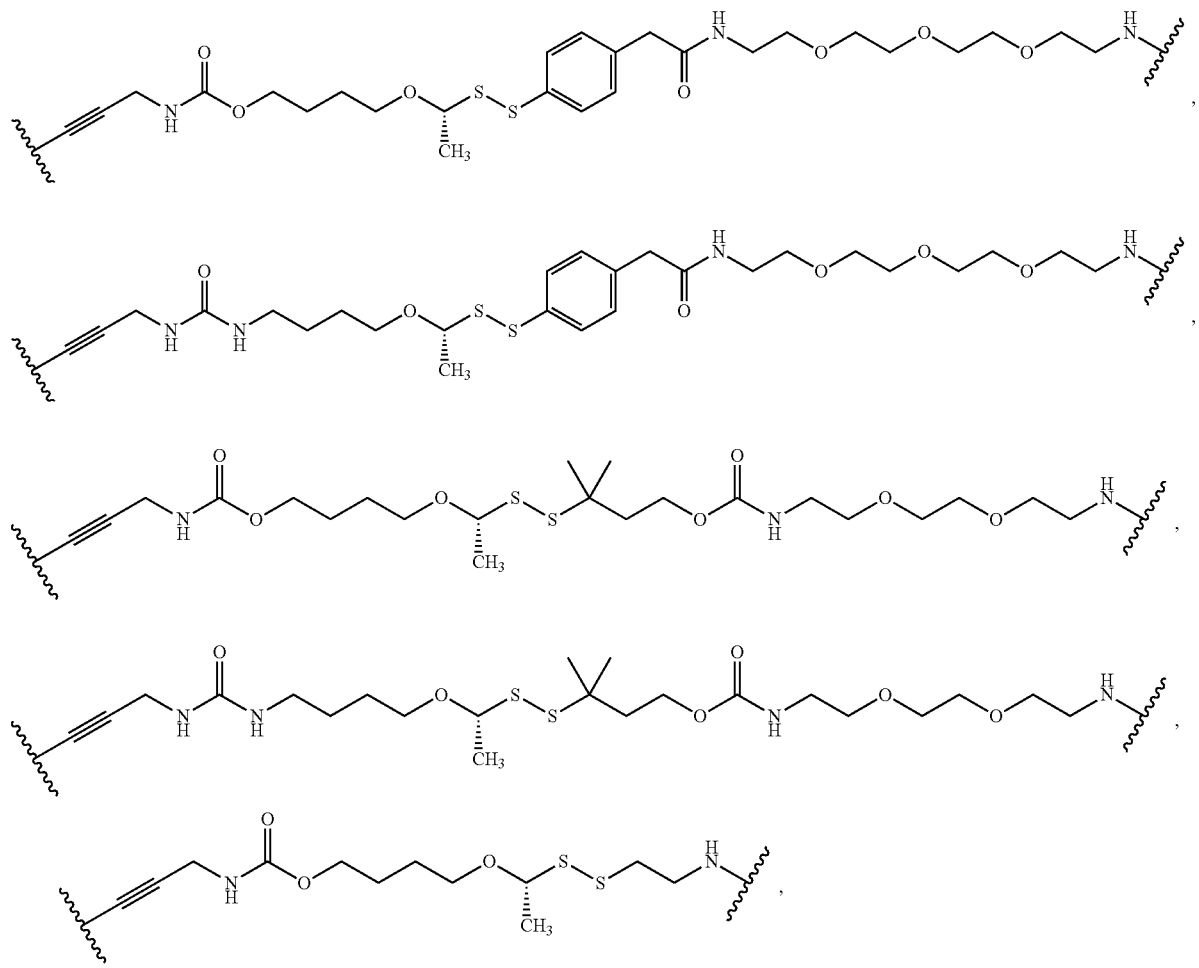

-continued
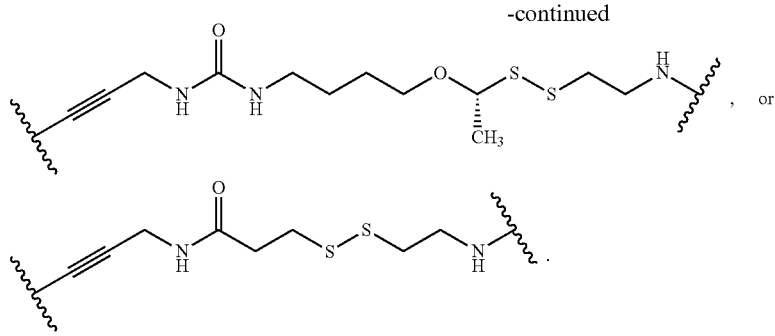, or
In embodiments, R⁴ is a fluorescent dye moiety. In embodiments, R⁴ is a detectable moiety described herein (e.g., Table 1). In embodiments, R⁴ is a detectable moiety described in Table 1.
In embodiments, R⁴ is
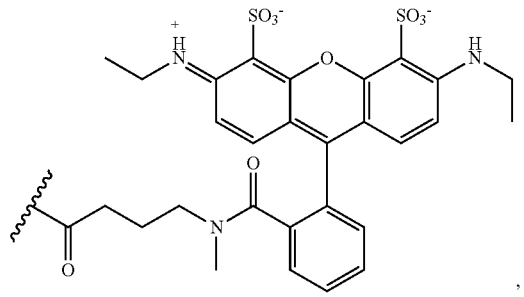,
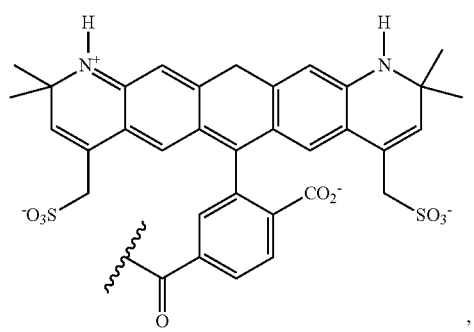,
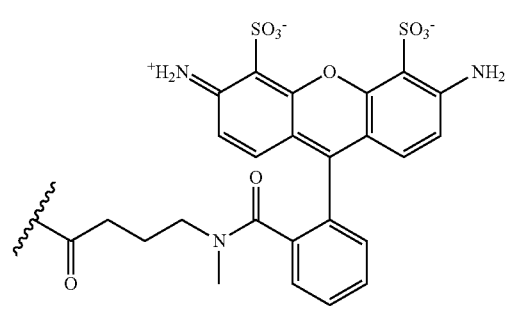, or
-continued
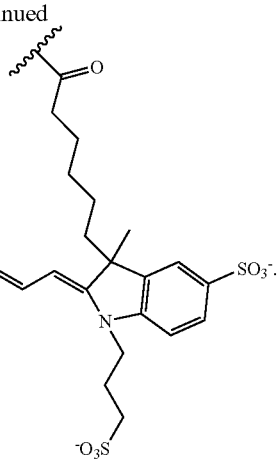
In embodiments, R⁴ is
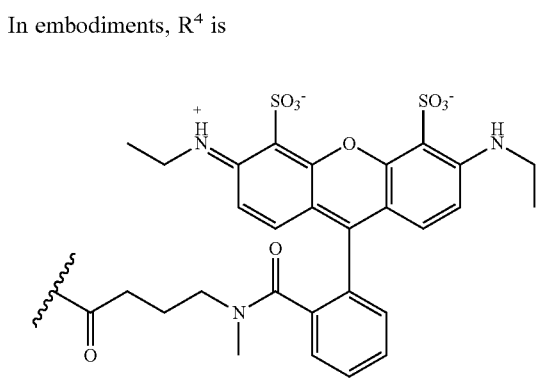
In embodiments, R⁴ is
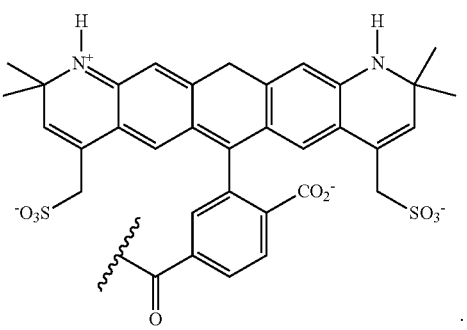

In embodiments, $R^4$ is

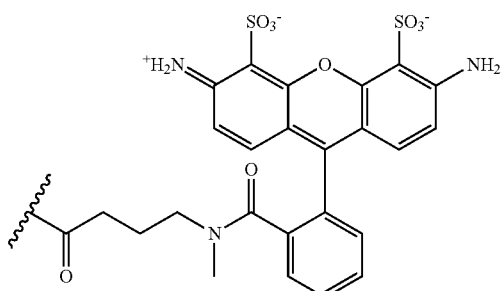

In embodiments, $R^4$ is

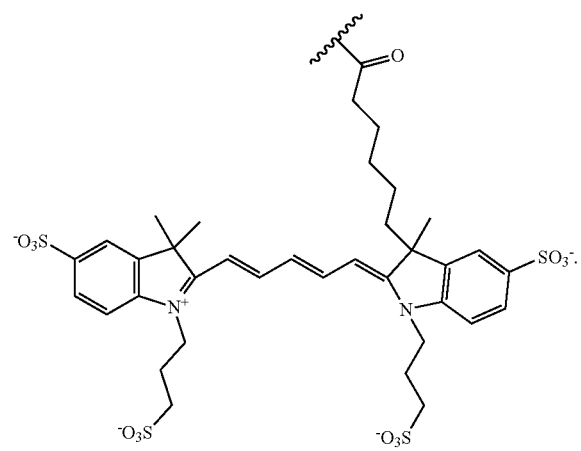

In embodiments, the compound has the formula:

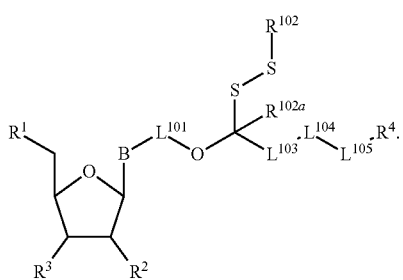

$R^1$, $R^2$, $R^3$, B, $L^{101}$, $R^{102}$, $R^{102a}$, $L^{103}$, $L^{104}$, $L^{105}$, and $R^4$ are as described herein, including in embodiments.

In embodiments, the compound has the formula:

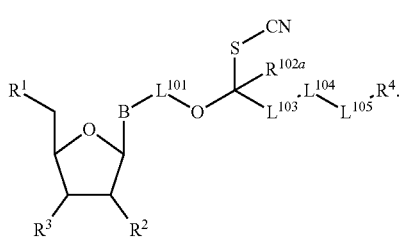

$R^1$, $R^2$, $R^3$, B, $L^{101}$, $R^{102}$, $R^{102a}$, $L^{103}$, $L^{104}$, $L^{105}$, and $R^4$ are as described herein, including in embodiments.

In embodiments, the compound has the formula:

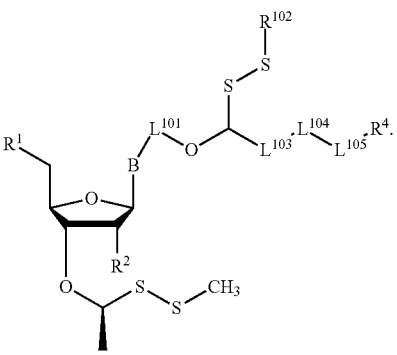

B, $R^1$, $R^2$, $L^{101}$, $L^{103}$, $L^{104}$, $L^{105}$, $R^{102}$, and $R^4$ are as described herein.

In embodiments, the compound has the formula:

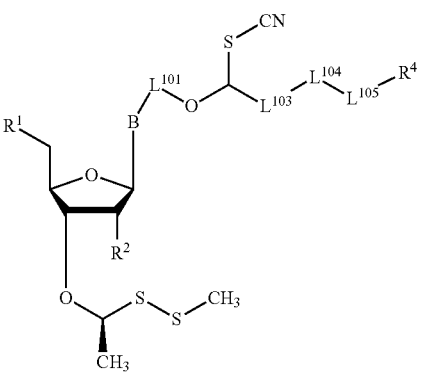

B, $R^1$, $R^2$, $L^{101}$, $L^{103}$, $L^{104}$, $L^{105}$, and $R^4$ are as described herein.

In embodiments, the compound has the formula:

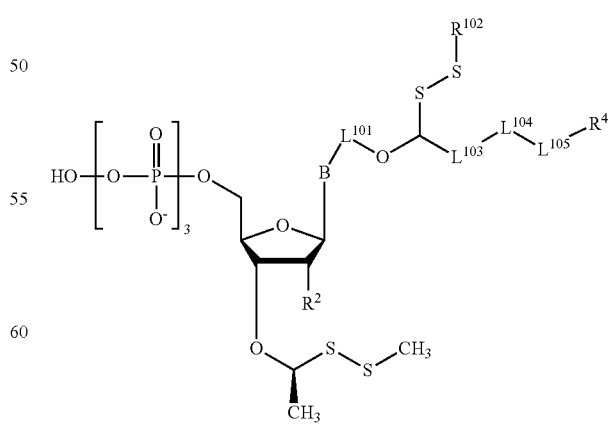

B, $R^2$, $L^{101}$, $L^{103}$, $L^{104}$, $L^{105}$, $R^{102}$, and $R^4$ are as described herein.

In embodiments the compound has the formula,

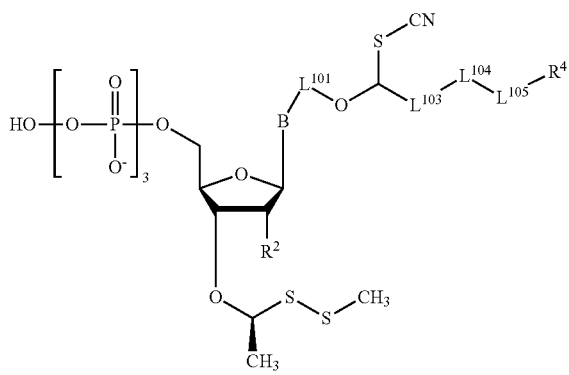

B, $R^2$, $L^{101}$, $L^{103}$, $L^{104}$, $L^{105}$, and $R^4$ are as described herein.

In embodiments, the compound has the formula:

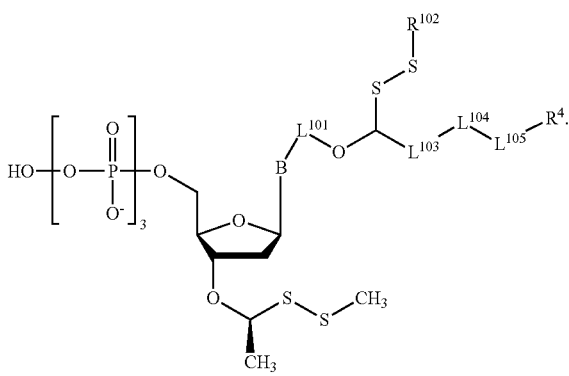

B, $L^{101}$, $L^{103}$, $L^{104}$, $L^{105}$, $R^{102}$, and $R^4$ are as described herein.

In embodiments, the compound has the formula:

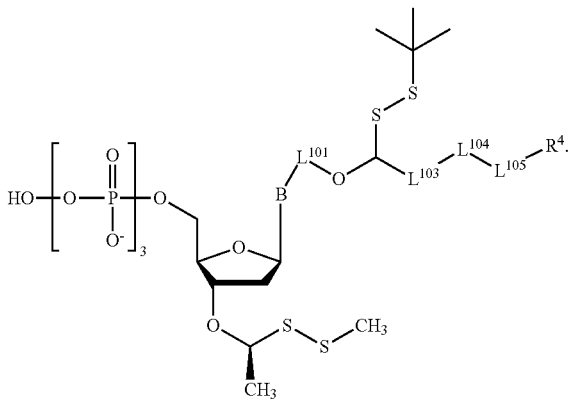

B, $L^{101}$, $L^{103}$, $L^{104}$, $L^{105}$, and $R^4$ are as described herein.

In embodiments, the compound has the formula:

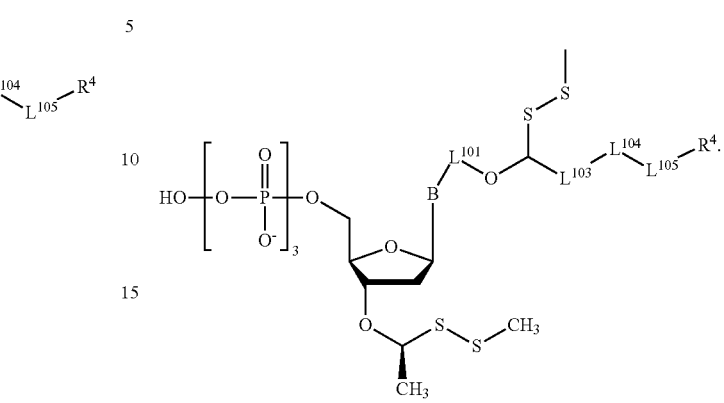

B, $L^{101}$, $L^{103}$, $L^{104}$, $L^{105}$, and $R^4$ are as described herein.

In embodiments, the compound has the formula:

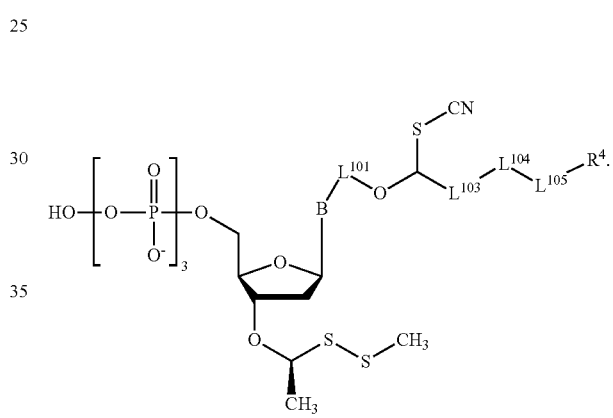

B, $L^{101}$, $L^{103}$, $L^{104}$, $L^{105}$, and $R^4$ are as described herein.

In embodiments, the compound has the formula:

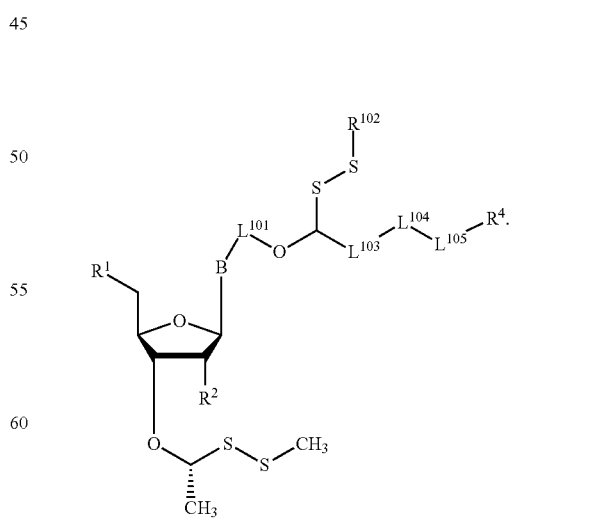

B, $R^1$, $R^2$, $L^{101}$, $L^{103}$, $L^{104}$, $L^{105}$, $R^{102}$, and $R^4$ are as described herein.

In embodiments, the compound has the formula:

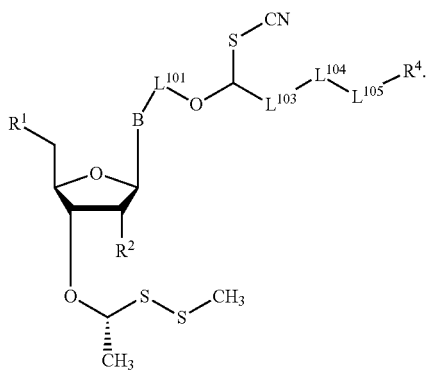

B, R¹, R², $L^{101}$, $L^{103}$, $L^{104}$, $L^{105}$, $R^{102}$, and $R^4$ are as described herein.

In embodiments, the compound has the formula:

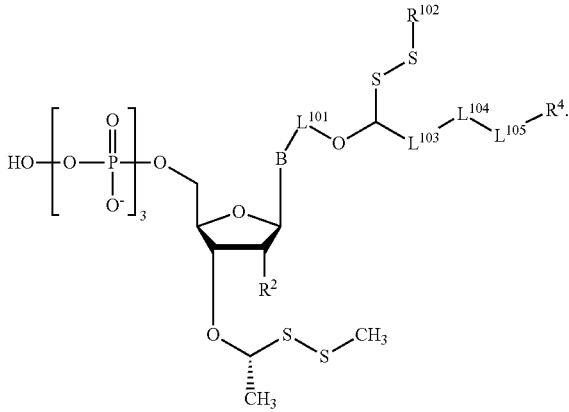

B, R², $L^{101}$, $L^{103}$, $L^{104}$, $L^{105}$, $R^{102}$, and $R^4$ are as described herein.

In embodiments, the compound has the formula:

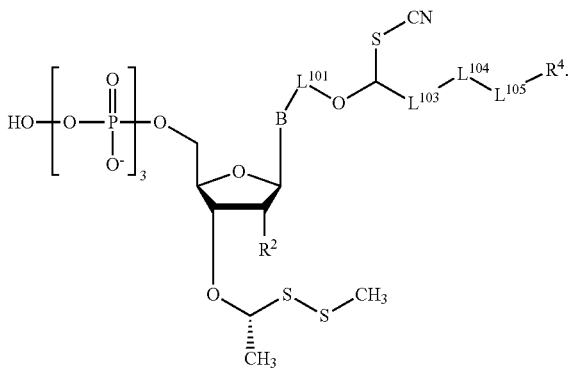

B, R², $L^{101}$, $L^{103}$, $L^{104}$, $L^{105}$, and $R^4$ are as described herein.

In embodiments, the compound has the formula:

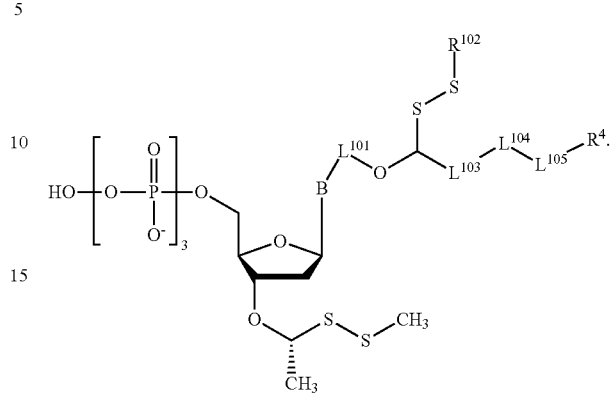

B, $L^{101}$, $L^{103}$, $L^{104}$, $L^{105}$, $R^{102}$, and $R^4$ are as described herein.

In embodiments, the compound has the formula:

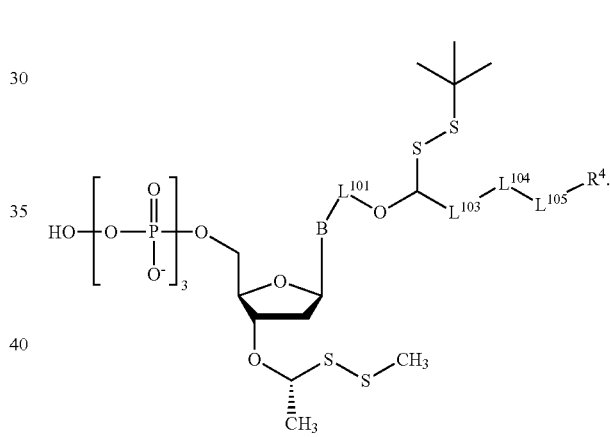

B, $L^{101}$, $L^{103}$, $L^{104}$, $L^{105}$, and $R^4$ are as described herein.

In embodiments, the compound has the formula:

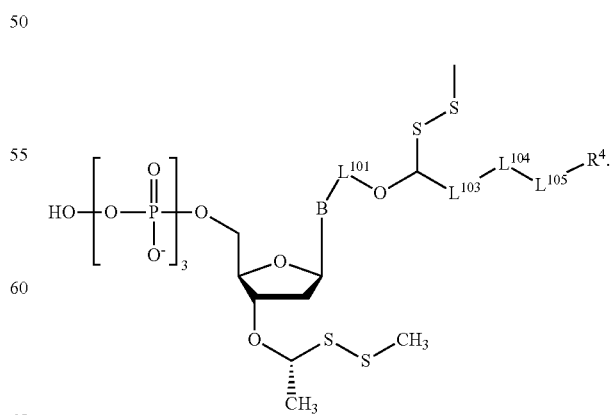

B, $L^{101}$, $L^{103}$, $L^{104}$, $L^{105}$, and $R^4$ are as described herein.

In embodiments, the compound has the formula:

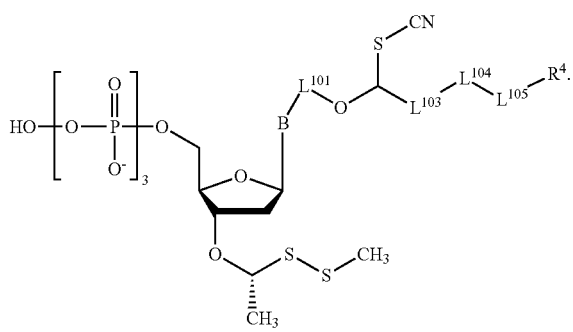

B, $L^{101}$, $L^{103}$, $L^{104}$, $L^{105}$, and $R^4$ are as described herein.

In embodiments, $R^2$ is hydrogen. In embodiments, $R^2$ is —OH.

In embodiments, $R^{102}$ is unsubstituted methyl. In embodiments, $R^{102}$ is unsubstituted ethyl. In embodiments, $R^{102}$ is unsubstituted propyl. In embodiments, $R^{102}$ is unsubstituted isopropyl. In embodiments, $R^{102}$ is unsubstituted butyl. In embodiments, $R^{102}$ is unsubstituted tert-butyl.

In embodiments, $L^{101}$ is

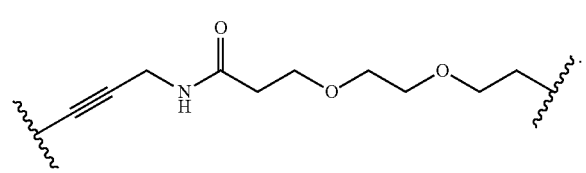 [SMILES: *C#CCNC(=O)CCOCCOCC*]

In embodiments, $L^{101}$ is

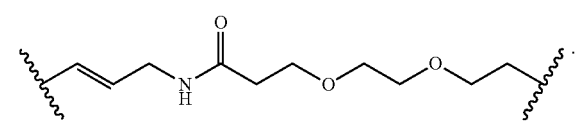 [SMILES: */C=C/CNC(=O)CCOCCOCC*]

In embodiments, $L^{101}$ is —CCCH$_2$—. In embodiments, $L^{101}$ is

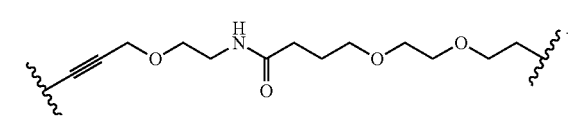 [SMILES: *C#CCOCCNC(=O)CCCOCCOCC*]

In embodiments, $L^{101}$ is

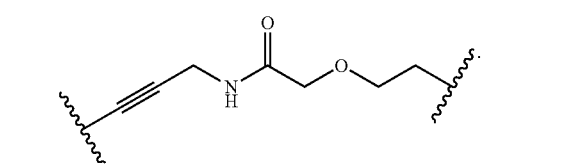 [SMILES: *C#CCNC(=O)COCC*]

In embodiments, $L^{101}$ is

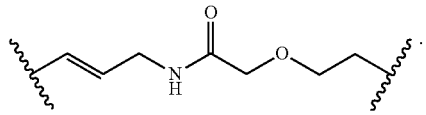 [SMILES: */C=C/CNC(=O)COCC*]

In embodiments, $L^{103}$ is

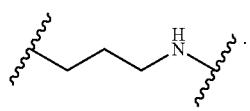 [SMILES: *CCCN*]

In embodiments, $L^{103}$ is

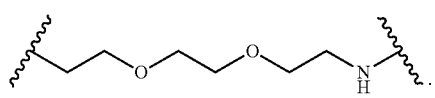 [SMILES: *CCOCCOCCN*]

In embodiments, $L^{103}$ is

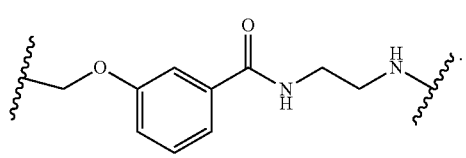 [SMILES: *COc1cccc(C(=O)NCCN*)c1]

In embodiments, $L^{103}$ is

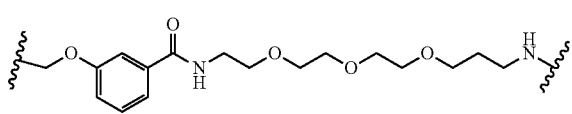

In embodiments, $L^{103}$ is

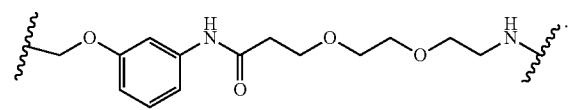 [SMILES: *COc1cccc(NC(=O)CCOCCOCCN*)c1]

In embodiments, $L^{103}$ is a bond.

In embodiments, $L^{104}$ is

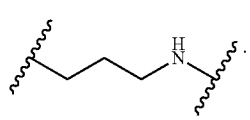 [SMILES: *CCCN*]

In embodiments, $L^{104}$ is

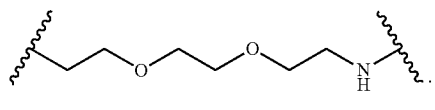 [SMILES: *CCOCCOCCN*]

In embodiments $L^{104}$ is
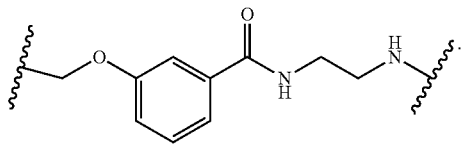 [SMILES: *COc1cccc(C(=O)NCCN*)c1]
In embodiments, $L^{104}$ is
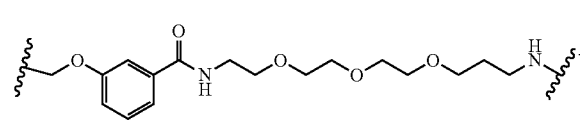 [SMILES: *COc1cccc(C(=O)NCCOCCOCCOCCCN*)c1]
In embodiments, $L^{104}$ is
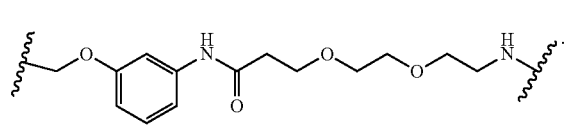 [SMILES: *COc1cccc(NC(=O)CCOCCOCCN*)c1]
In embodiments, $L^{1044}$ is a bond.
In embodiments, $L^{105}$ is
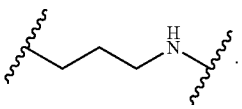 [SMILES: *CCCN*]
In embodiments, $L^{105}$ is
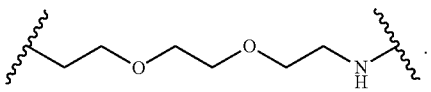 [SMILES: *CCOCCOCCN*]
In embodiments, $L^{105}$ is
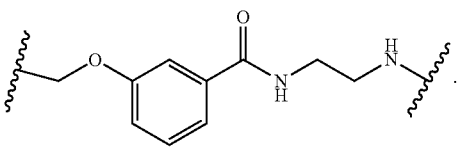 [SMILES: *COc1cccc(C(=O)NCCN*)c1]
In embodiments, $L^{105}$ is
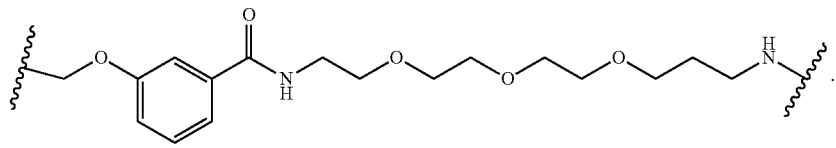 [SMILES: *COc1cccc(C(=O)NCCOCCOCCOCCCN*)c1]
In embodiments, $L^{105}$ is
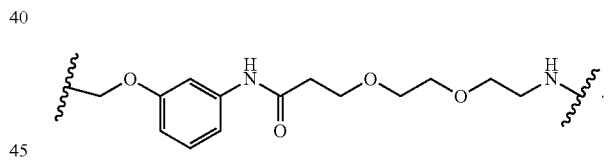
In embodiments, $L^{105}$ is a bond.
In embodiments, $L^{103}$-$L^{104}$-$L^{105}$- is
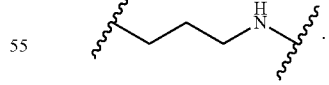
In embodiments, $L^{103}$-$L^{104}$-$L^{105}$- is
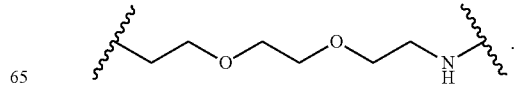

In embodiments, $L^{103}$-$L^{104}$-$L^{105}$- is

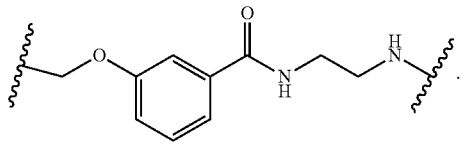 [SMILES: *COc1cccc(C(=O)NCCN*)c1]

In embodiments, $L^{103}$-$L^{104}$-$L^{105}$- is

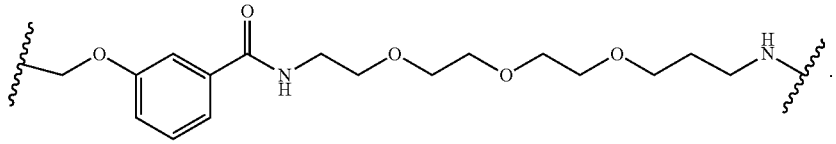 [SMILES: *COc1cccc(C(=O)NCCOCCOCCOCCCN*)c1]

In embodiments, $L^{103}$-$L^{104}$-$L^{105}$- is

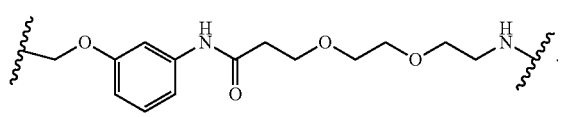 [SMILES: *COc1cccc(NC(=O)CCOCCOCCN*)c1]

In embodiments, the compound has the formula:

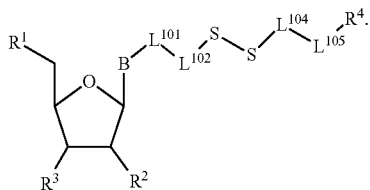

$R^1$, $R^2$, $R^3$, B, $L^{101}$, $L^{102}$, $L^{104}$, $L^{105}$, and $R^4$ are as described herein, including in embodiments.

In embodiments, the compound has the formula:

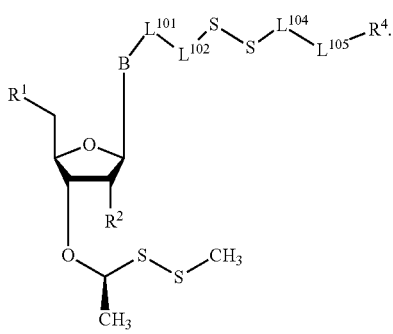

B, $R^1$, $R^2$, $L^{101}$, $L^{102}$, $L^{104}$, $L^{105}$, and $R^4$ are as described herein.

In embodiments, the compound has the formula:

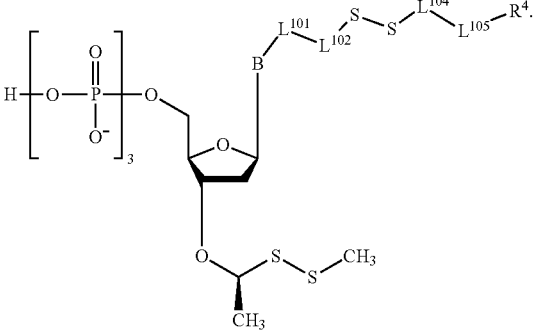

B, $R^2$, $L^{101}$, $L^{102}$, $L^{104}$, $L^{105}$, $R^{102}$, and $R^4$ are as described herein.

In embodiments, the compound has the formula:

B, $L^{101}$, $L^{102}$, $L^{104}$, $L^{105}$, and $R^4$ are as described herein.

In embodiments, the compound has the formula:
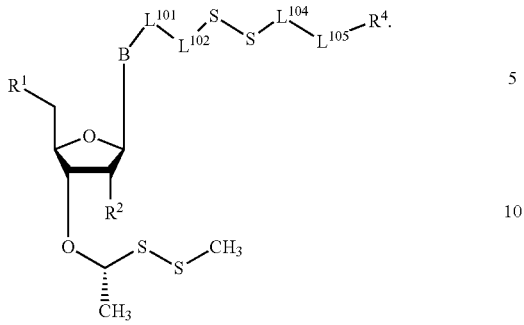
B, $R^1$, $R^2$, $L^{101}$, $L^{102}$, $L^{104}$, $L^{105}$, and $R^4$ are as described herein.
In embodiments, the compound has the formula:
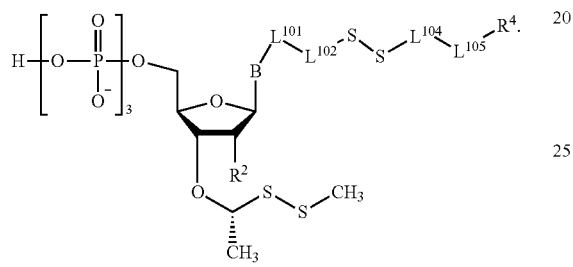
B, $R^2$, $L^{101}$, $L^{102}$, $L^{104}$, $L^{105}$, $R^{102}$, and $R^4$ are as described herein.
In embodiments, the compound has the formula:
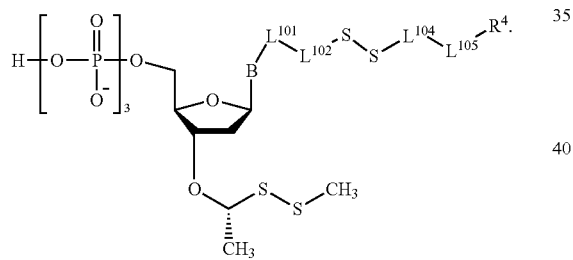
B, $L^{101}$, $L^{102}$, $L^{104}$, $L^{105}$, and $R^4$ are as described herein.
In embodiments, the compound has the formula:
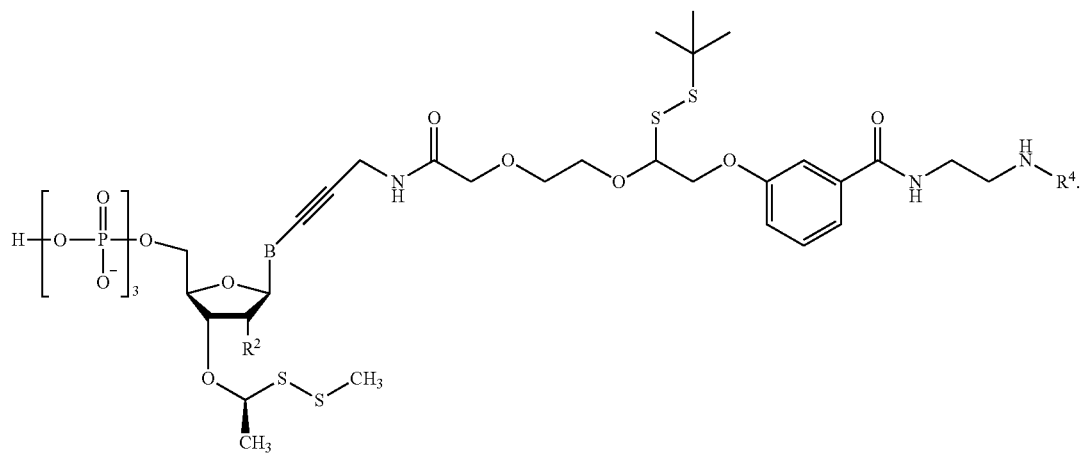

B, R² , and R⁴ are as described herein. In embodiments, R⁴ is a fluorescent dye moiety.

In embodiments, the compound has the formula:

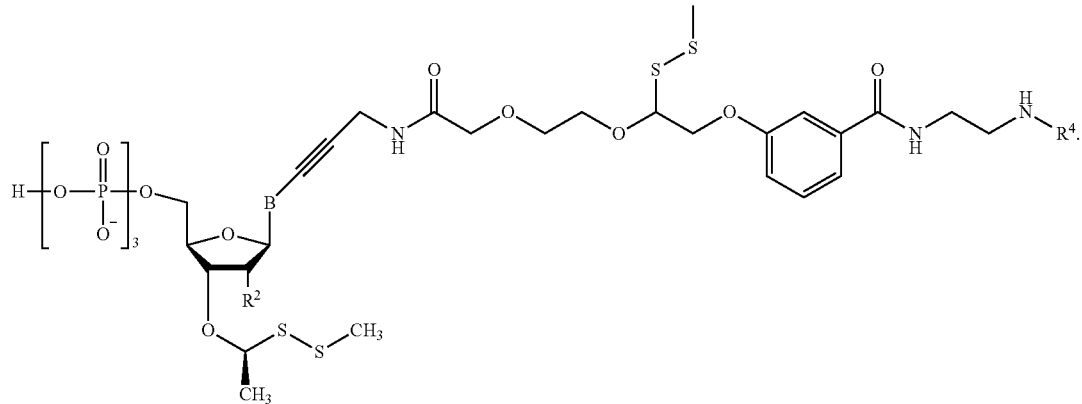

B, R² and R⁴ are as described herein. In embodiments, R⁴ is a fluorescent dye moiety.

In embodiments, the compound has the formula:

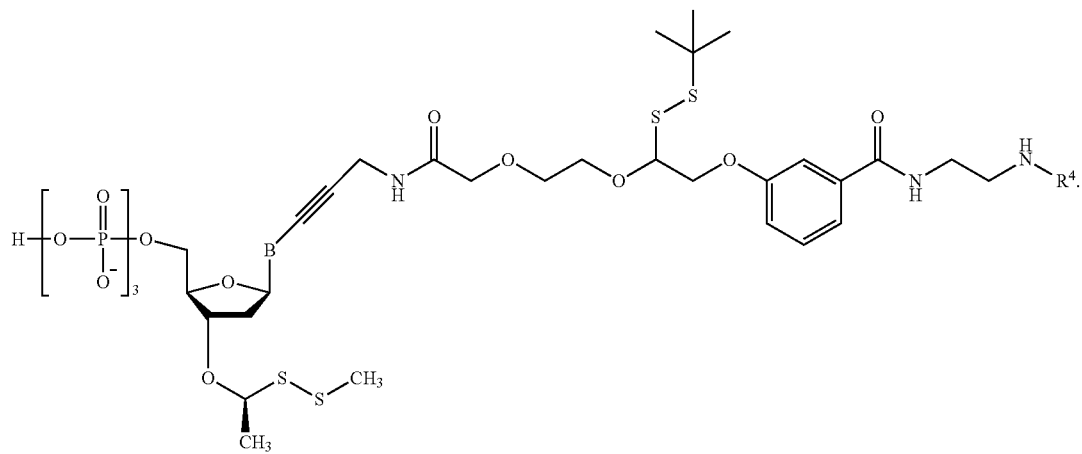

B and R⁴ are as described herein. In embodiments, R⁴ is a fluorescent dye moiety.

In embodiments, the compound has the formula:

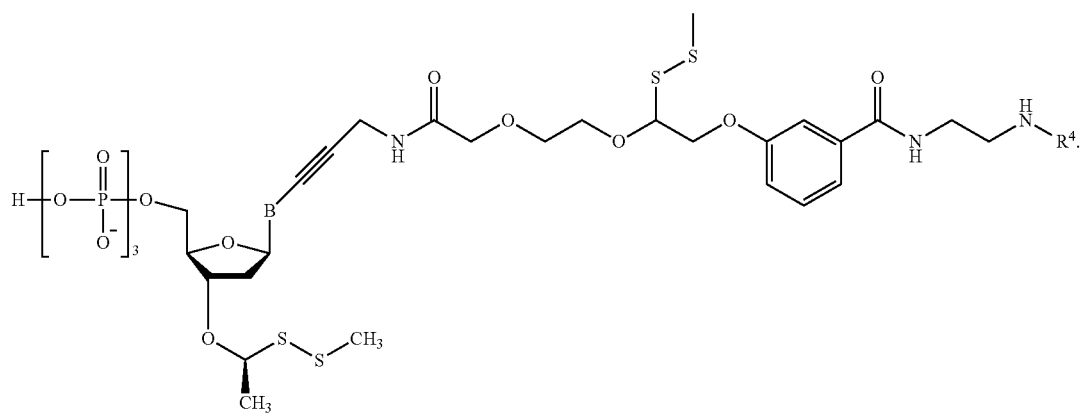

B and R⁴ are as described herein. In embodiments, R⁴ is a fluorescent dye moiety.

In embodiments, the compound has the formula:

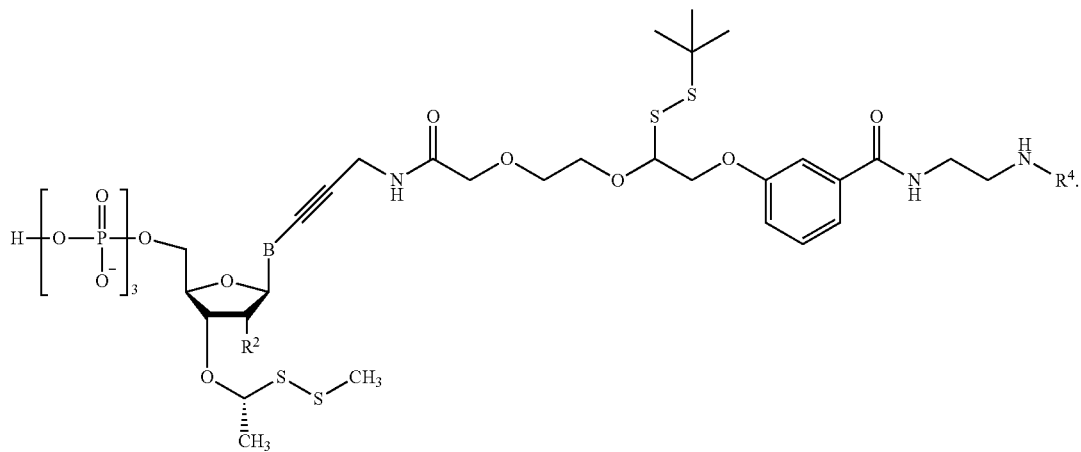

B, R², and R⁴ are as described herein. In embodiments, R⁴ is a fluorescent dye moiety.

In embodiments, the compound has the formula:

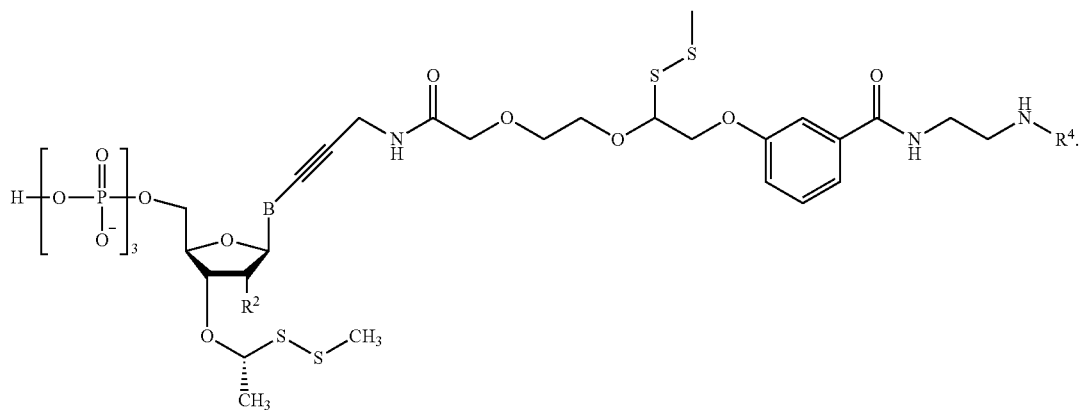

B, R², and R⁴ are as described herein. In embodiments, R⁴ is a fluorescent dye moiety.

In embodiments, the compound has the formula:

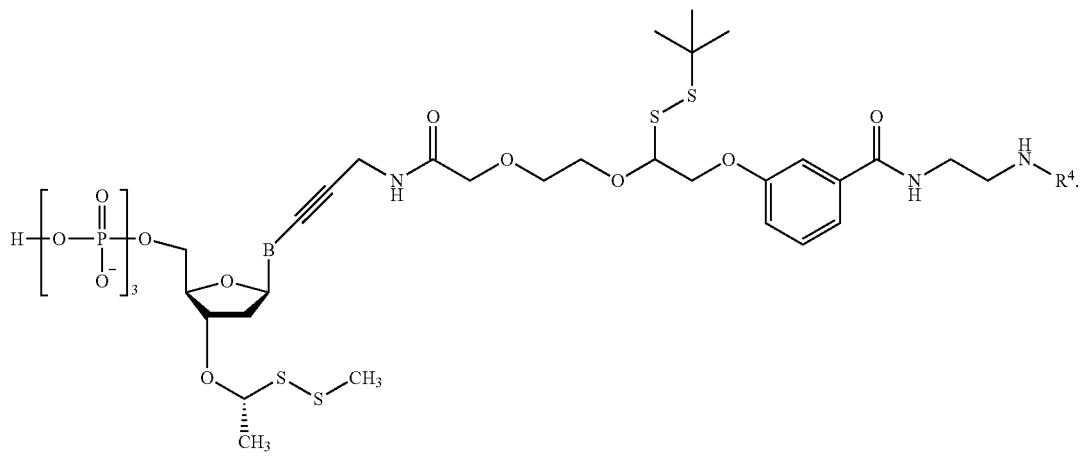

B and R⁴ are as described herein. In embodiments, R⁴ is a fluorescent dye moiety.

In embodiments, the compound has the formula:

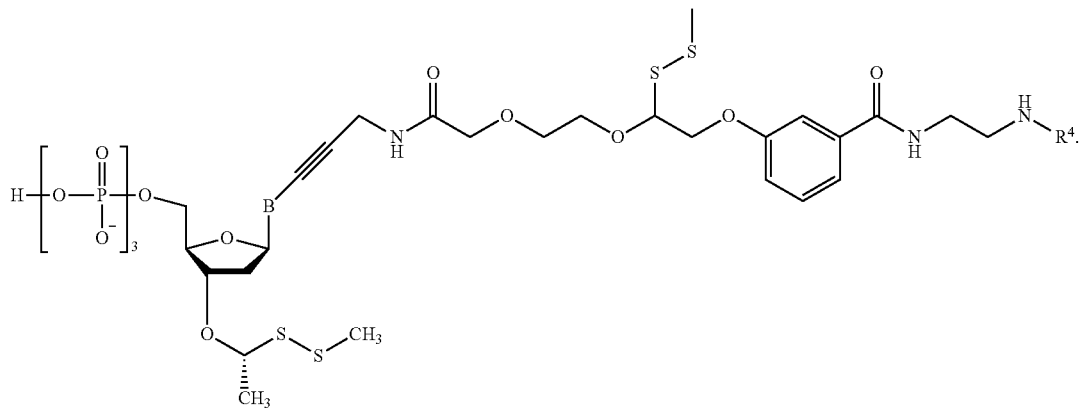

B and R⁴ are as described herein. In embodiments, R⁴ is a fluorescent dye moiety.

In embodiments, the compound has the formula:

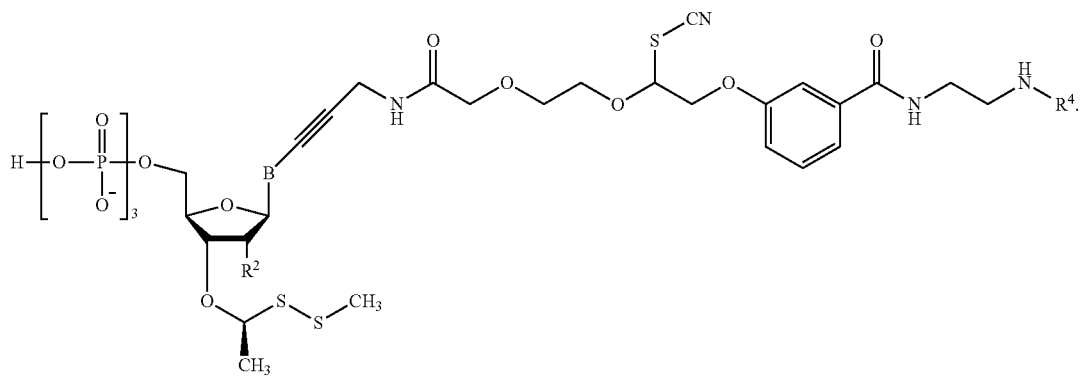

B, R², and R⁴ are as described herein. In embodiments, R⁴ is a fluorescent dye moiety.

In embodiments, the compound has the formula:

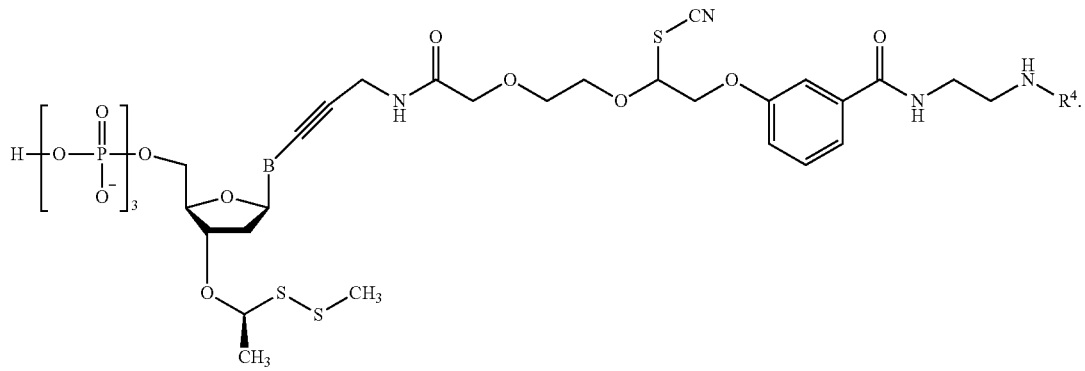

B and R⁴ are as described herein. In embodiments, R⁴ is a fluorescent dye moiety.

In embodiments, the compound has the formula:

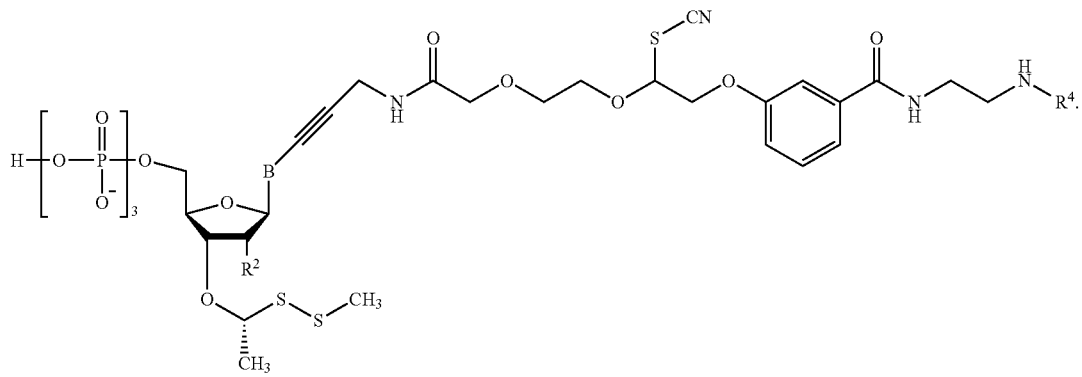

B, R², and R⁴ are as described herein. In embodiments, R⁴ is a fluorescent dye moiety.

In embodiments, the compound has the formula:

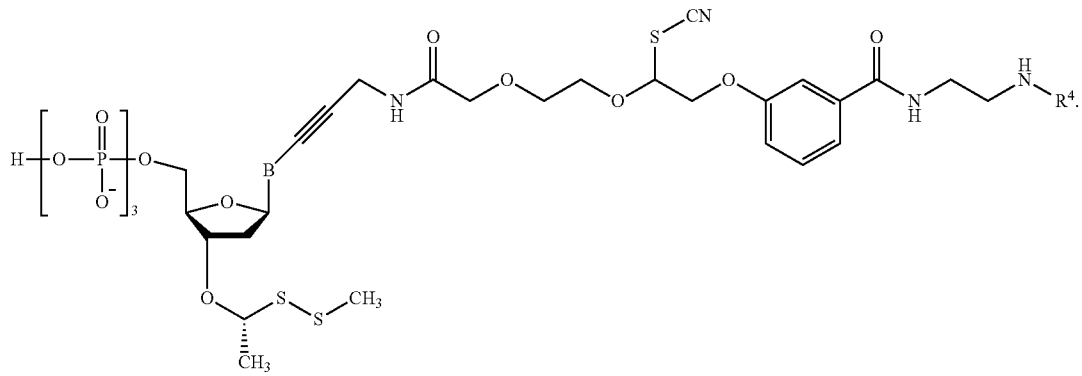

B and R⁴ are as described herein. In embodiments, R⁴ is a fluorescent dye moiety.

In embodiments, the compound is:

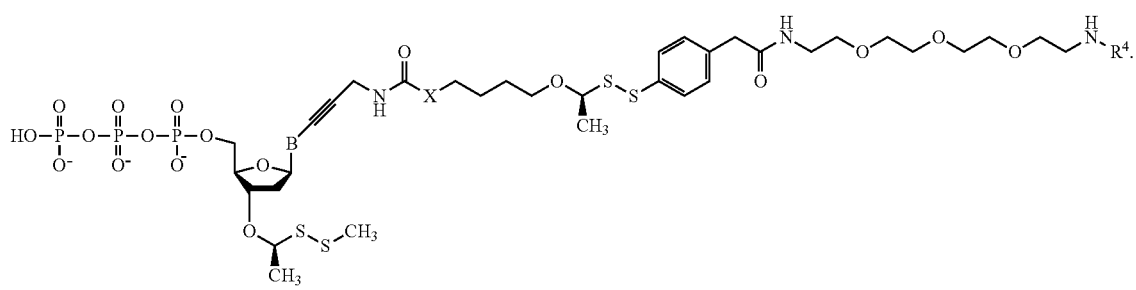

mixture of diastereoisomers (R and S)
or single diastereoisomer (R and S)

B and R⁴ are as described herein. X is O or NH in the formula above. In embodiments, R⁴ is a fluorescent dye moiety.

In embodiments, the compound is:

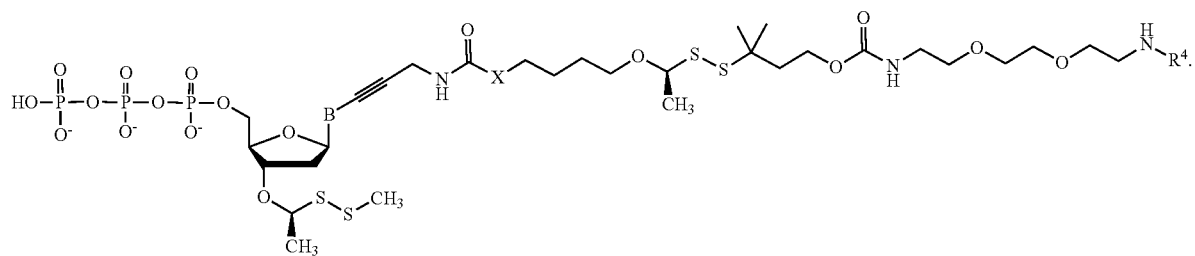

mixture of diastereoisomers (R and S)
or
single diastereoisomer (R or S)

B and R⁴ are as described herein. X is O or NH in the formula above. In embodiments, R⁴ is a fluorescent dye moiety.

In embodiments, the compound is:

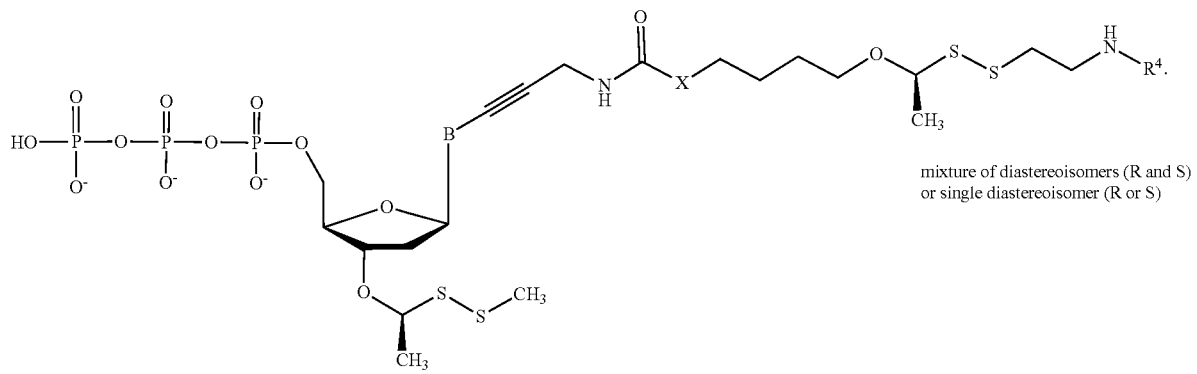

mixture of diastereoisomers (R and S)
or single diastereoisomer (R or S)

B and R⁴ are as described herein. X is O or NH in the formula above. In embodiments, R⁴ is a fluorescent dye moiety.

In embodiments, the compound is:

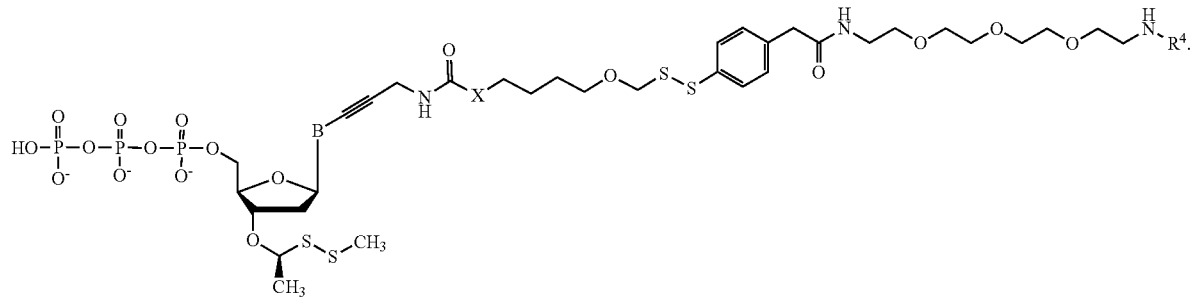

B and R⁴ are as described herein. X is O or NH in the formula above. In embodiments, R⁴ is a fluorescent dye moiety.

In embodiments, the compound is:

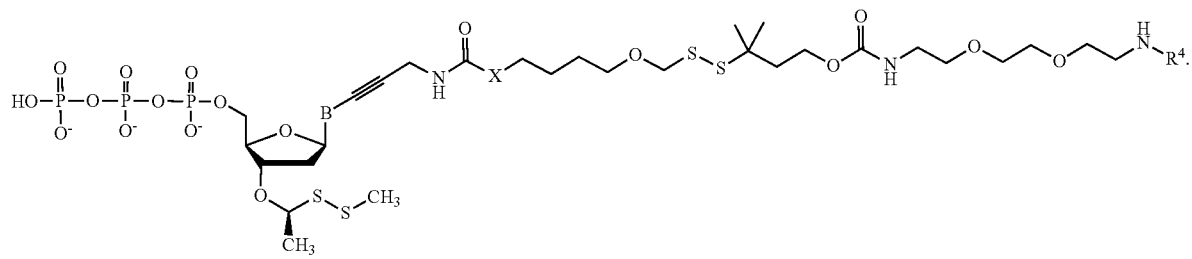

B and R⁴ are as described herein. X is O or NH in the formula above. In embodiments, R⁴ is a fluorescent dye moiety.

In embodiments, the compound is:

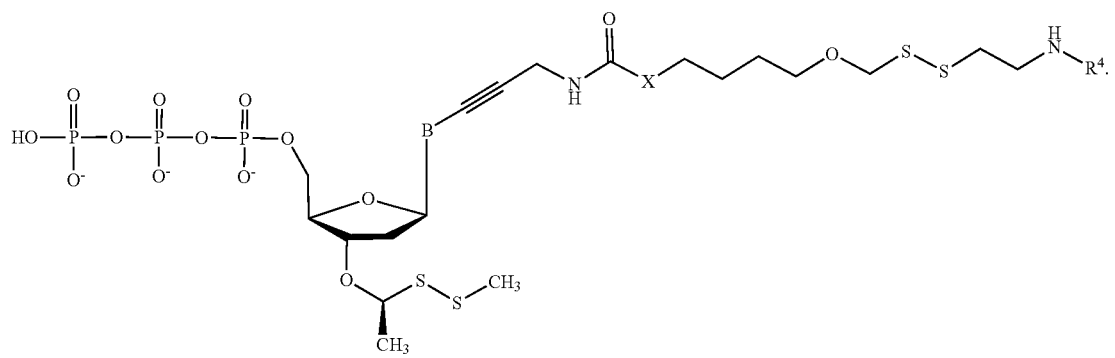

B and R⁴ are as described herein. X is O or NH in the formula above. In embodiments, R⁴ is a fluorescent dye moiety.

In embodiments, the compound is:

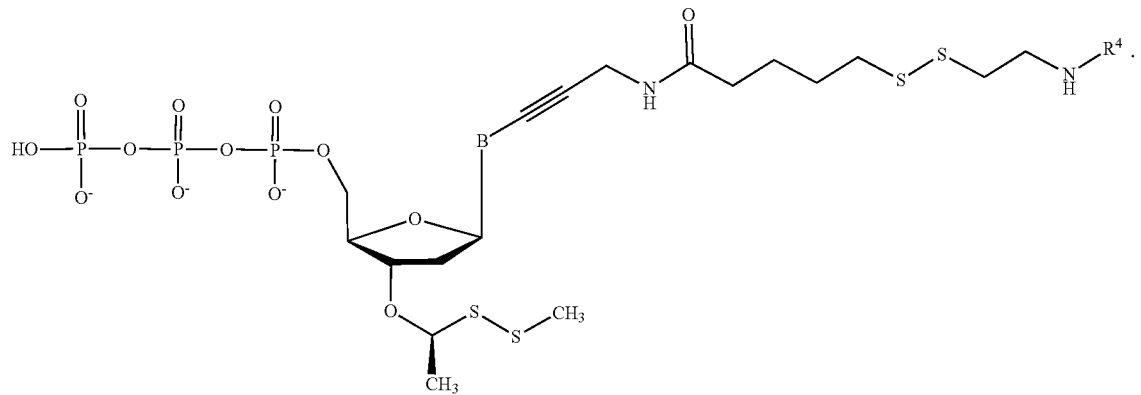

B and R⁴ are as described herein. X is O or NH in the formula above. In embodiments, R⁴ is a fluorescent dye moiety.

In embodiments, the compound is:

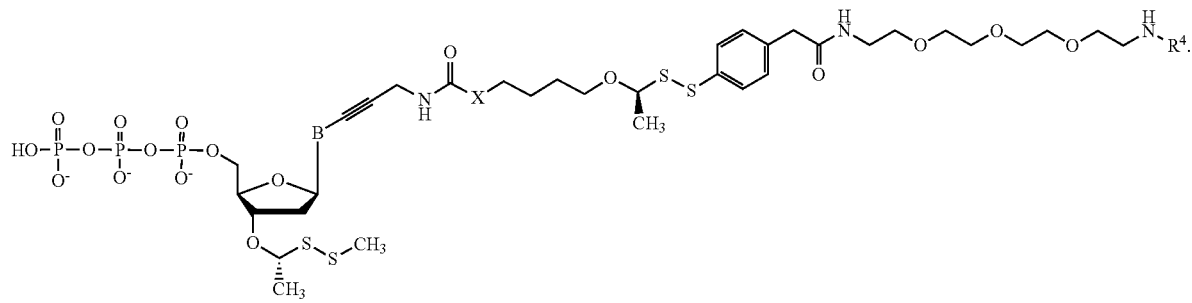

mixture of diastereoisomers (R and S)
or
single diastereoisomer (R or S)

B and $R^4$ are as described herein. X is O or NH in the formula above. In embodiments, $R^4$ is a fluorescent dye moiety.

In embodiments, the compound is:

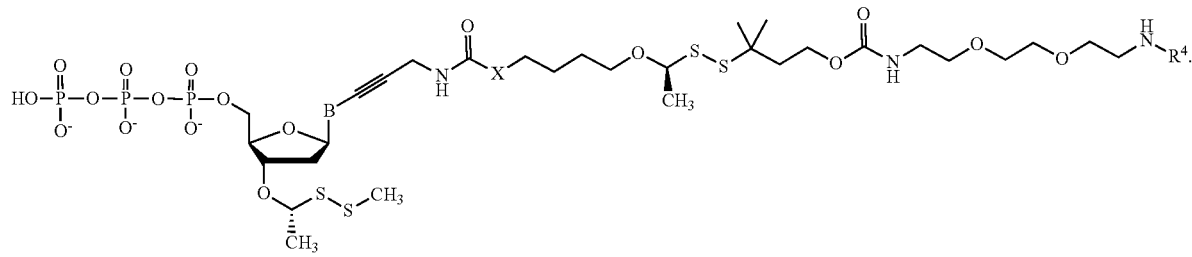

mixture of diastereoisomers (R and S)
or
single diastereoisomer (R or S)

B and $R^4$ are as described herein. X is O or NH in the formula above. In embodiments, $R^4$ is a fluorescent dye moiety.

In embodiments, the compound is:

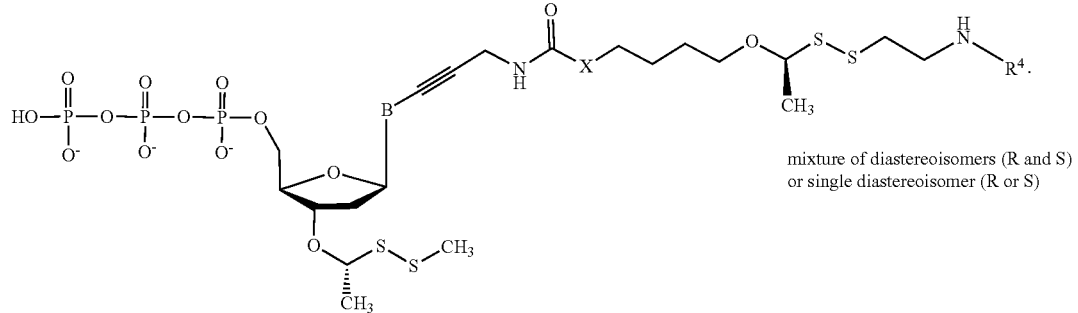

mixture of diastereoisomers (R and S)
or single diastereoisomer (R or S)

B and $R^4$ are as described herein. X is O or NH in the formula above. In embodiments, $R^4$ is a fluorescent dye moiety.

In embodiments, the compound is:

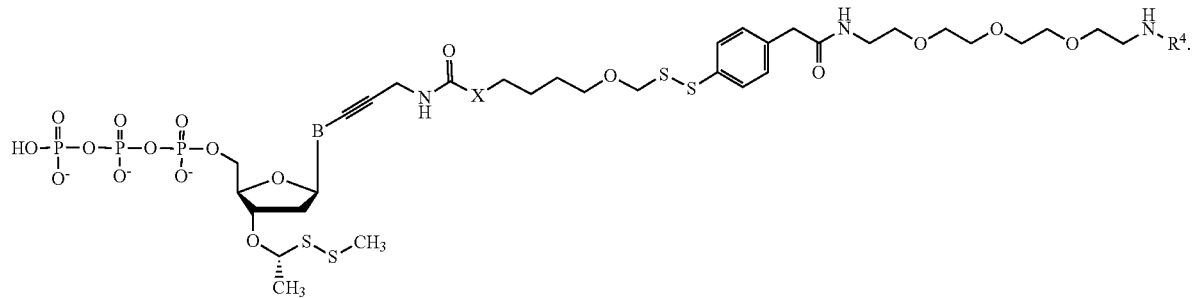

B and R⁴ are as described herein. X is O or NH in the formula above. In embodiments, R⁴ is a fluorescent dye moiety.

In embodiments, the compound is:

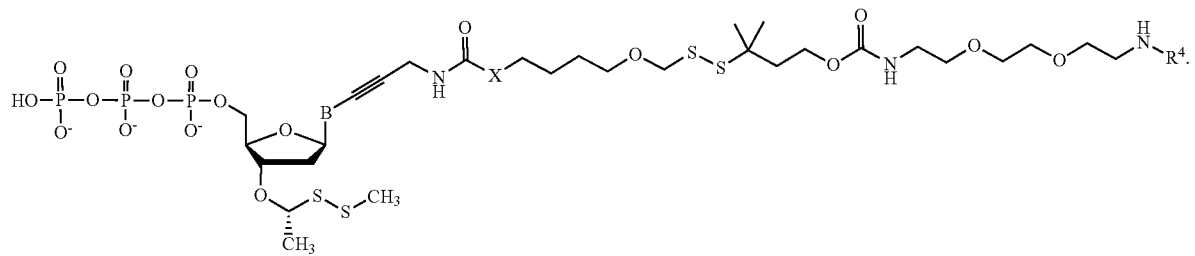

B and R⁴ are as described herein. X is O or NH in the formula above. In embodiments, R⁴ is a fluorescent dye moiety.

In embodiments, the compound is:

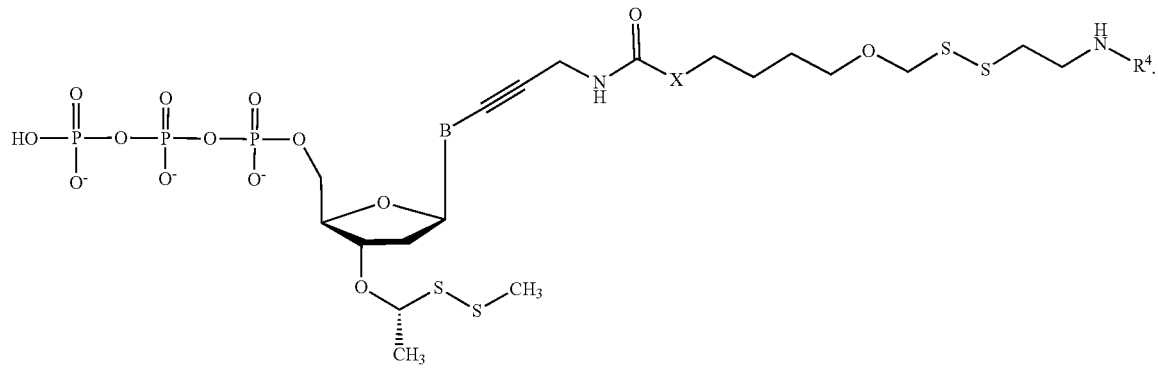

B and R⁴ are as described herein. X is O or NH in the formula above. In embodiments, R⁴ is a fluorescent dye moiety.

In embodiments, the compound is:

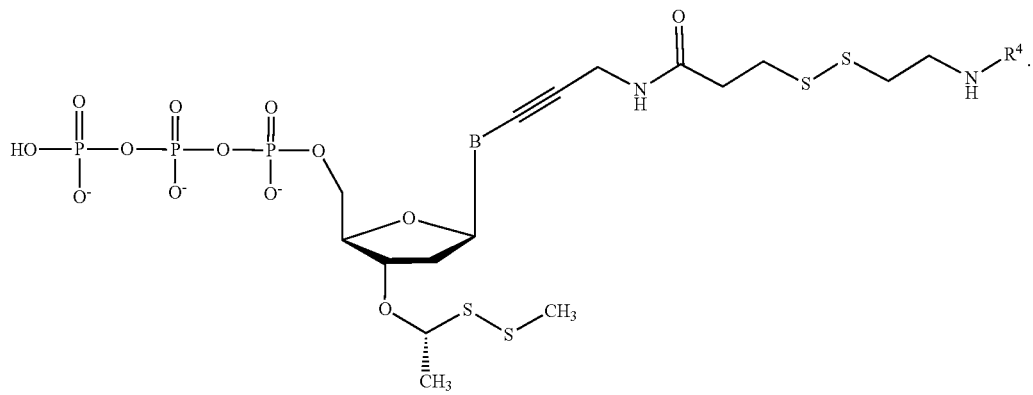

B and R⁴ areas described herein. X is O or NH in the formula above. In embodiments, R⁴ is a fluorescent dye moiety.

In embodiments, the compound is:

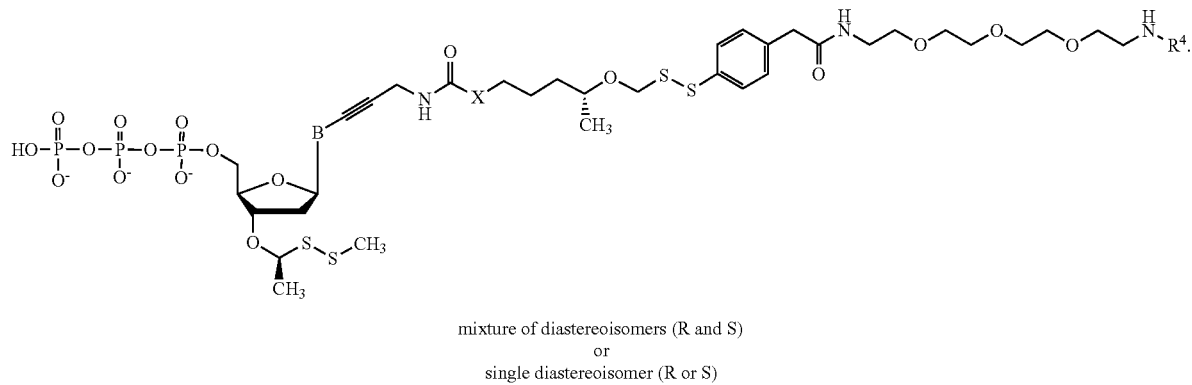

mixture of diastereoisomers (R and S)
or
single diastereoisomer (R or S)

B and R⁴ are as described herein. X is O or NH in the formula above. In embodiments, R⁴ is a fluorescent dye moiety.

In embodiments, the compound is:

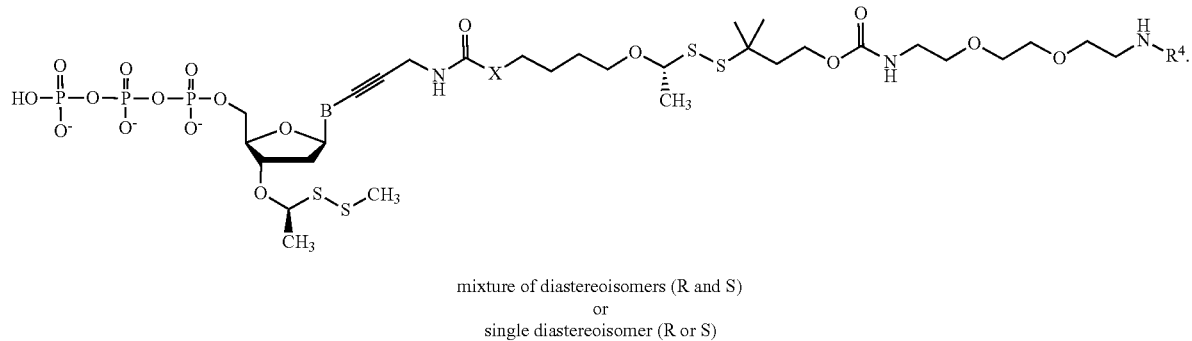

mixture of diastereoisomers (R and S)
or
single diastereoisomer (R or S)

B and R⁴ are as described herein. X is O or NH in the formula above. In embodiments, R⁴ is a fluorescent dye moiety.

In embodiments, the compound is:

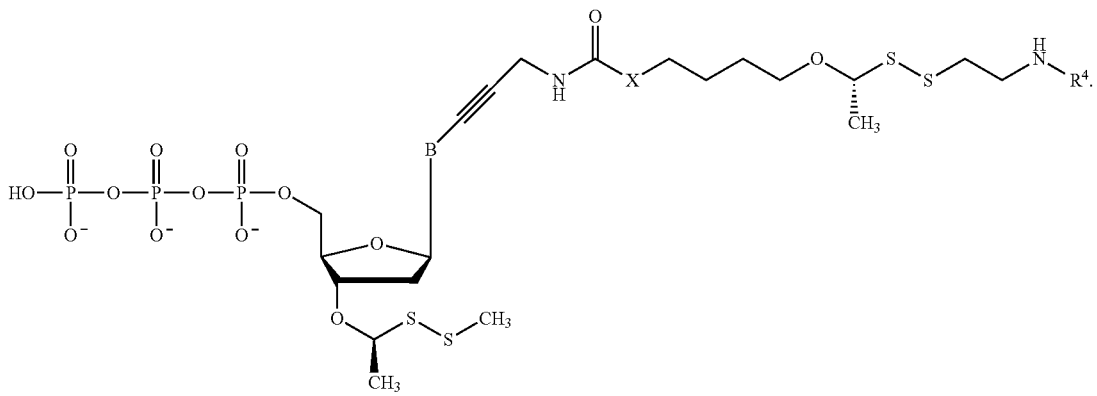

mixture of diastereoisomers (R and S) or single diastereoisomer (R or S)

B and R⁴ are as described herein. X is O or NH in the formula above. In embodiments, R⁴ is a fluorescent dye moiety.

In embodiments, the compound is:

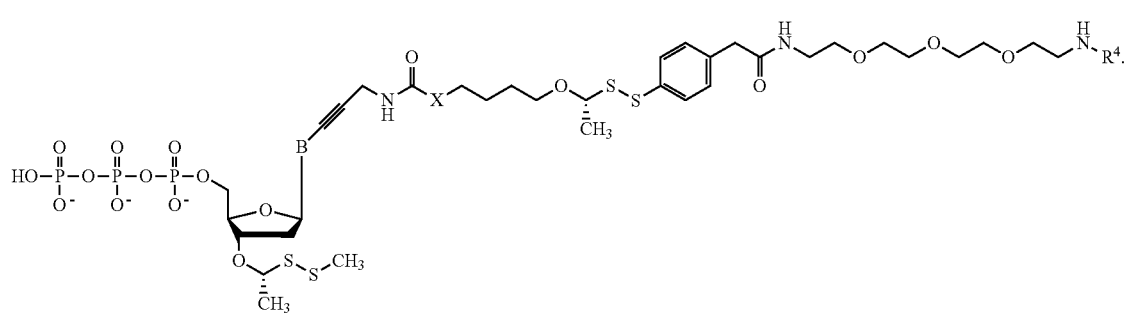

mixture of diastereoisomers (R and S) or single diastereoisomer (R or S)

B and R⁴ are as described herein. X is O or NH in the formula above. In embodiments, R⁴ is a fluorescent dye moiety.

In embodiments, the compound is:

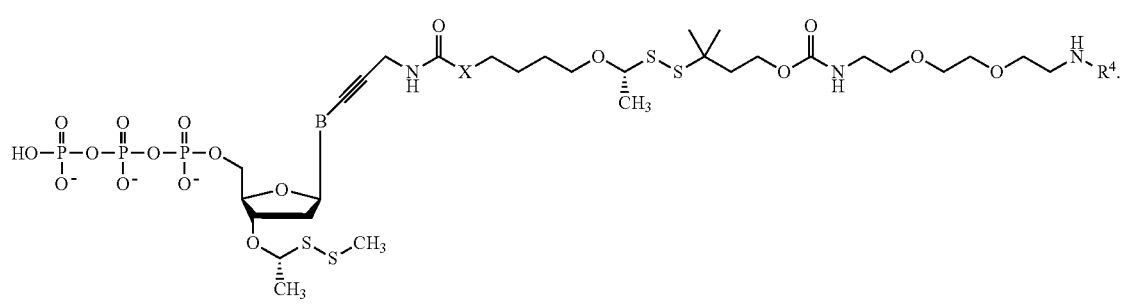

mixture of diastereoisomers (R and S) or single diastereoisomer (R or S)

B and R⁴ are as described herein. X is O or NH in the formula above. In embodiments, R⁴ is a fluorescent dye moiety.

In embodiments, the compound is:

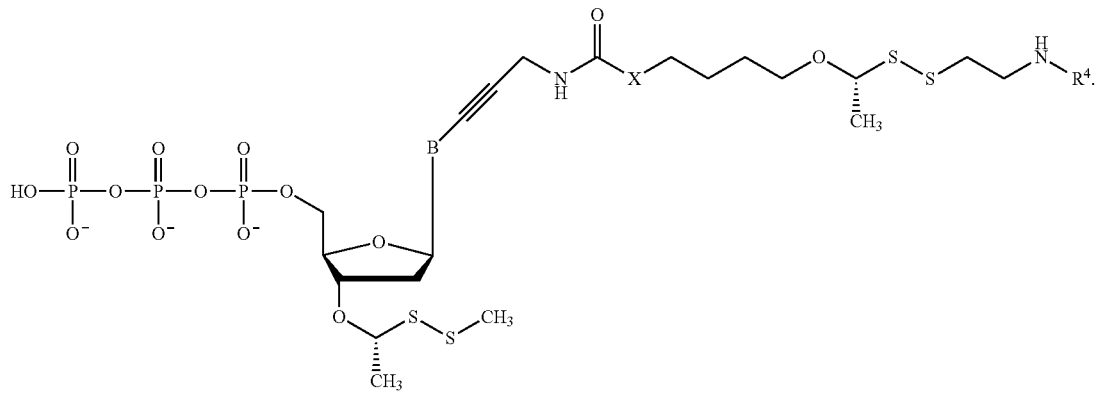

mixture of diastereoisomers (R and S) or single diastereoisomer (R or S)

B and R⁴ are as described herein. X is O or NH in the formula above. In embodiments, R⁴ is a fluorescent dye moiety.

In embodiments, the compound is:

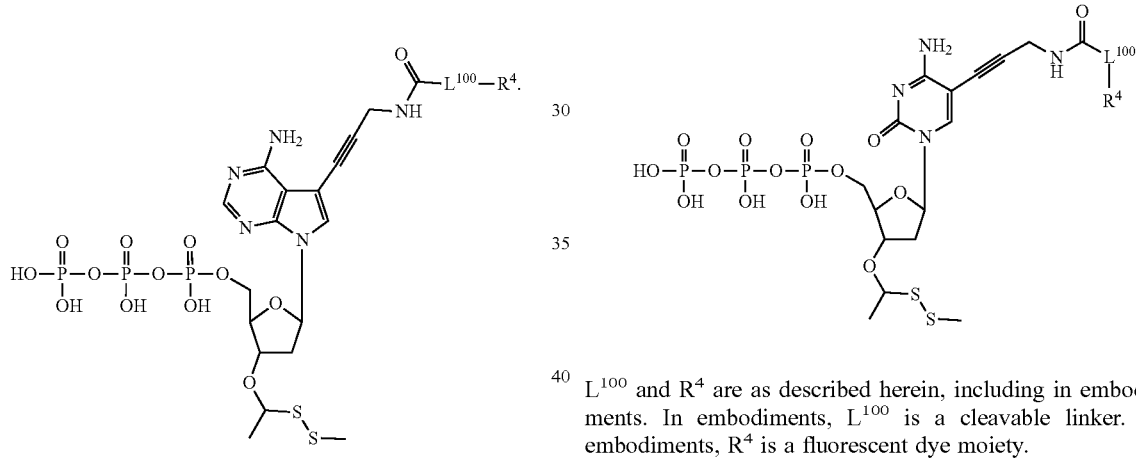

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

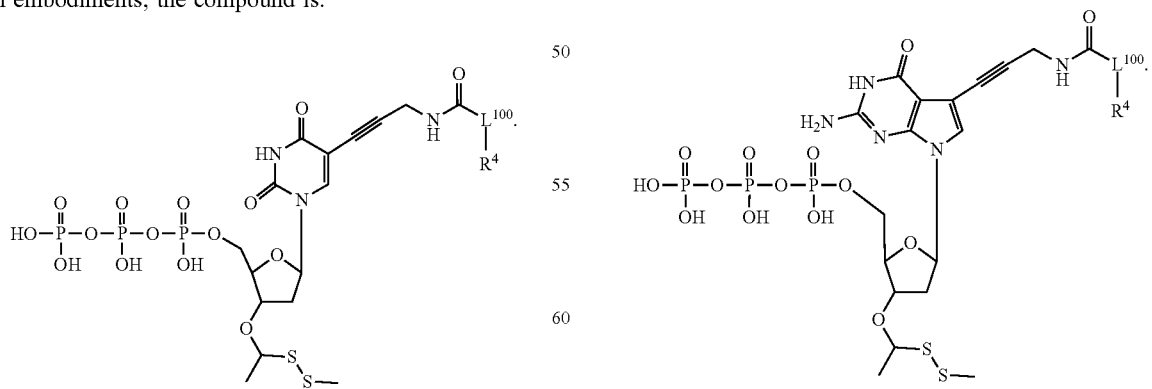

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

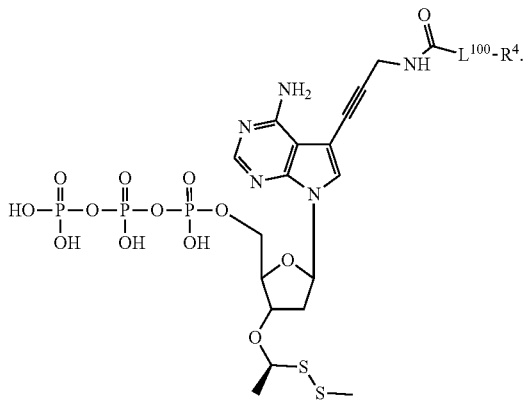

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

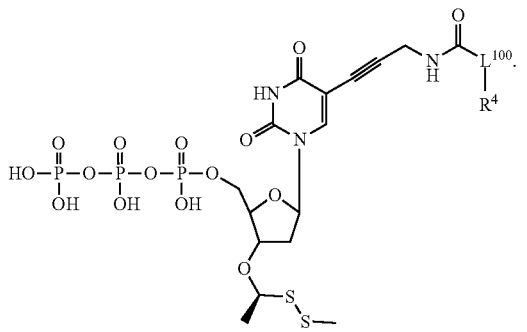

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

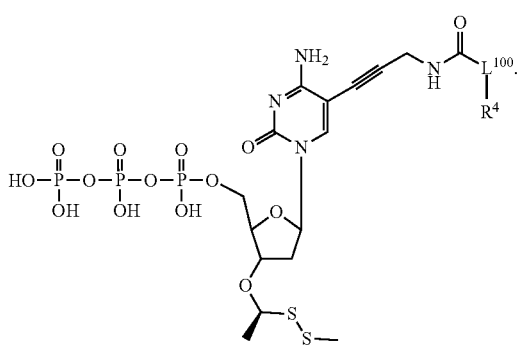

$L^{100}$ and $R^4$ are as described herein, including in embodiments. In embodiments, $L^{100}$ is a cleavable linker. In embodiments, Ra is a fluorescent dye moiety.

In embodiments, the compound is:

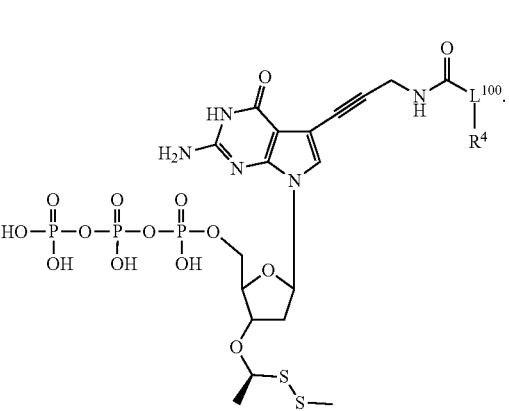

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

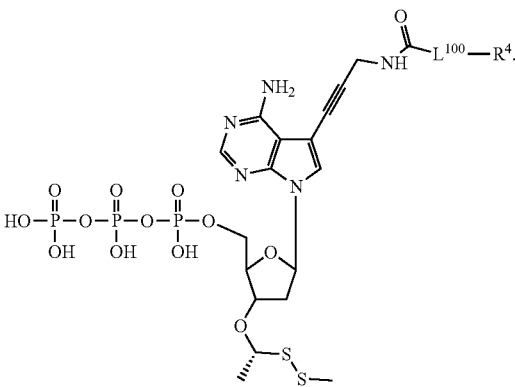

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

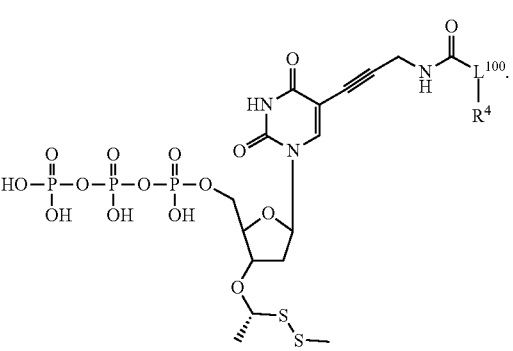

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

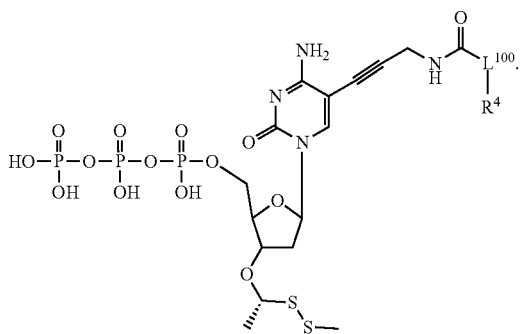

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

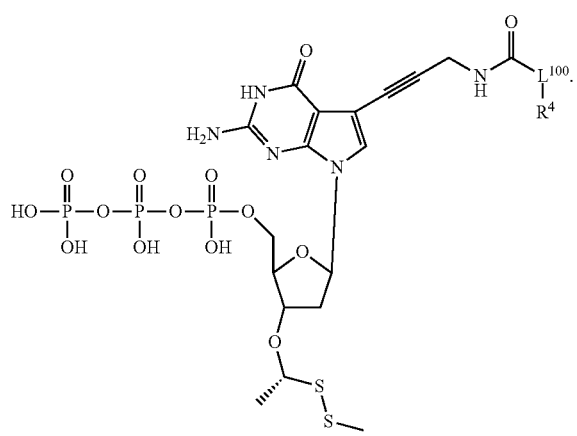

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

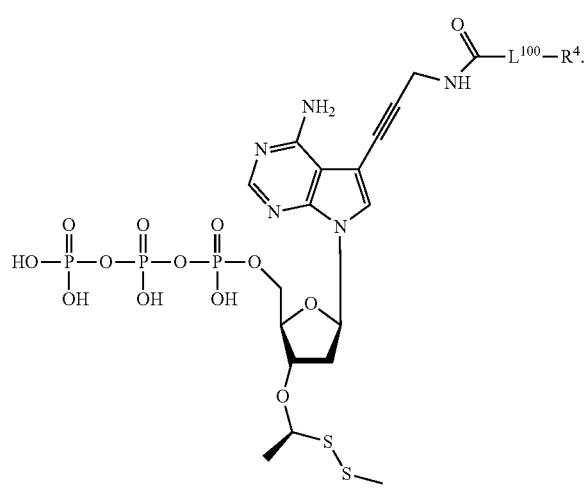

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

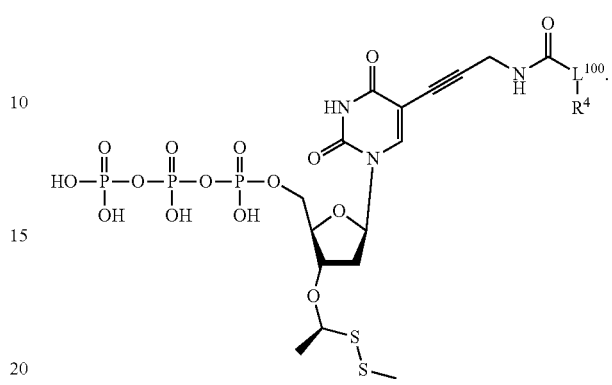

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

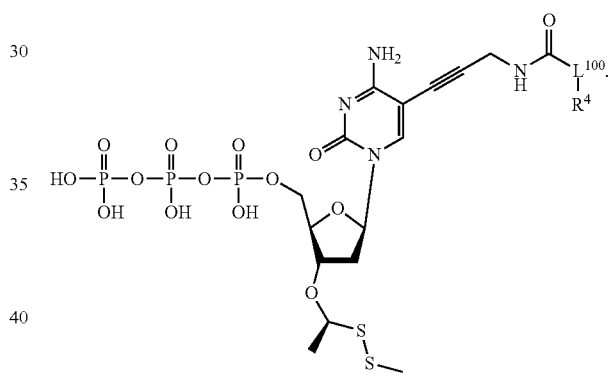

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

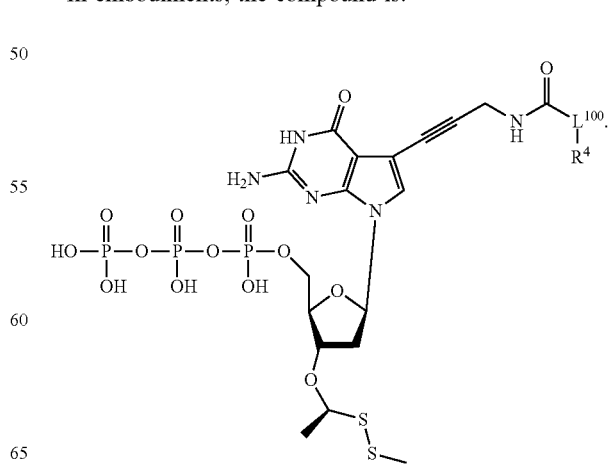

411

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

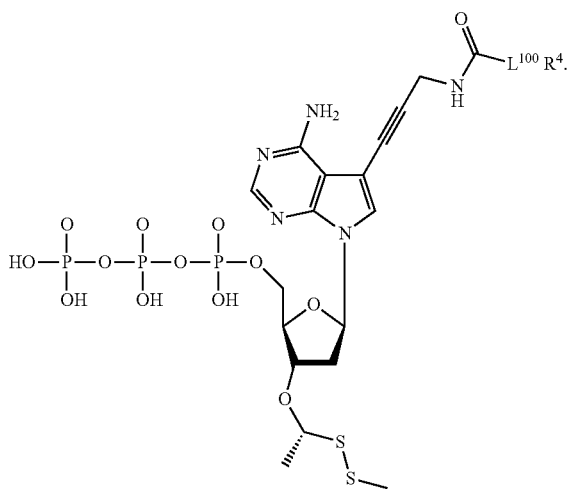

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

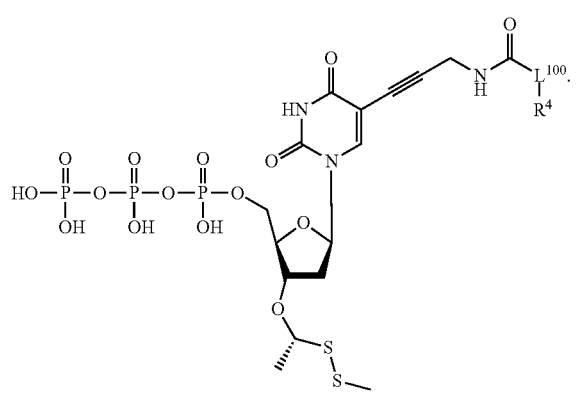

412

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

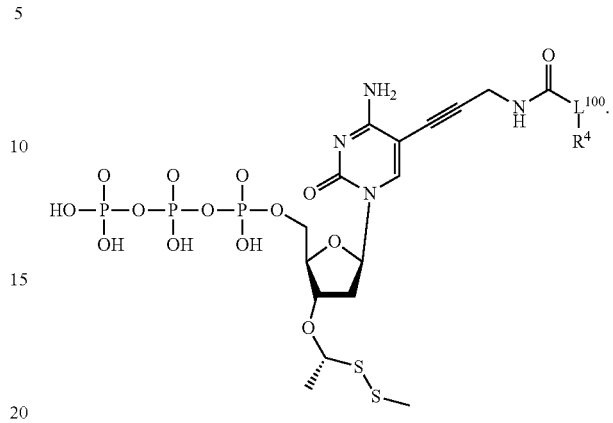

$L^{100}$ and $R^4$ are as described herein, including in embodiments. In embodiments, $L^{100}$ is a cleavable linker. In embodiments, $R^4$ is a fluorescent dye moiety.

In embodiments, the compound is:

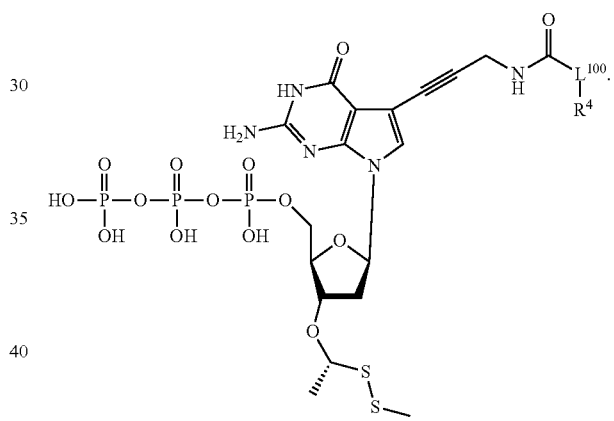

$L^{100}$ and $R^4$ are as described herein, including in embodiments. In embodiments, $L^{100}$ is a cleavable linker. In embodiments, $R^4$ is a fluorescent dye moiety.

In embodiments, $L^{100}$ is a cleavable linker, and the cleavable linker is

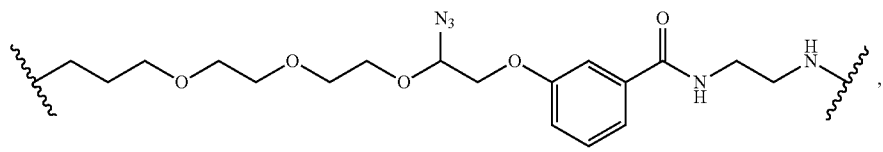

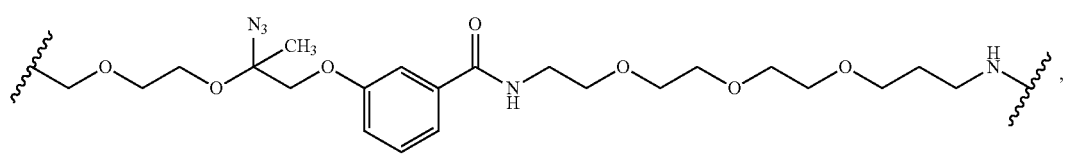

-continued
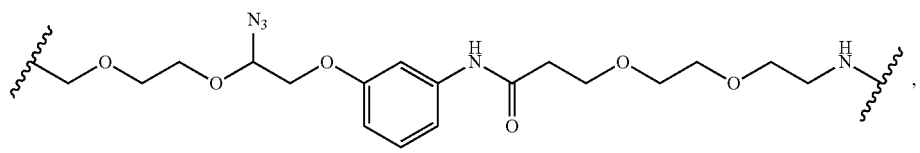
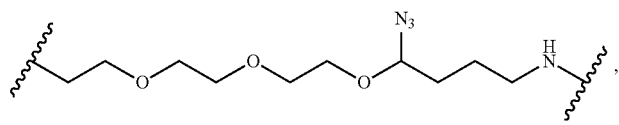
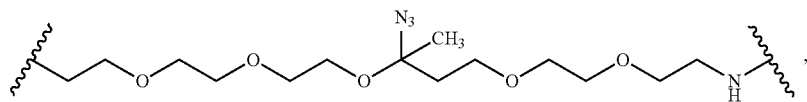
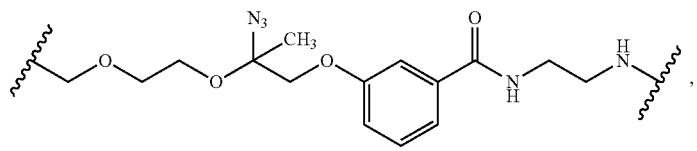
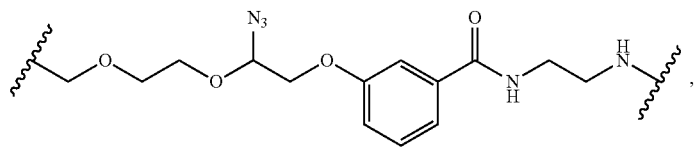
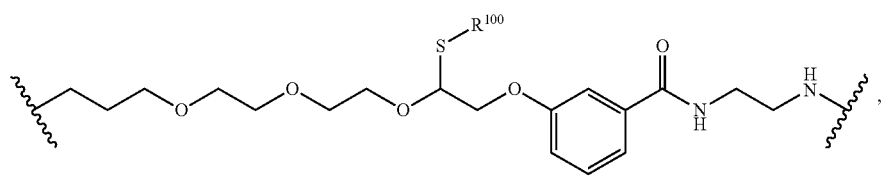
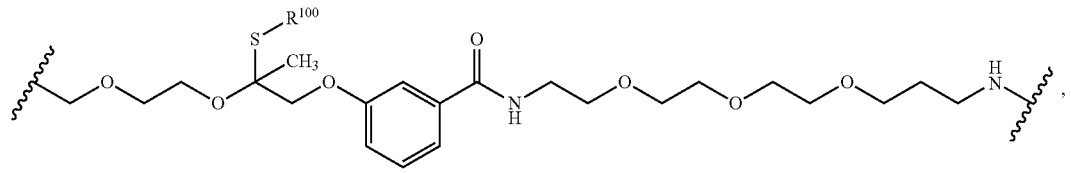
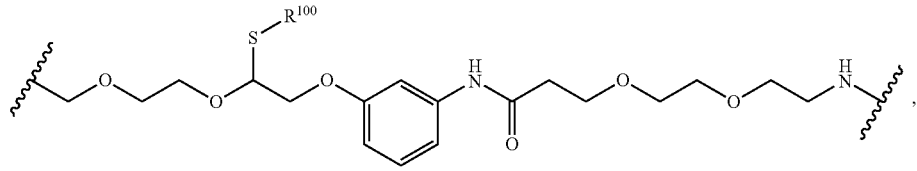
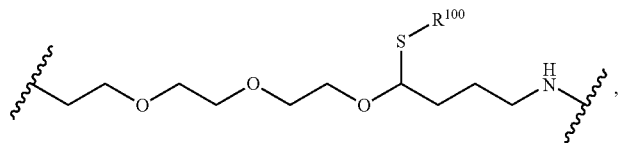
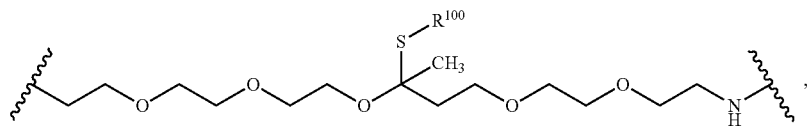
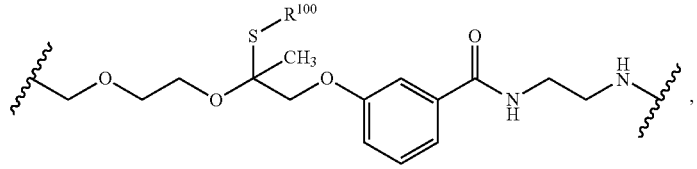

-continued
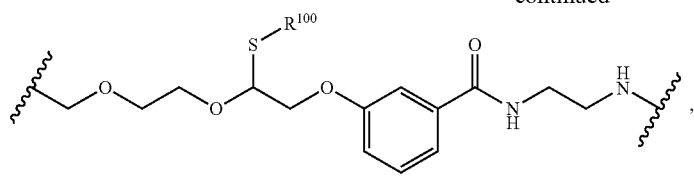
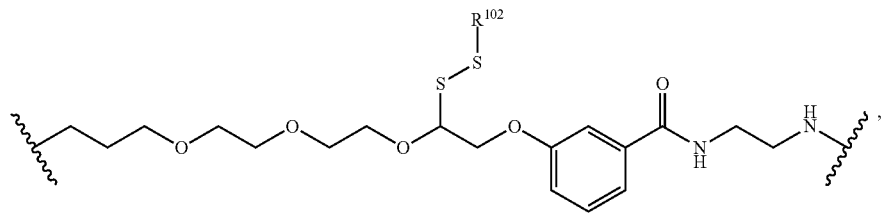
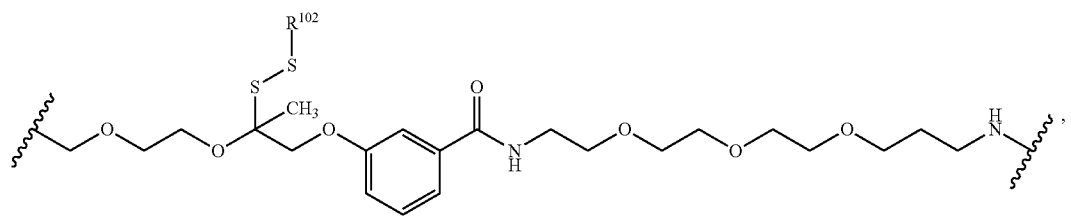
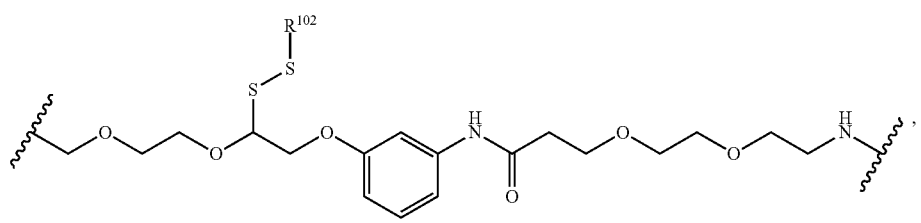
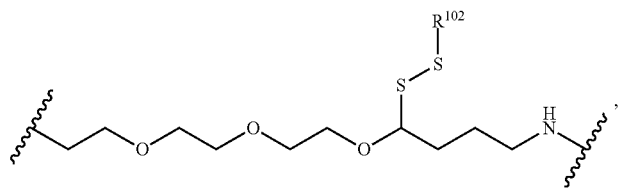
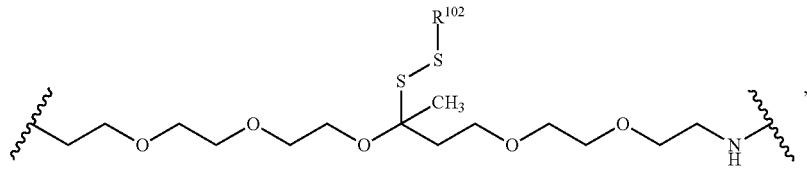
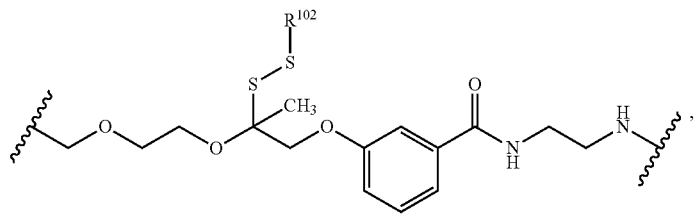
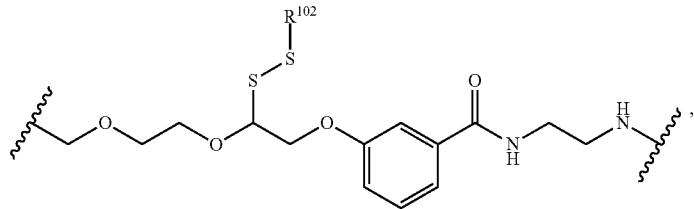

-continued
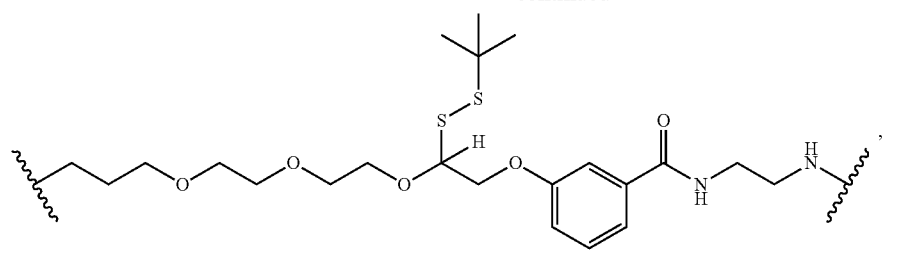
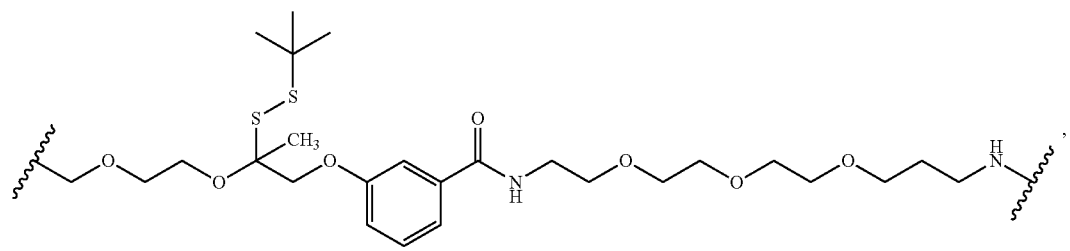
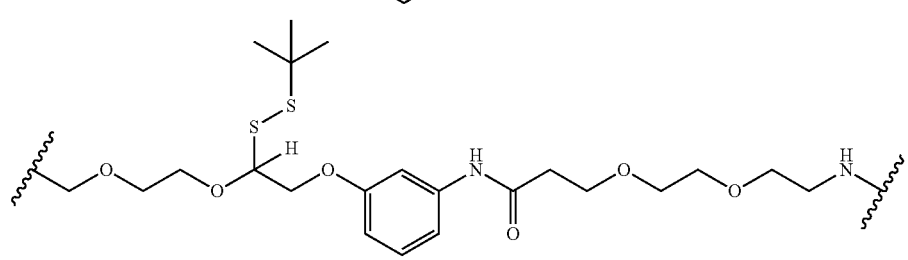
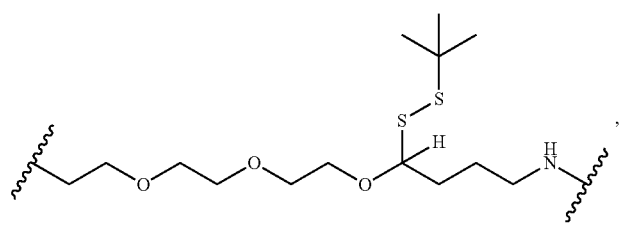
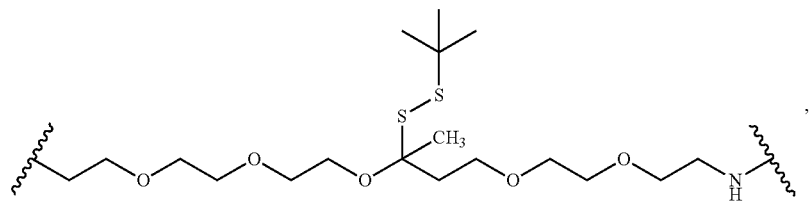
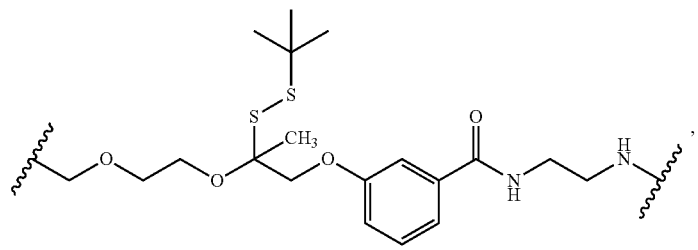
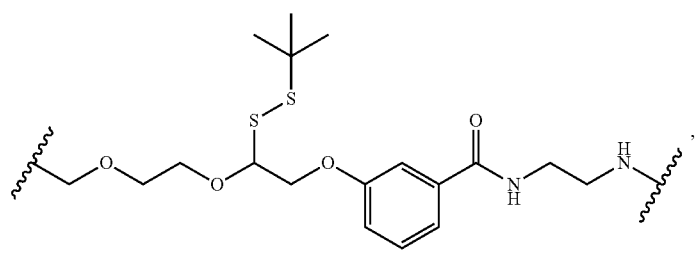

-continued
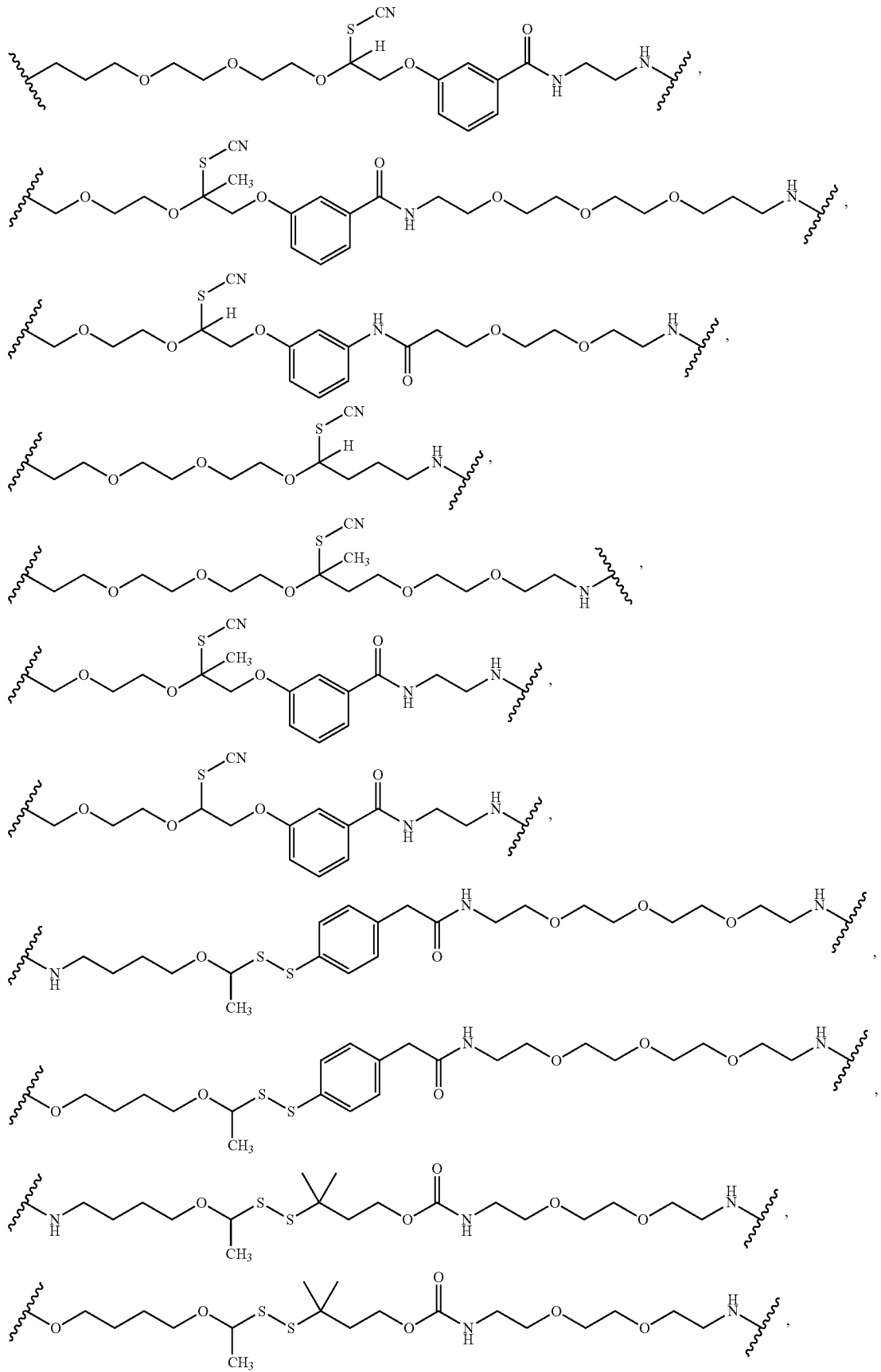

-continued

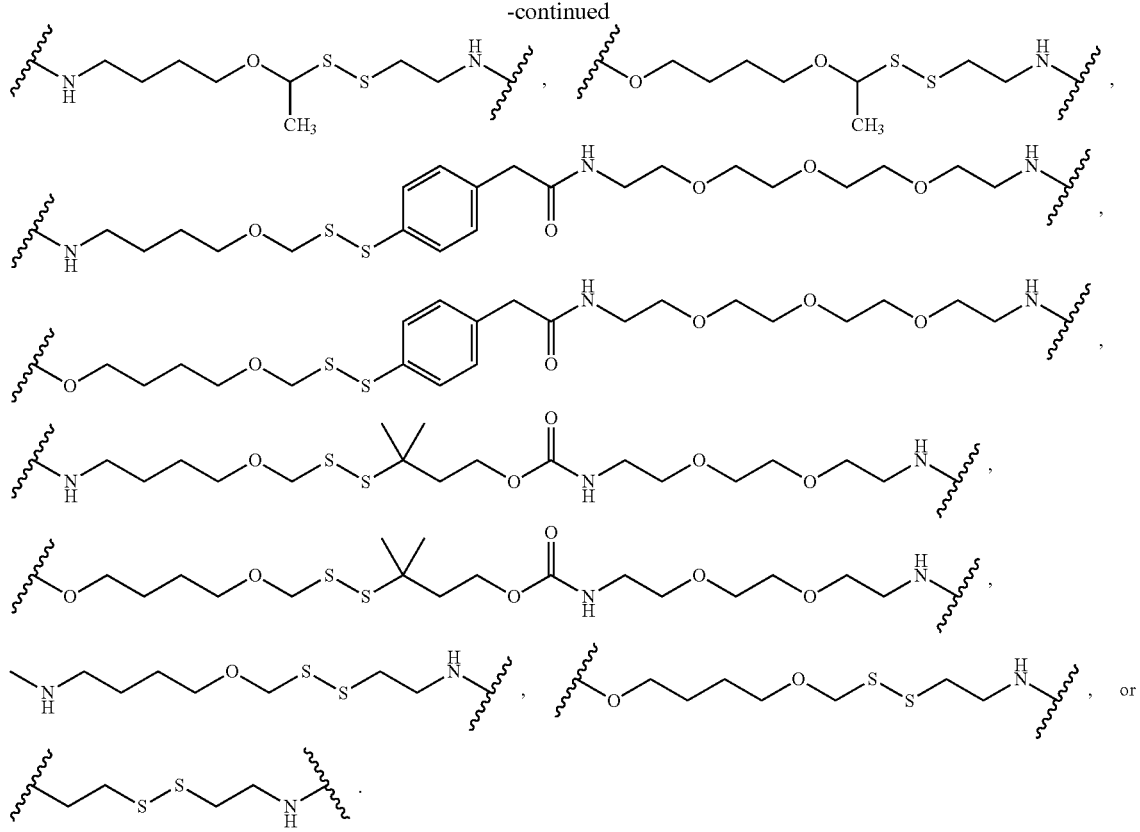

$R^{100}$ and $R^{102}$ are as described herein, including in embodiments.

In an aspect is provided a nucleic acid polymerase complex, wherein the nucleic acid polymerase is bound (e.g., non-covalently bound) to a compound described herein, including embodiments.

In embodiments, the nucleic acid polymerase is a Taq polymerase, Therminator γ, 9° N polymerase (exo-), Therminator II, Therminator III, or Therminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof.

In embodiments, the 3' moiety of a compound described herein is chemically cleaved faster than a 3'-OCH$_2$SSCH$_3$ (e.g., under identical cleavage conditions). In embodiments, a compound of formula I (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions). In embodiments, a compound of formula IA (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions). In embodiments, a compound of formula IB (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions). In embodiments, a compound of formula IAD (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions). In embodiments, a compound of formula IBD (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions). In embodiments, a compound described herein (e.g., in an aspect or embodiment) is chemically cleaved faster than an identical compound wherein the 3'-OCH(CH$_3$)SSCH$_3$ is replaced with a 3'-OCH$_2$SSCH$_3$ (e.g., under identical cleavage conditions).

In embodiments, chemical cleavage of a compound described herein (e.g., in an aspect or embodiment) is at least 1.1-fold (e.g., 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or 100000-fold) faster than chemical cleavage of an identical compound wherein the 3'-OCH(CH$_3$)SSCH$_3$ is replaced with a 3'-OCH$_2$SSCH$_3$ (e.g., under identical cleavage conditions). In embodiments, chemical cleavage of a compound described herein (e.g., in an aspect or embodiment) is about 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or about 100000-fold faster than chemical cleavage of an identical compound wherein the 3'-OCH(CH$_3$)SSCH$_3$ is replaced with a 3'-OCH$_2$SSCH$_3$ (e.g., under identical cleavage conditions). In embodiments, chemical cleavage of a compound described herein (e.g., in an aspect or embodiment) is 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or about 100000-fold faster than chemical cleavage of an identical compound wherein the 3'-OCH(CH$_3$)SSCH$_3$ is replaced with a 3'—OCH$_2$SSCH$_3$ (e.g., under identical cleavage conditions). In embodiments, chemical cleavage of a compound described herein (e.g., in an aspect or embodiment) is about 10-fold faster than chemical cleavage of an identical compound wherein the 3'-OCH(CH$_3$)SSCH$_3$ is replaced with a 3'-OCH$_2$SSCH$_3$ (e.g., under identical cleavage conditions). In embodiments, chemical cleavage of a compound described herein (e.g., in an aspect or embodiment) is at least 10-fold faster than chemical cleavage of an identical compound wherein the 3'-OCH(CH$_3$)SSCH$_3$ is replaced with a 3'-OCH$_2$SSCH$_3$ (e.g., under identical cleavage conditions). In embodiments, chemical cleavage of a compound described herein (e.g., in an aspect or embodiment) is 10-fold faster than chemical cleavage of an identical compound wherein the 3'-OCH(CH$_3$)SSCH$_3$ is replaced with a 3'-OCH$_2$SSCH$_3$ (e.g., under identical cleavage conditions). In embodiments, chemical cleavage is cleavage of the SS bond (e.g., in a 3' moiety). In embodiments, chemical cleavage is release of a 3' moiety from a nucleotide, nucleoside, or residue (e.g., from being bound to the 3' carbon of the sugar) to leave a 3'-OH on the nucleotide, nucleoside, or residue (e.g., attached to 3' carbon of the sugar). In embodiments, chemical cleavage is cleavage of the SS bond in a 3' moiety and release of a 3' moiety from a nucleotide, nucleoside, or residue (e.g., from being bound to the 3' carbon of the sugar) to leave a 3'-OH on the nucleotide, nucleoside, or residue (e.g., attached to 3' carbon of the sugar).

In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with a reducing agent. In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with THPP (e.g., about 10 mM THPP, at least 10 mM THPP). In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at around 55 degrees Celsius. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about 55 degrees Celsius. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at a temperature of at least 55 degrees Celsius. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at around pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at pH 9.5.

In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with a reducing agent. In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with THPP (e.g., about 10 mM THPP, at least 10 mM THPP). In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at around 55 degrees Celsius. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at a temperature of at least 55 degrees Celsius. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at around pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at pH 9.5.

In another aspect is provided a modified nucleotide or nucleoside, the nucleotide or nucleoside including a sugar moiety (e.g., a ribose or deoxyribose sugar moiety) having a 3'-0-polymerase-compatible cleavable moiety and a base (e.g., a purine, deazapurine, or pyrimidine base) linked via a covalent linker to a detectable moiety, wherein the covalent linker includes a thio-trigger moiety having the formula

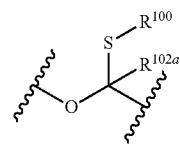

wherein $R^{100}$ is —$SR^{102}$ or —CN; and $R^{102}$ and $R^{102a}$ are as described herein, including embodiments. In embodiments, the thio-trigger moiety has the formula:

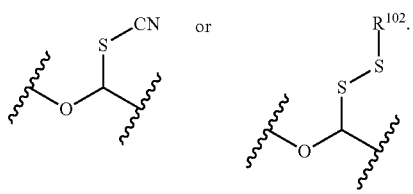

In an aspect is provided a kit. Some embodiments disclosed herein relate to kits including a labeled nucleoside or nucleotide including a linker between the fluorophore and the nucleoside or nucleotide, wherein the linker is a linker as described herein.

Some embodiments disclosed herein relate to kits including a labeled nucleoside or nucleotide including a linker between the fluorophore and the nucleoside or nucleotide, wherein the linker is a linker as described herein. In embodiments, the kit includes a compound described herein. In embodiments, the kit includes a plurality of compounds described herein.

III. Methods of Synthesis

In one aspect provided is a method of preparing or synthesizing a compound of Formula $I^P$,

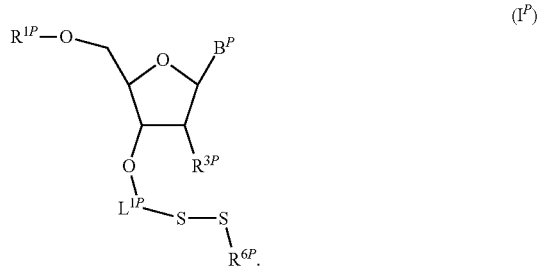

$B^P$ is a nucleobase, which may be optionally substituted. $L^{1P}$ is a covalent linker. $R^{1P}$ is independently hydrogen or 5'-nucleoside protecting group, or $-OR^{1P}$ is a monophosphate, or polyphosphate. $R^{3P}$ is hydrogen or $-OR^{3AP}$. $R^{3AP}$ is hydrogen or a polymerase-compatible cleavable moiety. $R^{6P}$ is a substituted or unsubstituted alkyl.

In embodiments, the method of synthesizing a compound of Formula $I^P$ by mixing compound ($IB^P$) and a thiolation reagent together in a reaction vessel, wherein compound of Formula $IB^P$ has the formula:

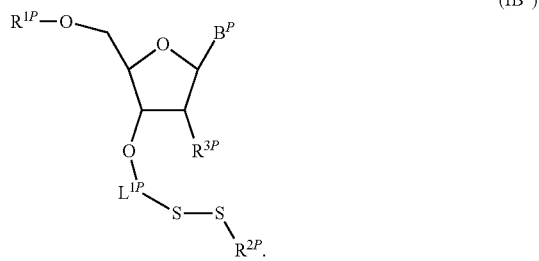

In embodiments, the thiolation reagent is

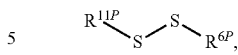

wherein $R^{6P}$ is as described herein. $R^{6P}$ is halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{11}$ is an unsubstituted heteroaryl (e.g., 5 to 10 membered heteroaryl, 5 to 9 membered heteroaryl, or 5 to 6 membered heteroaryl). In embodiments, $R^1$ is an unsubstituted alkyl (e.g., $C_1$-$C_8$ alkyl, $C_1$-$C_6$ alkyl, or $C_1$-$C_4$ alkyl).

In embodiments, the thiolation reagent is

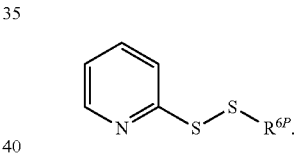

In embodiments the thiolation reagent is

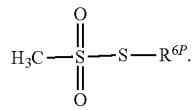

In embodiments, the thiolation reagent is

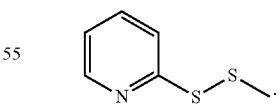

In embodiments, the thiolation reagent is

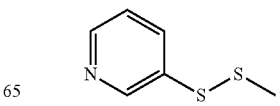

In embodiments, the thiolation reagent is

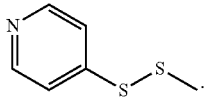

In embodiments, the thiolation reagent is

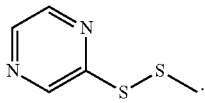

In embodiments, the thiolation reagent is

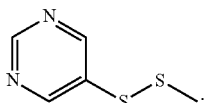

In embodiments, the thiolation reagent is

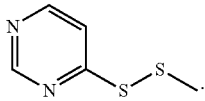

In embodiments, the thiolation reagent is

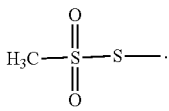

In embodiments, the thiolation reagent is

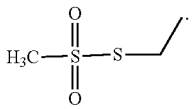

In embodiments, the thiolation reagent is a compound (e.g., a reagent) described in Mandal and Basu (RSC Adv., 2014, 4, 13854) or Musiejuk and Witt (Organic Preparations and Procedures International, 47:95-131, 2015), which are incorporated by reference in their entirety for all purposes.

In embodiments, the method of synthesizing a compound of Formula $I^P$ by mixing compound ($IB^P$) and compound ($II^P$) and/or compound ($III^P$) together in a reaction vessel, wherein compound of Formula $IB^P$ has the formula:

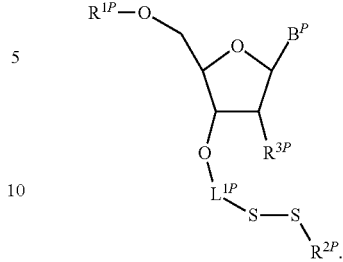
($IB^P$)

Compound $II^P$ has the formula:

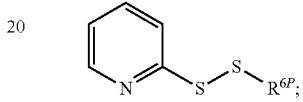
($II^P$)

and Compound $III^P$ has the formula:

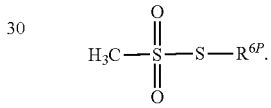
($III^P$)

In embodiments, the method of synthesizing a compound of Formula $I^P$ by mixing compound ($IB^P$) and compound ($II^P$) together in a reaction vessel, wherein compound of Formula $IB^P$ has the formula:

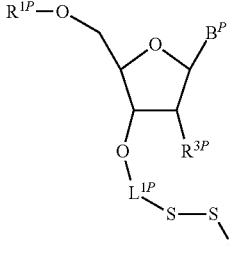
($IB^P$)

Compound $II^P$ has the formula:

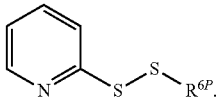
($II^P$)

In embodiments, the method of synthesizing a compound of Formula $I^P$ by mixing compound ($IB^P$) and compound ($III^P$) together in a reaction vessel, wherein compound of Formula $IB^P$ has the formula:

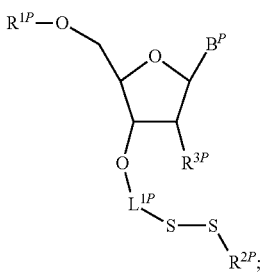

and Compound III$^P$ has the formula:

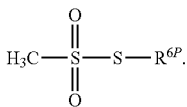

In embodiments, the method of synthesizing a compound of Formula I$^P$ includes contacting a compound of Formula IB$^P$:

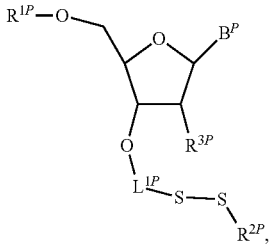

with a compound of Formula II$^P$:

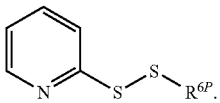

R$^{6P}$ is as described herein.

In embodiments, the method of synthesizing a compound of Formula I$^P$ includes contacting a compound of Formula IB$^P$:

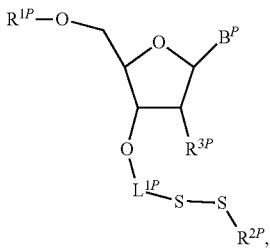

with a compound of Formula III$^P$:

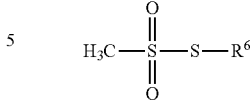

R$^{1P}$, R$^{2P}$, R$^{3P}$, R$^{6P}$, B$^P$ and L$^{1P}$ are as described herein. R$^{1P}$, R$^{3P}$, L$^{1P}$ and B$^P$ are described herein. R$^{2P}$ includes a protecting group. In embodiments, R$^{2P}$ is -L$^{2P}$-protecting group. In embodiments, R$^{2P}$ is -L$^{2P}$-R$^{4P}$, -L$^{2P}$-3'-nucleoside, -L$^{2P}$-3'-nucleotide, or -L$^{2P}$-3'-nucleic acid.

In embodiments, the method further includes deprotecting a compound of the formula IA$^P$:

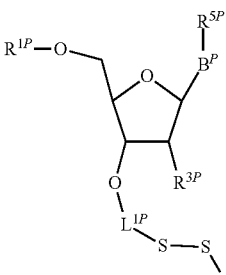

to form the compound of the formula IB$^P$. R$^{1P}$, R$^{2P}$, R$^{3P}$, R$^{5P}$, B$^P$ and L$^{1P}$ are as described herein.

In embodiments, the deprotecting includes contacting the compound of formula IA$^P$ with a deprotecting agent. In embodiments, the deprotecting agent includes concentrated ammonium hydroxide.

In embodiments, the concentrated ammonium hydroxide has a concentration greater than 1%. In embodiments, the concentrated ammonium hydroxide has a concentration greater than 2%. In embodiments, the concentrated ammonium hydroxide has a concentration greater than 3%. In embodiments, the concentrated ammonium hydroxide has a concentration greater than 4%. In embodiments, the concentrated ammonium hydroxide has a concentration greater than 5%. In embodiments, the concentrated ammonium hydroxide has a concentration ranging from 5 to 99%. In embodiments, the concentrated ammonium hydroxide has a concentration ranging from 5 to 95%. In embodiments, the concentrated ammonium hydroxide has a concentration ranging from 5 to 90%. In embodiments, the concentrated ammonium hydroxide has a concentration ranging from 5 to 85%. In embodiments, the concentrated ammonium hydroxide has a concentration ranging from 5 to 80%. In embodiments, the concentrated ammonium hydroxide has a concentration ranging from 5 to 75%. In embodiments, the concentrated ammonium hydroxide has a concentration ranging from 5 to 70%. In embodiments, the concentrated ammonium hydroxide has a concentration ranging from 5 to 65%. In embodiments, the concentrated ammonium hydroxide has a concentration ranging from 5 to 60%. In embodiments, the concentrated ammonium hydroxide has a concentration ranging from 5 to 55%. In embodiments, the concentrated ammonium hydroxide has a concentration ranging from 5 to 50%. In embodiments, the concentrated ammonium hydroxide has a concentration ranging from 5 to 45%. In embodiments, the concentrated ammonium hydroxide has a concentration ranging from 5 to 40%. In embodiments, the concentrated ammonium hydroxide has a concentration ranging from 5 to 35%. In embodiments, the concentrated ammonium hydroxide has a concentration ranging from 5 to 30%. In embodiments, the concentrated ammonium hydroxide is 25% ammonia in water.

In embodiments, the deprotecting agent may cleave propargyl amine moiety of $R^{5P}$. In embodiments, the deprotecting agent includes $K_2CO_2$ or $Na_2CO_3$. In embodiments, the deprotecting agent includes $K_2CO_2$ or $Na_2CO_3$ in methanol. In embodiments, the deprotecting agent includes $K_2CO_2$ or $Na_2CO_3$ in methanol and water. In embodiments, the deprotecting agent includes LiOH. In embodiments, the deprotecting agent includes LiOH and THF. In embodiments, the deprotecting agent includes LiOH, methanol, in methanol. In embodiments, the deprotecting agent includes LiOH, methanol, in methanol and water. In embodiments, the deprotecting agent includes $NH_3$. In embodiments, the deprotecting agent includes $NH_3$ in methanol. In embodiments, the deprotecting agent includes methylamine. In embodiments, the deprotecting agent includes methylamine in methanol. In embodiments, the deprotecting agent includes tert-butylamine. In embodiments, the deprotecting agent includes tert-butylamine in methanol. In embodiments, the deprotecting agent includes tert-butylamine in methanol and water.

In embodiments, the method further includes mixing compound of Formula $IB^P$ with a compound of Formula $II^P$ or $III^P$ in a reaction vessel.

In embodiments, the method includes synthesizing a compound of Formula $IC^P$:

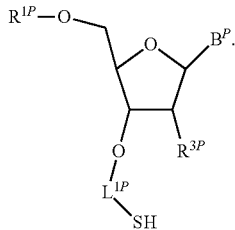

(IC$^P$)

$R^{1P}$, $R^{3P}$, $L^{1P}$ and $B^P$ are described herein.

In embodiments, the method of synthesizing a compound of Formula $I^P$ by mixing compound ($IC^P$) and compound ($II^P$) and/or compound ($III^P$) together in a reaction vessel, wherein compound of Formula $IB^P$ has the formula:

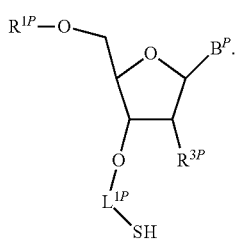

(IC$^P$)

Compound $II^P$ has the formula:

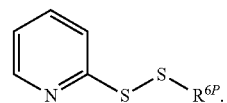

(II$^P$)

Compound $III^P$ has the formula:

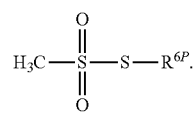

(III$^P$)

$R^{1P}$, $R^{2P}$, $R^{3P}$, $R^{6P}$, $B^P$ and $L^{1P}$ are as described herein.

In embodiments, the method of synthesizing a compound of Formula $I^P$ by contacting compound ($IC^P$) and compound ($II^P$) and/or compound ($III^P$) together in a reaction vessel, wherein compound of Formula $IB^P$ has the formula:

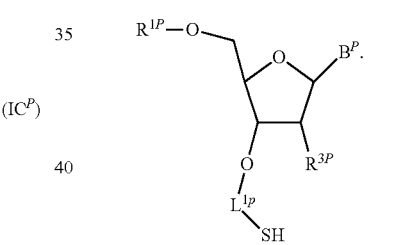

(IC$^P$)

Compound $II^P$ has the formula:

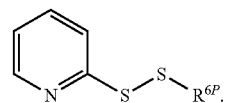

(II$^P$)

Compound $III^P$ has the formula:

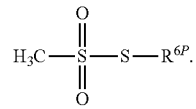

(III$^P$)

$R^{1P}$, $R^{3P}$, $R^{6P}$, $B^P$ and $L^{1P}$ are as described herein.

In embodiments, the method of synthesizing a compound of Formula $I^P$ includes contacting a compound of Formula $IC^P$:

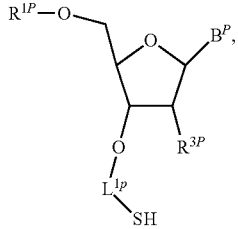

with a compound of Formula $II^P$:

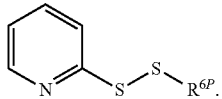

$R^{1P}$, $R^{3P}$, $R^{6P}$, $B^P$ and $L^{1P}$ are as described herein.

In embodiments, the method of synthesizing a compound of Formula $I^P$ includes contacting a compound of Formula $IB^P$:

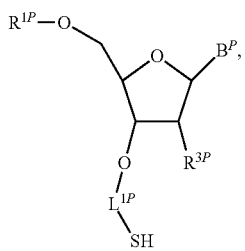

with a compound of Formula $III^P$:

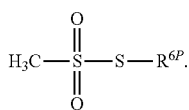

$R^{6P}$ is as described herein.

$R^{2P}$, $R^{3P}$, $L^{1P}$ and $B^P$ are described herein. $R^{2P}$ includes a protecting group. In embodiments, $R^{2P}$ is -$L^{2P}$-protecting group. In embodiments, $R^{2P}$ is -$L^{2P}$-$R^{4P}$, -$L^{2P}$-3'-nucleoside, -$L^{2P}$-3'-nucleotide, or -$L^{2P}$-3'-nucleic acid.

In embodiments, the method further includes deprotecting a compound of the formula $IA^P$:

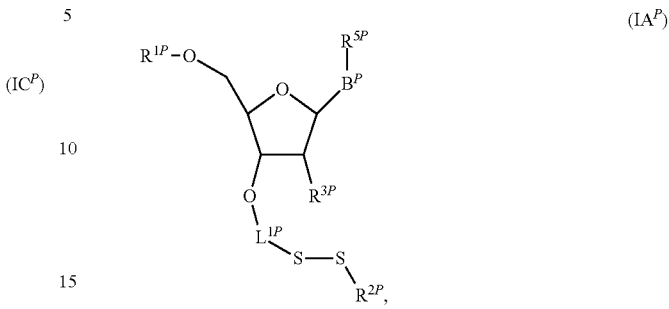

to form the compound of the formula $IB^P$. $R^{1P}$, $R^{2P}$, $R^{3P}$, $R^{5P}$, $B^P$ and $L^{1P}$ are as described herein.

In embodiments, the compound of Formula $IC^P$ is formed from the compound of Formula $IB^P$. In embodiments, the compound of Formula $IC^P$ is formed from the compound of Formula $IB^P$, wherein $L^{2P}$ is unsubstituted $C_1$-$C_4$ alkylene and $R^{2P}$ is -$L^{2P}$-3'-nucleoside, -$L^{2P}$-3'-nucleotide, or -$L^{2P}$-3'-nucleic acid. In embodiments, the compound of Formula $IC^P$ is formed from the compound of Formula $IB^P$, wherein $L^{2P}$ is —$CH_2$— or —$CH_2CH_2$— and $R^{2P}$ is -$L^{2P}$-3'-nucleoside, -$L^{2P}$-3'-nucleotide, or -$L^{2P}$-3'-nucleic acid. In embodiments, the compound of Formula IC is formed from the compound of Formula $IB^P$, wherein $L^{2P}$ is —$CH_2$—; and $R^{2P}$ is -$L^{2P}$-3'-nucleoside, -$L^{2P}$-3'-nucleotide, or -$L^{2P}$-3'-nucleic acid. In embodiments, the compound of Formula $IC^P$ is formed from the compound of Formula $IB^P$, wherein $L^{2P}$ is —$CH_2$—; and $R^{2P}$ is -$L^{2P}$-3'-nucleoside. In embodiments, the compound of Formula $IC^P$ is formed from the compound of Formula $IB^P$, wherein $L^{2P}$ is —$CH_2$—; and $R^{2P}$ is -$L^{2P}$-3'-nucleotide. In embodiments, the compound of Formula $IC^P$ is formed from the compound of Formula $IB^P$, wherein $L^{2P}$ is —$CH_2$—; and $R^{2P}$ is -$L^{2P}$-3'-nucleic acid. In embodiments, the compound of Formula $IC^P$ is formed from the compound of Formula $IB^P$, wherein $L^{2P}$ is —$CH_2CH_2$—; and $R^{2P}$ is -$L^{2P}$-3'-nucleoside, -$L^{2P}$-3'-nucleotide, or -$L^{2P}$-3'-nucleic acid. In embodiments, the compound of Formula $IC^P$ is formed from the compound of Formula $IB^P$, wherein $L^{2P}$ is —$CH_2CH_2$—; and $R^{2P}$ is -$L^{2P}$-3'-nucleoside. In embodiments, the compound of Formula $IC^P$ is formed from the compound of Formula $IB^P$, wherein $L^{2P}$ is —$CH_2CH_2$—; and $R^{2P}$ is -$L^{2P}$-3'-nucleotide. In embodiments, the compound of Formula $IC^P$ is formed from the compound of Formula $IB^P$, wherein $L^{2P}$ is —$CH_2CH_2$—; and $R^{2P}$ is -$L^{2P}$-3'-nucleic acid.

In embodiments, the compound of Formula $IC^P$ is formed from the compound of Formula $IB^P$, wherein the compound of Formula $IB^P$ having $R^{2P}$ of

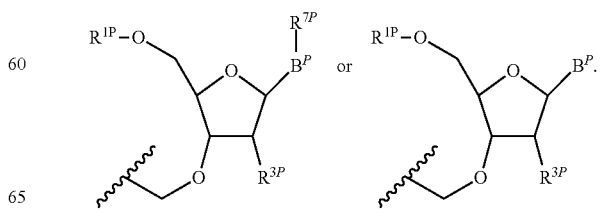

In embodiments, the compound of Formula IC$^P$ is

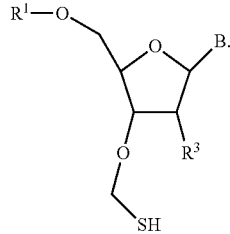
(IC$^P$)

R$^{1P}$, R$^{3P}$ and B$^P$ are described herein. In embodiments, the compound of Formula IC$^P$ is

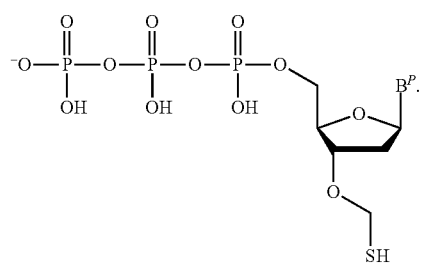
(IC$^{P''}$)

R$^{1P}$, R$^{2P}$, R$^{3P}$, R$^{6P}$, B$^P$ and L$^{1P}$ are as described herein.

In embodiments, the compound of Formula IC$^P$ is:

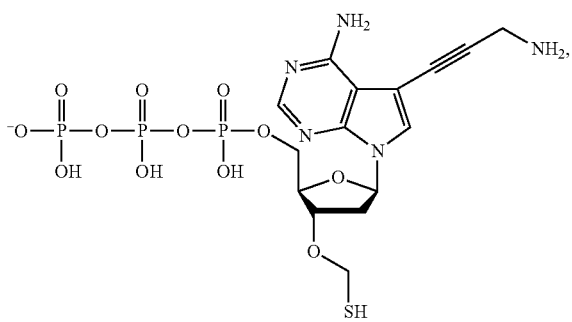

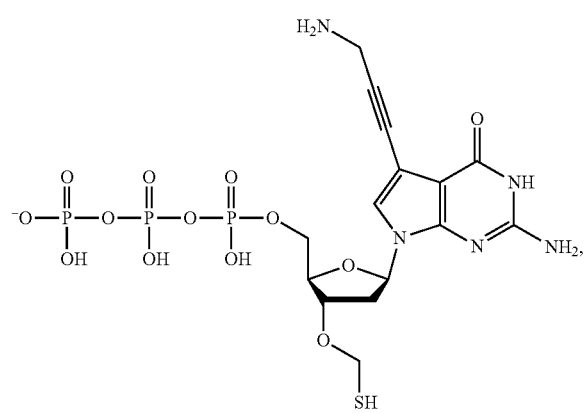

-continued

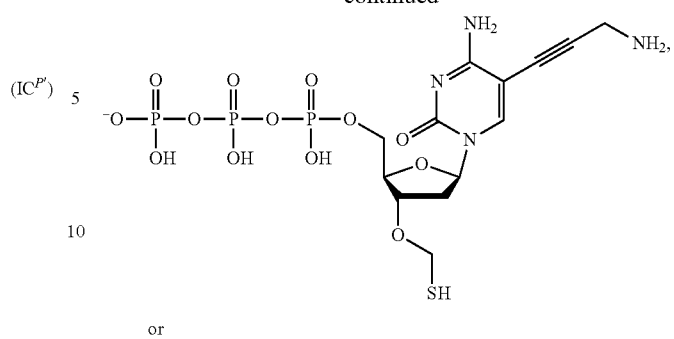

or

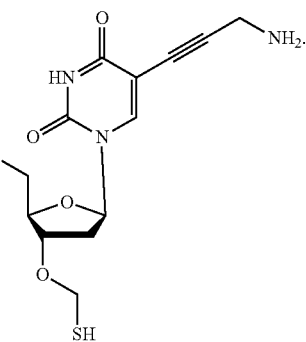

In embodiments, the compound of Formula IC$^P$ is:

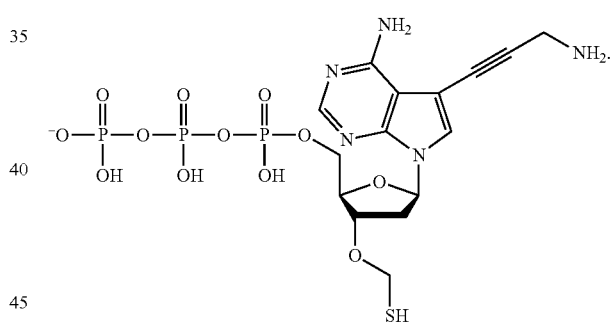

In embodiments, the compound of Formula IC$^P$ is:

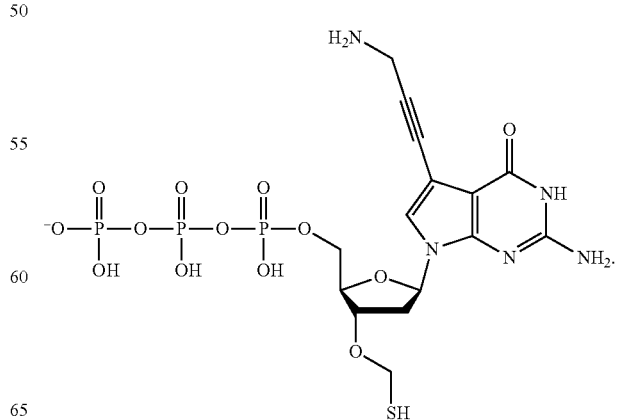

In embodiments, the compound of Formula IC$^P$ is:

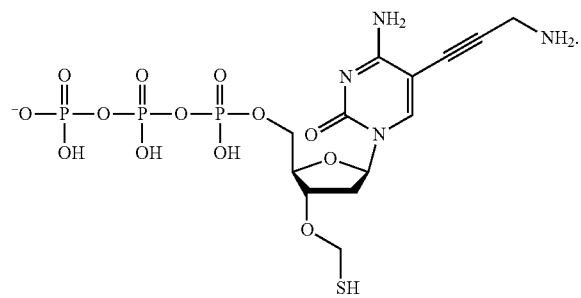

In embodiments, the compound of Formula IC$^P$ is:

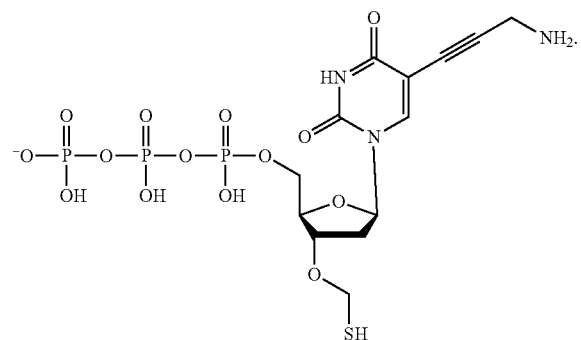

In another aspect is provided a method for sequencing a nucleic acid, including: (i) incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; and (ii) detecting the unique detectable label of each incorporated nucleotide analogue, so as to thereby identify each incorporated nucleotide analogue in the extension strand, thereby sequencing the nucleic acid; wherein each of the four different labeled nucleotide analogues is a nucleotide analogue described herein, including embodiments. In embodiments, the nucleotide analogues are compounds described herein. In embodiments, the labeled nucleotide analogues are compounds described herein. In embodiments, the four different labeled nucleotide analogues are four different compounds described herein (e.g., four different compounds described herein each including a different nucleobase and a different label (e.g., fluorescent dye moiety)). In embodiments, the four different labeled nucleotide analogues are four different compounds described herein (e.g., four different compounds described herein each including a different nucleobase). In embodiments, the four different labeled nucleotide analogues are four different compounds described herein (e.g., four different compounds described herein each including a different label (e.g., fluorescent dye moiety)).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

In an aspect is provided a method of preparing or synthesizing a compound of Formula XA,

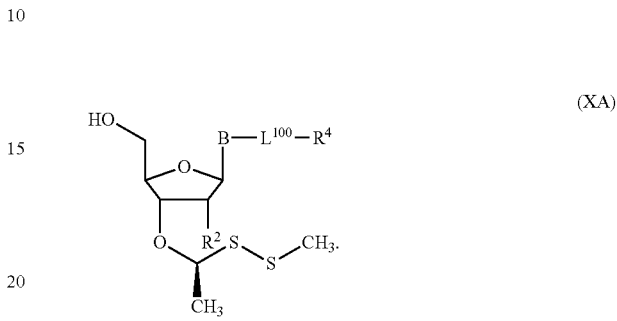

B, $L^{100}$, $R^2$, and $R^4$ are as described herein.

In embodiments, the method of synthesizing a compound of Formula XA includes mixing compound (XB) and a LG-$L^{100}$-$R^4$ together in a reaction vessel, wherein compound of Formula XB has the formula:

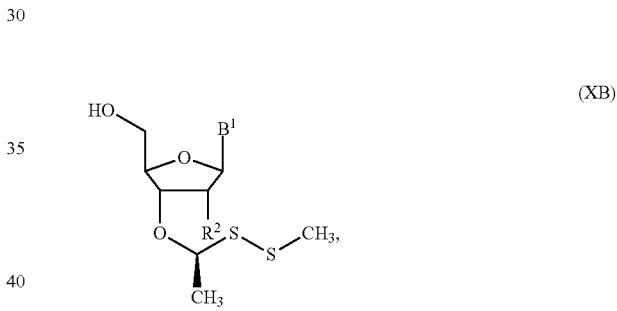

LG is a leaving group. $B^1$, $L^{100}$, $R^2$, and $R^4$ are as described herein. In embodiments, the leaving group is succinimidyl. In embodiments, the leaving group is —O-succinimide.

In embodiments, the method of synthesizing a compound of Formula XA includes a method of synthesizing a compound of formula XB, including mixing compound (XC) and a deprotecting reagent together in a reaction vessel, wherein compound of Formula XC has the formula:

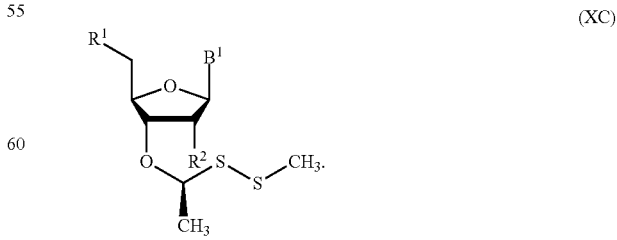

$R^1$, $B^1$, and $R^2$ are as described herein. In embodiments, $R^1$ is a 5'-nucleoside protecting group. In embodiments, $R^1$ is

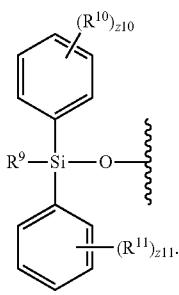

$R^9$, $R^{10}$, $R^{11}$, z10, and z11 are as described herein. In embodiments, the deprotecting reagent is tetra-n-butylammonium fluoride (TBAF). In embodiments, the deprotecting reagent is tetra-n-butylammonium fluoride (TBAF) and tetrahydrofuran (THF).

In embodiments, the method of synthesizing a compound of Formula XA includes a method of synthesizing a compound of formula XC, including mixing compound (XD) and a thiolation reagent together in a reaction vessel, wherein compound of Formula XD has the formula:

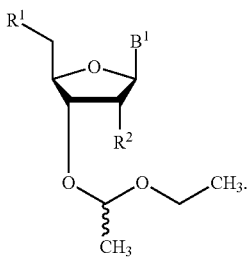

$R^1$, $B^1$, and $R^2$ are as described herein. In embodiments, the thiolation reagent is K-thiotosylate. In embodiments, the thiolation reagent is $NaSCH_3$. In embodiments, the method of synthesizing a compound of Formula XC includes mixing compound (XD) and TMSOTf, collidine, K-thiotosylate, 18-crown-6, and NaSMe; followed by purification (e.g., HPLC) of the stereoisomeric XC. In embodiments, the method of synthesizing a compound of Formula XC includes mixing compound (XD) and TMSOTf and collidine, followed by addition of K-thiotosylate and 18-crown-6, followed by addition of NaSMe, followed by purification (e.g., HPLC) of the stereoisomeric XC.

In embodiments, the method of synthesizing a compound of Formula XA includes a method of synthesizing a compound of formula XD, including mixing compound (XE) and a

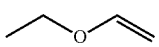

together in a reaction vessel, wherein compound of Formula XE has the formula:

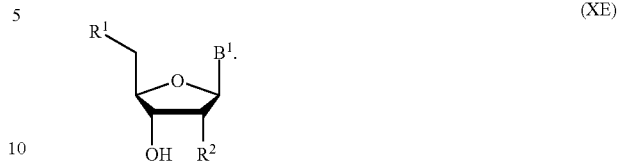

$R^1$, $B^1$, and $R^2$ are as described herein. In embodiments, compound XE is mixed with

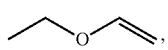

PPTS, and DCM.

In embodiments, the method of synthesizing a compound of Formula XA includes a method of synthesizing a compound of formula XE, including mixing compound (XF) and a protecting group reagent together in a reaction vessel, wherein compound of Formula XF has the formula:

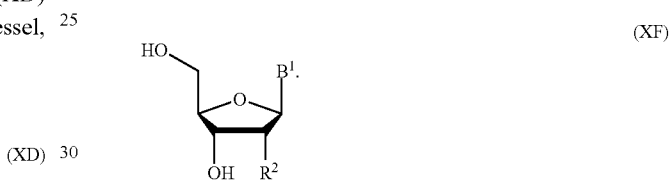

$R^1$, $B^1$, and $R^2$ are as described herein. In embodiments, the protecting group reagent is tert-butyl(chloro)diphenylsilane (TBDPSCl). In embodiments, the protecting group reagent is $R^9$-(chloro)diphenylsilane ($R^9$-DPSCl). In embodiments, the protecting group reagent is TBDPSCl, imidazole, and DMF.

In embodiments, the method of synthesizing a compound of Formula XA includes a method of adding a protecting group to $B^1$, including mixing compound (XE) and a protecting group reagent together in a reaction vessel. In embodiments, the protecting group reagent is

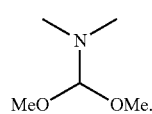

In an aspect is provided a method of preparing or synthesizing a compound of Formula XXA,

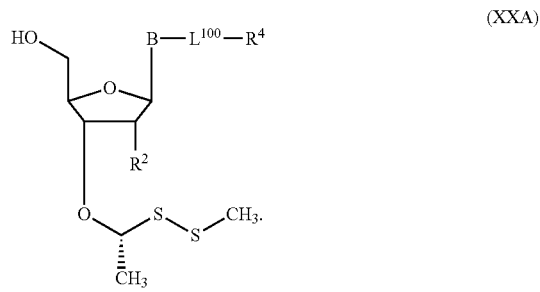

B, $L^{100}$, $R^2$, and $R^4$ are as described herein.

In embodiments, the method of synthesizing a compound of Formula XXA includes mixing compound (XXB) and a LG-$L^{100}$-$R^4$ together in a reaction vessel, wherein compound of Formula XXB has the formula:

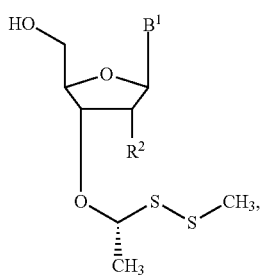

(XXB)

LG is a leaving group. $B^1$, $L^{100}$, $R^2$, and $R^4$ are as described herein. In embodiments, the leaving group is succinimidyl. In embodiments, the leaving group is —O-succinimide.

In embodiments, the method of synthesizing a compound of Formula XXA includes a method of synthesizing a compound of formula XB, including mixing compound (XXC) and a deprotecting reagent together in a reaction vessel, wherein compound of Formula XXC has the formula:

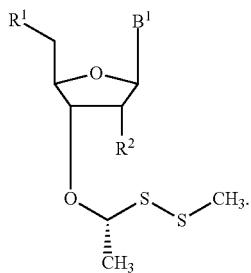

(XXC)

$R^1$, $B^1$, and $R^2$ are as described herein. In embodiments, $R^1$ is a 5'-nucleoside protecting group. In embodiments, $R^1$ is

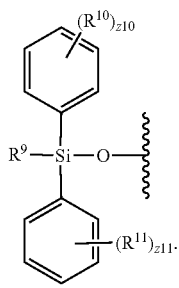

$R^9$, $R^{10}$, $R^{11}$, z10, and z11 are as described herein. In embodiments, the deprotecting reagent is tetra-n-butylammonium fluoride (TBAF). In embodiments, the deprotecting reagent is tetra-n-butylammonium fluoride (TBAF) and tetrahydrofuran (THF).

In embodiments, the method of synthesizing a compound of Formula XXA includes a method of synthesizing a compound of formula XXC, including mixing compound (XD) and a thiolation reagent together in a reaction vessel, wherein compound of Formula XD has the formula:

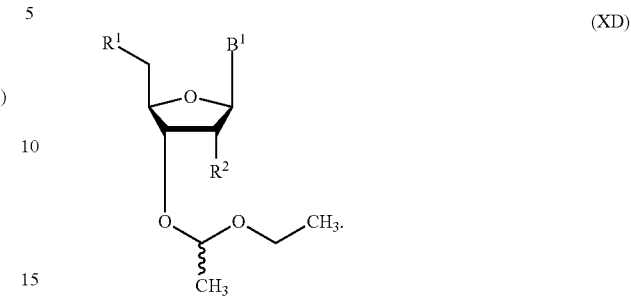

(XD)

$R^1$, $B^1$, and $R^2$ are as described herein. In embodiments, the thiolation reagent is K-thiotosylate. In embodiments, the thiolation reagent is $NaSCH_3$. In embodiments, the method of synthesizing a compound of Formula XC includes mixing compound (XD) and TMSOTf, collidine, K-thiotosylate, 18-crown-6, and NaSMe; followed by purification (e.g., HPLC) of the stereoisomeric XC. In embodiments, the method of synthesizing a compound of Formula XC includes mixing compound (XD) and TMSOTf and collidine, followed by addition of K-thiotosylate and 18-crown-6, followed by addition of NaSMe, followed by purification (e.g., HPLC) of the stereoisomeric XC.

In embodiments, the method of synthesizing a compound of Formula XXA includes a method of synthesizing a compound of formula XD, including mixing compound (XE) and

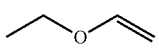

together in a reaction vessel, wherein compound of Formula XE has the formula:

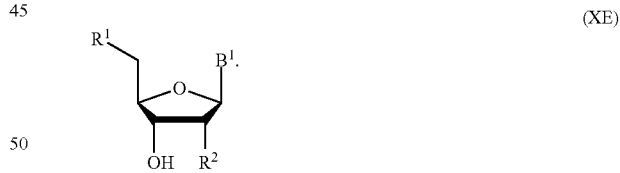

(XE)

$R^1$, $B^1$, and $R^2$ are as described herein. In embodiments, compound XE is mixed with

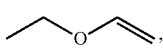

PPTS, and DCM.

In embodiments, the method of synthesizing a compound of Formula XXA includes a method of synthesizing a compound of formula XE, including mixing compound (XF) and a protecting group reagent together in a reaction vessel, wherein compound of Formula XF has the formula:

(XF)

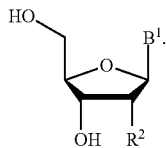

$R^1$, $B^1$, and $R^2$ are as described herein. In embodiments, the protecting group reagent is tert-butyl(chloro)diphenylsilane (TBDPSCl). In embodiments, the protecting group reagent is $R^9$-(chloro)diphenylsilane ($R^9$-DPSCl). In embodiments, the protecting group reagent is TBDPSCl, imidazole, and DMF.

In embodiments, the method of synthesizing a compound of Formula XXA includes a method of adding a protecting group to $B^1$, including mixing compound (XE) and a protecting group reagent together in a reaction vessel. In embodiments, the protecting group reagent is

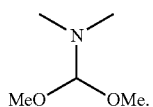

In embodiments, compound XA is (XAD)

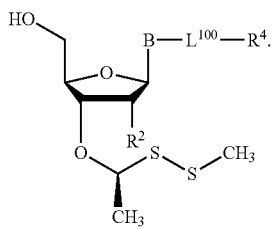

In embodiments, compound XB is (XBD)

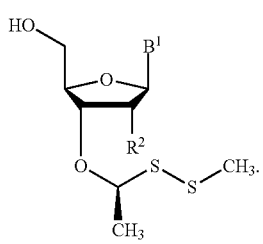

In embodiments, compound XC is (XCD)

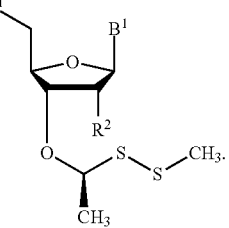

In embodiments, compound XD is (XDD)

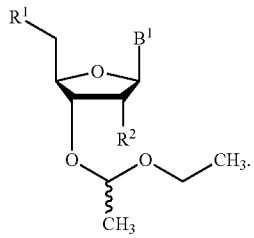

In embodiments, compound XE is (XED)

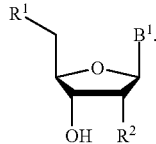

In embodiments, compound XF is (XFD)

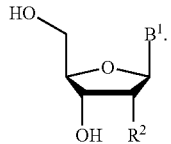

In embodiments, compound XXA is (XXAD)

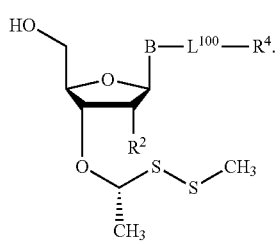

In embodiments, compound XXB is

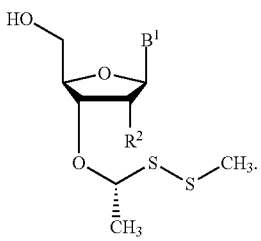
(XXBD)

In embodiments, compound XXC is

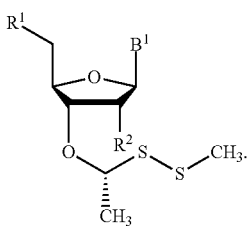
(XXCD)

In embodiments, the deprotecting includes contacting the compound of formula XA or XXA with a deprotecting reagent. In embodiments, the deprotecting reagent includes concentrated ammonium hydroxide.

In embodiments, the concentrated ammonium hydroxide has a concentration greater than 1%. In embodiments, the concentrated ammonium hydroxide has a concentration greater than 2%. In embodiments, the concentrated ammonium hydroxide has a concentration greater than 3%. In embodiments, the concentrated ammonium hydroxide has a concentration greater than 4%. In embodiments, the concentrated ammonium hydroxide has a concentration greater than 5%. In embodiments, the concentrated ammonium hydroxide has a concentration ranging from 5 to 99%. In embodiments, the concentrated ammonium hydroxide has a concentration ranging from 5 to 95%. In embodiments, the concentrated ammonium hydroxide has a concentration ranging from 5 to 90%. In embodiments, the concentrated ammonium hydroxide has a concentration ranging from 5 to 85%. In embodiments, the concentrated ammonium hydroxide has a concentration ranging from 5 to 80%. In embodiments, the concentrated ammonium hydroxide has a concentration ranging from 5 to 75%. In embodiments, the concentrated ammonium hydroxide has a concentration ranging from 5 to 70%. In embodiments, the concentrated ammonium hydroxide has a concentration ranging from 5 to 65%. In embodiments, the concentrated ammonium hydroxide has a concentration ranging from 5 to 60%. In embodiments, the concentrated ammonium hydroxide has a concentration ranging from 5 to 55%. In embodiments, the concentrated ammonium hydroxide has a concentration ranging from 5 to 50%. In embodiments, the concentrated ammonium hydroxide has a concentration ranging from 5 to 45%. In embodiments, the concentrated ammonium hydroxide has a concentration ranging from 5 to 40%. In embodiments, the concentrated ammonium hydroxide has a concentration ranging from 5 to 35%. In embodiments, the concentrated ammonium hydroxide has a concentration ranging from 5 to 30%. In embodiments, the concentrated ammonium hydroxide is 25% ammonia in water.

In embodiments, the deprotecting reagent includes $K_2CO_2$ or $Na_2CO_3$. In embodiments, the deprotecting reagent includes $K_2CO_2$ or $Na_2CO_3$ in methanol. In embodiments, the deprotecting reagent includes $K_2CO_2$ or $Na_2CO_3$ in methanol and water. In embodiments, the deprotecting reagent includes LiOH. In embodiments, the deprotecting reagent includes LiOH and THF. In embodiments, the deprotecting reagent includes LiOH, methanol, in methanol. In embodiments, the deprotecting reagent includes LiOH, methanol, in methanol and water. In embodiments, the deprotecting reagent includes $NH_3$. In embodiments, the deprotecting reagent includes $NH_3$ in methanol. In embodiments, the deprotecting reagent includes methylamine. In embodiments, the deprotecting reagent includes methylamine in methanol. In embodiments, the deprotecting reagent includes tert-butylamine. In embodiments, the deprotecting reagent includes tert-butylamine in methanol. In embodiments, the deprotecting reagent includes tert-butylamine.

In embodiments, the method of synthesizing a compound of Formula XA and/or XXA includes

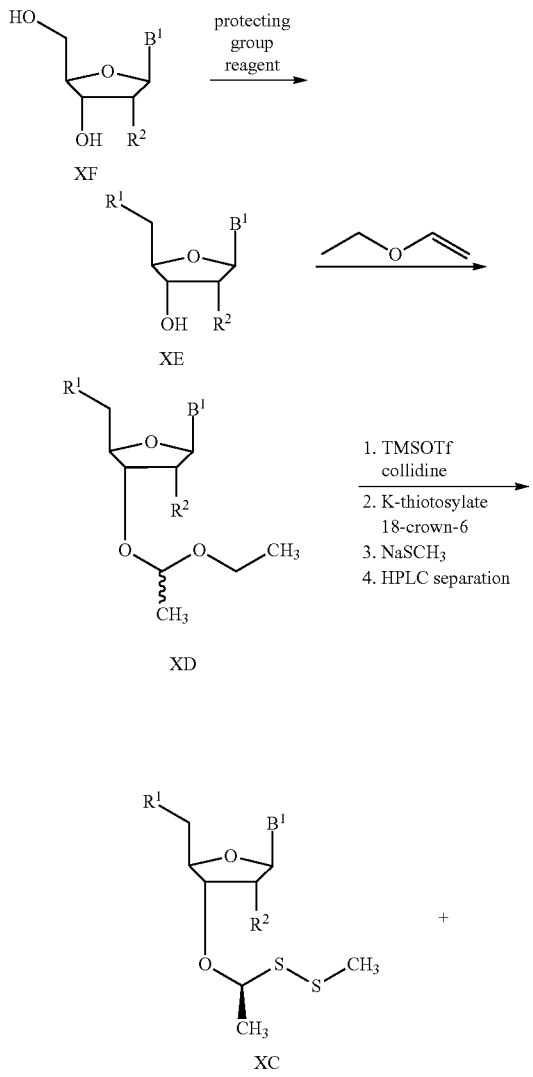

-continued
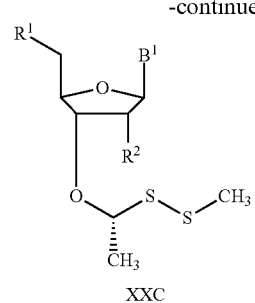
XXC
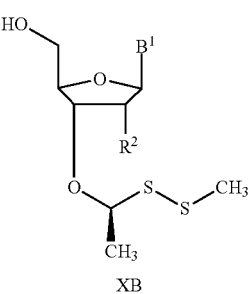
XB
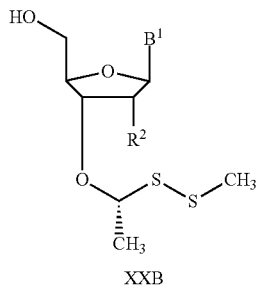
XXB
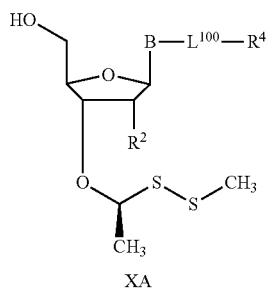
XA
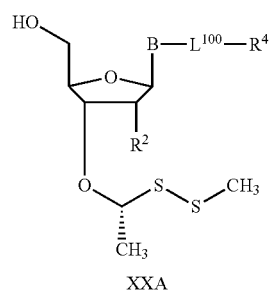
XXA
In embodiments, the method of synthesizing a compound of Formula XA and/or XXA includes
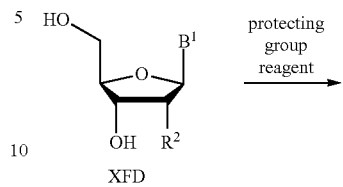
XFD
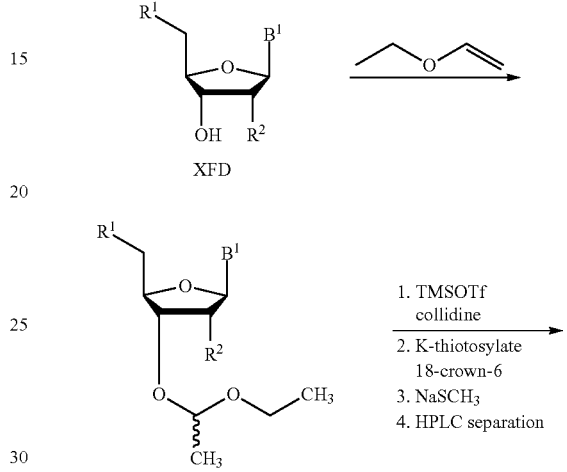
XFD
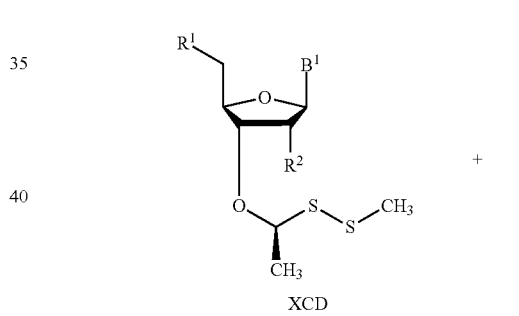
XED
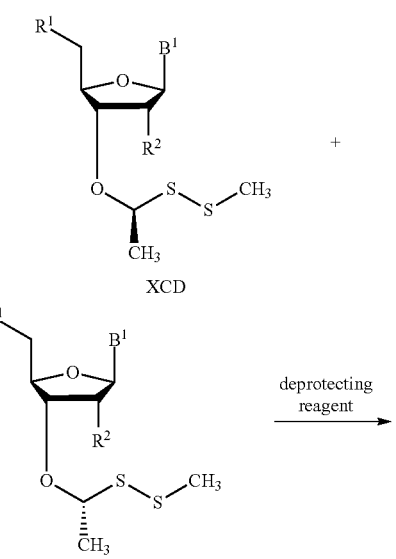
XCD
XXCD
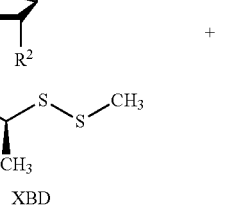
XBD

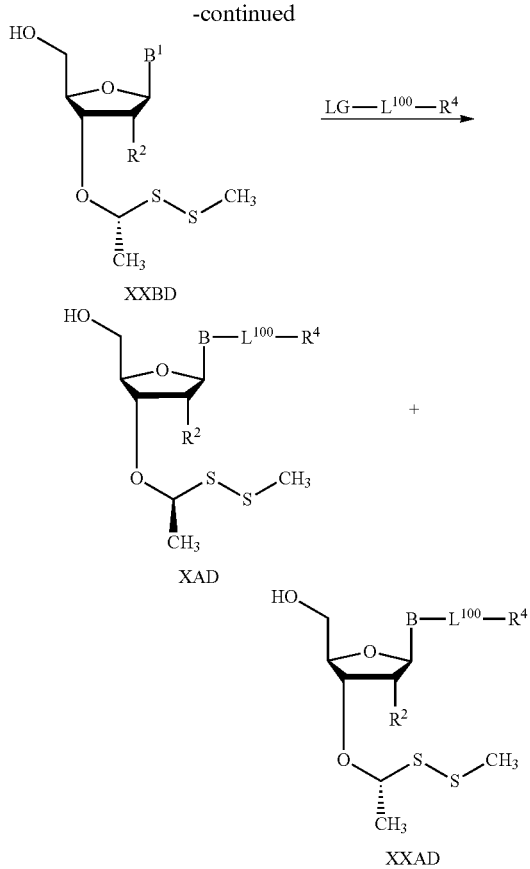

XXBD

XAD

XXAD

IV. Methods of Use

In an aspect is provided a method for sequencing a nucleic acid, including: (i) incorporating in series with a nucleic acid polymerase, within a reaction vessel, one of four different labeled nucleoside analogues into a primer to create an extension strand, wherein the primer is hybridized to the nucleic acid and wherein each of the four different labeled nucleoside analogues include a unique detectable label; and (ii) detecting the unique detectable label of each incorporated nucleoside analogue, so as to thereby identify each incorporated nucleoside analogue in the extension strand, thereby sequencing the nucleic acid; wherein each of the four different labeled nucleoside analogues is independently a compound described herein.

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In another aspect is provided a method of incorporating a nucleoside analogue into a primer, the method including combining a polymerase, a primer hybridized to nucleic acid template and a nucleoside analogue within a reaction vessel and allowing the polymerase to incorporate the nucleoside analogue into the primer thereby forming an extended primer, wherein the nucleoside analogue is a compound described herein, including embodiments.

In an aspect is provided a method for sequencing a nucleic acid, including: incorporating in series with a nucleic acid polymerase, within a reaction vessel, one of four different compounds into a primer to create an extension strand, wherein the primer is hybridized to the nucleic acid and wherein each of the four different compounds includes a unique detectable label; detecting the unique detectable label of each incorporated compound, so as to thereby identify each incorporated compound in the extension strand, thereby sequencing the nucleic acid; wherein each of the four different compounds is independently a compound described herein.

In an aspect is provided a method for sequencing a nucleic acid, including: incorporating in series with a nucleic acid polymerase, within a reaction vessel, a compound into a primer to create an extension strand, wherein the primer is hybridized to the nucleic acid and wherein the compound includes a detectable label; detecting the detectable label of the incorporated compound, so as to thereby identify the incorporated compound in the extension strand, thereby sequencing the nucleic acid; wherein the compound is independently a compound described herein. In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound described herein.

In an aspect is provided a nucleic acid polymerase complex including a nucleic acid polymerase, wherein the nucleic acid polymerase is bound to a compound described herein.

In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof.

In embodiments, the method includes simultaneously sequencing a plurality of different nucleic acids, including: a) extending a plurality of priming DNA strands hybridized to template DNAs, each of which includes one of the priming DNA strands, by incorporating a labeled nucleotide; and b) identifying each labeled nucleotide, so as to simultaneously sequence the plurality of different nucleic acids. In embodiments, the labeled nucleotide is a compound described herein.

In embodiments, the method further including, after the incorporating, cleaving the linker (e.g., $L^{100}$ or -($L^{101}$)-OC ($SR^{100}$)($R^{102a}$)-($L^{103}$)-($L^{104}$)-($L^{105}$)-) with a cleaving reagent (e.g., tris(hydroxypropyl)phosphine (THPP)). In embodiments, the cleaving reagent is an acid, base, oxidizing agent, reducing agent, Pd(0), tris-(2-carboxyethyl)phosphine, dilute nitrous acid, fluoride, tris(3-hydroxypropyl) phosphine), sodium dithionite ($Na_2S_2O_4$), or hydrazine ($N_2H_4$). In embodiments, the cleaving reagent is in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

In embodiments, the method further including, after the incorporating, cleaving the linker (e.g., $L^{100}$ or -($L^{101}$)-OC ($SR^{100}$)($R^{102a}$)-($L^{103}$)-($L^{104}$)-($L^{105}$)-) with a cleaving reagent (e.g., a water-soluble phosphine, such as tris(hydroxypropyl)phosphine (THPP)). In embodiments, the cleaving reagent is a reducing agent. In embodiments, the cleaving agent is a phosphine containing agent. In embodiments, the cleaving agent is a thiol containing agent. In embodiments, the cleaving agent is di-mercaptopropane sulfonate (DMPS). In embodiments, the cleaving reagent is Tris-(2-carboxyethyl)phosphines trisodium salt (TCEP), tris (hydroxypropyl)phosphine (THPP), guanidine, urea, cysteine, 2-mercaptoethylamine, or dithiothreitol (DTT). In embodiments, the cleaving reagent is an acid, base, oxidizing agent, reducing agent, Pd(0), tris-(2-carboxyethyl)phosphine, dilute nitrous acid, fluoride, tris(3-hydroxypropyl) phosphine), sodium dithionite ($Na_2S_2O_4$), or hydrazine ($N_2H_4$). In embodiments, the method includes contacting the compound (e.g., a compound described herein) with a reducing agent. In embodiments, the method further including, after the incorporating, cleaving the linker at about 55° C. In embodiments, the method further including, after the incorporating, cleaving the linker at about 55° C. to about 80° C. In embodiments, the method further including, after the incorporating, cleaving the linker at about 60° C. to about 70° C. In embodiments, the method further including, after the incorporating, cleaving the linker at about 65° C. to about 75° C. In embodiments, the method further including, after the incorporating, cleaving the linker at about 65° C. In embodiments, the method further including, after the incorporating, cleaving the linker at about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or about 80° C. In embodiments, the method further including, after the incorporating, cleaving the linker at a pH at about 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is about 60° C. to about 70° C.

In embodiments, the cleaving reagent cleaves both the linker and the polymerase-compatible cleavable moiety simultaneously.

In embodiments, the thermophilic nucleic acid polymerase is a Taq polymerase, Terminator γ, 9° N polymerase (exo-), Terminator II, Terminator III, or Terminator IX. In embodiments, the thermophilic nucleic acid polymerase is Terminator γ. In embodiments, the thermophilic nucleic acid polymerase is 9° N polymerase (exo-). In embodiments, the thermophilic nucleic acid polymerase is Terminator II. In embodiments, the thermophilic nucleic acid polymerase is Terminator III. In embodiments, the thermophilic nucleic acid polymerase is Terminator IX. In embodiments, the thermophilic nucleic acid polymerase is a Taq polymerase. In embodiments, the nucleic acid polymerase is a thermophilic nucleic acid polymerase. In embodiments, the nucleic acid polymerase is 9° N and mutants thereof. In embodiments, the nucleic acid polymerase is Phi29 and mutants thereof. In embodiments, the polymerase is a non-thermophilic nucleic acid polymerase.

In embodiments, chemical cleavage of a compound (e.g., cleavage of a polymerase-compatible cleavable moiety or cleavage of a linker of a compound described herein) described herein (e.g., in an aspect or embodiment) includes contacting the compound with a reducing agent. In embodiments, chemical cleavage of a (e.g., cleavage of a polymerase-compatible cleavable moiety or cleavage of a linker of a compound described herein) described herein (e.g., in an aspect or embodiment) includes contacting the compound with THPP (e.g., about 10 mM THPP, at least 10 mM THPP). In embodiments, chemical cleavage of a compound (e.g., cleavage of a polymerase-compatible cleavable moiety or cleavage of a linker of a compound described herein) described herein (e.g., in an aspect or embodiment) is performed at about 55 degrees Celsius. In embodiments, chemical cleavage of a compound (e.g., cleavage of a polymerase-compatible cleavable moiety or cleavage of a linker of a compound described herein) described herein (e.g., in an aspect or embodiment) is performed at a temperature of at least 55 degrees Celsius. In embodiments, chemical cleavage of a compound (e.g., cleavage of a polymerase-compatible cleavable moiety or cleavage of a linker of a compound described herein) described herein (e.g., in an aspect or embodiment) is performed at about pH 9.5 to 10.0. In embodiments, chemical cleavage of a compound (e.g., cleavage of a polymerase-compatible cleavable moiety or cleavage of a linker of a compound described herein) described herein (e.g., in an aspect or embodiment) is performed at a pH from 9.5 to 10.0. In embodiments, chemical cleavage of a compound (e.g., cleavage of a polymerase-compatible cleavable moiety or cleavage of a linker of a compound described herein) described herein (e.g., in an aspect or embodiment) is performed at pH 9.5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A method of making a compound of Formula I$^P$:

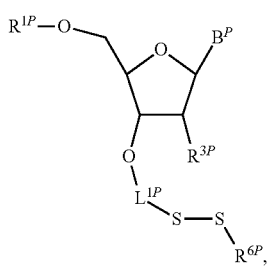
(I$^P$)

the method comprising mixing compound (IB$^P$) and compound (II$^P$) or compound (III$^P$) together in a reaction vessel;
wherein the compound of Formula IB$^P$ has the formula:

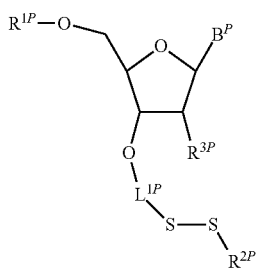
(IB$^P$)

the compound II$^P$ has the formula:

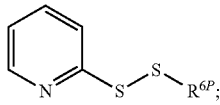
(II$^P$)

and/or
the compound III$^P$ has the formula:

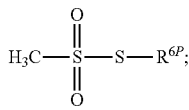
(III$^P$)

wherein
B$^P$ is a nucleobase;
R$^{1P}$ is independently hydrogen or 5'-nucleoside protecting group, or —OR$^{1P}$ is a monophosphate, or polyphosphate;
R$^{2P}$ is -L$^{2P}$-R$^{4P}$, -L$^{2P}$-3'-nucleoside, -L$^{2P}$-3'-nucleotide, or -L$^{2P}$-3'-nucleic acid;
R$^{3P}$ is independently hydrogen or —OR$^{3AP}$, wherein R$^{3AP}$ is hydrogen or a polymerase-compatible cleavable moiety;
R$^{4P}$ is substituted or unsubstituted C$_1$-C$_6$ alkyl;
R$^{6P}$ is —CH$_3$ or —CH$_2$CH$_3$;

L$^{1P}$ is substituted or unsubstituted C$_1$-C$_4$ alkylene; and
L$^{2P}$ is a bond, substituted or unsubstituted C$_1$-C$_4$ alkylene.

Embodiment P2. The method of embodiment P1, further comprising: deprotecting a compound of the formula IA$^P$:

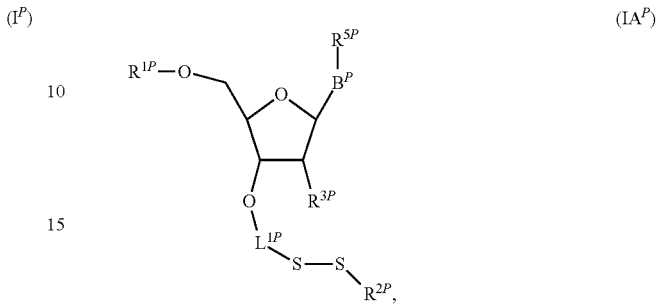
(IA$^P$)

to form the compound of the formula IB$^P$,
wherein R$^{5P}$ is a moiety comprising a protecting group.

Embodiment P3. The method of embodiment P2, wherein the deprotecting comprises contacting the compound of formula IA$^P$ with ammonium hydroxide.

Embodiment P4. The method of any one of embodiments P1 to P3, wherein L$^{1P}$ is unsubstituted methylene.

Embodiment P5. The method of any one of embodiments P1 to P3, wherein L$^{1P}$ is methylene which is substituted with C$_1$-C$_4$ haloalkyl or unsubstituted C$_1$-C$_4$ alkyl.

Embodiment P6. The method of any one of embodiments P1 to P5, wherein L$^{2P}$ is a bond.

Embodiment P7. The method of any one of embodiments P1 to P5, wherein R$^{4P}$ is unsubstituted C$_1$-C$_6$ alkyl.

Embodiment P8. The method of embodiment P7, wherein R$^{4P}$ is unsubstituted methyl, t-butyl, neopentyl, or thexyl.

Embodiment P9. The method of any one of embodiments P1 to P8, wherein R$^{3P}$ is hydrogen.

Embodiment P10. The method of claim any one of embodiments P1 to P9, the compound of Formula IB$^P$ has a structure of:

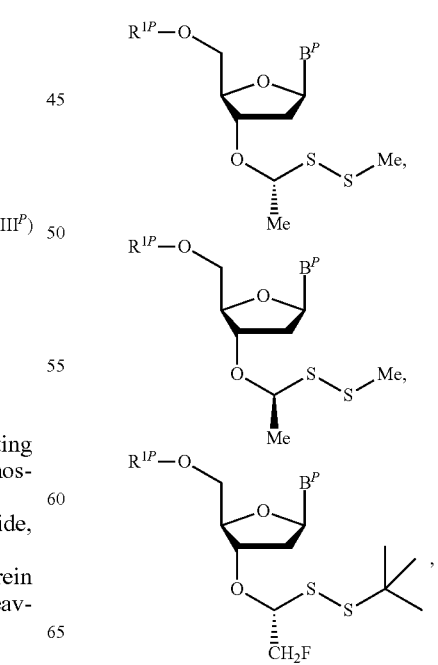

-continued

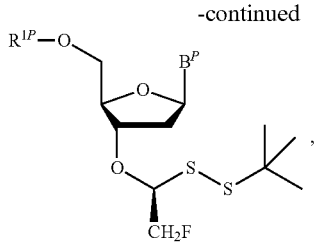,

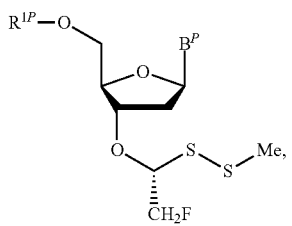,

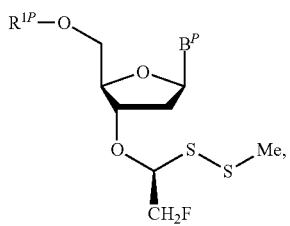,

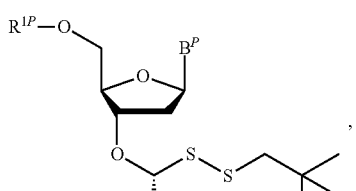,

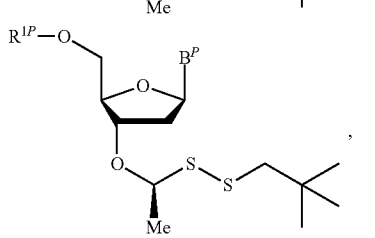,

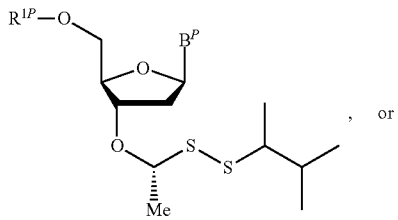, or

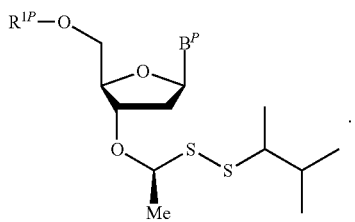.

Embodiment P11. The method of any one of embodiments P1 to P5, wherein $L^{2P}$ is unsubstituted methylene.

Embodiment P12. The method of any one of embodiments P1 to P5 and P11, wherein $R^{2P}$ is

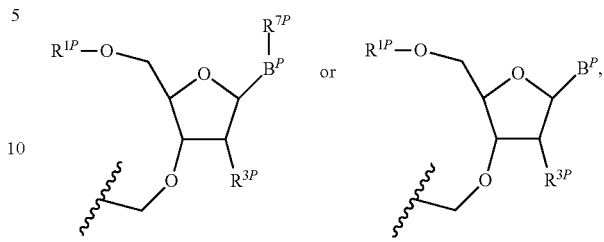

wherein $R^{7P}$ is a moiety comprising a protecting group.

Embodiment P13. The method of embodiment P1, further comprising contacting the compound of Formula $IB^P$ with tris(hydroxypropyl)phosphine (THPP).

Embodiment P14. The method of embodiment P13, comprising synthesis of compound of Formula $IC^P$:

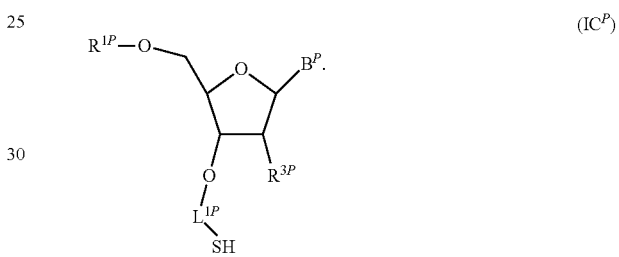

Embodiment P15. The method of embodiment P1, wherein $R^{6P}$ is —$CH_3$.

Embodiment P16. The method of embodiment P1, wherein $B^P$ is

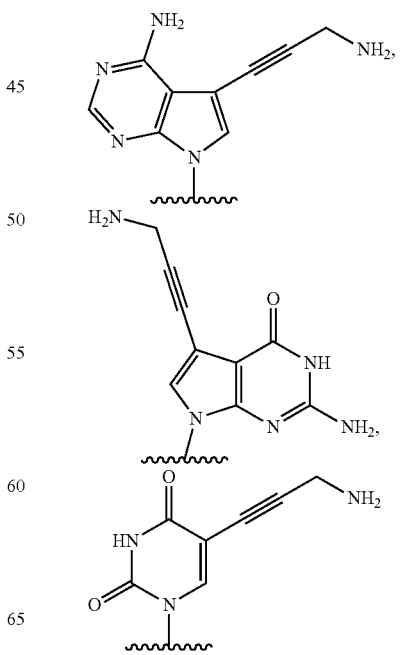

or

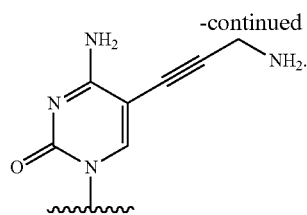
Embodiment P17. The method of embodiment P1, wherein the compound of Formula IB$^P$ is:
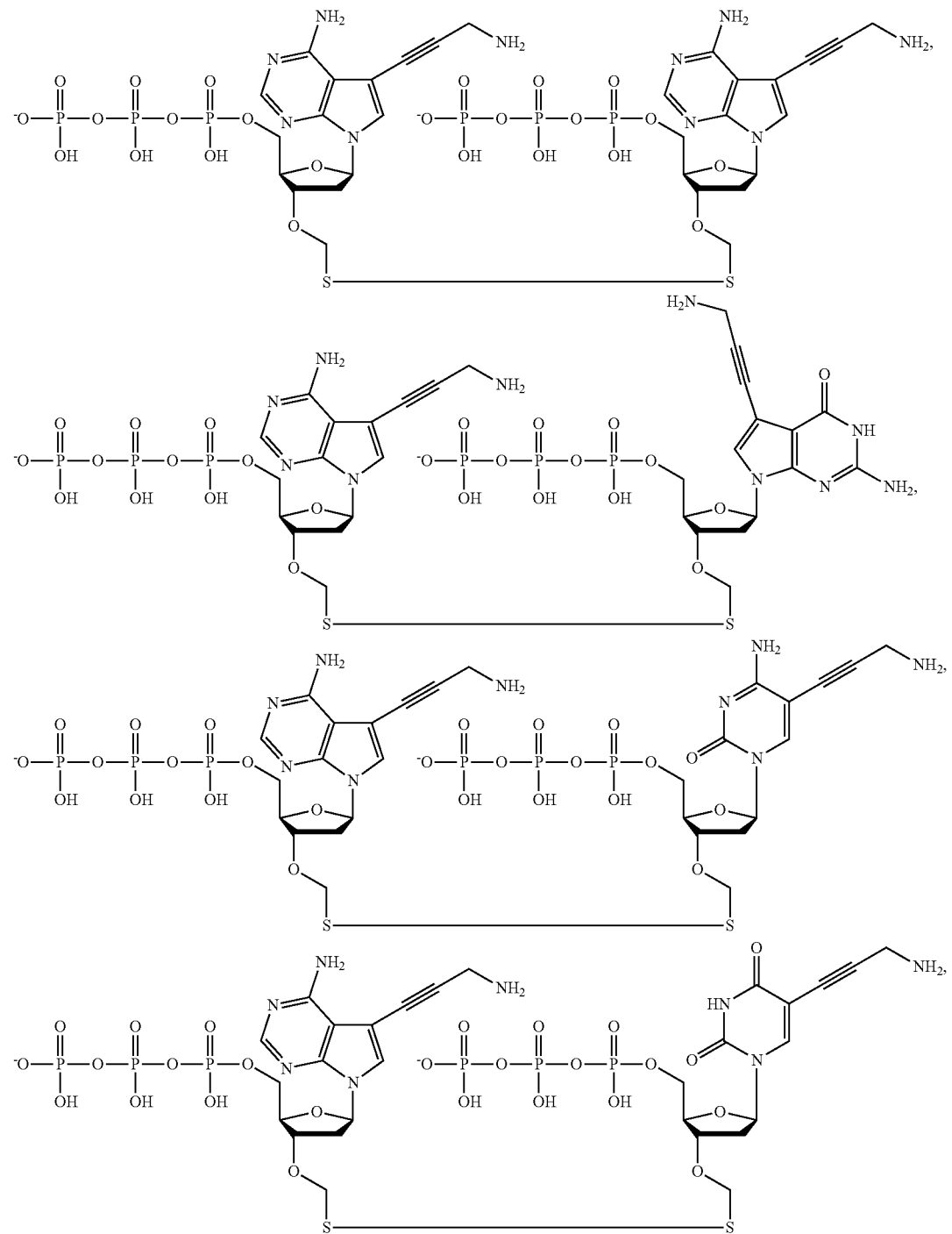

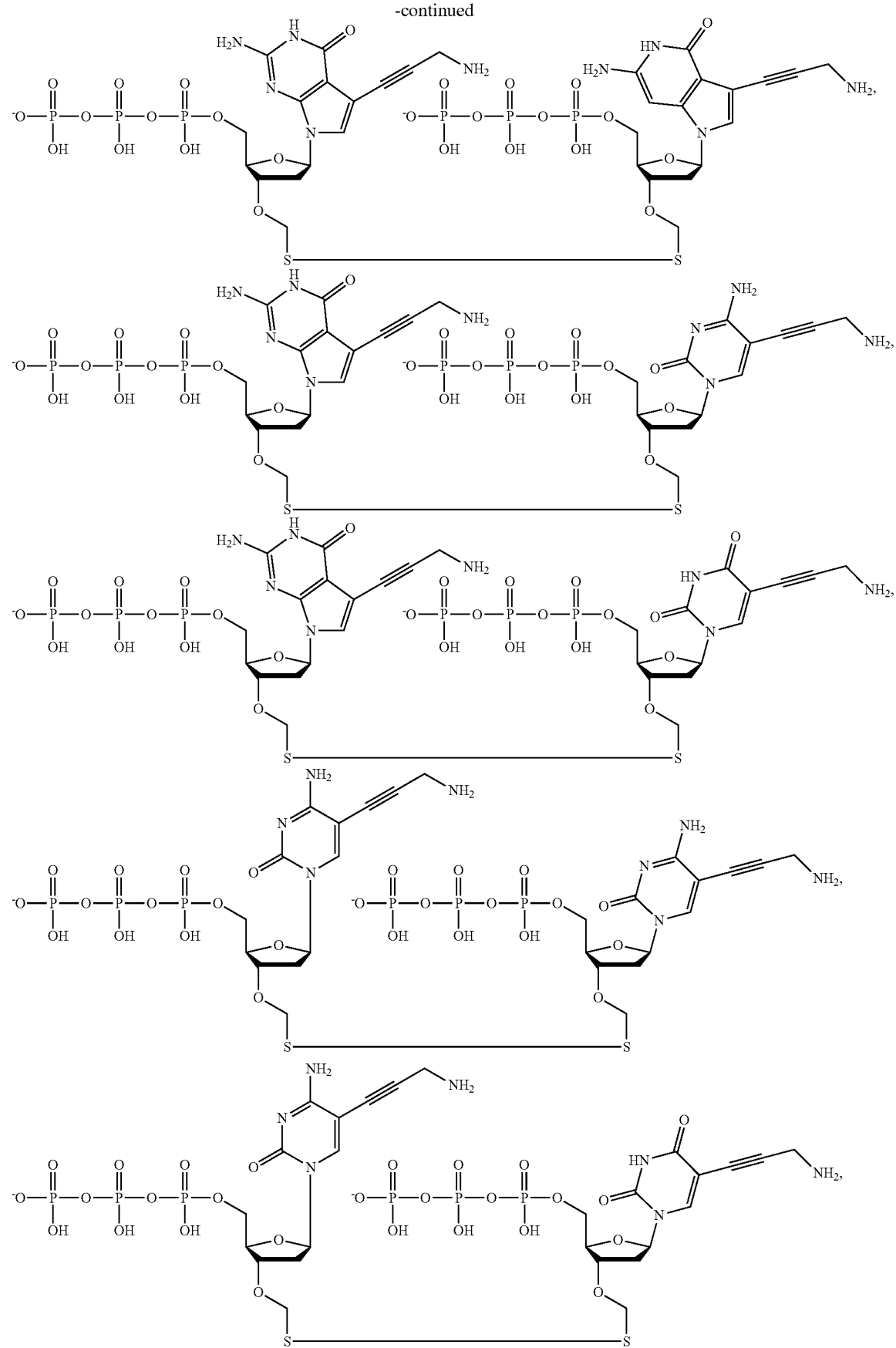

-continued
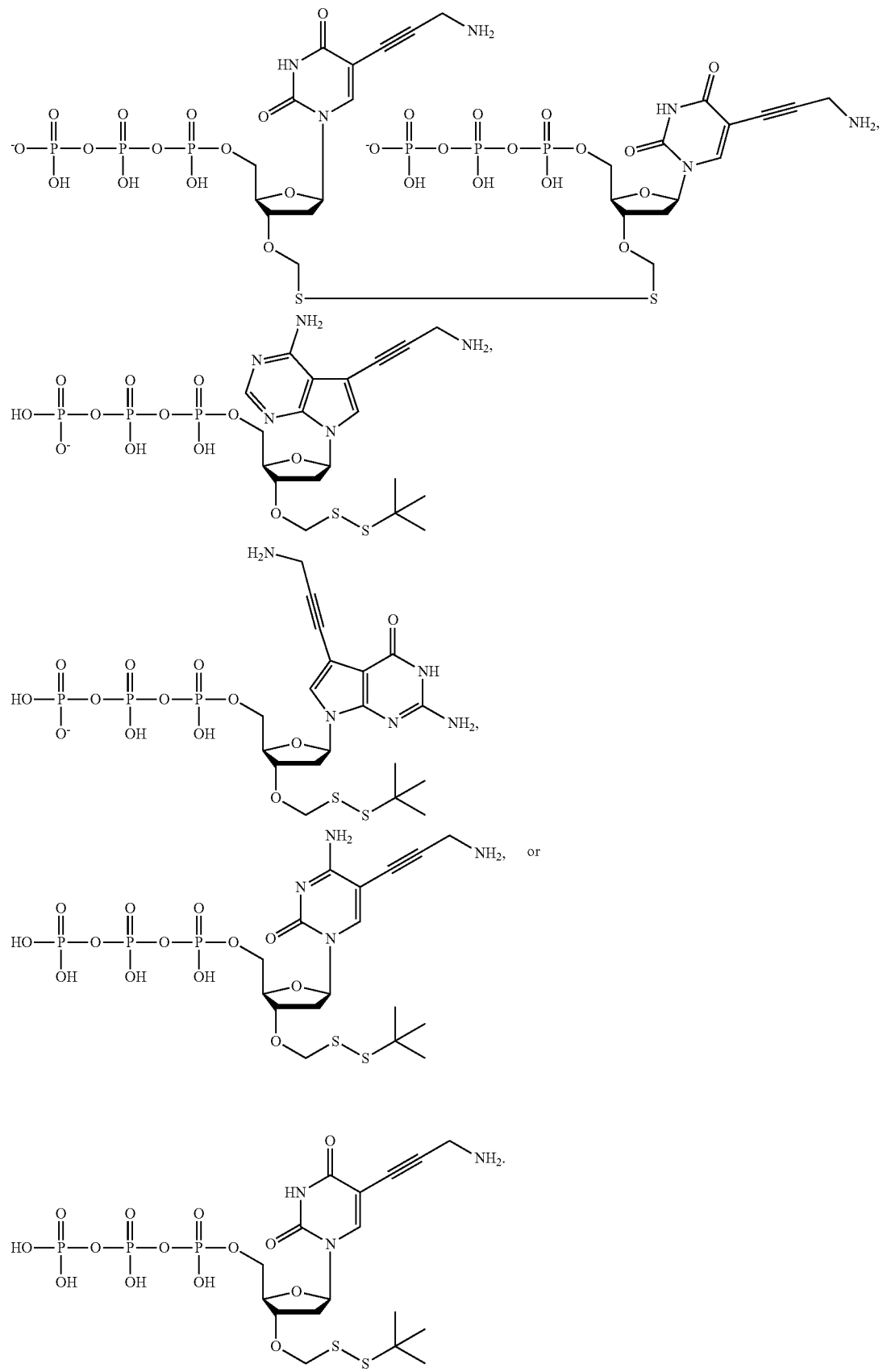

Embodiment P18. The method of embodiment P1, wherein the compound of Formula IB$^P$ is:

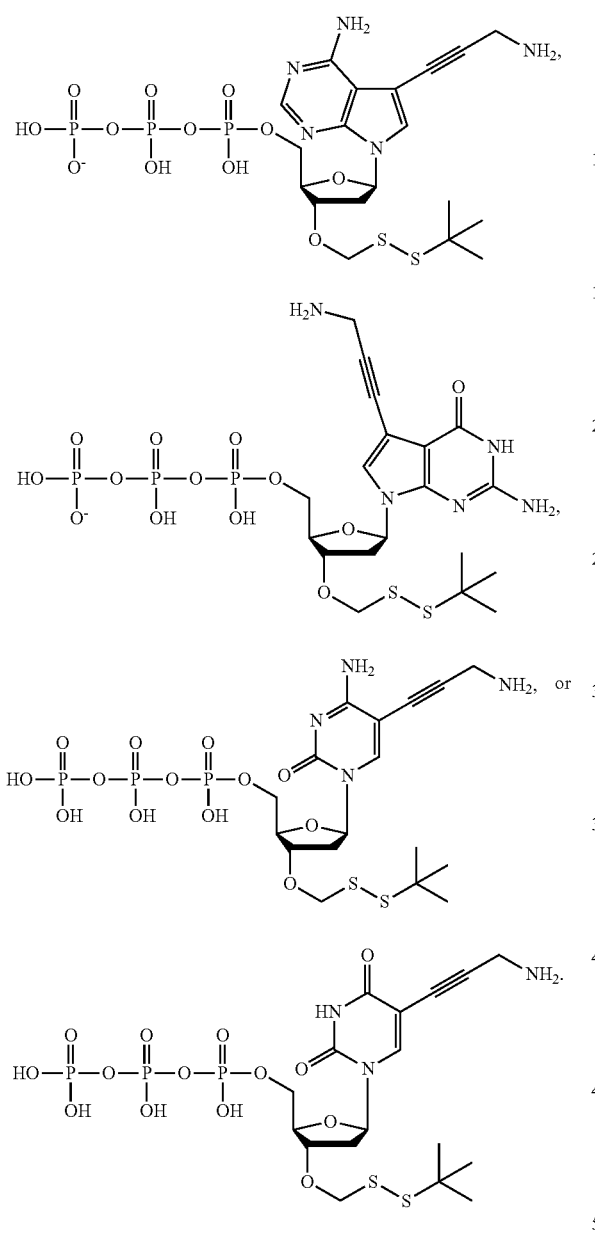

Embodiment Q1. A compound having the formula:

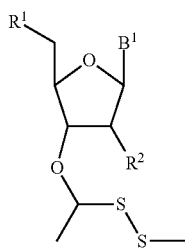

(I)

wherein,

B$^t$ is a monovalent nucleobase;

R$^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and R$^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or a —O-polymerase-compatible cleavable moiety.

Embodiment Q2. The compound of embodiment Q1, having the formula:

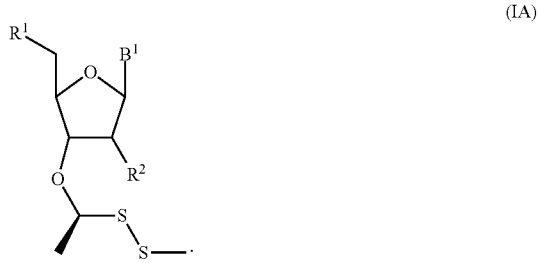

(IA)

Embodiment Q3. The compound of embodiment Q1, having the formula:

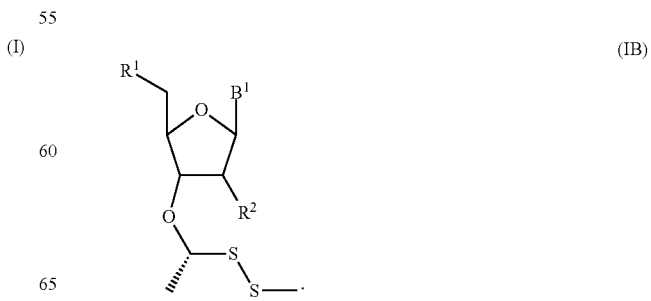

(IB)

Embodiment Q4. The compound of embodiment Q1, having the formula:

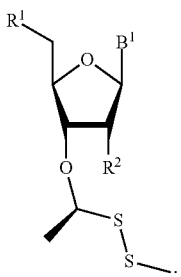

(IAD)

Embodiment Q5. The compound of embodiment Q1, having the formula:

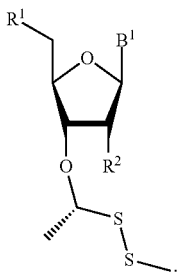

(IBD)

Embodiment Q6. The compound of one of embodiments Q1 to Q5, wherein $R^2$ is hydrogen.

Embodiment Q7. The compound of one of embodiments Q1 to Q5, wherein $R^2$ is —OH.

Embodiment Q8. The compound of one of embodiments Q1 to Q5, wherein $R^2$ is —O-polymerase-compatible cleavable moiety.

Embodiment Q9. The compound of one of embodiments Q1 to Q8, wherein $R^1$ is —OH.

Embodiment Q10. The compound of one of embodiments Q1 to Q8, wherein $R^1$ is a 5'-nucleoside protecting group.

Embodiment Q11. The compound of one of embodiments Q1 to Q8, wherein —$R^1$ is a monophosphate moiety.

Embodiment Q12. The compound of one of embodiments Q1 to Q8, wherein —$R^1$ is a polyphosphate moiety.

Embodiment Q13. The compound of one of embodiments Q1 to Q8, wherein —$R^1$ is a triphosphate moiety.

Embodiment Q14. The compound of one of embodiments Q1 to Q8, wherein $R^1$ is a nucleic acid moiety.

Embodiment Q15. The compound of one of embodiments Q1 to Q14, wherein $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof.

Embodiment Q16. The compound of one of embodiments Q1 to Q14, wherein $B^1$ is

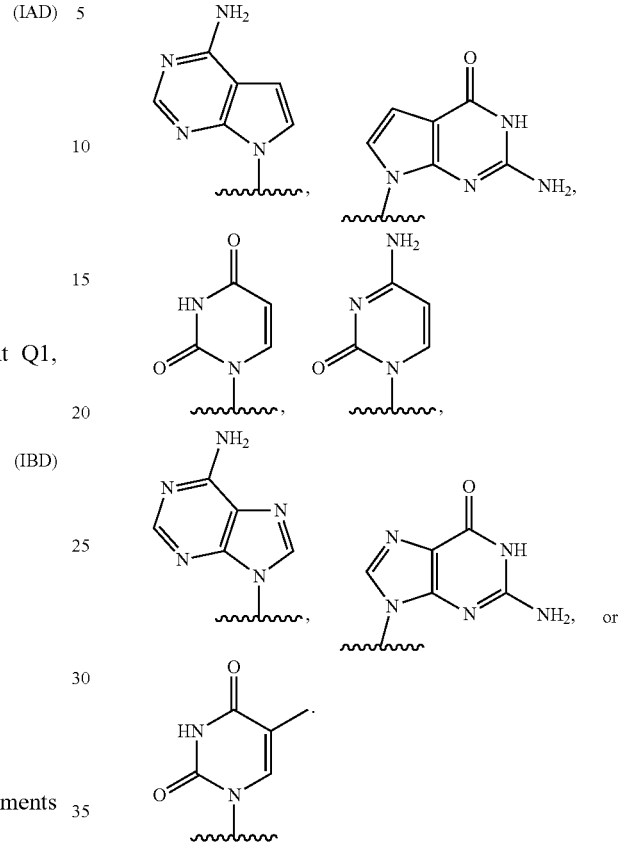

Embodiment Q17. The compound of one of embodiments Q1 to Q14, wherein $B^1$ is

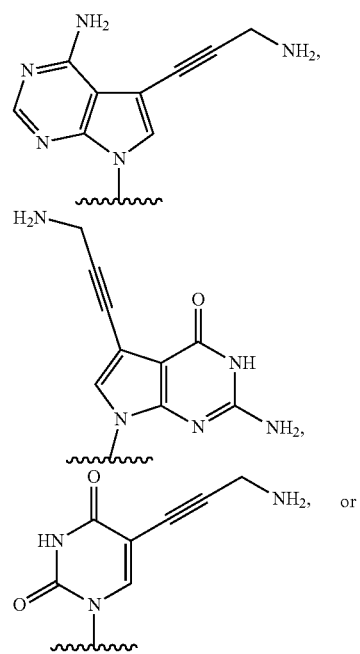

-continued

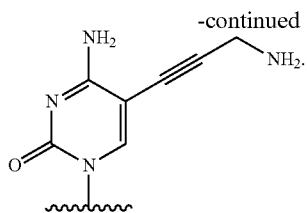

Embodiment Q18. The compound of one of embodiments Q1 to Q14, wherein $B^1$ is

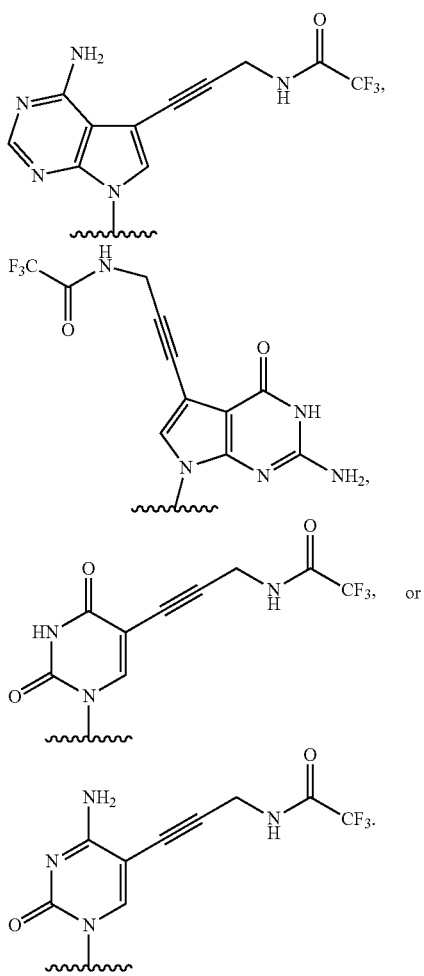

Embodiment Q19. The compound of one of embodiments Q1 to Q14, wherein
$B^1$ is —B-$L^{100}$-$R^4$;
B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof;
$L^{100}$ is a divalent linker; and
$R^4$ is a detectable moiety.

Embodiment Q20. The compound of embodiment Q19, wherein B is

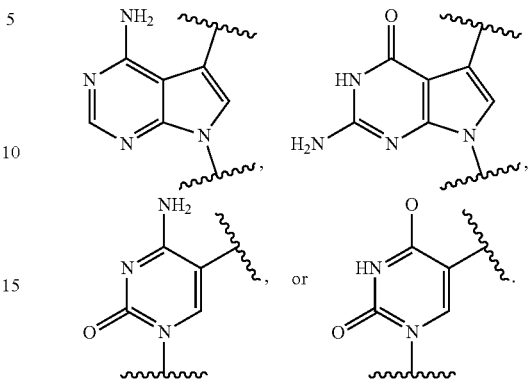

Embodiment Q21. The compound of one of embodiments Q19 to Q20, wherein $L^{100}$ is -$L^{101}$-$L^{102}$-$L^{103}$-$L^{104}$-$L^{105}$-;
$L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment Q22. The compound of one of embodiments Q19 to Q20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;
$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{100}$ is —$SR^{102}$ or —CN; and
$R^{102}$ is unsubstituted $C_1$-$C_4$ alkyl.

Embodiment Q23. The compound of one of embodiments Q19 to Q20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene;
$L^{105}$ is independently bond or substituted or unsubstituted 4 to 18 membered heteroalkylene;
$R^{100}$ is —$SR^{102}$ or —CN; and
$R^{102}$ is unsubstituted $C_1$-$C_4$ alkyl.

Embodiment Q24. The compound of one of embodiments Q19 to Q20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;
$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L¹⁰⁴ is unsubstituted phenylene;
R¹⁰⁰ is —SR¹⁰² or —CN; and
R¹⁰² is unsubstituted $C_1$-$C_4$ alkyl.

Embodiment Q25. The compound of one of embodiments Q19 to Q20, wherein L¹⁰⁰ is -L¹⁰¹-O—CH(N₃)-L¹⁰³-L¹⁰⁴-L¹⁰⁵-; and L¹⁰¹, L¹⁰³, L¹⁰⁴, and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment Q26. The compound of one of embodiments Q19 to Q20, wherein L¹⁰⁰ is -L¹⁰¹-O—CH(N₃)-L¹⁰³-L¹⁰⁴-L¹⁰⁵-;

L¹⁰¹ is independently a substituted or unsubstituted $C_1$-$C_4$ alkylene or substituted or unsubstituted 8 to 20 membered heteroalkylene;

L¹⁰³ is independently a bond or substituted or unsubstituted 2 to 10 membered heteroalkylene;

L¹⁰⁴ is independently a bond, substituted or unsubstituted 4 to 18 membered heteroalkylene, or substituted or unsubstituted phenylene; and L¹⁰⁵ is independently bond or substituted or unsubstituted 4 to 18 membered heteroalkylene.

Embodiment Q27. The compound of one of embodiments Q19 to Q20, wherein L¹⁰⁰ is -L¹⁰¹-O—CH(N₃)—CH₂—O-L¹⁰⁴-L¹⁰⁵-;

L¹⁰¹ and L¹⁰⁵ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and L¹⁰⁴ is unsubstituted phenylene.

Embodiment Q28. The compound of one of embodiments Q19 to Q20, wherein L¹⁰⁰ is

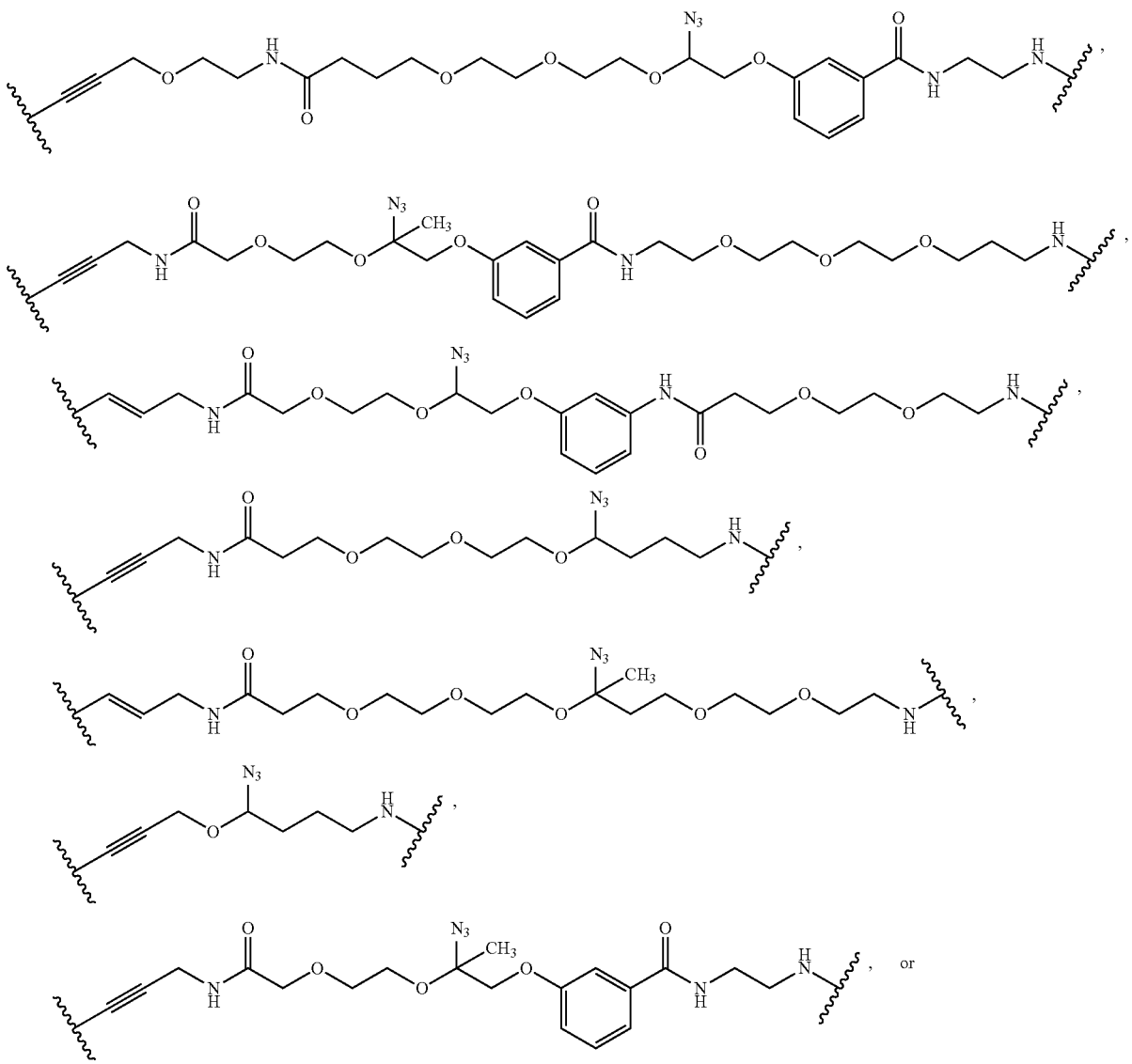

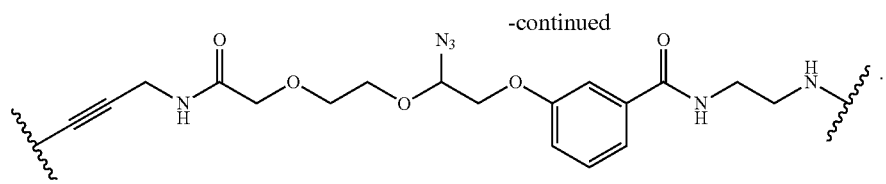
Embodiment Q29. The compound of one of embodiments Q19 to Q20, wherein $L^{100}$ is
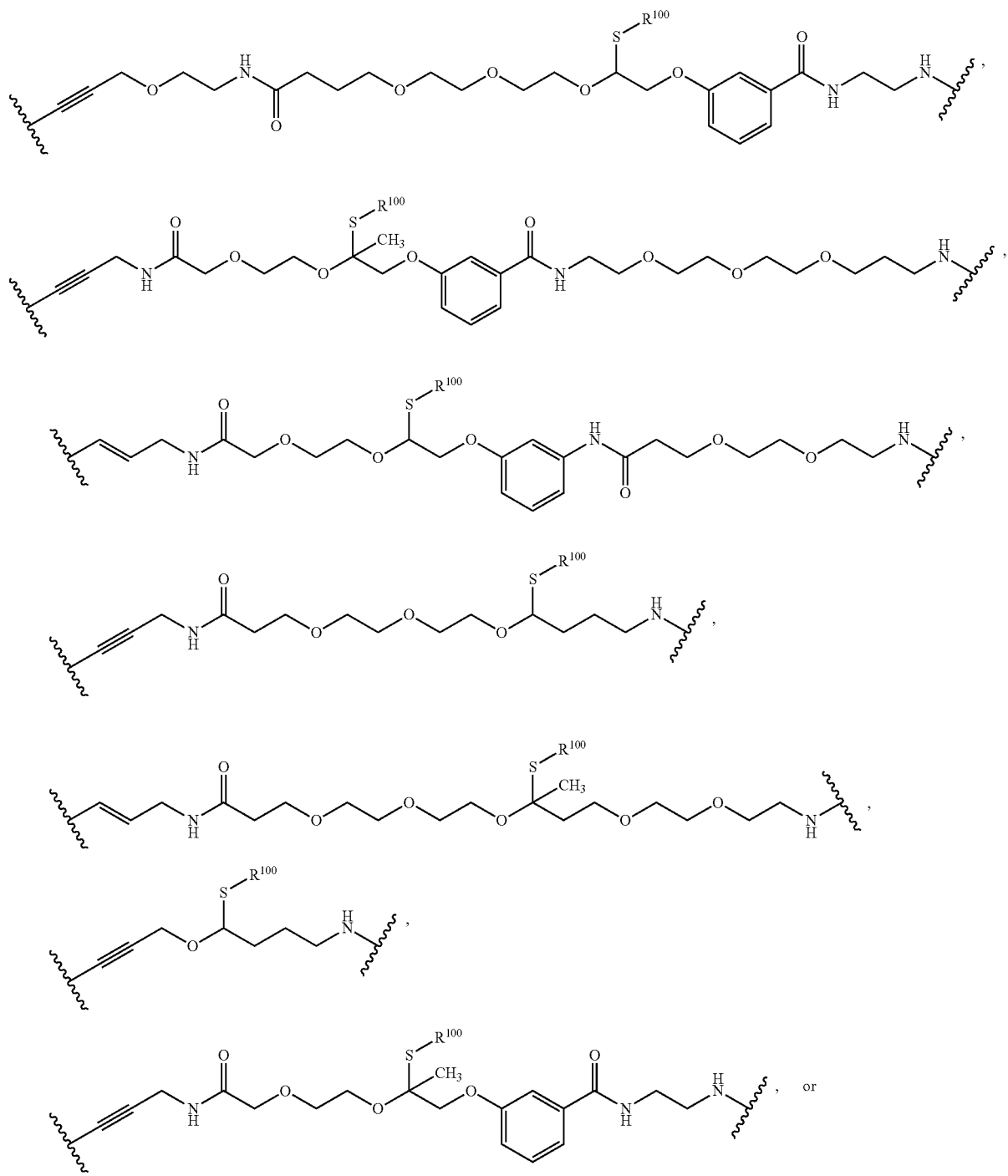

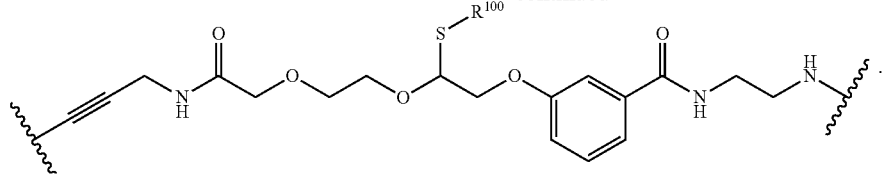
Embodiment Q30. The compound of one of embodiments Q19 to Q20, wherein $L^{100}$ is
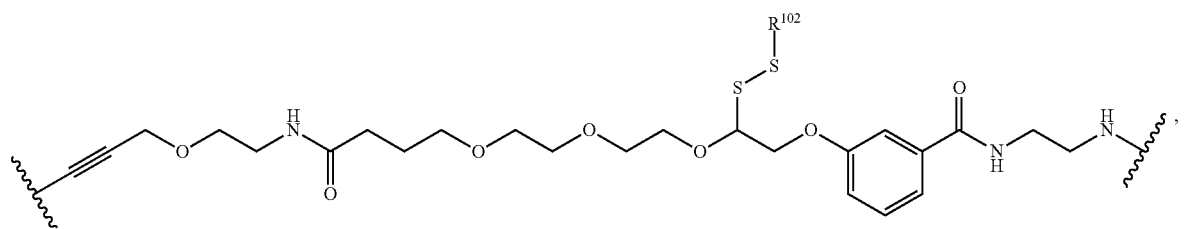
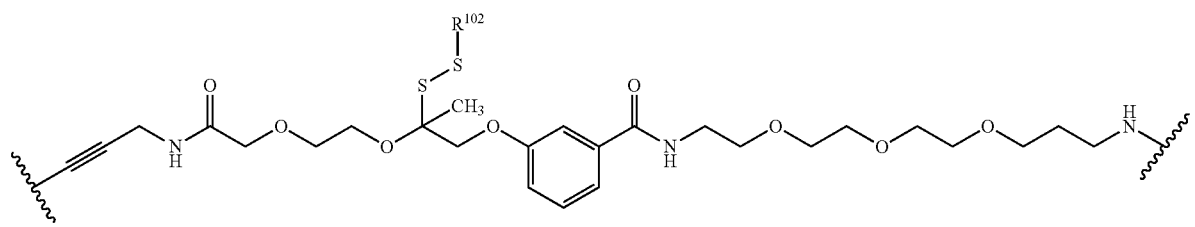
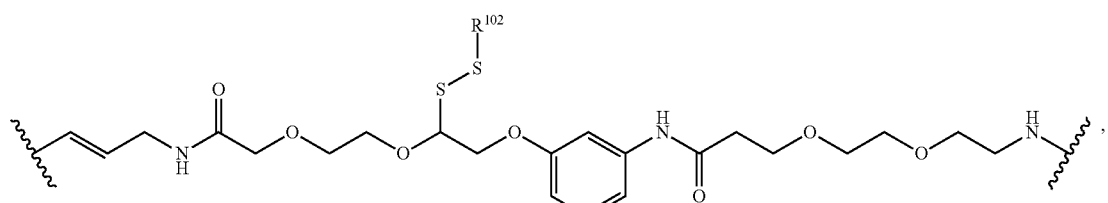
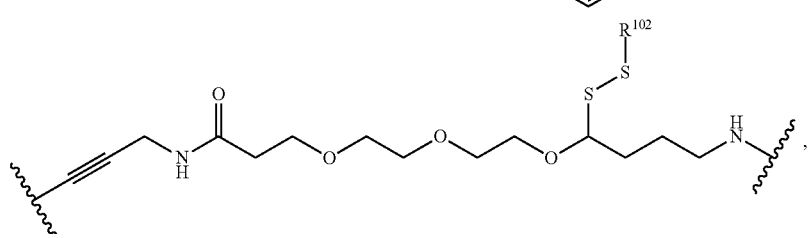
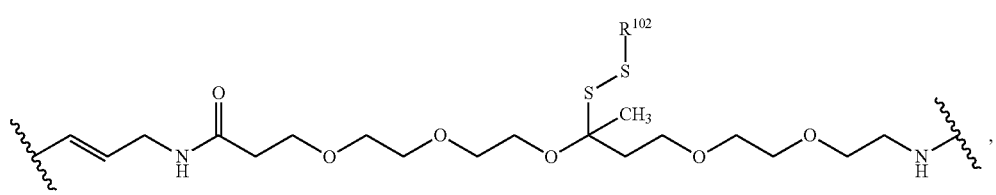
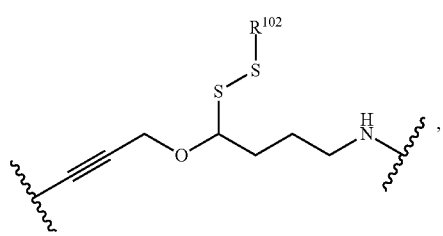

-continued
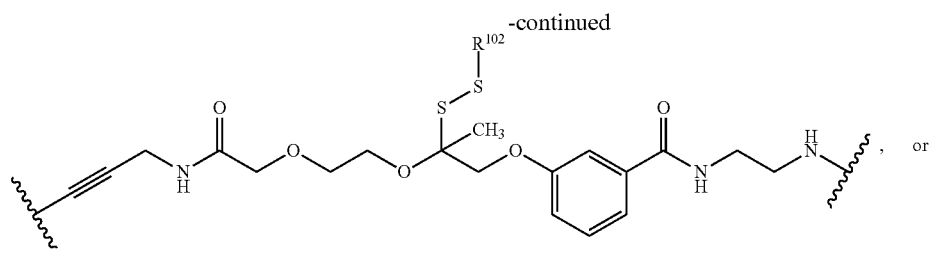
, or
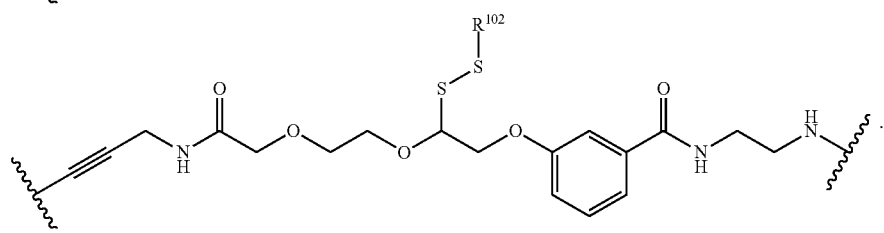
Embodiment Q31. The compound of one of embodiments Q19 to Q20, wherein $L^{100}$ is
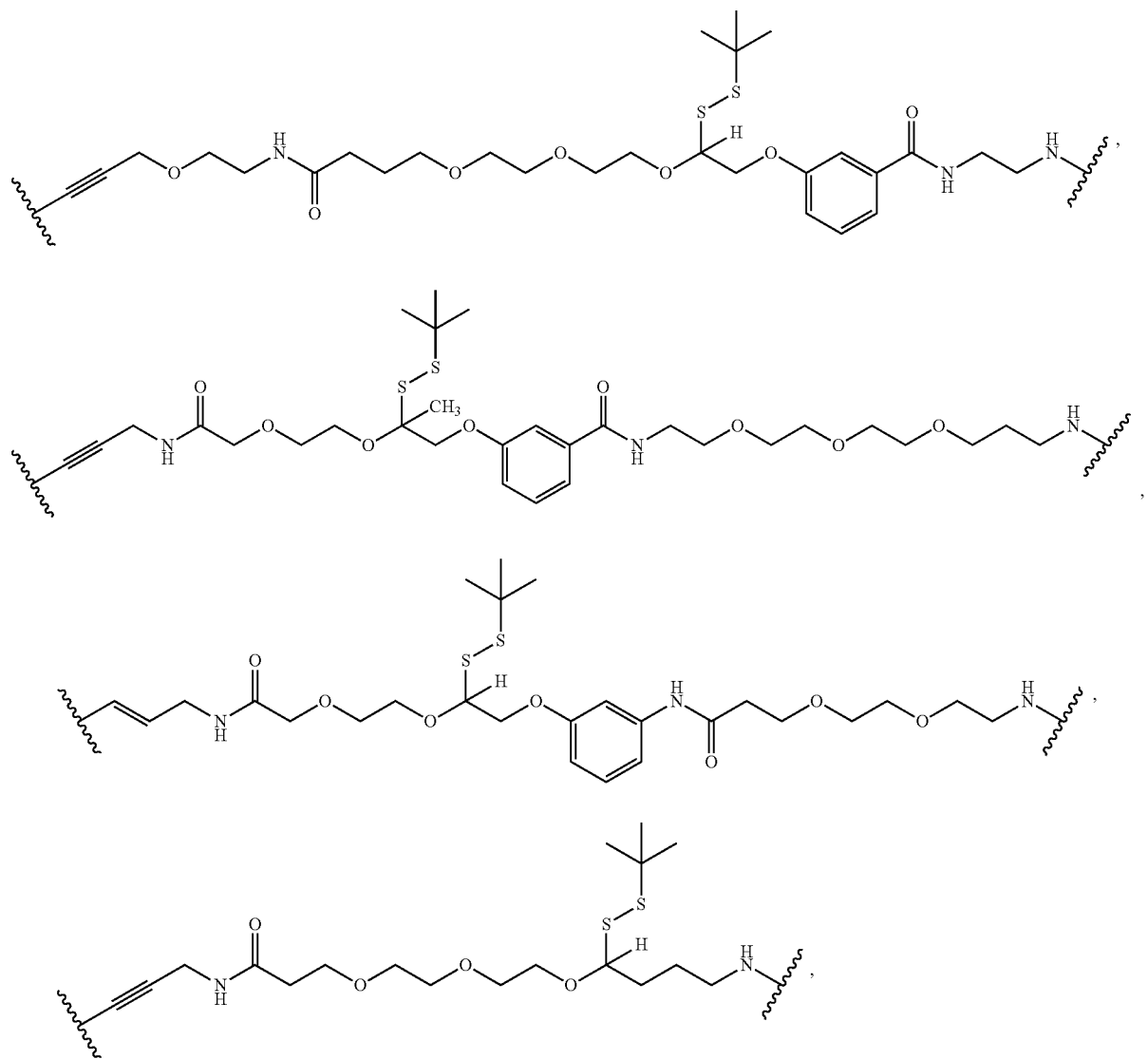

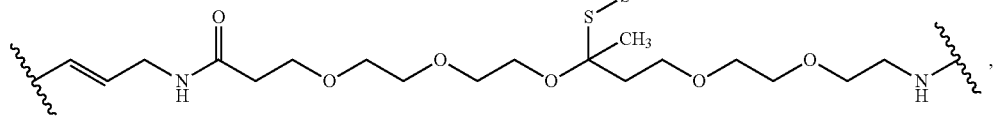
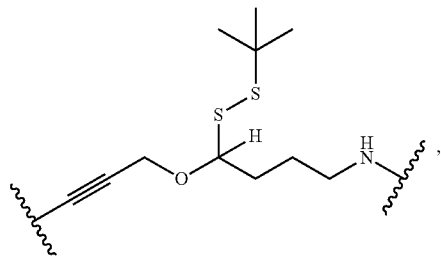
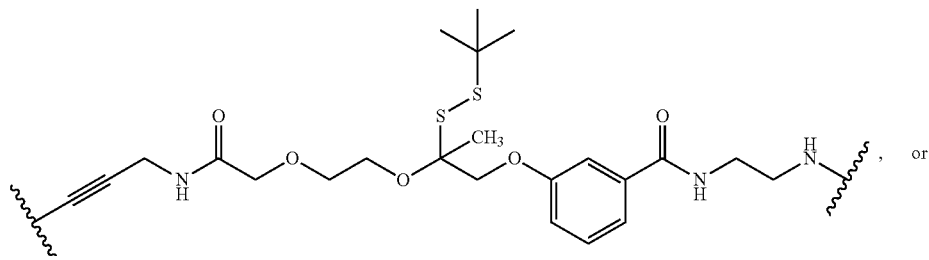, or
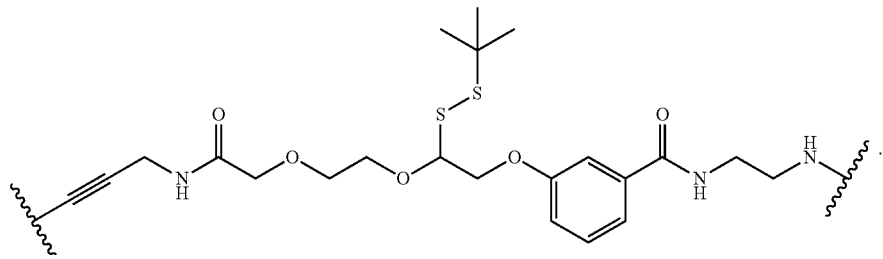.
Embodiment Q32. The compound of one of embodiments Q19 to Q20, wherein $L^{100}$ is
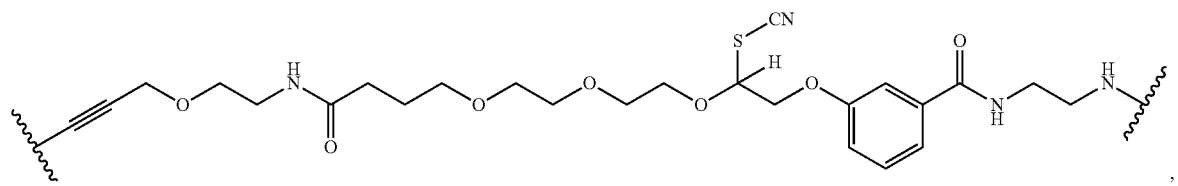,
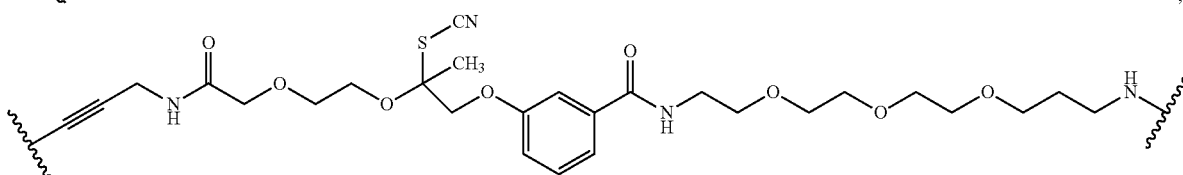,
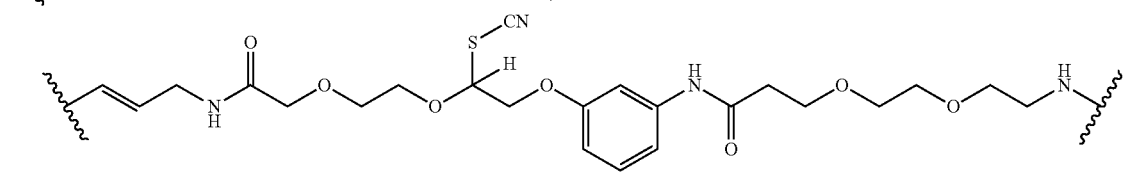, -continued
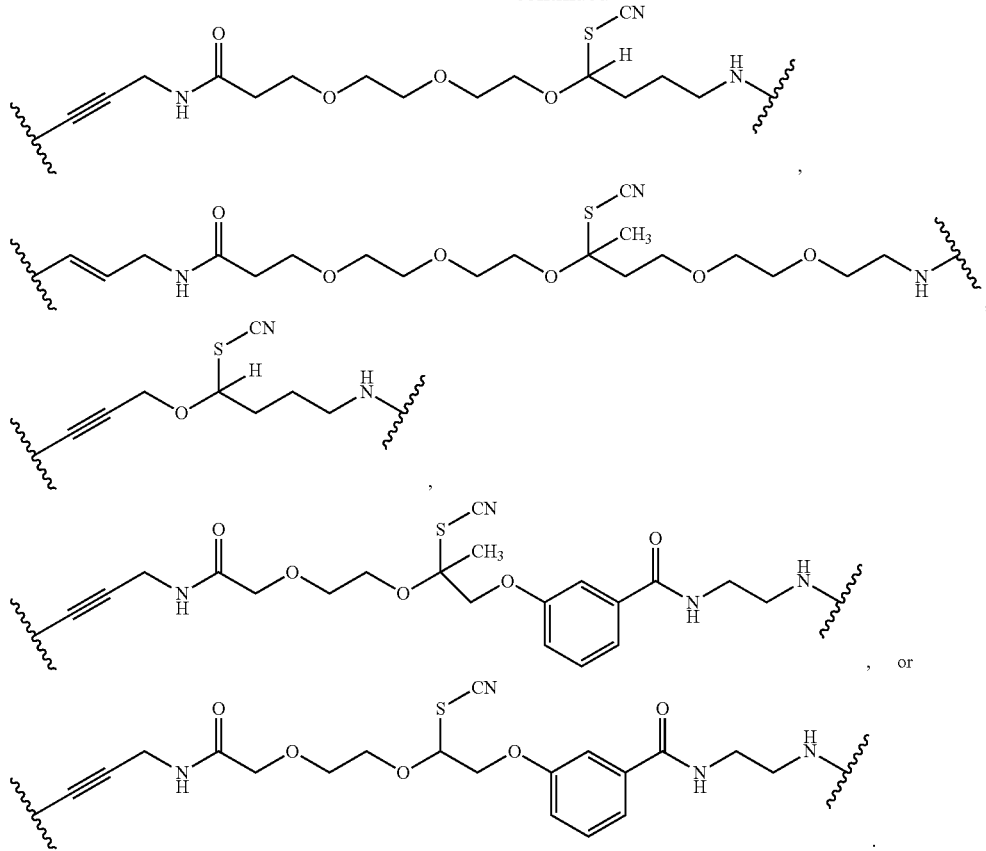
Embodiment Q33. The compound of one of embodiments Q19 to Q20, wherein $L^{100}$ is
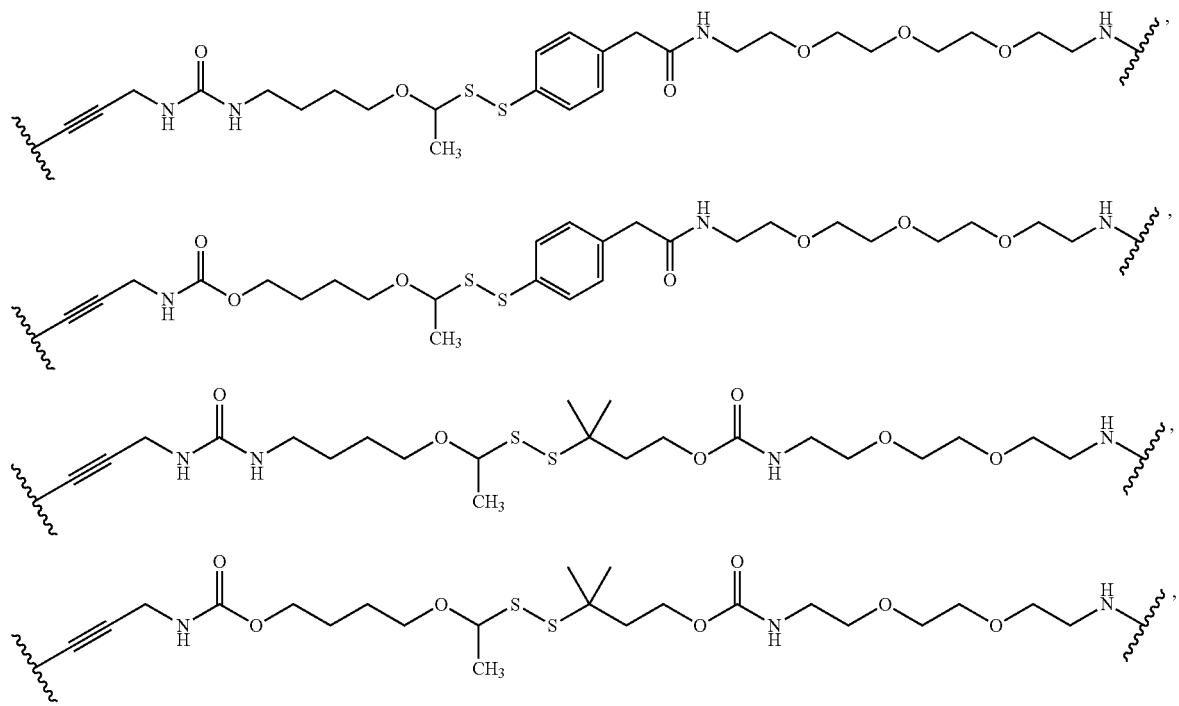

-continued
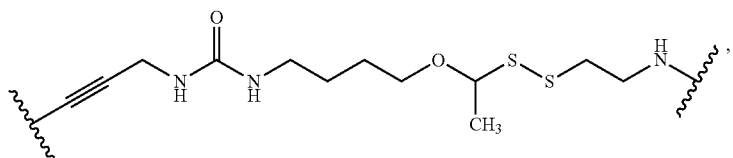
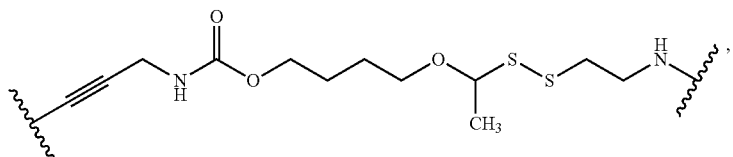
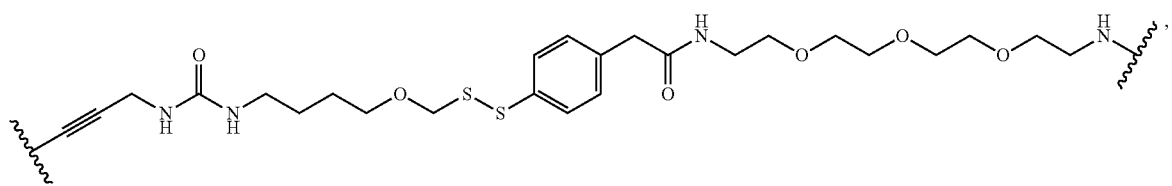
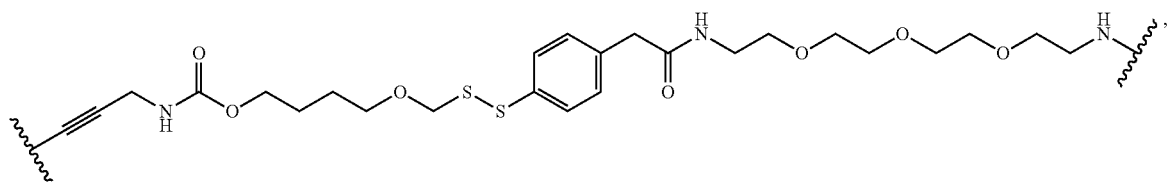
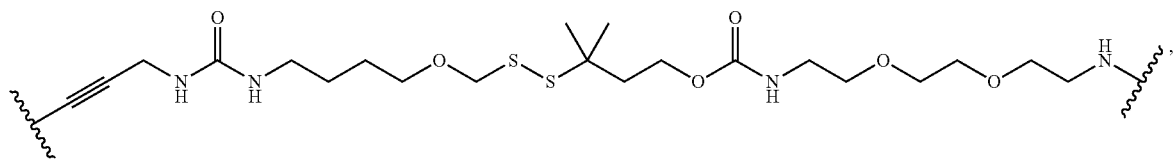
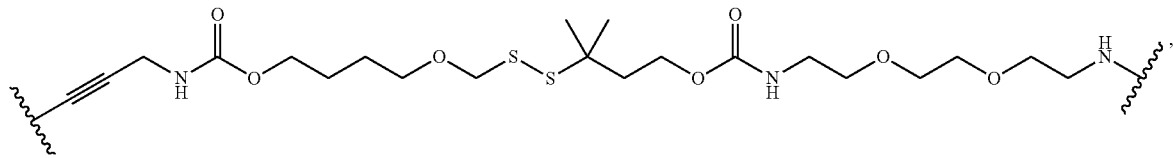
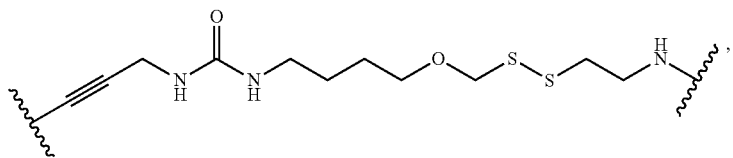
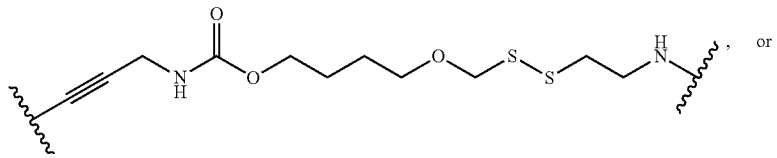
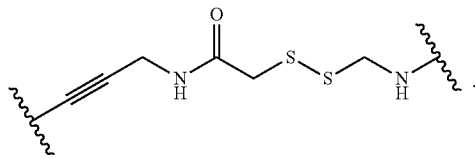

Embodiment Q34. The compound of one of embodiments Q19 to Q20, wherein $L^{100}$ is

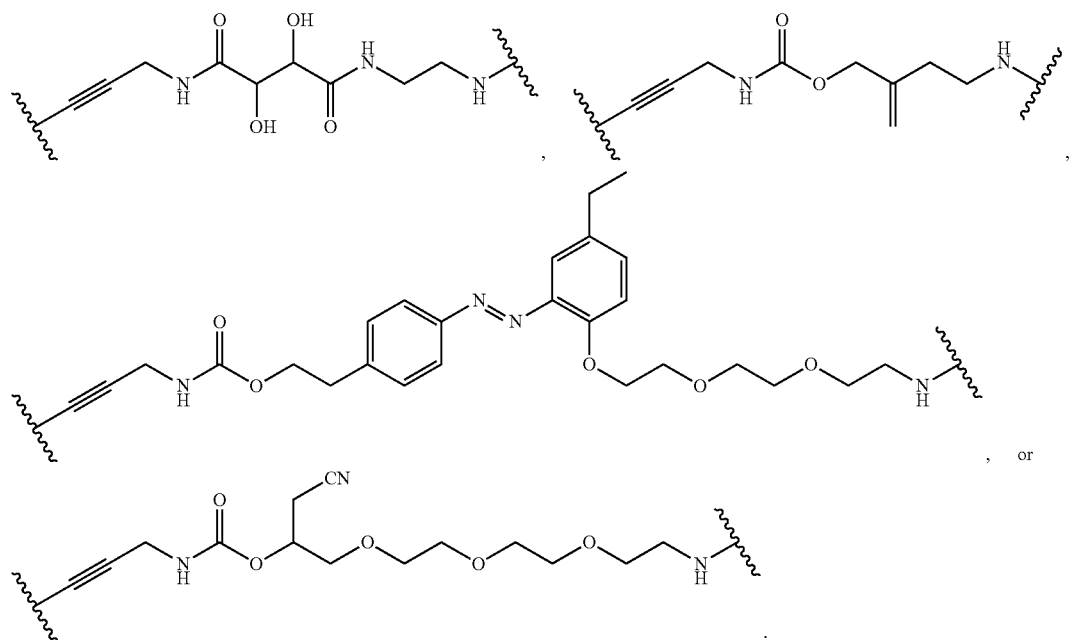

, or

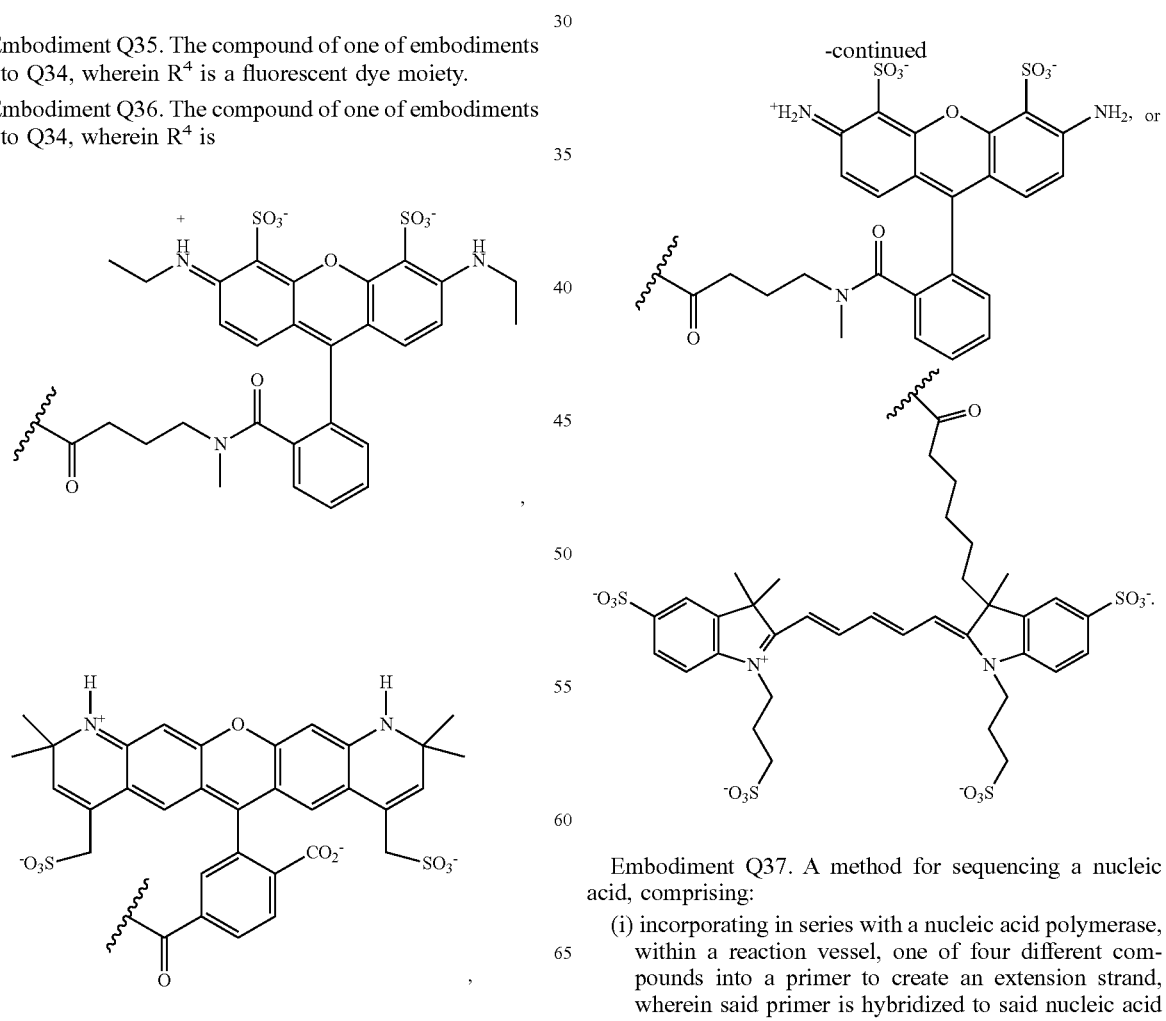

Embodiment Q35. The compound of one of embodiments Q1 to Q34, wherein $R^4$ is a fluorescent dye moiety.

Embodiment Q36. The compound of one of embodiments Q1 to Q34, wherein $R^4$ is

Embodiment Q37. A method for sequencing a nucleic acid, comprising:
  (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;

(ii) detecting said unique detectable label of each incorporated compound, so as to thereby identify each incorporated compound in said extension strand, thereby sequencing the nucleic acid;

wherein each of said four different compounds is independently a compound of one of embodiments Q1 to Q36.

Embodiment Q38. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments Q1 to Q36.

Embodiment Q39. A nucleic acid polymerase complex comprising a nucleic acid polymerase, wherein said nucleic acid polymerase is bound to a compound of one of embodiments Q1 to Q36.

Embodiment S1. A compound having the formula:

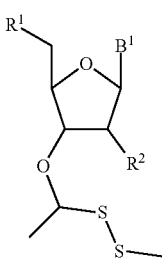

(I)

wherein, $B^1$ is a monovalent nucleobase;

$R^1$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and $R^2$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or a —O-polymerase-compatible cleavable moiety.

Embodiment S2. The compound of embodiment S1, having the formula:

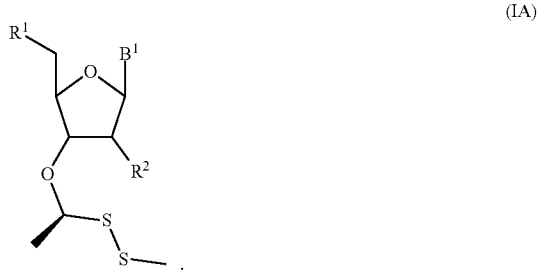

(IA)

Embodiment S3. The compound of embodiment S1, having the formula:

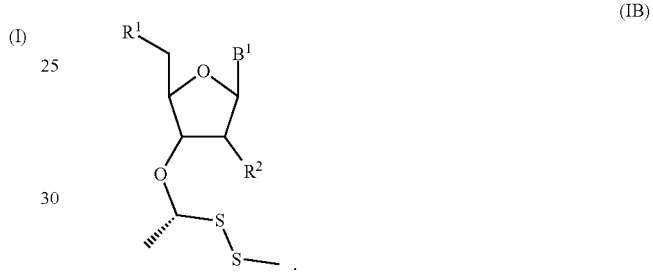

(IB)

Embodiment S4. The compound of embodiment S1, having the formula:

(IAD)

Embodiment S5. The compound of embodiment S1, having the formula:

(IBD)

Embodiment S6. The compound of one of embodiments S1 to S5, wherein $R^2$ is hydrogen.

Embodiment S7. The compound of one of embodiments S1 to S5, wherein $R^2$ is —OH.

Embodiment S8. The compound of one of embodiments S1 to S8, wherein $R^2$ is —O-polymerase-compatible cleavable moiety.

Embodiment S9. The compound of one of embodiments S1 to S8, wherein $R^1$ is —OH.

Embodiment S10. The compound of one of embodiments S1 to S8, wherein $R^1$ is a 5'-nucleoside protecting group.

Embodiment S11. The compound of one of embodiments S1 to S8, wherein —$R^1$ is a monophosphate moiety.

Embodiment S32. The compound of one of embodiments S1 to S8, wherein —$R^1$ is a polyphosphate moiety.

Embodiment S13. The compound of one of embodiments S1 to S8, wherein —$R^1$ is a triphosphate moiety.

Embodiment S14. The compound of one of embodiments S1 to S8, wherein $R^1$ is a nucleic acid moiety.

Embodiment S15. The compound of one of embodiments S1 to S14, wherein $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof.

Embodiment S16. The compound of one of embodiments S1 to S14, wherein $B^1$ is

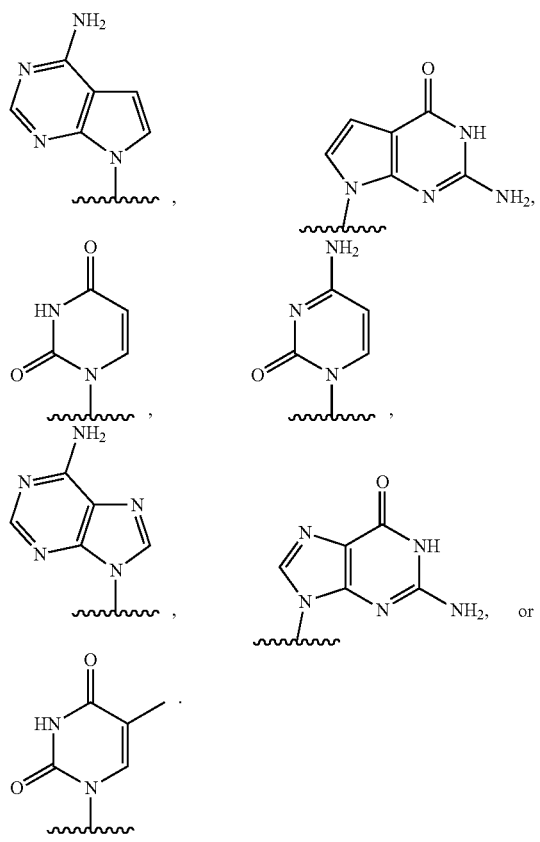

Embodiment S17. The compound of one of embodiments S1 to S14, wherein $B^1$ is

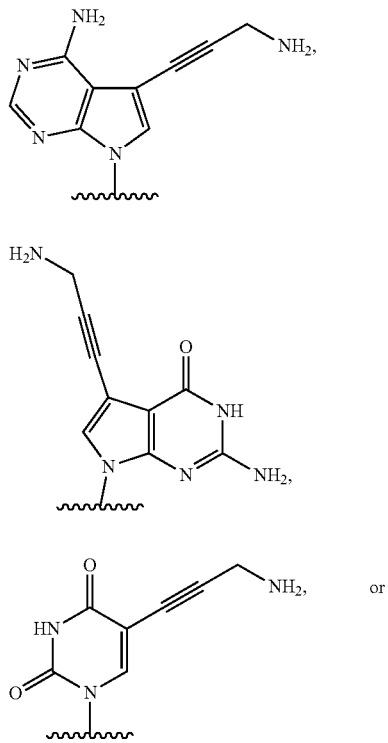

or

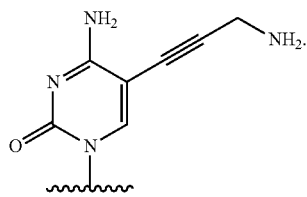

Embodiment S18. The compound of one of embodiments S1 to S14, wherein $B^1$ is

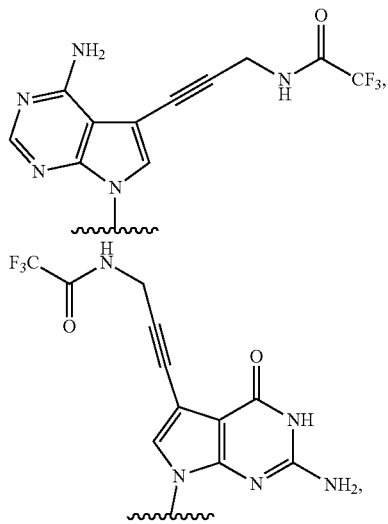

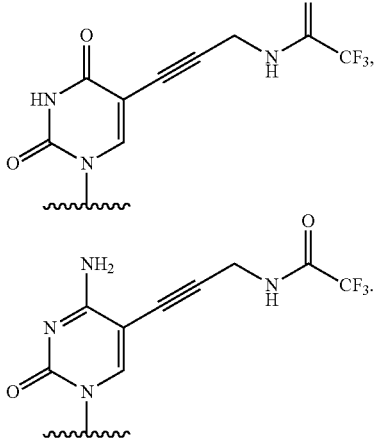

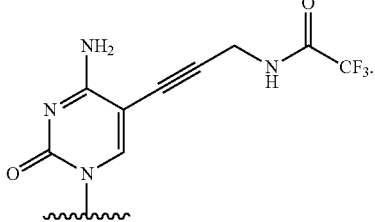

Embodiment S19. The compound of one of embodiments S1 to S14, wherein $B^1$ is —B-$L^{100}$-$R^4$;

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof;

$L^{100}$ is a divalent linker; and $R^4$ is a detectable moiety.

Embodiment S20. The compound of embodiment S19, wherein B is

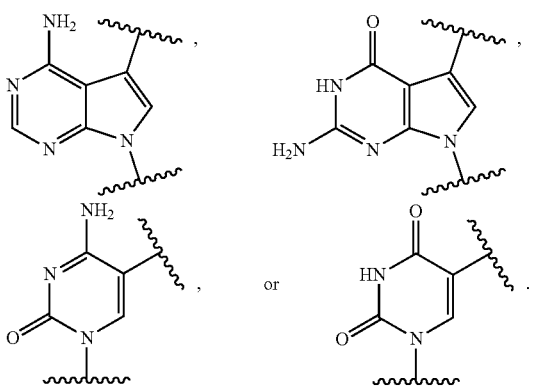

Embodiment S21. The compound of one of embodiments S19 to S20, wherein $L^{100}$ is -$L^{101}$-$L^{103}$-$L^{103}$-$L^{104}$-$L^{105}$-;

$L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment S22. The compound of one of embodiments S19 to S20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;

$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{100}$ is —$SR^{102}$ or —CN; and $R^{102}$ is unsubstituted $C_1$-$C_4$ alkyl.

Embodiment S23. The compound of one of embodiments S19 to S20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;

$L^{101}$ is independently a substituted or unsubstituted $C_1$-$C_4$ alkylene or substituted or unsubstituted 8 to 20 membered heteroalkylene;

$L^{103}$ is independently a bond or substituted or unsubstituted 2 to 10 membered heteroalkylene;

$L^{104}$ is independently a bond, substituted or unsubstituted 4 to 18 membered heteroalkylene, or substituted or unsubstituted phenylene;

$L^{105}$ is independently bond or substituted or unsubstituted 4 to 18 membered heteroalkylene;

$R^{100}$ is —$SR^{102}$ or —CN; and $R^{102}$ is unsubstituted $C_1$-$C_4$ alkyl.

Embodiment S24. The compound of one of embodiments S19 to S20, wherein $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-;

$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^{104}$ is unsubstituted phenylene;

$R^{100}$ is —$SR^{102}$ or —CN; and $R^{102}$ is unsubstituted $C_1$-$C_4$ alkyl.

Embodiment S25. The compound of one of embodiments S19 to S20, wherein $L^{100}$ is -$L^{101}$-O—CH($N_3$)-$L^{103}$-$L^{104}$-$L^{105}$-; and $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment S26. The compound of one of embodiments S19 to S20, wherein $L^{100}$ is -$L^{101}$-O—CH($N_3$)-$L^{103}$-$L^{104}$-$L^{105}$-;

$L^{101}$ is independently a substituted or unsubstituted $C_1$-$C_4$ alkylene or substituted or unsubstituted 8 to 20 membered heteroalkylene;

$L^{103}$ is independently a bond or substituted or unsubstituted 2 to 10 membered heteroalkylene;

$L^{104}$ is independently a bond, substituted or unsubstituted 4 to 18 membered heteroalkylene, or substituted or unsubstituted phenylene; and $L^{105}$ is independently bond or substituted or unsubstituted 4 to 18 membered heteroalkylene.

Embodiment S27. The compound of one of embodiments S19 to S20, wherein $L^{100}$ is -$L^{101}$-O—CH($N_3$)—$CH_2$—O-$L^{104}$-$L^{105}$-;

$L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{104}$ is unsubstituted phenylene.

Embodiment S28. The compound of one of embodiments S19 to S20, wherein $L^{100}$ is
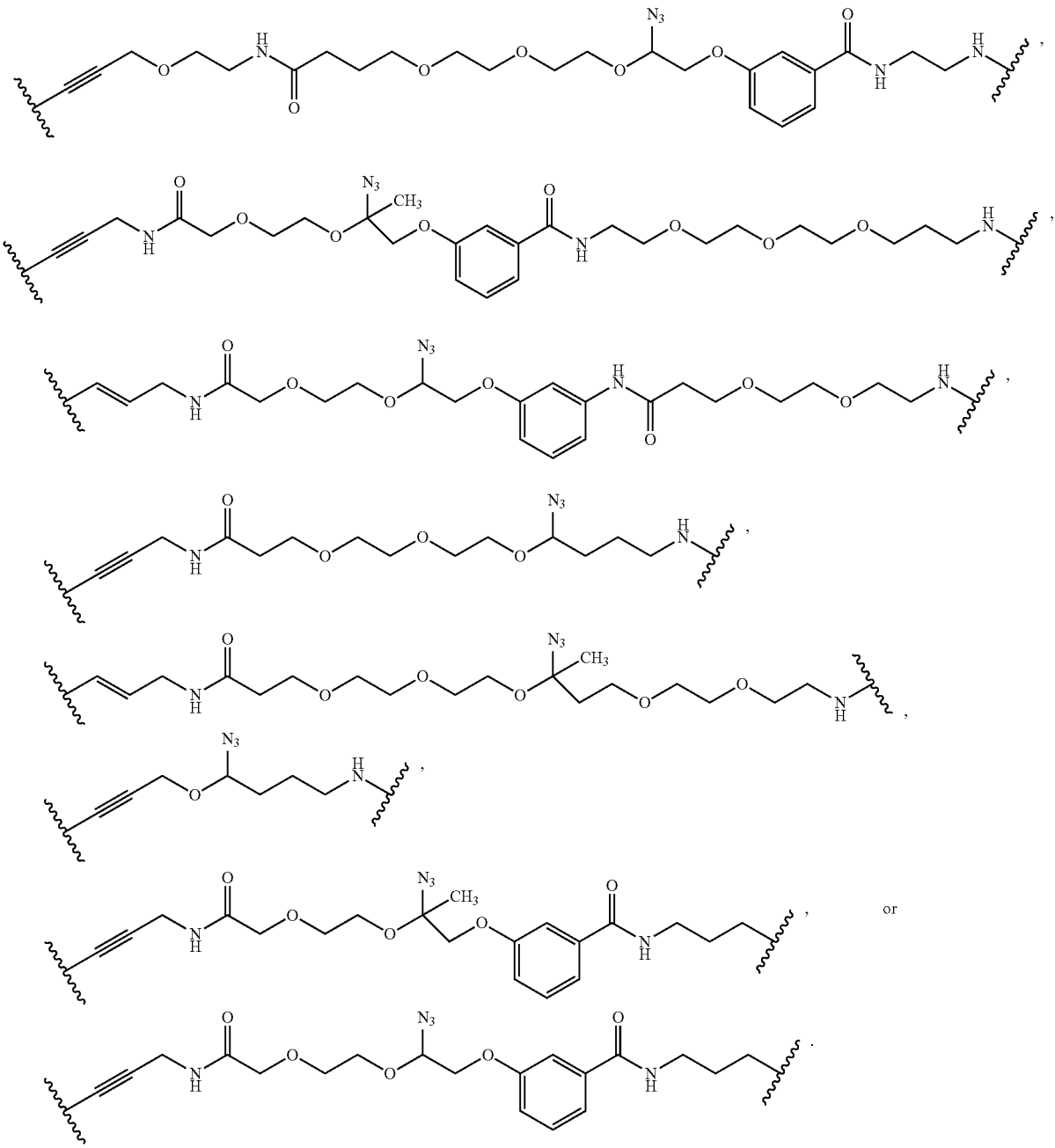
Embodiment S29. The compound of one of embodiments S19 to S20, wherein $L^{100}$ is
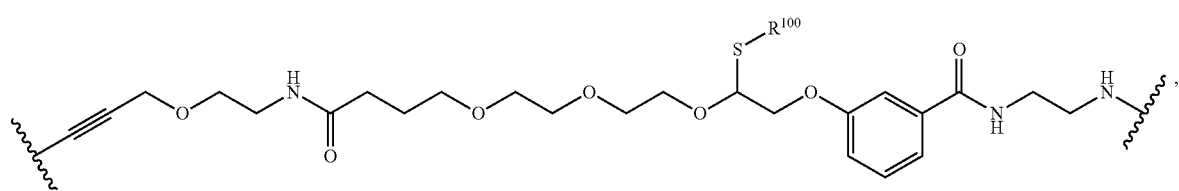

-continued
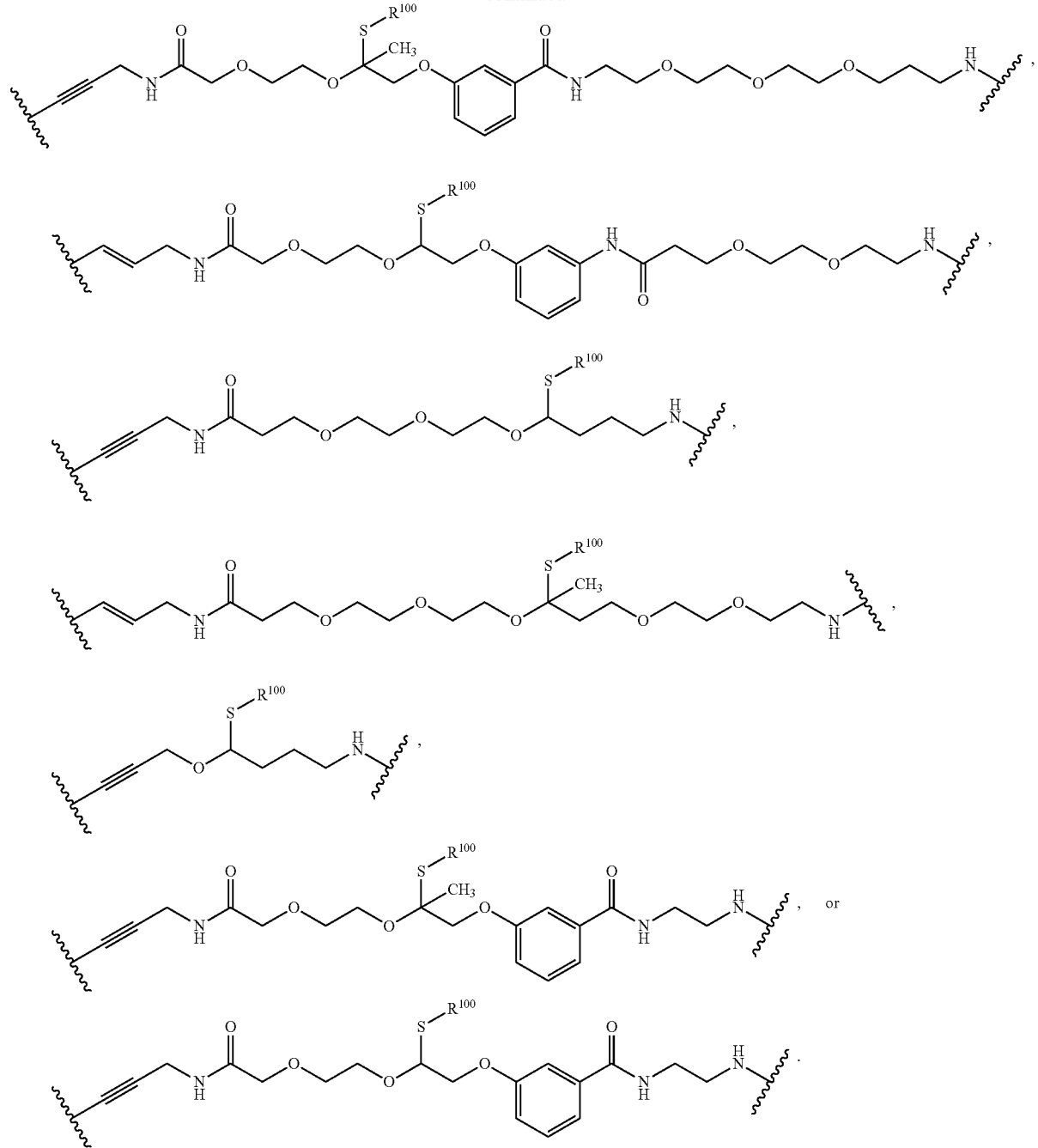
Embodiment S30. The compound of one of embodiments S19 to S20, wherein $L^{100}$ is
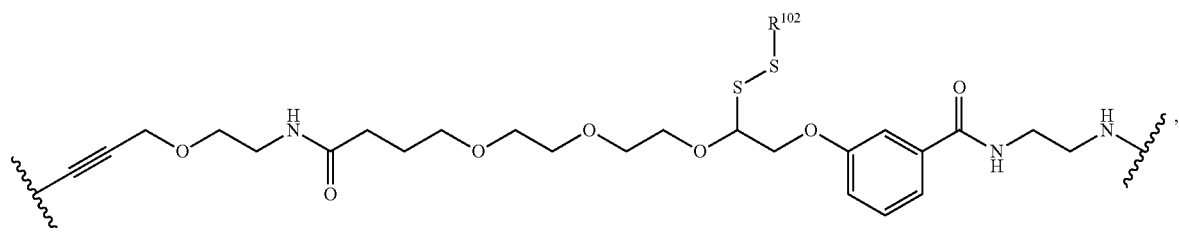

-continued
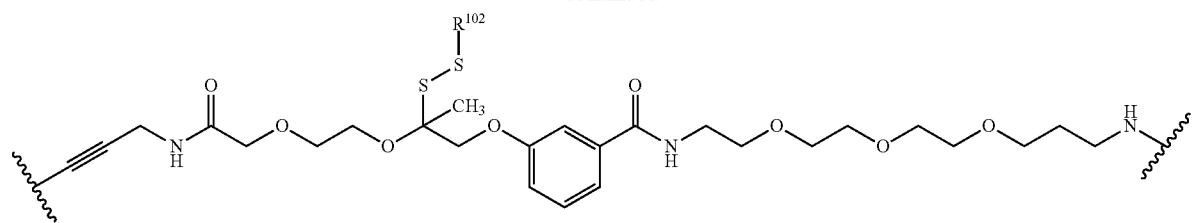
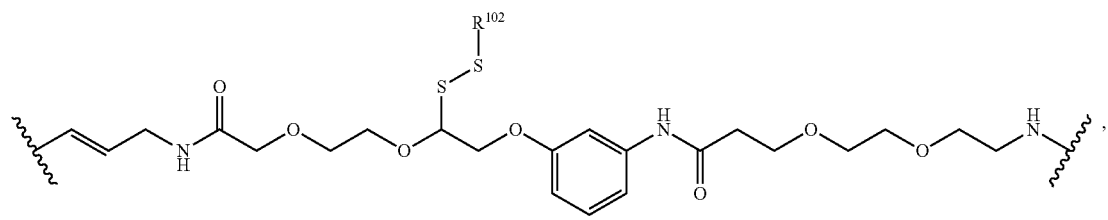
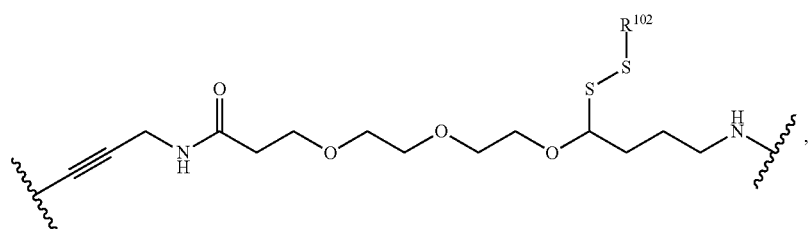
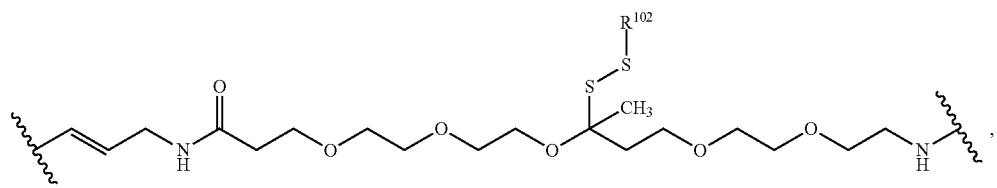
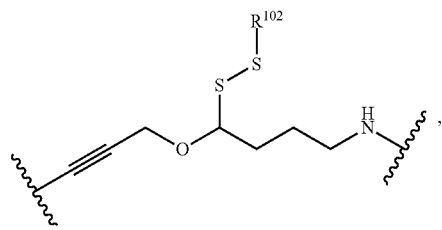
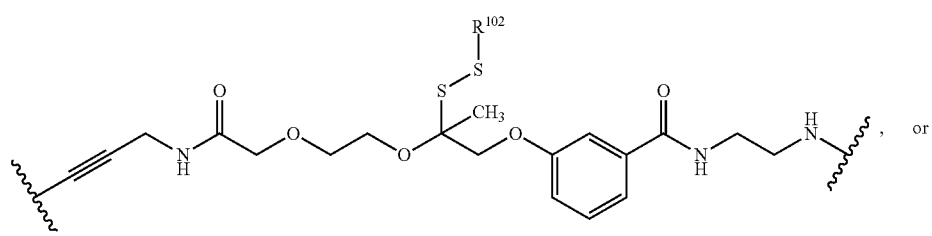
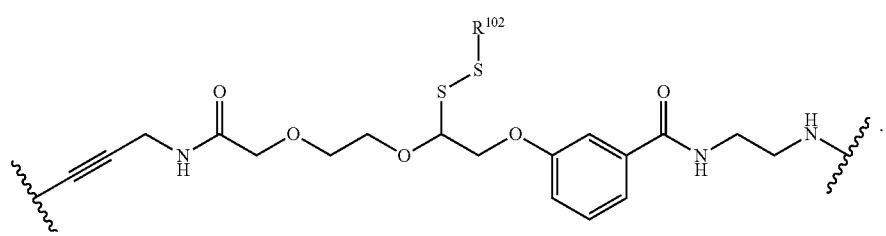

Embodiment S31. The compound of one of embodiments S19 to S20, wherein $L^{100}$ is
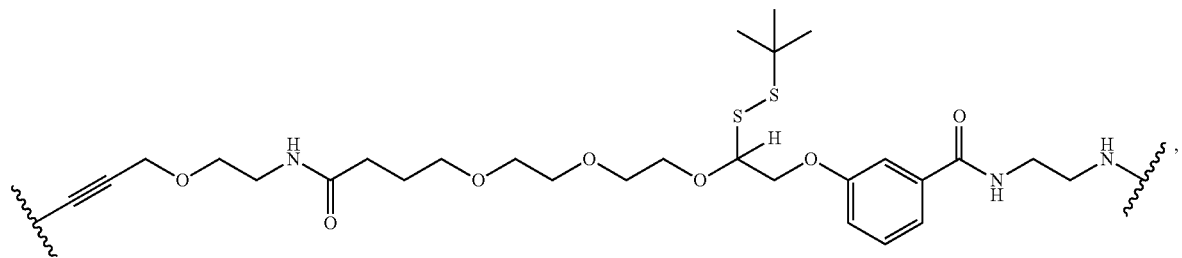
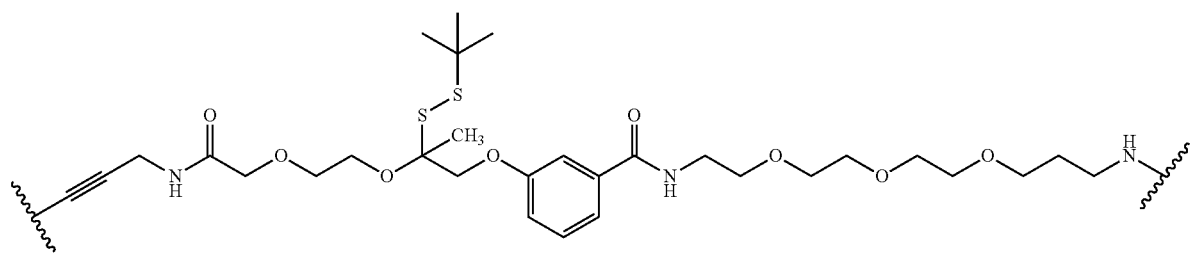
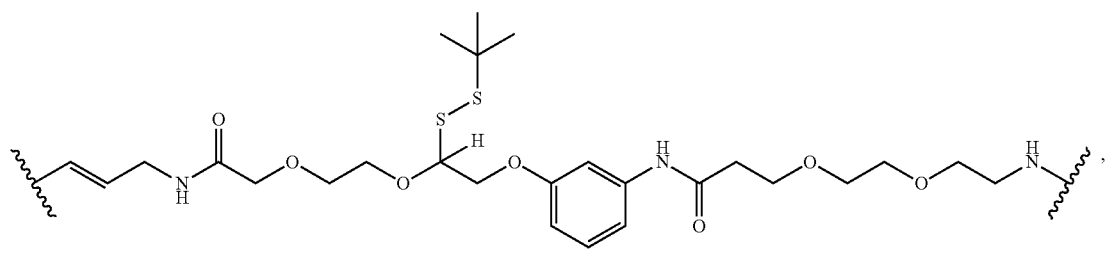
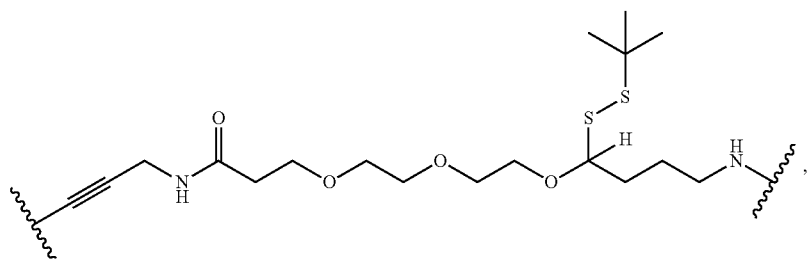
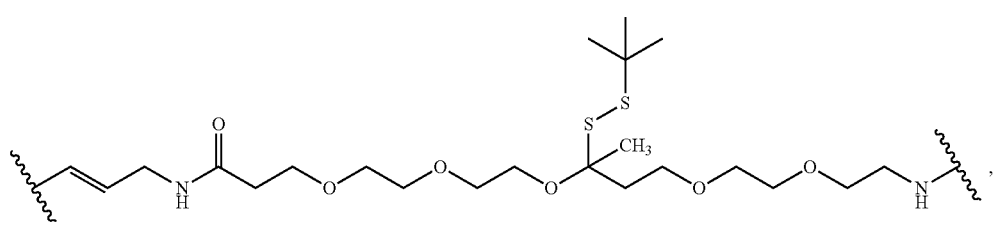
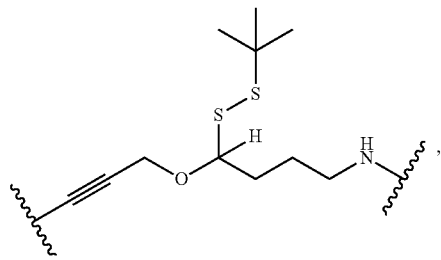

-continued
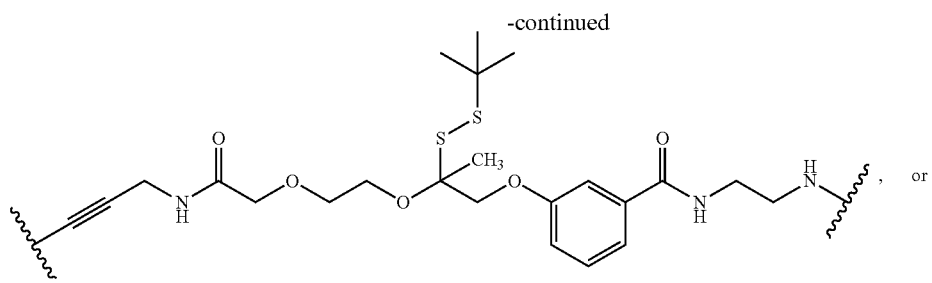
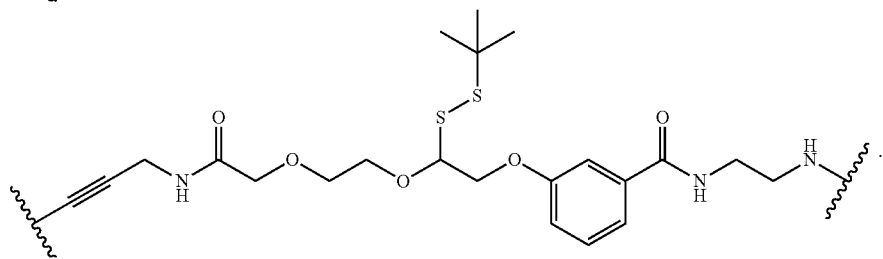
Embodiment S32. The compound of one of embodiments S19 to S20, wherein $L^{100}$ is
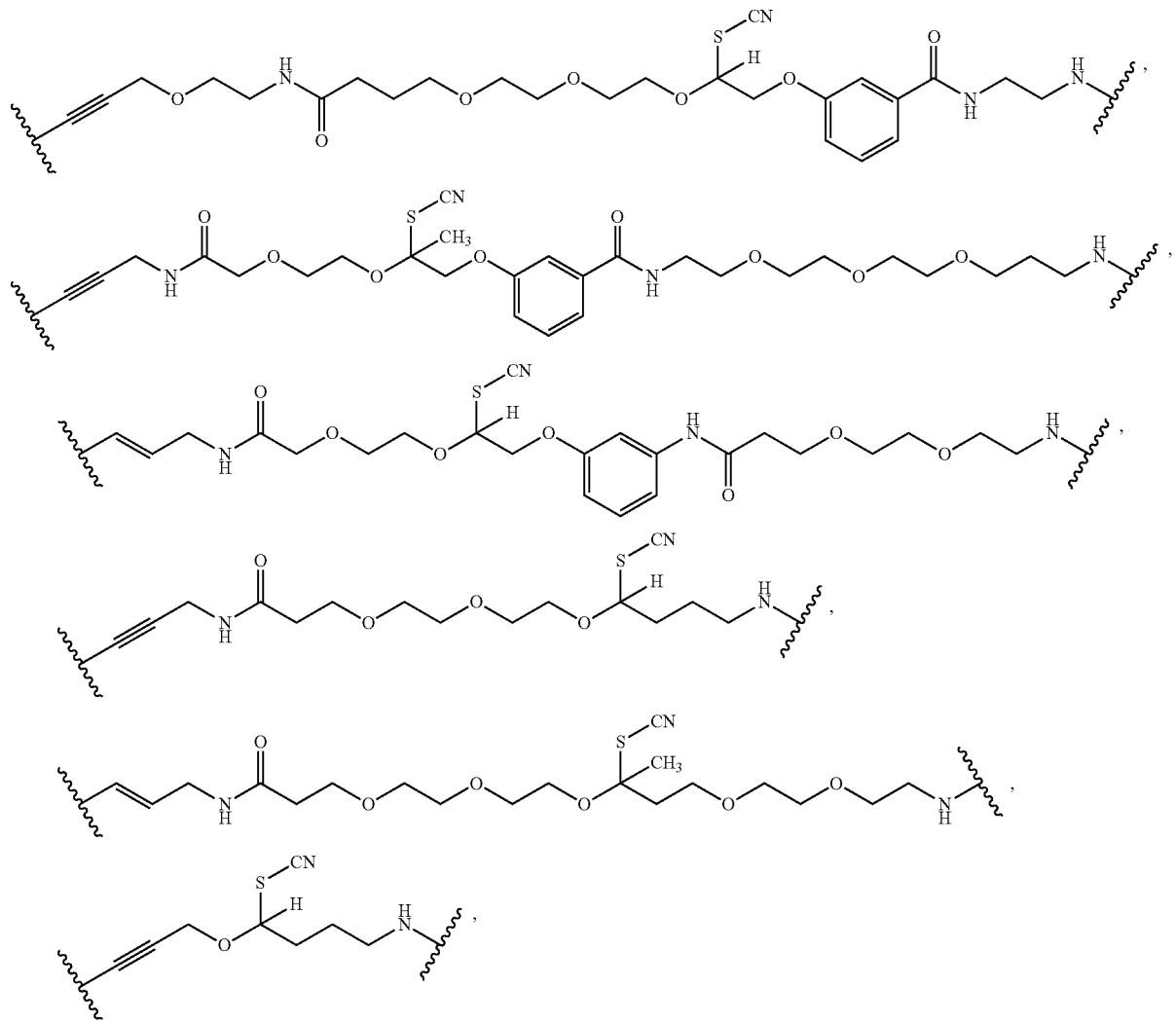

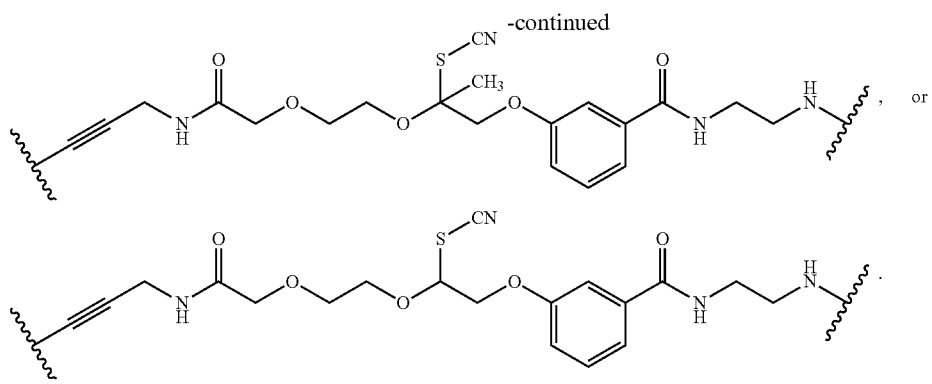
Embodiment S33. The compound of one of embodiments S19 to S20, wherein $L^{100}$ is
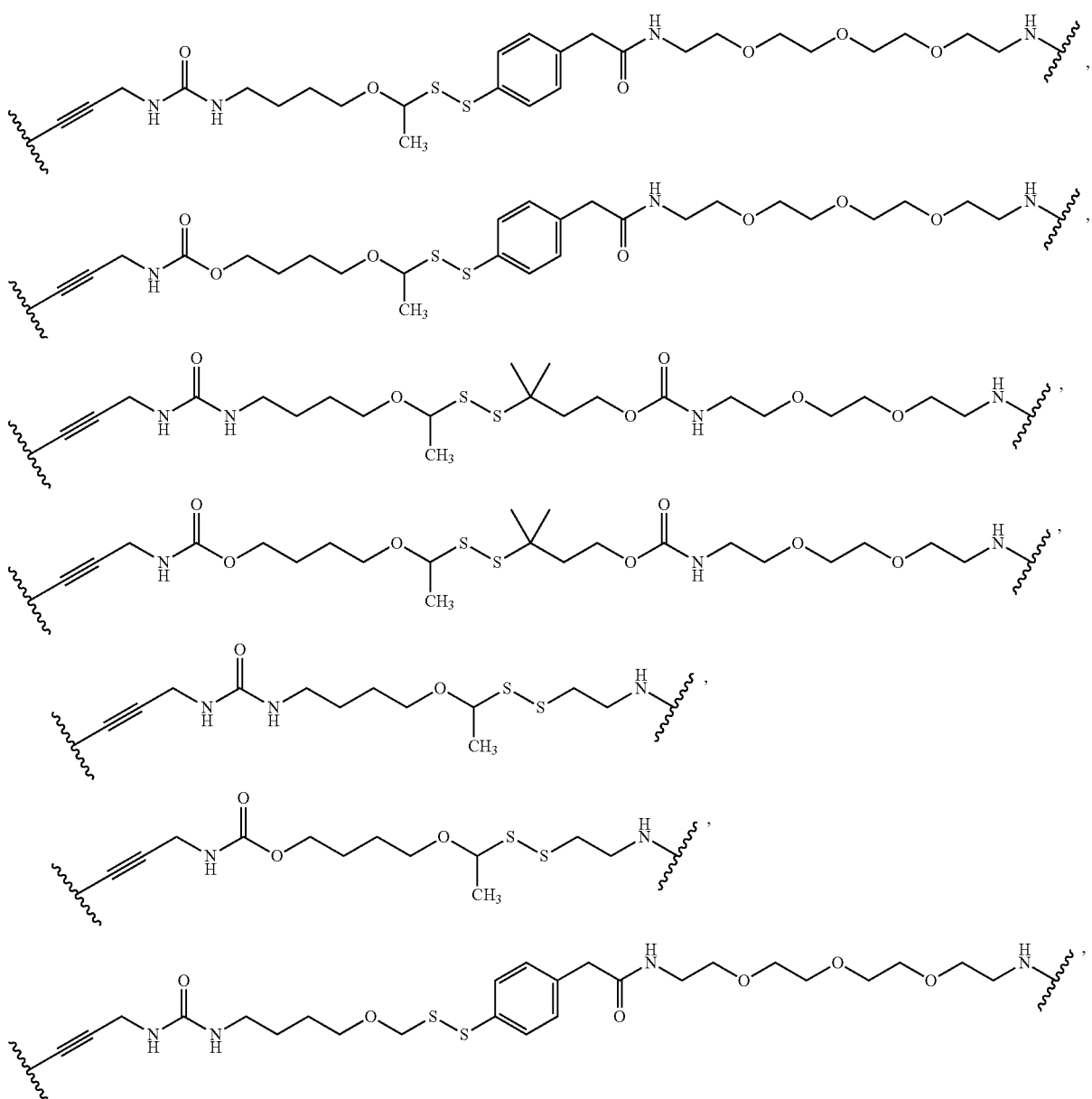

-continued
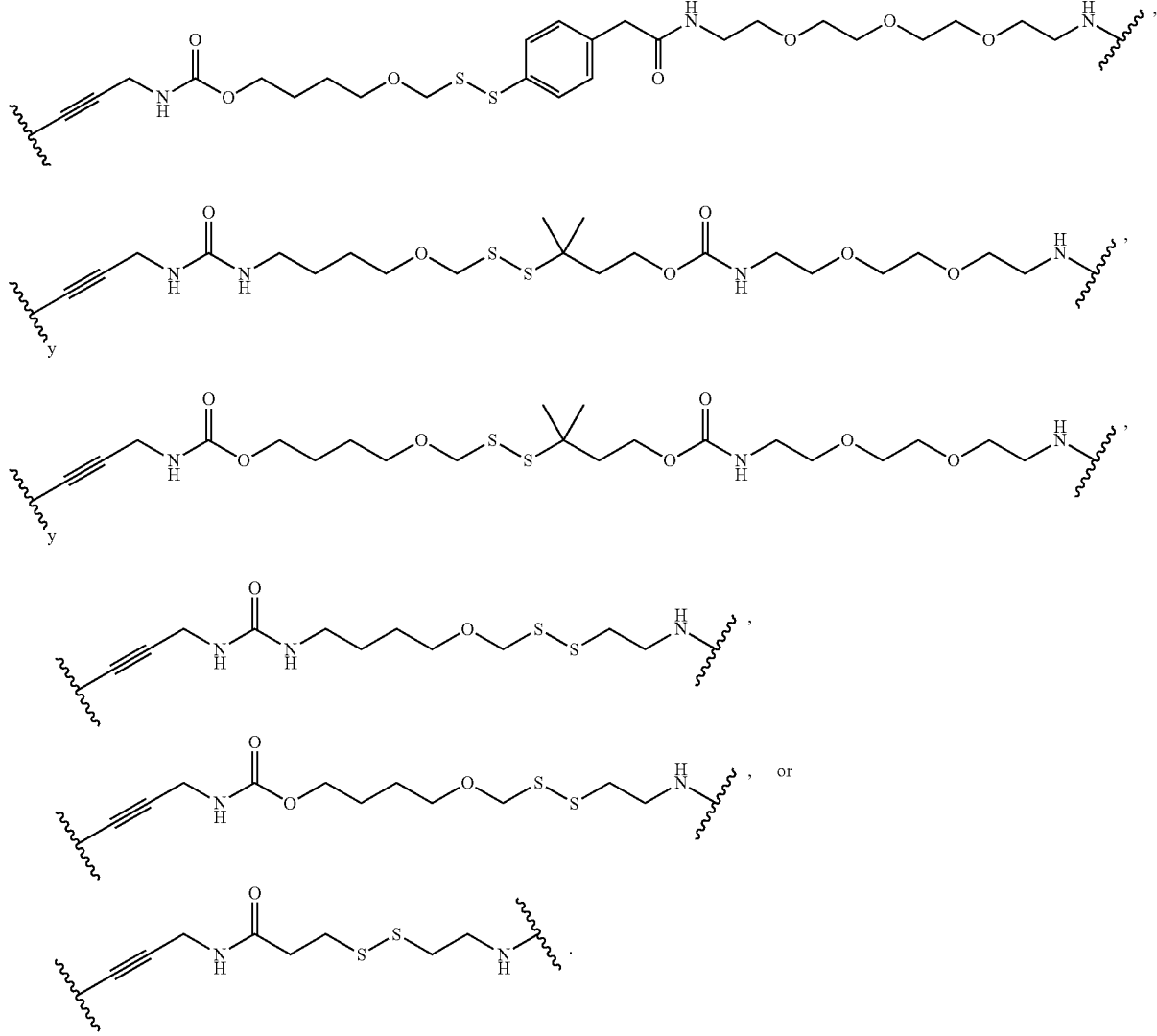
Embodiment S34. The compound of one of embodiments S19 to S20, wherein $L^{100}$ is
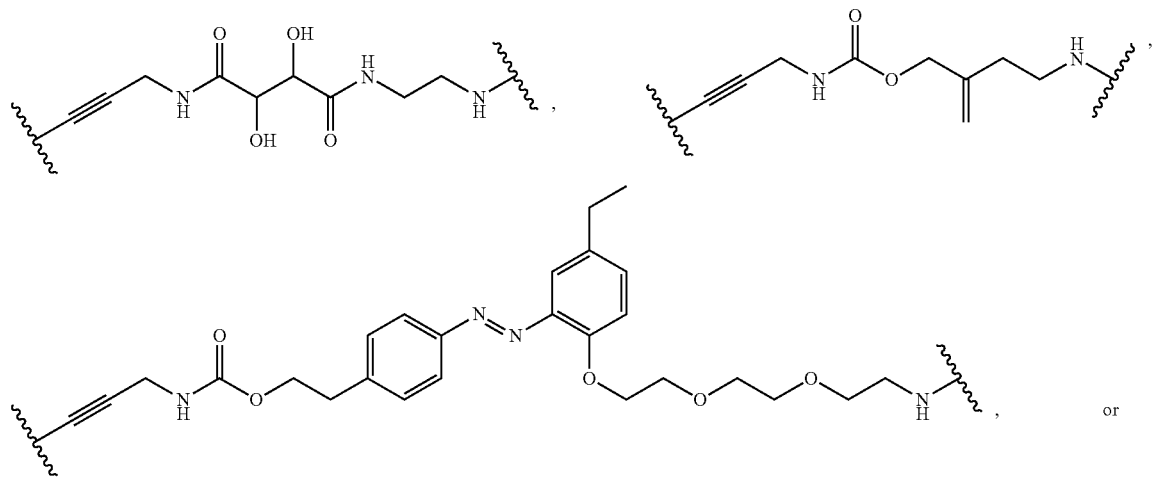

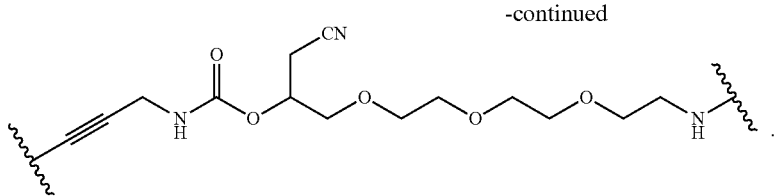

Embodiment S35. The compound of one of embodiments S1 to S34, wherein $R^4$ is a fluorescent dye moiety.

Embodiment S36. The compound of one of embodiments S1 to S34, wherein $R^4$ is

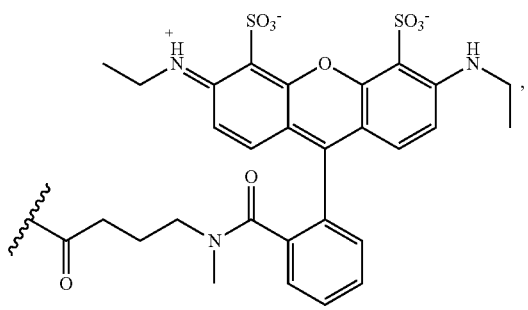

,

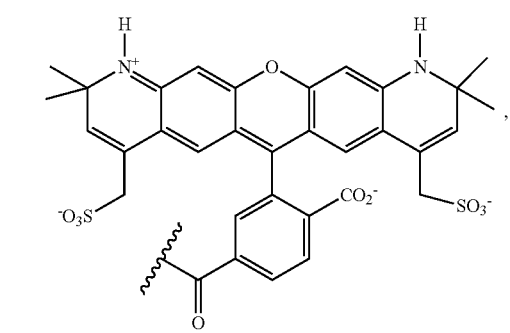

,

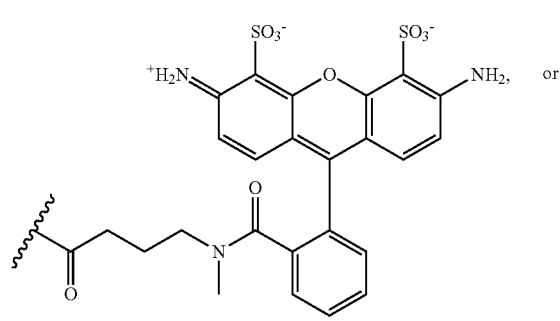

or

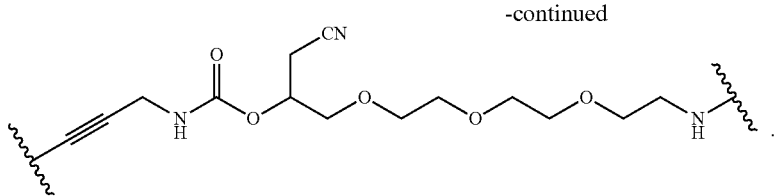

Embodiment S37. A method for sequencing a nucleic acid, comprising:

(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;

(ii) detecting said unique detectable label of each incorporated compound, so as to thereby identify each incorporated compound in said extension strand, thereby sequencing the nucleic acid;

wherein each of said four different compounds is independently a compound of one of embodiments S1 to S36.

Embodiment S38. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments S1 to S36.

Embodiment S39. A nucleic acid polymerase complex comprising a nucleic acid polymerase, wherein said nucleic acid polymerase is bound to a compound of one of embodiments S1 to S36.

VI. Additional Embodiments

Embodiment 1. A compound having the formula:

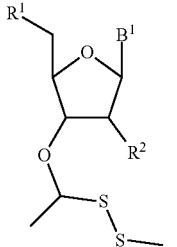
(I)

wherein
B¹ is a monovalent nucleobase;
R¹ is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and
R² is independently hydrogen, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SF₅, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or a —O-polymerase-compatible cleavable moiety.

Embodiment 2. The compound of embodiment 1, having the formula:

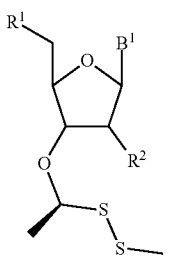
(IA)

Embodiment 3. The compound of embodiment 1, having the formula:

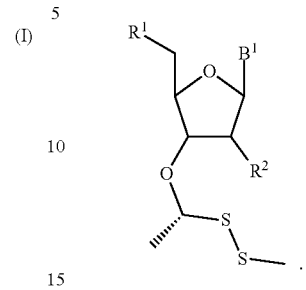
(IB)

Embodiment 4. The compound of embodiment 1, having the formula:

(IAD)

Embodiment 5. The compound of embodiment 1, having the formula:

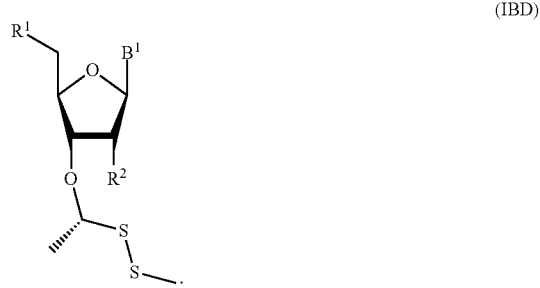
(IBD)

Embodiment 6. The compound of one of embodiments 1 to 5, wherein R² is hydrogen.
Embodiment 7. The compound of one of embodiments 1 to 5, wherein R² is —OH.
Embodiment 8. The compound of one of embodiments 1 to 5, wherein R² is —O-polymerase-compatible cleavable moiety.
Embodiment 9. The compound of one of embodiments 1 to 8, wherein R¹ is —OH.
Embodiment 10. The compound of one of embodiments 1 to 8, wherein R¹ is a 5'-nucleoside protecting group.
Embodiment 11. The compound of one of embodiments 1 to 8, wherein R¹ is a monophosphate moiety.
Embodiment 12. The compound of one of embodiments 1 to 8, wherein R¹ is a polyphosphate moiety.
Embodiment 13. The compound of one of embodiments 1 to 8, wherein R¹ is a triphosphate moiety.
Embodiment 14. The compound of one of embodiments 1 to 8, wherein R¹ is a nucleic acid moiety.

Embodiment 15. The compound of one of embodiments 1 to 14, wherein $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof.

Embodiment 16. The compound of one of embodiments 1 to 14, wherein $B^1$ is

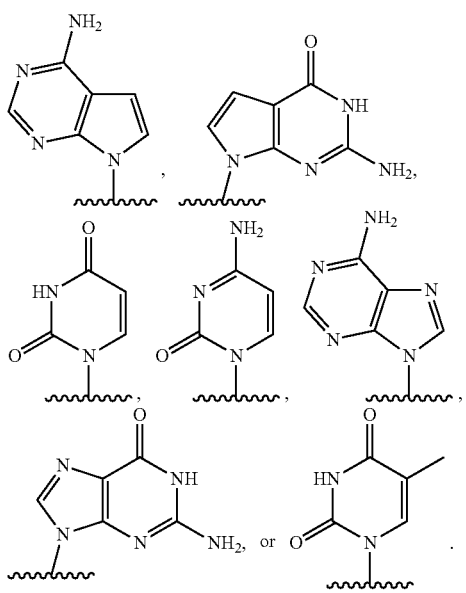

Embodiment 17. The compound of one of embodiments 1 to 14, wherein $B^1$ is

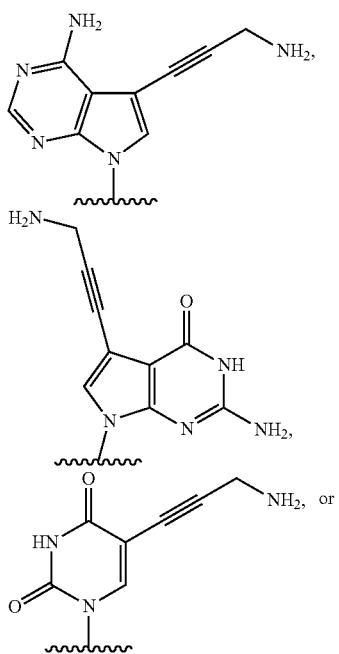

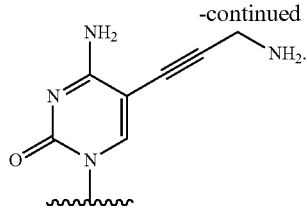

Embodiment 18. The compound of one of embodiments 1 to 14, wherein $B^1$ is

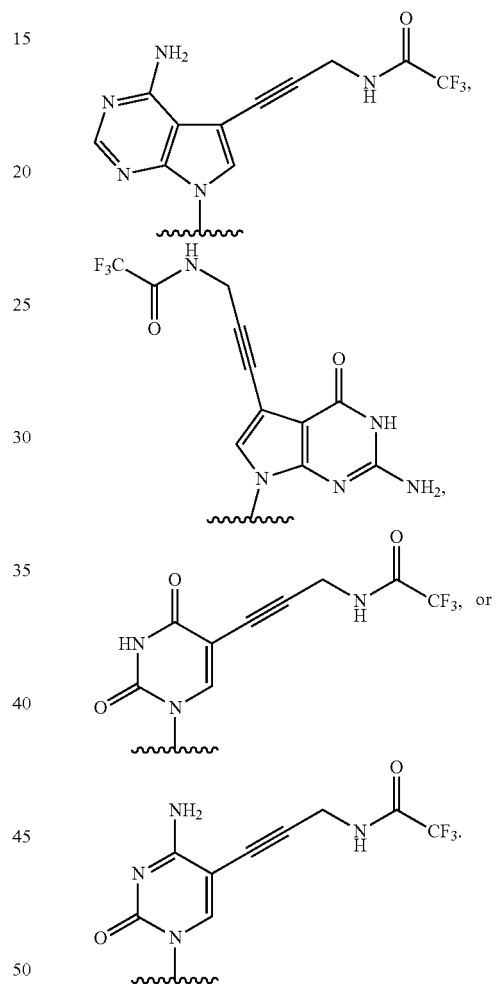

Embodiment 19. The compound of one of embodiments 1 to 14, wherein $B^1$ is —B-$L^{100}$-$R^4$;

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof;

$L^{100}$ is a divalent linker; and $R^4$ is a detectable moiety.

Embodiment 20. The compound of embodiment 19, wherein B is

511

[Chemical structures of four nucleobases: adenine-like (7-deazaadenine), guanine-like (7-deazaguanine), cytosine, and uracil/thymine-like bases, shown with wavy bond attachment points]

Embodiment 21. The compound of one of embodiments 19 to 20, wherein $L^{100}$ is $-L^{101}-L^{102}-L^{103}-L^{104}-L^{105}-$;
$L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 22. The compound of one of embodiments 19 to 20, wherein $L^{100}$ is $-L^{101}-O-CH(-SR^{100})-L^{103}-L^{104}-L^{105}-$ or $-L^{101}-O-C(CH_3)(-SR^{100})-L^{103}-L^{104}-L^{105}-$;
$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^{100}$ is —$SR^{102}$ or —CN; and
$R^{102}$ is unsubstituted $C_1$-$C_4$ alkyl.

Embodiment 23. The compound of one of embodiments 19 to 20, wherein $L^{100}$ is $-L^{101}-O-CH(-SR^{100})-L^{103}-L^{104}-L^{105}-$ or $-L^{101}-O-C(CH_3)(-SR^{100})-L^{103}-L^{104}-L^{105}-$;
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene;
$L^{105}$ is independently bond or substituted or unsubstituted 4 to 18 membered heteroalkylene;

512

$R^{100}$ is —$SR^{102}$ or —CN; and
$R^{102}$ is unsubstituted $C_1$-$C_4$ alkyl.

Embodiment 24. The compound of one of embodiments 19 to 20, wherein $L^{100}$ is $-L^{101}-O-CH(-SR^{100})-L^{103}-L^{104}-L^{105}-$ or $-L^{101}-O-C(CH_3)(-SR^{100})-L^{103}-L^{104}-L^{105}$;
$L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^{104}$ is unsubstituted phenylene;
$R^{100}$ is —$SR^{102}$ or —CN; and
$R^{102}$ is unsubstituted $C_1$-$C_4$ alkyl.

Embodiment 25. The compound of one of embodiments 19 to 20, wherein $L^{100}$ is $-L^{101}-O-CH(N_3)-L^{103}-L^{104}-L^{105}-$; and
$L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 26. The compound of one of embodiments 19 to 20, wherein $L^{100}$ is $-L^{101}-O-CH(N_3)-L^{103}-L^{104}-L^{105}$;
$L^{101}$ is independently a substituted or unsubstituted $C_1$-$C_4$ alkylene or substituted or unsubstituted 8 to 20 membered heteroalkylene;
$L^{103}$ is independently a bond or substituted or unsubstituted 2 to 10 membered heteroalkylene;
$L^{104}$ is independently a bond, substituted or unsubstituted 4 to 18 membered heteroalkylene, or substituted or unsubstituted phenylene; and
$L^{105}$ is independently bond or substituted or unsubstituted 4 to 18 membered heteroalkylene.

Embodiment 27. The compound of one of embodiments 19 to 20, wherein $L^{100}$ is $-L^{101}-O-CH(N_3)-CH_2-O-L^{104}-L^{105}-$;
$L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
$L^{104}$ is unsubstituted phenylene.

Embodiment 28. The compound of one of embodiments 19 to 20, wherein $L^{100}$ is

[Two chemical structures showing linker compounds with alkyne, PEG, azide, amide, and phenyl groups with wavy bond attachment points]

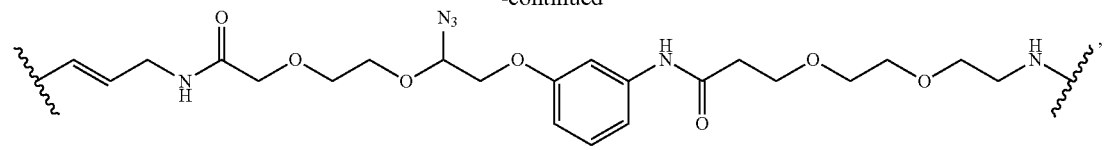
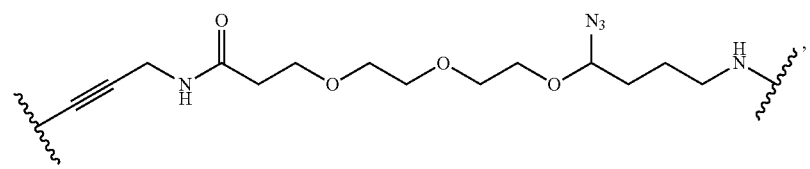
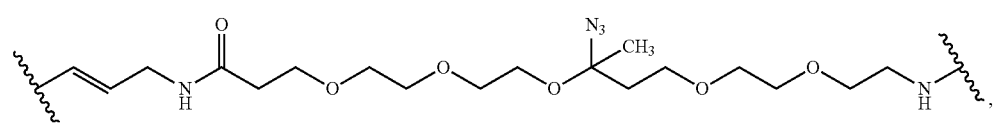
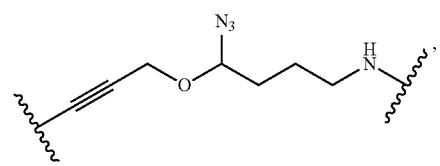
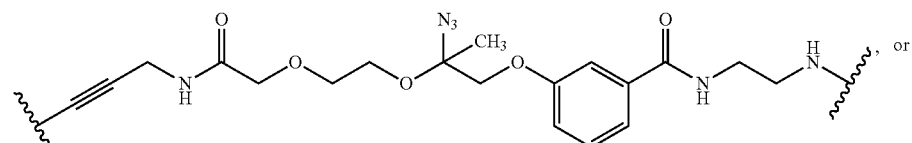
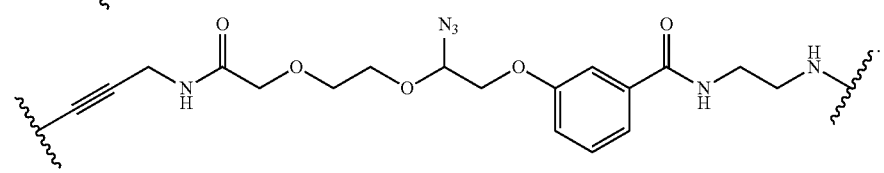
Embodiment 29. The compound of one of embodiments 19 to 20, wherein $L^{100}$ is
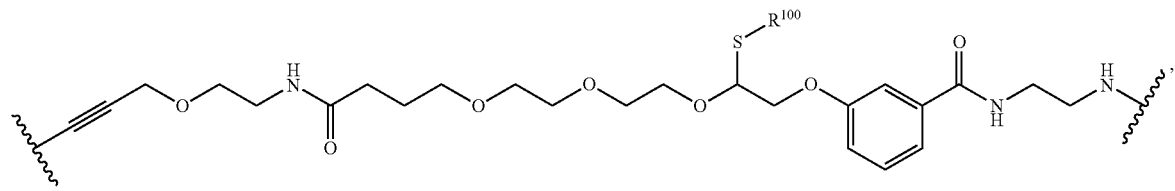
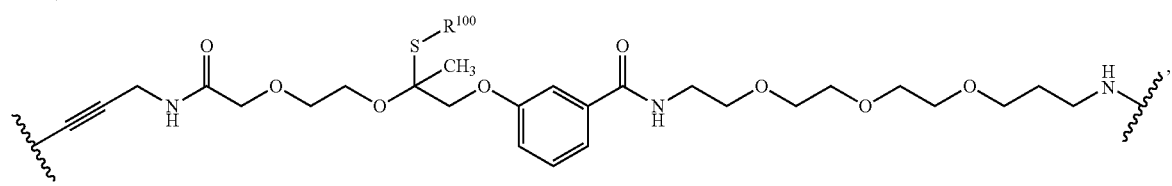
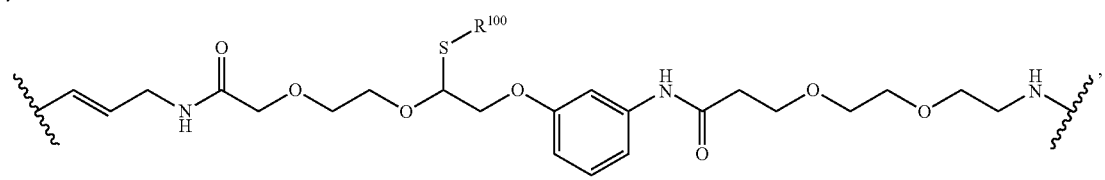

-continued
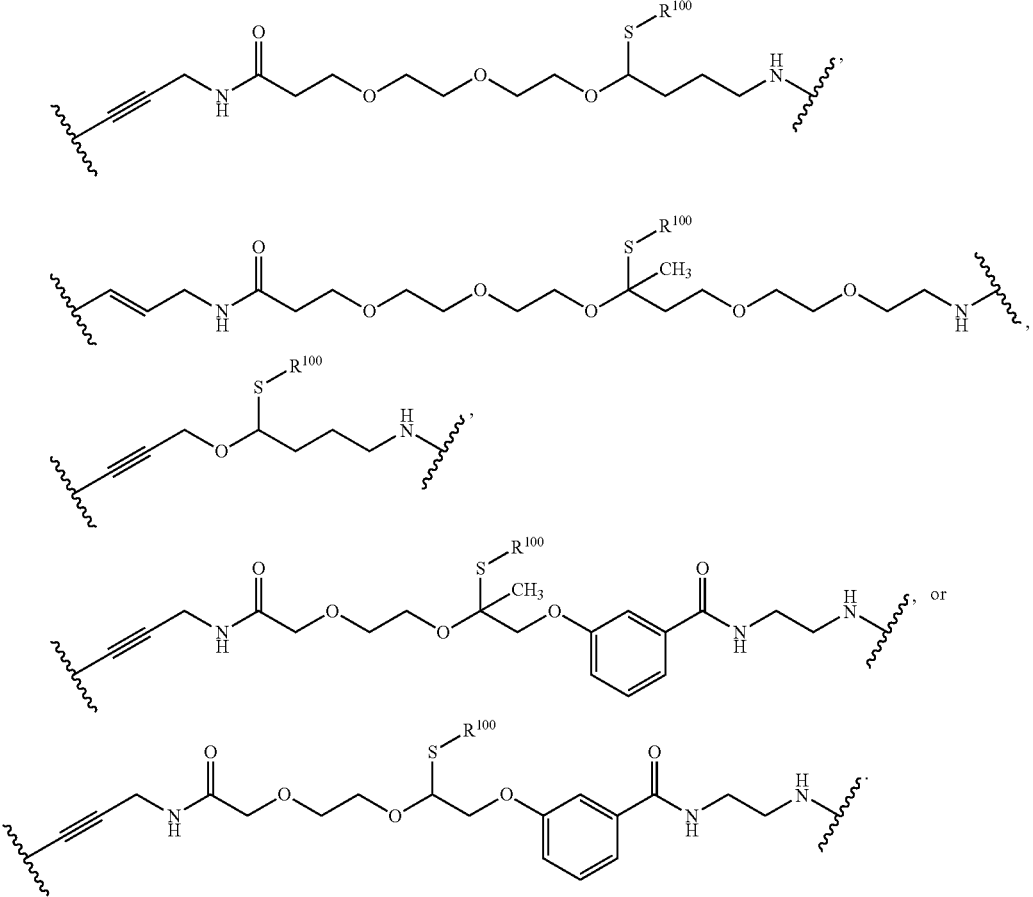
Embodiment 30. The compound of one of embodiments 19 to 20, wherein $L^{100}$ is
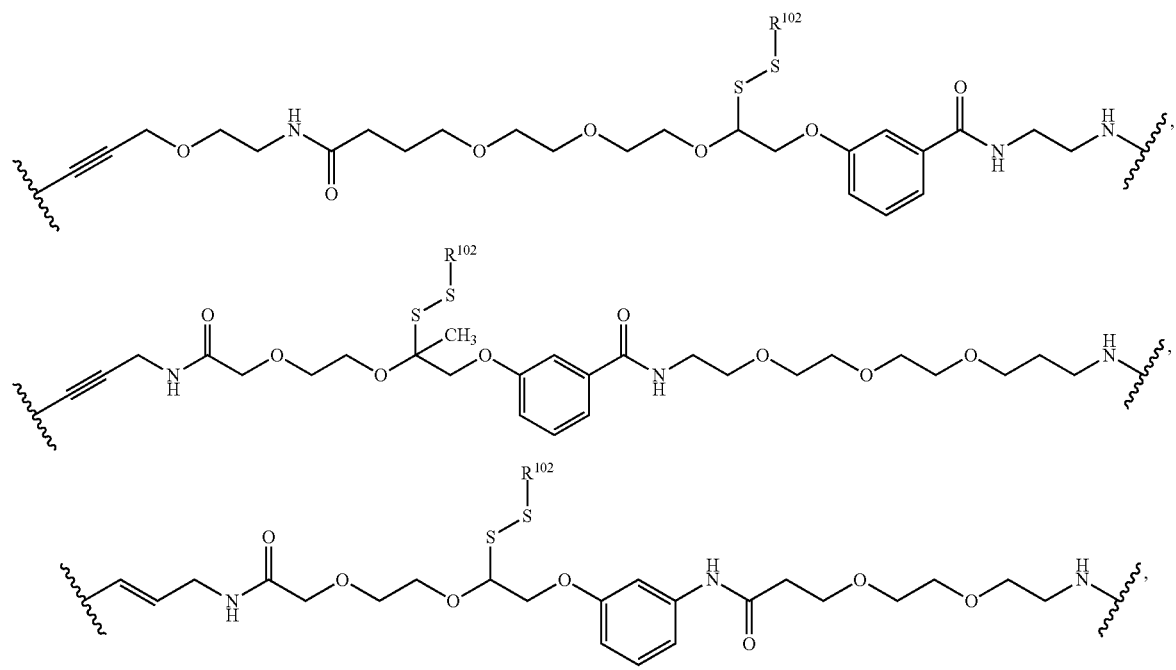

-continued
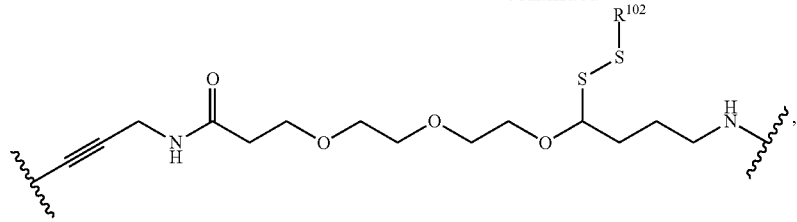
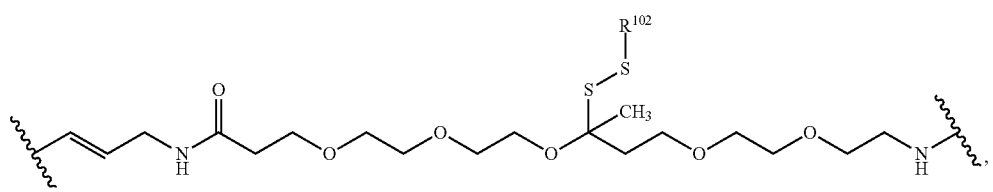
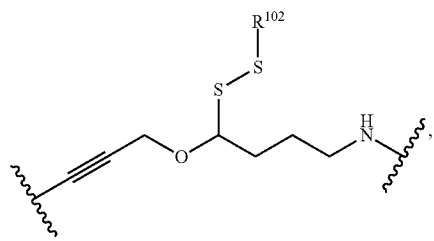
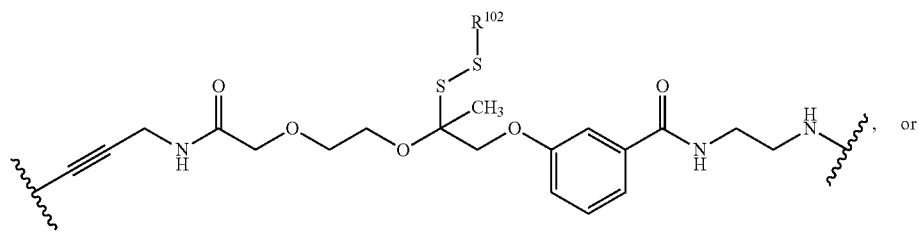, or
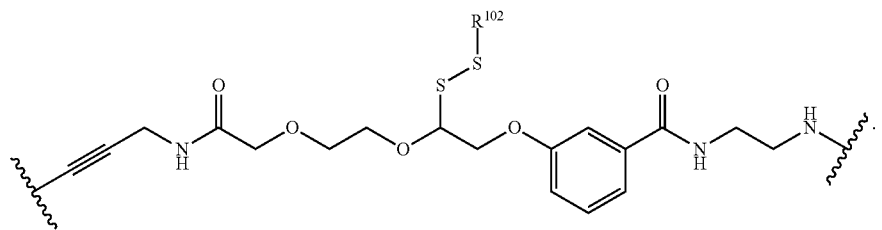.
Embodiment 31. The compound of one of embodiments 19 to 20, wherein $L^{100}$ is
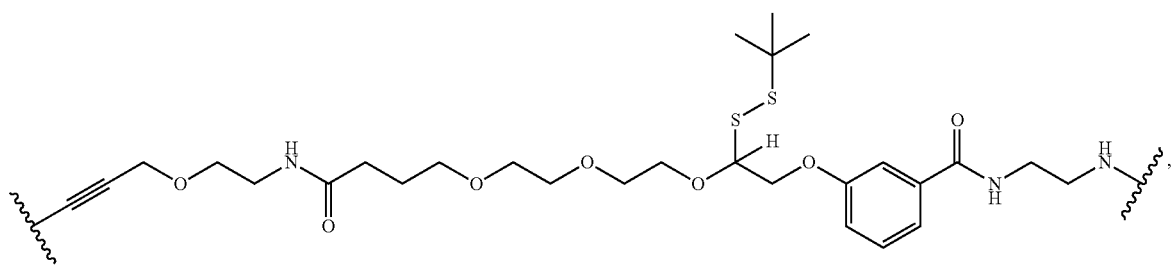,

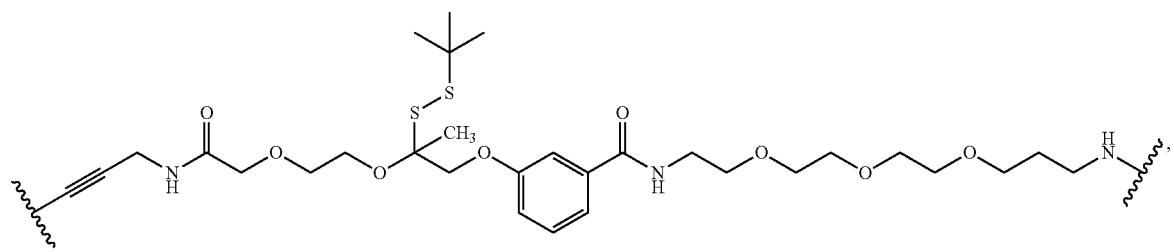
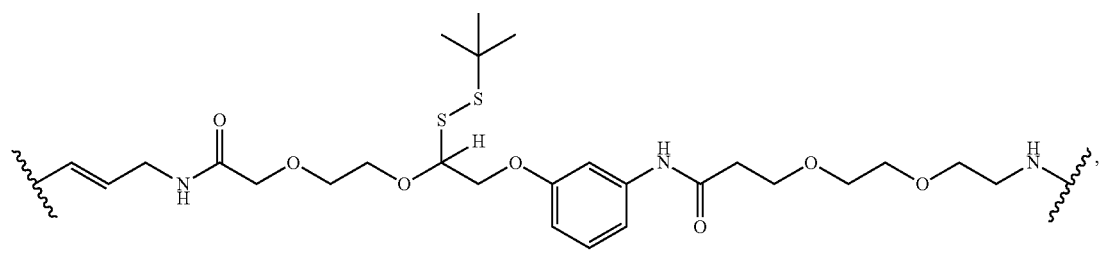
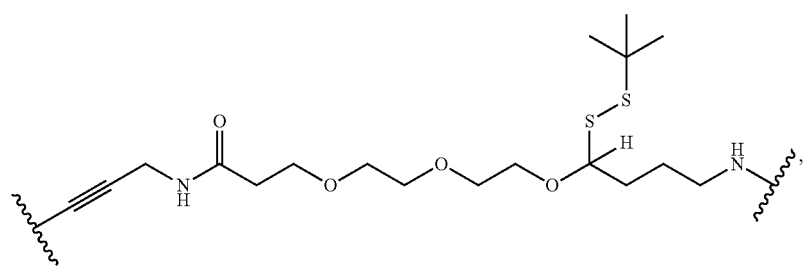
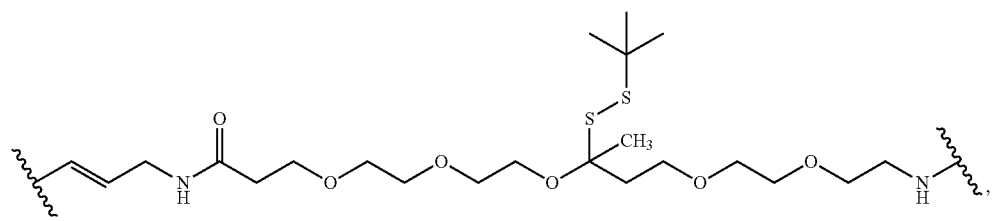
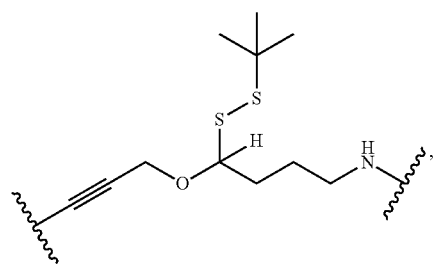
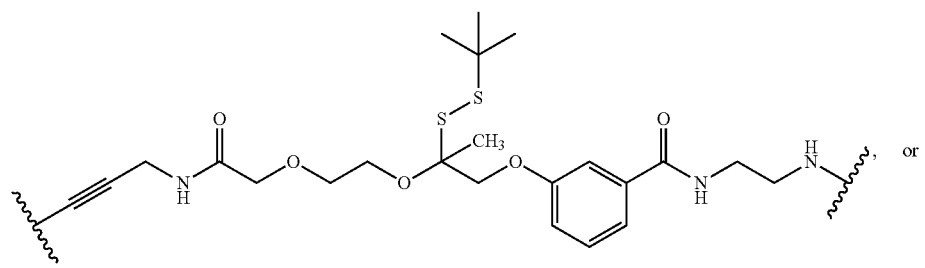

-continued
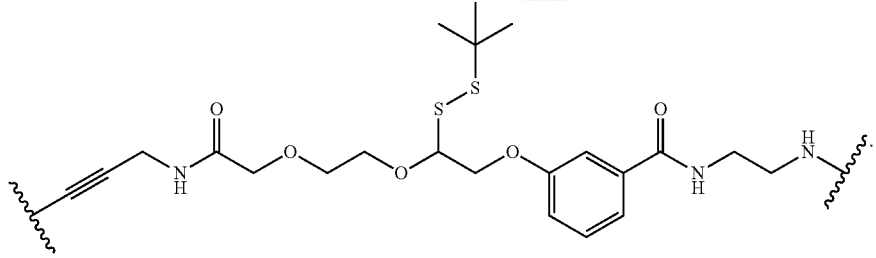
Embodiment 32. The compound of one of embodiments 19 to 20, wherein $L^{100}$ is
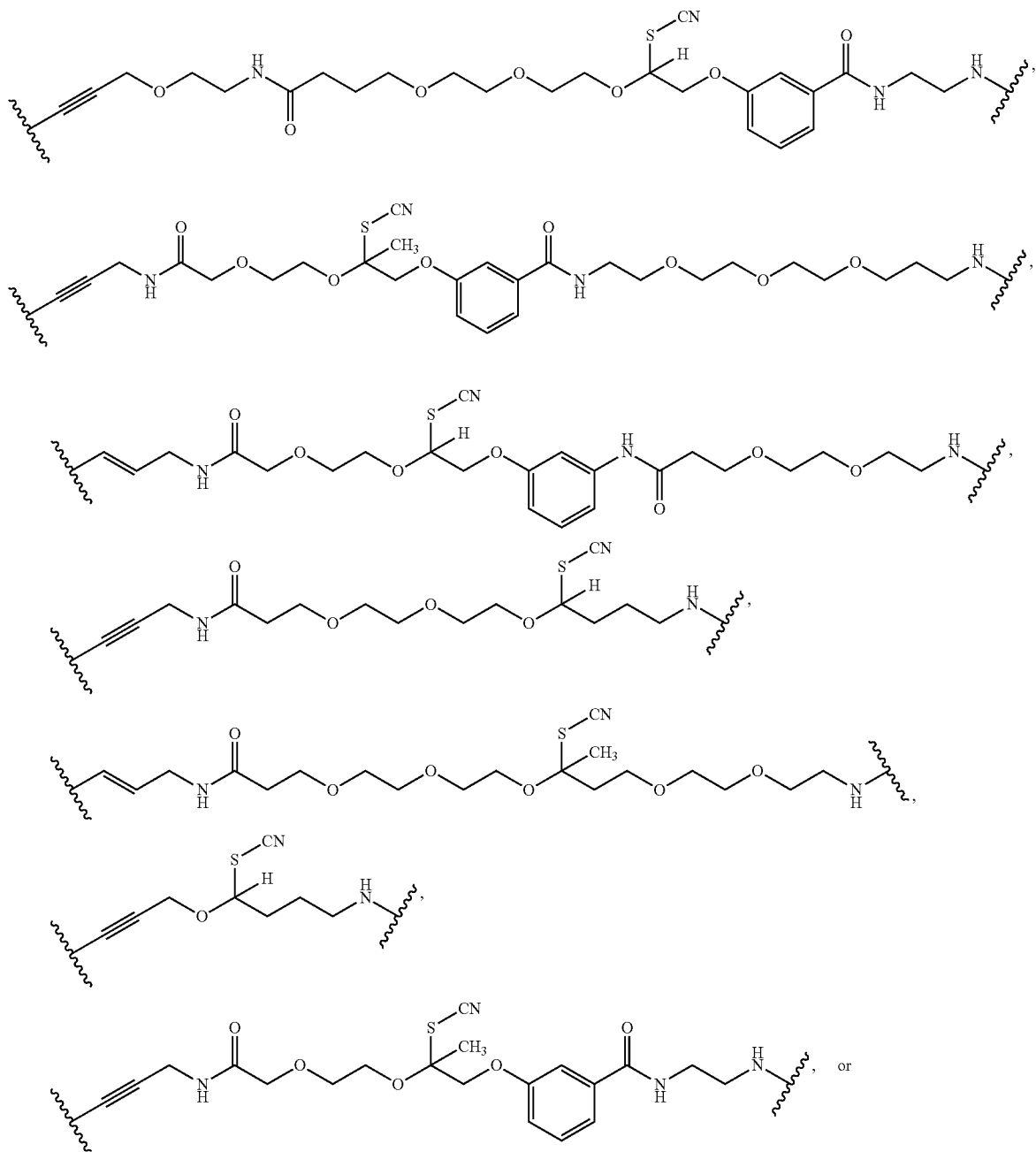

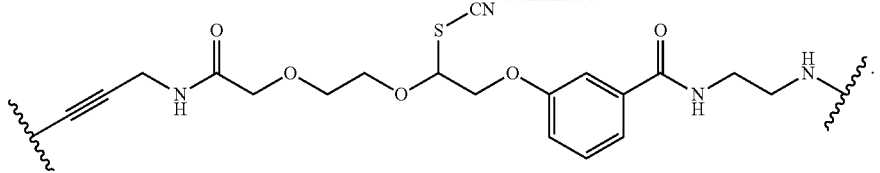
Embodiment 33. The compound of one of embodiments 19 to 20, wherein $L^{100}$ is
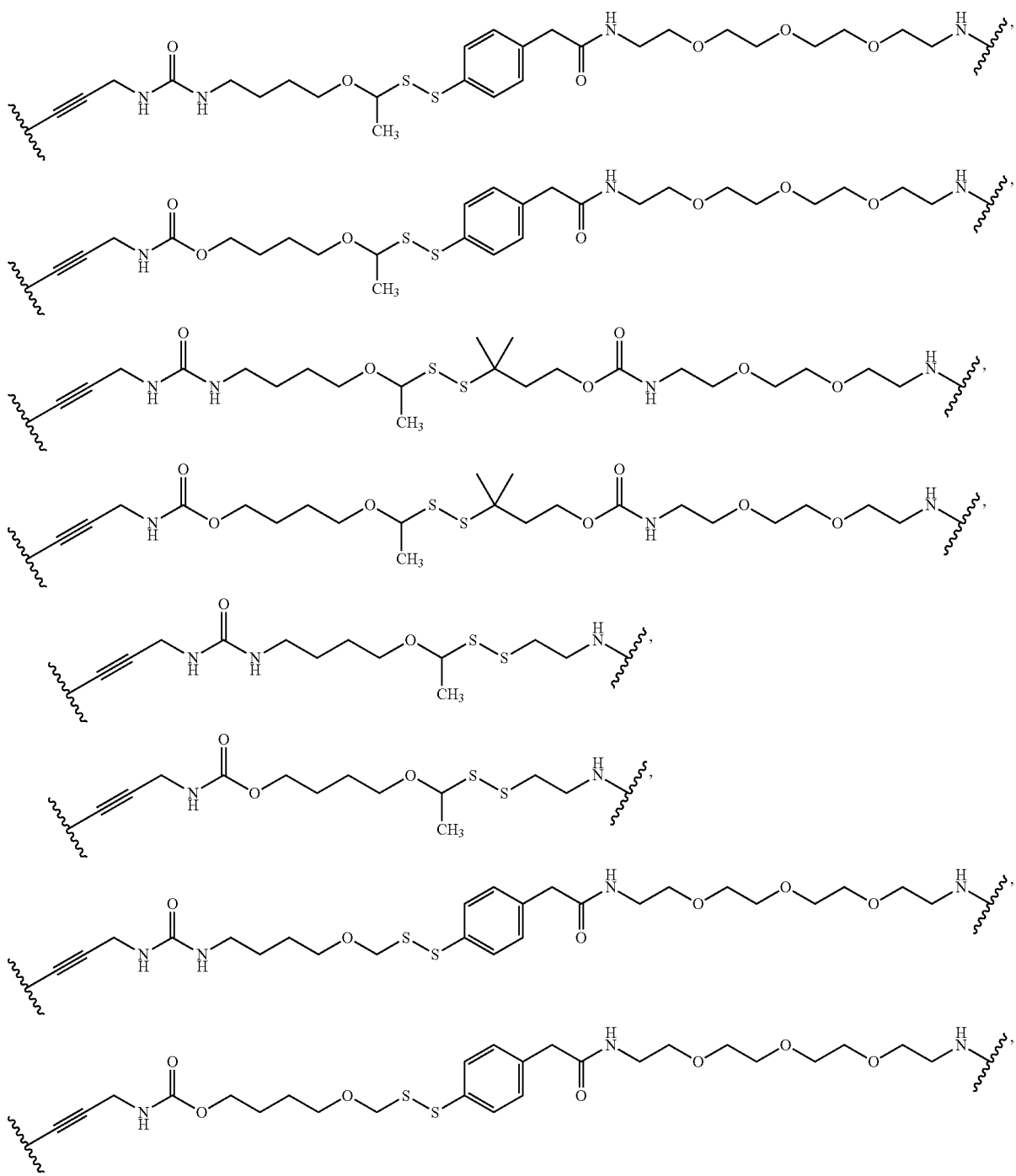

-continued
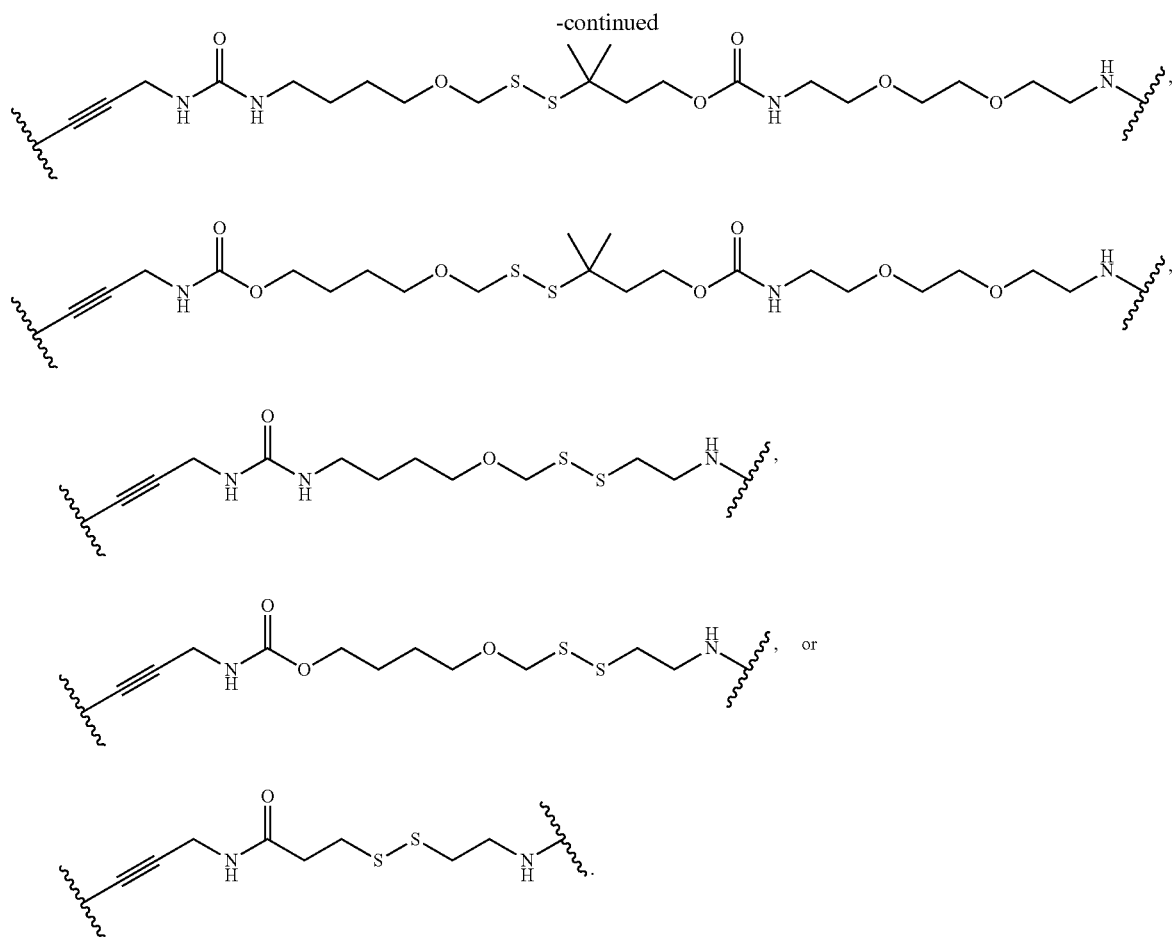
Embodiment 34. The compound of one of embodiments 19 to 20, wherein $R^{400}$ is
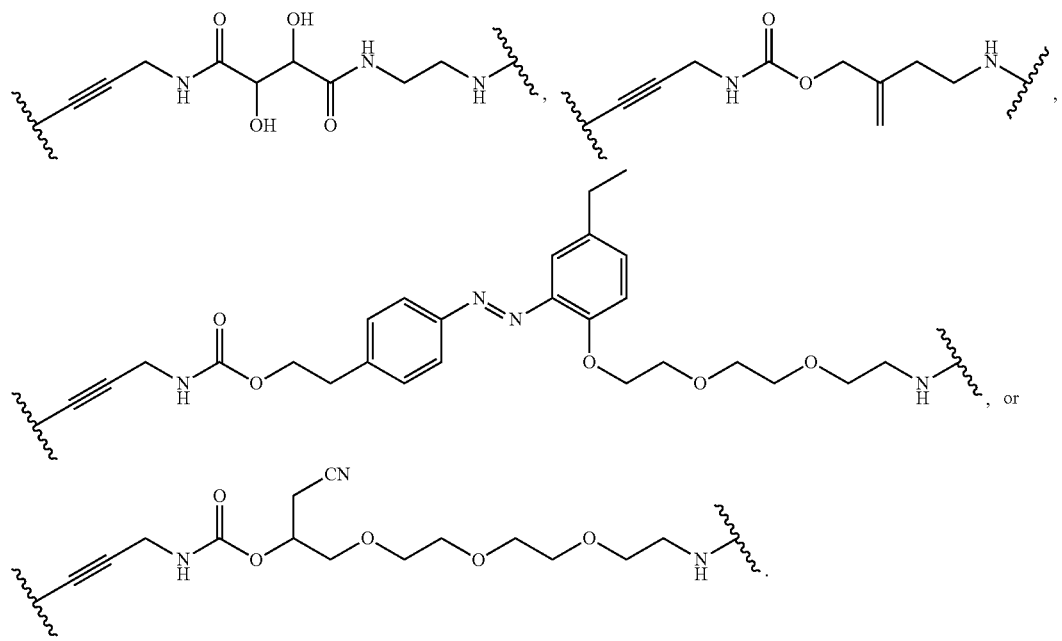

Embodiment 35. The compound of one of embodiments 19 to 34, wherein $R^4$ is a fluorescent dye moiety.

Embodiment 36. The compound of one of embodiments 19 to 34, wherein $R^4$ is

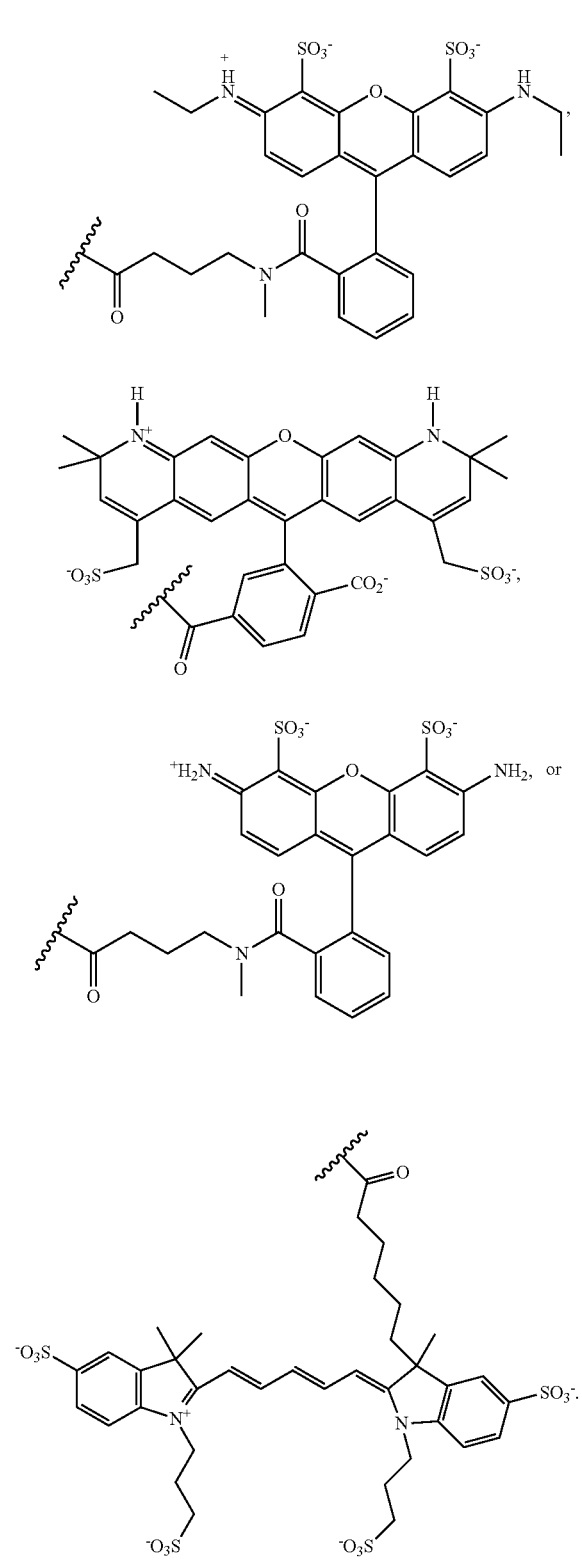

Embodiment 37. The compound of one of embodiments 19 to 36, having the formula:

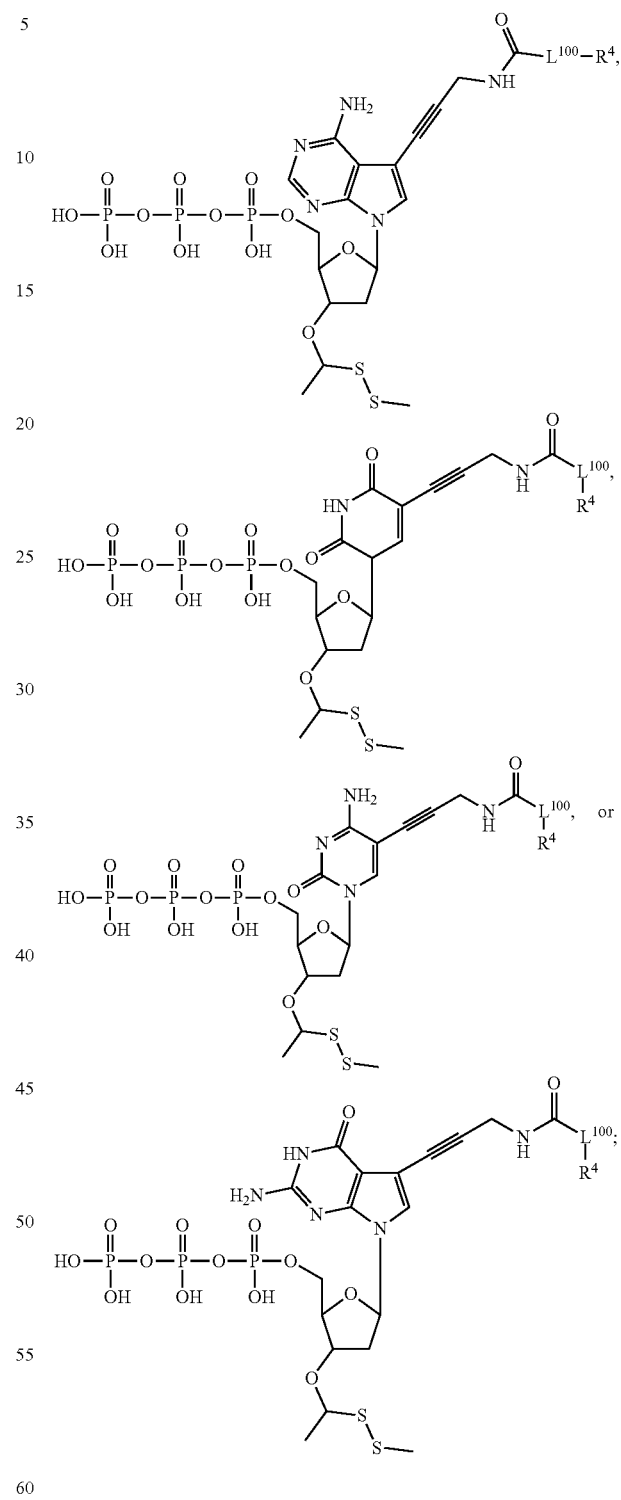

wherein $L^{100}$ is a cleavable linker.

Embodiment 38. A method for sequencing a nucleic acid, comprising:
(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;
(ii) detecting said unique detectable label of each incorporated compound, so as to thereby identify each incorporated compound in said extension strand, thereby sequencing the nucleic acid;
wherein each of said four different compounds is independently a compound of one of embodiments 1 to 37.

Embodiment 39. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of one of embodiments 1 to 37.

Embodiment 40. A nucleic acid polymerase complex comprising a nucleic acid polymerase, wherein said nucleic acid polymerase is bound to a compound of one of embodiments 1 to 37.

EXAMPLES

Example 1: Synthesis and Reaction Schemes

Methyldisulfanyl-Pyridine

The procedure for methyldisulfanyl-pyridine was adapted from the ethyldisulfanyl-pyridine procedure published in "A versatile post-synthetic method on a solid support for the synthesis of RNA containing reduction-responsive modifications" Organic & Biomolecular Chemistry 2016, vol. 14, pages 7010-7017.

Scheme 1

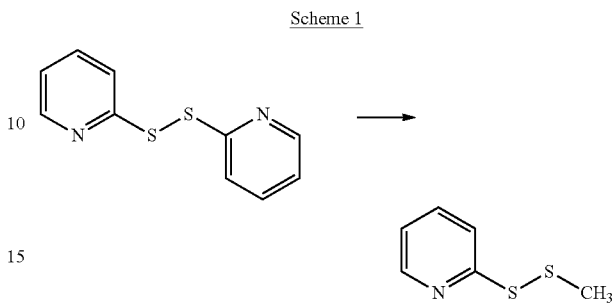

To a stirred solution of 2,2'-dithiodipyridine (0.66 g, 3 mmol) in methanol (16 mL), was added dropwise a solution of sodium methanethiolate (140 mg, 2 mmol) in methanol (4 mL). The yellow mixture was stirred under argon at room temperature for 30 minutes. The mixture was concentrated under reduced pressure. The crude material was purified by silica gel chromatography eluting with dichloromethane/methanol (99:1). $^1$HNMR (500 MHz, CDCl3) δ 8.45 (m, 1H), 7.64 (m, 2H), 7.06 (m, 1H), 2.48 (s, 3H). $^{13}$CNMR (125 MHz, CDCl3) δ 160.1, 149.9, 137.2, 120.7, 119.6, 23.1.

Scheme 2

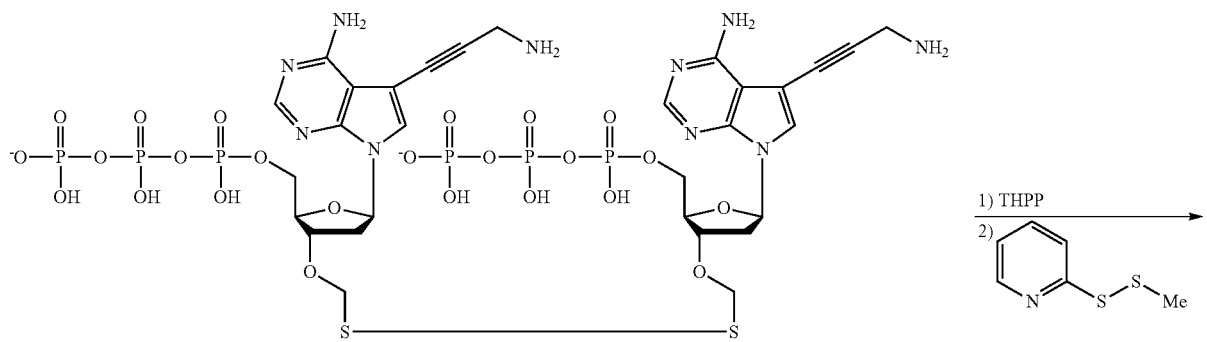

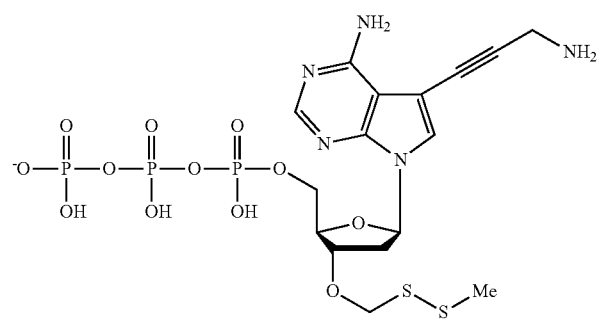

Scheme 2: Tris(hydroxypropyl)phosphine (THPP, 6 µL, 3 µmol, 0.5 M solution in water) was added to a solution of symmetrical dinucleotide (2 µmol, 105 µL, 19 mmol solution in water at room temperature. After 5 min an aliquot was removed and analyzed by C18 HPLC (MeCN/50 mM TEAA, 2:98 to 50:50 over 20 min). The intermediate "OCH2SH" slowly hydrolyzed and so methyldisulfanyl-pyridine (1 mg, 6 µmol) was added before the HPLC run finished. After 20 min the crude product was purified by semi-prep C18 HPLC (MeCN/50 mM TEAA, 2:98 to 40:60 over 40 min). The fraction eluting at 21 min was collected, concentrated and desalted on a plug of C18 (933 nmol, 47%). The structure was confirmed by LCMS [M−H]⁻ calculated 634 found 634.

Scheme 3: tBuSS_dATP_PA (10 µmol, 100 µL, 100 mM in water) was treated with THPP (20 uL, 0.5 M in water). After 5 min an aliquot was removed and checked by C18 HPLC (2:98 to 50:50 over 20 min). The intermediate "OCH2SH" slowly hydrolyzed and so methyldisulfanyl-pyridine (20 µL, 6 µmol) was added before the HPLC run finished. After 20 min the crude product was purified by semi-prep C18 HPLC (MeCN/50 mM TEAA, 2:98 to 40:60 over 40 min). The fraction eluting at 21 min was collected, concentrated and desalted on a plug of C18 (4.3 umol, 43%). The structure was confirmed by LCMS [M−H]⁻ calculated 634 found 634.

Scheme 3

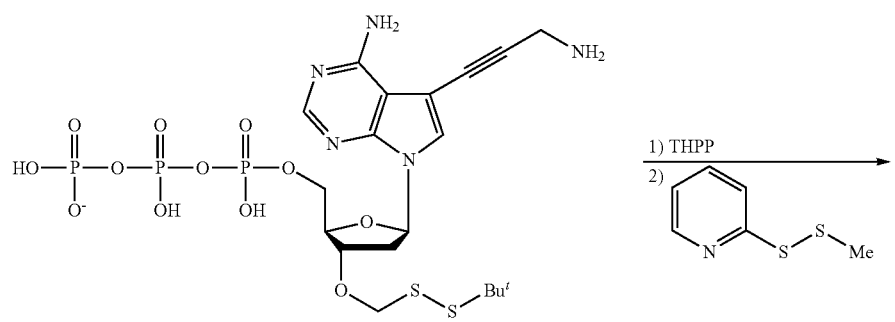

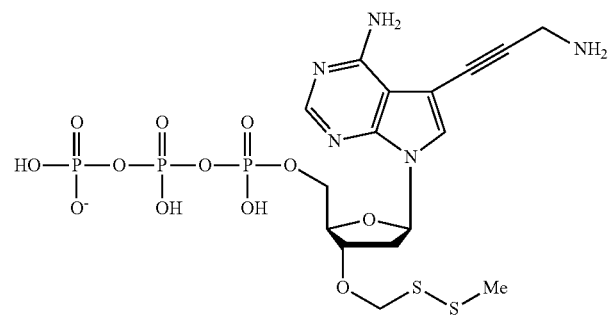

Scheme 4

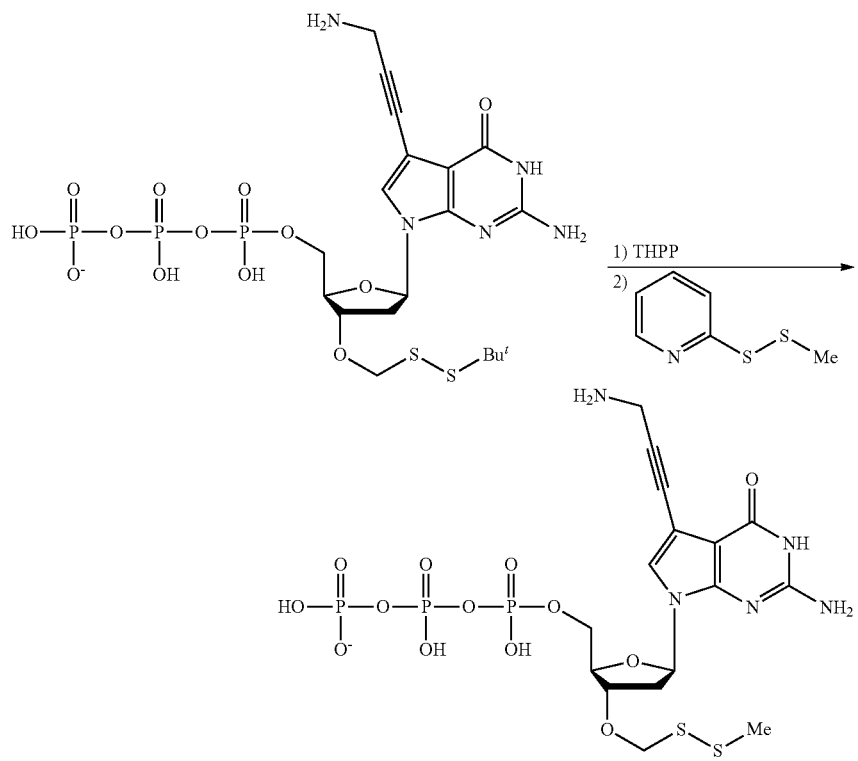

Scheme 4: tBuSS_dGTP_PA (12.7 µmol, 440 µL, 29 mM in water) was treated with THPP (12.7 µmol, 26 µL, 0.5 M in water). After 5 min an aliquot was removed and checked by C18 HPLC (2:98 to 50:50 over 20 min). The intermediate "OCH2SH" slowly hydrolyzed and so methyldisulfanyl-pyridine (2 mg, 13 µmol) was added before the HPLC run was finished. After 20 min the crude product was purified by semi-prep C18 HPLC (MeCN/50 mM TEAA, 2:98 to 40:60 over 60 min). The fraction eluting at 30 min was collected, concentrated and desalted on a plug of C18 (3.6 µmol, 28%). The structure was confirmed by LCMS [M−H]− calculated 650 found 650.

Scheme 5

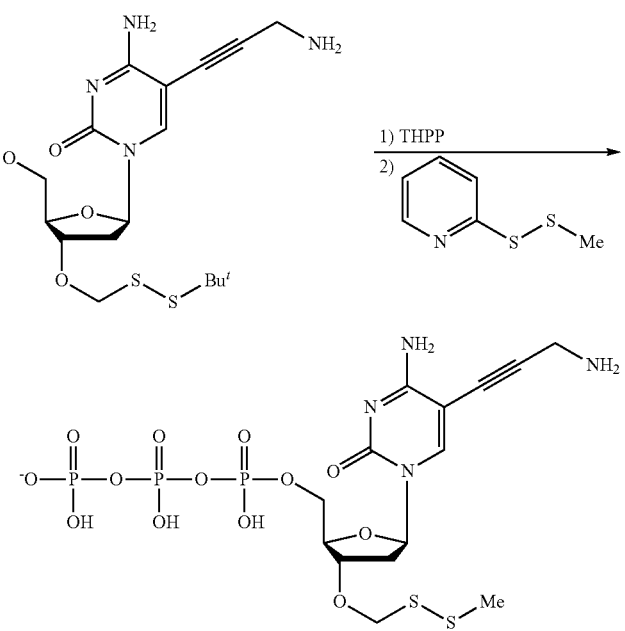

Scheme 5: tBuSS_dCTP_PA (5 μmol, 100 μL, 50 mM in water) was treated with THPP (5 μmol, 10 μL, 0.5 M in water). After 5 min an aliquot was removed and checked by C18 HPLC (2:98 to 50:50 over 20 min). The intermediate "OCH2SH" slowly hydrolyzed and so methyldisulfanyl-pyridine (2 mg, 13 μmol) was added before the HPLC run was finished. After 20 min the crude product was purified by semi-prep C18 HPLC (MeCN/50 mM TEAA, 2:98 to 40:60 over 60 min). The fraction eluting at 28 min was collected, concentrated and desalted on a plug of C18 (2 μmol, 20%).

The structure was confirmed by LCMS [M−H] calculated 611 found 611.

Example 2: Intermediate Formation

THPP cleavage of SS may proceed via the "SH" intermediate. The "SH" intermediate could be trapped before it 3′ MeSS. The stability of the 3′ tBuSS may be controlled by protecting group cleavage conditions and the 3′ tBuSS may be converted into 3′ MeSS afterwards.

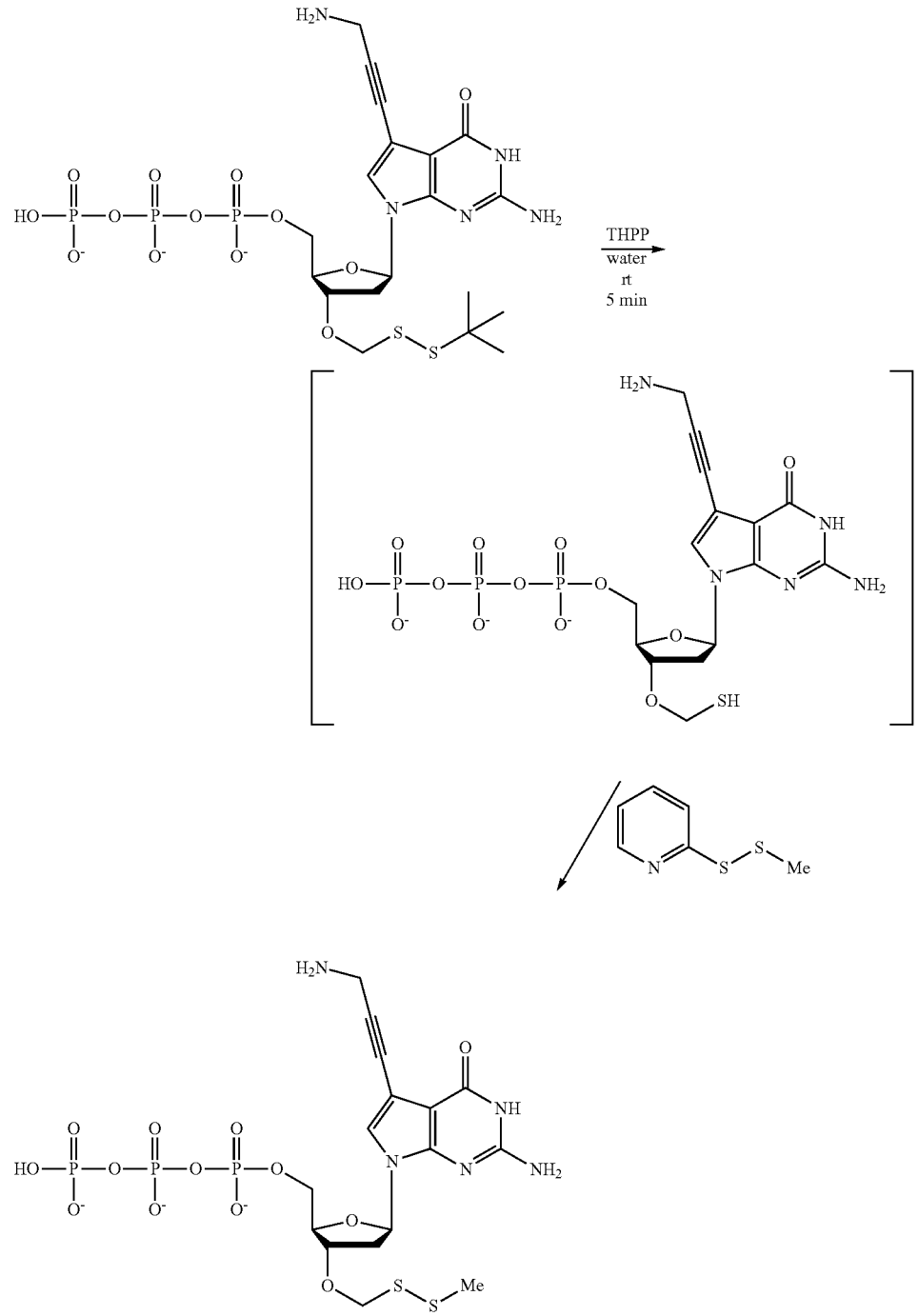

Scheme 6

Scheme 6 shows an intermediate formation from the reaction of Scheme 4.
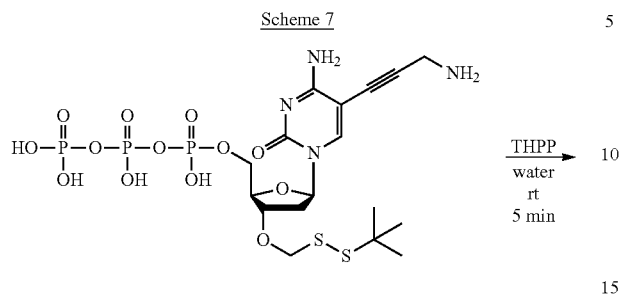
Scheme 7
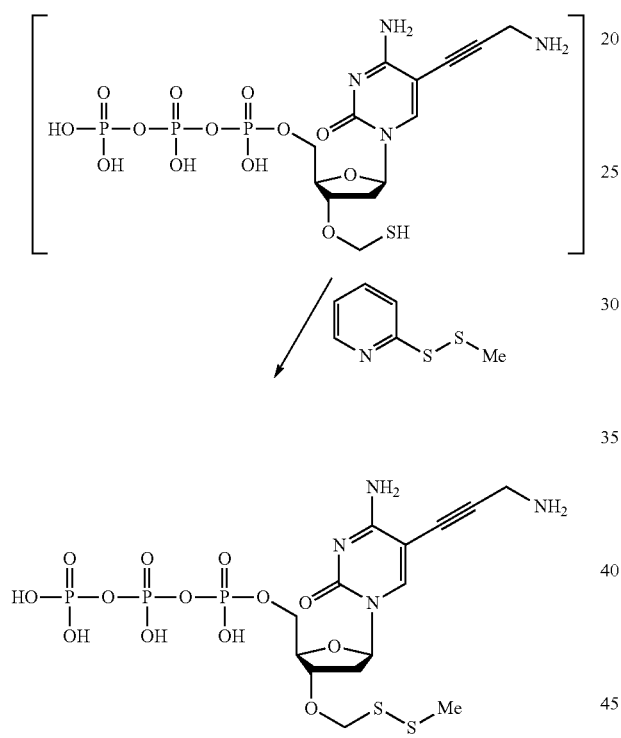
Scheme 7 shows an intermediate formation from the reaction of Scheme 5.
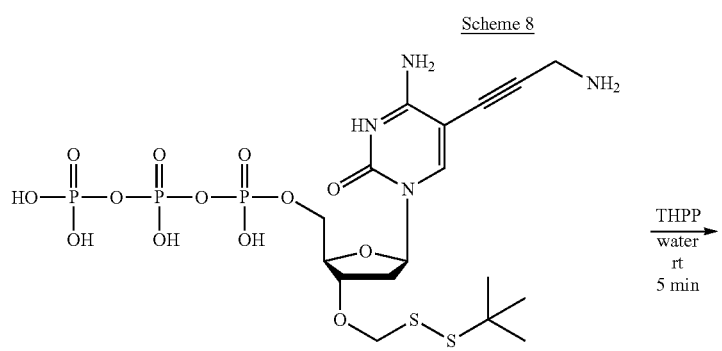
Scheme 8

-continued
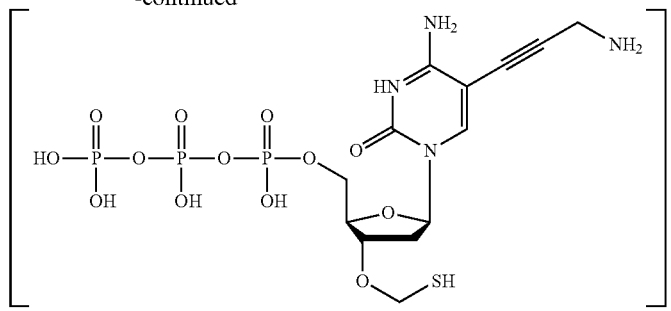
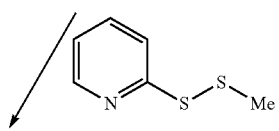
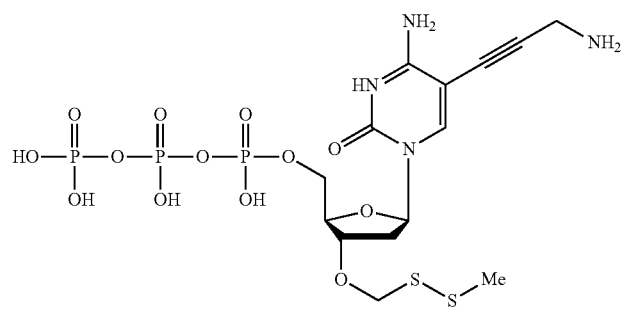
Scheme 8 shows an exemplary intermediate formation.
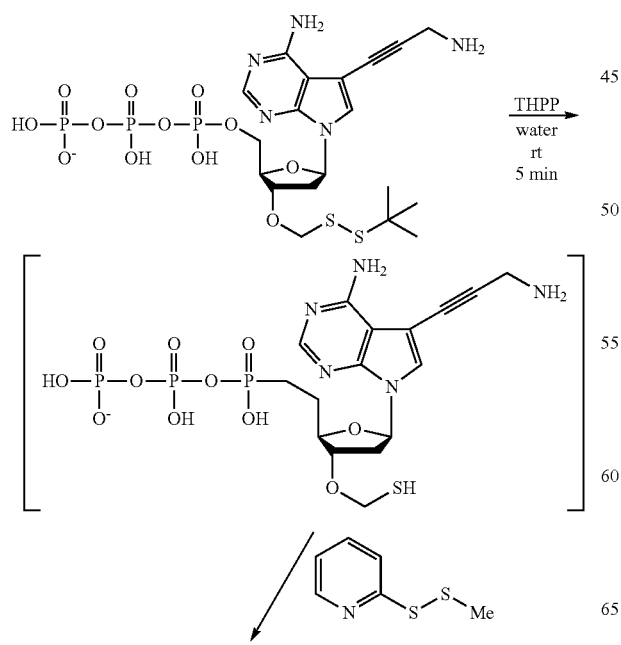

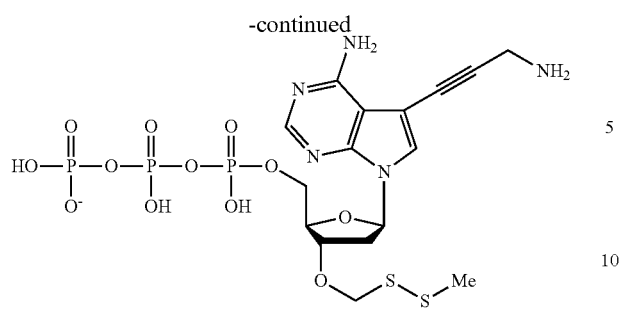
Scheme 9 shows an intermediate formation from the reaction of Scheme 3.
Example 3: Dimer Formation
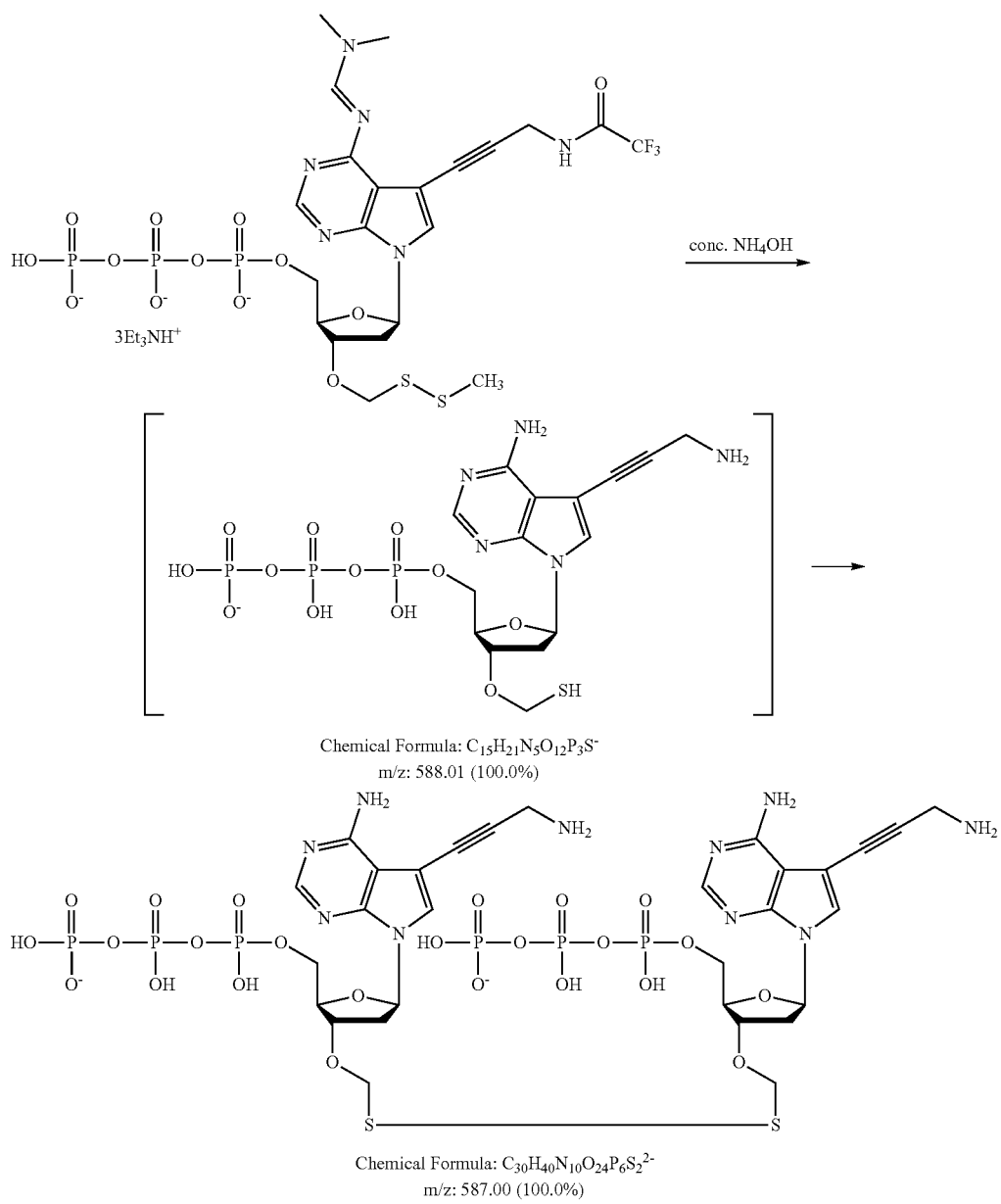

Dissolve anhydrous bis(tributylammonium) pyrophosphate (99 mg, 180 μmol) in anhydrous acetonitrile (200 μL) and tributylamine (72 μL, 300 μmol). Dissolve salicyl chlorophosphite (37 mg, 180 μmol) in anhydrous acetonitrile (100 μL) and transfer dropwise the pyrophosphate solution. Stir 20 min. Transfer the solution dropwise to 3'MeSS_dA (dmf)_PA(tfa) (33 mg, 60 mmol) dissolved in anhydrous acetonitrile (200 μL). After stirring 60 min add iodine solution (1 mL, 0.05% in 9:1 pyridine/water) and then add triethylammonium bicarbonate solution (1 mL, 1 M). Stir overnight. Evaporate the buffer, acetonitrile and pyridine. Triturate the residue with ethyl ether (3×10 mL) to remove salicylic acid. Add concentrated ammonium hydroxide (3 mL, 30%) and stir 1 hour. Evaporate the ammonium hydroxide. Dissolve the residue in water and purify by C18 reverse phase HPLC (MeCN/50 mM TEAA, 2:98 to 40:60 over 60 min). Collect the fraction eluting from 22 to 23 minutes. Yield 3.8 μmol, 6%. LCMS calculated 587.0 [m/2z]⁻, observed 587.1 [m/2z]⁻. The structures of the intermediates with 3' MeSH and the dimer were confirmed by LCMS [M–H].

Scheme 11

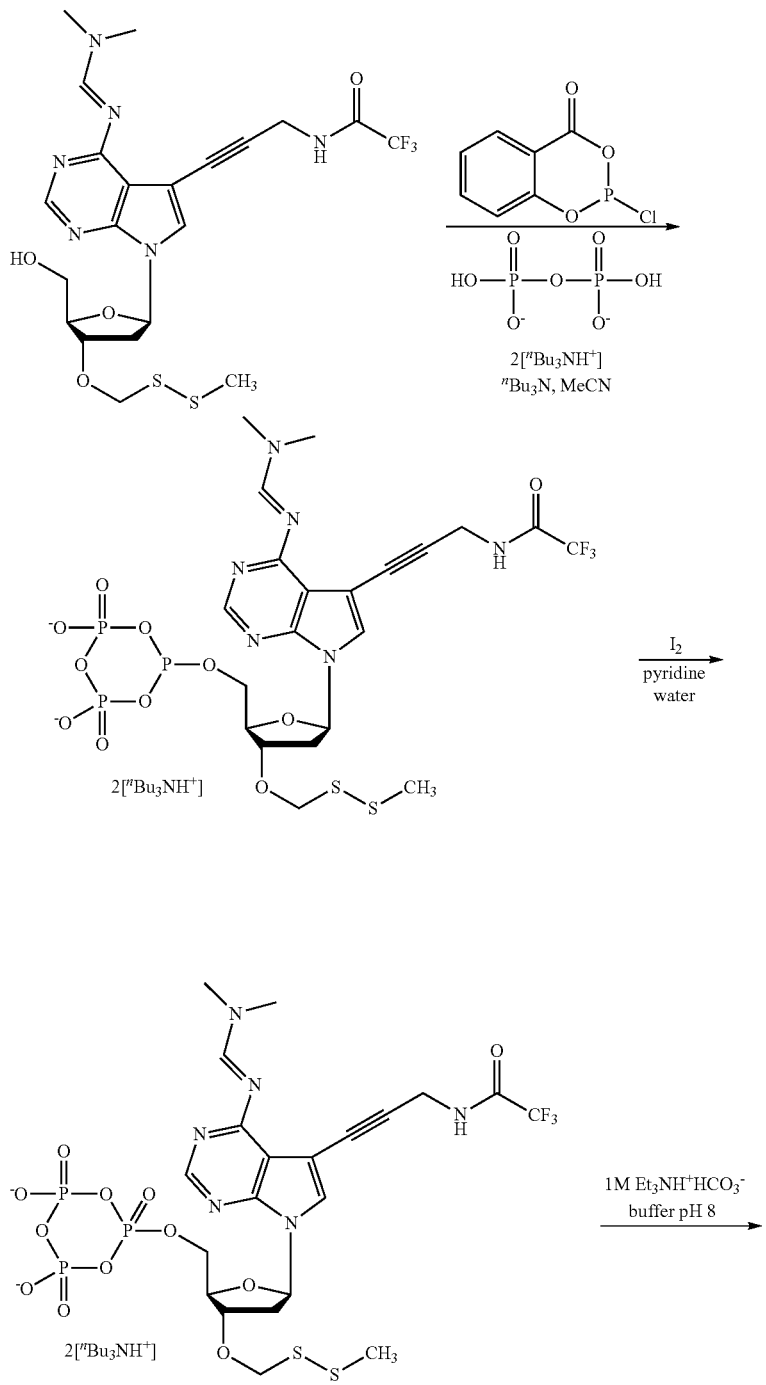

-continued
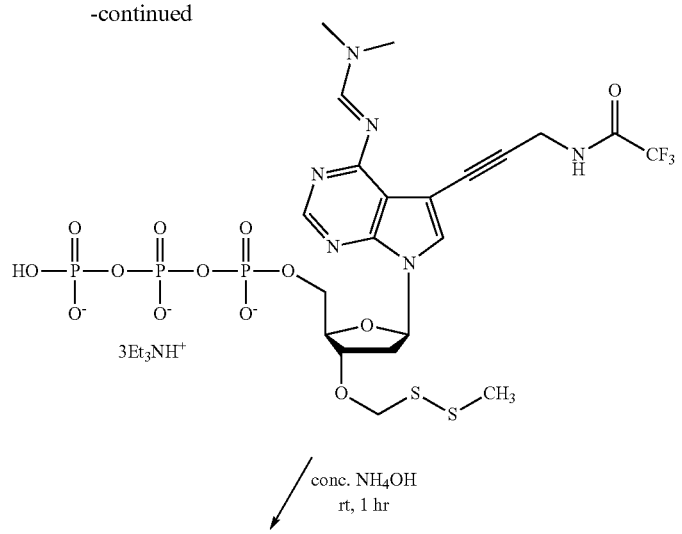
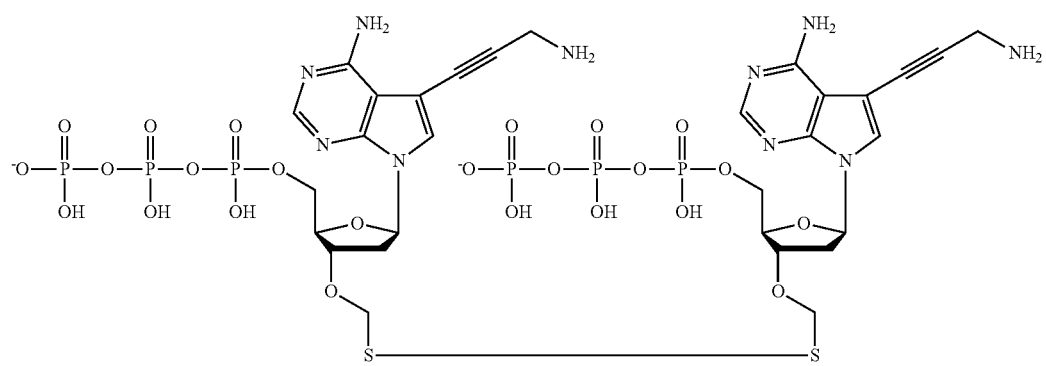
Scheme 11 shows synthetic procedure forming the dimer.
Scheme 12
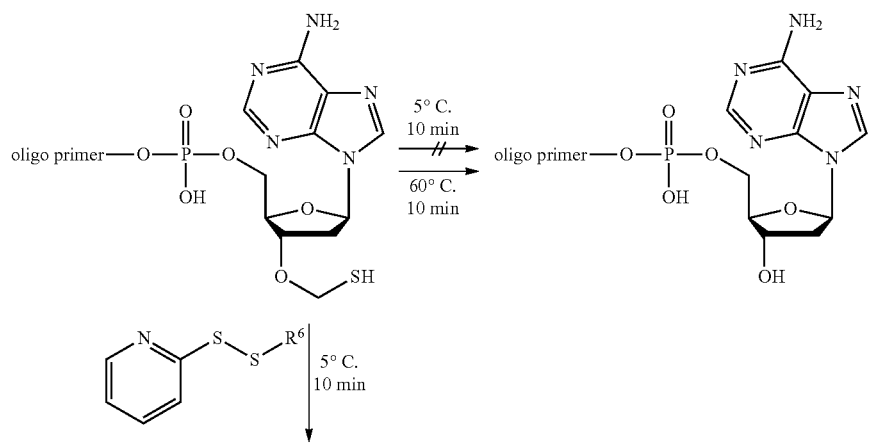

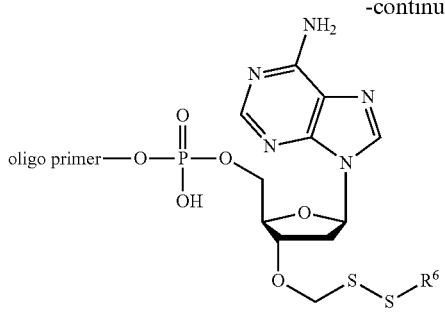

Scheme 12 shows synthetic procedure forming a nucleic acid including an oligo primer and a nucleotide including 3'-O—CH$_2$—S—SR that cleaves to 3' OH over 10 min when at 60° C.

Example 4: Synthesis of Labeled Nucleosides

The process for using polymerase-compatible cleavable moiety containing molecules generally involves incorporation of a labeled nucleotide analog into the growing polynucleotide chain, followed by detection of the label, then cleavage of the nucleotide analog to remove the covalent modification blocking continued synthesis (e.g., polymerase-compatible cleavable moiety). The cleaving step may be accomplished using an enzyme or by chemical cleavage. Modifications of nucleotides may be made on the 5' terminal phosphate or the 3' hydroxyl group. Developing a truly reversible set of nucleotide terminators has been a goal for many years. Despite the recent advances only a few solutions have been presented, most of which cause other problems, including inefficient or incomplete incorporation by the polymerase, inefficient or incomplete cleavage of the removable group, or harsh conditions needed to for the cleaving step causing spurious problems with the remainder of the assay and/or fidelity of the target sequence. Disclosed herein is a new class of fluorescently labeled nucleotides that include a methyl disulfanyl moiety bonded to the 3' oxygen,

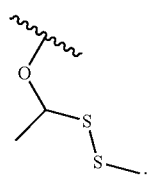 [SMILES: *OC(C)SSC ; "."]

Scheme 13. Part 1 of 2 MeSS_CHCH3_dAPT scheme

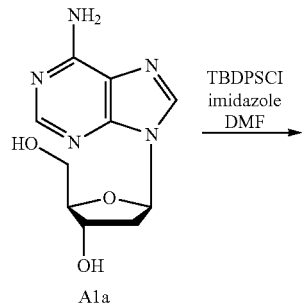

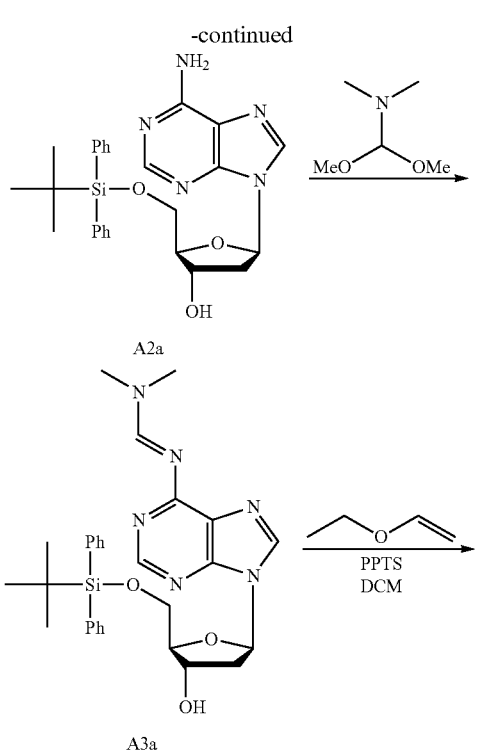

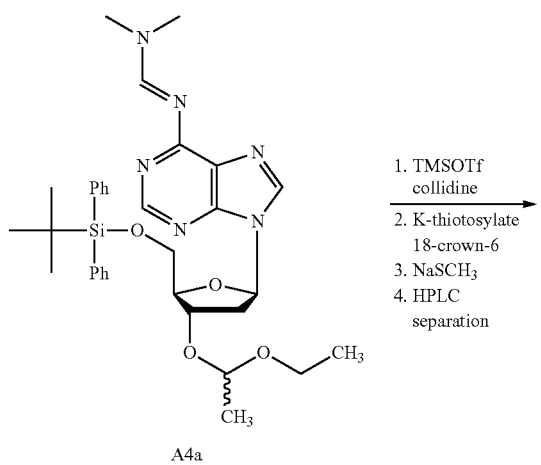

549
-continued
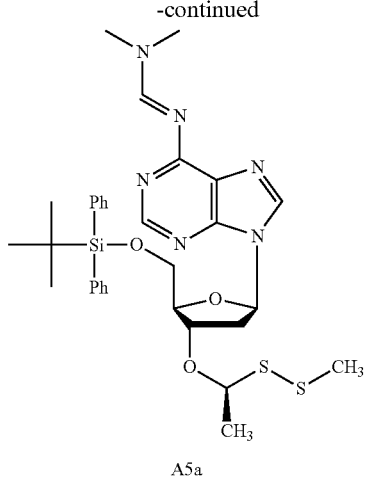
A5a
+
550
-continued
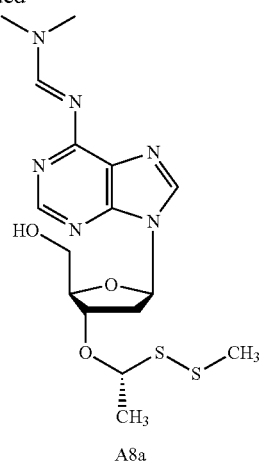
A8a
Scheme 14. Part 2 of 2 MeSS_CHCH3_dATP scheme
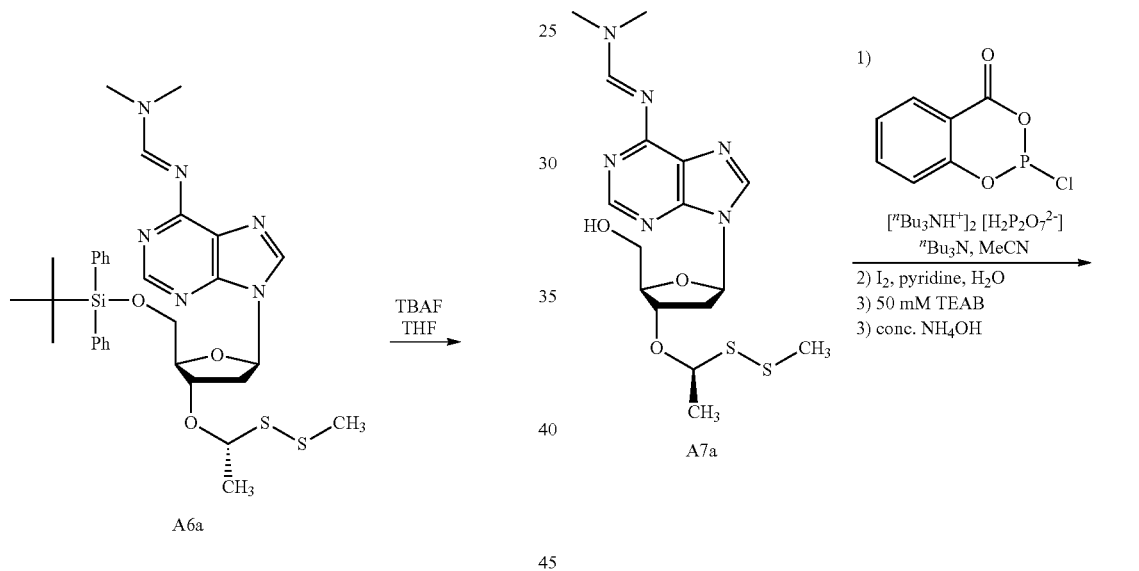
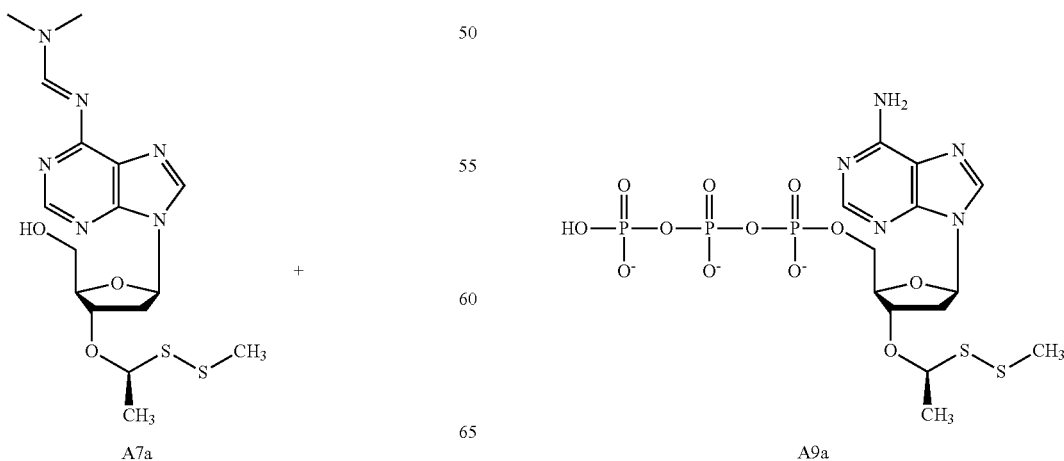

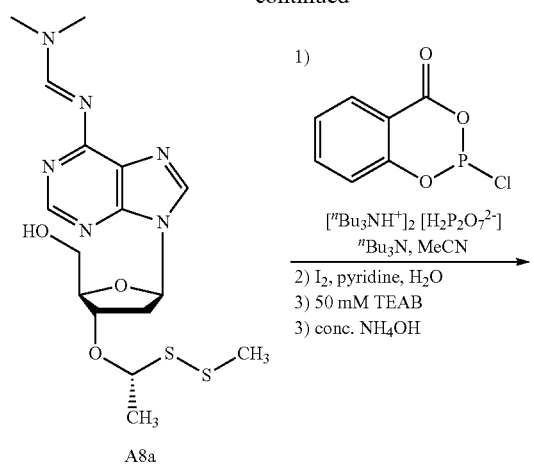
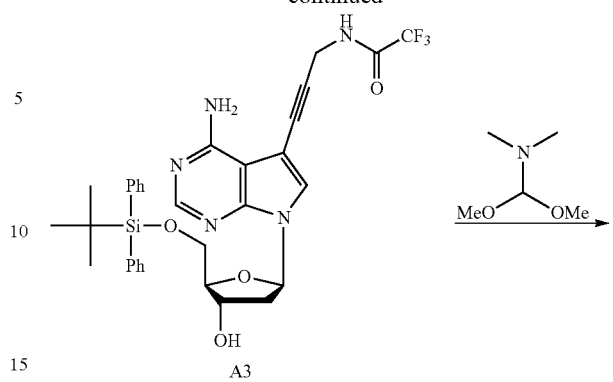
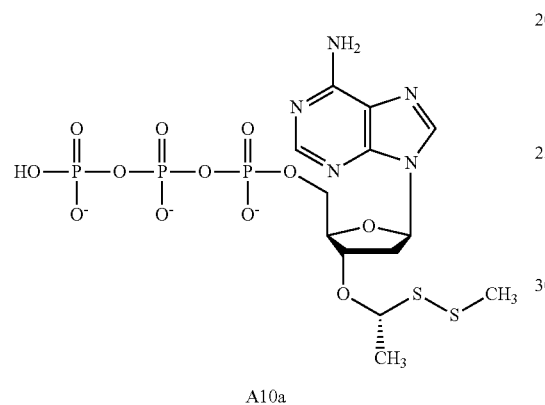
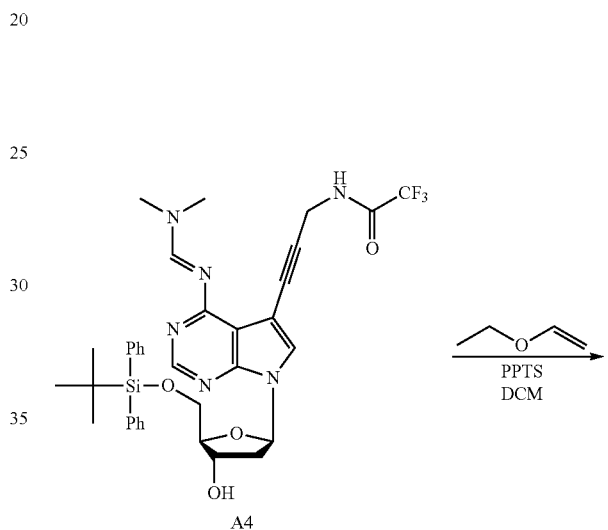
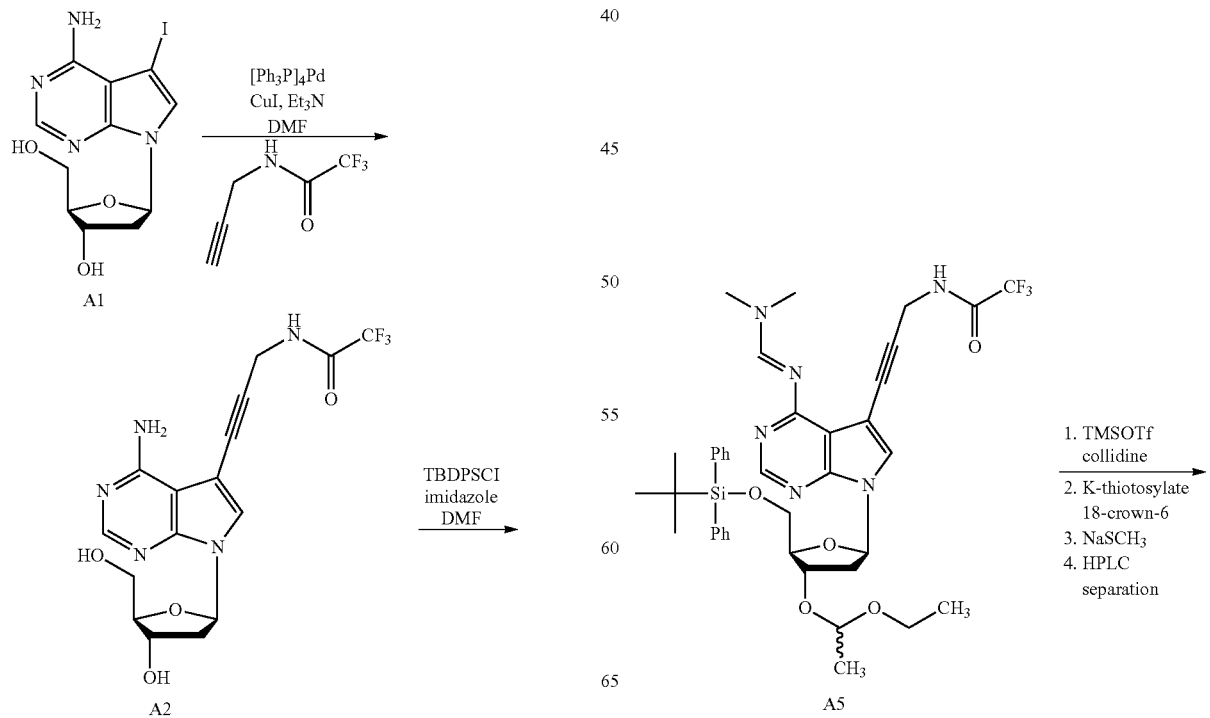

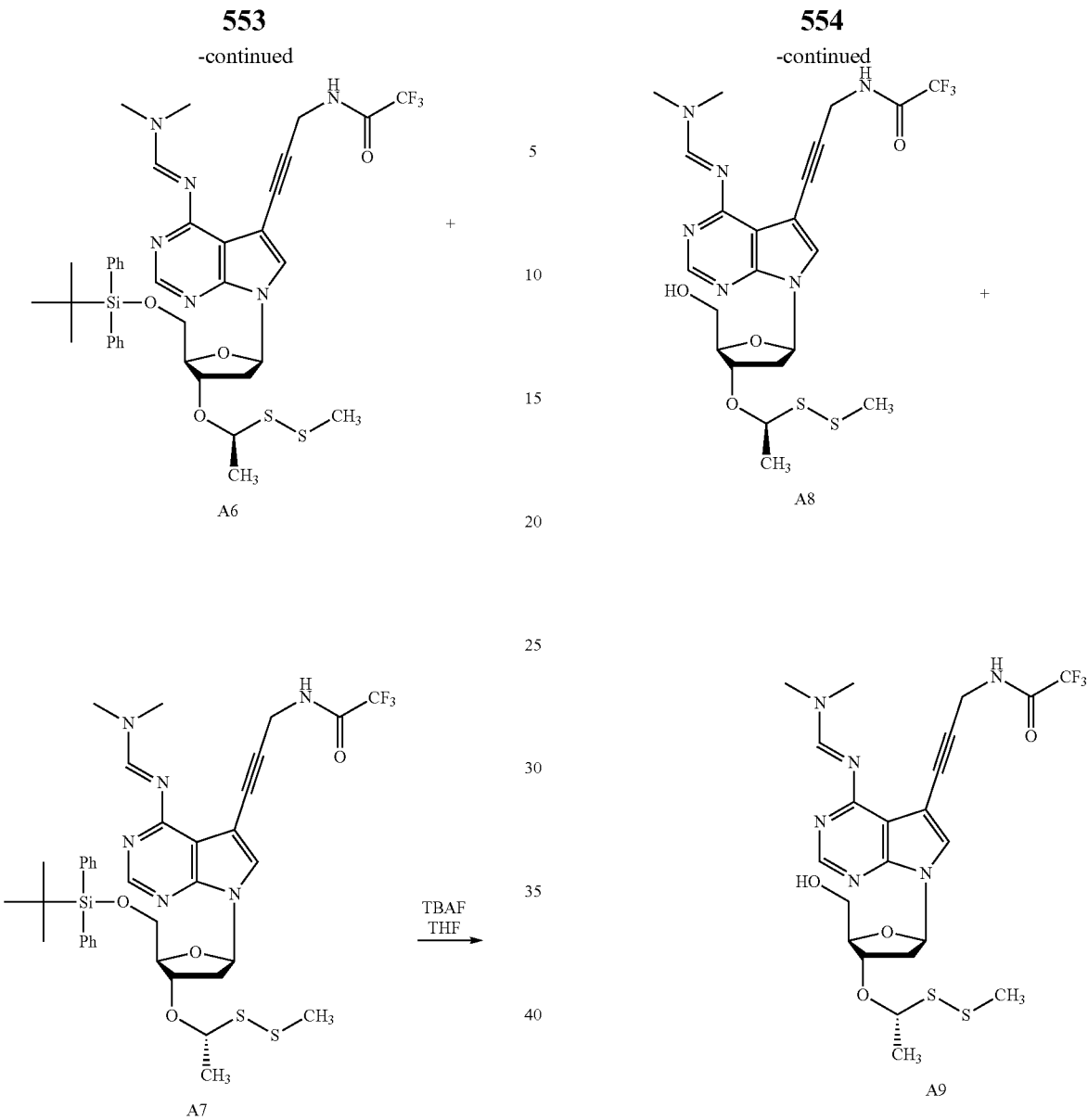
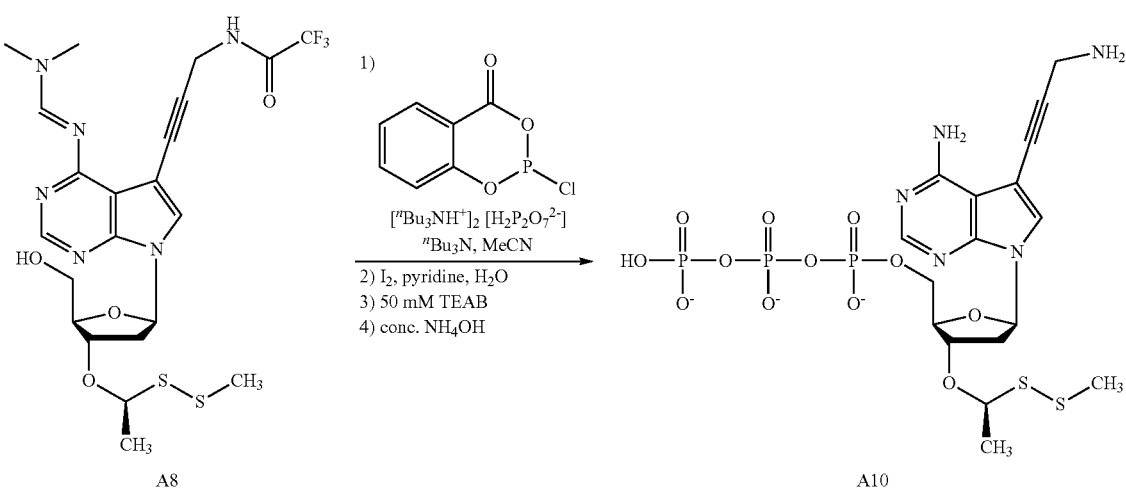
Scheme 16. Part 2 of 5 MeSS_CHCH3_dATP_N3 linker scheme 555 556
-continued
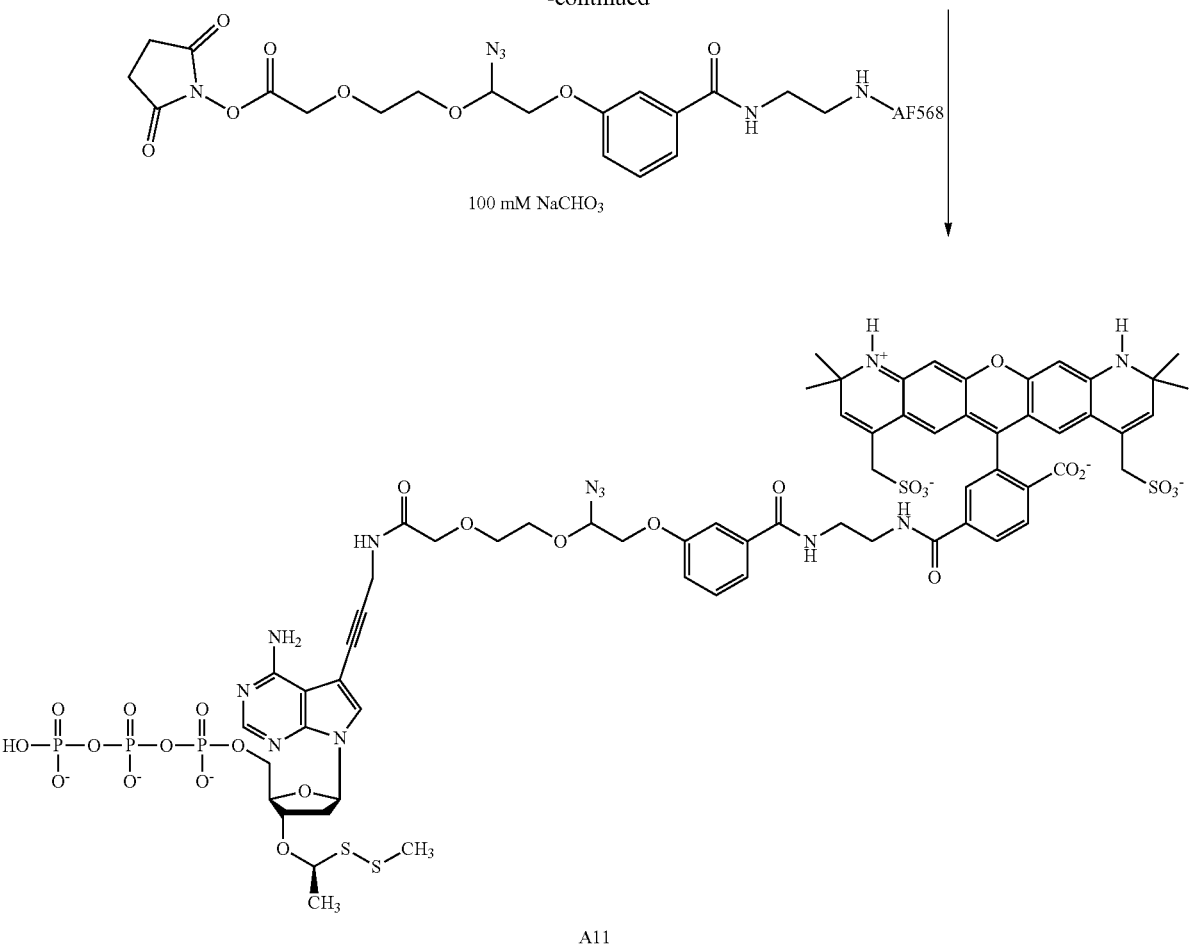
Scheme 17. Part 3 of 5 MeSS_CHCH3_dATP_N3 linker scheme
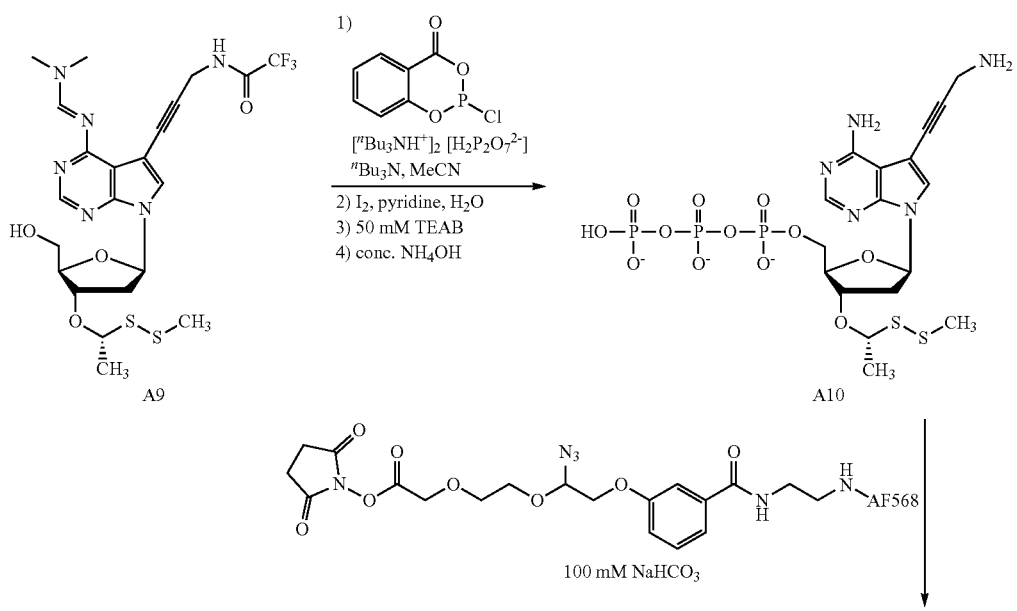

-continued
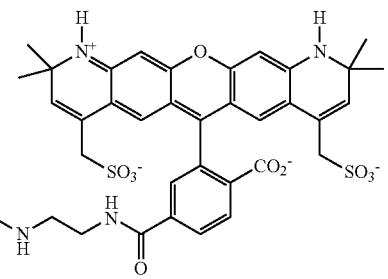
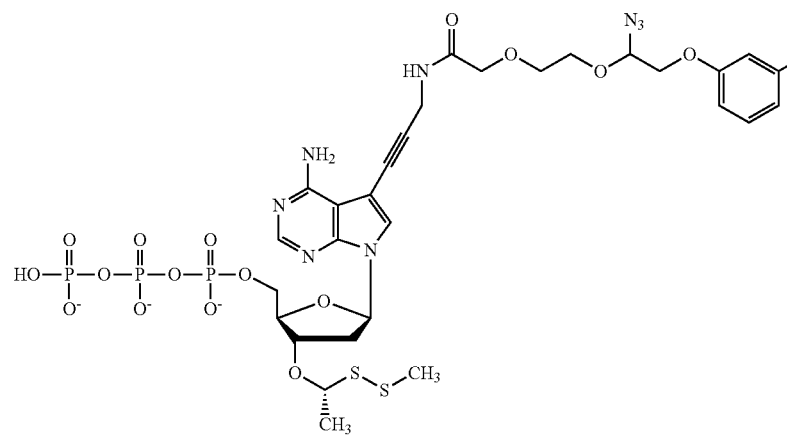
A13
Scheme 18. Part 4 of 5 MeSS_CHCH3_dATP_thio -trigger containing linker scheme
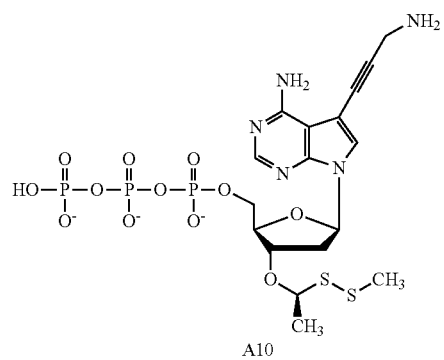
A10
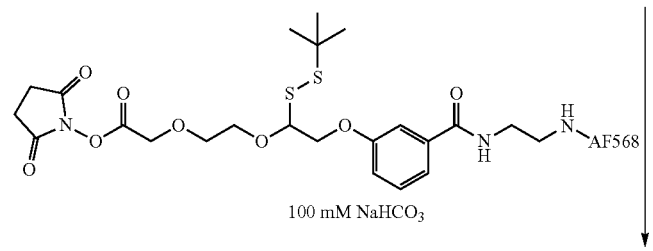
100 mM NaHCO₃

-continued
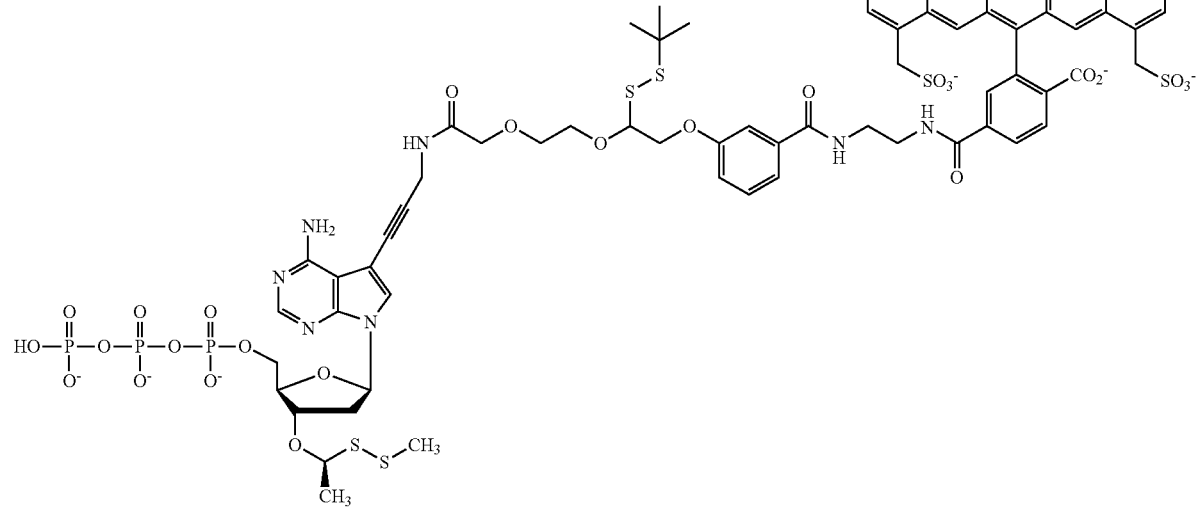
A14
Scheme 19. Part 5 of 5 MeSS_CHCH3_dATP_thio -trigger containing linker scheme
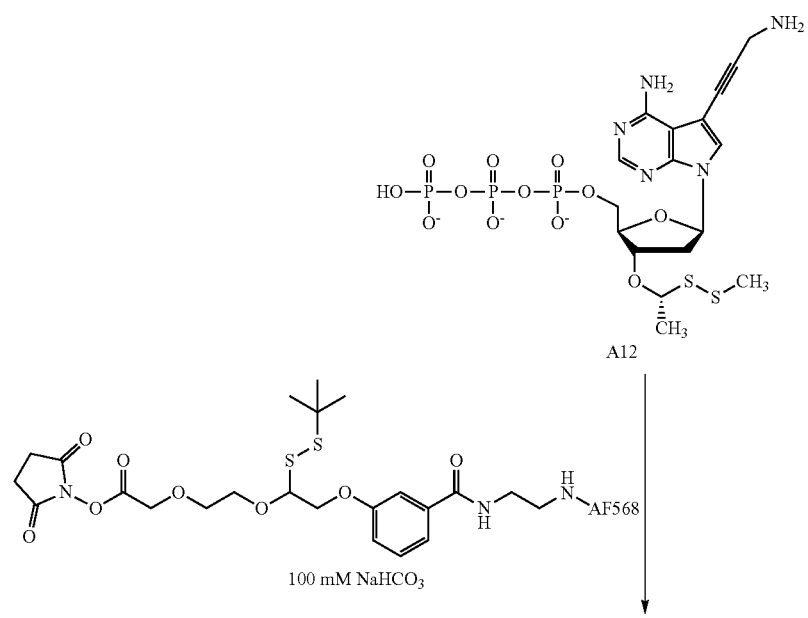
A12
100 mM NaHCO₃

-continued
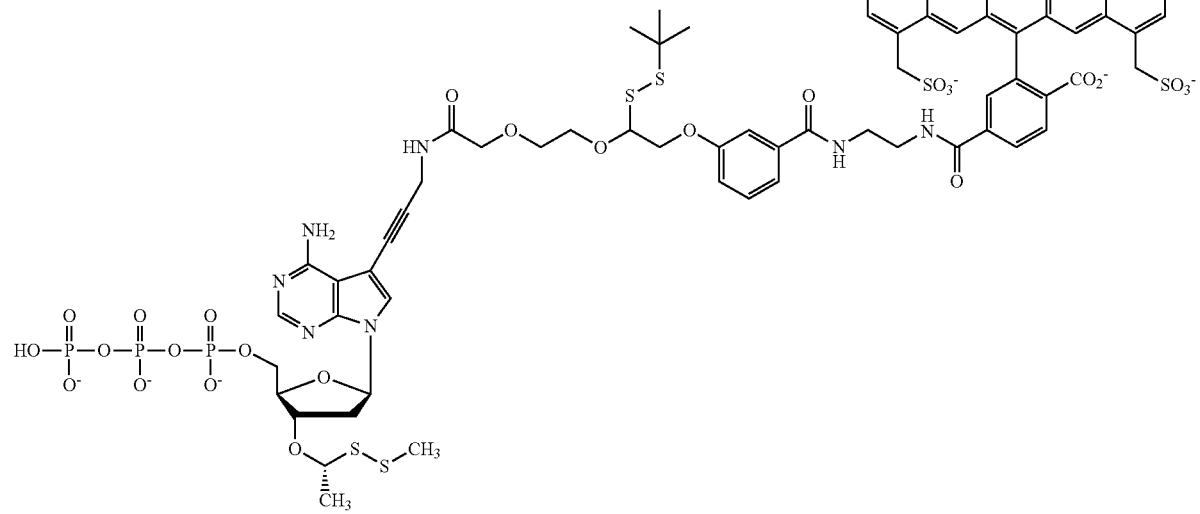
A15
Scheme 20. Part 1 of 2 MeSS_CHCH3_dCTP scheme
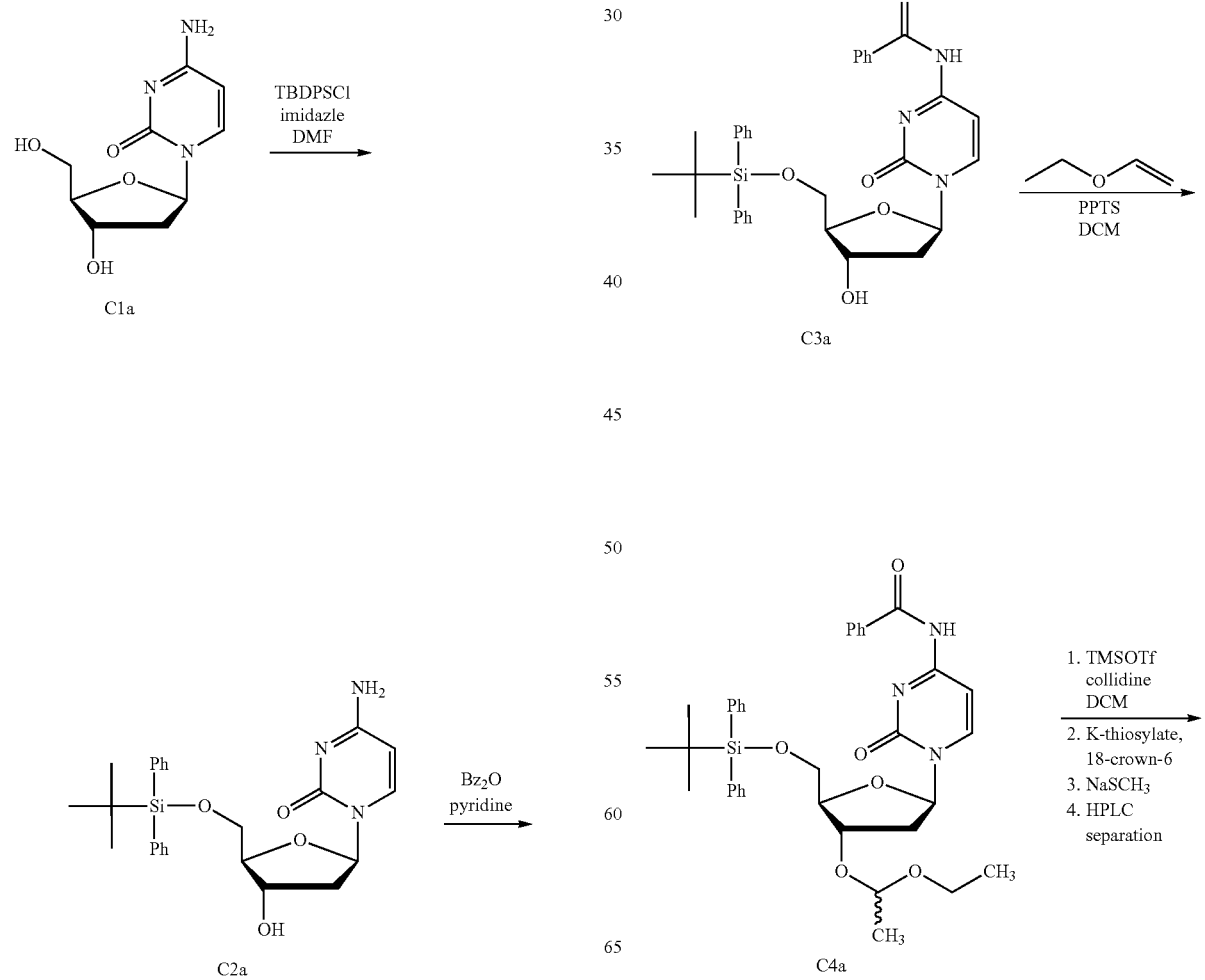

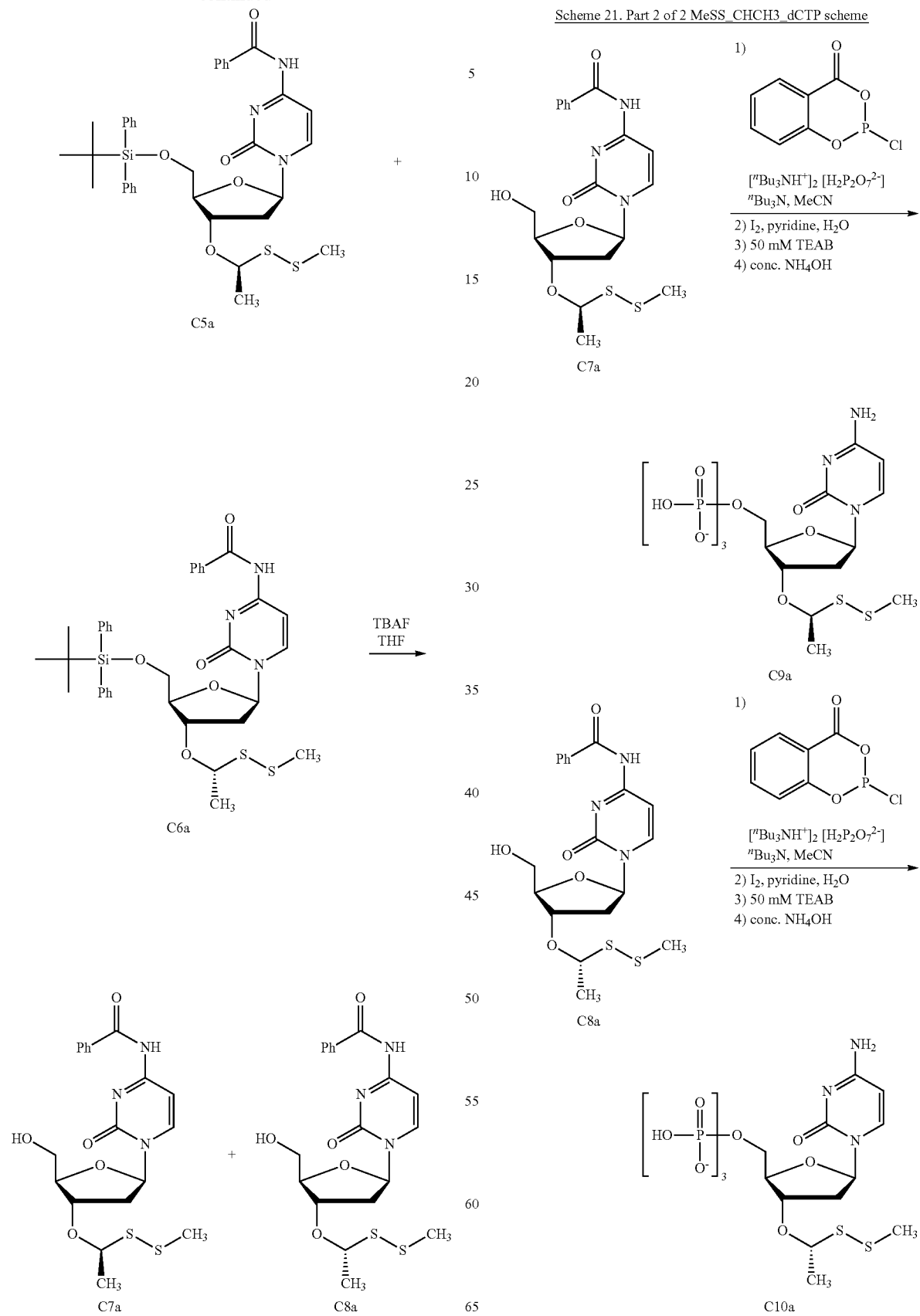
Scheme 21. Part 2 of 2 MeSS_CHCH3_dCTP scheme

Scheme 22. Part 1 of 5 MeSS_CHCH3_dCTP_N3 linker scheme
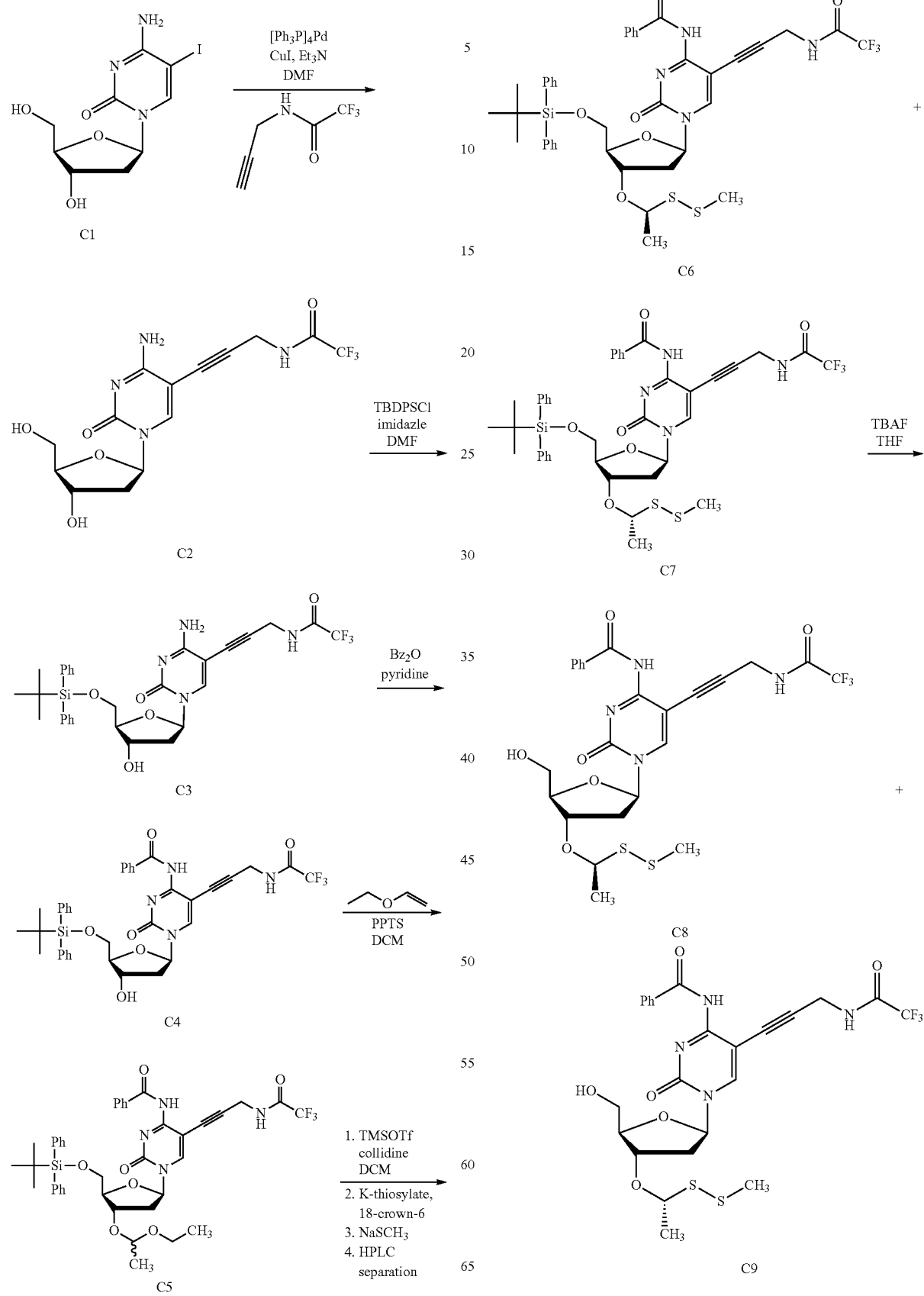

Scheme 23. Part 2 of 5 MeSS_CHCH3_dCTP_N3 linker scheme
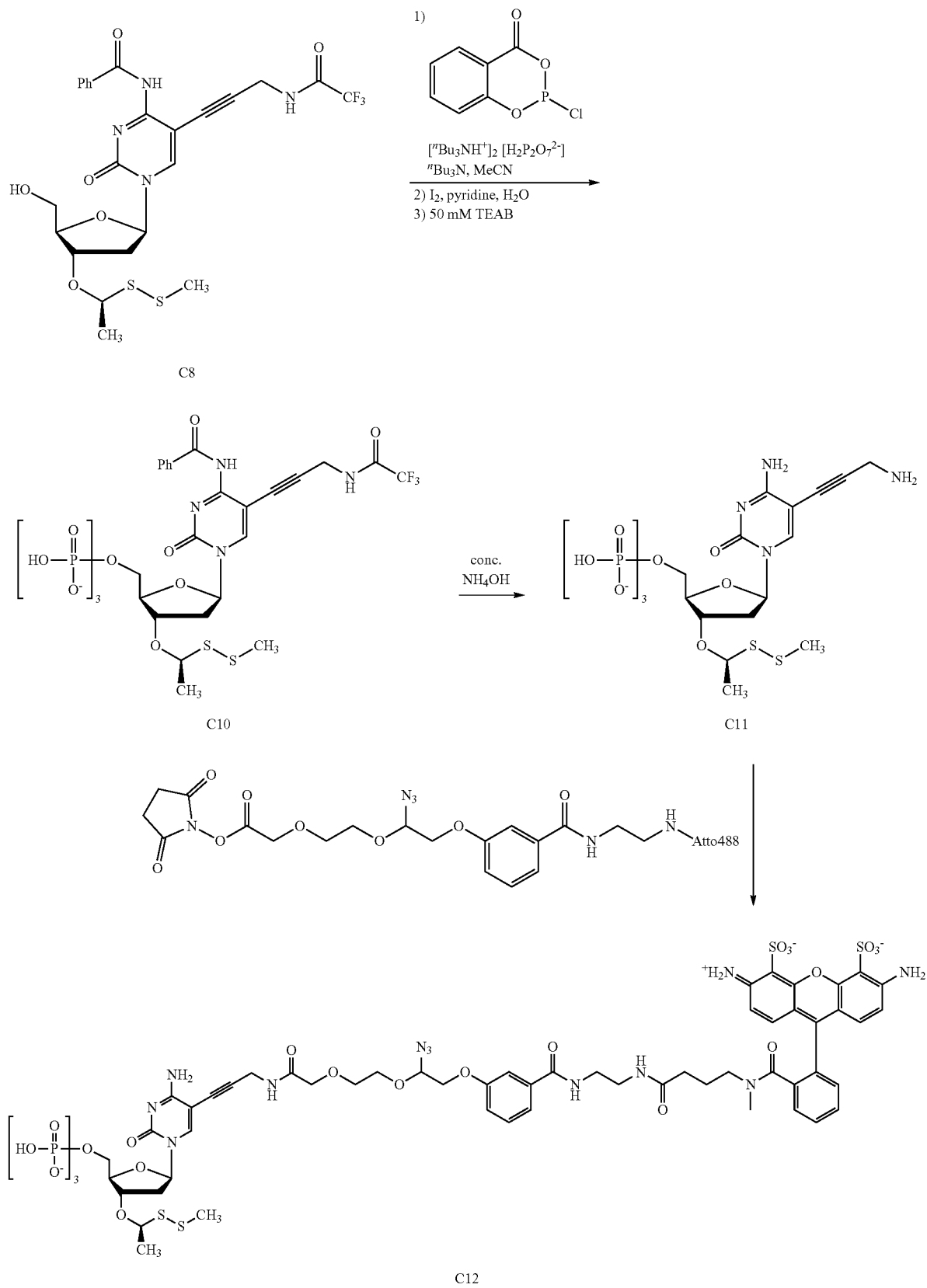

Scheme 24. Part 3 of 5 MeSS_CHCH3_dCTP_N3 linker scheme
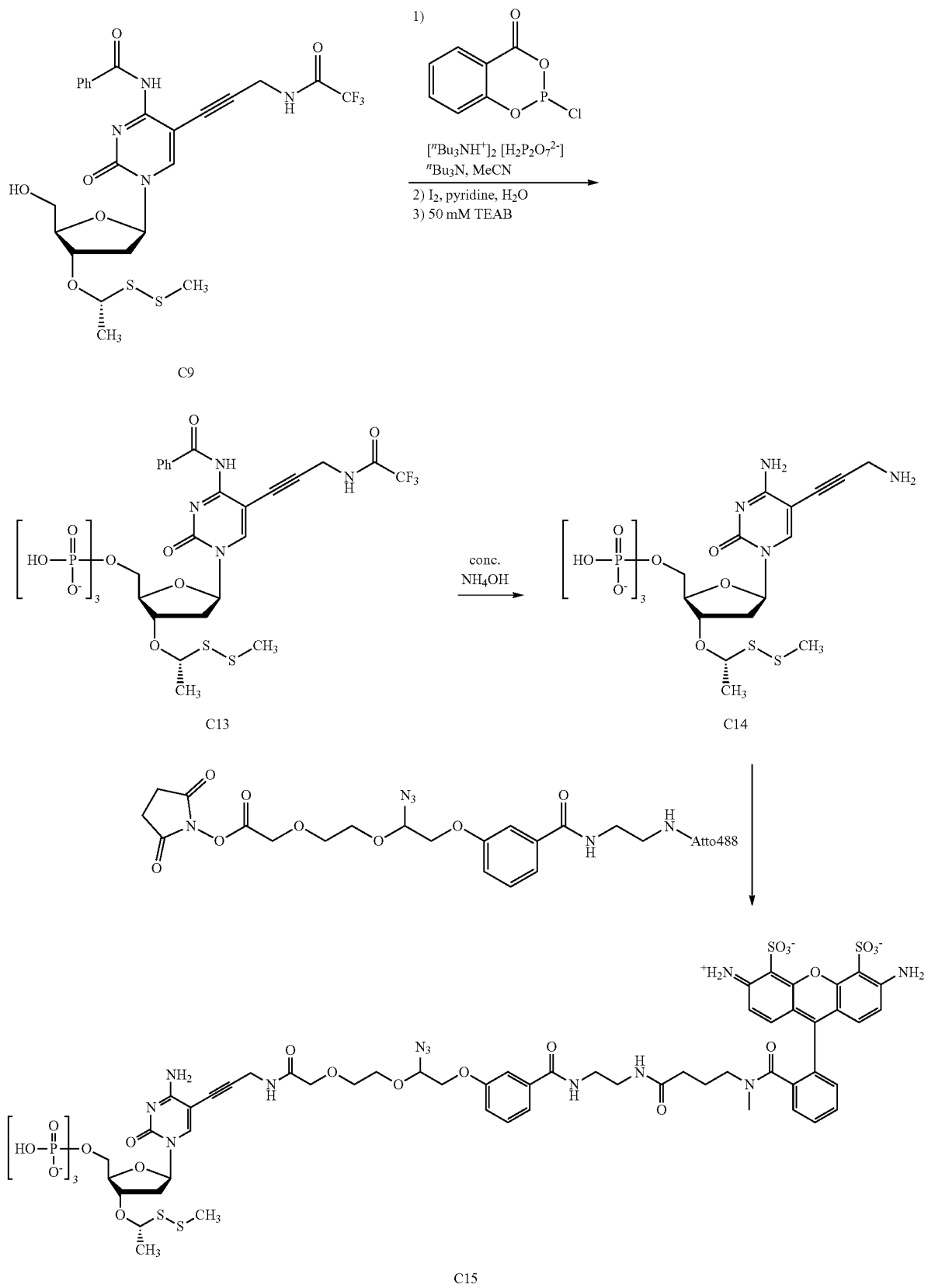

Scheme 25. Part 4 of 5 MeSS_CHCH3_dCTP_thio-trigger containing linker scheme
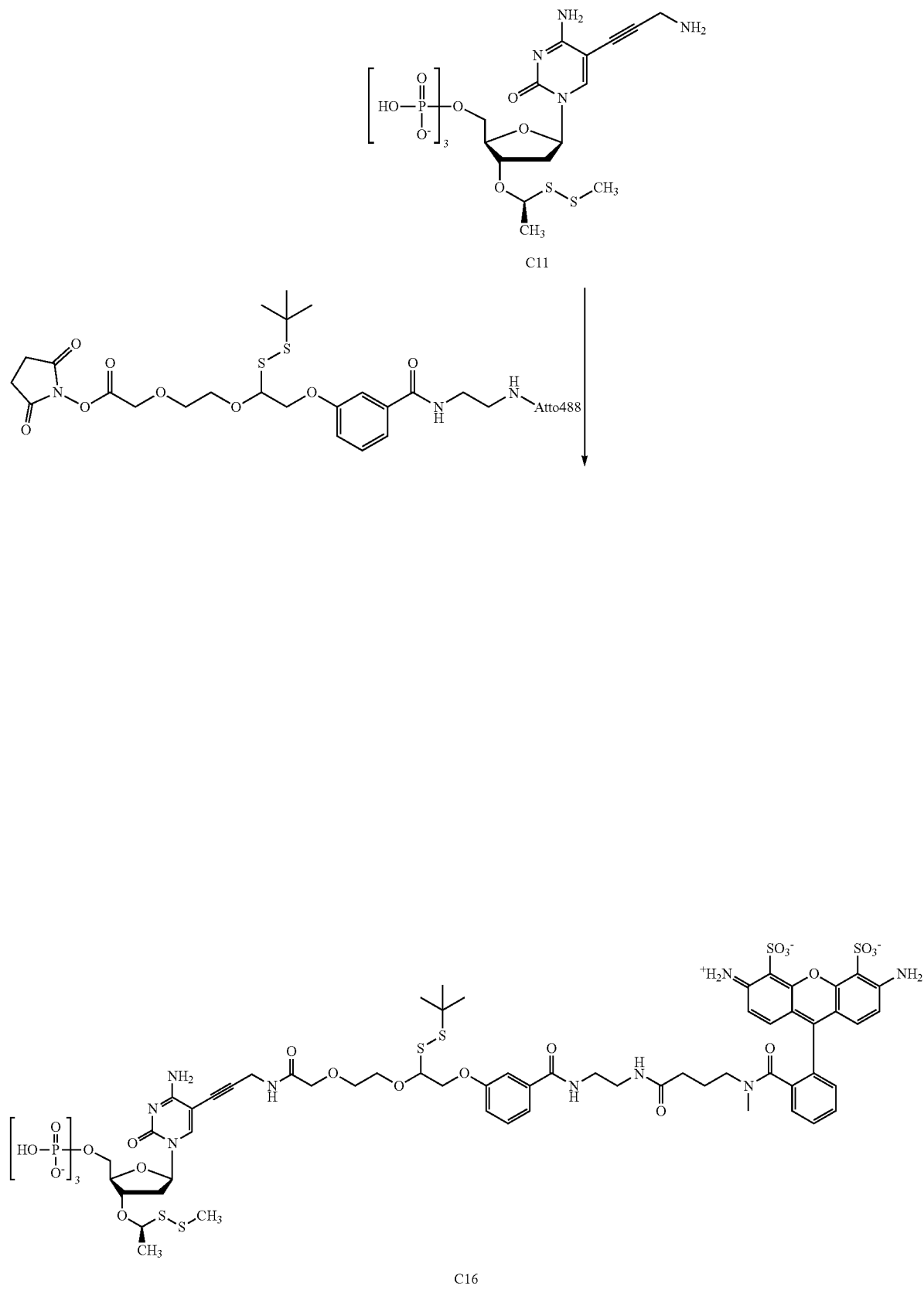

Scheme 26. Part 5 of 5 MeSS_CHCH3_dCTP_thio-trigger containing linker scheme
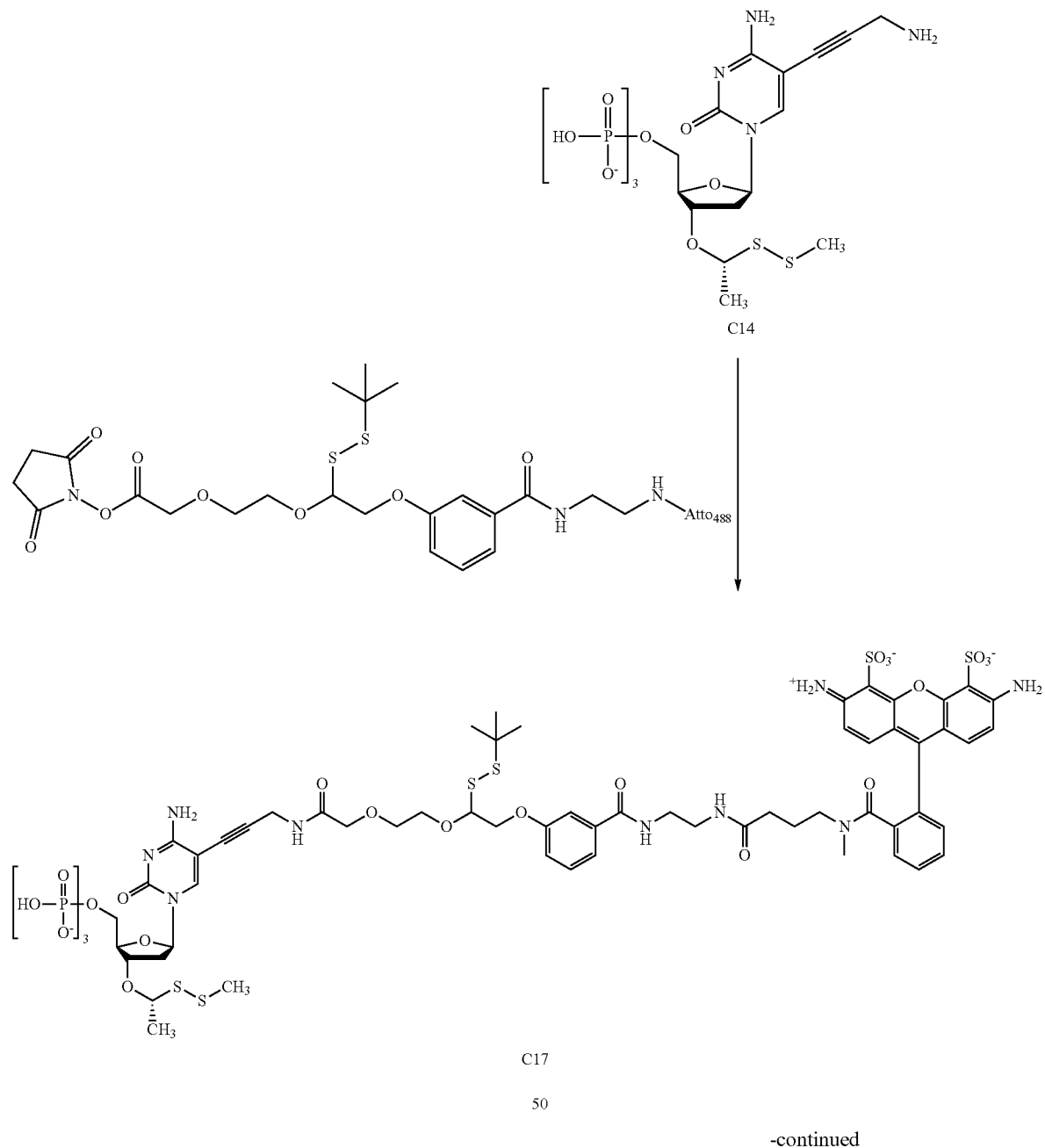
C14
C17
Scheme 27. Part 1 of 2 MeSS_CHCH3_dGTP scheme
-continued
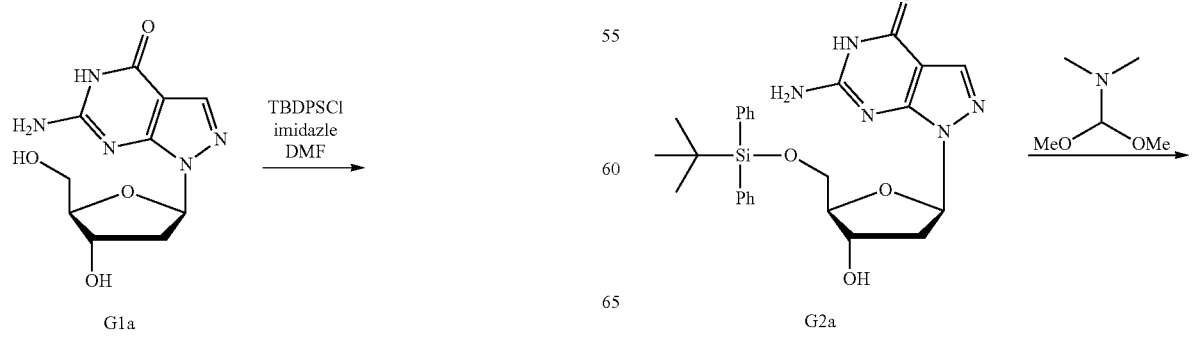
G1a
G2a

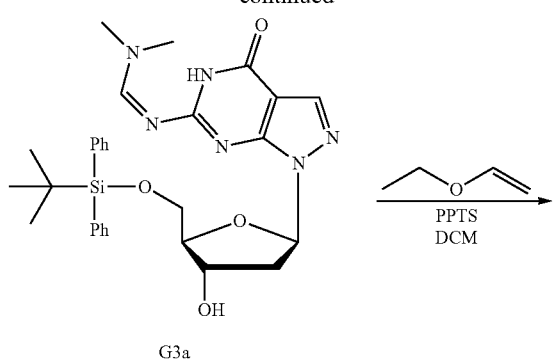
G3a
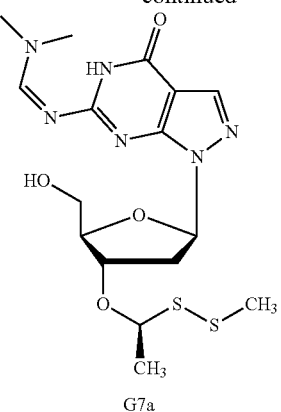
G7a
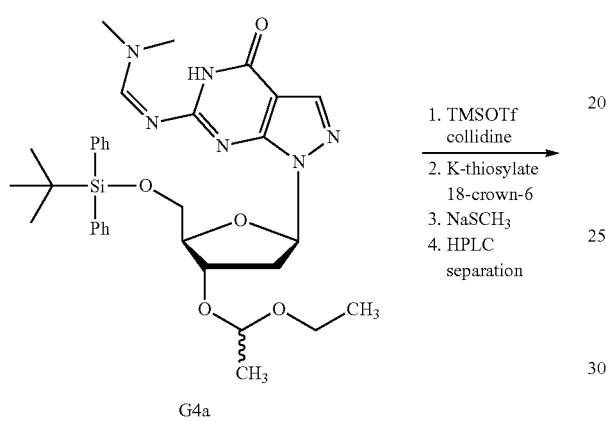
G4a
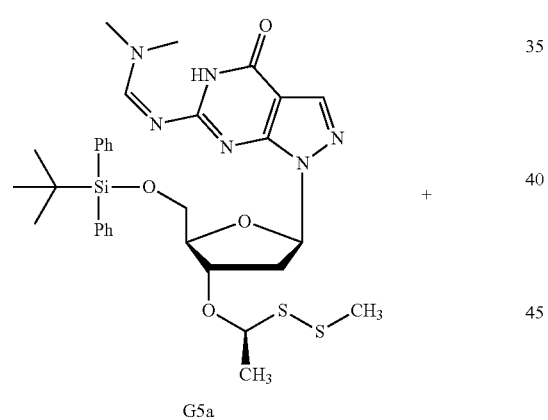
G5a
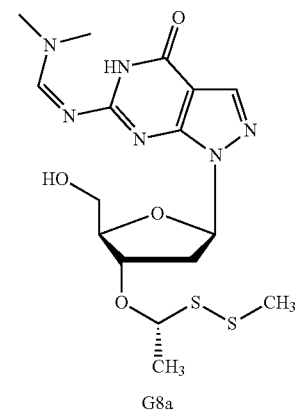
G8a
Scheme 28. Part 2 of 2 MeSS_CHCH3_dGTP scheme
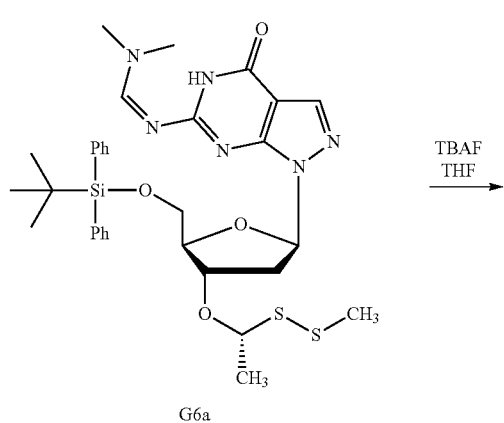
G6a
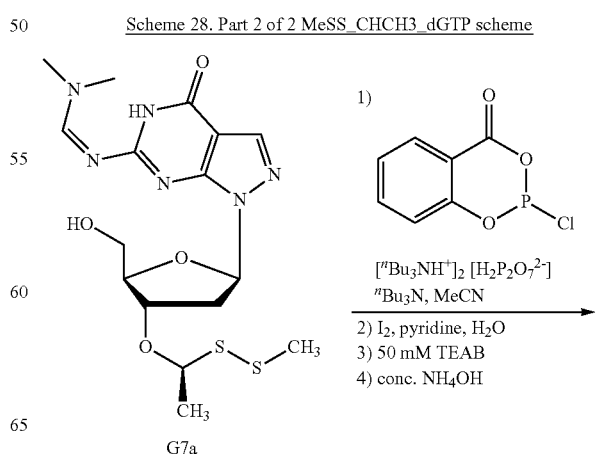
G7a 577
-continued
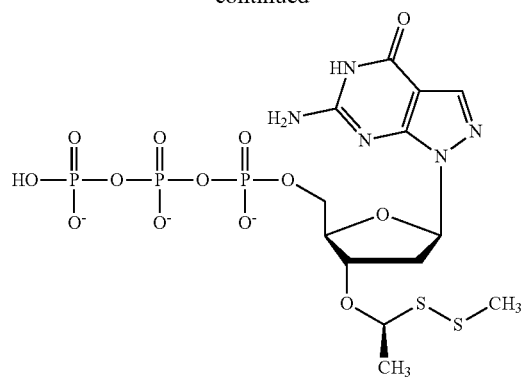
G9a
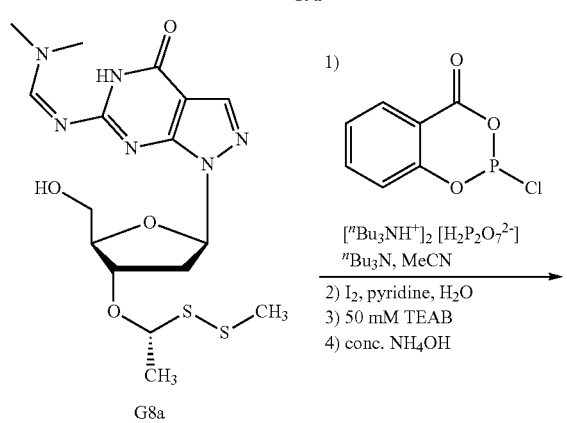
G8a
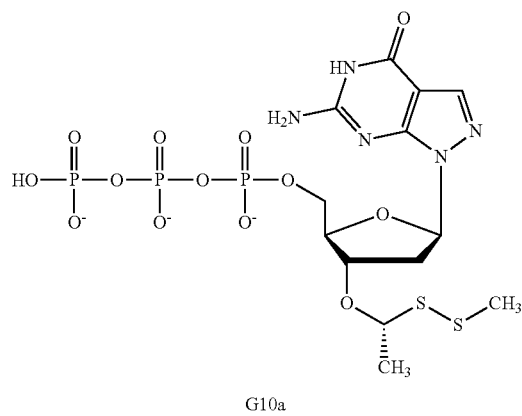
G10a
Scheme 29. Part 1 of 5 MeSS_CHCH3_dGTP_N3 linker scheme
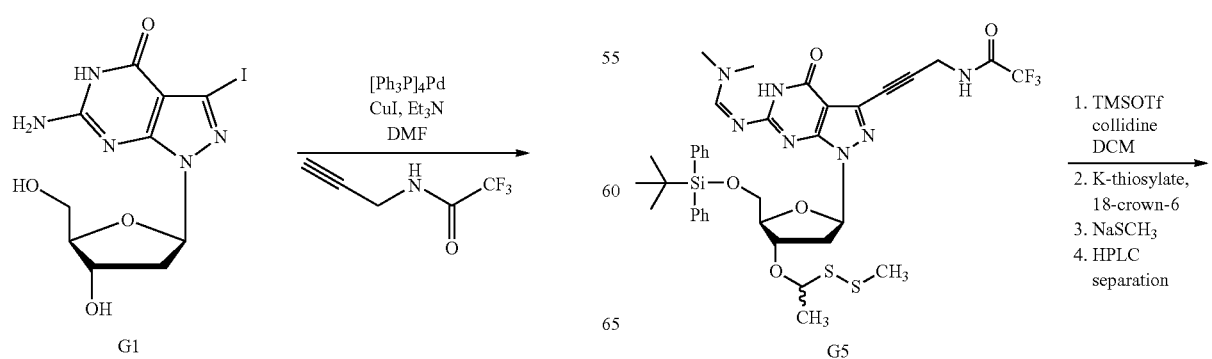
G1
578
-continued
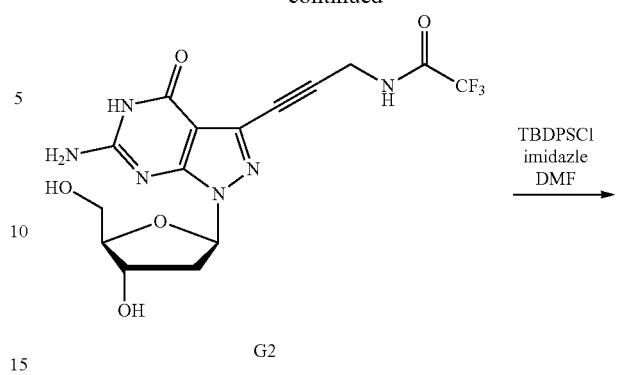
G2
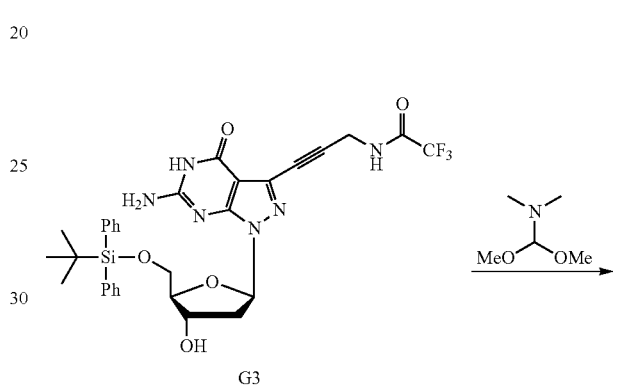
G3
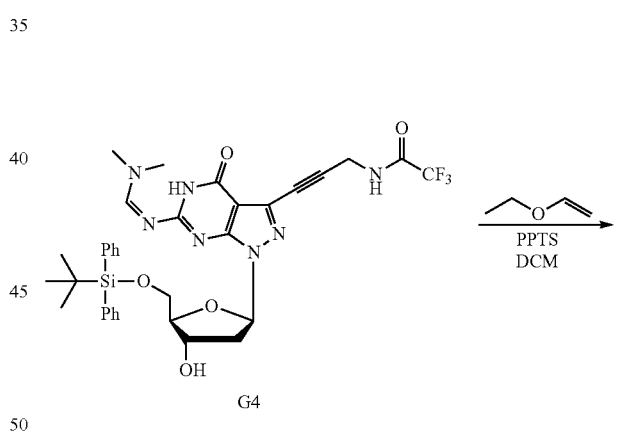
G4
G5

579
-continued
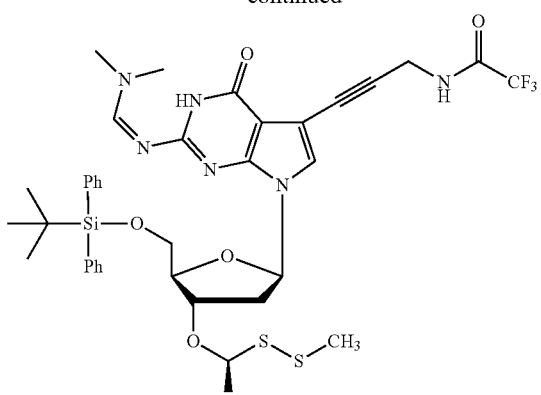
G6
580
-continued
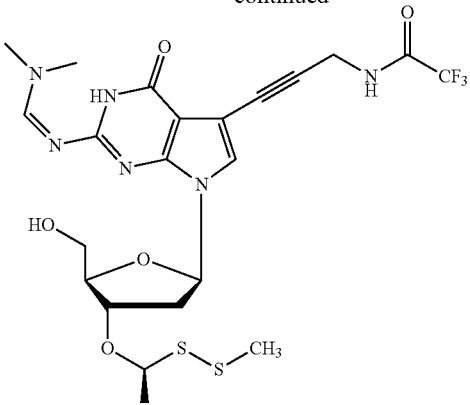
G8
+
+
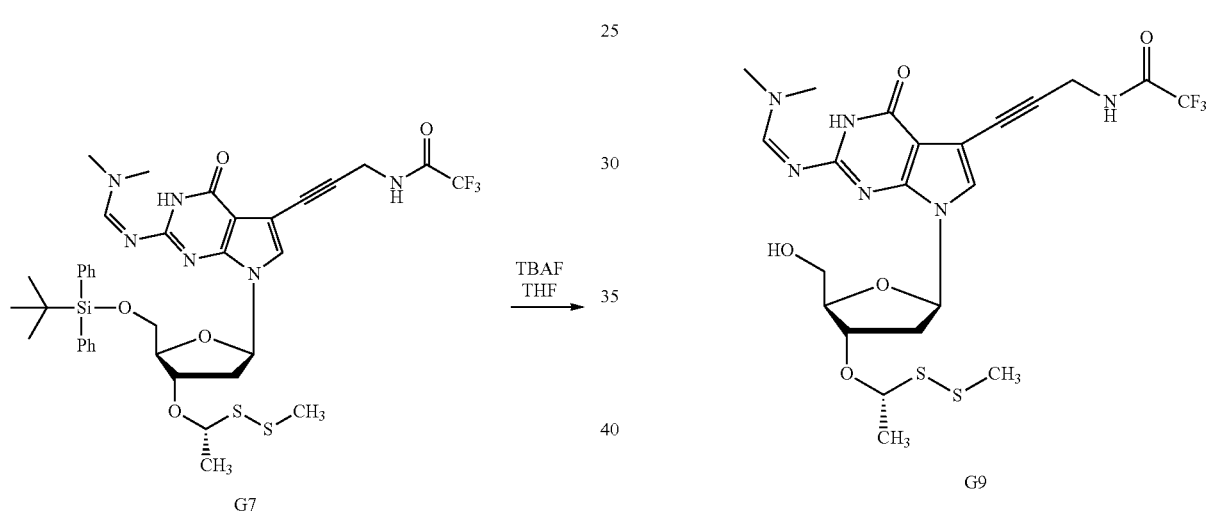
Scheme 30. Part 2 of 5 MeSS_CHCH3_dGTP_N3 linker scheme
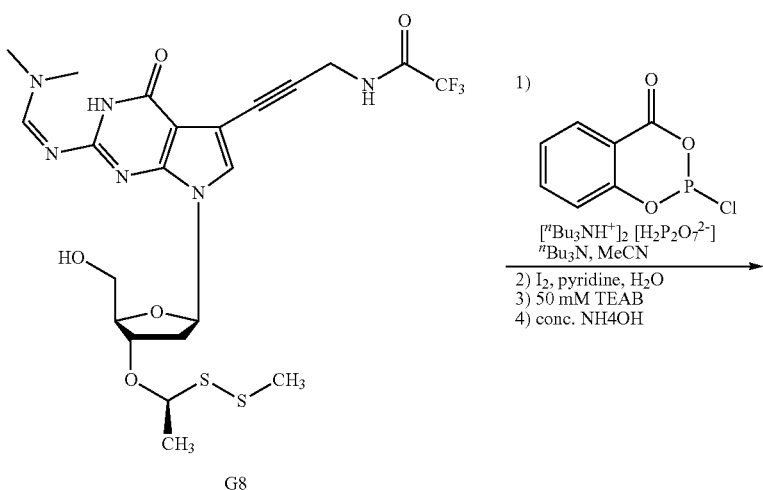
G8
1)
[nBu3NH+]2 [H2P2O7^{2-}]
nBu3N, MeCN
2) I2, pyridine, H2O
3) 50 mM TEAB
4) conc. NH4OH -continued
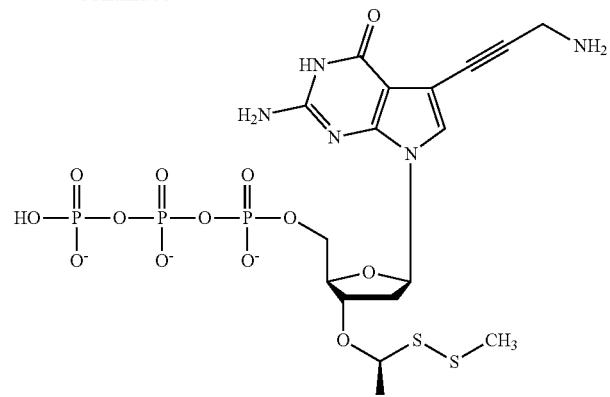
G10
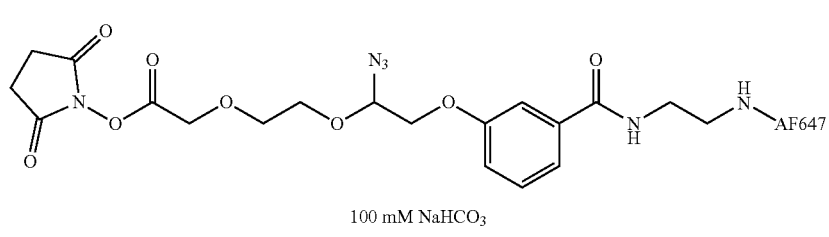
100 mM NaHCO₃
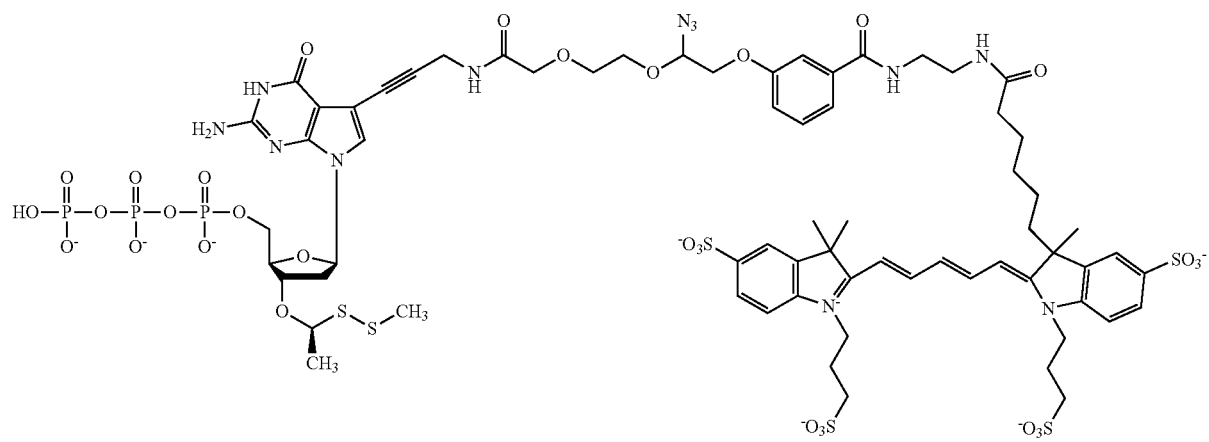
G11

Scheme 31. Part 3 of 5 MeSS_CHCH3_dGTP_N3 linker scheme
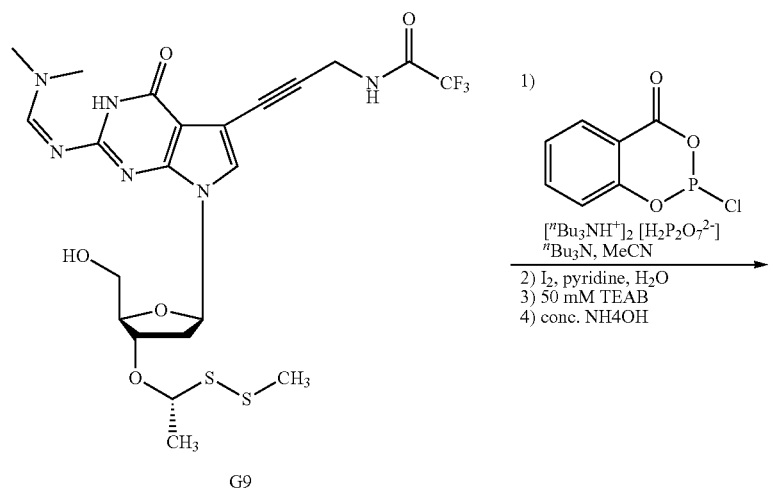
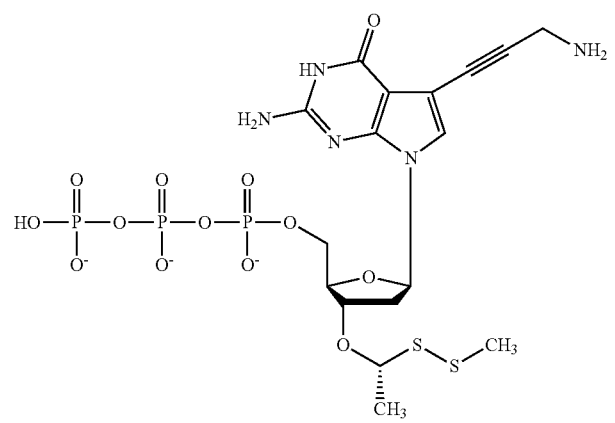
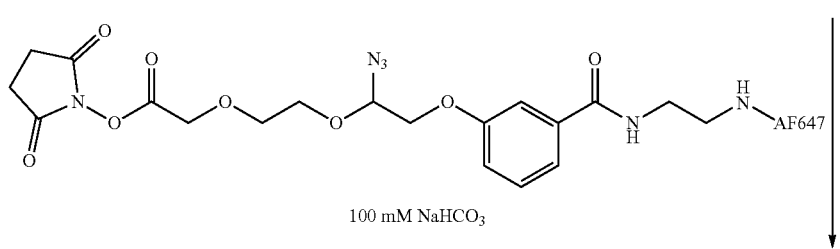

585
-continued
586
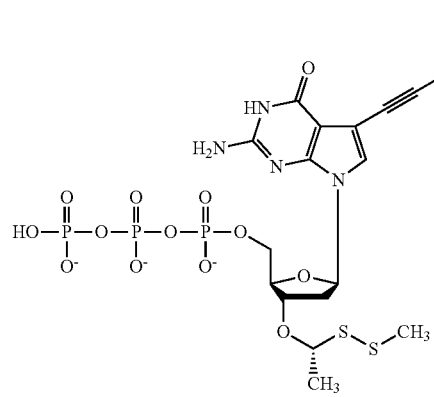
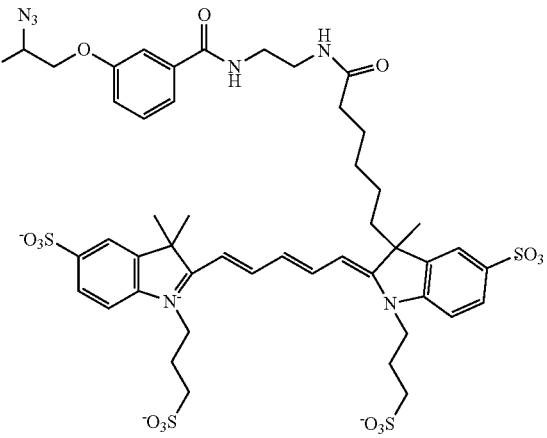
G13
Scheme 32. Part 4 of 5 MeSS_CHCH3_dGTP_thio-trigger containing linker scheme
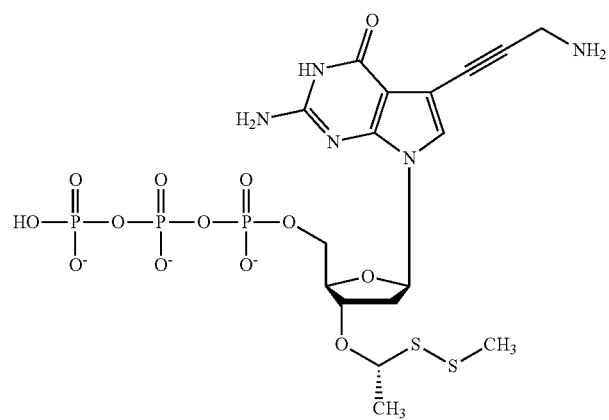
G12
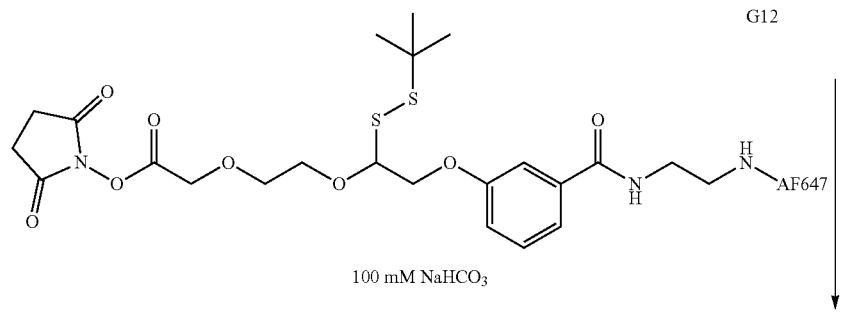
100 mM NaHCO₃

-continued
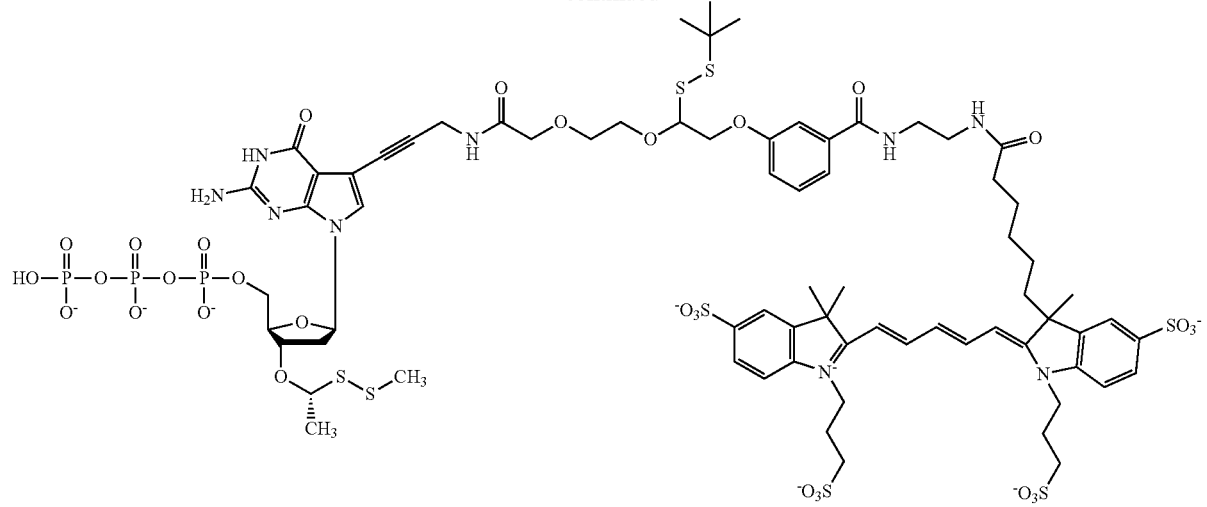
G14
Scheme 33. Part 5 of 5 MeSS_CHCH3_dGTP_thio-trigger containing linker scheme
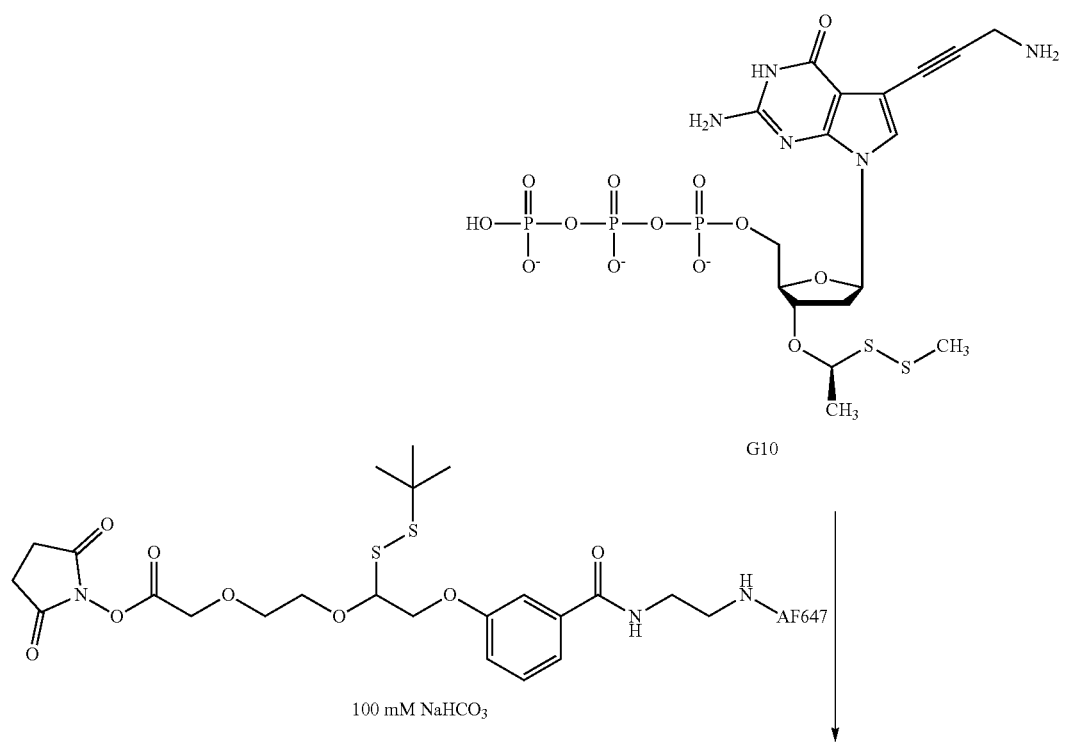
G10
100 mM NaHCO₃

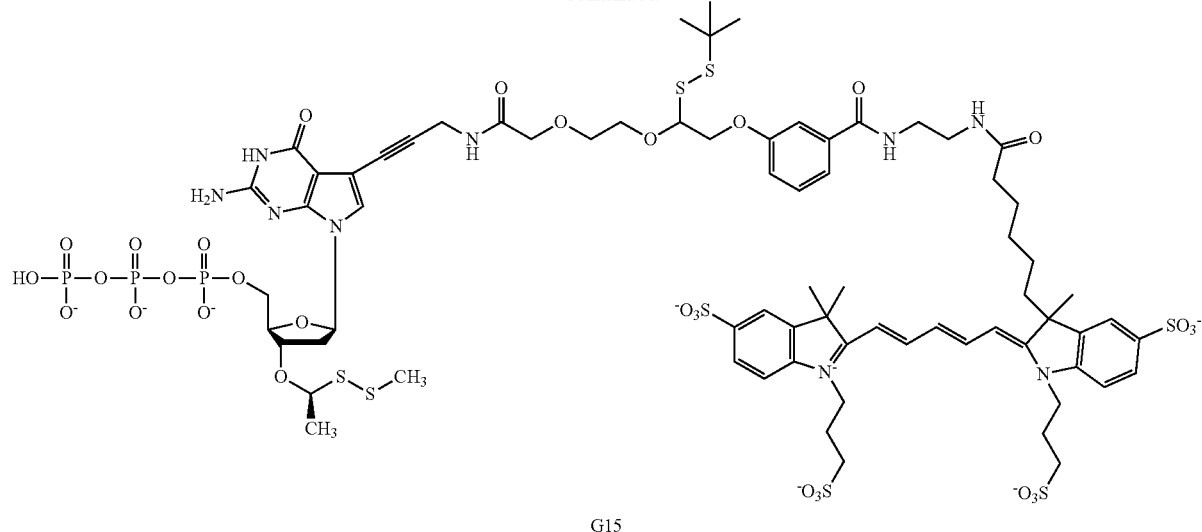
G15
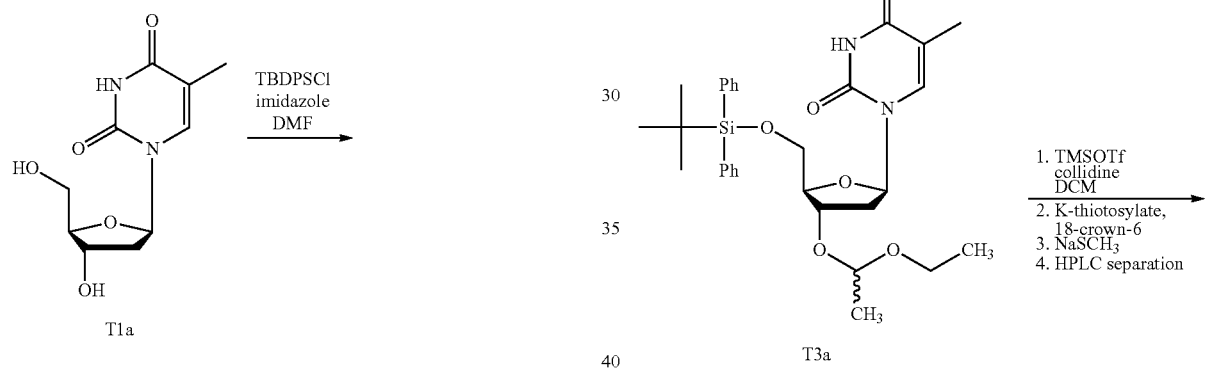
Scheme 34. Part 1 of 2 MeSS_CHCH3_dTTP scheme
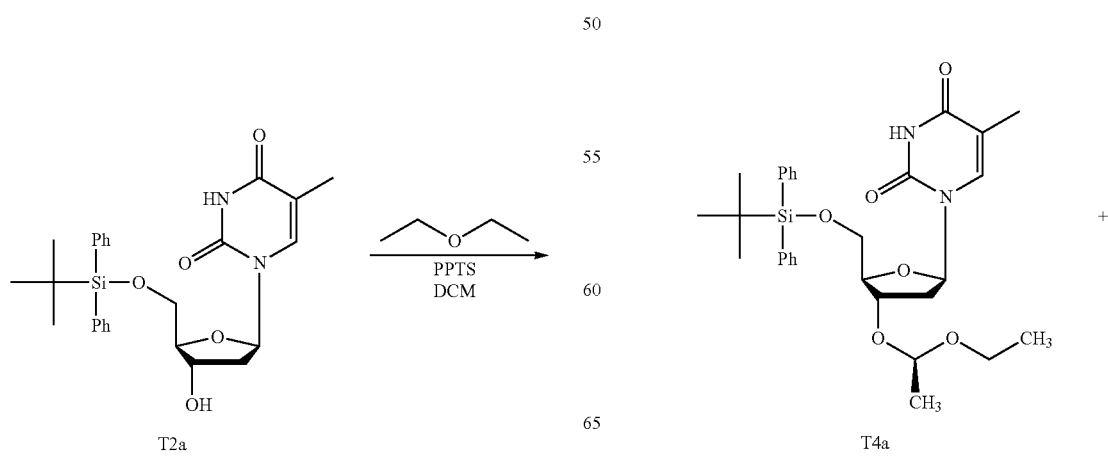

Scheme 35. Part 2 of 2 MeSS_CHCH3_dTTP scheme
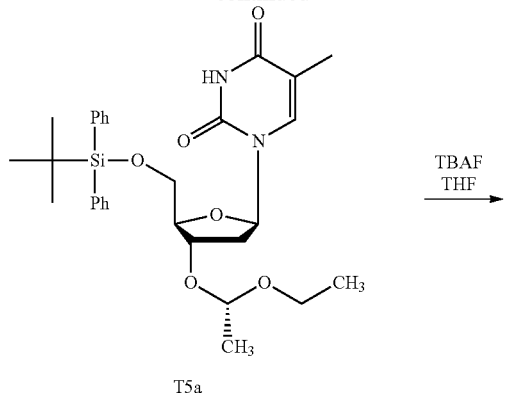
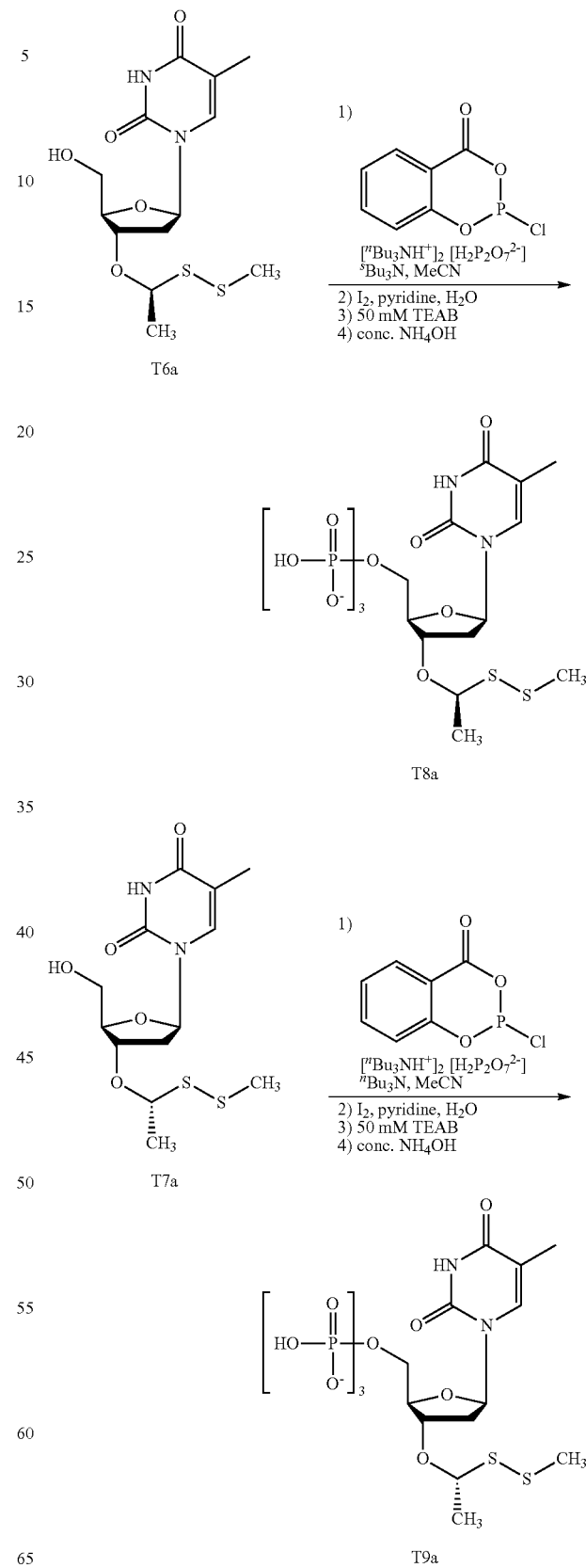

Scheme 36. Part 1 of 5 MeSS_CHCH3_dTTP_N3 linker scheme
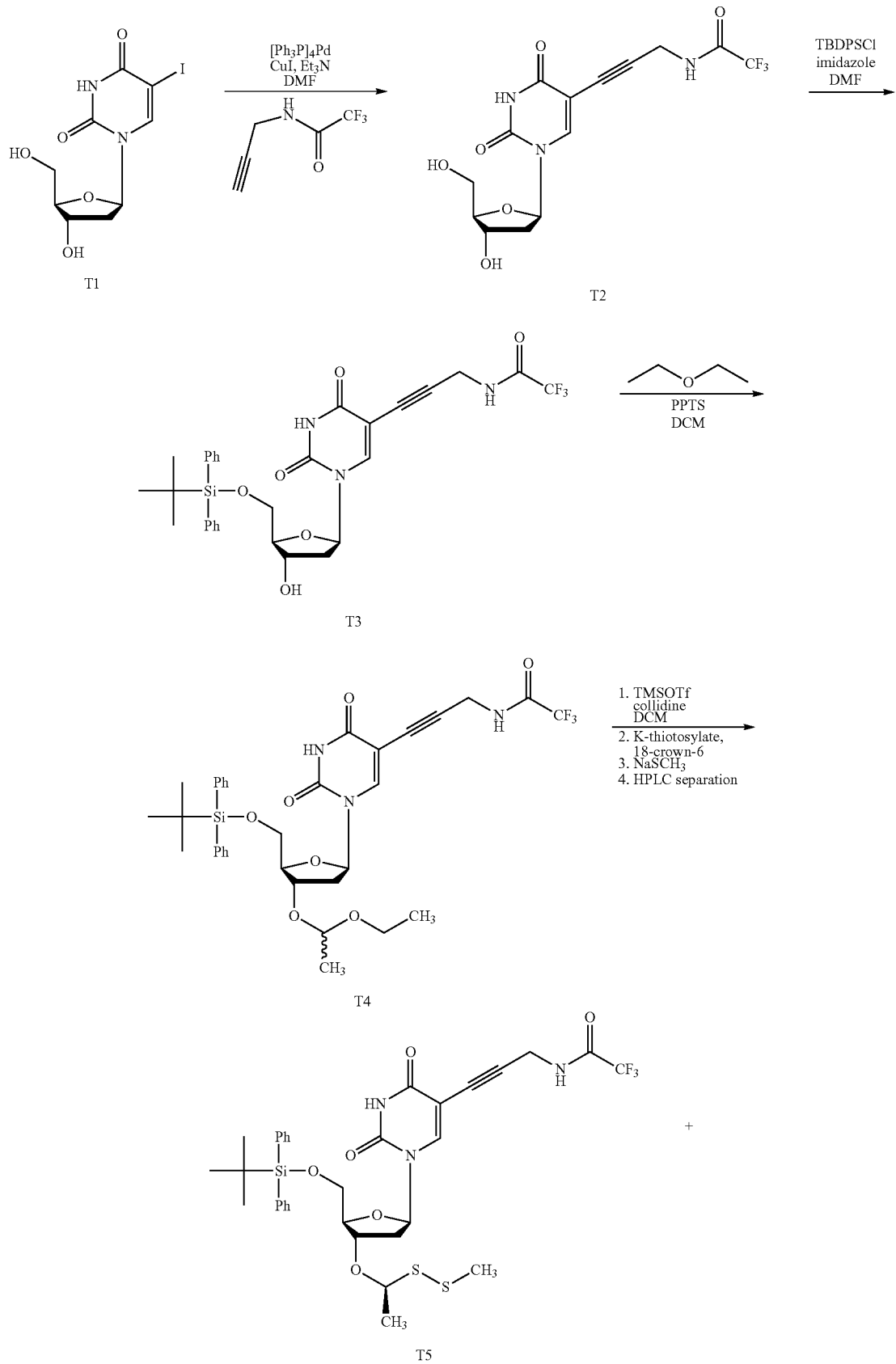

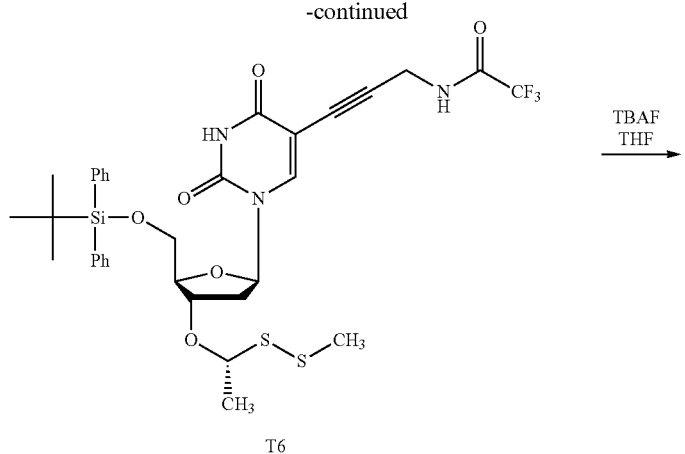
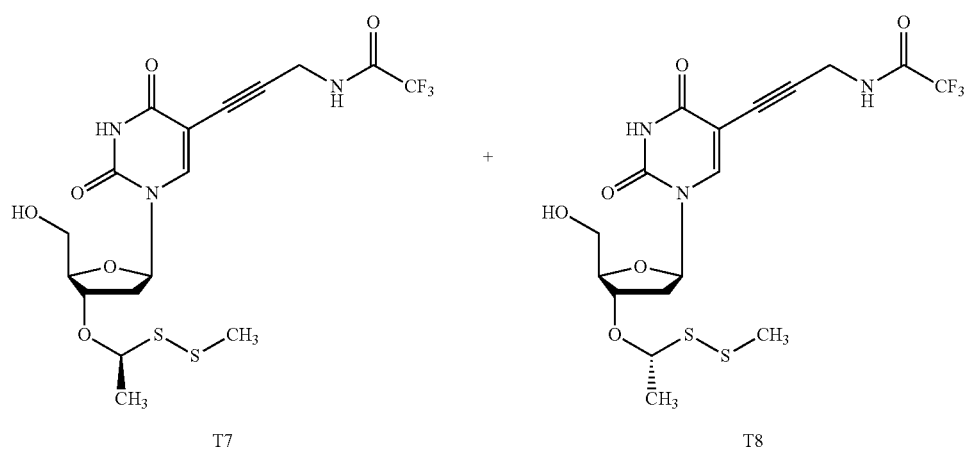
Scheme 37. Part 2 of 5 MeSS_CHCH3_dTTP_N3 linker scheme
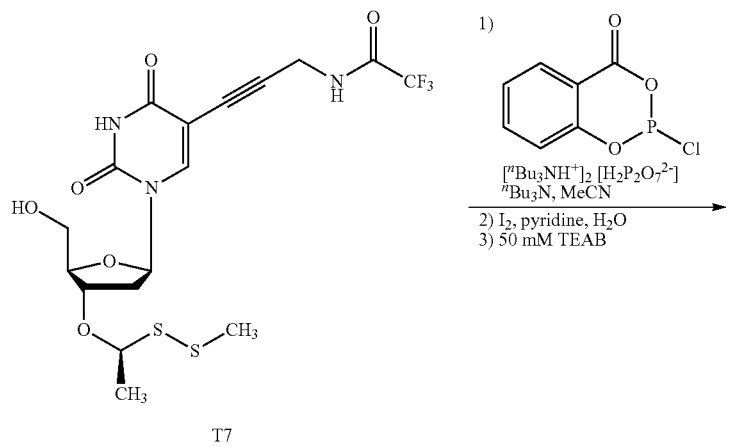

597 598
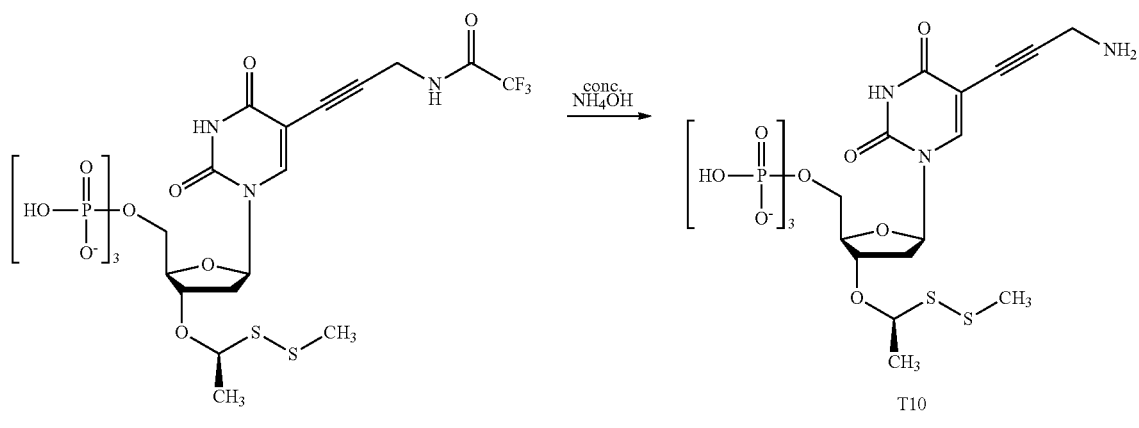
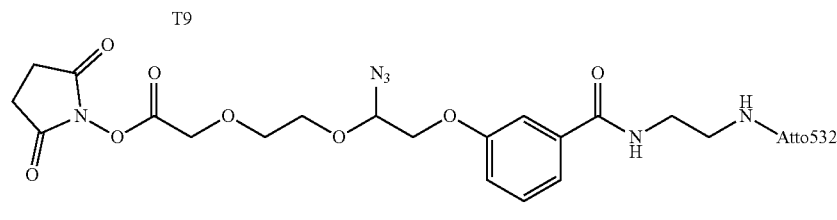
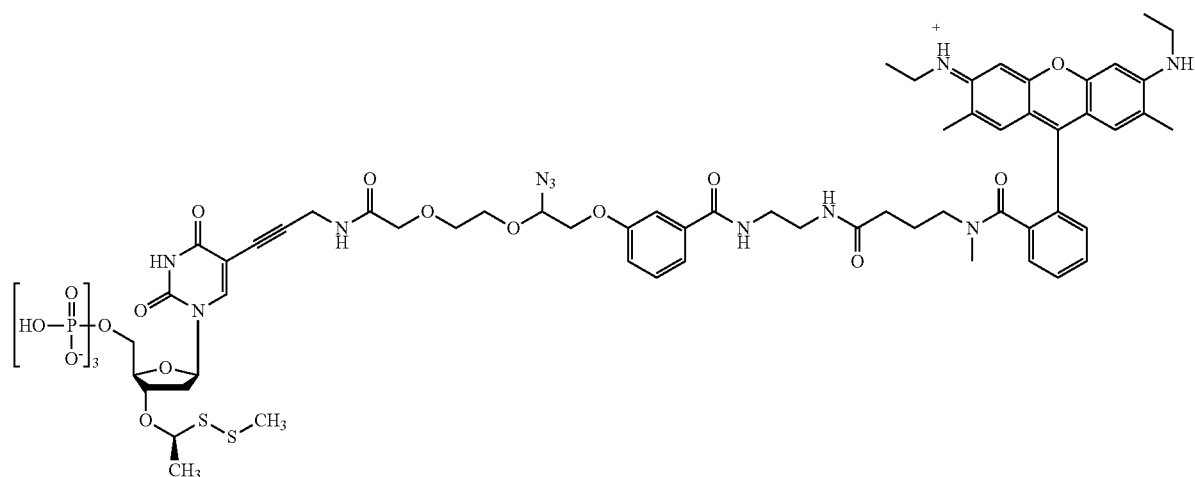

Scheme 38. Part 3 of 5 MeSS_CHCH3_dTTP_N3 linker scheme
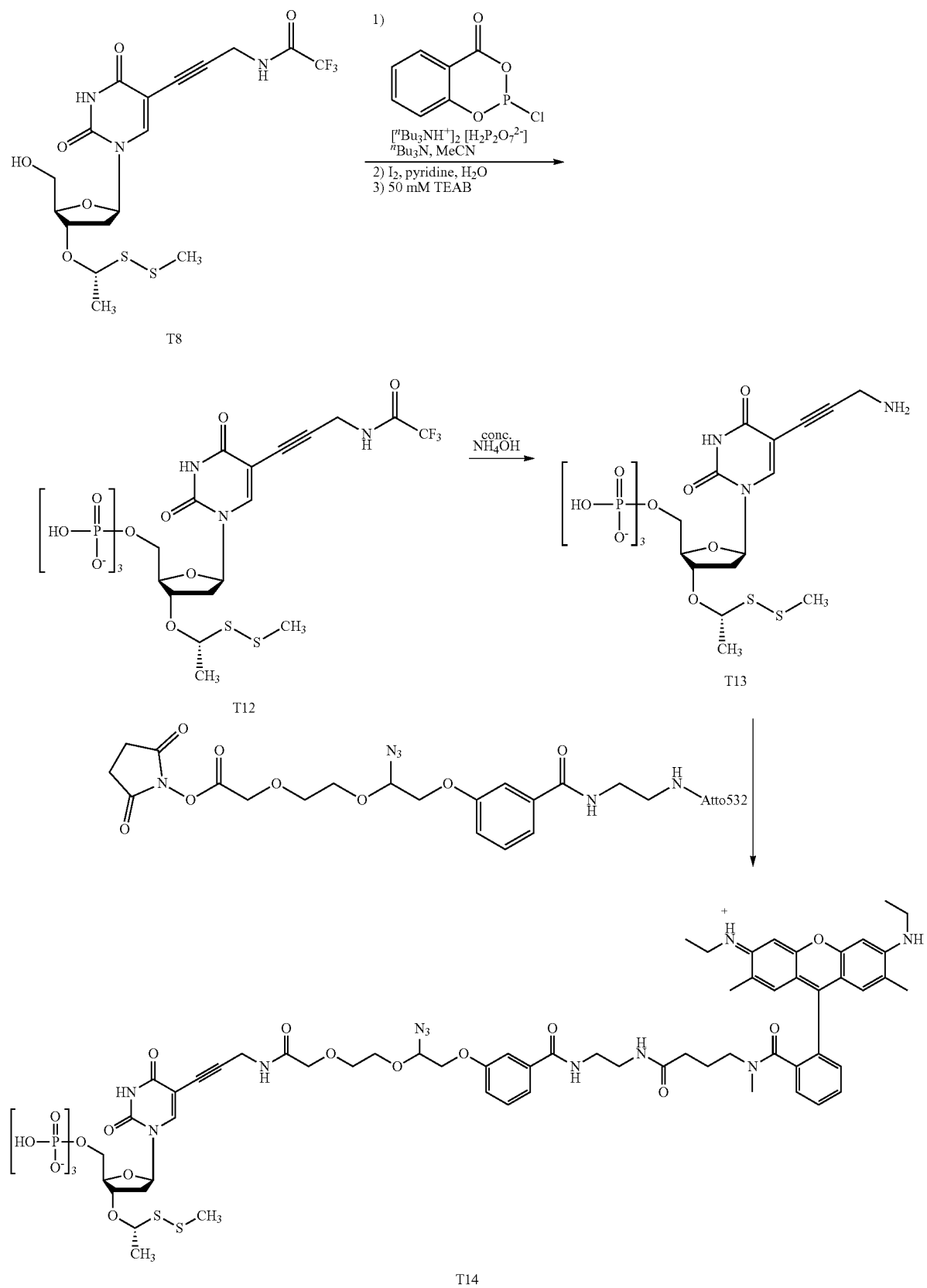

Scheme 39. Part 4 of 5 MeSS_CHCH3_dTTP thio-trigger containing linker
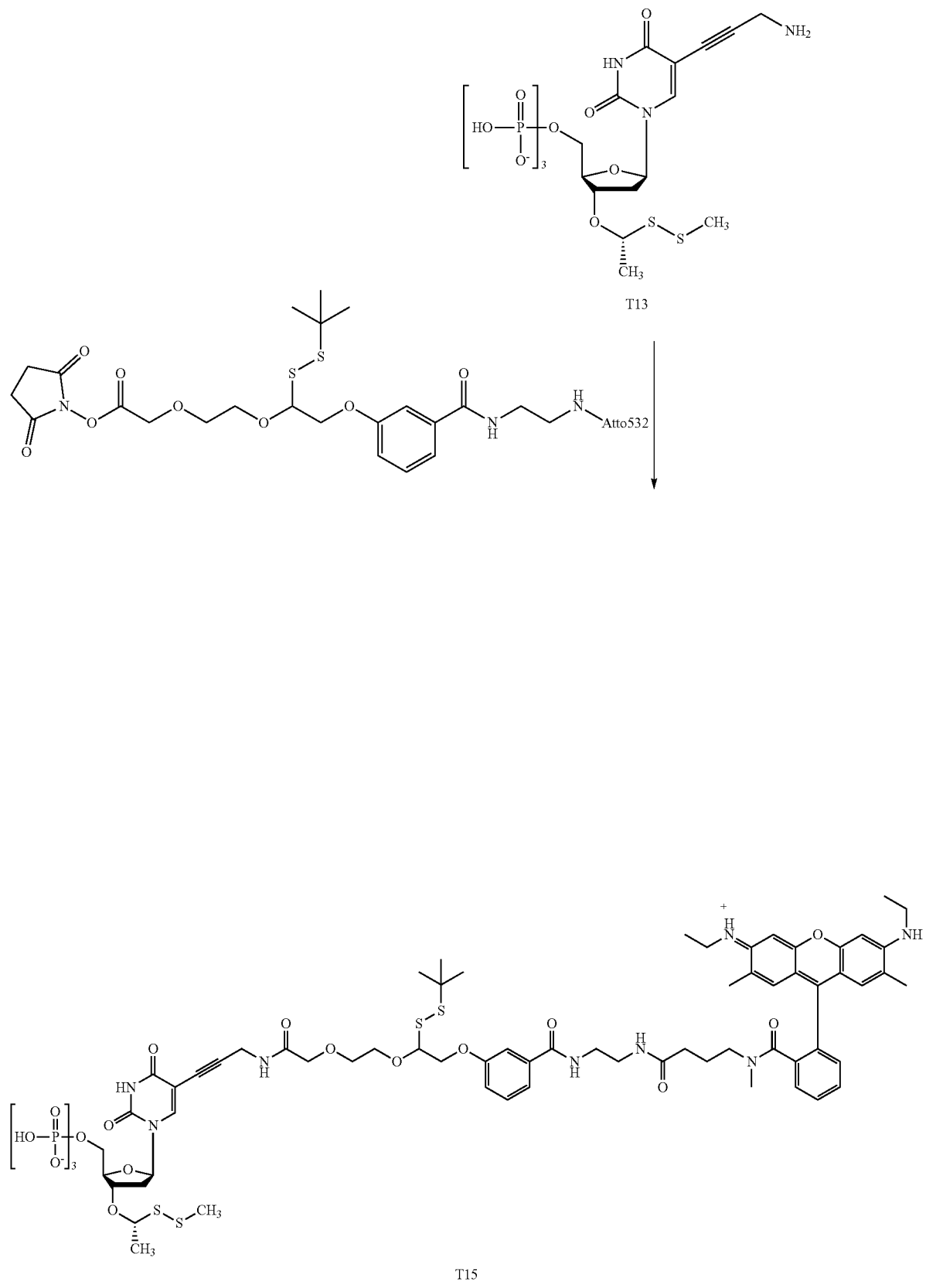

Scheme 40. Part 5 of 5 MeSS_CHCH3_dTTP thio-trigger containing linker scheme

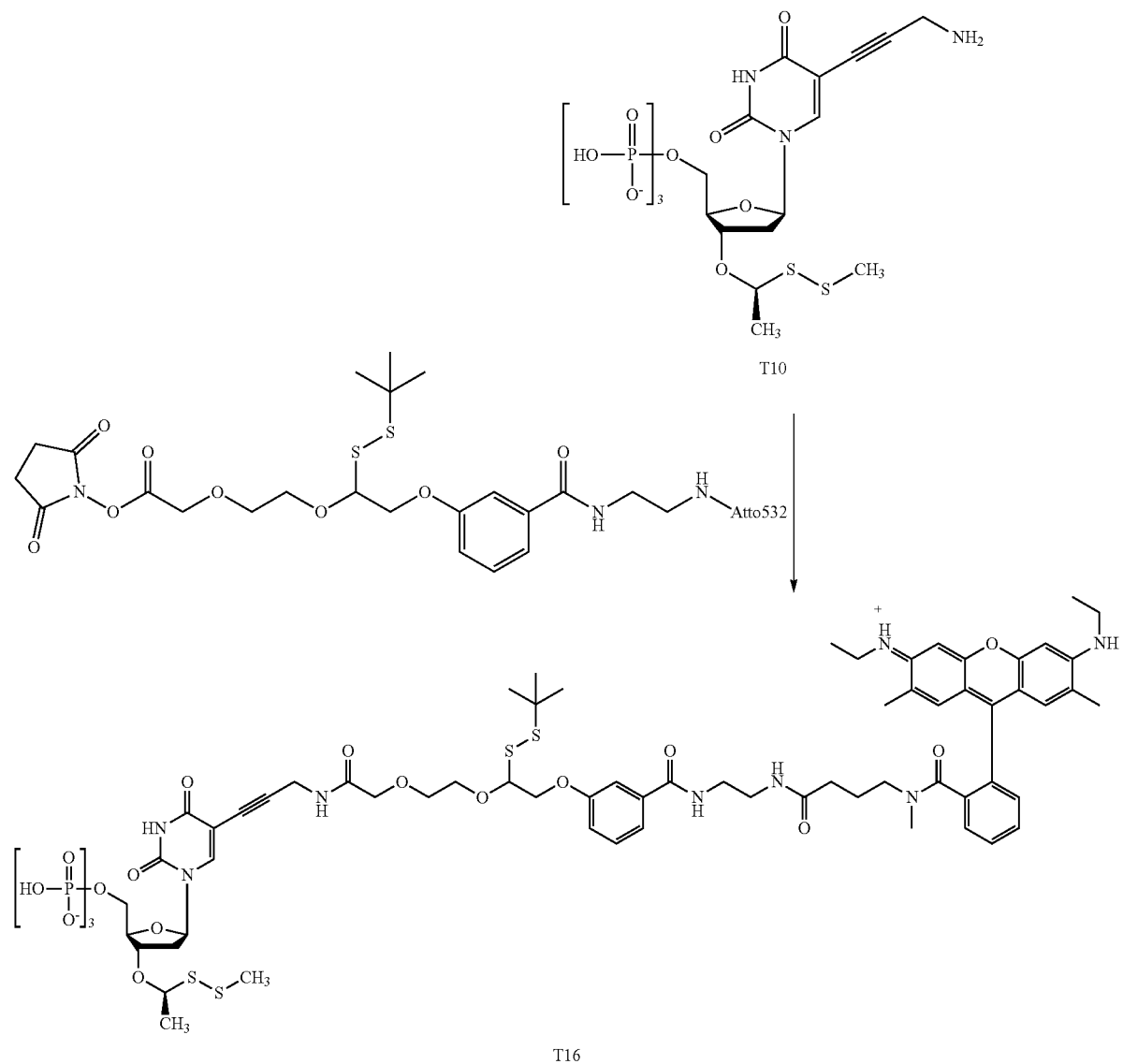

Preparation of T3a. T2a (1.0 g, 2.08 mmol) was suspended in dichloromethane (4 mL) and ethyl vinyl ether (2 mL). Pyridinium p-toluenesulfonate (26 mg, 0.1 mmol) was added and the reaction mixture was stirred at ambient temperature. After 1 hour the reaction mixture was clear, and the solvent was evaporated. The residue was dissolved in ether (25 mL) and washed with 0.1 M NaHCO3 (2×25 mL) followed by brine (25 mL) and dried over magnesium sulfate. The crude product was purified by chromatography on silica gel eluting with dichloromethane/methanol (98:2) to afford T3a as a white foam (0.92 g, 1.66 mmol, 80%). LCMS observed m/z 552 calculated m/z 552. $^1$H NMR (500 MHz, CDCl$_3$) δ 9.80 (q, J=3.0 Hz, 1H), 7.99 (br s, 1H), 7.67-7.64 (m, 4H), 7.48-7.39 (m, 7H), 6.37 (dd, J=8.0, 5.5 Hz, 1H), 4.58-4.57 (m, 1H), 4.05-3.96 (m, 2H), 3.88-3.85 (m, 1H), 2.40-2.36 (m, 1H), 2.24-2.17 (m, 1H), 2.21 (d, J=3.0 Hz, 3H), 1.65 (d, J=1.0 Hz, 3H), 1.21 (d, J=6.5 Hz, 6H), 1.09 (s, 9H).

Preparation of T4a and T5a. T3a (542 mg, 0.982 mmol) was dissolved in anhydrous dichloromethane (4 mL) and cooled in an ice bath. Collidine (583 µL, 4.42 mmol) was added followed by dropwise addition of trimethylsilyl triflate (533 µL, 2.95 mmol). After stirring 30 min, 18-crown-6 (528 mg, 2 mmol) was added followed by potassium p-toluenethiosulfonate (452 mg, 2 mmol). The reaction mixture was warmed to room temperature and stirred for 30 min. Sodium thiomethoxide (210 mg, 3 mmol) was added and the reaction mixture was stirred at room temperature for 1 hour. The reaction mixture was added directly to a silica gel column and eluted with dichloromethane/methanol (97:3). The product was further purified by reverse phase HPLC eluting with acetonitrile/water 60:40 to 98:2 over 40 min. The fraction eluting between 23 and 27 minutes contained a mixture of T4a and T5a (209 mg, 36%). LCMS observed m/z 586 calculated m/z 586.

Preparation of T6a and T7a. A mixture of T4a and T5a (209 mg, 0.357 mmol) was dissolved in anhydrous tetrahydrofuran (2 mL). Tetrabutylammonium fluoride (0.536 mL, 1 M in THF) was added and the reaction mixture was left to sit for 1 hour at room temperature. The tetrahydrofuran was evaporated, and the crude product was triturated with ethyl ether (3×10 mL) and then purified by reverse phase HPLC eluting with acetonitrile/water (20:80 to 30:70 over 40 min). The fraction eluting between 22 and 26 minutes contained a mixture of T6a and T7a (81 mg, 0.233 mmol, 65%). LCMS observed m/z 348 calculated m/z 348. $^1$H NMR (500 MHz, CDCl3) δ 9.28 (br s, 2H), 7.45 (d, J=1.5 Hz, 1H), 7.36 (d, J=1.0 Hz, 1H), 6.16-6.13 (m, 2H), 4.73 (q, J=6.0 Hz, 1H), 4.69 (q, J=6.0 Hz, 1H), 4.10-4.09 (m, 1H), 4.06-4.04 (m, 1H), 3.94-3.90 (m, 2H), 3.83-3.75 (m, 2H), 3.03 (br s, 1H), 2.85 (br s, 1H), 2.429 (s, 1H), 2.425 (s, 1H), 2.41-2.38 (m, 4H), 1.89 (s, 3H), 1.88 (s, 3H), 1.62 (d, J=6.0 Hz, 3H), 1.61 (d, J=6.0 Hz, 3H). $^{13}$C NMR (125 MHz, CDCl3) δ 164.1, 150.7, 137.1, 136.9, 111.3, 87.2, 86.7, 86.2, 86.0, 85.5, 85.0, 77.4, 76.9, 62.9, 62.4, 38.3, 37.2, 24.7, 24.6, 22.9, 22.8, 12.7.

Preparation of T8a and T9a. A solution of 2-chloro-4-H-1,3,2-benzodioxaphosphorin-4-one (44 mg, 0.216 mmol) in anhydrous acetonitrile (0.12 mL) was added dropwise to a solution of tributylammonium pyrophosphate (158 mg, 0.287 mmol) in anhydrous tributylamine (137 μL, 0.575 mmol) and anhydrous acetonitrile (0.3 mL). After stirring for 20 min at room temperature the solution was transferred to a solution of T6a and T7a (25 mg, 72 μmol) in anhydrous acetonitrile (0.2 mL). The reaction mixture was stirred for 30 minutes and then iodine solution (1 mL, 50 mM in 9:1 pyridine/water) was added. After 30 minutes water (1 mL) was added and the reaction mixture was stirred for 1 hour. The reaction mixture was concentrated to near dryness and the residue was triturated with ether (3×5 mL). The crude product was purified by reverse phase HPLC eluting with acetonitrile/50 mM TEAB (2:98 to 30:70 over 40 min). The fraction eluting at 22 minutes contained T8a (5 μmol, 7%) and the fraction eluting at 24 minutes contained T9a (4.4 μmol, 6%). LCMS observed m/z 587 calculated m/z 587.

Experimental Procedures for S—S Linker

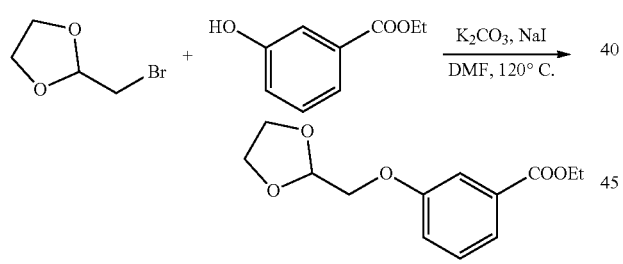

Sodium iodide (1.5 g, 10.0 mmol) and potassium carbonate (6.9 g, 50 mmol) were added to a stirred solution of ethyl 3-hydroxybenzoate (4.15 g, 25 mmol), 2-bromomethyl-1,3-dioxolane (10.4 mL, 100 mmol) in DMF (15 mL) and was heated to 120° C. The progress of the reaction was monitored by HPLC (100 mM TEAA/MeCN, 60% to 100% over 15 min, hold for 5 min at 100%). The reaction mixture was cooled to room temperature when the amount of ethyl-3-hydroxybenzoate was less than 5%. The suspension was filtered and washed with ether (2×50 mL). The combined filtrates were washed with water (3×50 mL) and brine (50 mL), dried over sodium sulfate and concentrated in vacuo. The crude product was purified by silica gel chromatography (hexanes/ethyl acetate, 80:20) to obtain the desired compound, ethyl 3-((1,3-dioxolan-2-yl)methoxy)benzoate as colorless clear liquid (5.57 g, 88%). $^1$H NMR (500 MHz, DMSO) δ 7.59-7.52 (m, 1H), 7.48-7.39 (m, 2H), 7.25 (ddd, J=8.3, 2.7, 1.0 Hz, 1H), 5.22 (t, J=3.9 Hz, 1H), 4.35-4.25 (m, 2H), 4.07 (d, J=3.9 Hz, 2H), 4.01-3.91 (m, 2H), 3.86 (ddd, J=15.2, 9.1, 5.6 Hz, 2H), 1.31 (q, J=7.2 Hz, 3H); MS: calc'd for [$C_{13}H_{16}O_5$+Na]: 275.1, found 275.3.

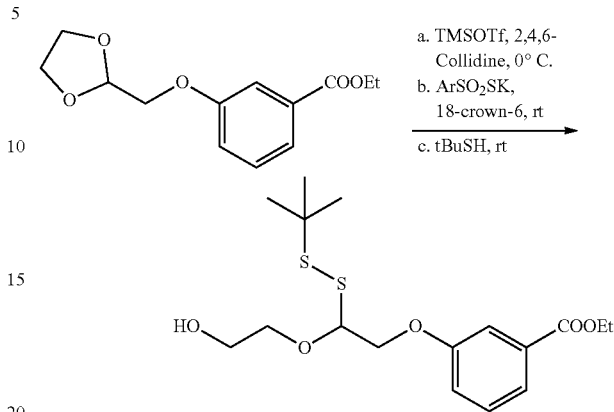

2,4,6-Collidine (2.38 mmol, 3.0 equiv.) was added to a stirred solution of ethyl 3-((1,3-dioxolan-2-yl)methoxy)benzoate (0.2 g, 0.79 mmol) in DCM (0.1 M) at 0° C. under Ar atmosphere followed by the addition of trimethylsilyl triflate (1.59 mmol, 2.0 equiv.). The mixture was stirred at the same temperature until the disappearance of an acetal on TLC and formation of highly polar compound was observed, after which potassium thiotosylate (1.59 mmol, 2.0 equiv.) and 18-crown-6 (1.59 mmol, 2.0 equiv.) were added to the reaction mixture. Disappearance of the polar component was confirmed by TLC, after which tert-butyl thiol (1.59 mmol, 2.0 equiv.) was added. The reaction mixture was loaded on to silica gel column upon completion of the reaction and the desired product, ethyl 3-(2-(tert-butyldisulfaneyl)-2-(2-hydroxyethoxy)ethoxy)benzoate was eluted with 20% ethyl acetate and hexanes mixture as a colorless oil (235.6 mg, 63% yield). $^1$H NMR (500 MHz, DMSO) δ 7.57 (dd, J=6.6, 1.2 Hz, 1H), 7.51-7.42 (m, 2H), 7.27 (ddd, J=8.2, 2.7, 0.8 Hz, 1H), 4.92 (t, J=5.4 Hz, 1H), 4.69 (t, J=5.4 Hz, 1H), 4.35-4.25 (m, 4H), 3.89-3.80 (m, 1H), 3.61-3.49 (m, 3H), 1.37-1.28 (m, 12H). MS: calc'd for [$C_{17}H_{26}O_5S_2$+Na]: 397.1, found 397.3.

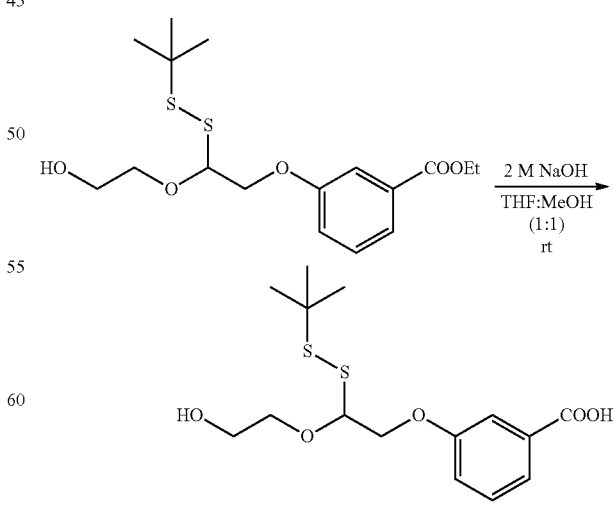

Sodium hydroxide (0.7 mL, 2 M) was added to a stirred solution of ethyl 3-(2-(tert-butyldisulfaneyl)-2-(2-hydroxyethoxy)ethoxy)benzoate (131 mg, 0.35 mmol) in 1:1 methanol (0.33 mL) and THF (0.33 mL) mixture. The solution was initially heterogeneous but became homogenous after 1 hour of stirring. The reaction progress was monitored by HPLC (100 mM TEAA/MeCN, 60% to 100% over 15 min, hold for 5 min at 100%). Upon completion, the reaction mixture was concentrated and HCl (1 M, 1.382 mL) was added dropwise with stirring until the milky swirl persisted. The aqueous suspension was extracted with DCM (3×15 mL) and the extracts were dried over sodium sulfate. The crude product was purified using silica gel chromatography (50% ethyl acetate:hexanes) and 3-(2-(tert-butyldisulfaneyl)-2-(2-hydroxyethoxy)ethoxy)benzoic acid was obtained as a colorless oil (87 mg, 72% yield). $^1$H NMR (500 MHz, DMSO) δ 13.00 (s, 1H), 7.58-7.52 (m, 1H), 7.47 (dt, J=11.9, 6.1 Hz, 1H), 7.42 (t, J=7.9 Hz, 1H), 7.21-7.19 (m, 1H), 4.92 (t, J=5.4 Hz, 1H), 4.69 (s, 1H), 4.34-4.24 (m, 2H), 3.88-3.82 (m, 1H), 3.61-3.50 (m, 3H), 1.35-1.26 (m, 9H). MS: calc'd for $[C_{15}H_{22}O_5S_2+Na]$: 369.1, found 369.2.

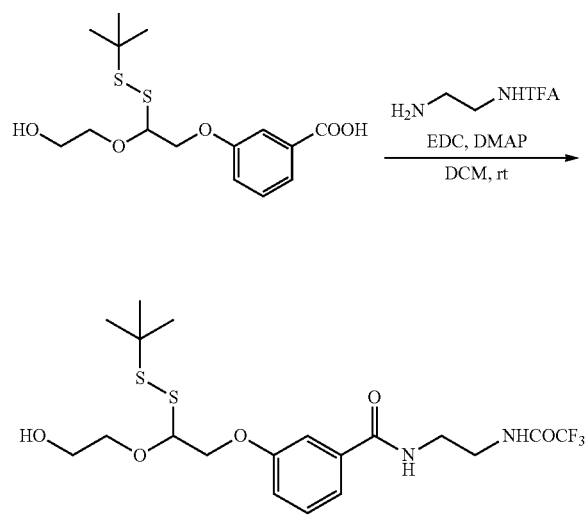

To a mixture of 3-(2-(tert-butyldisulfaneyl)-2-(2-hydroxyethoxy)ethoxy)benzoic acid (43 mg, 0.124 mmol), N-(2-aminoethyl)-2,2,2-trifluoroacetamide (28.6 mg, 0.148 mmol, 1.2 equiv.), 4-N,N-dimethylaminopyridine (4.5 mg, 0.037 mmol, 0.3 equiv.) in DCM (0.2 mL, 0.6 M) at 0° C., was added N-(3-dimethylaminopropyl)-N'-ethylcarbodiimide hydrochloride (33 mg, 0.174 mmol, 1.4 equiv.) in DCM dropwise. The reaction was stirred at room temperature until the disappearance of the starting material as monitored by HPLC (100 mM TEAA/MeCN, 60% to 100% over 15 min, hold for 5 min at 100%). The reaction mixture was diluted with water and extracted with ethyl acetate (3×15 mL) and dried over sodium sulfate. The crude was purified by silica gel chromatography (60% ethyl acetate: hexanes) and 3-(2-(tert-butyldisulfaneyl)-2-(2-hydroxyethoxy)ethoxy)-N-(2-(2,2,2-trifluoroacetamido)ethyl)benzamide was obtained as colorless liquid (38 mg, 63.3% yield). $^1$H NMR (500 MHz, DMSO) δ 9.49 (d, J=5.5 Hz, 1H), 8.59 (t, J=5.5 Hz, 1H), 7.40 (dq, J=22.8, 7.7 Hz, 3H), 7.12 (dd, J=8.0, 1.6 Hz, 1H), 4.92 (t, J=5.4 Hz, 1H), 4.70 (t, J=5.3 Hz, 1H), 4.35-4.19 (m, 2H), 3.87 (dt, J=9.6, 4.3 Hz, 1H), 3.62-3.50 (m, 3H), 3.43-3.33 (m, 4H), 1.31 (s, 9H). MS: calc'd for $[C_{19}H_{27}F_3N_2O_5S_2+Na]$: 507.1, found 507.2.

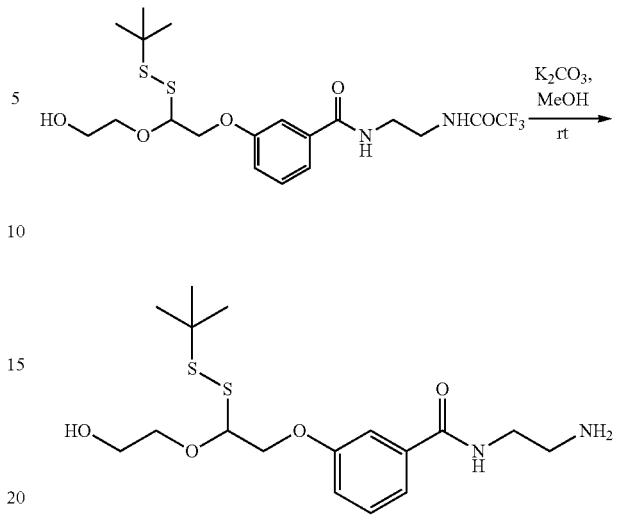

To a stirred solution of 3-(2-(tert-butyldisulfaneyl)-2-(2-hydroxyethoxy)ethoxy)-N-(2-(2,2,2-trifluoroacetamido)ethyl)benzamide (55 mg, 0.115 mmol) in methanol (0.5 mL), potassium carbonate (45.5 mg, 0.329 mmol, 2.9 equiv.) was added. The reaction progress was monitored by HPLC (100 mM TEAA/MeCN, 60% to 100% over 15 min, hold for 5 min at 100%) and upon completion, the reaction mixture was diluted with water and extracted with ethyl acetate (3×5 mL). The organic fractions were collected, dried over sodium sulfate and purified by HPLC to obtain N-(2-aminoethyl)-3-(2-(tert-butyldisulfaneyl)-2-(2-hydroxyethoxy)ethoxy)benzamide as colorless liquid. $^1$H NMR (500 MHz, DMSO) δ 8.43 (d, J=5.0 Hz, 1H), 7.45 (t, J=5.8 Hz, 2H), 7.37 (t, J=7.8 Hz, 1H), 7.11 (dd, J=7.8, 2.1 Hz, 1H), 4.92 (t, J=5.3 Hz, 1H), 4.71 (s, 1H), 4.28 (d, J=5.9 Hz, 2H), 3.87 (dt, J=9.4, 4.2 Hz, 1H), 3.63-3.50 (m, 3H), 3.32-3.22 (m, 4H), 2.71 (t, J=6.5 Hz, 2H), 1.31 (s, 9H). MS: calc'd for $[C_{17}H_{28}N_2O_4S_2+H]$: 389.2, found 389.4.

Scheme 41. SCN linker scheme

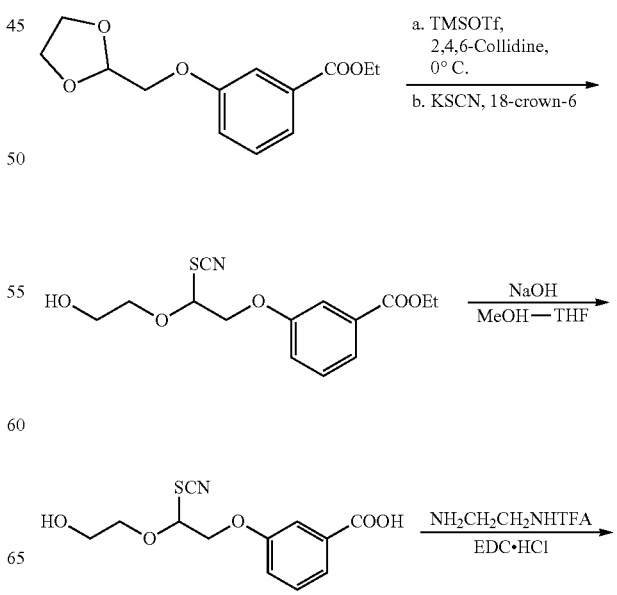

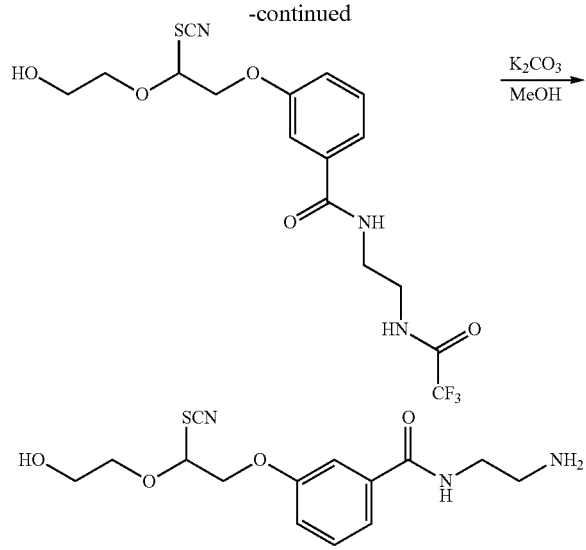

Experimental Procedures for S—S Linker

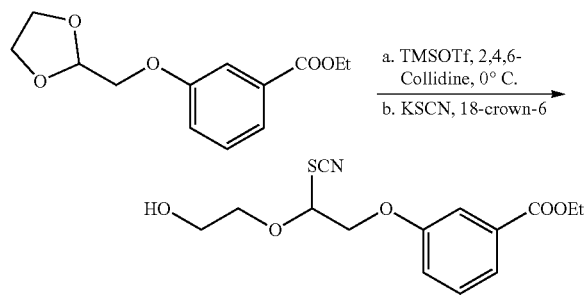

2,4,6-Collidine (0.59 mmol, 3.0 equiv.) was added to a stirred solution of ethyl 3-((1,3-dioxolan-2-yl)methoxy)benzoate (0.05 g, 0.79 mmol) in DCM (0.1 M) at 0° C. under Ar atmosphere followed by the addition of trimethylsilyl triflate (0.4 mmol, 2.0 equiv.). The mixture was stirred at the same temperature until the disappearance of an acetal on TLC and formation of highly polar compound was observed, after which a solution of potassium thiocyanate (0.99 mmol, 5.0 equiv.) and 18-crown-6 (0.99 mmol, 5.0 equiv.) in acetone (0.2 mL) was added to it. Disappearance of the polar component was confirmed by TLC. The product formation was confirmed by mass analysis, MS: calc'd for $[C_{14}H_{17}NO_5S-H]^-$: 311.0, found 310.0.

TABLE 1

Detectable moieties to be used in selected embodiments.

| Nucleoside/ nucleotide abbreviation | Dye name | λmax (nm) |
| --- | --- | --- |
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |

TABLE 1-continued

Detectable moieties to be used in selected embodiments.

| Nucleoside/ nucleotide abbreviation | Dye name | λmax (nm) |
| --- | --- | --- |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

Example 5: Cleavage Kinetics

An important property of a reversible terminator on a nucleotide is that it can be rapidly cleaved under conditions that do not adversely affect the DNA. FIG. 1 shows the cleavage kinetics of two —O-polymerase-compatible cleavable moieties, RT #1 and RT #2. RT #1 is

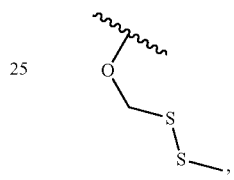

wherein the oxygen is attached to the 3' position of the deoxyribose. RT #2 is a 3' moiety of a compound as described herein, e.g., having the formula

Figure 4:
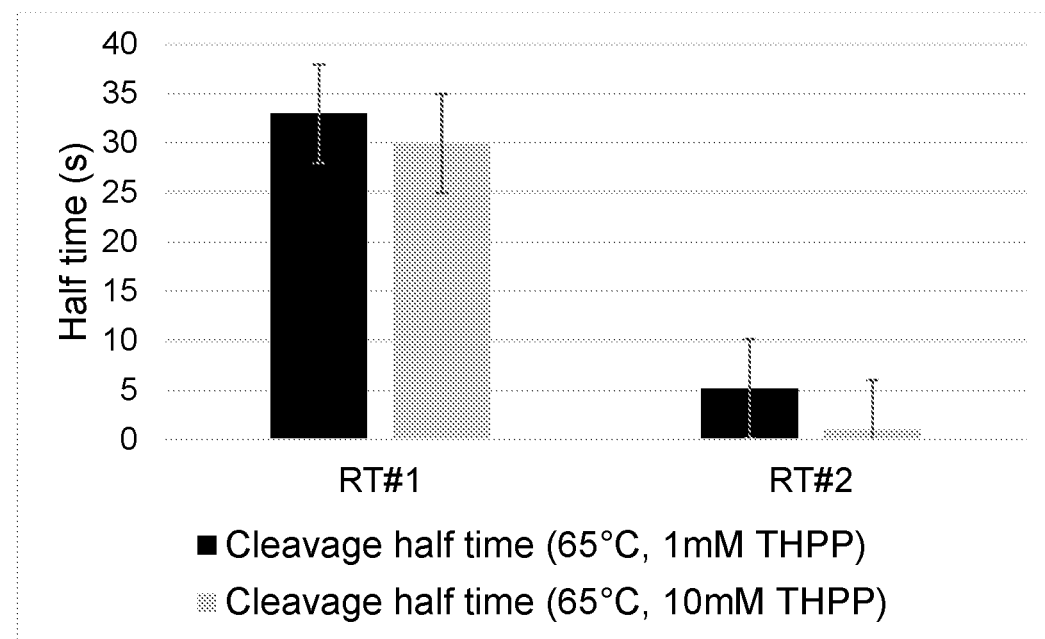
FIG. 4. Cleavage half time of two reversible terminators, RT #1 and RT #2.

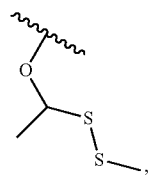 [SMILES: *OC(C)SSC ; ","]

wherein the oxygen is attached to the 3' position of the deoxyribose. In both cases, a dTTP nucleotide with each 3' moiety was incorporated into a growing DNA strand immobilized on a solid support. Excess nucleotides were washed away. Next, a cleavage solution containing 10 mM THPP as a reducing agent was introduced for controlled periods of time. The cleavage reaction was carried out at 55° C., in a buffer solution at 9.5 pH. The degree of cleavage is measured as the percent of DNA strands with a free 3'OH group on the nucleotide available for addition of a subsequent nucleotide. As seen in FIG. 1, the cleavage occurs approximately 10-fold faster with RT #2. This can be further observed by calculating the halftime, as depicted in FIG. 4, which shows a drastic improvement in the kinetics (i.e., a reduction in halftime) of RT #2 compared to RT #1. While the cleavage of the disulfide bond (reversible terminator) is rapid in both cases, the subsequent hydrolysis reaction that removes the residual portion of the 3' moiety is much faster with the new 3' moiety (i.e., RT #2). Modifying the reaction conditions (e.g., elevating the temperature to 65° C., increasing the pH, increasing the amount of reducing agent) results in faster cleavage. For example, data presented in FIG. 4 shows that by varying the amount of reducing agent and keeping the constant at 65° C., the kinetics can be further improved. Increasing the amount of reducing agent THPP from 1 mM to 10 mM results in a further reduction in halftime of RT #2 compared to RT #1.

Example 6: Chemical Stability

Another important property of a reversible terminator (e.g., 3' cleavable moiety as described herein) is chemical stability during storage and use. Any degradation that results in loss of the eversible terminator (e.g., 3' cleavable moiety as described herein) is particularly problematic, as the unterminated nucleotides will be incorporated during the sequencing reaction, causing some of the growing DNA strands to be extended by two bases rather than one, in what is known as a dephasing or leading effect. A dTTP nucleotide with the new reversible terminator (e.g., 3' cleavable moiety as described herein) was tested for stability at the three conditions listed in the table below, and no degradation was observed even at elevated temperature. The test was done by carrying out a single cycle extension reaction with the test solution, and then confirming that the incorporated nucleotide was terminated.

TABLE 2

| Stability Test | Result |
| --- | --- |
| 7 days at 4° C. | No degradation observed |
| 7 days at 25° C. | No degradation observed |
| 4 hours at 65° C. | No degradation observed |

Example 7. Incorporation

Another important property of a nucleotide with a reversible terminator (e.g., 3' cleavable moiety as described herein) is the ability to be rapidly incorporated by a DNA polymerase. Naturally occurring DNA polymerases are typically not capable of incorporating nucleotides modified with reversible terminator (e.g., 3' cleavable moiety as described herein) at the 3' position on the ribose of the nucleotide. As known in the art, a number of thermophilic polymerases have been engineered to enable the incorporation of nucleotides modified with 3' terminators. The table below shows the half-time for incorporation of RT #1, and two isomers of RT #2 by a modified thermophilic polymerase (Therminator 3, from New England BioLabs). The reaction was carried out in a buffered solution at pH 8.5, with nucleotides at 200 nM concentration, 4 mM Mg, at a temperature of 55° C. The polymerase was pre-bound to the primed DNA template. All three terminated nucleotides are efficiently incorporated by the modified DNA polymerase. The polymerase can be further modified for desired properties such as incorporation rate and accuracy.

TABLE 3

| Reversible Terminator | Incorporation half-time |
| --- | --- |
| RT #1 | 14 +/− 3 sec |
| RT #2, Isomer A | 9 +/− 3 sec |
| RT #2, Isomer B | 12 +/− 3 sec |

What is claimed is:

1. A kit comprising a labeled nucleotide, wherein the labeled nucleotide comprises:
   (i) a cleavable moiety covalently bound to the 3' oxygen of said labeled nucleotide, wherein the cleavable moiety has the formula -$L^{1P}$-S—S—$R^{6P}$(I); and
   (ii) a nucleobase linked via a covalent linker to a first detectable moiety, wherein said covalent linker comprises

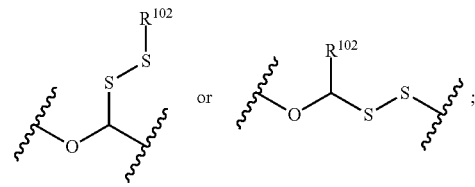

wherein,
$R^{102}$ is unsubstituted $C_1$-$C_4$ alkyl;
$L^{1P}$ is a substituted methylene, wherein $L^{1P}$ is substituted with a substituted or unsubstituted alkyl, or a substituted or unsubstituted heteroalkyl; and
$R^{6P}$ is unsubstituted methyl or unsubstituted ethyl.

2. The kit of claim 1, wherein the labeled nucleotide comprises a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

3. The kit of claim 1, wherein the labeled nucleotide is labeled adenine nucleotide, a labeled cytosine nucleotide, a labeled thymidine nucleotide, or a labeled guanosine nucleotide.

4. The kit of claim 1, wherein the kit comprises
   a labeled adenine nucleotide comprising the cleavable moiety of formula (I), wherein the labeled adenine nucleotide is linked via the covalent linker to the first detectable moiety,
   a labeled cytosine nucleotide comprising the cleavable moiety of formula (I), wherein the labeled cytosine nucleotide is linked via the covalent linker to a second detectable moiety,
   a labeled thymidine nucleotide comprising the cleavable moiety of formula (I), wherein the labeled thymidine nucleotide is linked via the covalent linker to a third detectable moiety, and
   a labeled guanosine nucleotide comprising the cleavable moiety of formula (I), wherein the labeled guanosine nucleotide is linked via the covalent linker to a fourth detectable moiety
   wherein the first detectable moiety, the second detectable moiety, the third detectable moiety, and the fourth detectable moiety are optionally different.

5. The kit of claim 4, wherein $L^{1P}$ is substituted with unsubstituted alkyl or unsubstituted heteroalkyl.

6. The kit of claim 4, wherein $L^{1P}$ is substituted with unsubstituted alkyl.

7. The kit of claim 1, wherein $L^{1P}$ is
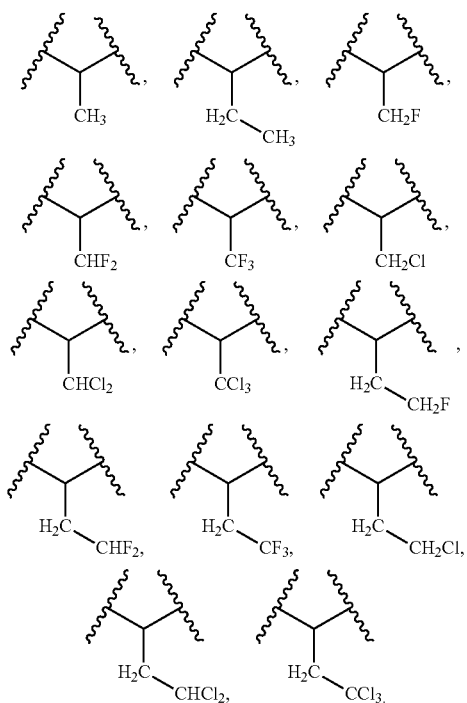
8. The kit of claim 1, wherein $L^{1P}$ is
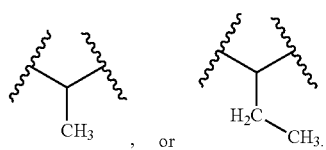
9. The kit of claim 1, wherein $L^{1P}$-S—S—$R^{6P}$ is:
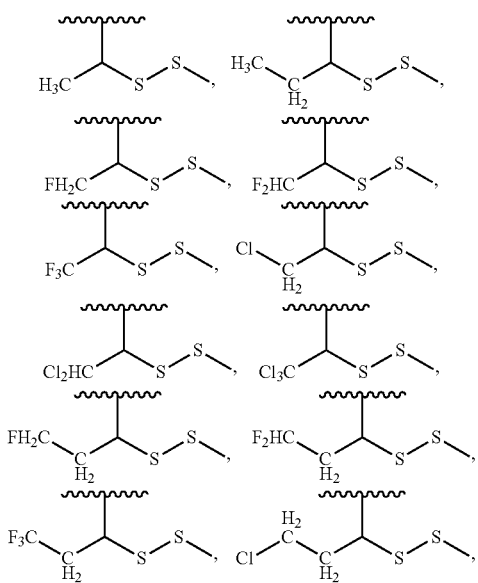
-continued
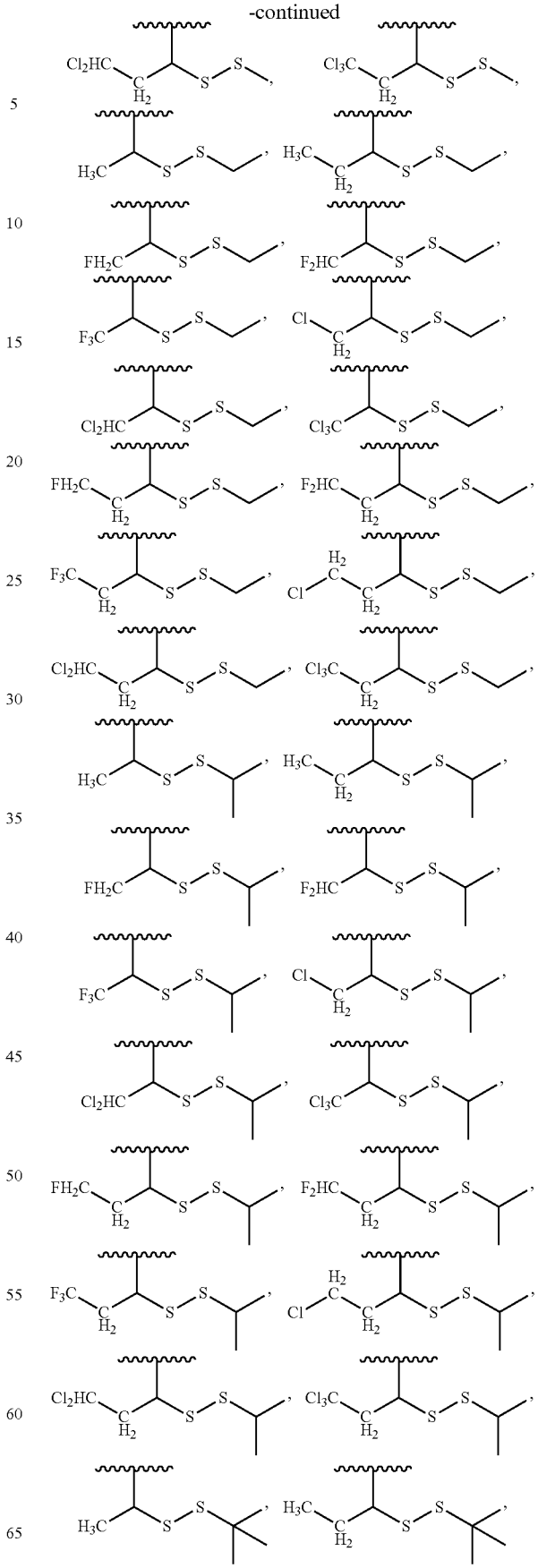

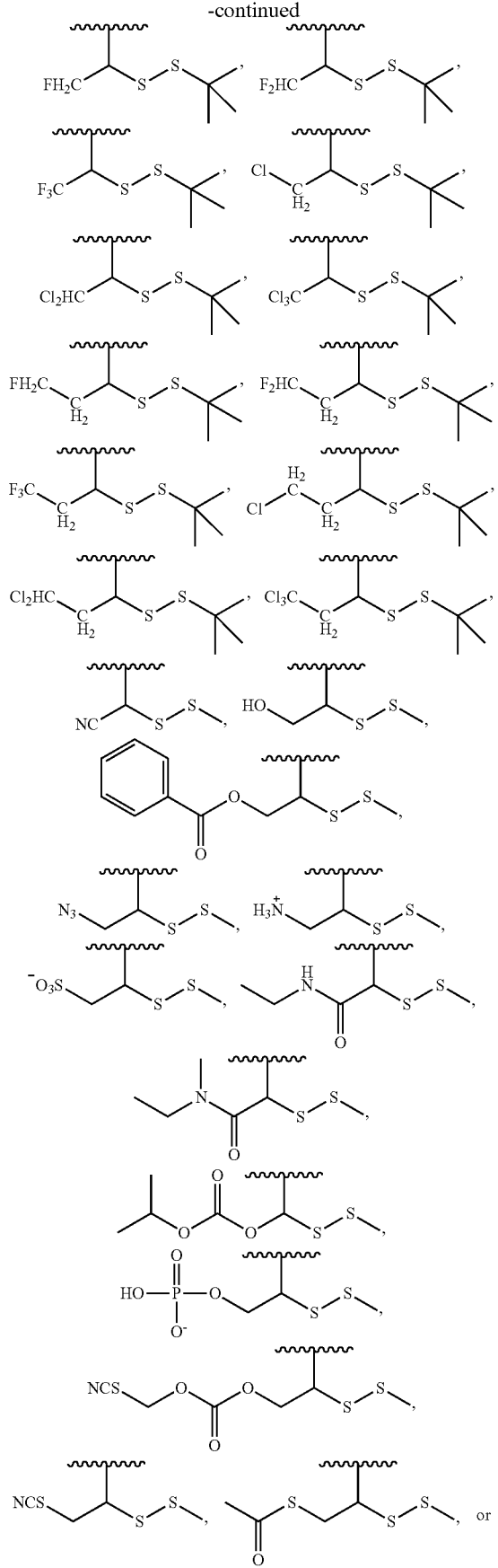
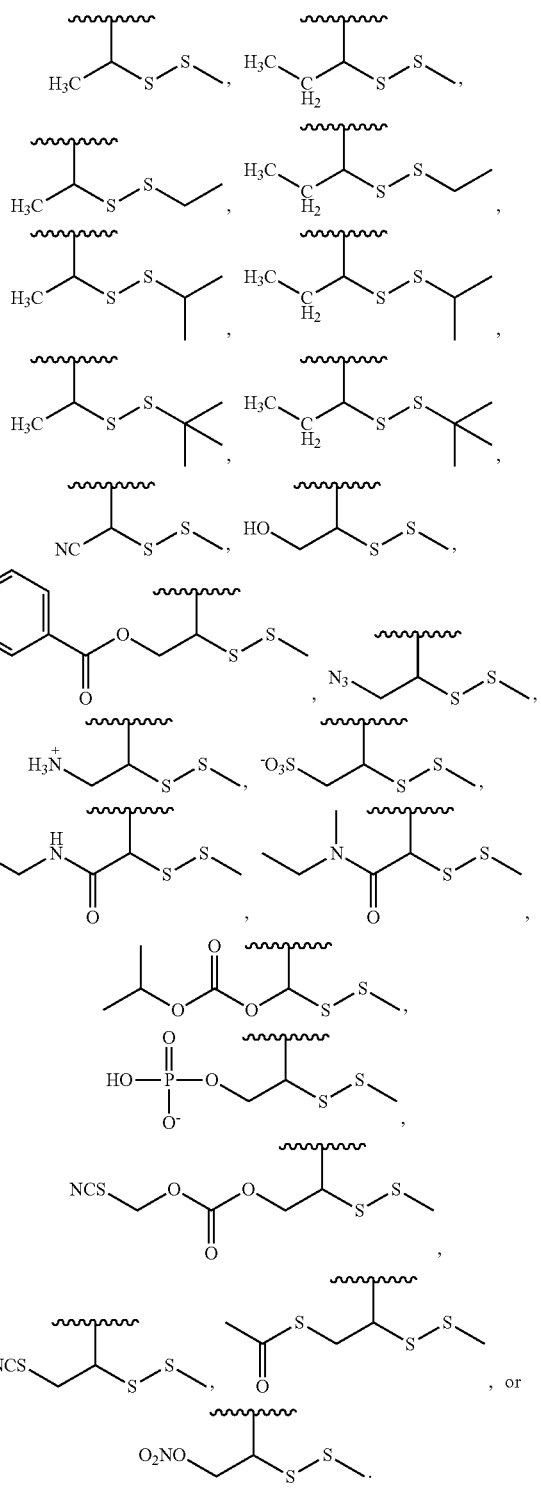
10. The kit of claim 1, wherein -L$^{1P}$-S—S—R$^{6P}$ is:

11. The kit of claim 1, wherein -L$^{1P}$-S—S—R$^{6P}$ is:

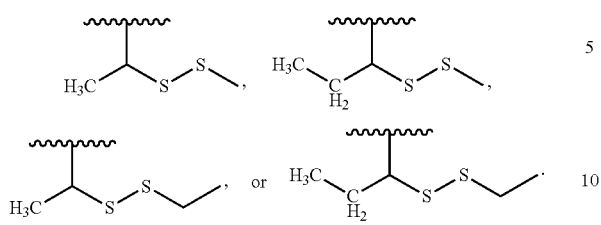

12. The kit of claim 1, wherein the first detectable moiety is a xanthene derivative, cyanine derivative, naphthalene derivative, coumarin derivative, oxadiazole derivative, anthracene derivative, pyrene derivative, oxazine derivative, acridine derivative, arylmethine derivative, or tetrapyrrole derivative.

13. The kit of claim 11, wherein said first detectable moiety is a xanthene derivative, cyanine derivative, naphthalene derivative, coumarin derivative, oxadiazole derivative, anthracene derivative, pyrene derivative, oxazine derivative, acridine derivative, arylmethine derivative, or tetrapyrrole derivative.

14. The kit of claim 1, wherein the detectable moiety is a xanthene derivative or cyanine derivative.

15. The kit of claim 4, wherein the detectable moiety is a xanthene derivative or cyanine derivative.

16. The kit of claim 1, further comprising a polymerase and a solid substrate.

17. The kit of claim 4 comprising

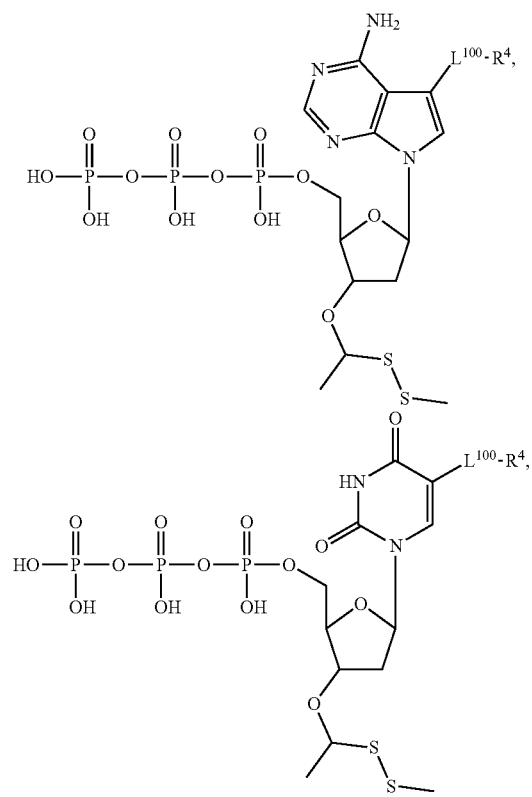

-continued

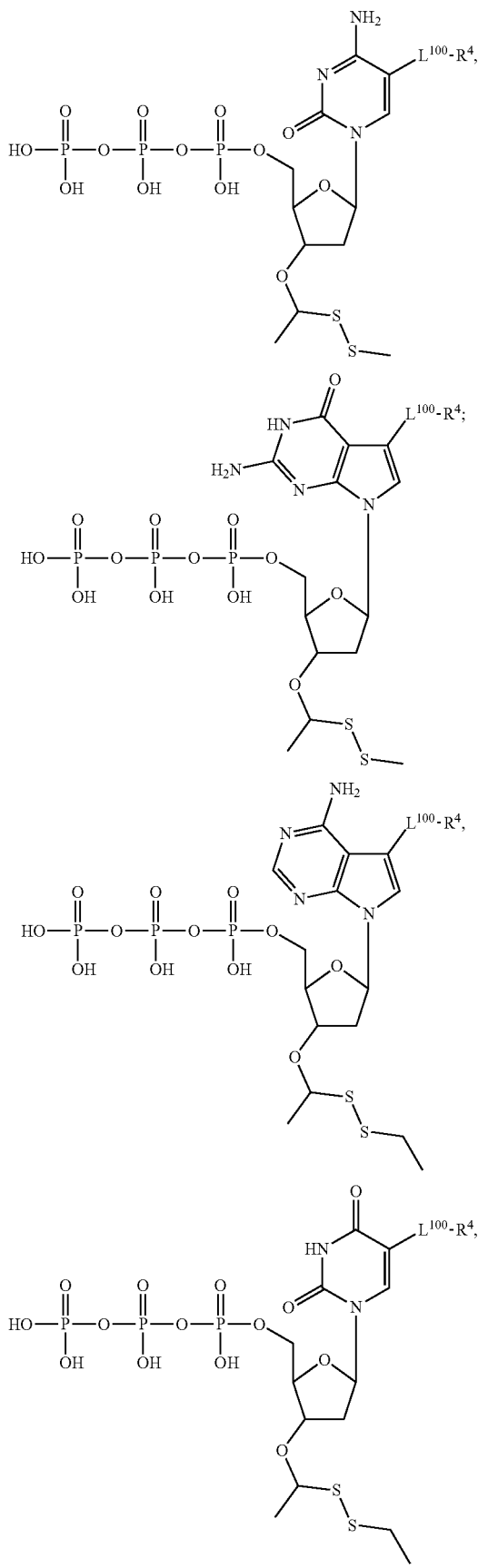

619
-continued

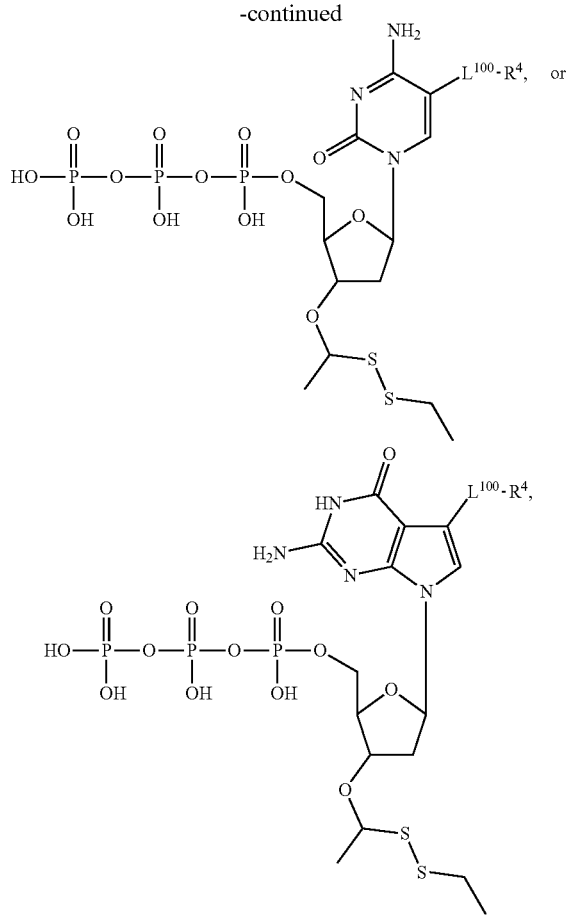

wherein
L$^{100}$ is said covalent linker and R$^4$ is independently said first detectable moiety, said second detectable moiety, third detectable moiety, or said fourth detectable moiety.

18. The kit of claim 1, wherein the covalent linker comprises

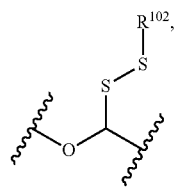

wherein R$^{102}$ is unsubstituted C$_1$-C$_4$ alkyl.

19. The kit of claim 1, wherein L$^{1P}$

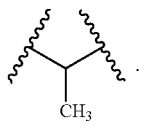

20. The kit of claim 1, wherein the covalent linker comprises

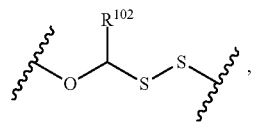

wherein R$^{102}$ is unsubstituted C$_1$-C$_4$ alkyl.

21. The kit of claim 20, wherein R$^{102}$ is unsubstituted methyl, unsubstituted ethyl, or unsubstituted propyl.

* * * * *